(12) United States Patent
Vos et al.

(10) Patent No.: US 7,375,125 B2
(45) Date of Patent: May 20, 2008

(54) MELANOCORTIN-4 RECEPTOR BINDING COMPOUNDS AND METHODS OF USE THEREOF

(75) Inventors: Tricia J. Vos, Medford, MA (US); Michael E. Solomon, Nashua, NH (US); Christopher F. Claiborne, Cambridge, MA (US); Martin P. Maguire, Woburn, MA (US); Mingshi Dai, Billerica, MA (US); Michael Patane, Andover, MA (US); Thomas H. Marsilje, San Diego, CA (US)

(73) Assignee: Ore Pharmaceuticals, Inc., Gaithersburg, MD (US)

( * ) Notice: Subject to any disclaimer, the term of this patent is extended or adjusted under 35 U.S.C. 154(b) by 228 days.

(21) Appl. No.: 10/462,436

(22) Filed: Jun. 16, 2003

(65) Prior Publication Data

US 2004/0082779 A1 Apr. 29, 2004

Related U.S. Application Data

(63) Continuation-in-part of application No. 09/778,468, filed on Feb. 7, 2001, now Pat. No. 6,699,873, which is a continuation-in-part of application No. 09/632,309, filed on Aug. 4, 2000, now abandoned.

(60) Provisional application No. 60/223,277, filed on Aug. 3, 2000, provisional application No. 60/147,288, filed on Aug. 4, 1999.

(51) Int. Cl.
C07D 233/20 (2006.01)
A61K 31/4164 (2006.01)

(52) U.S. Cl. .................. 514/401; 514/402; 548/311.4; 548/354.1

(58) Field of Classification Search ............. 548/311.4, 548/354.1; 514/401, 402
See application file for complete search history.

(56) References Cited

U.S. PATENT DOCUMENTS

| 4,598,077 | A | * | 7/1986 | Fujii et al. ................ 514/235.8 |
| 5,731,408 | A | | 3/1998 | Hadley et al. |
| 2003/0096827 | A1 | | 5/2003 | Yu et al. |

FOREIGN PATENT DOCUMENTS

| GB | 1418053 | | 12/1975 |
| JP | 05156475 | | 6/1993 |
| WO | WO-97/47316 | | 12/1997 |
| WO | WO-99/64002 | | 12/1999 |
| WO | WO 01/10842 | * | 2/2001 |
| WO | WO 02/062766 | * | 8/2002 |

OTHER PUBLICATIONS

Vergoni et al., PubMed Abstract (Eur J Pharmacol. 405(1-3):25-32) Sep. 2000.*
Ramos et al., PubMed Abstract (Curr Opin Clin Nutr Metab Care. 7(4):427-34) Jul. 2004.*
Lechan et al., Editorial: Hypothalamic Melanocortin Signalling in Cachexia, Endocrinology, 142(8):3288-3291, Aug. 2001.*
Hagan et al., Long-term orexigenic effects of AgRP-(83-132) involve mechanisms other than melanocortin receptor blockade, Am J Physiol Integrative Comp Physiol. 279: R47-R52, 2000.*
Yamaguchi, CAPLUS Abstract 120:220508, 1994.*
Scholz et al., "Inhibition of FceRl-Mediated Activation of Mast Cells by 2,3,4-Tryhydropyrimidino[ 2,1-a]isoquinolines," *Journal of Medicinal Chemistry.* 47(7), pp. 1050-1059, Mar. 1998.
Legrand, Chemical Abstract 87:5904, 1977.
Bednarek, Maria A. et al. "Analogs of MTII, Lactam Derivatives of . alpha.-Melanotrophin Modified at the N-terminu, and Their Selectively at Human Melanocortin Receptors 3, 4, and 5." *Biochemical and Biophysical Research Communications.* vol. 261, pp. 209-213 (1999).
Kask, Ants et al., "Selective Antagonist for the MelanoCortin 4 Receptor (HS014) Increase Food Intake in Free-Feeding Rats." *Biochemical and Biophysical Research Communications.* vol. 245, pp. 90-93 (1998).
Haskell-Luevano, Carrie et al., "Biological and Conformational Examination of Stereochemical Modifications Using the Template Melanotropin Peptide, Ac-Nle-c-[Asp-His-Phe-Arg-Trp-Ala-Lys]-NH2, on Human Melanocortin Receptors." *Journal of Medicinal Chemistry.* vol. 40, pp. 1738-1748 (1997).
Vos, T.J. et al., "Identification of 2-'2-'2-(5-Bromo-2-methoxyphenyl)-ethyl-3-fluoro-phenyl-4,5-dihydro-1H-imidazole (ML00253764), a Small Molecule Melanocortin Receptor Antagonist That Effectively Reduces Tumor Induced Weight Loss in a Mouse Model." *Journal of Medicinal Chemistry.* vol. 47(7), pp. 1602-1604 (2004).

* cited by examiner

*Primary Examiner*—Deepak Rao
(74) *Attorney, Agent, or Firm*—Venable LLP; Keith G. Haddaway

(57) ABSTRACT

Provided are MC4-R binding compounds of the formula XVII:

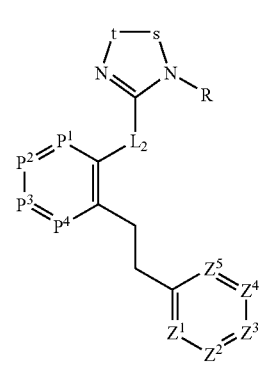

wherein $L_2$ is a linker group, and $P^1$, $P^2$, $P^3$, $P^4$, $Z^1$, $Z^2$, $Z^3$, $Z^4$, $Z^5$, t, s, and R are as described in the specification. Methods of using the compounds to treat MC4-R associated disorders, such as disorders associated with weight loss, are also provided.

30 Claims, 2 Drawing Sheets

MELANOCORTIN-4 RECEPTOR BINDING COMPOUNDS AND METHODS OF USE THEREOF

RELATED APPLICATIONS

This application is a continuation-in-part of U.S. patent application Ser. No. 09/778,468, entitled "Melanocortin-4 Receptor Binding Compounds and Methods of Use Thereof," filed on Feb. 7, 2001 now U.S. Pat. No. 6,699,873; which is a continuation-in-part of U.S. patent application Ser. No. 09/632,309, entitled "Melanocortin-4 Receptor Binding Compounds and Methods of Use Thereof," filed on Aug. 4, 2000 now abandoned; which claims priority to U.S. Provisional Application Ser. No. 60/223,277, entitled "Melanocortin-4 Receptor Binding Compounds and Methods of Use Thereof," filed on Aug. 3, 2000; and U.S. Provisional Application Ser. No. 60/147,288, entitled "Melanocortin-4 Receptor Binding Compounds and Methods of Use Thereof," filed on Aug. 4, 1999; the entire contents of all of the aforementioned applications are hereby incorporated herein by reference.

BACKGROUND

Melanocortins are known to have a broad array of physiological actions (Nakanishi, et al. *Nature* (1979) 278:423-427). Aside from their well known effects on adrenal cortical functions and on melanocytes, melanocortins have been shown to affect behavior, learning, memory, control of the cardiovascular system, analgesia, thermoregulation, and the release of other neurohumoral agents including prolactin, luetinizing hormone, and biogenic amines (De Weid et al. *Methods Achiev. Exp. Pathol.* (1991) 15:167-199; De Weid et al. *Physiol. Rev.* (1982) 62:977-1059; Gruber, K. A. et al. *Am. J. Physiol.* (1989) 257:R681-R694; Murphy et al. *Science* (1980) 210:1247-1249; Murphy et al. *Science* (1983) 221:192-193; Ellerkmann, E. et al. *Endocrinol.* (1992) 130:133-138; Versteeg, D. H. G. et al. *Life Sci.* (1986) 835-840). Peripherally, melanocortins have been identified to have immunomodulatory and neurotrophic properties, and to be involved in events surrounding partition (Cannon, J. G. et al. *J. Immunol.* (1986) 137:2232-2236; Gispen, W. H. *Trends Pharm. Sci.* (1992) 11:221-222; Wilson, J. F. *Clin. Endocrinol.* (1982) 17:233-242; Clark, D. et al. *Nature* (1978) 273:163-164; Silman, R. E. et al. *Nature* (1976) 260:716-718). Furthermore, melanocortins are present in a myriad of normal human tissues including the brain, ovary, lung, thyroid, liver, colon, small intestine and pancreas (Tatro, J. B. et al. *Endocrinol.* (1987) 121:1900-1907; Mountjoy, K. G. et al. *Science* (1992) 257:1248-1251; Chhajlani, V. et al., *FEBS Lett.* (1992) 309:417-420; Gantz, L. et al., *J. Biol. Chem.* (1993) 268:8246-8250; Gantz, L. et al, *J. Biol. Chem.* (1993) 268:15174-15179).

Recent studies have described an unexpected diversity of subtypes of receptors for the melanocortin peptides and determined that they belong to the superfamily of seven transmembrane G-protein linked cell surface receptors (Mountjoy, K. G. et al., *Science* (1992), supra; Chhajlani, V. et al., *FEBS Lett.* (1992), supra). Five melanocortin receptor subtypes have been cloned. The melanocortin-1 (MC1) receptor is found in melanoma cells, where it has a role in mediating pigmentation. The melanocortin-2 receptor (MC2-R or ACTH receptor) is found in the adrenal glands where it mediates the effects of ACTH (adrenocorticotrophic hormone). The melanocortin-3 receptor (MC3-R) is primarily found in the central nervous system (CNS) (Gantz, L. et al., *J. Biol. Chem.* (1993) 268:8246-8250), but its physiological function is still unknown. The melanocortin-4 receptor (MC4-R) has been found in the brain, where it is widely distributed in several areas, including the cortex, thalamus, hypothalamus, brain stem, and spinal cord (Gantz, L. et al. *J. Biol. Chem.* (1993) 268:15174-15179; Mountjoy, K. G. et al. *Mol. Endocrinol.* (1994) 8:1298-1308). MC4-R has recently been related to weight homeostasis. MC4-R "knock out" mice have been shown to develop obesity (Huszar et al. *Cell* (1997) 88:131-141). The feeding behavior leading to the obesity can be inhibited by injection of MSH peptides (Vergoni et al. *Neuropeptides* (1986) 7:153-158; Vergoni et al. *Eur. J. Pharmacol.* (1990) 179:347-355; Fan et al. *Nature* (1997) 385:165-168). The melanocortin-5 receptor (MC5-R) has a wide peripheral distribution and is believed to participate in the regulation of the exocrine gland function (Chen et al. *Cell* (1997) 91:789-798).

SUMMARY

In one aspect, the invention pertains to a method for treating a melanocortin-4 receptor (MC4-R) associated state in a mammal. The method involves administering an effective amount of a MC4-R binding compound to a mammal, such that the MC4-R associated state is treated. The MC4-R binding compound is of the formula (I):

B-Z-E                  (I)

wherein B is an anchor moiety, Z is a central moiety, E is a MC4-R interacting moiety, and pharmaceutically acceptable salts, thereof.

In a further embodiment, the MC4-R binding compound is of the formula (II):

B-A-E                  (II)

wherein B is an anchor moiety, A is cyclic moiety, E is a MC4-R interacting moiety, and pharmaceutically acceptable salts, thereof.

In another embodiment, the invention pertains to another method for treating an MC4-R associated state in a mammal, by administering to a mammal an effective amount of a MC4-R binding compound of formula (III):

$B\text{-}L_1\text{-}A\text{-}L_2\text{-}E$                  (III)

wherein B is an anchor moiety, $L_1$ and $L_2$ are linking moieties, A is a cyclic moiety, E is a MC4-R interacting moiety, and pharmaceutically acceptable salts thereof.

The invention also pertains to treating MC4-R associated states with an MC4-R binding compound of formula III, wherein B is substituted or unsubstituted biaryl, unsubstituted or substituted heterocyclic, or unsubstituted or substituted phenyl, wherein one or more of said substituents are halogens, hydroxy, alkyl, alkynyl, alkoxy, aryl, amino, cyano, or nitro; $L_1$ is a covalent bond, $C_1\text{-}C_{10}$ branched or unbranched alkyl, wherein one or two of the carbons are optionally replaced with oxygen, sulfur or nitrogen atoms; $L_2$ is a covalent bond, substituted or unsubstituted amino, ether, thioether, or alkyl; E is substituted or unsubstituted alkyl, amino, amidino, guanidino, heterocyclic, or aryl, wherein said substituents are amino, arylalkyl, aminoalkyl, alkyl, aryl, alkenyl, or alkynyl; and A is a substituted or unsubstituted phenyl, heteroaryl, cycloalkyl, or biaryl, and pharmaceutically acceptable salts thereof.

In another embodiment, the invention pertains to a method for treating an MC4-R associated state in a mammal by administering an effective amount of a MC4-R binding compound to a mammal, such that the MC4-R associated state is treated. In this embodiment, the compound is of the formula (IV):

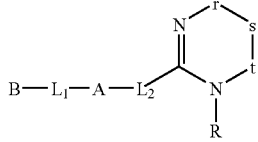

(IV)

wherein B is substituted or unsubstituted alkyl, cycloalkyl, alkenyl, alkynyl, aryl, or heteroaryl; A is aryl, heteroaryl, biaryl, cycloalkyl, heterocyclic, or cycloalkenyl; $L_1$ and $L_2$ are selected from the group consisting of a covalent bond, $C_1$-$C_6$ branched or unbranched alkyl, wherein one or two of the carbons are optionally replaced with oxygen, sulfur or nitrogen atoms; r is a covalent bond, CH, $CH_2$, $CHR^1$, $CR^1R^2$, or H; t is CH, $CH_2$, $CHR^3$, $CR^3R^4$, or H; s is $CHR_5$, $CR^5$, $CR^5R^6$ or absent (e.g., leaving a non-cyclic diamine); R is H, substituted or unsubstituted alkyl, arylalkyl, or heteroalkyl, and may optionally be linked to A, B, $L_1$, or $L_2$; $R^1$, $R^2$, $R^3$, $R^4$, $R^5$, and $R^6$ are each substituted or unsubstituted alkyl, alkenyl, halogen, thiol, thioether, thioalkyl, or alkoxy, and may optionally be linked to form a carbocyclic or heterocyclic ring. Pharmaceutically acceptable salts of the MC4-R binding compound are also included.

The invention also pertains to methods for treating an MC4-R associated state in a mammal by administering an effective amount of a MC4-R binding compound of the formula (V):

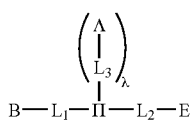

(V)

wherein B is substituted or unsubstituted biaryl, unsubstituted or substituted heterocyclic, or unsubstituted or substituted phenyl, wherein one or more of said substituents are halogens, alkyl, alkynyl, alkoxy, aryl, amino, cyano, or nitro; $L_1$ is a covalent bond, $C_1$-$C_{10}$ branched or unbranched alkyl, wherein one or two of the carbons are optionally replaced with oxygen, sulfur or nitrogen atoms; $L_2$ is a covalent bond, substituted or unsubstituted amino, ether, thioether, or alkyl; E is substituted or unsubstituted alkyl, amino, amidino, guanidino, heterocyclic, or aryl, wherein said substituents are amino, arylalkyl, aminoalkyl, alkyl, aryl, alkenyl, or alkynyl; Π is a covalent bond, a carbon atom, a nitrogen atom, heterocyclic, alkyl, cycloalkyl, or aryl; $L_3$ is a covalent bond, $C_1$-$C_6$ branched, unbranched or cyclic alkyl, wherein one, two or three of the carbons are optionally replaced with oxygen, sulfur or nitrogen atoms, carbonyl, aminocarbonyl, aminocarbonylamino, aminocarbonyloxy, or aminothiocarbonyl; and Λ is heterocyclic, aryl, alkoxy, amino, alkyl, alkenyl, alkynyl, or hydrogen; and λ is 0, 1 or 2, and pharmaceutically acceptable salts thereof.

In yet another embodiment, the invention also pertains to a method for treating an MC4-R associated state in a mammal by administering an effective amount of a MC4-R binding compound to a mammal, wherein the compound is an MC4-R antagonist, and is of the formula (VI):

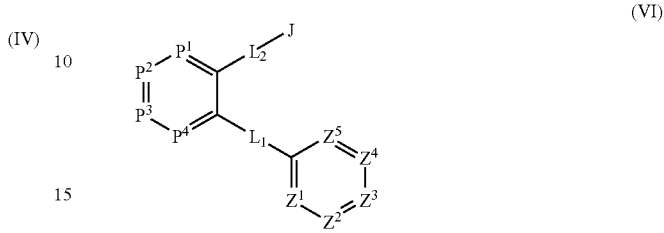

(VI)

wherein
$P^1$, $P^2$, $P^3$, and $P^4$ are optionally substituted carbon, sulfur, or nitrogen, and wherein one of $P^1$, $P^2$, $P^3$ and $P^4$ may represent a covalent bond; $Z^1$, $Z^2$, $Z^3$, $Z^4$, and $Z^5$ are optionally substituted carbon or nitrogen; $L_1$ is a covalent bond, $C_1$-$C_{10}$ branched or unbranched alkyl, wherein one or two of the carbons are optionally replaced with oxygen, sulfur or nitrogen atoms; $L_2$ is a covalent bond, substituted or unsubstituted amino, ether, thioether, or alkyl; and J is an unsubstituted or substituted nitrogen containing heterocycle or a substituted or unsubstituted amino group, and pharmaceutically acceptable salts thereof.

In another embodiment, the MC4-R binding compound is of formula (VII):

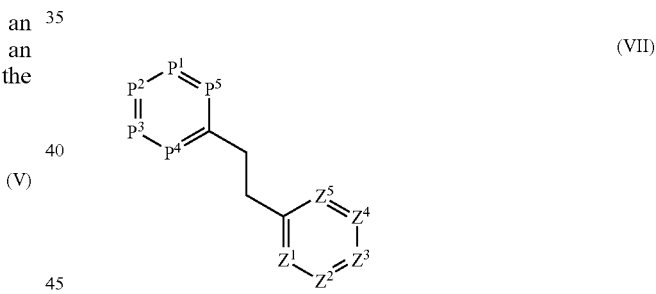

(VII)

wherein
$Z^1$, $Z^2$, $Z^3$, $Z^4$, and $Z^5$ are CH, N, or substituted carbon; and
$P^1$, $P^2$, $P^3$, $P^4$, and $P^5$ are CH, N or substituted carbon.

In another embodiment, the MC4-R binding compound is of formula (VIII):

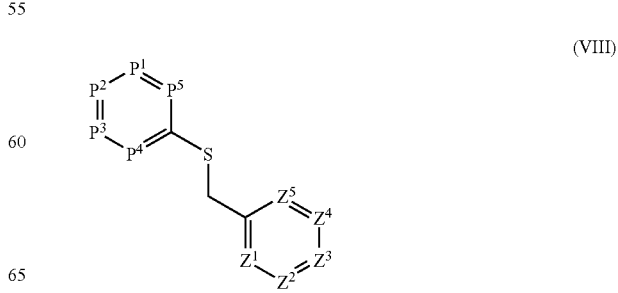

(VIII)

wherein $Z^1$, $Z^2$, $Z^3$, $Z^4$, and $Z^5$ are CH, N, or substituted carbon; and $P^1$, $P^2$, $P^3$, $P^4$, and $P^5$ are CH, N or substituted carbon.

The invention also pertains to MC4-R binding compound of the formula (IX):

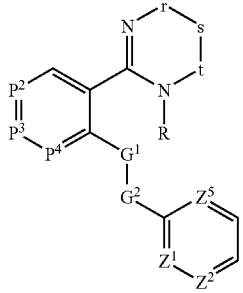

(IX)

wherein:

$P^2$ is CH, CF, CCl, CBr, C-alkyl, C-aryl, C-alkoxy, C—CN, C—OH, CI, or a covalent bond;

$P^3$ is CH, CF, CCl, CBr, C-alkyl, C-aryl, C-alkoxy, C—CN, C—OH, or CI;

$P^4$ is CH, CCl, CBr, CF, C-alkyl, C-aryl, C-alkoxy, C—CN, C—OH, CI, or a sulfur atom;

$G^1$ and $G^2$ are each independently $CH_2$, S, or O;

r is a covalent bond or $CH_2$;

t is $CH_2$, $CHR^3$, or $CR^3R^4$;

s is $CH_2$, $CHR^5$ or $CR^5R^6$;

R is hydrogen, alkyl, alkoxycarbonyl, or alkylcarbonyl;

$Z^1$ is CH, or covalently linked to $Z^2$ to form a naphthyl ring;

$Z^2$ is CH, C—(C≡CH), CCl, CBr, CI, CF, or covalently linked to $Z^1$ to form a naphthyl ring;

$Z^5$ is CH, C-alkoxy or C—OMe;

$R^3$, $R^4$, $R^5$, and $R^6$ are methyl, ethyl, hydroxyl, alkoxy, halogen, cyano, nitro, or amino, or pharmaceutically acceptable salts thereof.

In still another embodiment the MC4R binding compound is of the formula XVII:

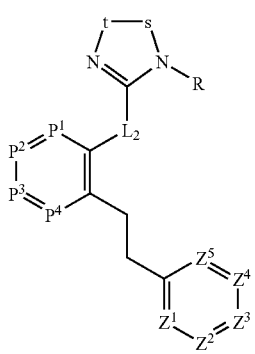

XVII wherein $P^1$, $P^2$, $P^3$, and $P^4$ are each selected from a substituted or unsubstituted carbon, wherein one of $P^1$-$P^4$ is optionally replaced by a nitrogen atom, or the ring bearing $P^1$-$P^4$ is a thiophene ring, wherein $P^3$-$P^4$ together are replaced by a sulfur atom;

$Z^1$ is CH or a carbon substituted with $R^7$;

$Z^2$ is CH or a carbon substituted with $R^8$;

$Z^3$, $Z^4$ and $Z^5$ are each independently selected from CH or a carbon substituted with $R^9$;

$R^7$ is $C_{1-3}$ alkoxy, $C_{1-3}$ haloalkoxy, cyano, $C_{1-3}$ cyanoalkyl, halo, $C_{1-3}$ alkyl, or $C_{1-3}$ haloalkyl;

$R^8$ is halo, $C_{1-3}$ alkyl, $C_{1-3}$ haloalkyl, or $R^7$ and $R^8$ are optionally taken together with their intervening atoms to form a fused, 5-6 membered aromatic or nonaromatic ring having 0-2 ring heteroatoms selected from oxygen, nitrogen or sulfur;

each $R^9$ is independently selected from halo, cyano, trialkylsiloxy, $C_{1-6}$ alkyl, $C_{1-6}$ haloalkyl, $C_{1-6}$ alkoxy, $C_{1-6}$ haloalkoxy, $C_{1-6}$ alkynyl, $N(R^{10})_2$, $(C_{1-6}$ alkyl$)$-$N(R^{10})_2$, $O(C_{1-6}$ alkyl$)$-$N(R^{10})_2$, $C_{1-6}$ alkylsulfonyl, $C_{1-6}$ alkylthio, or phenyl;

Each $R^{10}$ is independently selected from hydrogen, $C_{1-4}$ alkyl, or two $R^{10}$ on the same nitrogen are taken together with their intervening nitrogen to form a 5-6 membered ring having 1-2 ring heteroatoms selected from oxygen, nitrogen or sulfur;

$L_2$ is a covalent bond, a substituted or an unsubstituted 1-2 carbon chain or a 2 carbon carbonyl chain, wherein one of the carbons along with the hydrogen attached thereto is optionally replaced by oxygen, $N(R^{10})$, or sulfur;

t is $CH_2$, $CHR^3$, or $CR^3R^4$, and s is $CH_2$, $CHR^5$, or $CR^5R^6$, or t-s taken together is CH=CH, $CR^3$=CH, CH=$CR^5$ or $CR^3$=$CR^5$;

$R^3$, $R^4$, $R^5$, and $R^6$ are each independently selected from $C_{1-4}$ alkyl, $C_{1-4}$ alkylcarboxyl, $C_{1-4}$ alkylcarboxamide, or two of $R^3$, $R^4$, $R^5$, and $R^6$ are taken together with their intervening atom or atoms to form a fused 3-7 membered aromatic or nonaromatic or 3-7 membered spirocyclic ring, having 0-2 ring heteroatoms selected from oxygen, nitrogen or sulfur;

R is hydrogen or a $C_{1-8}$ alkyl or $C_{1-8}$ alkylcarbonyl that is substituted with 0-2 $R^{11}$, or R and $R^5$ are taken together with their intervening atoms to form a fused pyrrolidino or piperidino ring, or R and $L_2$ are taken together with their intervening atoms to form a fused five membered ring having 1-2 ring heteroatoms selected from oxygen, nitrogen or sulfur;

each $R^{11}$ is independently selected from $C_{1-3}$ alkyl, cyano, halo, haloalkyl, $N(R^{10})_2$, (C=O)$N(R^{10})_2$, OC(=O)$N(R^{10})_2$, OH, S($C_{1-6}$ alkyl), $SO_2(C_{1-6}$ alkyl), $SO_2N(R^{10})_2$, $C_{1-6}$ alkoxy, $C_{1-6}$ alkylcarbonyl, $C_{1-6}$ alkylcarboxyl, $C_{1-6}$ alkoxycarboxyl, $C_{5-6}$ aryl, $C_{6-10}$ arylalkyl, or a 3-6 membered heterocyclyl having 1 or 2 heteroatoms;

or a pharmaceutically acceptable salt thereof.

The invention also features a pharmaceutical composition for the treatment of a MC4-R associated state in a mammal. The pharmaceutical compositions contain a pharmaceutically acceptable carrier and a MC4-R binding compound. The compounds are described herein in the context of the description of the method but it should be understood that the invention further pertains to pharmaceutical compositions containing the compounds and the compounds per se. For example, pharmaceutical compositions of the invention include a pharmaceutically acceptable carrier and an effective amount of at least one MC4-R binding compound of the formula (I):

B-Z-E (I)

wherein B is an anchor moiety, Z is an central moiety, E is a MC4-R interacting moiety, and pharmaceutically acceptable salts thereof.

DETAILED DESCRIPTION OF THE INVENTION

Figure 1A:
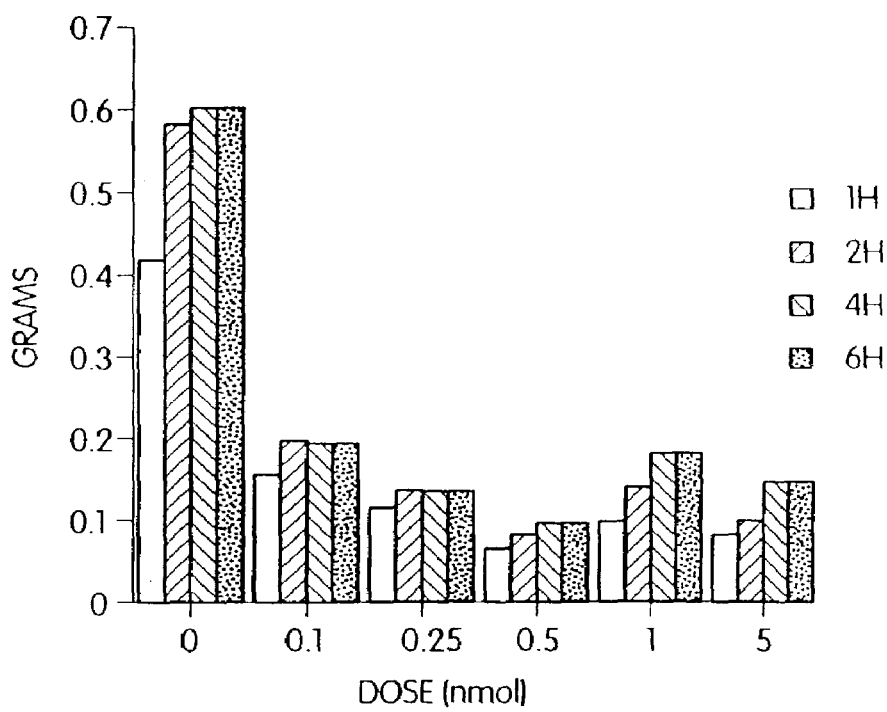
FIGS. 1a and 1b are bar graphs showing the effects of MT II (a MC4-R agonist) on food intake in lean mice.

In one aspect, the invention pertains to a method for treating a melanocortin-4 receptor (MC4-R) associated state in a mammal. The method involves administering an effective amount of a MC4-R binding compound to a mammal, such that the MC4-R associated state is treated. The MC4-R binding compound is of the formula (I):

B-Z-E            (I)

wherein B is an anchor moiety, Z is a central moiety, E is a MC4-R interacting moiety, and pharmaceutically acceptable salts thereof.

The term "MC4-R" includes receptors for α-melanocyte stimulating hormone. The MC4-R is usually found in the brain where it is widely distributed (Mountjoy et al. *Mol. Endocrinol.* (1994) 8:1298-1308). Melanocortins are peptide hormones that play an important role in regulating melanocyte pigmentation as well as memory and thermoregulation. They consist of various peptides, such as α-melanocyte stimulating hormone, that are cleaved from the polypeptide precursor prooptiomelanocortin (POMC). The effects of melanocortins are mediated via stimulation of adenylate cyclase via the activation of the melanocortin receptors.

The melancortin-4 receptor (MC4-R) is a G-protein coupled receptor (GPCR) expressed in brain tissue. The specific role of the MC4-R protein in vivo was investigated by engineering MC4-R "knock out" mice. The mice were unable to produce functional MC4-R protein, because the endogenous MC4-R gene coding sequence was deleted.

The knock-out mice were produced by using human MC4-r gene sequences to isolate and clone the murine MC4-r gene. A murine MC4-r targeting construct was then generated which was designed to delete the majority of the murine MC4-r coding sequence upon homologous recombination with the endogenous murine MC4-r gene. Embryonic stem (ES) cells containing the disrupted MC4-r gene were produced, isolated and microinjected into murine blastocysts to yield mice chimeric for cells containing a disrupted MC4-r gene. Offspring of the chimeric mice resulting from germline transmission of the ES genome were obtained and animals heterozygous for the disrupted MC4-R were identified.

To assess the role of MC4-R in vivo, the animals heterozygous for the MC4-r disrupted gene were bred together, producing litters containing wild-type mice, mice heterozygous for the MC4-r mutation and mice homozygous for the MC4-R mutation. The weight gain of the animals was monitored regularly. Homozygous null MC4-R mutants showed an increase in weight compared to mice heterozygous for MC4-R deletion and wild type mice as early as 25 days of age. By 54-58 days of age, MC4-R deficient mice exhibited, on average, a 55-70% greater weight relative to wild type mice, and an approximately 50% greater weight compared to mice heterozygous for the MC4-R deletion.

The language "MC4-R associated states" includes those states, disorders, or diseases characterized by aberrant or undesirable activity or expression of MC4-Rs. It also includes those states, disorders and diseases associated with MC4-R ligands (e.g., α-melanocyte stimulating hormone). The language also includes prevention of states, disorders and diseases characterized by aberrant or undesirable activity of MC4-Rs or its ligands. Examples of MC4-R associated states include, but are not limited to, disorders involving or associated with pigmentation, bones, pain, and weight homeostasis, e.g., weight loss or obesity. MC4-R associated states include the unhealthy decrease in body weight that can occur during an acute inflammatory response or that occurs in a cancer patient as a result of cachexia, radiotherapy or chemotherapy, or to the undesirable decrease in body mass due to simulated or actual weightlessness, such as occurs during space travel.

Other examples of unhealthy decreases in weight occur in some patients during advance stages of illnesses such as AIDS. Physiologically, this may be a result from any one of a number of complex factors, such as loss of appetite and possibly abnormal catabolism. This cachexia, may be slowed by MC4-R binding compounds. In a preferred embodiment of the invention, the weight loss is a result of old age (e.g., sarcopenia or age associated involuntary weight loss), anorexia nervosa, or cachexia (e.g., cachexia associated with cancer or HIV).

Examples of MC4-R associated disorders include feeding and wasting disorders, such as cachexia (e.g., chronic disease associated cachexia including cancer cachexia, AIDS cachexia, CHF cachexia, etc.), anorexia, catabolic wasting, aging associated involuntary weight loss, and sarcopenia. Recent studies have demonstrated that the central melanocortin signaling system, in particular MC4-R contributes to animal models of cachexia. Wisse B E, et al. *Endocrinology* 142:3292-3301 (2001); Marks D L, et al. *Cancer Res* 61:1432-1438 (2001); Vergoni A V, et al. *Eu J Pharm* 369:11-15 (1999).

Cachexia is a common pathological syndrome associated with cancer and other chronic illnesses (e.g., AIDS, chronic heart failure, chronic infection, etc), which encompasses both the loss of appetite and the inability to conserve energy. A hallmark of the disorder is loss of fat and lean body mass, contributing to morbidity, mortality, and reduced quality of life in afflicted patients. Ronald M. L. and J. B. Tatro, *Diabetes,* 8: 267-271, (1999); Tisdale M J *Nutrition* 17: 438-442 (2001). Physiologically, this may be a result from any one of a number of complex factors, such as loss of appetite and possibly abnormal catabolism.

Sarcopenia is a generic term for failure to thrive (e.g., due to loss of lean body mass, in particular skeletal muscle mass) that occurs with age. For example, loss of muscle mass, quality, and strength can ultimately contribute and lead to frailty in the elderly.

Accordingly the instant invention provides compounds, compositions, and methods effective for increasing feeding behavior and body weight, which are particularly useful in treating those disorders or diseases associated with weight loss and wasting (e.g., cachexia (e.g., chronic disease associated cachexia including cancer cachexia, AIDS cachexia, CHF cachexia, etc.), anorexia, catabolic wasting, aging associated involuntary weight loss, and sarcopenia.

In one further embodiment, the MC4-R associated state is not weight loss.

In an embodiment, the MC4-R associated disorder is a bone associated disorder. MC4-R knockout mice have been shown to have enhanced bone thickness (Ducy et al. *Science*, (September, 2000) 289:1501-1504). Examples of bone associated disorders which may be treated with MC4-R binding compounds of the invention include disorders and states where the formation, repair or remodeling of bone is advantageous. For examples bone associated states include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone associated disorders include all states in which the formation, repair or remodeling of bone is advantageous to the subject as well as all other disorders associated with the bones or skeletal system of a subject which can be treated with the compounds of the invention.

Melanocortins increase neuropathic pain in animal models and antagonize opiate analgesia, and antagonists counteract neuropathic pain. Vrinten D H, et al. *J Neurosci* 20:8131-8137 (2000); Adan R A H in *The melanocortin receptors*. Cone R D, ed. Totowa, N.J.: Humana Press; 109-141 (2000). Additionally, patients with cancer might have the additional benefit of improved pain control when treated with melanocortin receptor antagonists undergoing a cancer cachexia treatment regimen. Thus, the methods and compositions described herein may be useful in the treatment of MC4-R associated pain or neuronal disorders, including neuropathic pain.

The term "mammal" includes organisms which express the MC4-R. Examples of mammals include mice, rats, cows, sheep, pigs, goats, horses, bears, monkeys, dogs, cats and, preferably, humans. Transgenic organisms which express the MC4-R are also included in this definition.

The language "MC4-R binding compound" includes those compounds which interact with the MC4-R resulting in modulation of the activity of the MC4-R. In an embodiment, the MC4-R binding compounds are antagonists of the MC4-R. The term "antagonist" includes compounds which interact with the MC4-R and modulate, e.g., inhibit or decrease, the ability of a second compound, e.g., α-melanocyte stimulating hormone or another MC4-R ligand, to interact with the MC4-R. In another embodiment, the MC4-R binding compounds is an agonist of the MC4-R. The term "agonists" includes compounds which interact with the MCR-4 and modulate, e.g., increase or stimulate, its activity and/or its ability to interact with a second compounds, e.g., α-melanocyte stimulaturing hormone.

MC4-R binding compounds can be identified through both in vitro (e.g., cell and non-cell based) and in vivo methods. These methods are described in detail in Examples 4, 5, 6, and 7.

The Scincillation Proximity Assay (SPA) is a non-cell based in vitro assay, described in Example 4. It can be used to identify compounds that interact with, e.g., bind to MC4-R. Such compounds may act as antagonists or agonists of MC4-R activity and may be used in the treatment of body weight disorders. One example of a qualitative measure of binding affinity of a MC4-R binding compound to MC4-R is its $IC_{50}$ Preferably, the MC4-R binding compound binds to the MC4-R with a binding affinity, for example, of about 50 μM or less, 20 μM or less, 10 μM or less, 5 μM or less, 2.5 μM or less, or 1 μM or less. In an advantageous embodiment, the $IC_{50}$ of a MC4-R binding compounds is about 0.5 μM or less, about 0.3 μM or less, about 0.1 μM or less, about 0.08 μM or less, about 0.06 μM or less, about 0.05 μM or less, about 0.04 μM or less, or, preferably, about 0.03 μM or less.

In the SPA, isolated membranes are used to identify compounds that interact with MC4-R. For example, in a typical experiment using isolated membranes, 293 cells may be genetically engineered to express the MC4-R. Membranes are be harvested by standard techniques and used in an in vitro binding assay. $^{125}$I-labeled ligand (e.g., $^{125}$I-labeled α-MSH, β-MSH, or ACTH) is bound to the membranes and assayed for specific activity; specific binding is determined by comparison with binding assays performed in the presence of excess unlabelled ligand.

To identify MC4-R binding compounds, membranes are incubated with labeled ligand in the presence or absence of test compound. Compounds that bind to the receptor and compete with labeled ligand for binding to the membranes reduced the signal compared to the vehicle control samples. Preferably, the screens are designed to identify compounds that antagonize the interaction between MC4-R and MC4-R ligands such as α-MSH, β-MSH and ACTH. In such screens, the MC4-R ligands are labeled and test compounds can be assayed for their ability to antagonize the binding of labeled ligand to MC4-R.

Cell based assay systems can also be used to identify MC4-R binding compounds. An example of a cell based assay system is the cAMP assay described in detail in Example 5. Cell based methods may use cells that endogenously express MC4-R for screening compounds which bind to MC4-R. Alternatively, cell lines, such as 293 cells, COS cells, CHO cells, fibroblasts, and the like, genetically engineered to express the MC4-R can also be used for screening purposes. Preferably, host cells genetically engineered to express a functional receptor that responds to activation by melanocortin peptides can be used as an endpoint in the assay; e.g., as measured by a chemical, physiological, biological, or phenotypic change, induction of a host cell gene or a reporter gene, change in cAMP levels, adenylyl cyclase activity, host cell G protein activity, extracellular acidification rate, host cell kinase activity, proliferation, differentiation, etc.

To be useful in screening assays, the host cells expressing functional MC4-R should give a significant response to MC4-R ligand, preferably greater than 5-fold induction over background. Host cells should preferably possess a number of characteristics, depending on the readout, to maximize the inductive response by melanocortin peptides, for example, for detecting a strong induction of a CRE reporter gene: (a) a low natural level of cAMP, (b) G proteins capable of interacting with the MC4-R, (c) a high level of adenylyl cyclase, (d) a high level of protein kinase A, (e) a low level of phosphodiesterases, and (f) a high level of cAMP response element binding protein would be advantageous. To increase response to melanocortin peptide, host cells could be engineered to express a greater amount of favorable factors or a lesser amount of unfavorable factors. In addition, alternative pathways for induction of the CRE reporter could be eliminated to reduce basal levels.

In using such cell systems, the cells expressing the melanocortin receptor are exposed to a test compound or to vehicle controls (e.g., placebos). After exposure, the cells can be assayed to measure the expression and/or activity of components of the signal transduction pathway of the melanocortin receptor, or the activity of the signal transduction pathway itself can be assayed. For example, after exposure, cell lysates can be assayed for induction of cAMP. The ability of a test compound to increase levels of cAMP, above those levels seen with cells treated with a vehicle control, indicates that the test compound induces signal transduction mediated by the melanocortin receptor expressed by the host cell. In screening for compounds that may act as antagonists of MC4-R, it is necessary to include ligands that activate the MC4-R, e.g., α-MSH, β-MSH or ACTH, to test for inhibition of signal transduction by the test compound as compared to vehicle controls.

When it is desired to discriminate between the melanocortin receptors and to identify compounds that selectively agonize or antagonize the MC4-R, the assays described above may be conducted using a panel of host cells, each genetically engineered to express one of the melanocortin receptors (MC1-R through MC5-R). Expression of the human melanocortin receptors is preferred for drug discovery purposes. To this end, host cells can be genetically engineered to express any of the amino acid sequences shown for melanocortin receptors 1 through 5. The cloning and characterization of each receptor has been described: MC1-R and MC2-R (Mountjoy., 1992, Science 257: 1248-1251; Chhajlani & Wikberg, 1992 FEBS Lett. 309: 417-420); MC3-R (Roselli-Rehfuss et al., 1993, Proc. Natl. Acad. Sci., USA 90: 8856-8860; Gantz et al., 1993, J. Biol. Chem. 268: 8246-8250); MC4-R (Gantz et al., 1993, J. Biol. Chem. 268: 15174-15179; Mountjoy et al., 1994, Mol. Endo. 8: 1298-1308); and MC5-R (Chhajlani et al., 1993, Biochem. Biophys. Res. Commun. 195: 866-873; Gantz et al., 1994, Biochem. Biophys. Res. Commun. 200; 1234-1220), each of which is incorporated by reference herein in its entirety. Thus, each of the foregoing sequences can be utilized to engineer a cell or cell line that expresses one of the melanocortin receptors for use in screening assays described herein. To identify compounds that specifically or selectively regulate MC4-R activity, the activation, or inhibition of MC4-R activation is compared to the effect of the test compound on the other melanocortin receptors. In certain embodiments, it may be advantageous to select compounds of the invention selective for MC4-R, or, alternatively, it may be useful to select compounds which interact with other receptors as well.

In one further embodiment, the MC4-R binding compounds of the invention are more selective for the MC4-R than at least one other MC receptors, for example, more than twice as selective, at least ten times as selective, at least twenty times as selective, at least fifty times as selective, or at least one hundred times as selective.

In one further embodiment, the MC4-R binding compounds of the invention are more selective for the MC4-R than the MC1-R, for example, more than twice as selective, at least ten times as selective, at least twenty times as selective, at least fifty times as selective, or at least one hundred times as selective.

In one further embodiment, the MC4-R binding compounds of the invention are more selective for the MC4-R than the MC3-R, for example, more than twice as selective, at least ten times as selective, at least twenty times as selective, at least fifty times as selective, or at least one hundred times as selective.

In one further embodiment, the MC4-R binding compounds of the invention are more selective for the MC4-R than the MC5-R, for example, more than twice as selective, at least ten times as selective, at least twenty times as selective, at least fifty times as selective, or at least one hundred times as selective.

In yet another further embodiment, the MC4-R binding compounds of the invention are more selective for the MC4-R receptor than at least one, two or three other MC receptors (such as, for example, MC1-R, MC3-R, or MC5-R). In a further embodiment, the MC4-R binding compounds are more selective for the MC4-R than MC1-R, MC3-R, and MC5-R. In a further embodiment, the MC4-R binding compounds as at least ten times as selective, at least twenty times as selective, at least fifty times as selective, or at least one hundred times as selective for the MC4-R than the MC1-R, MC3-R and the MC5-R.

As stated above, in an embodiment, the MC4-R binding compound includes compounds of the formula (I):

wherein B is an anchor moiety, Z is a central moiety, E is a MC4-R interacting moiety, and pharmaceutically acceptable salts thereof.

The language "anchor moiety" ("B") includes moieties which interact with the MC4-R, which may, advantageously, result in the binding of the MC4-R binding compound to the MC4-R. Examples of anchor moieties include substituted or unsubstituted alkyl (e.g., branched, straight chain, or cyclic (e.g., cyclohexane, cyclopentane)), alkenyl, alkynyl, aryl (e.g., substituted or unsubstituted phenyl, naphthyl, biphenyl, anthracenyl, fluorenyl, etc.), heterocyclic (e.g., thienyl, morpholinyl, piprazinyl, piperidinyl, etc.), and multicyclic (e.g., indolyl, benzothioenyl, etc.) moieties. Other examples of anchor moieties include carbonyl moieties, thiol groups, cyano groups, amino groups, and hydrogen atoms.

In a further embodiment, the anchor moiety ("B") includes substituted or unsubstituted carbocyclic aryl moieties, e.g., phenyl, naphthyl, etc. Examples of substituents include halogens (e.g., fluorine, chlorine, iodine, bromine, etc.), alkoxy (e.g., methoxy, ethoxy, isopropoxy, n-propyloxy, n-butyloxy, pentoxy, cyclopentoxy, arylalkyloxy, etc.) hydroxy, alkylcarbonyl, cyano, nitro, thiol, thioether, thioalkyl, alkenyl, alkynyl (e.g., ethynyl, etc.), alkylcarbonyloxy, arylcarbonyloxy, alkoxycarbonyloxy, aryloxycarbonyloxy, carboxylate, alkoxycarbonyl, aminocarbonyl, alkylthiocarbonyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, trifluoromethyl, azido, heterocyclyl, alkylaryl, heteroaryl, alkyl (e.g., unsubstituted (e.g., methyl, ethyl, propyl, butyl, hexyl, etc.) or substituted, e.g., halogen substituted, e.g., trifluoromethyl, trichloromethyl), aryl (e.g., substituted and unsubstituted phenyl, heteroaryl (e.g., thienyl, pyridinyl, etc.), arylalkyl, arylalkenyl, arylalkynyl, or combinations thereof. In yet another further embodiment, the anchor moiety substituent can be substituted itself with one or more halogen, nitro, alkyl, alkenyl, alkynyl, aryl or alkoxy groups, or combinations thereof. In certain embodiments, the aryl moiety is fused to another ring which can be substituted or unsubstituted, carbocyclic or heterocyclic, aromatic or non-aromatic.

In a further embodiment, the anchor moiety is substituted with at least one halogen, alkoxy group, or alkyl (e.g., substituted or unsubstituted) group. Examples of halogen substituted phenyl anchor moieties include o-iodophenyl, m-iodophenyl, o-bromophenyl, m-bromophenyl, o-chlorophenyl, m-chlorophenyl, o-fluorophenyl, m-fluorophenyl, p-fluorophenyl, m-nitrophenyl, or o-methoxy. The anchor moiety may also comprise more than one substituent, e.g. two halogens, e.g., two fluorines, a fluorine and a chlorine.

Other examples of anchor moieties include 2-methoxy-5-bromophenyl, 2-methoxy-5-fluorophenyl, 2-methoxy-5-iodophenyl, 2-methoxy-5-fluorophenyl, 2-ethoxy-5-bromophenyl, 2-methoxy-6-bromophenyl, 3-methoxy-6-bromophenyl, 2-isopropyl-5-bromophenyl, 2-n-propyl-5-bromophenyl, and 2-cyclopentyloxy-5-bromophenyl.

Other examples of anchor moieties include, but are not limited to, 2-methoxy-5-cyanophenyl, 2-chloro-5-chlorophenyl, 2-methoxy-6-methoxyphenyl, 2-methoxy-5-nitrophenyl, 2-methoxy-5-phenyl phenyl, 2-methoxy-5-3'-thiofuranyl phenyl, 2-methoxy-5-methylcarbonyl phenyl, 3,5-dimethyloxy phenyl, 2-methoxyphenyl, 2,5-dimethoxy phenyl, 2-fluoro-6-chlorophenyl, and 3-chloro-4-fluorophenyl.

In another further embodiment, the anchor moiety includes substituted and unsubstituted heterocycles. Examples of such heterocycles include, but are not limited to, furanyl, imidazolyl, benzothiophenyl, benzofuranyl, quinolinyl, isoquinolinyl, benzodiozanyl, benzoxazolyl, benzothiazolyl, methylenedioxyphenyl, ethylenedioxyphenyl, indolyl, thienyl, pyrimidyl, pyrazinyl, purinyl, deazapurinyl, morpholine, piprazine, piperidine, thiomorpholine, and thioazolidine. Examples of substituents include alkyl (e.g., substituted or unsubstituted, branched straight chain or cyclic, e.g., methyl, ethyl, propyl, butyl, pentyl, etc.), alkenyl, alkynyl, halogens (e.g., fluorine, chlorine, bromine, iodine, etc.), hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, azido, heterocyclyl, alkylaryl, aryl and heteroaryl groups.

In another further embodiment, the anchor moiety ("B") is a substituted or unsubstituted fused aryl or biaryl moiety. Biaryl moieties include moieties with two or more aromatic rings, which may be fused or connected through one or more covalent bonds. Examples include biphenyl, fluorene, anthracenyl, benzoquinazolinyl, and naphthyl. Examples of substituents of biaryl moieties include alkyl (e.g., substituted and unsubstituted, branched or straight chain, methyl, ethyl, propyl, butyl, pentyl, etc.), alkoxy (e.g., methoxy, ethoxy, propoxy, butoxy, pentoxy, cyclopentoxy, etc.), alkenyl, alkynyl, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, an aromatic heteroaromatic moiety, halogens (e.g., fluorine,. chlorine, bromine, iodine, etc.), combinations thereof and other groups which allow the MC4-R binding compound to perform its intended function. Biaryl moieties also include moieties which comprise one or more heterocycles, such as, benzothiofuranyl, benzothienyl, quinolinyl, benzothiophenyl, benzofuranyl, isoquinolinyl, benzodiozanyl, benzoxazolyl, benzothiazolyl, methylenedioxyphenyl, ethylenedioxyphenyl, and indolyl. Examples of biaryl anchor moieties include naphthyl, 2-methoxynaphthyl, 2-methoxy-5-phenyl phenyl, 2-ethoxynaphthyl, 2-methoxy-5-thiofuranyl phenyl, 2-methyl naphthyl, 2-n-propyl naphthyl, benxothiofuranyl, 2-phenyl phenyl, 2-methoxy-5-4'methoxy-phenyl phenyl; 2-methoxy-5-(3'-fluoro-4'-phenyl) phenyl phenyl; 2-cyclopentoxynaphthyl; quinolinyl; and 2-methoxy-5-(3'-chloro-4'fluoro)phenyl phenyl.

Furthermore, the anchor moiety can be multicyclic and comprise a combination of one or more aromatic, non-aromatic, heterocyclic, and heteroaryl rings, which can be fused, bridged, or linked together through covalent bonds. The multicyclic anchor moiety may also be substituted with substituents such as alkyl (e.g., substituted or unsubstituted, branched straight chain or cyclic, e.g., methyl, ethyl, propyl, butyl, pentyl, etc.), alkenyl, alkynyl, halogens (e.g., fluorine, chlorine, bromine, iodine, etc.), hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, azido, heterocyclyl, alkylaryl, aryl and heteroaryl groups.

The term "central moiety" ("Z") includes moieties which covalently attach the anchor moiety to the MC4-R interacting moiety. Examples of central moieties include cyclic moieties, optionally substituted amines (e.g., tertiary amino, aminoalkylamino, dialkylaminoalkylamino, aminocarbonylamino, aminocarbonylamino; arylaminocarbonylamino groups; arylaminothiocarbonylamino), optionally substituted alkyl groups (e.g., carbon atoms with substituted or unsubstituted alkyl, aryl (e.g., phenyl, naphthyl), heterocyclic moieties (e.g., morpholinyl, piprazinyl, etc.), and carbonyl groups, etc. Examples of substituents of the central moiety include, for example, alkyl (e.g., straight, branched or cyclic, substituted or unsubstituted, methyl, ethyl, propyl, butyl, cyclopropyl, cyclobutyl, cyclopentyl, cyclohexyl), alkenyl (ethenyl, propenyl, butenyl, etc.), alkynyl (e.g., ethynyl, propynyl, etc.), halogen (e.g., chlorine, fluorine, iodine, bromine), hydroxyl, alkoxy (e.g., methoxy, ethoxy, trifluoromethoxy, trichloromethoxy, propoxy, butoxy, cyclopropoxy, etc.), alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, arylalkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, azido, heterocyclyl (e.g., morpholinyl, piprazinyl, etc.), arylalkyl, alkylaryl and aryl (e.g., substituted or unsubstituted phenyl (e.g., alkyl, halogen, alkoxy substituted), naphthyl, anthracene, etc.) and heteroaryl moieties. Furthermore, the central moiety may further comprise one or more linking moieties. For example, the linking moieties may covalently link the cyclic moiety to the anchor moiety and/or the MC4-R interacting moiety.

The term "central moiety" also includes moieties of the formula (XII):

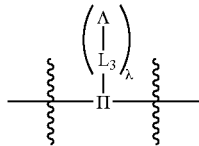

(XII)

wherein

Π is a covalent bond, a carbon atom, a nitrogen atom, heterocyclic, alkyl, carbocyclic, or aryl;

$L_3$ is a covalent bond, $C_1$-$C_6$ branched, unbranched or cyclic alkyl(wherein one, two or three of the carbons are optionally replaced with oxygen, sulfur or nitrogen atoms), carbonyl, aminocarbonyl, aminocarbonylamino, aminocarbonyloxy, or aminothiocarbonyl moiety;

Λ is substituted or unsubstituted heterocyclic, aryl, alkoxy, amino, alkyl, alkenyl, alkynyl, or hydrogen; and λ is 0, 1 or 2.

In a further embodiment, Π is a carbon or nitrogen atom. In other embodiments, Π is alkyl, carbocyclic, heterocyclic (e.g., piprazinyl, morphonlinyl, piperidinyl, etc.).

In another further embodiment, Λ is heterocyclic (e.g., non-aromatic, e.g., substituted or unsubstituted, bridged, fused, or monocyclic, morpholinyl, piperidinyl, azetidinyl, piprazinyl, etc. or aromatic, e.g., pyridinyl, pyrimidinyl, pyrrolyl, etc.), aryl e.g., phenyl, naphthyl) or amino (e.g., substituted or unsubstituted, e.g., alkylamino, dialkyl amino, etc.).

The language "cyclic moiety" includes heterocyclic and carbocyclic groups, such as substituted or unsubstituted phenyl, heteroaryl, or biaryl moieties. Examples of cyclic moieties include those without aromaticity (e.g., cyclohexane, cyclopentane, etc.) and those with aromaticity, e.g. moieties that have at least one aromatic ring. Cyclic moieties may include one or more heteroatoms. Examples include phenyl, pyrrole, furan, thiophene, imidazole, benzoxazole, benzothiazole, triazole, tetrazole, pyrazole, pyridine, pyrazine, pyridazine, pyrimidine, naphthyl, quinolyl, indolyl, and the like. The cyclic moiety can be substituted at one or more ring positions with such substituents such as, for example, alkyl (e.g., substituted or unsubstituted methyl, ethyl, propyl, butyl), alkenyl (ethenyl, propenyl, butenyl, etc.), alkynyl (e.g., ethynyl, propynyl, etc.), halogen (e.g., chlorine, fluorine, iodine, bromine), hydroxyl, alkoxy (e.g., methoxy, ethoxy, trifluoromethoxy, trichloromethoxy, propoxy, butoxy, cyclopropoxy, etc.), aryloxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, azido, heterocyclyl, alkylaryl, and aryl (e.g., substituted or unsubstituted phenyl, naphthyl) and heteroaryl moieties. The cyclic moiety can also be fused or bridged with alicyclic or heterocyclic rings which are not aromatic so as to form a polycycle (e.g., tetralin, or fluorene).

In an embodiment, the cyclic moiety of the present invention is substituted or unsubstituted phenyl, heteroaryl, or biaryl. The language "cyclic moiety" also includes non-aromatic cyclic moieties, such as, substituted or unsubstituted cyclic alkanes, (e.g., cyclohexane, and cyclopentane), cyclic alkenes (e.g., cyclohexene), and substituted or unsubstituted heterocycles (e.g., thiofuran, pyrimidine, pyrazine, pyrrole, imidazole, quinoxaline, etc.). The language "cyclic moiety" comprises not only the heterocyclic or carbocyclic moieties, but also may additionally include moieties which further comprise linking moieties, such as $L_1$ and $L_2$ which, for example, may link the anchor moiety to the carbocyclic or heterocyclic cyclic portion of the cyclic moiety. Furthermore, linking moieties may also link the heterocyclic or carbocyclic cyclic moiety to the MC4-R interacting moiety. Examples of cyclic moieties include unsubstituted phenyl, halogenated phenyl (e.g., fluoro, bromo, chloro and iodo phenyl), alkyl substituted phenyl (e.g., methyl, ethyl, propyl, etc.),amino substituted phenyl, heteroaryls (e.g., thiofuran, pyridine, quinoxaline, pyrazine, pyrrole, etc.).

The language "MC4-R interacting moiety" ("E") includes moieties which permit the MC4-R binding compound to perform its intended function, e.g., interact with the MC4-R. Examples of MC4-R interacting moieties include substituted or unsubstituted alkyl (e.g., substituted with amino, cyano, nitro, hydroxy, etc.), aryl (e.g., phenyl, heteroaryl), amino (e.g., 3-aminopropylamino, dimethyl amino, diethyl amino), amidino, guanidino, carbocyclic and heterocyclic moieties. The language "MC4-R interacting moiety" is not intended to suggest that this moiety is the active pharmacophore of the molecule, responsible for the pharmacological, binding or other properties of the MC4-R binding compound.

In one embodiment, the MC4-R interacting moiety is cyclic, e.g., aryl, alkyl, biaryl, polycyclic, heteroaromatic, or heterocyclic. Examples of heterocyclic MC4-R interacting moieties include heterocycles which contain nitrogen atoms, such as, substituted and unsubstituted imidazolyl, imidazolinyl, pyridinyl, pyrrolyl, piprazinyl, imidoazopyridinyl, pyrrolloimidazolyl, pyrrolyl, azetidinyl, azapanyl, pyrimidinyl, pyridinyl, morpholinyl, diazapanyl, and piperidinyl moieties. The MC4-R interacting moiety may be bicyclic, polycyclic, bridged or a fused ring system. Examples of fused and bridged heterocycles include:

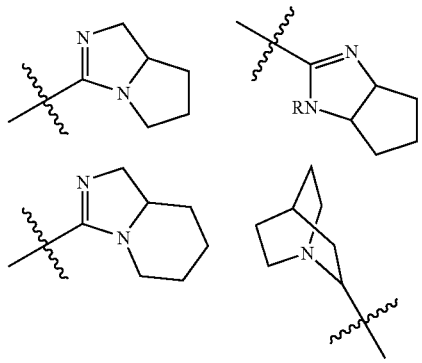

-continued

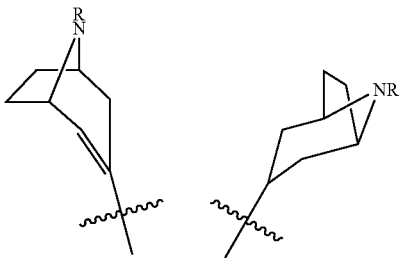

The substituent R includes substituted and unsubstituted alkyl (e.g., methyl, ethyl, etc.), arylcarbonyl, alkoxycarbonyl, alkylcarbonyl, arylalkylcarbonyl, and other groups which allow the MC4-R interacting moiety to perform its intended function.

The MC4-R interacting moiety can be substituted with substituents such as, but not limited to, halogens (e.g., fluorine, chlorine, bromine, iodine, etc.), alkyl (e.g., substituted or unsubstituted, branched straight chain or cyclic, e.g., methyl, ethyl, propyl, butyl, pentyl, etc.), alkenyl, alkynyl, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, aminoalkyl, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, azido, heterocyclyl, alkylaryl, aryl, heteroaryl moieties and combinations thereof.

In another embodiment, the MC4-R interacting moiety is not cyclic, e.g., the MC4-R interacting moiety is alkyl, unsubstituted amino, alkylamino, dialkylamino, amidino, guanidino, etc. Examples of alkyl MC4-R interacting moieties include straight and branched chain alkyls such as n-butyl, n-pentyl, and n-hexyl.

In another embodiment, the MC4-R interacting moiety contains one or more nitrogen atoms, e.g., pyridinyl, pyrrolyl, pyrazinyl, imidazolyl, imidazolinyl, quinoxalinyl, or pyrimidinyl. In a further embodiment, the MC4-R interacting moiety is of the formula (XIII):

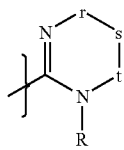

(XIII)

wherein
r is a covalent bond, CH, $CH_2$, $CHR^1$, $CR^1R^2$, or H;
t is CH, $CH_2$, $CHR^3$, $CR^3R^4$, or H;
s is CH, $CH_2$, $CHR^5$, $CR^5R^6$, or absent;
R is hydrogen, alkyl, alkenyl, arylalkyl, arylcarbonyl, alkoxycarbonyl, arylalkylcarbonyl, alkylcarbonyl, optionally linked to A, B, $L_1$, $L_2$, $R^1$, $R^2$, $R^3$, $R^4$, $R^5$, or $R^6$ to form one or more rings;
$R^1$, $R^2$, $R^3$, $R^4$, $R^5$, and $R^6$ are each substituted or unsubstituted alkyl, alkenyl, alkynyl, heterocyclic, halogen, thiol, thioether, thioalkyl, hydroxyl, nitro, amino, cyano, or alkoxy, and may optionally be linked to form a carbocyclic or heterocyclic ring. The carbocyclic ring that is formed through the linkage of R, $R^1$, $R^2$, $R^3$, $R^4$, $R^5$, or $R^6$ may be bridged, fused, or spiro.

In one embodiment, the MC4-R interacting moiety is represented by the formula (XIV) below, when s is absent:

(XIV)

For example, in another further embodiment, the MC4-R interacting moiety may be bicyclic, e.g., biheterocyclic, for example, quinoxalinyl. The language "linked to form a ring" refers to moieties covalently connected through a chain of atoms (e.g., carbon atoms and/or heteroatoms). The chain of atoms can comprise any number of atoms, which allow the MC4-R binding moiety to perform its intended function. In a further embodiment, the chain of atoms is selected such that a ring with three, four, five, six, seven, or eight members are formed. The ring that can be formed may be spiro (e.g., connected through the same carbon atom), fused (connected through adjacent carbon atoms), or bridged (e.g., connected through carbon atoms which are neither identical nor adjacent). In an embodiment, R and t are linked, e.g., to for a bicyclic moiety. Examples of bicyclic moieties include, but are not limited to, imidazopyridinyl, pyrrolloimidazolyl, cyclopentaimidazolyl, pyridopyrimidinyl, etc.

In a further embodiment R is H, alkyl, benzocarboxy, alkylcarboxy, or arylalkylcarboxy. In another further embodiment, s is $CR^5R^6$ and $R^5$ and $R^6$ are each methyl. In another further embodiment, r is a covalent bond, and at least one of t and s are $CH_2$. In another, t, r, and s are each $CH_2$. In another, r is a covalent bond, and t and s are linked through a 4 carbon chain. In another further embodiment, at least one R group is OH. In an embodiment, r is a covalent bond, t is $CR^3R^4$, and s is $CR^5R^6$, wherein $R^3$, $R^4$, $R^5$ and $R^6$ are each independently hydrogen or alkyl (e.g., methyl, ethyl, propyl, or butyl).

Examples of MC4-R interacting moieties include, but are not limited to, the following structures:

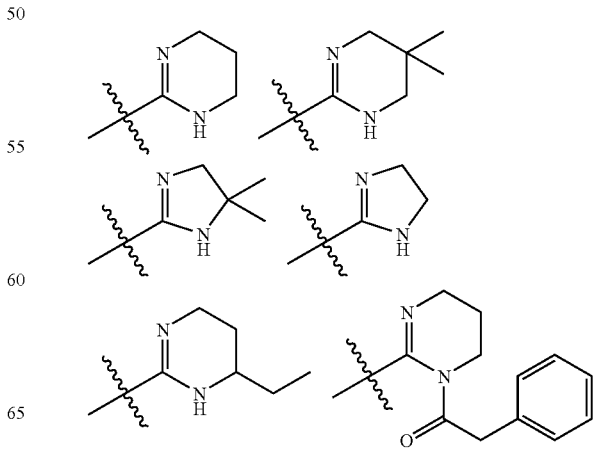

-continued

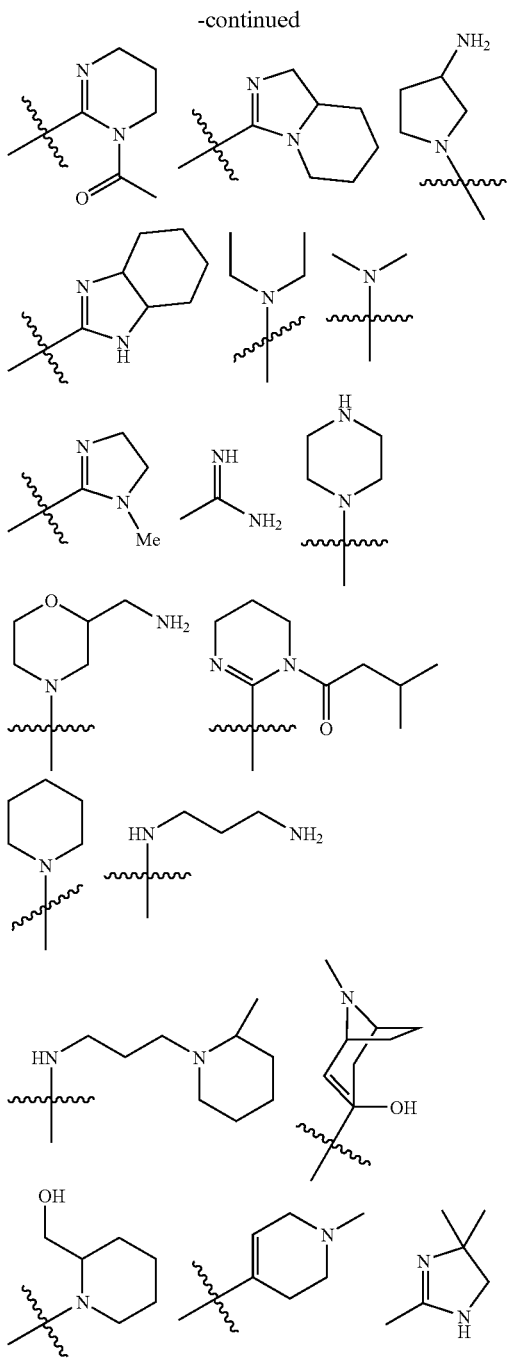

In another embodiment, the invention pertains to a method for treating an MC4-R associated state in a mammal, by administering an effective amount of a MC4-R binding compound to a mammal, such that the MC4-R associated state is treated. Examples of MC4-R binding compounds include compounds comprising the formula (II):

B-A-E     (II)

wherein:
B is a anchor moiety;
A is a cyclic moiety; and
E is a MC4-R interacting moiety, and pharmaceutically acceptable salts thereof.

The MC4-R binding compounds of formula (II), may further comprise linking moieties, $L_1$ and $L_2$. Such MC4-R binding compounds include compounds of the formula (III):

B-$L_1$-A-$L_2$-E     (III)

wherein B is an anchor moiety (as described above), $L_1$ and $L_2$ are linking moieties, A is a cyclic moiety (as described above), and E is a MC4-R interacting moiety. Pharmaceutically acceptable salts of the MC4-R binding compound are also included.

The language "linking moiety" includes moieties which link, preferably covalently, the MC4-R interacting moiety, the cyclic moiety, and the anchor moiety of the invention. Examples of linking moieties include covalent bonds, 1-10 atom chains which may be branched or unbranched, substituted or unsubstituted alkyl, heterocyclic, alkenyl, or alkynyl. The chains may be substituted with 0-3 heteroatoms or other moieties which allow the MC4-R binding compound to perform its intended function. Examples of suitable heteroatoms include sulfur, oxygen, nitrogen, and phosphorous. The invention contemplates MC4-R binding compounds which comprises more than two linking moieties.

In an embodiment, $L_1$ is a chain of 1-10 atoms (e.g., such as carbon, nitrogen, oxygen, or sulfur atoms), e.g., 1, 2, 3, 4, 5, 6, 7, 8, 9 or 10 atoms. In an embodiment, $L_1$ is selected from the group consisting of a covalent bond, $C_1$-$C_6$, $C_1$-$C_5$, $C_1$-$C_4$, $C_1$-$C_3$, $C_1$-$C_2$, branched or unbranched alkyl, wherein one, two or three of the carbons are optionally replaced with any combination of substituted or unsubstituted oxygen, sulfur or nitrogen atoms. In a further embodiment, $L_1$ is a thioether (e.g., —S—$CH_2$—, S—$CH(CH_3)$—, —$CH_2$—S—$CH_2$, —S—, or —S—CH—$(C_6H_5)$—), an ether (e.g., —O—$CH_2$ or —$CH_2$—O—$CH_2$—), a sulfoxide, a sulfone, an amine (e.g., —NH—, —NH—$CH_2$—, —NMe—$CH_2$—, $CH_2$—NH—$CH_2$—, etc.) or alkyl (e.g., —$CH_2$—$CH_2$—, —$CH_2$—, or —$CH_2$—$CH_2$—$CH_2$—). In another embodiment, $L_1$ comprises a sulfonyl group. Furthermore, $L_1$ can be substituted or unsubstituted (e.g., a hydrogen can be replaced by another moiety), such that the MC4-R binding compound is capable of performing its intended function, e.g., bind to or interact with the MC4-R. Examples of substituents include, but are not limited to, halogens (e.g., fluorine, chlorine, bromine, iodine, etc.), alkyl (e.g., substituted or unsubstituted, branched straight chain or cyclic, e.g., methyl, ethyl, propyl, butyl, pentyl, etc.), alkenyl, alkynyl, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, azido, heterocyclyl, alkylaryl, aryl heteroaryl moieties, or combinations thereof.

In an embodiment, examples of $L_2$ include a covalent bond, a chain of 1-10 atoms (e.g., such as carbon, nitrogen, oxygen, or sulfur atoms), e.g., 1, 2, 3, 4, 5, 6, 7, 8, 9 or 10 atoms. In an embodiment, $L_1$ is selected from the group consisting of a covalent bond, $C_1$-$C_6$, $C_1$-$C_5$, $C_1$-$C_4$, $C_1$-$C_3$, $C_1$-$C_2$, branched or unbranched alkyl, wherein one, two or three of the carbons are optionally replaced with any combination of substituted or unsubstituted oxygen, sulfur or nitrogen atoms. In a further embodiment, $L_2$ is a covalent bond, —$CH_2$— or —NH—. Furthermore, $L_2$ may also comprise one or more carbonyl groups. For example, $L_2$ linkers include substituted urea groups (NH—C=O—NH), oxycarbonylamino groups (—O—C=O—NH), thiocarboynl groups, etc.

Furthermore, like $L_1$, $L_2$ can be substituted with any substituent such that the MC4-R binding compound is capable of performing its intended function. Examples of substituents include, but are not limited to, halogens (e.g., fluorine, chlorine, bromine, iodine, etc.), alkyl (e.g., substituted or unsubstituted, branched straight chain or cyclic, e.g., methyl, ethyl, propyl, butyl, pentyl, etc.), alkenyl, alkynyl, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, azido, heterocyclyl, alkylaryl, aryl and heteroaryl moieties.

In a further embodiment, the MC4-R binding compound is of formula (III) (e.g., B-$L_1$-A-$L_2$-E), wherein B is substituted or unsubstituted biaryl (e.g., substituted or unsubstituted biphenyl, naphthyl, fluorenyl), unsubstituted or substituted heteroaryl (e.g., thienyl, benzothienyl, furanyl, pyrazinyl, pyrrolyl, pyrrolidinyl, etc.), unsubstituted or substituted phenyl, wherein one or more of said substituents are selected from the group consisting of halogens (e.g., bromine, fluorine, chlorine, iodine, etc.), alkyl groups (e.g., branched, straight chain or cyclic, substituted or unsubstituted, methyl, ethyl, propyl, butyl, etc.), alkoxy groups (e.g., substituted or unsubstituted alkoxy, e.g., methoxy, ethoxy, isopropoxy, n-propoxy, isobutoxy, n-butoxy, pentoxy, cyclopentoxy, methylenedioxy, ethylenedioxy, etc.), aryl groups (e.g., substituted or unsubstituted phenyl, heterocyclic groups), alkenyl, alkynyl, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, thiol, thioether, thioalkyl, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, and azido;

$L_1$ is a covalent bond, $C_1$-$C_{10}$ branched or unbranched alkyl, wherein one or more of the carbons are optionally replaced with oxygen, sulfur or nitrogen atoms;

A is a substituted or unsubstituted phenyl, heteroaryl (e.g., pyrrolyl, pyrazinyl, thienyl, pyridinyl, etc.), bicyclic (e.g., methylenedioxyphenyl, isoindole, indole, and indan )or biaryl (e.g., naphthyl, quinoxalinyl, purinyl, etc.) wherein said substituent is selected from the group consisting of halogens (e.g., bromine, fluorine, chlorine, iodine, etc.), alkyl groups (e.g., branched, straight chain or cyclic, substituted or unsubstituted, methyl, ethyl, propyl, butyl, etc.), alkoxy groups (e.g., substituted or unsubstituted alkoxy, e.g., methoxy, ethoxy, isopropoxy, n-propoxy, isobutoxy, n-butoxy, pentoxy, cyclopentoxy, methylenedioxy, ethylenedioxy, etc.), aryl groups (e.g., substituted or unsubstituted phenyl, heterocyclic groups), alkenyl, alkynyl, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, and azido;

$L_2$ is a covalent bond, a chain of 1-10 atoms (e.g., such as carbon, nitrogen, oxygen, or sulfur atoms), e.g., 1, 2, 3, 4, 5, 6, 7, 8, 9 or 10 atoms. In an embodiment, $L_1$ is selected from the group consisting of a covalent bond, $C_1$-$C_6$, $C_1$-$C_5$, $C_1$-$C_4$, $C_1$-$C_3$, $C_1$-$C_2$, branched or unbranched alkyl, wherein one, two or three of the carbons are optionally replaced with oxygen, sulfur or nitrogen atoms, substituted or unsubstituted amino (e.g., —NH—, —NH—$CH_2$), ether, thioether, or alkyl (e.g., $C_1$-$C_{10}$, —$CH_2$—, —$CH_2$—$CH_2$—, or —$CH_2$—$CH_2$—$CH_2$—, etc.);

E is unsubstituted amino, unsubstituted and substituted alkylamino (e.g., 3-aminopropylamino), dialkylamino (e.g., dimethyl amino, diethyl amino), amidino, guanidino, heterocyclic (e.g., substituted and unsubstituted imidazolyl, imidazolinyl, piprazinyl, morpholinyl, piperidinyl, imidoazopyridinyl, pyrolloimidazolyl, pyridinyl, or pyrimidinyl) moieties, aryl (e.g., phenyl, heteroaromatic, e.g., substituted and unsubstituted pyrazinyl, imidazolyl, quinoxalinyl, or pyrimidinyl), wherein said substituents include, but are not limited to, amino (e.g., unsubstituted amino, alkylamino, dialkyl amino), aminoalkyl (e.g., methylamino, ethylamino, propylamino, etc.), alkyl (e.g., branched and straight chain, substituted and unsubstituted (e.g., carboxy, hydroxy, halogen, amino, cyano, nitro, etc. substituted), methyl, ethyl, propyl, butyl, etc.), aryl (e.g., phenyl, heteroaromatic), alkenyl (e.g., branched or straight chain, substituted or unsubstituted), alkynyl, etc, and pharmaceutically acceptable salts thereof.

In another embodiment, the invention pertains to a method for treating an MC4-R associated state in a mammal by administering an effective amount of a MC4-R binding compound to a mammal, such that the MC4-R associated state is treated. In an embodiment, the compound is of the formula (IV):

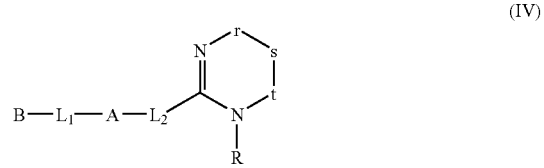

(IV)

wherein

A is a substituted or unsubstituted phenyl, heteroaryl (e.g., pyrrolyl, pyrazinyl, pyridinyl, etc.), or biaryl (e.g., naphthyl, quinoxalinyl, purinyl, etc.) wherein said substituent is selected from the group consisting of halogens (e.g., bromine, fluorine, chlorine, iodine, etc.), alkyl groups (e.g., branched, straight chain or cyclic, substituted or unsubstituted, methyl, ethyl, propyl, butyl, etc.), alkoxy groups (e.g., substituted or unsubstituted alkoxy, e.g., methoxy, ethoxy, isopropoxy, n-propoxy, isobutoxy, n-butoxy, pentoxy, cyclopentoxy, methylenedioxy, ethylenedioxy, etc.), aryl groups (e.g., substituted or unsubstituted phenyl, heterocyclic groups), alkenyl, alkynyl, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, and azido;

B is substituted or unsubstituted biaryl (e.g., substituted or unsubstituted biphenyl, naphthyl, fluorenyl), unsubstituted or substituted heteroaryl (e.g., thienyl, benzothienyl, furanyl, pyrazinyl, pyrrolyl, pyrrolidinyl, etc.), unsubstituted or substituted phenyl, wherein one or more of said substituents are selected from the group consisting of halogens (e.g., bromine, fluorine, chlorine, iodine, etc.), alkyl groups (e.g., branched, straight chain or cyclic, substituted or unsubstituted, methyl, ethyl, propyl, butyl, etc.), alkoxy groups (e.g., substituted or unsubstituted alkoxy, e.g., methoxy, ethoxy, isopropoxy, n-propoxy, isobutoxy, n-butoxy, pentoxy, cyclopentoxy, methylenedioxy, ethylenedioxy, etc.), aryl groups (e.g., substituted or unsubstituted phenyl, heterocyclic groups), alkenyl, alkynyl, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, thiol, thioether, thioalkyl, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, and azido;

$L_1$ and $L_2$ are selected from the group consisting of a covalent bond, $C_1$-$C_4$ branched or unbranched, substituted or unsubstituted alkyl, wherein one or two of the carbons are optionally replaced with oxygen, sulfur or nitrogen atoms;

r is a covalent bond, CH, $CH_2$, $CHR^1$, $CR^1R^2$, or H;

t is CH, $CH_2$, $CHR^3$, $CR^3R^4$, or H;

s is $CHR_5$, $CR_5R_6$ or absent (e.g., leaving a non-cyclic diamine);

R is H, substituted or unsubstituted alkyl, arylalkyl, or heteroalkyl, and may optionally be linked to A, B, $L_1$, or $L_2$;

$R^1$, $R^2$, $R^3$, $R^4$, $R^5$, and $R^6$ are each substituted or unsubstituted alkyl, halogen, thiol, thioether, thioalkyl, alkoxy, and may be optionally linked to each other to form additional ring moieties, e.g., quinoxalinyl. Pharmaceutically acceptable salts of the MC4-R binding compounds are also included.

In one further embodiment, A is substituted or unsubstituted phenyl. Examples of substituents include halogens (e.g., fluorine, chlorine, iodine, bromine), alkoxy, alkyl (e.g., methyl, trifluoromethyl), and amino moieties. In other embodiments, A is heteroaromatic, (e.g., thienyl), or biaryl, (e.g., napthyl or quinoxalinyl).

The invention also pertains to methods for treating an MC4-R associated state in a mammal comprising by administering an effective amount of a MC4-R binding compound of the formula (V):

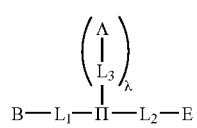

(V)

B is substituted or unsubstituted biaryl, unsubstituted or substituted heterocyclic, or unsubstituted or substituted phenyl, wherein one or more of said substituents are halogens, alkyl alkynyl, alkoxy, aryl, amino, thiol, thioether, thioalkyl, cyano, or nitro;

$L_1$ is a covalent bond, $C_1$-$C_{10}$ branched or unbranched alkyl, wherein one or two of the carbons are optionally replaced with oxygen, sulfur or nitrogen atoms;

$L_2$ is a covalent bond, substituted or unsubstituted amino, ether, thioether, or alkyl;

E is substituted or unsubstituted alkyl, amino, amidino, guanidino, heterocyclic, or aryl, wherein said substituents are amino, arylalkyl, aminoalkyl, alkyl, aryl, alkenyl, or alkynyl;

Π is a covalent bond, a carbon atom, a nitrogen atom, heterocyclic, alkyl, carbocyclic, or aryl;

$L_3$ is a covalent bond, $C_1$-$C_6$ branched, unbranched or cyclic alkyl (wherein one, two or three of the carbons are optionally replaced with oxygen, sulfur or nitrogen atoms), carbonyl, aminocarbonyl, aminocarbonylamino, aminocarbonyloxy, or an aminothiocarbonyl moiety; and Λ is substituted or unsubstituted heterocyclic, aryl, alkoxy, amino, alkyl, alkenyl, alkynyl, or hydrogen; and λ is 0, 1 or 2, and pharmaceutically acceptable salts thereof.

Examples of MC4-R binding compounds with this structure include, but are not limited to, compounds, wherein Π is a carbon atom, $L_3$ is aminocarbonyloxy, Λ is substituted aryl, λ is one, $L_1$ and $L_2$ are each $CH_2$, and B and E are each pipridinyl. Examples of substituents for Λ include but are not limited to, alkoxy (e.g., $C_1$-$C_{10}$ alkoxy, e.g., methoxy, ethoxy, propoxy, butoxy, pentoxy, hexoxy, heptoxy, octoxy, nonoxy, and decoxy), cyano, halogens (e.g., fluorine, chlorine, bromine, iodine), alkyl (e.g., straight or branched chain, etc.), aryl, alkenyl, alkynyl, nitro, amino, or any other substituents which enables the MC4-R binding compound to perform its intended function, e.g., treat an MC4-R associated state.

Other examples of compounds of formula (V) include, but are not limited to, compounds wherein Π, $L_2$ and $L_3$ together are a single covalent bond, E is alkyl, and B is substituted or unsubstituted heterocyclic. In other compounds of formula (V), Π is a nitrogen atom, $L_2$, $L_1$ and $L_3$ are each alkyl, E is substituted amino (e.g., alkyl substituted), or heterocyclic (e.g., piprazinyl, piperidinyl, morpholinyl, etc.) and B and Λ are each aryl (e.g., phenyl, anthracenyl, biaryl, e.g., naphthyl).

In another further embodiment, the invention pertains to yet another method for treating an MC4-R associated state in a mammal by administering to a mammal an effective amount of a MC4-R binding compound of the formula (VI):

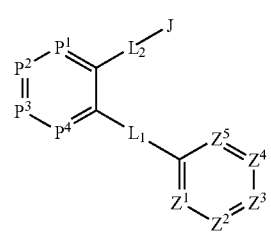

(VI)

wherein $P^1$, $P^2$, $P^3$, and $P^4$ are optionally substituted carbon, sulfur, or nitrogen, and wherein one of $P^1$, $P^2$, $P^3$, and $P^4$ may represent a covalent bond;

$Z^1, Z^2, Z^3, Z^4$, and $Z^5$ are optionally substituted carbon or nitrogen;

$L^1$ is a covalent bond, $C_1$-$C_6$ branched or unbranched alkyl, wherein one or two of the carbons are optionally replaced with oxygen, sulfur or nitrogen atoms;

$L_2$ is a covalent bond, substituted or unsubstituted amino, ether, thioether, or alkyl;

J is an unsubstituted or substituted nitrogen containing heterocycle or a substituted or unsubstituted amino group, and pharmaceutically acceptable salts thereof.

Examples of substituents of $P^1, P^2, P^3, P^4, Z^1, Z^2, Z^3, Z^4$, and $Z^5$ include halogens (e.g., bromine, fluorine, chlorine, iodine, etc.), alkyl groups (e.g., branched, straight chain or cyclic, substituted or unsubstituted, methyl, ethyl, propyl, butyl, etc.), alkoxy groups (e.g., substituted or unsubstituted alkoxy, e.g., methoxy, ethoxy, isopropoxy, n-propoxy, isobutoxy, n-butoxy, pentoxy, cyclopentoxy, methylenedioxy, ethylenedioxy, etc.), aryl groups (e.g., substituted or unsubstituted phenyl, heterocyclic groups), alkenyl, alkynyl, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, and azido groups.

In a further embodiment, $P^1, P^2, P^3$, and $P^4$ are each substituted or unsubstituted carbon (e.g., CH). For example, $P^1$ and $P^3$ may be CH. In another further embodiment, $P^2$ and $P^4$ are each CH, CF, CCl, CBr, CI, C-aryl, C-alkyl (e.g., C-Me, C-ethyl, C-propyl, etc.) C-alkoxy (e.g., C—OMe, C—O-ethyl, C—OCF$_3$, etc.). In a further embodiment, $P^2$ is CH and $P^4$ is CCl or CF. In an embodiment, $P^1$ is a covalent bond, $P^2$ and $P^3$ are each optionally substituted carbon, and $P^4$ is S (e.g., thienyl).

In a third further embodiment, $Z^3$ and $Z^4$ are each CH.

In a fourth further embodiment, $Z^1$ is CH, or covalently linked to $Z^2$ to form a naphthyl ring. Examples of $Z^2$ include CH, C—(C≡CH), CCl, CBr, CI, and CF. Furthermore, $Z^2$ may be substituted with a chain of atoms which covalently links it to $Z^1$ to form a naphthyl ring.

Examples of $Z^5$ include, but are not limited to, CH and C-alkoxy. The term "C-alkoxy" includes carbon atoms covalently bound to an alkoxy group, as described below. Examples of alkoxy groups include methoxy, ethoxy, propoxy, butoxy, etc.

In yet another further embodiment, $L_2$ is a covalent bond.

Examples of J include, but are not limited to, substituted or unsubstituted piprazinyl, imidoazopyridinyl, pyrrolimidazolyl, pyrrolyl, azetidinyl, azapanyl, diazapanyl, pyrimidinyl, pyridinyl, morpholinyl, or piperidinyl. Furthermore, J may be a substituted or unsubstituted fused ring or bridged heterocycle.

In a further embodiment, each of $P^1, P^2, P^3$, and $P^4$ are each optionally substituted carbon; $Z^1, Z^2, Z^3, Z^4$, and $Z^5$ are each also optionally substituted carbon (e.g., alkoxy substituted, halogen substituted or linked to form a ring); wherein $L_1$ is either —S—CH$_2$—, or CH$_2$—CH$_2$. In a further embodiment, $L_2$ is a covalent bond and J is a moiety of formula XIII, as described above.

In another embodiment, the MC4-R binding compound is of formula (VII):

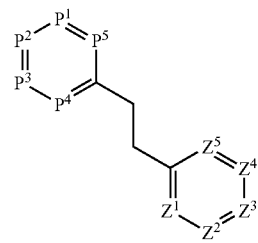

(VII)

wherein $Z^1, Z^2, Z^3, Z^4$, and $Z^5$ are CH, N, or substituted carbon; and $P^1, P^2, P^3, P^4$, and $P^5$ are CH, N or substituted carbon.

Examples of substituents of $Z^1, Z^2, Z^3, Z^4, Z^5, P^1, P^2, P^3, P^4$, and $P^5$ include halogens (e.g., bromine, fluorine, chlorine, iodine, etc.), alkyl groups (e.g., branched, straight chain or cyclic, substituted or unsubstituted, methyl, ethyl, propyl, butyl, etc.), alkoxy groups (e.g., substituted or unsubstituted alkoxy, e.g., methoxy, ethoxy, isopropoxy, n-propoxy, isobutoxy, n-butoxy, pentoxy, cyclopentoxy, methylenedioxy, ethylenedioxy, etc.), aryl groups (e.g., substituted or unsubstituted phenyl, heterocyclic groups), alkenyl, alkynyl, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, and azido groups.

In a further embodiment, $P^1, P^2, P^3, P^4$ and $P^5$ are each substituted or unsubstituted carbon (e.g., CH). For example, $P^1$ and $P^3$ may be CH. In another further embodiment, $P^2$ and $P^4$ are each CH, CF, CCl, CBr, or CI. Furthermore, $P^1, P^2, P^3$, and $P^4$ can be linked covalently to form a bicyclic ring.

In a third further embodiment, $Z^3$ and $Z^4$ are each CH.

In a fourth further embodiment, $Z^1$ is CH, or covalently linked to $Z^2$ to form a naphthyl ring. Examples of $Z^2$ include CH, C—(C≡CH), CCl, CBr, CI, and CF. Furthermore, $Z^2$ may be substituted with a chain of atoms which covalently links it to $Z^1$ to form a naphthyl ring.

In a further embodiment, $P^5$ is C-$L_2$-J, wherein C is a carbon atom, $L_2$ is a linking moiety, e.g., a covalent bond, substituted or unsubstituted amino, ether, thioether, or alkyl; and J is an unsubstituted or substituted nitrogen containing heterocycle or a substituted or unsubstituted amino group. In yet a further embodiment, $L_2$ is a covalent bond and J is a moiety of formula (XIII):

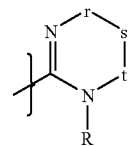

(XIII)

wherein r is a covalent bond, CH, CH$_2$, CHR$^1$, CR$^1$R$^2$, or H;

t is CH, CH$_2$, CHR$^3$, CR$^3$R$^4$, or H;

s is CH, CH$_2$, CHR$^5$, CR$^5$R$^6$, or absent;

R is hydrogen, alkyl, alkenyl, arylalkyl, arylcarbonyl, alkoxycarbonyl, arylalkylcarbonyl, alkylcarbonyl, optionally linked to A, B, L$_1$, L$_2$, R$^1$, R$^2$, R$^3$, R$^4$, R$^5$, or R$^6$ to form one or more rings;

R$^1$, R$^2$, R$^3$, R$^4$, R$^5$, and R$^6$ are each halogen, thiol, thioether, thioalkyl, alkoxy, alkyl, alkenyl, alkynyl, heterocyclic, hydroxyl, nitro, amino, cyano, aryl, optionally linked to form a ring with R, R$^1$, R$^2$, R$^3$, R$^4$, R$^5$, or R$^6$.

In a further embodiment, compounds of formula VII also include compounds wherein J is

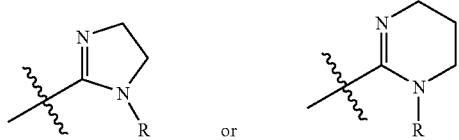

wherein R is alkyl (e.g., methyl, ethyl, propyl, butyl, etc.) or hydrogen. In another embodiment, the compounds include those in which P$^1$, P$^2$, and P$^3$ are each CH, and P$^4$ is CCl. Furthermore, the compounds also include those wherein Z$^1$, Z$^3$, and Z$^4$ are each CH, Z$^5$ is COMe, and Z$^2$ is CBr, as well as those wherein Z$^1$ is covalently linked to Z$^2$ to form a naphthyl ring, and Z$^3$, Z$^4$ and Z$^5$ are each CH.

In another embodiment, the MC4-R binding compound is of formula (VIII):

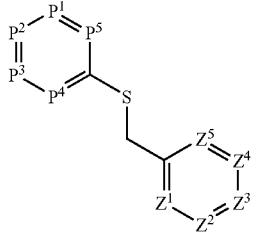

(VIII)

wherein

Z$^1$, Z$^2$, Z$^3$, Z$^4$, and Z$^5$ are CH, N, or substituted carbon; and

P$^1$, P$^2$, P$^3$, P$^4$, and P$^5$ are CH, N or substituted carbon.

Examples of substituents of Z$^1$, Z$^2$, Z$^3$, Z$^4$, Z$^5$, P$^1$, P$^2$, P$^3$, P$^4$, and P$^5$ include halogens (e.g., bromine, fluorine, chlorine, iodine, etc.), alkyl groups (e.g., branched, straight chain or cyclic, substituted or unsubstituted, methyl, ethyl, propyl, butyl, etc.), alkoxy groups (e.g., substituted or unsubstituted alkoxy, e.g., methoxy, ethoxy, isopropoxy, n-propoxy, isobutoxy, n-butoxy, pentoxy, cyclopentoxy, methylenedioxy, ethylenedioxy, etc.), aryl groups (e.g., substituted or unsubstituted phenyl, heterocyclic groups), alkenyl, alkynyl, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, and azido groups.

In a further embodiment, P$^1$, P$^2$, P$^3$, and P$^4$ are each substituted or unsubstituted carbon (e.g., CH). For example, P$^1$ and P$^3$ may be CH. In another further embodiment, P$^2$ and P$^4$ are each CH, CF, CCl, CBr, or CI. Furthermore, P$^1$, P$^2$, P$^3$, and P$^4$ can be linked covalently to form a bicyclic ring.

In a third further embodiment, Z$^3$ and Z$^4$ are each CH.

In a fourth further embodiment, Z$^1$ is CH, or covalently linked to Z$^2$ to form a naphthyl ring. Examples of Z$^2$ include CH, C—(C≡CH), CCl, CBr, CI, and CF. Furthermore, Z$^2$ may be substituted with a chain of atoms which covalently links it to Z$^1$ to form a naphthyl ring.

In a further embodiment, P$^5$ is C-L$_2$-J, wherein C is a carbon atom, L$_2$ is a linking moiety, e.g., a covalent bond, substituted or unsubstituted amino, ether, thioether, or alkyl; and J is an unsubstituted or substituted nitrogen containing heterocycle or a substituted or unsubstituted amino group. In yet a further embodiment, L$_2$ is a covalent bond and J is a moiety of formula (XIII):

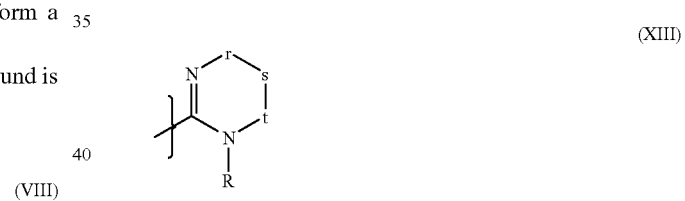

(XIII)

wherein r is a covalent bond, CH, CH$_2$, CHR$^1$, CR$^1$R$^2$, or H;

t is CH, CH$_2$, CHR$^3$, CR$^3$R$^4$, or H;

s is CH, CH$_2$, CHR$^5$, CR$^5$R$^6$, or absent;

R is hydrogen, alkyl, alkenyl, arylalkyl, arylcarbonyl, alkoxycarbonyl, arylalkylcarbonyl, alkylcarbonyl, optionally linked to A, B, L$_1$, L$_2$, R$^1$, R$^2$, R$^3$, R$^4$, R$^5$, or R$^6$ to form one or more rings;

R$^1$, R$^2$, R$^3$, R$^4$, R$^5$, and R$^6$ are each halogen, thiol, thioether, thioalkyl, alkoxy, alkyl, alkenyl, alkynyl, heterocyclic, aryl, hydroxyl, nitro, amino, cyano, optionally linked to form a ring with R, R$^1$, R$^2$, R$^3$, R$^4$, R$^5$, or R$^6$.

In another embodiment, the invention pertains to MC4-R binding compounds of formulae VII and VIII. Examples of MC4-R binding compound of these formulae include, for example, compounds wherein P$^5$ is a carbon covalently bonded to a moiety of formula XIII. In a further embodiment, the moiety of formula XIII is not benzoimidazole. In another further embodiment, Z$^3$ is not ethoxy. In another embodiment, the invention pertains to both methods of using and MC4-R binding compounds of formula (IX):

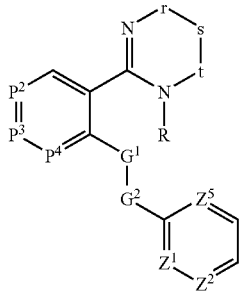

(IX)

wherein:

$P^2$ is CH, CF, CCl, CBr, C-alkyl, C-aryl, C-alkoxy, C—CN, C—OH, CI, or a covalent bond;

$P^3$ is CH, CF, CCl, CBr, C-alkyl, C-aryl, C-alkoxy, C—CN, C—OH, or CI;

$P^4$ is CH, CCl, CBr, CF, C-alkyl, C-aryl, C-alkoxy, C—CN, C—OH, or CI;

$G^1$ and $G^2$ are each independently $CH_2$, S, or O;

r is a covalent bond or $CH_2$;

t is $CH_2$, $CHR^3$, or $CR^3R^4$;

s is $CH_2$, $CHR^5$ or $CR^5R^6$;

R is hydrogen alkyl, alkoxycarbonyl, or alkylcarbonyl;

$Z^1$ is CH, or covalently linked to $Z^2$ to form a naphthyl ring;

$Z^2$ is CH, C—(C≡CH), CCl, CBr, CI, CF, or covalently linked to $Z^1$ to form a naphthyl ring;

$Z^5$ is CH, C-alkoxy (e.g., C—OMe);

$R^3$, $R^4$, $R^5$, and $R^6$ are methyl, ethyl, hydroxyl, alkoxy, halogen, cyano, nitro, amino, or pharmaceutically acceptable salts thereof.

The language "linked to form a naphthyl ring" includes moieties which join $Z^1$ and $Z^2$ to form a naphthyl (fused) ring system. Examples of such $Z^1$ and $Z^2$ groups include, but are not limited to, —CH=CH—CH=CH—.

In a further embodiment, $Z^1$ is CH; $Z^2$ is CBr; and $Z^5$ is C—OMe.

In another further embodiment, $P^2$ is CH. In another, $P^4$ is CCl or CF. $G^1$ and $G^2$ are each $CH_2$. In another, $G^1$ and $G^2$ together are —$CH_2$—$CH_2$—, —$CH_2$O—, —O—$CH_2$—, —$CH_2$—S— or —S—$CH_2$—. In another, $Z^1$ and $Z^2$ are linked to form a naphthyl ring.

In an embodiment, r is a covalent bond, s is $CR^5R^6$, and t is $CR^3R^4$, wherein $R^3$, $R^4$, $R^5$, and $R^6$ are each independently hydrogen or alkyl (e.g., methyl, ethyl, propyl, or butyl). In another embodiment, R is hydrogen or alkyl (e.g., methyl, ethyl, propyl or butyl, etc.)

The invention pertains to MC4-R binding compound of the formula (VII):

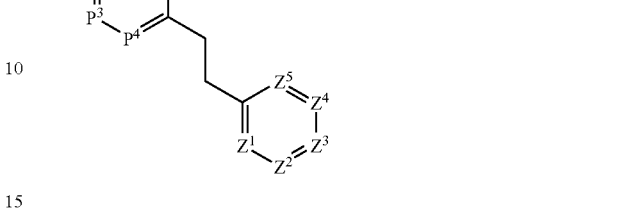

(VII)

wherein $Z^1$, $Z^2$, $Z^3$, $Z^4$, and $Z^5$ are CH, N, or substituted carbon; and $P^1$, $P^2$, $P^3$, $P^4$, and $P^5$ are CH, N or substituted carbon.

$P^5$ is C-$L_2$-J, wherein $L_2$ is a covalent bond, alkyl (e.g., $C_1$-$C_3$), amino, ether, carbonyl, etc., and wherein J is a moiety of the formula (XIII):

(XIII)

wherein r is a covalent bond, CH, $CH_2$, $CHR^1$, $CR^1R^2$, or hydrogen to provide an acyclic group;

t is CH, $CH_2$, $CHR^3$, $CR^3R^4$, or hydrogen to provide an acyclic group;

s is CH, $CH_2$, $CHR^5$, $CR^5R^6$, or absent;

R is hydrogen, alkyl, alkenyl, arylalkyl, arylcarbonyl, alkoxycarbonyl, arylalkylcarbonyl, alkylcarbonyl, optionally linked to $R^1$, $R^2$, $R^3$, $R^4$, $R^5$, or $R^6$ to form one or more rings; and $R^1$, $R^2$, $R^3$, $R^4$, $R^5$, and $R^6$ are each halogen, thiol, thioether, thioalkyl, alkoxy, alkyl, alkenyl, alkynyl, heterocyclic, hydroxyl, nitro, amino, cyano, aryl, optionally linked to form a ring with R, $R^1$, $R^2$, $R^3$, $R^4$, $R^5$, or $R^6$.

The invention also pertains to MC4-R binding compound of the formula (VIII):

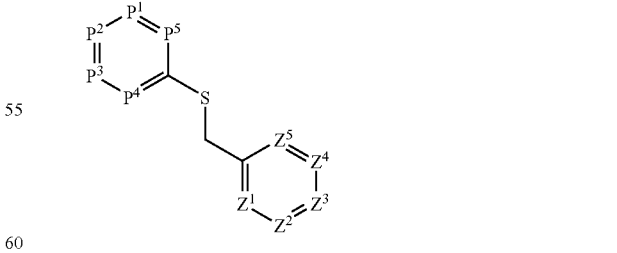

(VIII)

wherein $Z^1$, $Z^2$, $Z^3$, $Z^4$, and $Z^5$ are CH, N, or substituted carbon; $P^1$, $P^2$, $P^3$, and $P^4$ are CH, N or substituted carbon; and $P^5$ is C-$L_2$-J, wherein $L_2$ is a covalent bond, alkyl (e.g., $C_1$-$C_3$), amino, ether, carbonyl, etc., and wherein J is a moiety of the formula (XIII):

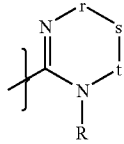

(XIII)

wherein r is a covalent bond, CH, CH$_2$, CHR$^1$, CR$^1$R$^2$, or hydrogen to provide an acyclic group;

t is CH, CH$_2$, CHR$^3$, CR$^3$R$^4$, or hydrogen to provide an acyclic group;

s is CH, CH$_2$, CHR$^5$, CR$^5$R$^6$, or absent;

R is hydrogen, alkyl, alkenyl, arylalkyl, arylcarbonyl, alkoxycarbonyl, arylalkylcarbonyl, alkylcarbonyl, optionally linked to R$^1$, R$^2$, R$^3$, R$^4$, R$^5$, or R$^6$ to form one or more rings; and R$^1$, R$^2$, R$^3$, R$^4$, R$^5$, and R$^6$ are each halogen, thiol, thioalkyl, thioether, alkoxy, alkyl, alkenyl, alkynyl, heterocyclic, hydroxyl, nitro, amino, cyano, aryl, optionally linked to form a ring with R, R$^1$, R$^2$, R$^3$, R$^4$, R$^5$, or R$^6$.

The invention also pertains to MC4-R binding compound of the formula (XV):

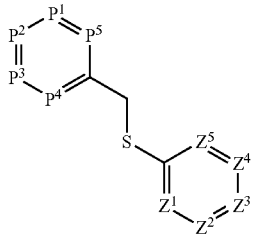

(XV)

wherein

Z$^1$, Z$^2$, Z$^3$, Z$^4$, and Z$^5$ are CH, N, or substituted carbon;

P$^1$, P$^2$, P$^3$, and P$^4$ are CH, N or substituted carbon; and

P$^5$ is C-L$_2$-J, wherein L$_2$ is a covalent bond, alkyl (e.g., C$_1$-C$_3$), amino, ether, carbonyl, etc., and wherein J is a moiety of the formula (XIII):

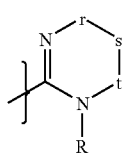

(XIII)

wherein r is a covalent bond, CH, CH$_2$, CHR$^1$, CR$^1$R$^2$, or hydrogen to provide an acyclic group;

t is CH, CH$_2$, CHR$^3$, CR$^3$R$^4$, or hydrogen to provide an acyclic group;

s is CH, CH$_2$, CHR$^5$, CR$^5$R$^6$, or absent;

R is hydrogen, alkyl, alkenyl, arylalkyl, arylcarbonyl, alkoxycarbonyl, arylalkylcarbonyl, alkylcarbonyl, optionally linked to R$^1$, R$^2$, R$^3$, R$^4$, R$^5$, or R$^6$ to form one or more rings; and R$^1$, R$^2$, R$^3$, R$^4$, R$^5$, and R$^6$ are each halogen, thiol, thioalkyl, thioether, alkoxy, alkyl, alkenyl, alkynyl, heterocyclic, hydroxyl, nitro, amino, cyano, aryl, optionally linked to form a ring with R, R$^1$, R$^2$, R$^3$, R$^4$, R$^5$, or R$^6$.

The invention also pertains to MC4-R binding compound of the formula (XVI):

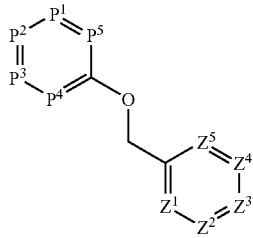

(XVI)

wherein

Z$^1$, Z$^2$, Z$^3$, Z$^4$, and Z$^5$ are CH, N, or substituted carbon;

P$^1$, P$^2$, P$^3$, and P$^4$ are CH, N or substituted carbon; and

P$^5$ is C-L$_2$-J, wherein L$_2$ is a covalent bond, alkyl (e.g., C$_1$-C$_3$), amino, ether, carbonyl, etc., and wherein J is a moiety of the formula (XIII):

(XIII)

wherein r is a covalent bond, CH, CH$_2$, CHR$^1$, CR$^1$R$^2$, or hydrogen to provide an acyclic group;

t is CH, CH$_2$, CHR$^3$, CR$^3$R$^4$, or hydrogen to provide an acyclic group;

s is CH, CH$_2$, CHR$^5$, CR$^5$R$^6$, or absent;

R is hydrogen, alkyl, alkenyl, arylalkyl, arylcarbonyl, alkoxycarbonyl, arylalkylcarbonyl, alkylcarbonyl, optionally linked to R$^1$, R$^2$, R$^3$, R$^4$, R$^5$, or R$^6$ to form one or more rings; and R$^1$, R$^2$, R$^3$, R$^4$, R$^5$, and R$^6$ are each halogen, thiol, thioalkyl, thioether, alkoxy, alkyl, alkenyl, alkynyl, heterocyclic, hydroxyl, nitro, amino, cyano, aryl, optionally linked to form a ring with R, R$^1$, R$^2$, R$^3$, R$^4$, R$^5$, or R$^6$.

In a further embodiment, the invention includes compounds wherein P$^1$, P$^2$, P$^3$, and P$^4$ of any one of formulas VII, VIII, XV, or XVI are each substituted or unsubstituted carbon. For example, in one embodiment, P$^1$ is CH. In another example, at least one of P$^2$, P$^3$ and P$^4$ is a substituted carbon. In a further embodiment, P$^2$, P$^3$ and P$^4$ are selected from the group consisting of CH, CF, Cl, CBr, C-alkyl, C-alkoxy, or CI.

In another embodiment, the compounds of formulae VII, VIII, XV, or XVI, include compounds wherein Z$^3$ and Z$^4$ are each CH. In another further embodiment of the formulae, Z$^1$ is CH. For example, in another further embodiment, Z$^1$ is covalently linked to Z$^2$ to form a naphthyl ring. Z$^2$ is CH, C—(C≡CH), CCl, CBr, CI, and CF.

In another further embodiment, the compounds of the invention include compounds of formulae VII, VIII, XV, or XVI, wherein $L_2$ is a covalent bond. Also included are compounds wherein R is H, alkyl, benzocarboxy, alkylcarboxy, or arylalkylcarboxy.

In another further embodiment, the compounds of the invention include compounds of formulae VII, VIII, XV, or XVI, wherein s is $CR^5R^6$ and $R^5$ and $R^6$ are each methyl. In another example r is a covalent bond. Alternatively, each of t, r and s may be $CH_2$.

Another embodiment of the invention pertains to compounds of the formula XVII:

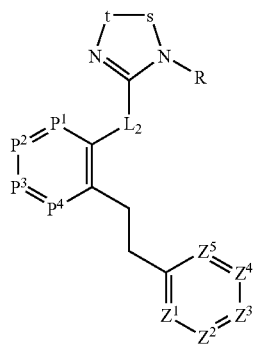

XVII wherein:

$P^1$, $P^2$, $P^3$, and $P^4$ are each selected from a substituted or unsubstituted carbon, wherein one of $P^1$-$P^4$ is optionally replaced by a nitrogen atom, or the ring bearing $P^1$-$P^4$ is a thiophene ring, wherein $P^3$-$P^4$ together are replaced by a sulfur atom;

$Z^1$ is CH or a carbon substituted with $R^7$;

$Z^2$ is CH or a carbon substituted with $R^8$;

$Z^3$, $Z^4$ and $Z^5$ are each independently selected from CH or a carbon substituted with $R^9$;

$R^7$ is $C_{1-3}$ alkoxy, $C_{1-3}$ haloalkoxy, cyano, $C_{1-3}$ cyanoalkyl, halo, $C_{1-3}$ alkyl, or $C_{1-3}$ haloalkyl;

$R^8$ is halo, $C_{1-3}$ alkyl, $C_{1-3}$ haloalkyl, or $R^7$ and $R^8$ are taken together with their intervening atoms to form a fused, 5-6 membered aromatic or nonaromatic, ring having 0-2 ring heteroatoms selected from oxygen, nitrogen or sulfur;

each $R^9$ is independently selected from halo, cyano, trialkylsiloxy, $C_{1-6}$ alkyl, $C_{1-6}$ haloalkyl, $C_{1-6}$ alkoxy, $C_{1-6}$ haloalkoxy, $C_{1-6}$ alkenyl, $C_{1-6}$ alkynyl, $N(R^{10})_2$, $(C_{1-6}$ alkyl)-$N(R^{10})_2$, $O(C_{1-6}$ alkyl)-$N(R^{10})_2$, $C_{1-6}$ alkylsulfonyl, $C_{1-6}$ alkylthio, or phenyl, or two $R^9$ on neighboring carbons are taken together to form a fused, 5-6 membered aromatic or nonaromatic ring having 0-2 ring heteroatoms selected from oxygen, nitrogen, or sulfur;

each $R^{10}$ is independently selected from hydrogen, $C_{1-4}$ alkyl, or two $R^{10}$ on the same nitrogen are taken together with their intervening nitrogen to form a 5-6 membered ring having 1-2 ring heteroatoms selected from oxygen, nitrogen or sulfur;

$L_2$ is a covalent bond, a substituted or unsubstituted 1-2 carbon chain or a 2 carbon carbonyl chain, wherein one of the carbons along with the hydrogen attached thereto is optionally replaced by oxygen, $N(R^{10})$, or sulfur;

t is $CH_2$, $CHR^3$, or $CR^3R^4$, and s is $CH_2$, $CHR^5$, or $CR^5R^6$, or t-s taken together is CH=CH, $CR^3$=CH, CH=$CR^5$ or $CR^3$=$CR^5$;

$R^3$, $R^4$, $R^5$, and $R^6$ are each independently selected from $C_{1-4}$ alkyl, $C_{1-4}$ alkylcarboxyl, $C_{1-4}$ alkoxycarbonyl, $C_{1-4}$ alkylcarboxamide, or two of $R^3$, $R^4$, $R^5$, and $R^6$ are taken together with their intervening atom or atoms to form a fused 3-7 membered aromatic or non-aromatic ring or 3-7 membered spirocyclic ring, having 0-2 ring heteroatoms selected from oxygen, nitrogen or sulfur;

R is hydrogen or a $C_{1-8}$ alkyl or $C_{1-8}$ alkylcarbonyl that is substituted with 0-2 $R^{11}$, or R and $R^5$ are taken together with their intervening atoms to form a fused pyrrolidino or piperidino ring, or R and $L_2$ are taken together with their intervening atoms to form a fused five membered ring having 1-2 ring heteroatoms selected from oxygen, nitrogen or sulfur;

each $R^{11}$ is independently selected from $C_{1-3}$ alkyl, cyano, halo, haloalkyl, $N(R^{10})_2$, (C=O)$N(R^{10})_2$, OC(=O)$N(R^{10})_2$, OH, S($C_{1-6}$ alkyl), $SO_2(C_{1-6}$ alkyl), $SO_2N(R^{10})_2$, $C_{1-6}$ alkoxy, $C_{1-6}$ alkylcarbonyl, $C_{1-6}$ alkylcarboxyl, $C_{1-6}$ alkoxycarboxyl, $C_{5-6}$ aryl, $C_{6-10}$ arylalkyl, or a 3-6 membered heterocyclyl having 1 or 2 heteroatoms selected from oxygen, nitrogen or sulfur; or a pharmaceutically acceptable salt thereof.

In certain embodiments, where carbon chains or R groups (e.g, $L_2$, R, $R^3$, $R^4$, $R^5$, $R^6$, etc.) contain an alkyl or an aryl, they may be substituted or unsubstituted with one or more substituents. In certain embodiments where R groups are taken together to form a ring (e.g., $R^7$ and $R^8$ are taken together to form a ring), the resulting ring may be substituted or unsubstituted. Examples of substituents (e.g., of $P^1$, $P^2$, $P^3$, $P^4$, $P^5$, $Z^3$, $Z^4$, $Z^5$, R, $R^3$, $R^4$, $R^5$, $R^6$, $R^7$, $R^8$, $R^9$, $R^{10}$ and $R^{11}$) include halogens (e.g., bromine, fluorine, chlorine, iodine, etc.), oxygen, sulfur, alkyl groups (e.g., branched, straight chain or cyclic, substituted or unsubstituted, methyl, ethyl, propyl, butyl, etc.), alkoxy groups (e.g., substituted or unsubstituted alkoxy, e.g., methoxy, ethoxy, isopropoxy, n-propoxy, isobutoxy, n-butoxy, pentoxy, cyclopentoxy, methylenedioxy, ethylenedioxy, etc.), aryl groups (e.g., substituted or unsubstituted phenyl, heterocyclic groups), alkenyl, alkynyl, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, and azido groups.

In certain embodiments, $P^1$, $P^2$, $P^3$ and $P^4$ are each independently selected from a substituted (e.g, CF) or unsubstituted (e.g., CH) carbon. For example, $P^1$ $P^2$ and $P^3$ can be CH. Specific examples of $P^2$ and $P^4$ independently include CH, CF, CCl, CBr, or CI.

In a further embodiment, the compound of formula (XVII) has one or more features selected from:

(a) $Z^1$ is a carbon substituted with $R^7$;

(b) $Z^2$, $Z^3$ and $Z^5$ are each CH;

(c) $Z^4$ is a carbon substituted with $R^9$;

(d) $L^2$ is a covalent bond;

(e) t is $CH_2$;

(f) s is $CH_2$; and (g) R is hydrogen or $C_{1-8}$ alkyl that is substituted with 0-2 $R^{11}$.

In one embodiment, the compound has all of the above features (a)-(g), and $P^1$, $P^2$, $P^3$ and $P^4$ are each independently selected from a substituted (e.g, CF) or unsubstituted (e.g., CH) carbon. In one aspect, R is hydrogen. In another aspect, $R^7$ is alkoxy. In another aspect, $R^9$ is halo cyano or alkynyl. Specific examples of $R^9$ include F, Br, or Cl.

In yet another aspect, the compound of Formula (XVII) has one or more (a)-(g); and further include one or more of the specific features (h)-(k):

(h) $P^1$, $P^2$, and $P^3$ are each an unsubstituted carbon, and $P^4$ is an unsubstituted carbon, or a carbon substituted with a halogen or alkoxy;
(i) $R^7$ is alkoxy;
(j) $R^9$ is a halo, cyano or alkynyl; and
(k) R is hydrogen, or $C_{1-4}$ alkyl that is substituted with 0-2 $R^{11}$, wherein $R^{11}$ can be $C_{1-3}$ alkyl, cyano, halo, $C_{1-4}$ alkoxy, or a 5-6 membered heterocyclyl having 1 or 2 heteroatoms selected from oxygen, nitrogen or sulfur.

In one aspect the compound has all of the above features (h)-(k). In another aspect, $P^1$, $P^2$, and $P^3$ are each an unsubstituted carbon; $P^4$ is CH, CF, or Cl. In yet a further aspect, $R^7$ is alkoxy. In another aspect R is $C_{1-4}$ alkyl that is substituted with 0-2 $R^{11}$, wherein $R^{11}$ can be $C_{1-3}$ alkyl, cyano, halo, $C_{1-4}$ alkoxy, or a 5-6 membered heterocyclyl having 1 or 2 heteroatoms selected from nitrogen, oxygen or sulfur. Specific examples of $R^9$ include F, Cl, or Br.

Yet another embodiment of the invention includes compounds of Formula (XVII) having one or more of the following features:

(a) $Z^1$ is a carbon substituted with $R^7$, $Z^2$ is a carbon substituted with $R^8$, and $R^7$ and $R^8$ are taken together to form a fused, 5-6 membered aromatic or nonaromatic ring having 0-2 ring heteroatoms selected from oxygen, nitrogen or sulfur;
(b) $Z^3$ and $Z^5$ are each CH;
(c) $Z^4$ is a carbon substituted with $R^9$;
(d) $L_2$ is a covalent bond;
(e) t is $CH_2$;
(f) s is $CH_2$; and
(g) R is hydrogen or $C_{1-8}$ alkyl that is substituted with 0-2 $R^{11}$.

In one aspect, the compound has all of the above features (a)-(g) and $P^1$, $P^2$, $P^3$ and $P^4$ are each independently selected from a substituted (e.g, CF) or unsubstituted (e.g., CH) carbon. In another aspect the compound of Formula (XVII) has one or more of the features (a)-(g), wherein one or more of (h)-(k) are included:

(h) $P^1$, $P^2$, and $P^3$ are each an unsubstituted carbon, and $P^4$ is an unsubstituted carbon, or a carbon substituted with a halogen or alkoxy;
(i) $R^7$ and $R^8$ are taken together to form a substituted or unsubstituted benzo, furano, thieno, dioxolo ring.
(j) $R^9$ is halo cyano or alkynyl; and
(k) R is hydrogen, or $C_{1-4}$ alkyl that is substituted with 0-2 $R^{11}$, and $R^{11}$ is $C_{1-3}$ alkyl, cyano, halo, $C_{1-4}$ alkoxy, or a 5-6 membered heterocyclyl having 1 or 2 heteroatoms selected from nitrogen, oxygen or sulfur. In still another aspect, the compound has all of features (a)-(k). In still a more specific aspect, $P^1$, $P^2$, and $P^3$ are each an unsubstituted carbon and $P^4$ is CH, CF, CCl, or CBr. In still another aspect, $R^7$ and $R^8$ are taken together to form a substituted or unsubstituted benzo, furano, thieno, dioxolo ring. Specific examples of $R^9$ include F, Cl, Br or cyano. In yet another aspect, R is $C_{1-4}$ alkyl that is substituted with 0-1 $R^{11}$ and $R^{11}$ is $C_{1-3}$ alkyl, cyano, halo, or a 5-6 membered heterocyclyl having 1 or 2 heteroatoms selected from nitrogen, oxygen or sulfur.

In still a further embodiment, a compound of Formula (XVII) has one or more of the following features:
(a) $Z^1$ is a carbon substituted with $R^7$;
(b) $Z^2$, $Z^3$ and $Z^5$ are each CH;
(c) $Z^4$ is a carbon substituted with $R^9$;
(d) L is a covalent bond;
(e) t is $CH_2$ or $CHR^3$;
(f) s is $CHR^5$, or $CR^5R^6$, and
(g) R is hydrogen or $C_{1-8}$ alkyl that is substituted with 0-2 $R^{11}$, wherein $R^3$ and $R^5$ are optionally taken together with their intervening atom or atoms to form a fused 3-7 membered aromatic or non-aromatic ring having 0-2 ring heteroatoms selected from oxygen, nitrogen, or sulfur or R and $R^5$ are taken together with their intervening atoms to form a fused pyrrolidino or piperidino ring.

In one aspect, the compound has all of the above features (a)-(g). In another aspect, the compound has one or more of the features (a)-(g) and one or more of features (h)-(k):
(h) $P^1$, $P^2$, and $P^3$ are each an unsubstituted carbon, and $P^4$ is an unsubstituted carbon, or a carbon substituted with a halogen or alkoxy;
(i) $R^7$ is alkoxy;
(j) $R^9$ is a halo, cyano or alkynyl; and
(k) s is $CHR^5$. In certain aspects, $R^5$ is taken together with $R^3$ to form a fused 5-6 membered non-aromatic ring. In other aspects, $R^5$ is taken together with R with their intervening atoms to form a fused pyrrolidino or piperidino ring. In a further aspect, the compound has all of the features (h)-(k). In yet a more specific aspect, L is a covalent bond, $P^1$, $P^2$, and $P^3$ are each CH, and $P^4$ is an CH, CF, CCl, or CBr, $R^7$ is alkoxy; t is $CHR^3$; s is $CHR^5$, wherein $R^5$ is taken together with $R^3$ to form a fused 5-6 membered non-aromatic ring; $Z^1$ is a carbon substituted with $R^7$; $Z^2$, $Z^3$ and $Z^5$ are each CH; $Z^4$ is a carbon substituted with $R^9$ and $R^9$ is Br, Cl, F or cyano; and R is hydrogen or $C_{1-8}$ alkyl that is substituted with 0-2 $R^{11}$. In yet another more specific aspect, $L^2$ is a covalent bond; $P^1$, $P^2$, and $P^3$ are each CH, and $P^4$ is an CH, CF, CCl, or CBr; $R^7$ is alkoxy; s is $CHR^5$, wherein $R^5$ is taken together with R with their intervening atoms to form a fused pyrrolidino or piperidino ring; t is $CH_2$; $Z^1$ is a carbon substituted with $R^7$; $Z^2$, $Z^3$ and $Z^5$ are each CH; and $Z^4$ is a carbon substituted with $R^9$ and $R^9$ is Br, Cl, F, or cyano.

Yet another embodiment of the invention includes compounds of Formula (XVII) having one or more of the following features:
(a) $Z^1$ is a carbon substituted with $R^7$, $Z^2$ is a carbon substituted with $R^8$, and $R^7$ and $R^8$ are taken together to form a fused, 5-6 membered aromatic or nonaromatic ring having 0-2 ring heteroatoms;
(b) $Z^3$ and $Z^4$ are each CH;
(c) $Z^5$ is a carbon substituted with $R^9$;
(d) $L^2$ is a covalent bond;
(e) t is $CH_2$ or $CHR^3$;
(f) s is $CHR^5$, or $CR^5R^6$, and
(g) R is hydrogen or $C_{1-8}$ alkyl that is substituted with 0-2 $R^{11}$.

In certain aspects, $R^3$ and $R^5$ can be taken together with their intervening atom or atoms to form a fused 3-7 membered aromatic or non-aromatic ring having 0-2 ring heteroatoms. Specific heteroatoms include oxygen, nitrogen, or sulfur. In other certain aspects, R and $R^5$ are taken together with their intervening atoms to form a fused pyrrolidino or piperidino ring.

In one aspect the compound has all of the above features (a)-(g). In another aspect, the compound has one or more features (a)-(g), and $P^1$, $P^2$, and $P^3$ are each an unsubstituted carbon, and $P^4$ is an unsubstituted carbon, or a carbon substituted with a halogen or alkoxy. Examples of $R^9$ include halo cyano or alkynyl. Specific $R^9$ include Br, Cl, F or cyano.

In one specific aspect, $R^7$ and $R^8$ are taken together to form a substituted or unsubstituted benzo, furano, thieno, dioxolo ring. In another specific aspect, s is $CHR^5$, wherein $R^5$ is taken together with $R^3$ to form a fused 5-6 membered non-aromatic ring. In yet another aspect, s is $CHR^5$, wherein $R^5$ is taken together with R with their intervening atoms to form a fused pyrrolidino or piperidino ring. In a more specific aspect, the compound has one or more features (a)-(g); $P^1$, $P^2$, and $P^3$ are each an unsubstituted carbon, and $P^4$ is an unsubstituted carbon, or a carbon substituted with a halogen or alkoxy; and one or more of the following features (h)-(j):

(h) $R^7$ and $R^8$ are taken together to form a substituted or unsubstituted benzo, furano, thieno, dioxolo ring;

(i) $R^9$ is halo cyano or alkynyl;

(j) s is $CHR^5$, wherein $R^5$ is taken together with $R^3$ to form a fused 5-6 membered non-aromatic ring or $R^5$ is taken together with R with their intervening atoms to form a fused pyrrolidino or piperidino ring. In still another more aspect, the compound has all of the features of (a)-(j). In still a further aspect, the compound has all of the features of (a)-(j) wherein $R^5$ is taken together with $R^3$ to form a fused 5-6 membered non-aromatic ring. In another another further specific aspect, the compound has all of the features of (a)-(j), wherein $R^5$ is taken together with R with their intervening atoms to form a fused pyrrolidino or piperidino ring.

Another embodiment of the invention includes compounds of the Formula (XVII) having one or more of the following features:

(a) $Z^1$ is a carbon substituted with $R^7$, $Z^2$ is a carbon substituted with $R^8$, and $R^7$ and $R^8$ are taken together to form a substituted or unsubstituted benzo, furano, thieno, dioxolo ring;

(b) $Z^3$ and $Z^5$ are each CH;

(c) $Z^4$ is a carbon substituted with $R^9$ and $R^9$ is halo cyano or alkynyl;

(d) $L^2$ is a covalent bond;

(e) t is $CH_2$;

(f) s is $CHR^5$;

(g) R and $R^5$ are taken together with their intervening atoms to form a fused pyrrolidino or piperidino ring; and (h) $P^1$, $P^2$, and $P^3$ are each CH, and $P^4$ is CH, CBr, CCl, CF, or C-alkoxy.

In one aspect, the compound has all of features (a)-(h).

Still a further embodiment of the invention includes compounds of Formula (XVII) having one or more of the following features:

(a) $Z^1$ is a carbon substituted with $R^7$, $Z^2$ is a carbon substituted with $R^8$, and $R^7$ and $R^8$ are taken together to form a substituted or unsubstituted benzo, furano, thieno, dioxolo ring;

(b) $Z^3$ and $Z^4$ are each CH;

(c) $Z^5$ is a carbon substituted with $R^9$ and $R^9$ is halo cyano or alkynyl;

(d) $L^2$ is a covalent bond;

(e) t is $CHR^3$;

(f) s is $CHR^5$, wherein $R^3$ and $R^5$ are taken together with their intervening atom or atoms to form a fused 3-7 membered non-aromatic ring having 0-2 ring heteroatoms selected from oxygen, nitrogen, or sulfur;

(g) R is hydrogen or $C_{1-8}$ alkyl that is substituted with 0-2 $R^{11}$; and (h) $P^1$, $P^2$, and $P^3$ are each CH, and $P^4$ is CH, CBr, CCl, CF, or C-alkoxy.

In one aspect, the invention includes compounds having all of features (a)-(h).

In a further embodiment, the MC4-R binding compounds of the invention of formula VII do not include benzimadazole as the moiety of formula XIII, when $P^1$, $P^2$ $P^3$, $P^4$, $Z^1$, $Z^2$, $Z^4$, $Z^3$, and $Z^5$ are each CH. Furthermore, in another further embodiment, the compounds of the invention do not include compounds wherein the moiety of formula XIII is tetrahydropyrimidine, when $P^1$, $P^2$, $P^3$, $P^4$, $Z^1$, $Z^2$, $Z^4$, and $Z^5$ are each CH and $Z^3$ is C—OEt or CH.

In another further embodiment, the MC4-R binding compounds of the invention of formula VIII, do not include compounds wherein the moiety of formula XIII is benzoimidazolyl. In another further embodiment, the MC4-R binding compounds of the invention of formula VIII, do not include compounds wherein $P^2$ is not Cl, if $P^1$, $P^3$, or $P^4$ are CH. In another further embodiment, the MC4-R binding compounds of the invention of formula VIII, do not include compounds wherein $P^1$, $P^2$, $P^3$, $P^4$, $Z^1$, $Z^2$, $Z^4$, $Z^3$, and $Z^5$ are each CH, when the moiety of formula XIII is tetrahydropyrimidine. In another further embodiment, the compounds of formula VIII of the invention do not include compounds wherein the moiety of formula is 4,5-dihydro-1H-imidazole, when $P^1$, $P^2$, $P^3$, and $P^4$ are each CH, and wherein one or two of $Z^1$, $Z^2$, or $Z^3$ is CCl, and the remaining Z groups are CH. In another further embodiments, the MC4-R binding compounds of formula VIII of the invention, do not include compounds wherein the moiety of formula XIII is tetrahydropyrimidine, and when $P^1$, $P^2$, $P^3$, and $P^4$ are each CH, and $Z^2$ is CCl and the remaining Z groups are CH. In another further embodiments, the compounds of formula VIII of the invention, do not include compounds wherein when the moiety of formula XIII is tetrahydropyrimidine, and when $P^1$, $P^2$, $P^3$, and $P^4$ are each CH, and $Z^1$ and one of $Z^4$ or $Z^5$ are CCl and the remaining Z groups are CH.

In another further embodiment, the MC4-R binding compounds of the invention do not include compounds of formula XV, wherein the moiety of formula VIII is not benzoimidazole if $P^1$, $P^2$, $P^3$, $P^4$ are each CH, and wherein $Z^2$ is CMe and the remaining Z groups are CH.

In another further embodiment, the MC4-R binding compounds of the invention do not include compounds of formula XVI, wherein the moiety of formula XVI, wherein $L_2$ is not NH (e.g., amino), if $P^1$, $P^2$, $P^3$, $P^4$, $Z^1$, $Z^2$, $Z^4$, $Z^3$, and $Z^5$ are each CH. In another embodiment, the MC4-R binding compounds of formula XVI of the invention do not include compounds wherein P groups are substituted to form a naphthyl ring.

In another embodiment, the invention features a method for treating an MC4-R associated state in a mammal by administering an effective amount of a MC4-R binding compound to a mammal. Compounds of formula (X) are also included in the invention. In this embodiment, the compound is of the formula (X):

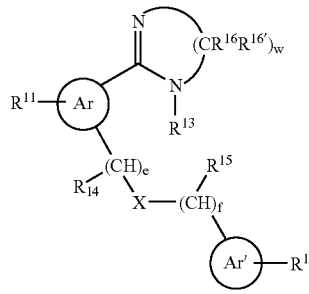
(X)

wherein
Ar and Ar' are aromatic groups;
$R^{11}$ is selected independently for each position capable of substitution from the group hydrogen, cyano, nitro, alkoxy, halogen, alkyl, amino, or aryloxy.
$R^{12}$ is selected for each position capable of substitution from the group consisting of hydrogen, halogen, alkoxy, acetylenic, nitro, aryl, alkyl, alkenyl, alkynyl, cyano, acyl, or carbonyl;
$R^{13}$ is hydrogen, alkenyl, alkynyl, aralkyl, nitro, cyano, alkyl (e.g., $C_1$-$C_{10}$ alkyl, e.g., methyl, ethyl, etc.) acyl, carbonyl, or $SO_2CH_3$, and may optionally be linked to an $R^{16}$ or an $R^{16'}$ group;
$R^{16}$ and $R^{16'}$ are each independently selected for each position capable of substitution from the group consisting of hydrogen, alkyl, alkenyl, alkynyl, aryl, heterocyclic, carbonyl, or acyl, and may optionally be connected through an alkyl chain to $R^{13}$ or another $R^{16}$ or $R^{16'}$ group, to form a fused or spiro ring system;
X is $NR^{17}$, S, O or a covalent bond;
$R^{17}$ is hydrogen, alkyl, alkenyl, alkynyl, acyl, heterocyclic, or carbonyl;
$R^{14}$ and $R^{15}$ are each independently selected from the group consisting of hydrogen, alkyl, alkenyl, heteroaromatic, halogen, nitro, cyano, amino, or aryl, for each occurrence;
w is 0, 1, 2, 3, or 4;
e is 0, 1, 2, or 3;
f is 0, 1, 2, or 3, and pharmaceutically acceptable salts thereof.
Examples of Ar groups include:

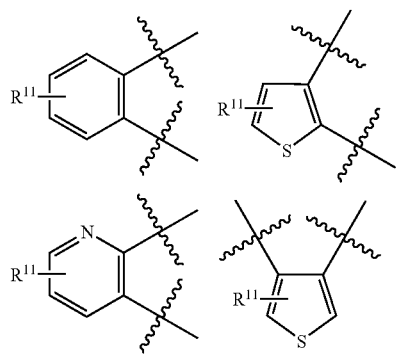

-continued

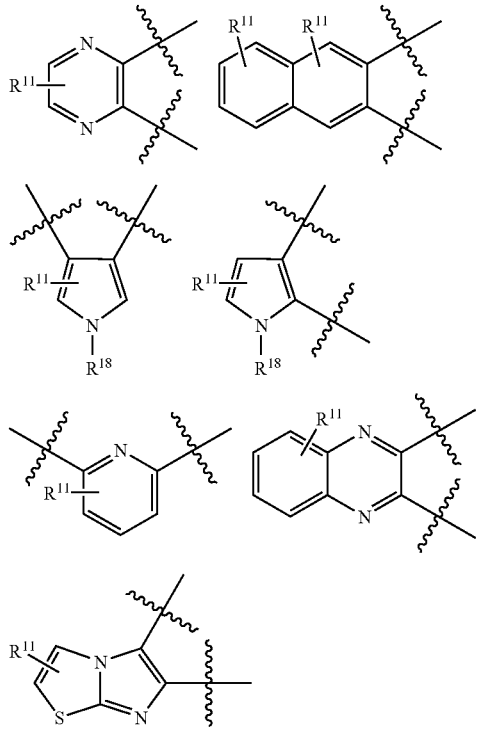

wherein $R^{18}$ is acyl, alkyl or hydrogen.
In a further embodiment, Ar is,

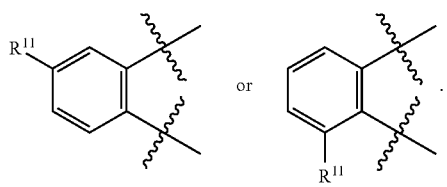

$R^{11}$ is selected independently for each aromatic position capable of substitution. Exemplary $R^{11}$ groups include, but are not limited to, hydrogen, halogen (e.g., fluorine, chlorine, or bromine), alkyl, amino, and benzyloxy.
Examples of Ar' groups include:

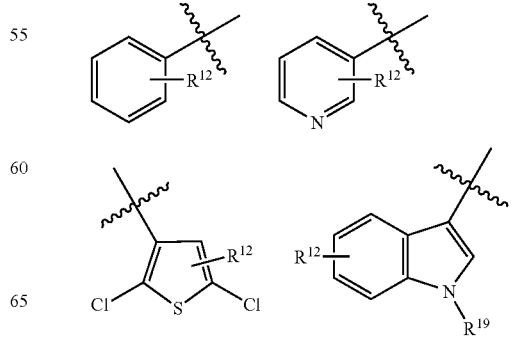

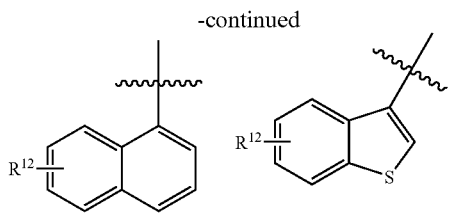

wherein $R^{19}$ is hydrogen, alkyl, acyl, aryl, alkenyl, or alkynyl.

In a further embodiment, each $R^{12}$ group is selected independently from the group consisting of hydrogen, alkoxy, halogen (e.g., fluorine, bromine, chlorine, or iodine), and cyano. Examples of alkoxy groups include $C_1$-$C_{10}$ alkoxy, such as, methoxy, ethoxy, n-propoxy, i-propoxy, and cyclopentoxy.

Examples of X include covalent bond, S, O and $NR^{17}$. Examples of $R^{17}$ include hydrogen, alkyl (e.g., $C_1$-$C_{10}$ alkyl, e.g., methyl), or acyl.

Examples of $R^{16}$ and $R^{16'}$ include alkyl and hydrogen. Each $R^{16}$ and $R^{16'}$ group is selected independently for each occurrence. In a further embodiment, at least one of $R^{16}$ or $R^{16'}$ are at least once hydrogen. In another embodiment, at least one of $R^{16}$ or $R^{16'}$ are at least once $C_1$-$C_{10}$ alkyl, e.g., methyl or ethyl.

In yet another further embodiment, $R^{14}$ and $R^{15}$ are each independently hydrogen, alkyl (e.g., $C_1$-$C_{10}$, e.g., methyl) or phenyl for each occurrence.

In yet another further embodiment, $R^{13}$ is hydrogen, acyl, alkyl (e.g., $C_1$-$C_{10}$ alkyl, e.g., methyl, ethyl, etc.) acyl, carboxy, or $SO_2CH_3$. Examples of acyl group include, but are not limited to, optionally substituted $C_1$-$C_{10}$alkyl acyl (e.g., i-propylcarbonyl and benzylcarbonyl).

In yet another further embodiment, w is 2 or 3. In yet another further embodiment, e is 0 or 1. In yet another further embodiment, f is 0 or 1.

In another embodiment, the invention features a method for treating an MC4-R associated state in a mammal by administering an effective amount of a MC4-R binding compound to a mammal. In this embodiment, the compound is of the formula (XI):

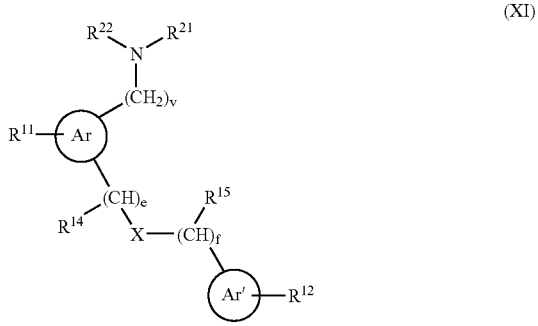

(XI)

wherein

Ar and Ar' are aromatic groups, as described above;

$R^{11}$ is selected independently for each position capable of substitution from the group hydrogen, halogen, alkyl, amino, cyano, or aryloxy.

$R^{12}$ is selected for each position capable of substitution from the group consisting of hydrogen, halogen, alkoxy, acetylenic, nitro, aryl, alkyl, alkenyl, alkynyl, cyano, acyl, or carbonyl;

X is $NR^{17}$, S, O or a covalent bond;

$R^{17}$ is hydrogen, alkyl, acyl, heterocyclic, or carbonyl;

$R^{14}$ and $R^{15}$ are each independently selected from the group consisting of hydrogen, alkyl, alkenyl, or aryl, for each occurrence;

$R^{20}$ and $R^{21}$ are each independently selected from the group consisting of substituted or unsubstituted alkyl, alkenyl, alkynyl, aryl, hydrogen, or carbonyl, and may optionally be linked to form a heterocycle (e.g., morphonlinyl, piperazinyl, piperidinyl, etc.);

v is 0, 1, 2, 3, 4, 5, or 6;

e is 0, 1, 2, or 3;

f is 0, 1, 2, or 3, and pharmaceutically acceptable salts thereof.

Examples of Ar, Ar', $R^{11}$, $R^{12}$, $R^{14}$, $R^{15}$ and X moieties include those described for formula (X).

Other examples of MC4-R binding compounds include compounds of the formula (XVIII):

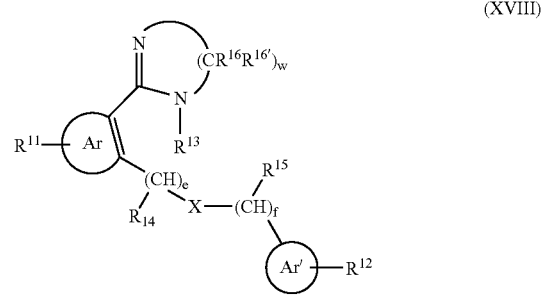

(XVIII)

wherein

Ar and Ar' are aromatic groups;

$R^{11}$ is selected independently for each position capable of substitution from the group hydrogen, cyano, alkoxy, nitro, halogen, alkyl, amino, or aryloxy;

$R^{12}$ is selected for each position capable of substitution from the group consisting of hydrogen, halogen, alkoxy, acetylenic, nitro, aryl, alkyl, alkenyl, alkynyl, cyano, acyl, or carbonyl;

$R^{13}$ is hydrogen, alkenyl, alkynyl, aralkyl, nitro, cyano, alkyl, acyl, carbonyl, or $SO_2CH_3$, and may optionally be linked to an $R^{16}$ or an $R^{16'}$ group;

$R^{16}$ and $R^{16'}$ are each independently selected for each position capable of substitution from the group consisting of hydrogen, alkyl, alkenyl, alkynyl, hydroxyl, cyano, aryl, heterocyclic, carbonyl, or acyl, and may optionally be connected through an alkyl chain to $R^{13}$ or another $R^{16}$ or $R^{16'}$ group, to form a fused or spiro ring system;

X is $NR^{17}$, S, O or a covalent bond;

$R^{17}$ is hydrogen, alkyl, or carbonyl;

$R^{14}$ and $R^{15}$ are each independently hydrogen, halogen, or alky;

w is 1, 2, 3, or 4;

e is 0 or 1;

f is 0 or 1, wherein both e and f are not both 0 if X is a covalent bond, and pharmaceutically acceptable salts thereof.

Examples of Ar, Ar', $R^{11}$, $R^{12}$, $R^{14}$, $R^{15}$, $R^{16}$ and $R^{16'}$ and X moieties include those described for formula (X).

The invention also pertains to the following compounds:

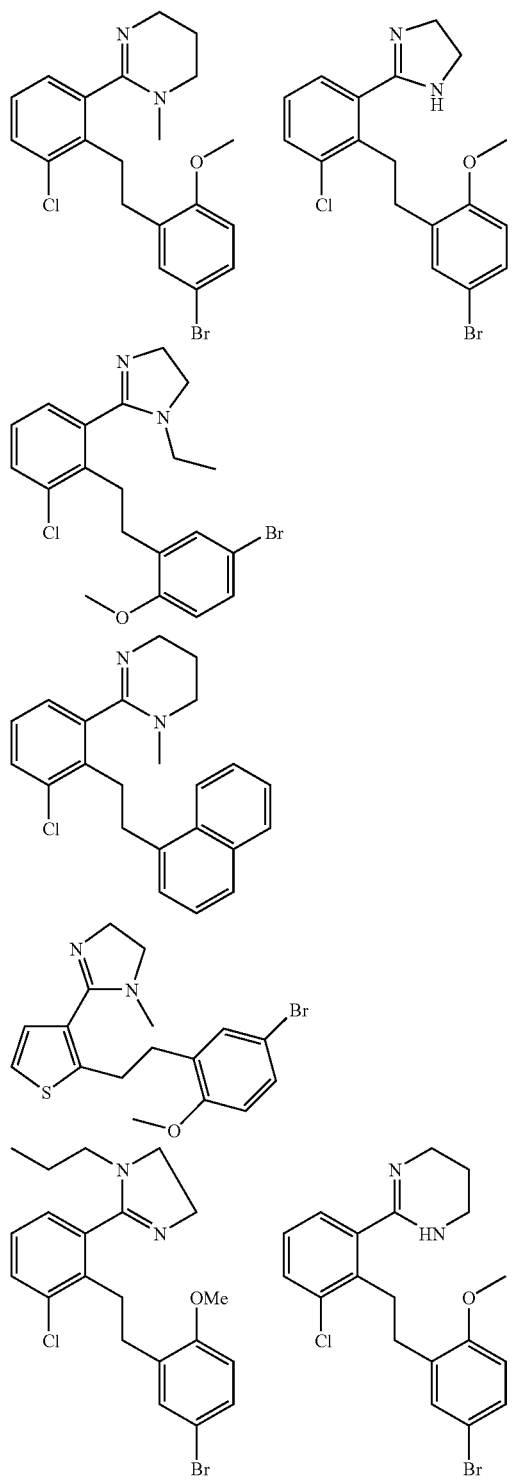

Other examples of MC4-R binding compounds include compounds of the formulae:

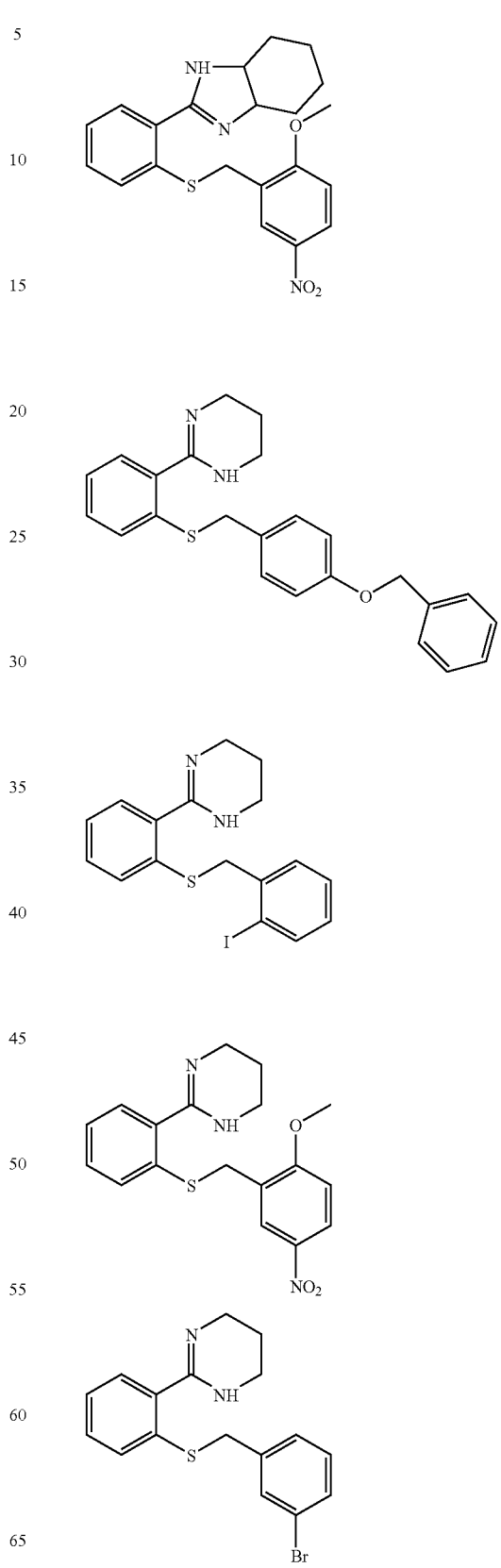

The invention also pertains to methods of using these compounds in methods for treating MC4-R associated states in a mammal by administering an effective amount of the compound to a mammal, such that the MC4-R associated state is treated, as well as pharmaceutical compositions comprising these compounds.

-continued
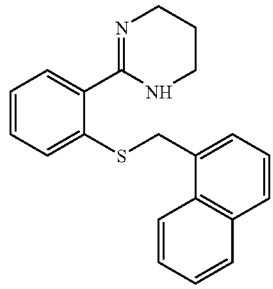
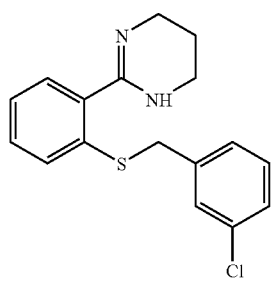
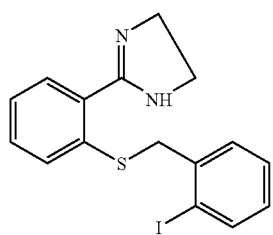
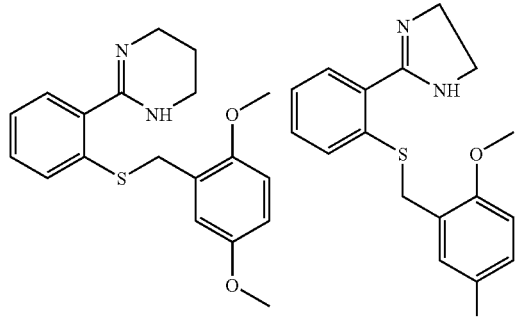
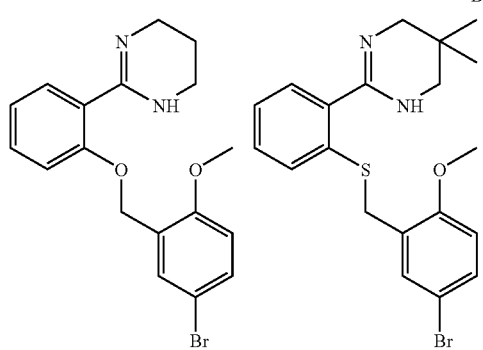
-continued
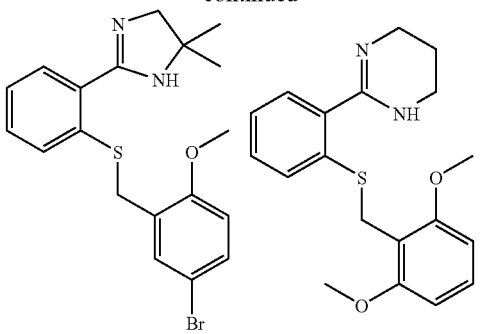
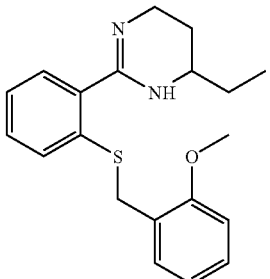
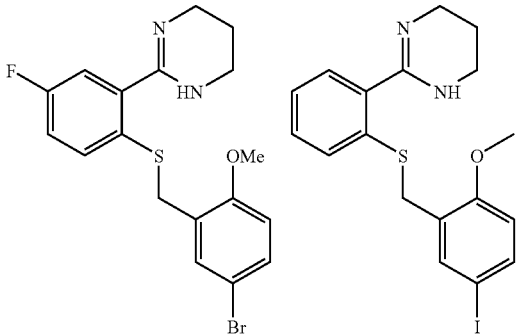
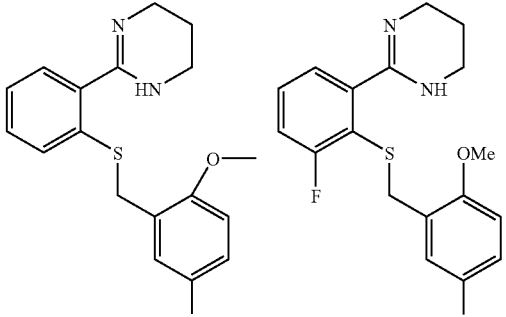
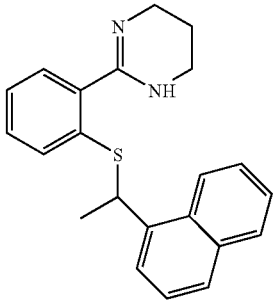

-continued
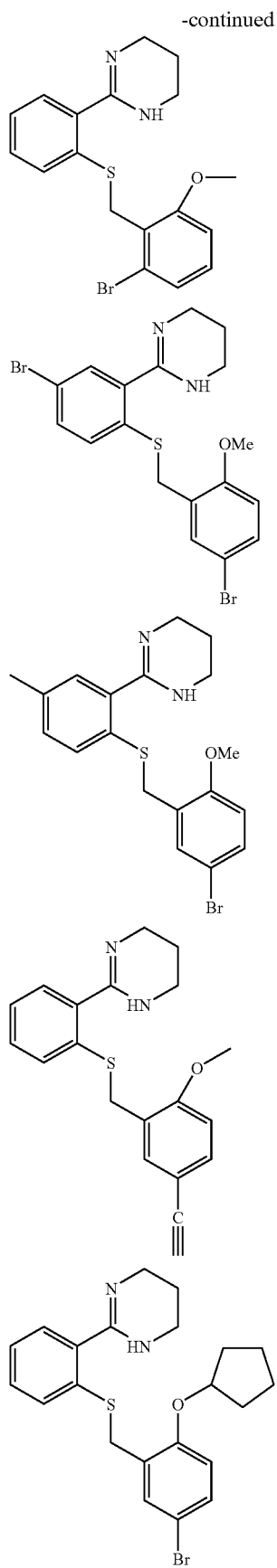
-continued
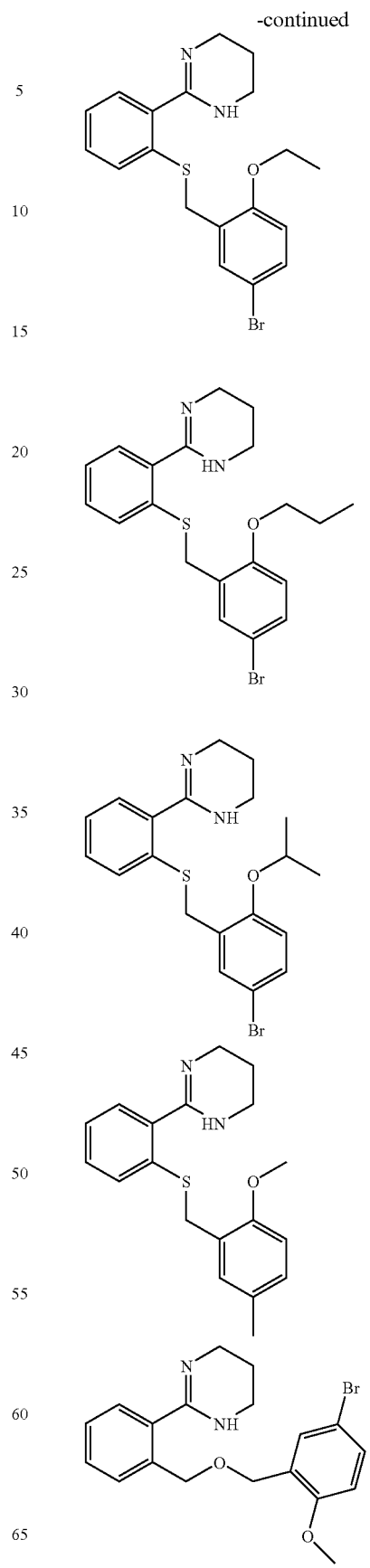

-continued
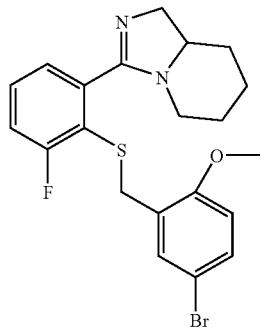
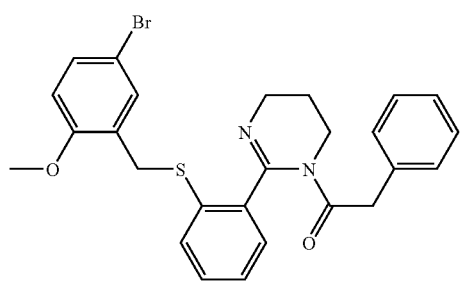
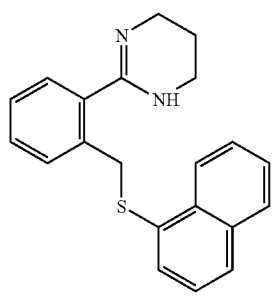
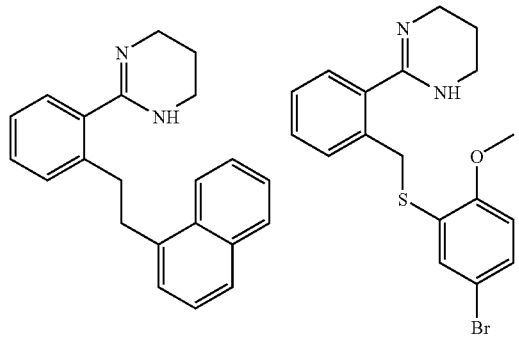
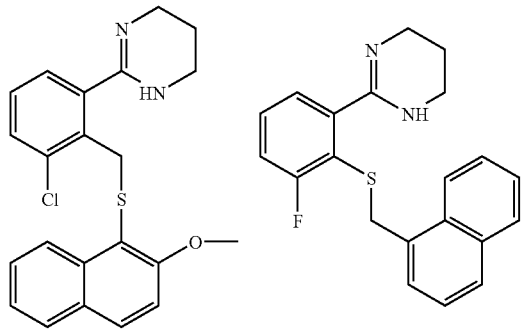
-continued
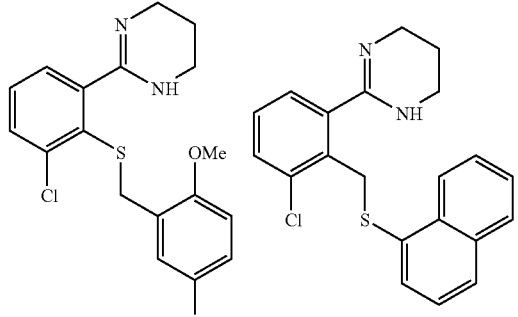
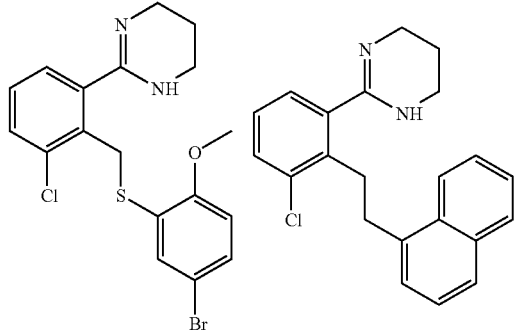
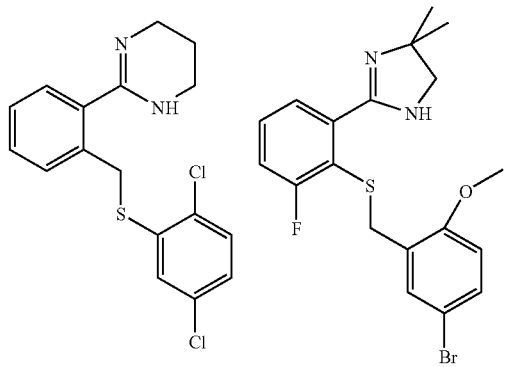
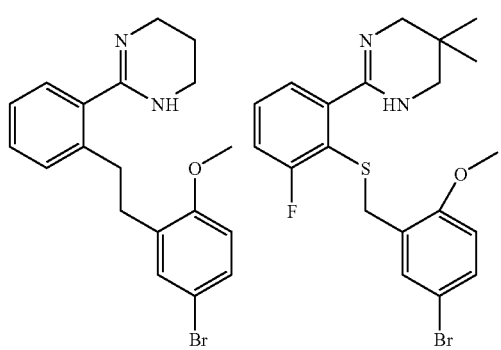

-continued
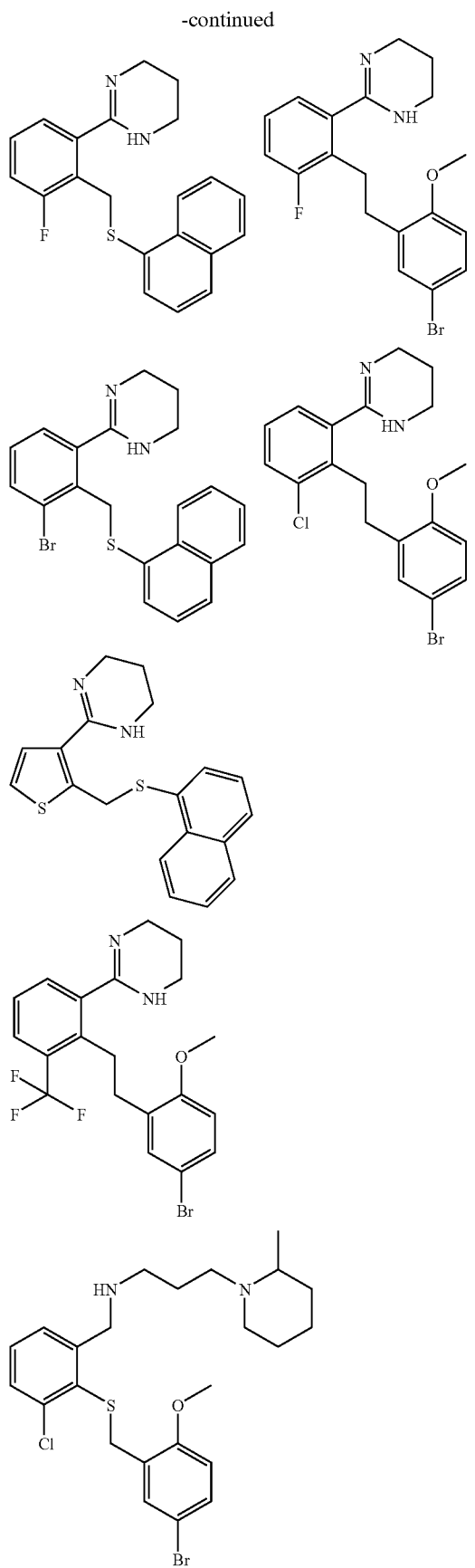
-continued
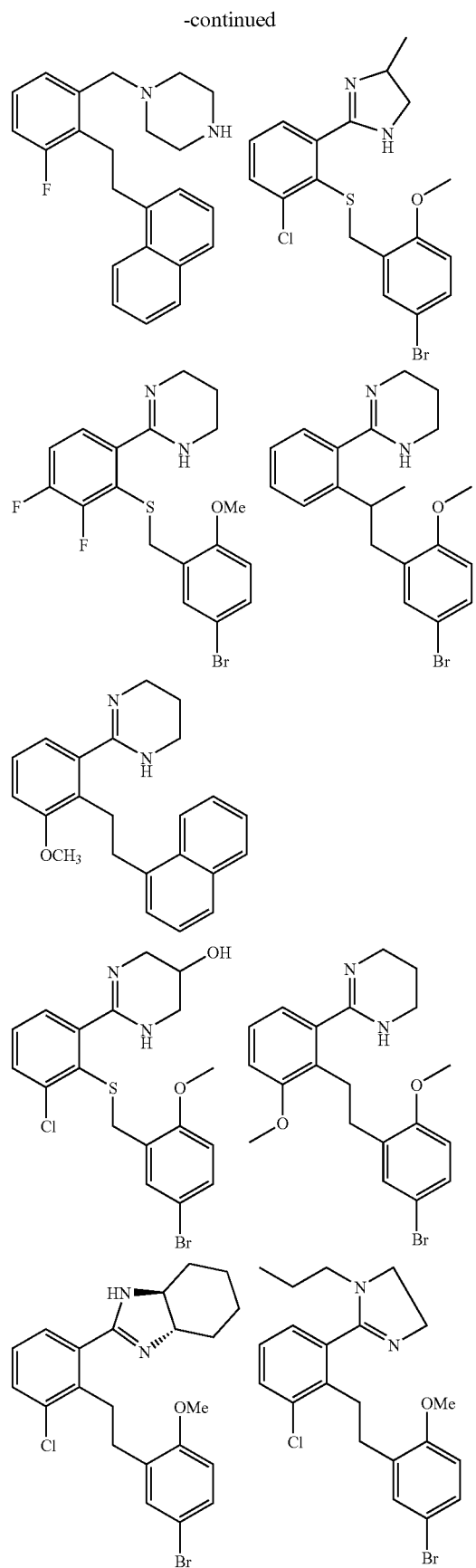

-continued
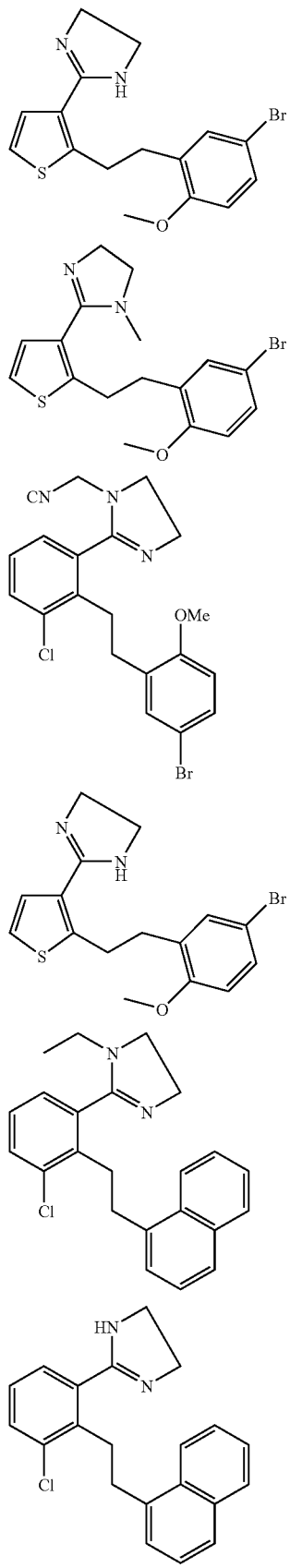
-continued
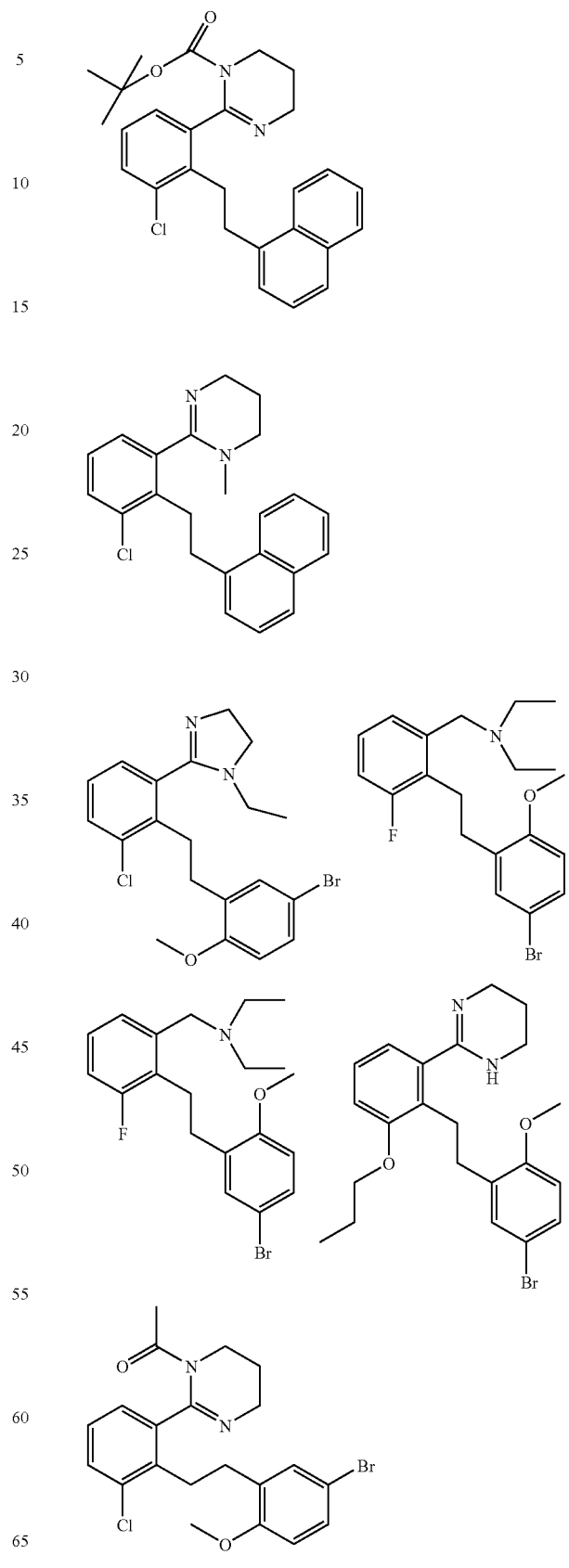

-continued
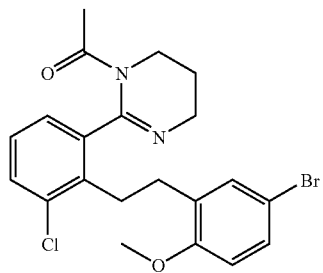
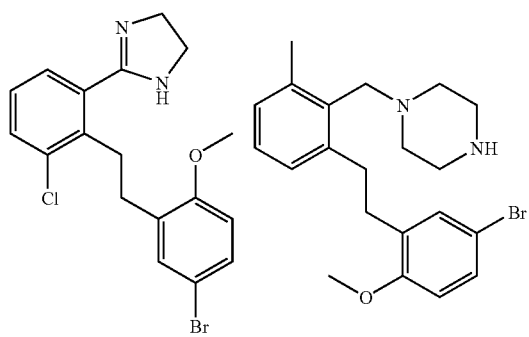
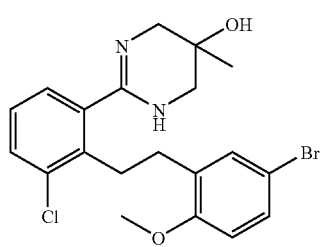
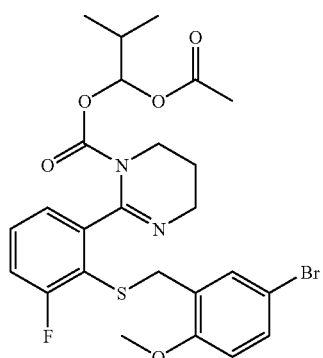
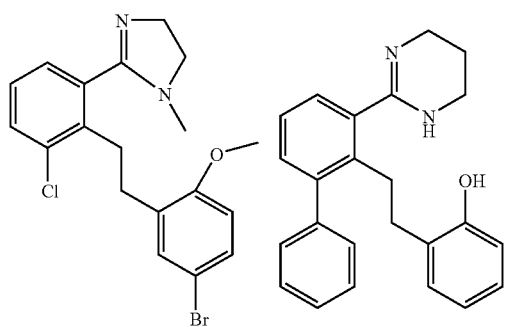
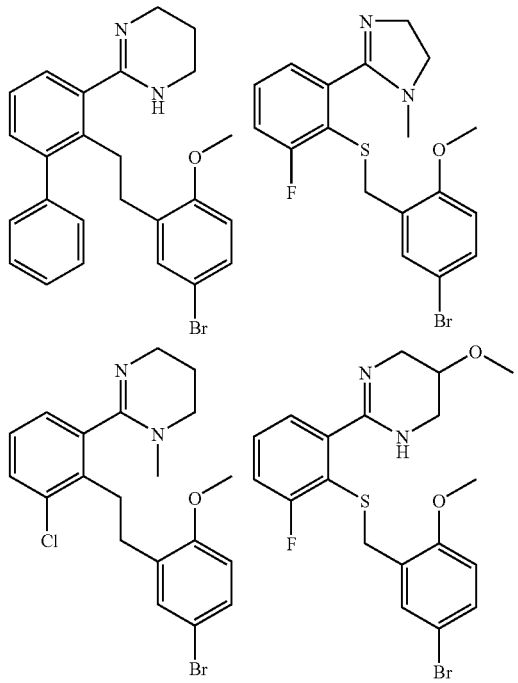
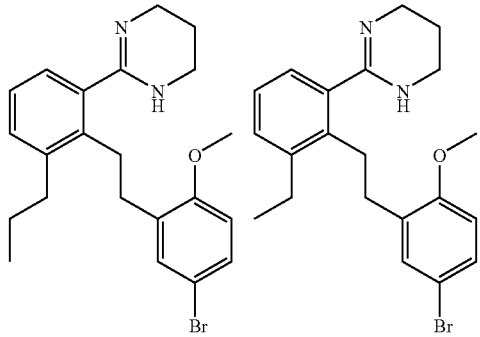
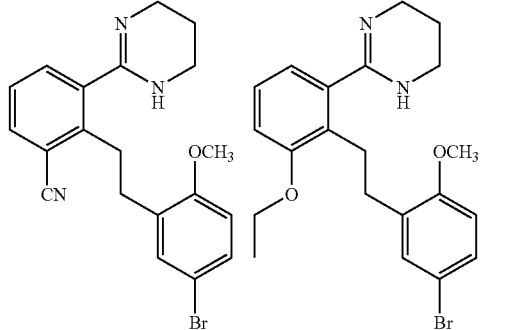
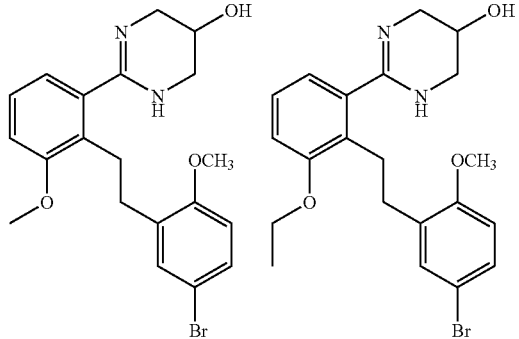

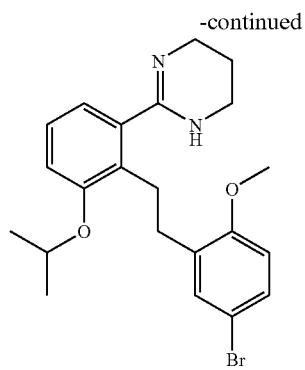
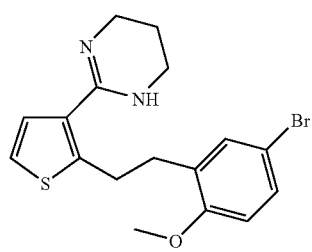
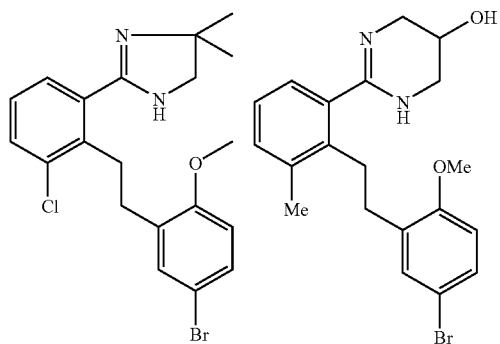
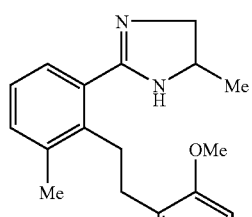
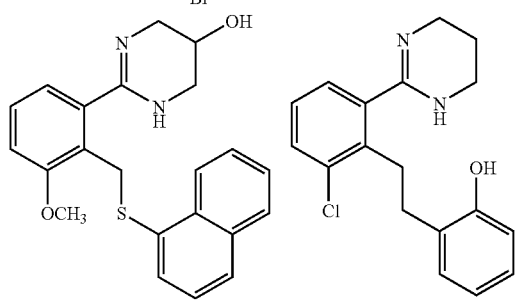
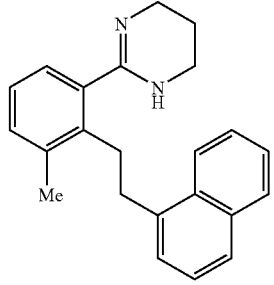
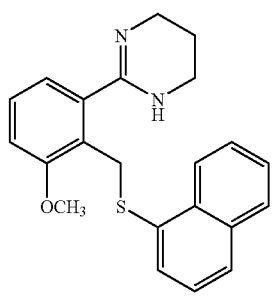
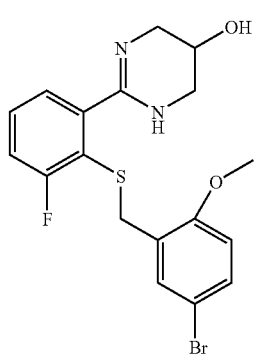
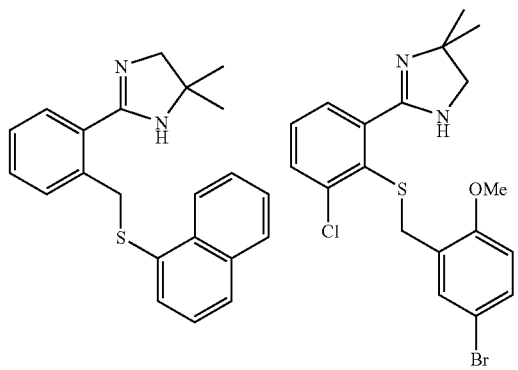

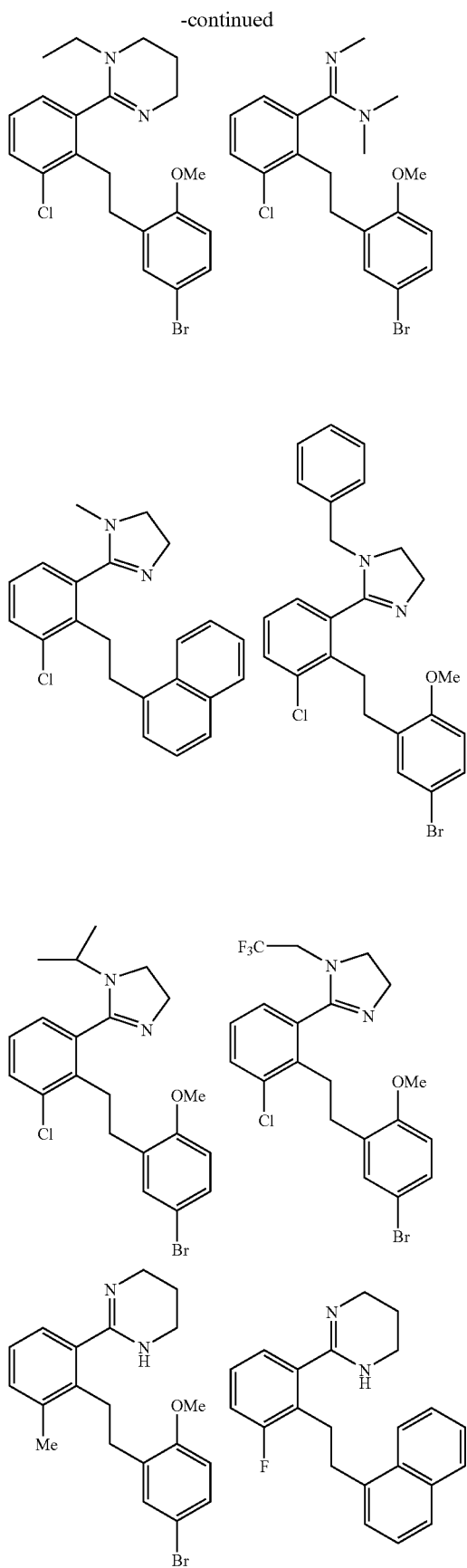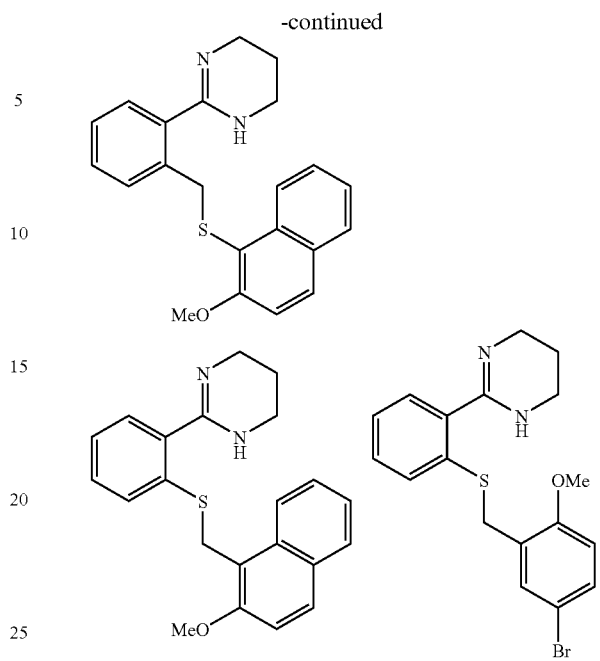
and pharmaceutically acceptable salts thereof.
Still further examples of MC4-R binding compounds include compounds of the formulae:
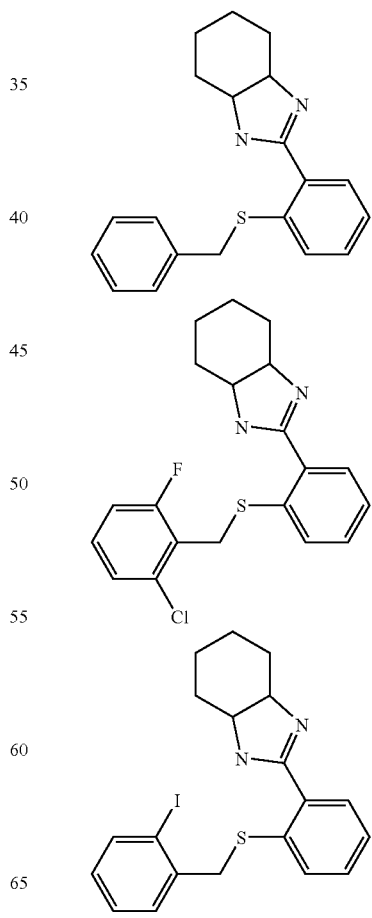

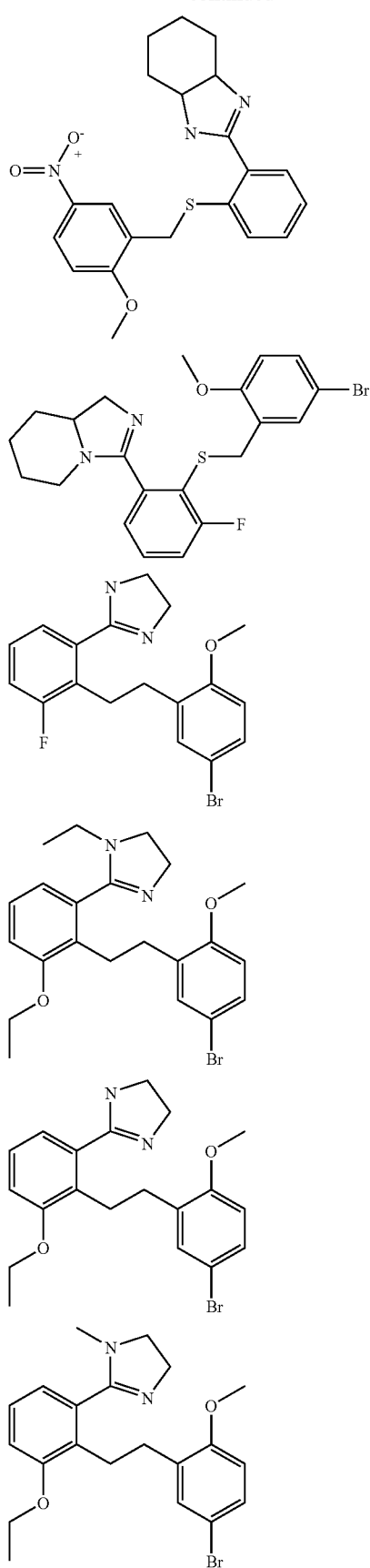
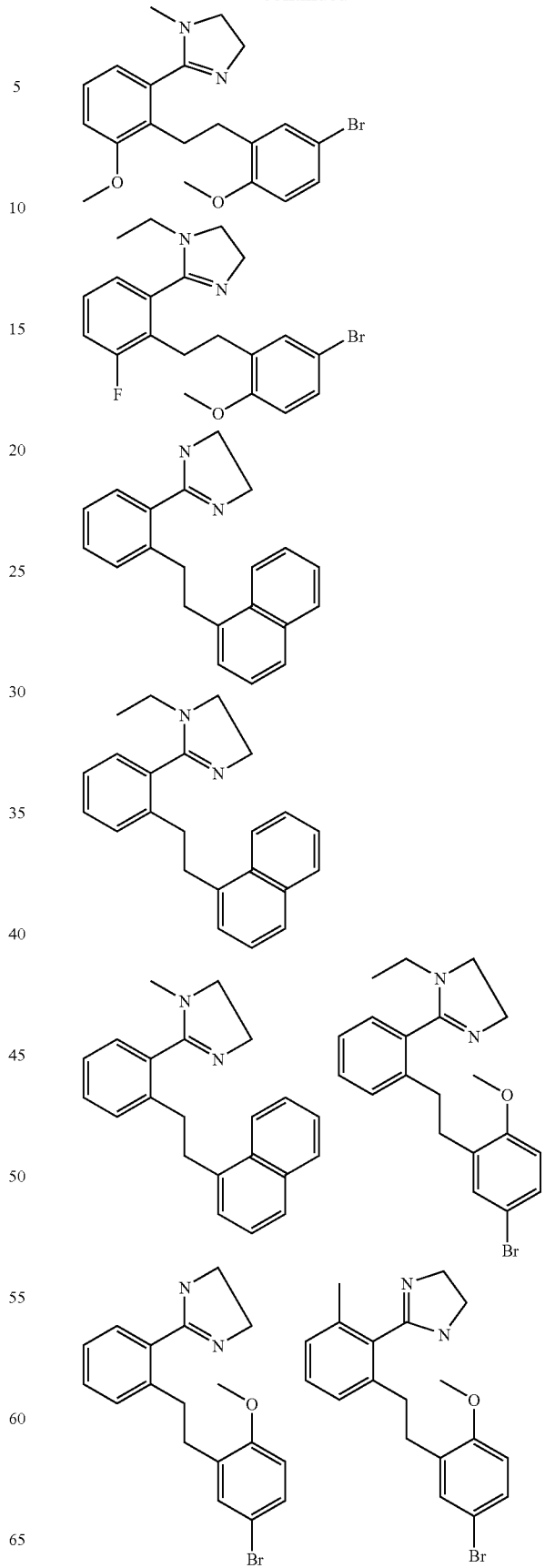

-continued
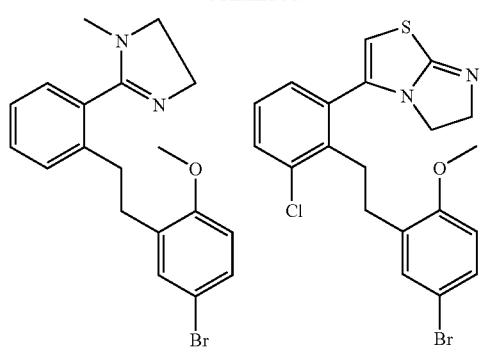
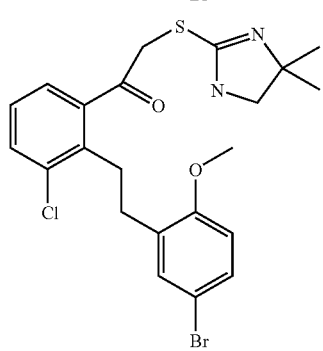
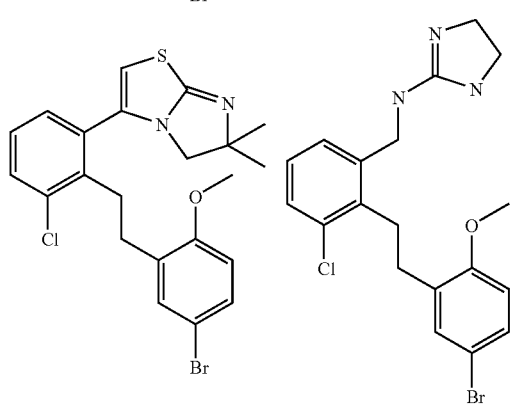
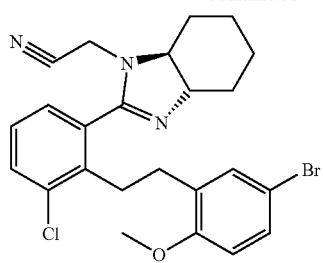
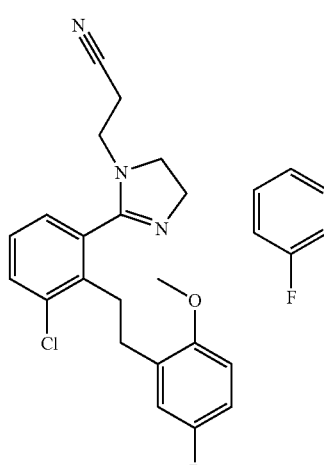
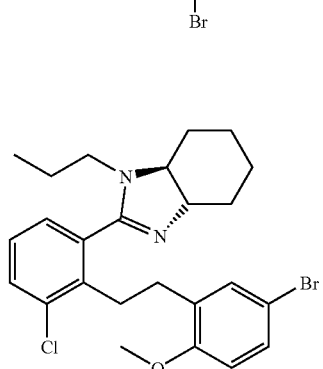
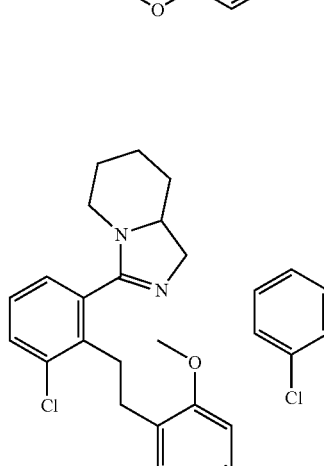

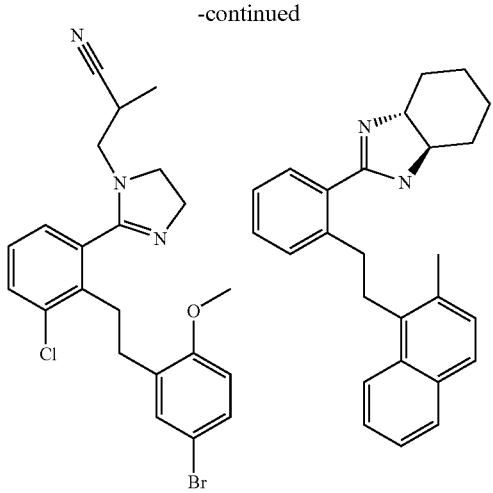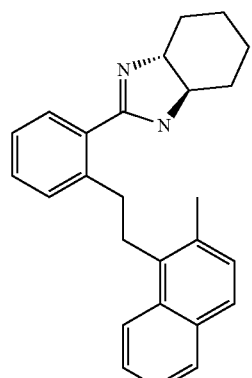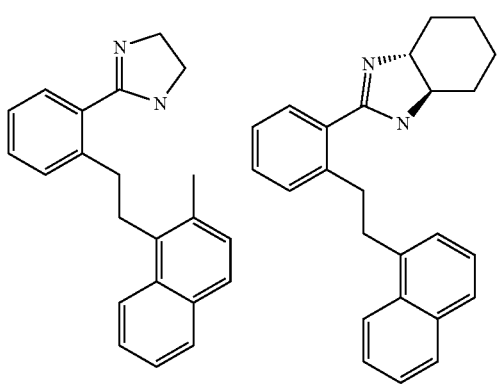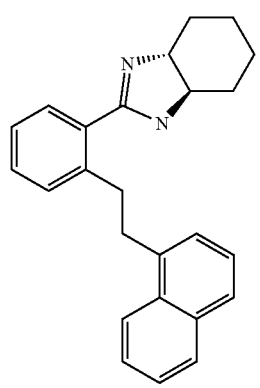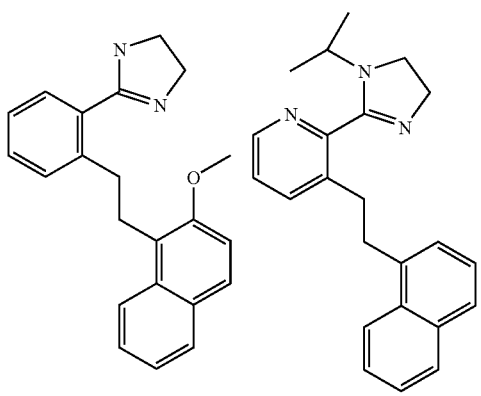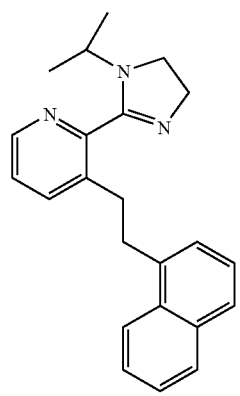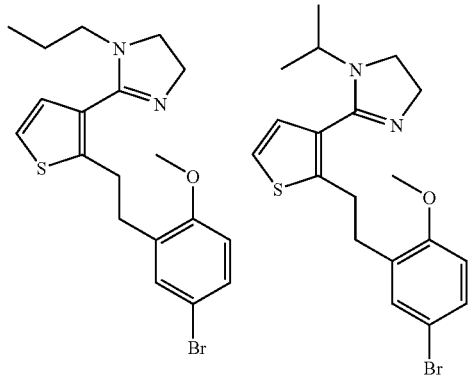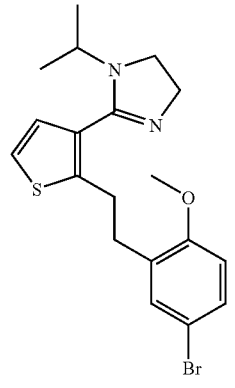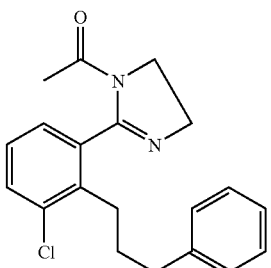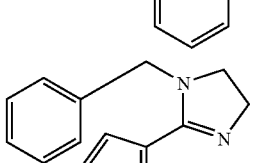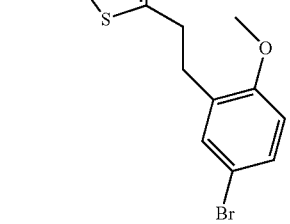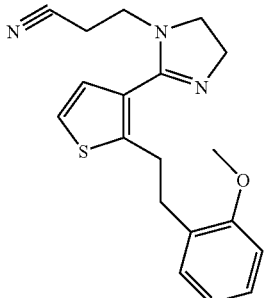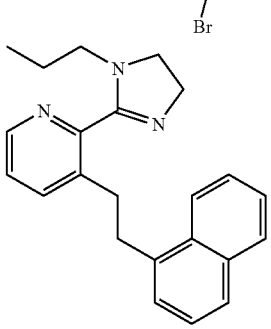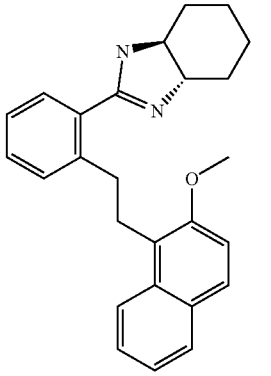

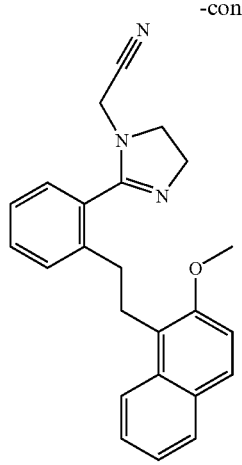
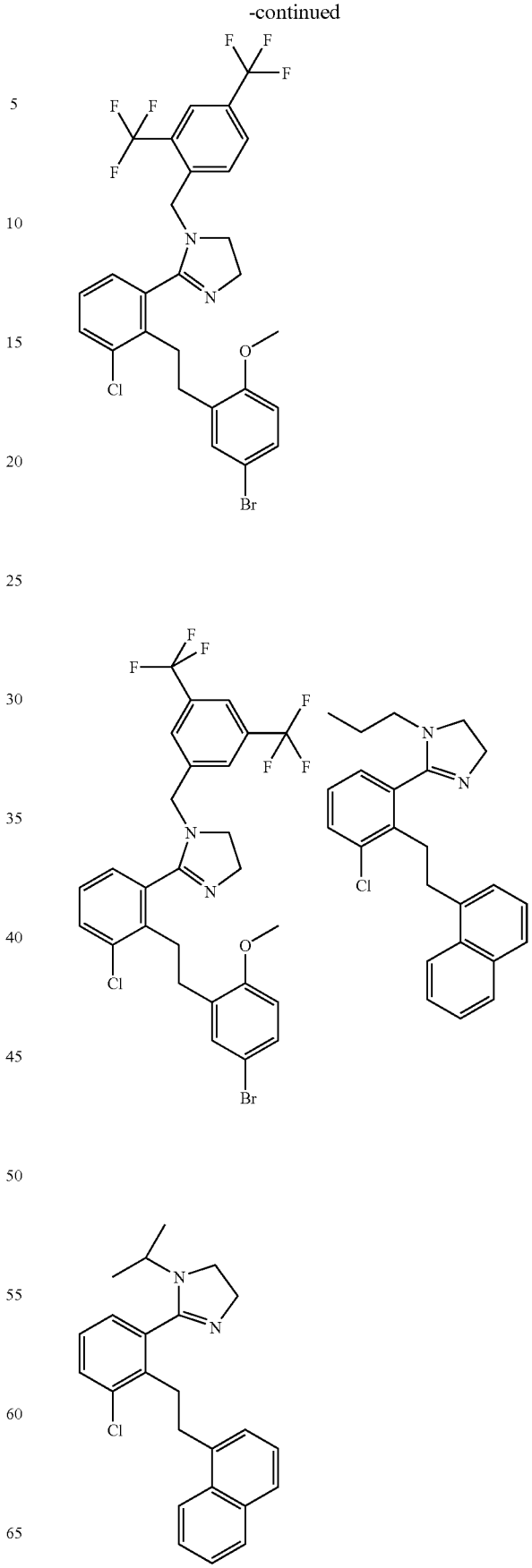

69
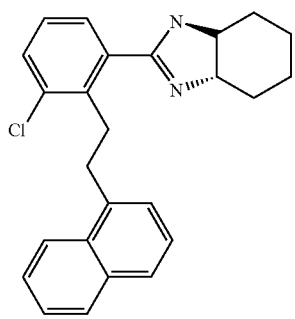
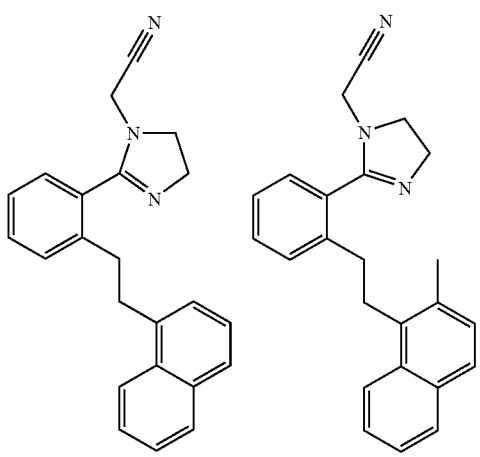
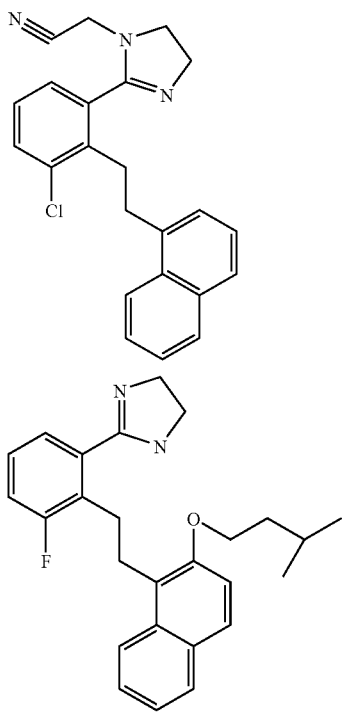
70
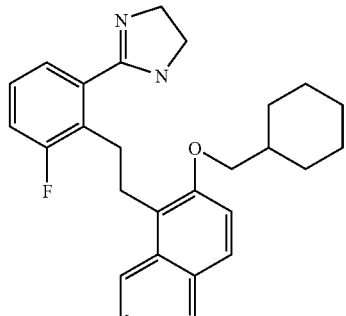
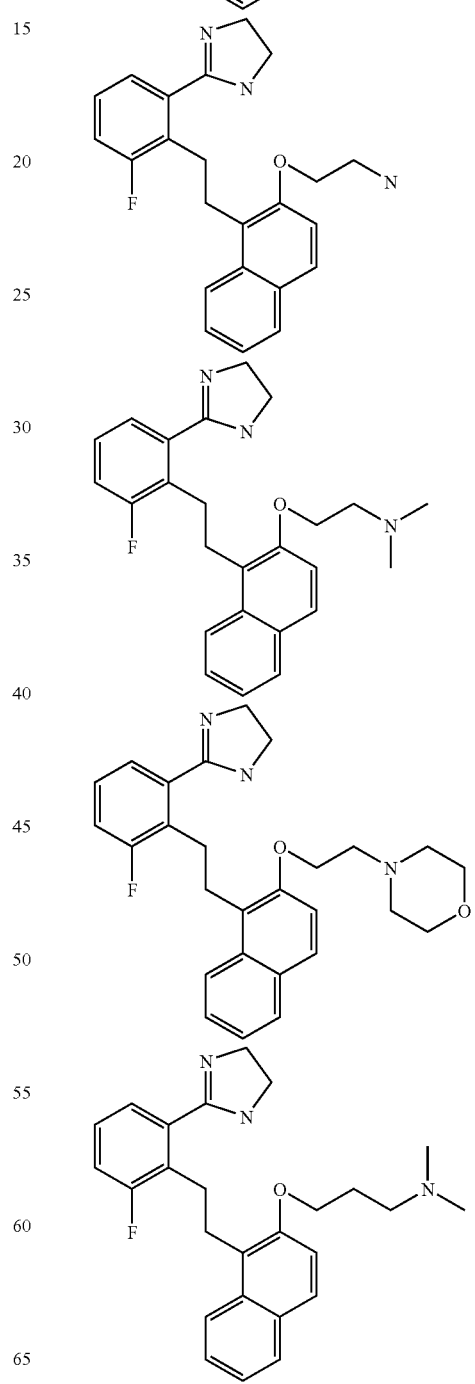

-continued
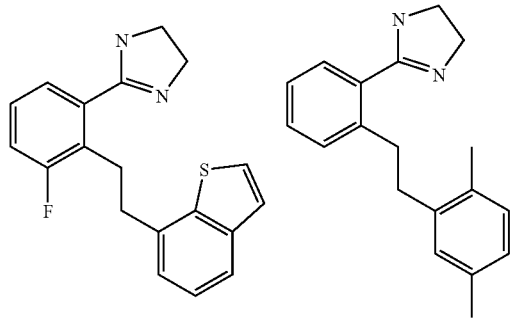
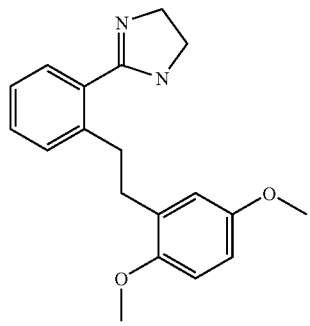
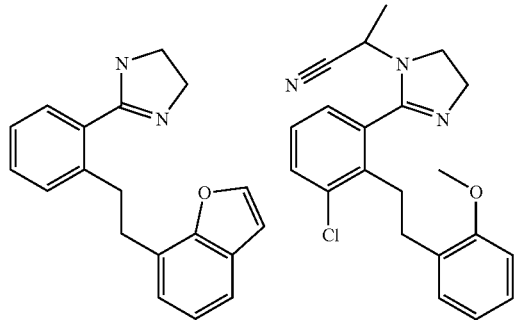
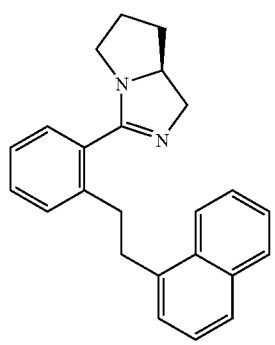
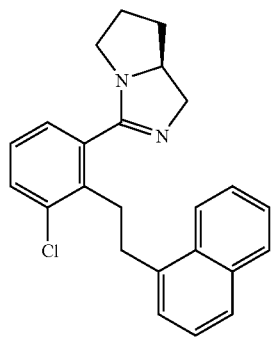
-continued
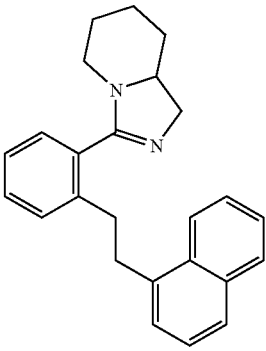
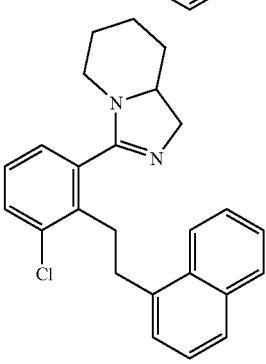
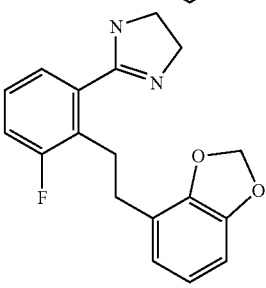
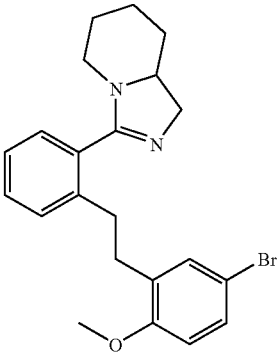
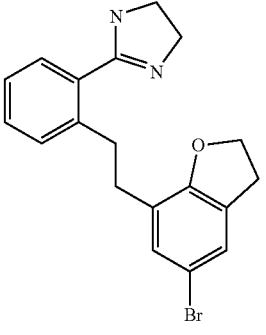
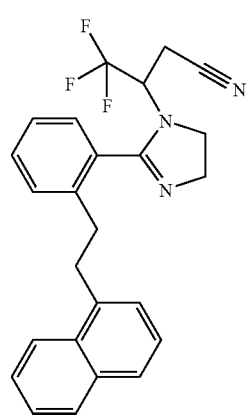

73
-continued
74
-continued
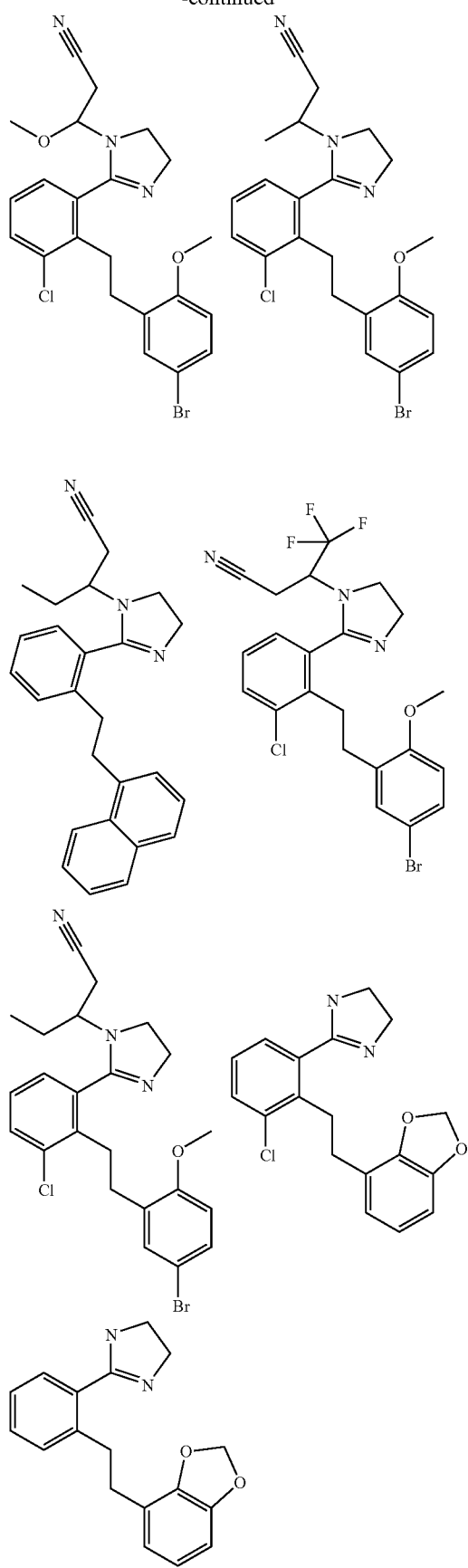
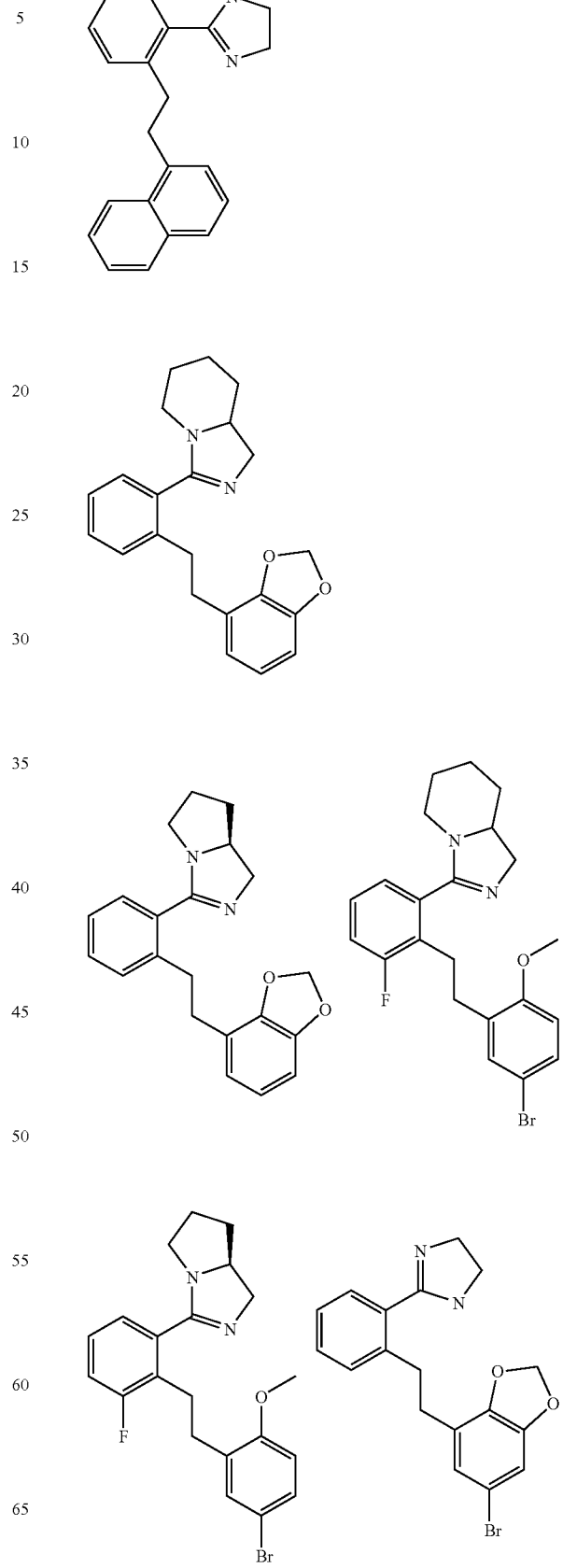

75
-continued
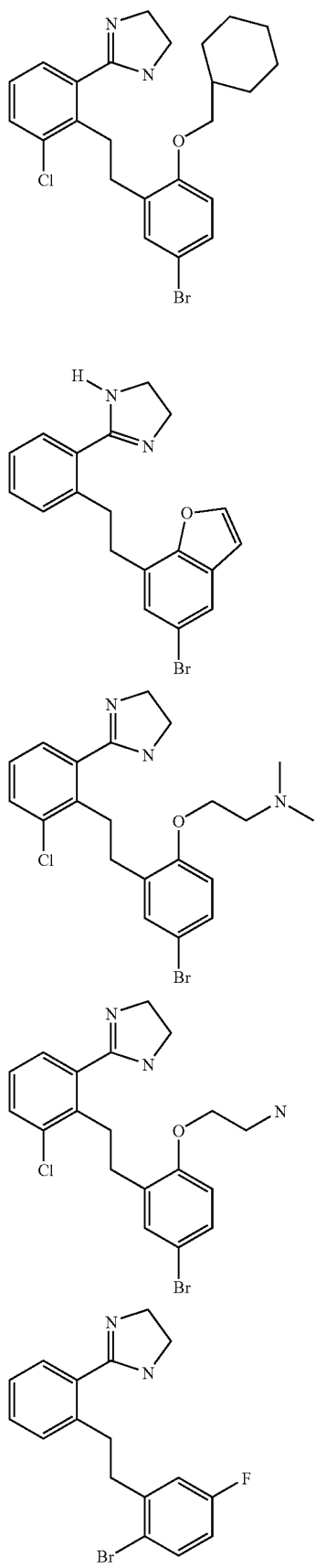
76
-continued
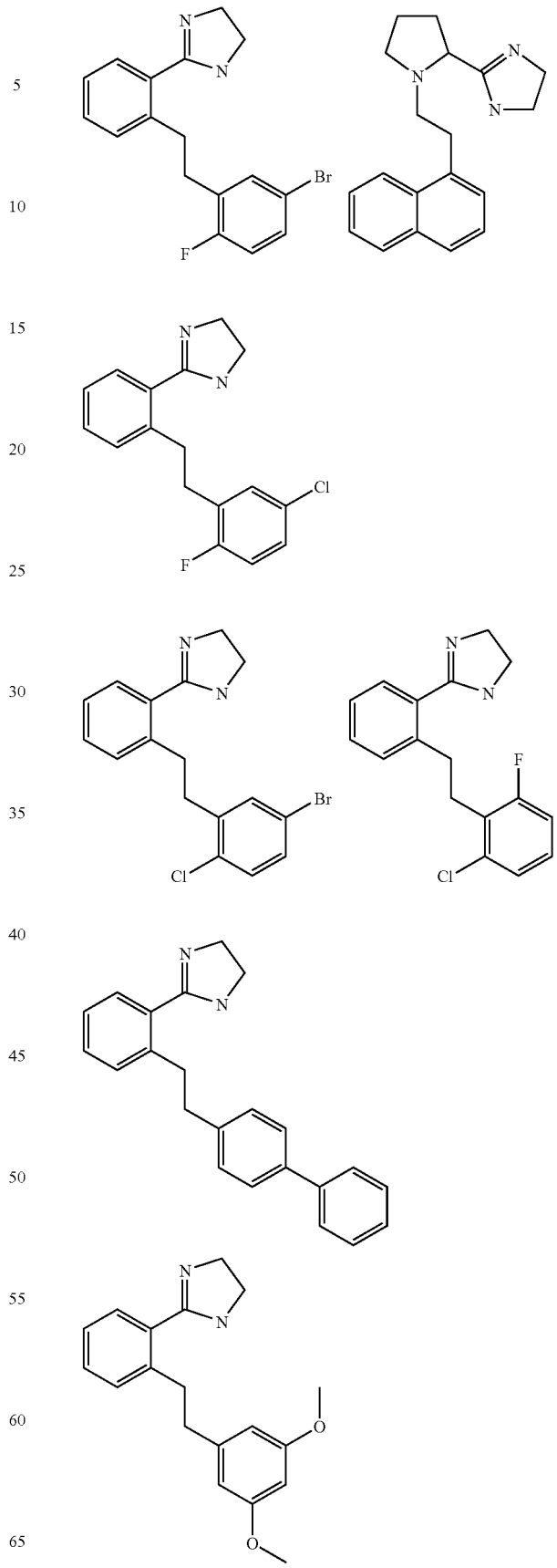

77
-continued
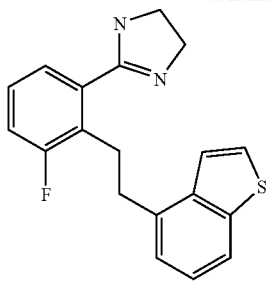
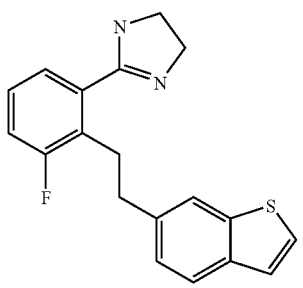
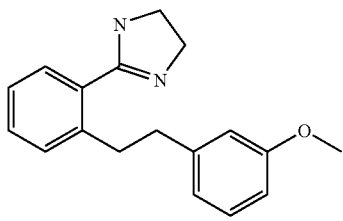
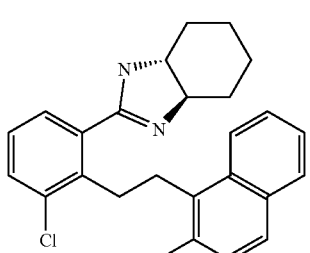
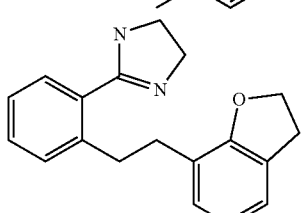
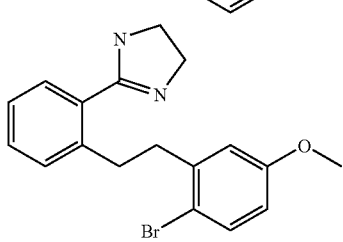
78
-continued
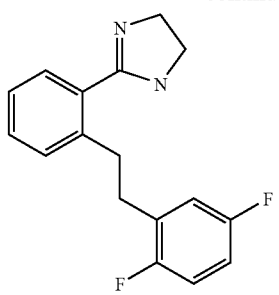
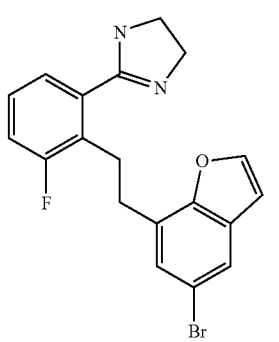
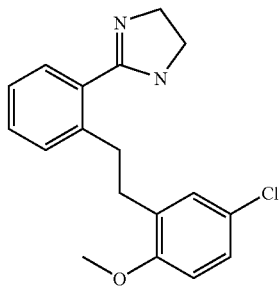
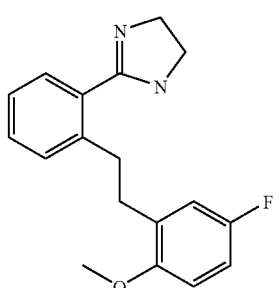
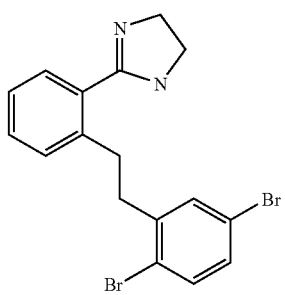

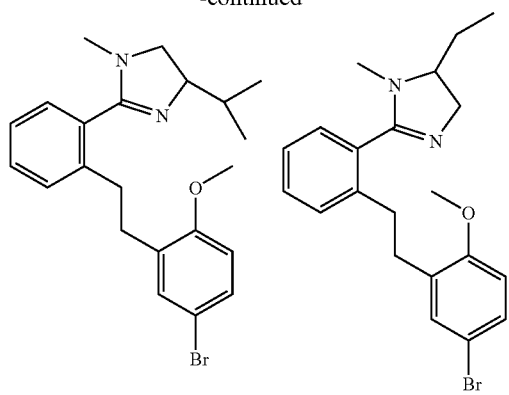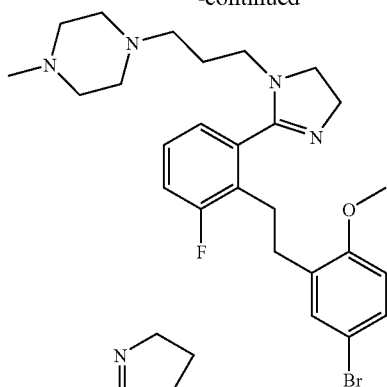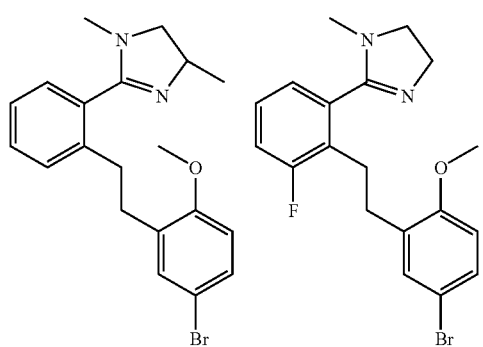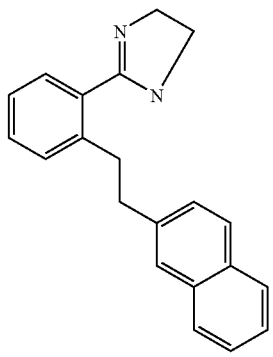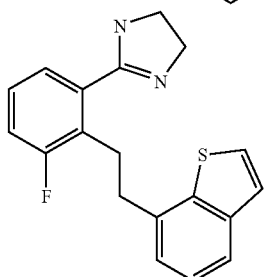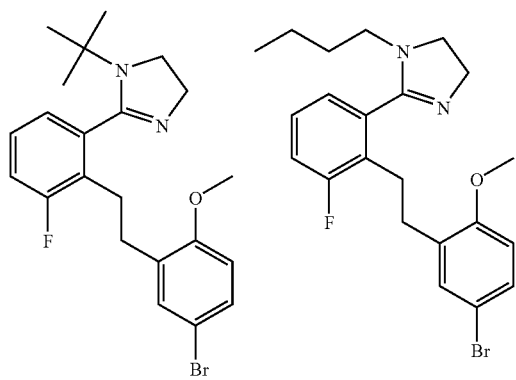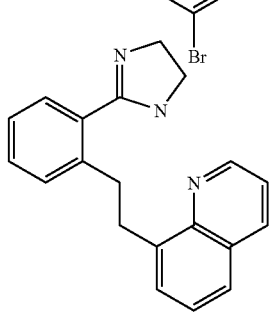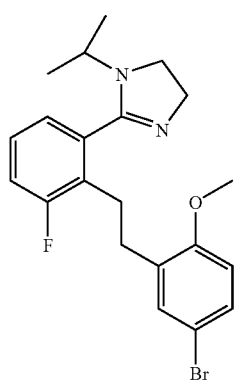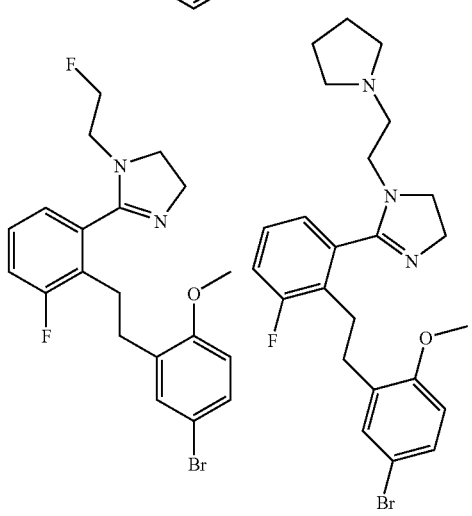

-continued
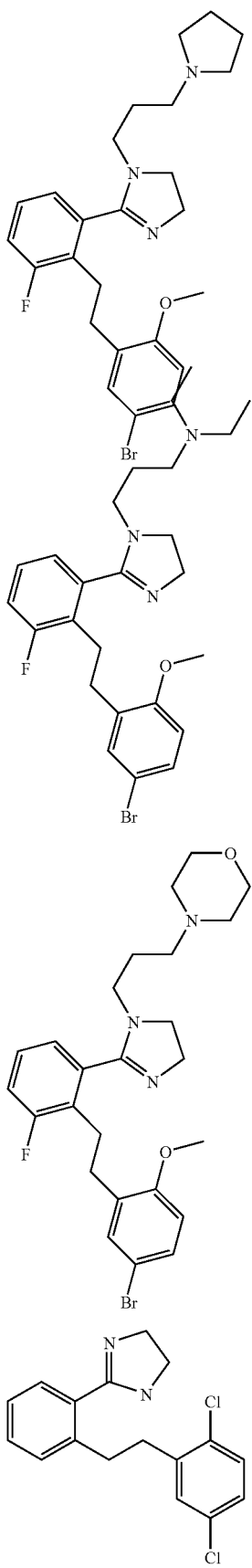
-continued
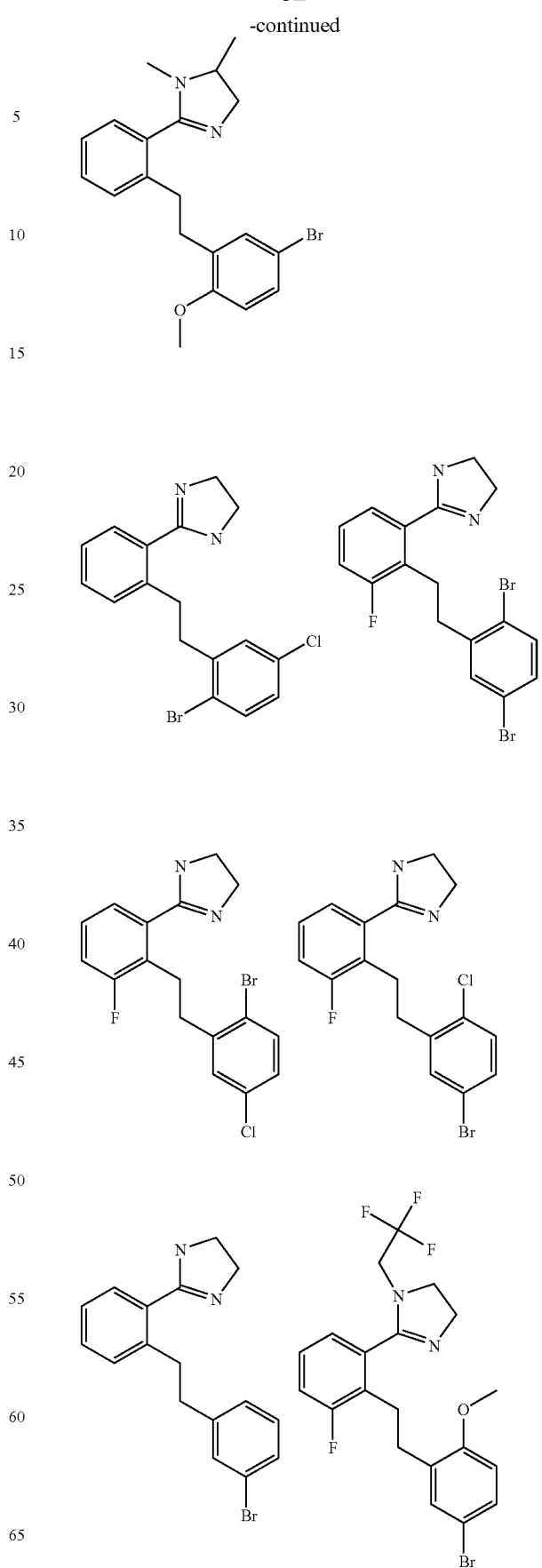

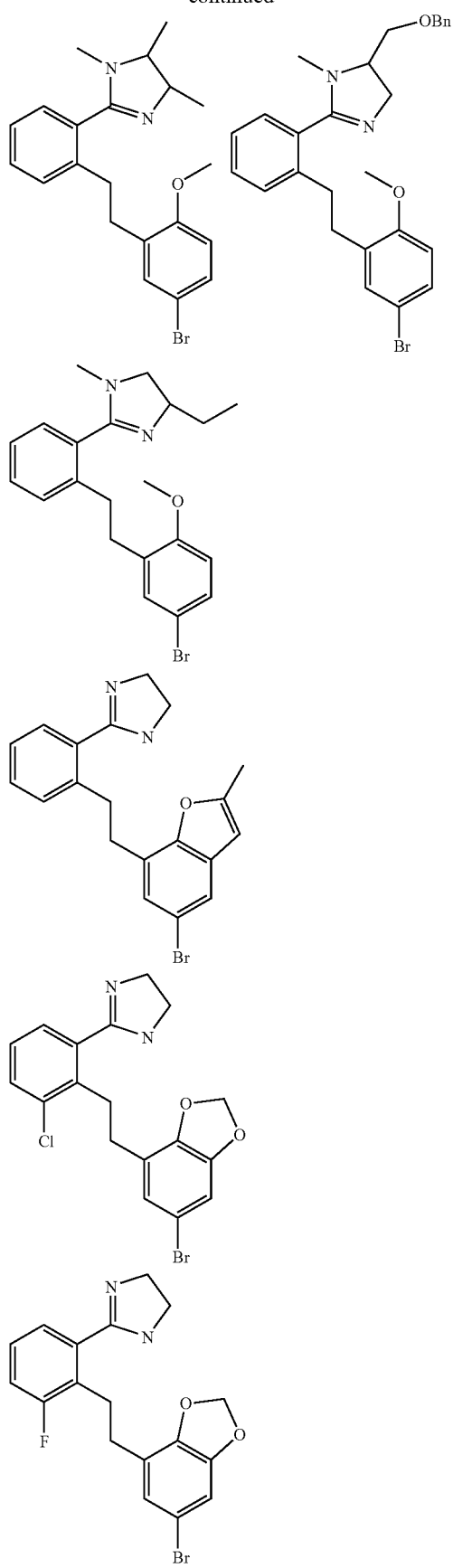
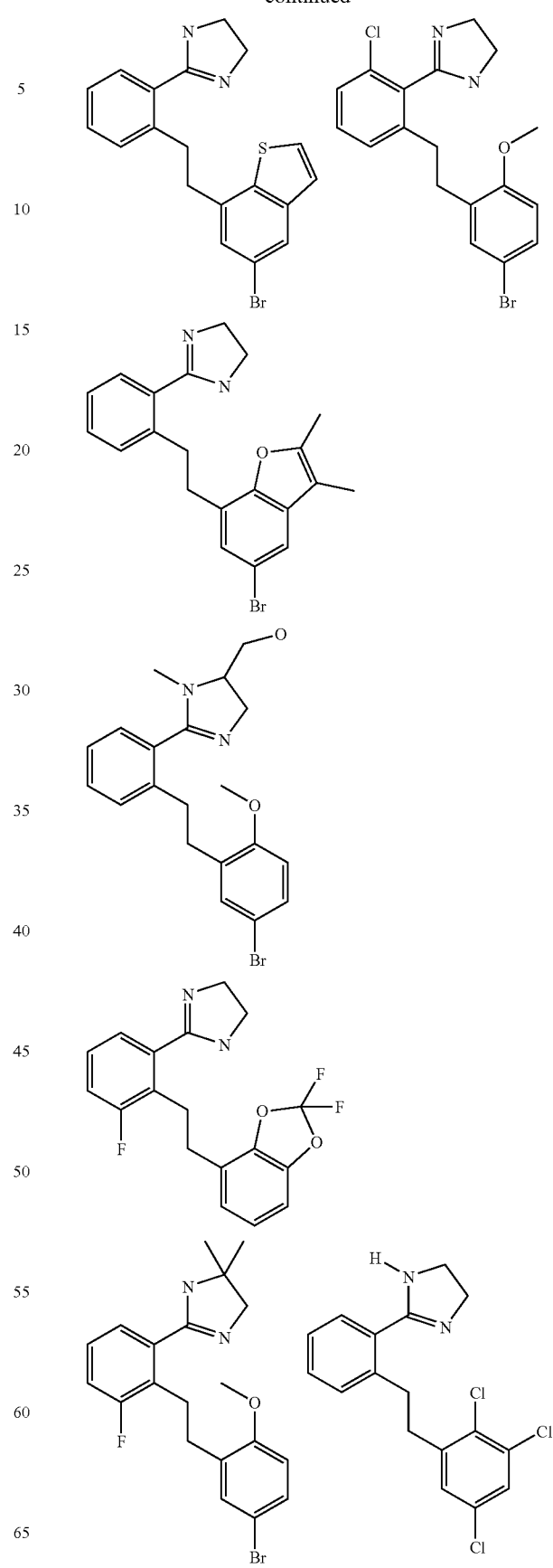

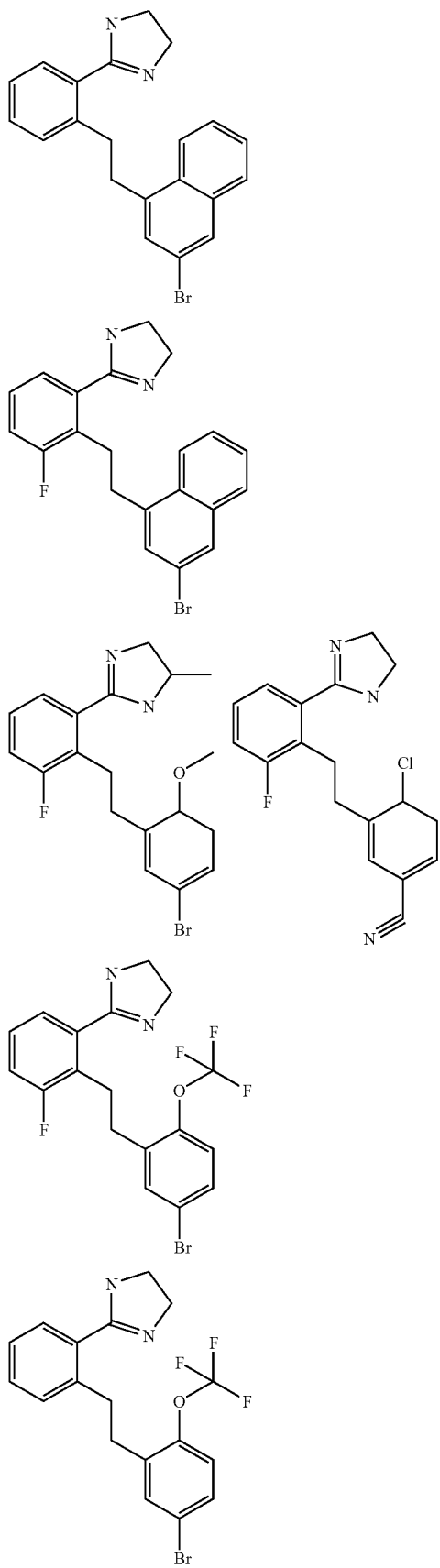
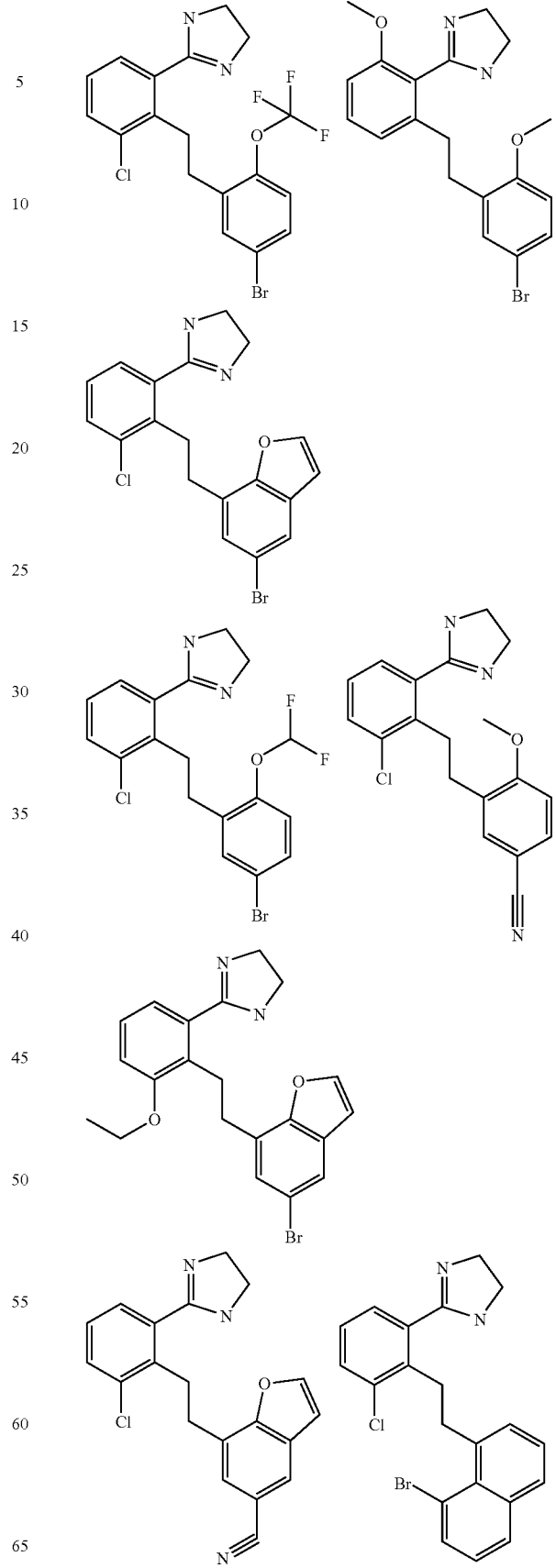

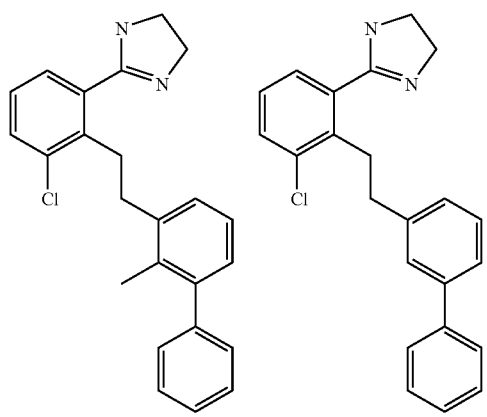
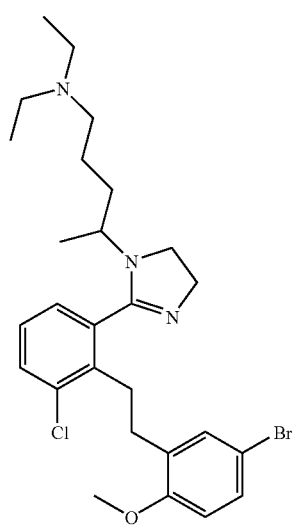
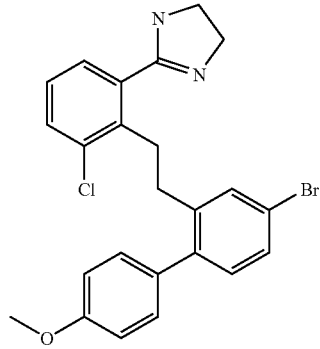
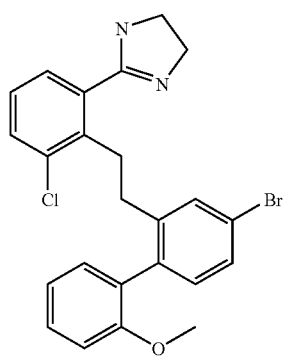
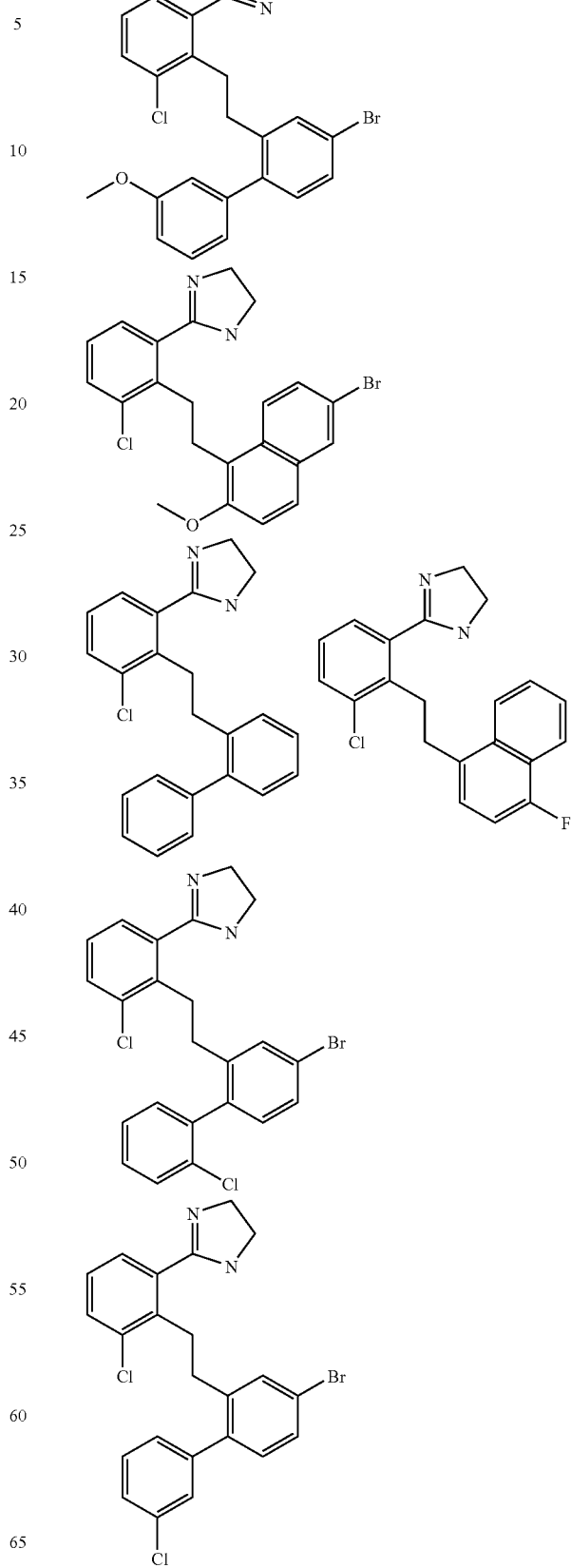

89
-continued
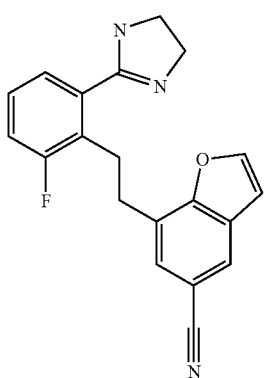
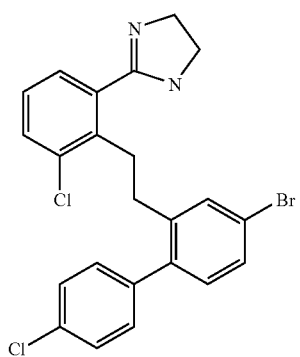
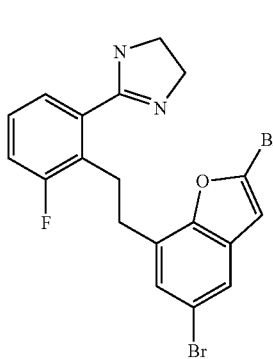
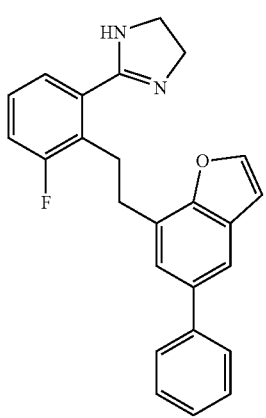
90
-continued
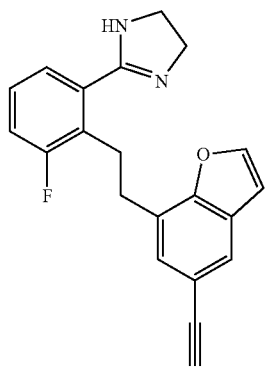
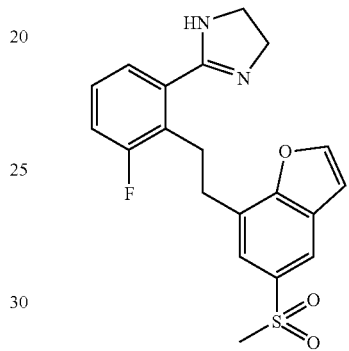
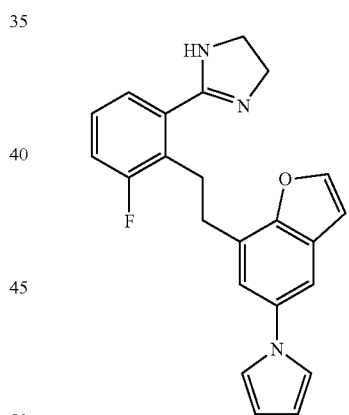
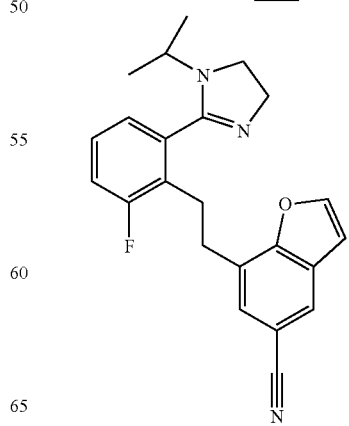

91
-continued
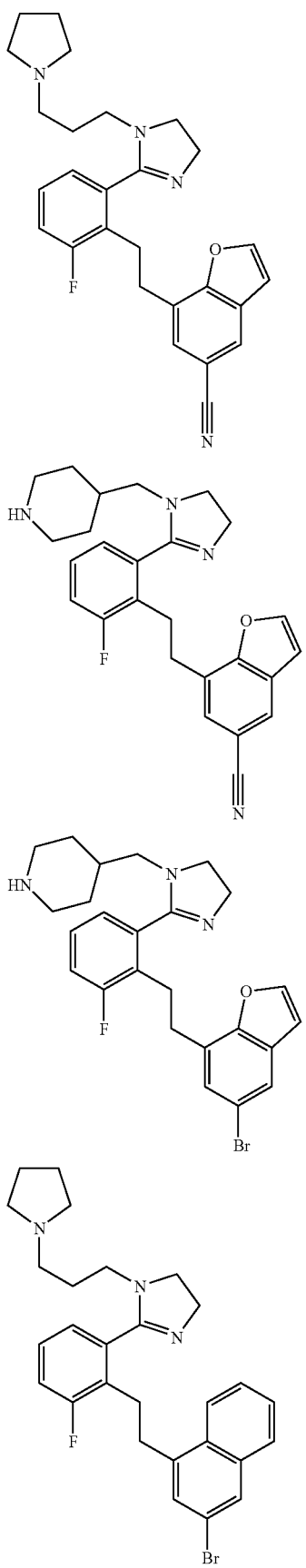
92
-continued
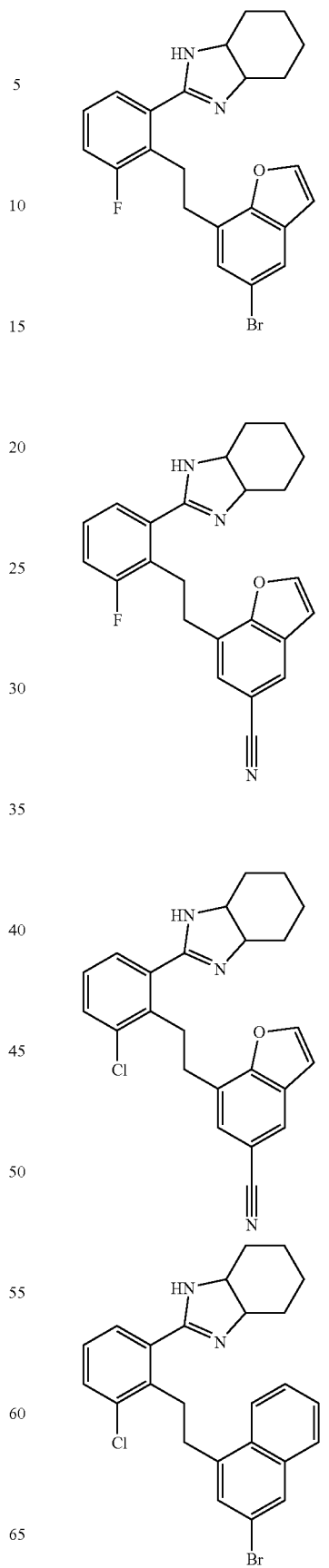

93
-continued
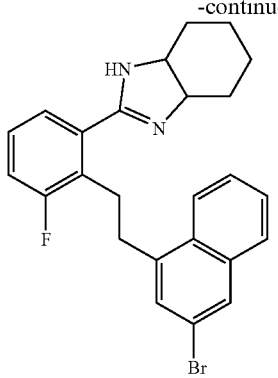
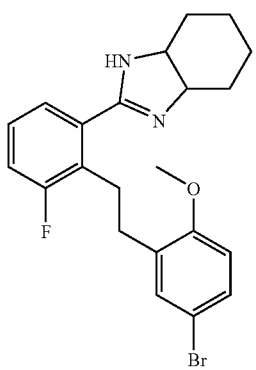
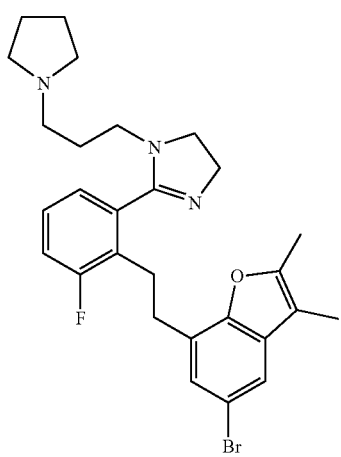
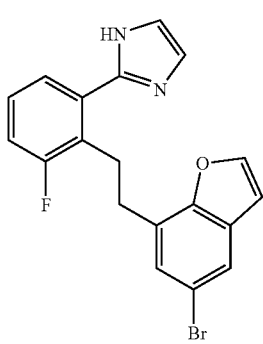
94
-continued
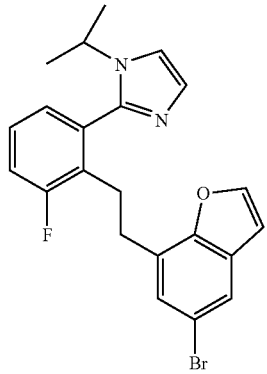
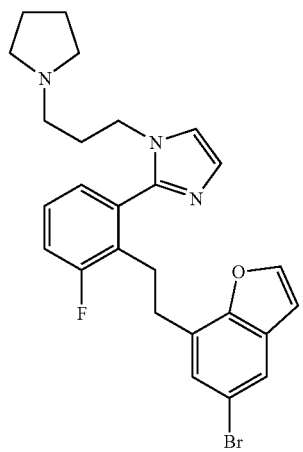
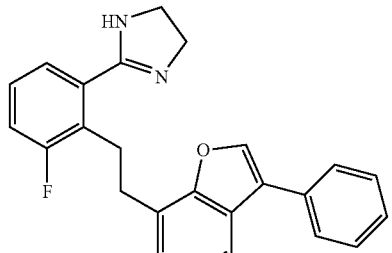
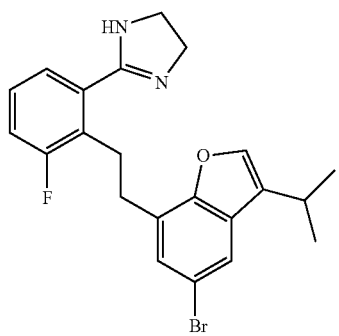

95
-continued
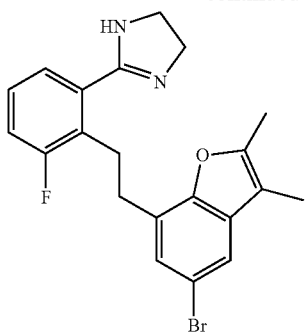
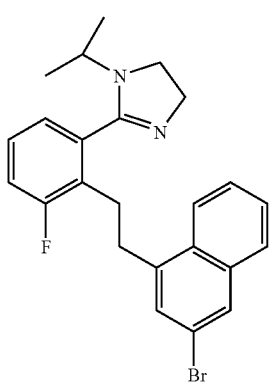
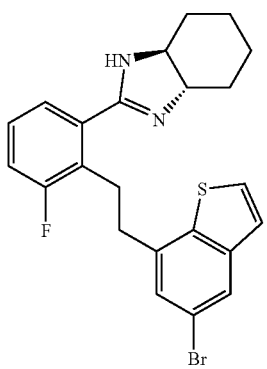
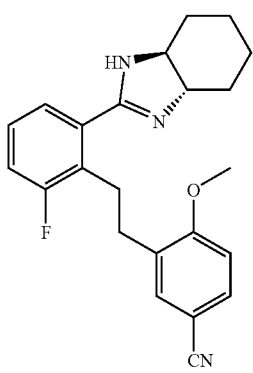
96
-continued
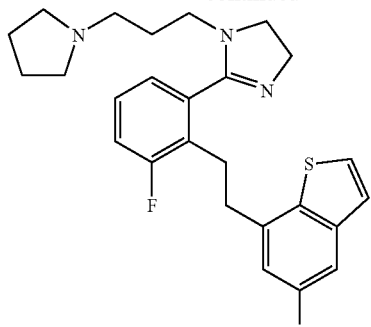
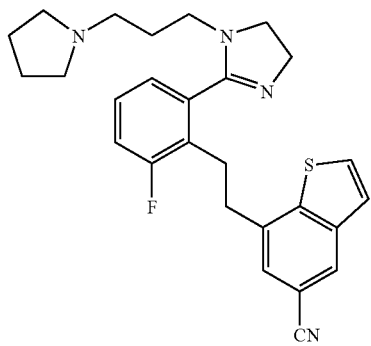
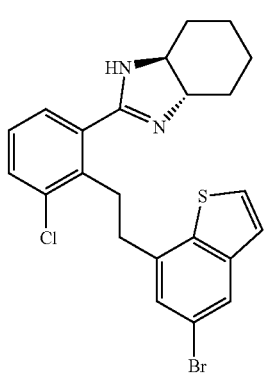
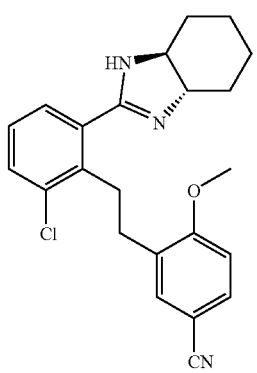

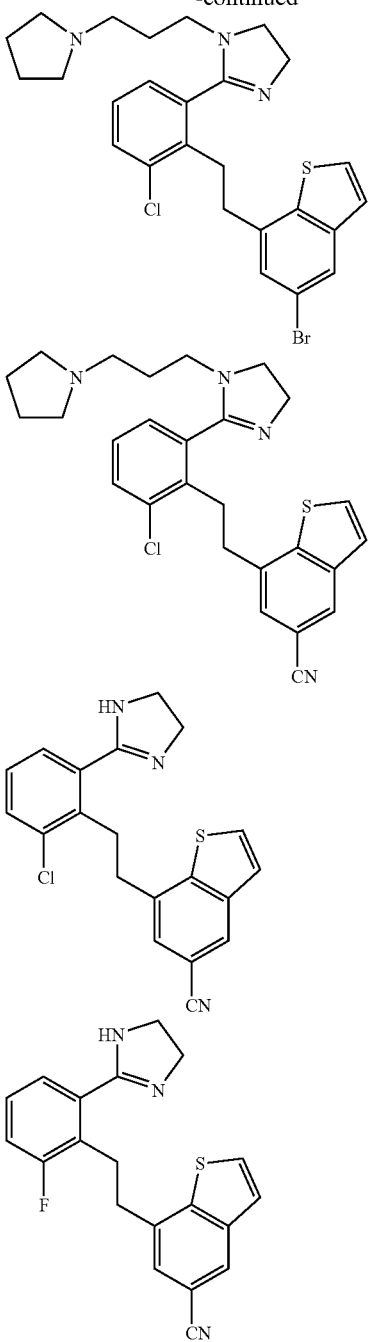

and pharmaceutically acceptable salts thereof.

The invention also includes MC4-R binding compounds such as:

2-[2-(4-benzyloxy-benzylsulfanyl)-phenyl]-1,4,5,6-tetrahydro-pyrimidine;
2-[2-(2-iodo-benzylsulfanyl)-phenyl]-1,4,5,6-tetrahydropyrimidine;
2-[2-(2-methoxy-5-nitro-benzylsulfanyl)-phenyl]-1,4,5,6-tetrahydro-pyrimidine;
2-[2-(naphthalen-1-ylmethylsulfanyl)-phenyl]-1,4,5,6-tetrahydro-pyrimidine;
2-[2-(3-chloro-benzylsulfanyl)-phenyl]-1,4,5,6-tetrahydro-pyrimidine;
2-[2-(2,5-dimethoxy-benzylsulfanyl)-phenyl]-1,4,5,6-tetrahydro-pyrimidine;
2-[2-(3-bromo-benzylsulfanyl)-phenyl]-1,4,5,6-tetrahydro-pyrimidine;
2-[2-(2-iodo-benzylsulfanyl)-phenyl]-4,5-dihydro-1H-imidazole;
2-[2-(2-methoxy-5-nitro-benzylsulfanyl)-phenyl]-4,5-dihydro-1H-imidazole;
2-[2-(2-methoxy-5-nitro-benzyloxy)-phenyl]-1,4,5,6-tetrahydropyrimidine;
2-[2-(2-bromo-benzylsulfanyl)-phenyl]-1,4,5,6-tetrahydro-pyrimidine;
2-[2-(3-iodo-benzylsulfanyl)-phenyl]-1,4,5,6-tetrahydro-pyrimidine;
2-[2-(2-methoxy-5-nitro-benzylsulfanyl)-phenyl]-3a,4,5,6,7,7a-hexahydro-1H-benzoimidazole;
2-{2-[2-(2-methoxy-naphthalen-1-yl)-ethyl]-phenyl}-1,4,5,6-tetrahydropyrimidine;
2-[2-(5-bromo-2-methoxy-benzylsulfanyl)-phenyl]-1,4,5,6,-tetrahydropyrimidine;
2-{2-[2-(2-methyl-naphthalen-1-yl)-ethyl]-phenyl}-1,4,5,6-tetrahydropyrimidine;
2-{2-[2-(2,3-dihydro-benzo[1,4]dioxin-5-yl)-ethyl]-phenyl}-1,4,5,6-tetrahydropyrimidine;
2-[2-(2-methoxy-napthalen-1-ylmethylsulfanyl)-phenyl]-1,4,5,6-tetrahydropyrimidine;
2-(2-Benzylsulfanyl-phenyl)-1,4,5,6-tetrahydro-pyrimidine;
2-(2-Pentadecylsulfanyl-phenyl)-1,4,5,6-tetrahydro-pyrimidine;
2-(2-Cyclohexylmethylsulfanyl-phenyl)-1,4,5,6-tetrahydro-pyrimidine;
2-[2-(2-Methyl-benzylsulfanyl)-phenyl]-1,4,5,6-tetrahydro-pyrimidine;
2-[2-(3-Nitro-benzylsulfanyl)-phenyl]-1,4,5,6-tetrahydro-pyrimidine;
2-[2-(3,5-Dimethoxy-benzylsulfanyl)-phenyl]-1,4,5,6-tetrahydro-pyrimidine;
2-[2-(4-Fluoro-benzylsulfanyl)-phenyl]-1,4,5,6-tetrahydro-pyrimidine;
2-[2-(2-Chloro-benzylsulfanyl)-phenyl]-1,4,5,6-tetrahydro-pyrimidine;
2-[2-(2-Fluoro-benzylsulfanyl)-phenyl]-1,4,5,6-tetrahydro-pyrimidine;
2-[2-(2,4-Bis-trifluoromethyl-benzylsulfanyl)-phenyl]-1,4,5,6-tetrahydro-pyrimidine;
2-[2-(3-Methoxy-benzylsulfanyl)-phenyl]-1,4,5,6-tetrahydro-pyrimidine;
2-[2-(3,5-Bis-trifluoromethyl-benzylsulfanyl)-phenyl]-1,4,5,6-tetrahydro-pyrimidine;
2-[2-(2-Methoxy-5-nitro-benzyloxy)-phenyl]-1,4,5,6-tetrahydro-pyrimidine;
2-[2-(2-Chloro-6-fluoro-benzylsulfanyl)-phenyl]-4,5-dihydro-1H-imidazole;
2-(2-Benzylsulfanyl-phenyl)-4,5-dihydro-1H-imidazole;
2-[2-(2,6-Difluoro-benzylsulfanyl)-phenyl]-1,4,5,6-tetrahydro-pyrimidine;
2-[2-(Naphthalen-1-ylmethoxy)-phenyl]-1,4,5,6-tetrahydro-pyrimidine;
2-[2-(2-Methyl-naphthalen-1-ylmethylsulfanyl)-phenyl]-1,4,5,6-tetrahydro-pyrimidine;
1-{2-[2-(2-Chloro-6-fluoro-benzylsulfanyl)-phenyl]-5,6-dihydro-4H-pyrmidin-1-yl}-ethanone;
2-[2-(2-Chloro-6-fluoro-benzylsulfanyl)-phenyl]-3a,4,5,6,7,7a-hexahydro-1H-benzoimidazole;
2-[2-(2-Iodo-benzylsulfanyl)-phenyl]-3a,4,5,6,7,7a-hexahydro-1H-benzoimidazole;

2-[2-(2,5-Dimethyl-benzylsulfanyl)-phenyl]-1,4,5,6-tetrahydro-pyrimidine;
4-[2-(1,4,5,6-Tetrahydro-pyrimidin-2-yl)-phenylsulfanylmethyl]-quinoline;
2-[2-(2-Methoxy-5-nitro-benzylsulfanyl)-pyridin-3-yl]-1,4,5,6-tetrahydro-pyrimidine;
2-[2-(2-Methoxy-benzylsulfanyl)-phenyl]-1,4,5,6-tetrahydro-pyrimidine;
2-[2-(2-Cyclopentyloxy-benzylsulfanyl)-phenyl]-1,4,5,6-tetrahydro-pyrimidine;
2-[2-(2,3-Dihydro-benzo[1,4]dioxin-5-ylmethylsulfanyl)-phenyl]-1,4,5,6-tetrahydro-pyrimidine;
2-[2-(6-Methoxy-2,3-dihydro-benzo[1,4]dioxin-5-ylmethylsulfanyl)-phenyl]-1,4,5,6-tetrahydro-pyrimidine;
2-[2-(5-fluoro-2-methoxy-benzylsulfanyl)-phenyl]-4,5-dihydro-1H-imidazole;
1-Methyl-2-[2-(naphthalen-1-ylmethylsulfanyl)-phenyl]-1,4,5,6-tetrahydro-pyrimidine;
2-[2-(5-Bromo-2-methoxy-benzylsulfanyl)-phenyl]-4,5-dihydro-1H-imidazole;
2-[2-(5-Bromo-2-methoxy-benzyloxy)-phenyl]-1,4,5,6-tetrahydro-pyrimidine;
2-[2-(Naphthalen-1-yloxymethyl)-phenyl]-1,4,5,6-tetrahydro-pyrimidine;
2-[2-(5-Bromo-2-methoxy-benzylsulfanyl)-phenyl]-5,5-dimethyl-1,4,5,6-tetrahydro-pyrimidine;
2-[2-(5-Bromo-2-methoxy-benzylsulfanyl)-phenyl]-5,5-dimethyl-4,5-dihydro-1H-imidazole;
2-[2-(2,6-Dimethoxy-benzylsulfanyl)-phenyl]-1,4,5,6-tetrahydro-pyrimidine;
2-[2-(2-Bromo-6-methoxy-benzylsulfanyl)-phenyl]-1,4,5,6-tetrahydro-pyrimidine;
2-[5-Bromo-2-(5-bromo-2-methoxy-benzylsulfanyl)-phenyl]-4,5-dihydro-1H-imidazole;
2-[5-Bromo-2-(5-bromo-2-methoxy-benzylsulfanyl)-phenyl]-1,4,5,6-tetrahydro-pyrimidine;
2-[4-Bromo-2-(5-bromo-2-methoxy-benzylsulfanyl)-phenyl]-1,4,5,6-tetrahydro-pyrimidine;
2-[2-(2-Bromo-5-methoxy-benzylsulfanyl)-phenyl]-1,4,5,6-tetrahydro-pyrimidine;
2-[2-(5-Bromo-2-methoxy-benzylsulfanyl)-5-methyl-phenyl]-1,4,5,6-tetrahydro-pyrimidine;
2-[2-(Biphenyl-3-ylmethylsulfanyl)-phenyl]-1,4,5,6-tetrahydro-pyrimidine;
2-[2-(5-Chloro-2-methoxy-benzylsulfanyl)-phenyl]-1,4,5,6-tetrahydro-pyrimidine;
2-[2-(2-Methoxy-5-thiophen-3-yl-benzylsulfanyl)-phenyl]-1,4,5,6-tetrahydro-pyrimidine;
2-[2-(Biphenyl-2-ylmethylsulfanyl)-phenyl]-1,4,5,6-tetrahydro-pyrimidine;
2-[2-(5-Iodo-2-methoxy-benzylsulfanyl)-phenyl]-1,4,5,6-tetrahydro-pyrimidine;
2-[2-(5-Bromo-2-methoxy-benzylsulfanyl)-5-fluoro-phenyl]-1,4,5,6-tetrahydro-pyrimidine;
2-[2-(5-Bromo-2-methoxy-benzylsulfanyl)-3-fluoro-phenyl]-1,4,5,6-tetrahydro-pyrimidine;
2-[2-(4,4'-Dimethoxy-biphenyl-3-ylmethylsulfanyl)-phenyl]-1,4,5,6-tetrahydro-pyrimidine;
2-[2-(9H-Fluoren-9-ylsulfanyl)-phenyl]-1,4,5,6-tetrahydro-pyrimidine;
2-[2-(3'-Chloro-4'-fluoro-4-methoxy-biphenyl-3-ylmethylsulfanyl)-phenyl]-1,4,5,6-tetrahydro-pyrimidine;
2-[2-(1-Naphthalen-1-yl-ethylsulfanyl)-phenyl]-1,4,5,6-tetrahydro-pyrimidine;
2-[2-(5-Bromo-2-methoxy-benzylsulfanyl)-5-fluoro-phenyl]-4,5-dihydro-1H-imidazole;
2-(2-Benzhydrylsulfanyl-phenyl)-1,4,5,6-tetrahydro-pyrimidine;
2-[2-(2'-Fluoro-4''-methoxy-[1,1';4',1'']terphenyl-3''-ylmethylsulfanyl)-phenyl]-1,4,5,6-tetrahydro-pyrimidine;
2-(5-Bromo-2-methoxy-benzylsulfanyl)-benzamidine;
2-[4-(Naphthalen-1-ylmethylsulfanyl)-phenyl]-1,4,5,6-tetrahydro-pyrimidine;
2-[2-(5-Ethynyl-2-methoxy-benzylsulfanyl)-phenyl]-1,4,5,6-tetrahydro-pyrimidine;
2-[2-(5-Bromo-2-methoxy-benzylsulfanyl)-benzyl]-1,4,5,6-tetrahydro-pyrimidine;
2-[2-(5-Bromo-2-cyclopentyloxy-benzylsulfanyl)-phenyl]-1,4,5,6-tetrahydro-pyrimidine;
2-[2-(5-Bromo-2-ethoxy-benzylsulfanyl)-phenyl]-1,4,5,6-tetrahydro-pyrimidine;
2-[2-(5-Bromo-2-propoxy-benzylsulfanyl)-phenyl]-1,4,5,6-tetrahydro-pyrimidine;
[2-(5-Bromo-2-methoxy-benzylsulfanyl)-benzyl]-diethylamine;
1-[2-(5-Bromo-2-methoxy-benzylsulfanyl)-benzyl]-piperazine;
C-{4-[3-(5-Bromo-2-methoxy-benzylsulfanyl)-quinoxalin-2-yl]-morpholin-2-yl}-methylamine;
2-[2-(2-Methoxy-5-methyl-benzylsulfanyl)-phenyl]-1,4,5,6-tetrahydro-pyrimidine;
2-[2-(5-Bromo-2-methoxy-benzyloxymethyl)-phenyl]-1,4,5,6-tetrahydro-pyrimidine;
[2-(5-Bromo-2-methoxy-benzylsulfanyl)-benzyl]-dimethylamine;
2-[2-(5-Bromo-2-isopropoxy-benzylsulfanyl)-phenyl]-1,4,5,6-tetrahydro-pyrimidine;
2-[2-(2-Ethoxy-naphthalen-1-ylmethylsulfanyl)-phenyl]-1,4,5,6-tetrahydro-pyrimidine;
2-[2-(2-Propoxy-naphthalen-1-ylmethylsulfanyl)-phenyl]-1,4,5,6-tetrahydro-pyrimidine;
4-Methoxy-3-[2-(1,4,5,6-tetrahydro-pyrimidin-2-yl)-phenylsulfanylmethyl]-benzonitrile;
1-{4-Methoxy-3-[2-(1,4,5,6-tetrahydro-pyrimidin-2-yl)-phenylsulfanylmethyl]-phenyl}-ethanone;
2-[2-(Naphthalen-1-ylsulfanylmethyl)-phenyl]-1,4,5,6-tetrahydro-pyrimidine;
1-[2-(5-Bromo-2-methoxy-benzylsulfanyl)-benzyl]-piperidine;
C-{4-[2-(2-Methoxy-naphthalen-1-ylmethylsulfanyl)-benzyl]-morpholin-2-yl}-methylamine;
1-[2-(5-Bromo-2-methoxy-benzylsulfanyl)-benzyl]-pyrrolidin-3-ylamine;
1-[2-(2-Methoxy-naphthalen-1-ylmethylsulfanyl)-benzyl]-pyrrolidin-3-ylamine;
3-[2-(5-Bromo-2-methoxy-benzylsulfanyl)-3-fluoro-phenyl]-1,5,6,7,8,8a-hexahydro-imidazo[1,5-a]pyridine;
3-[2-(5-Bromo-2-methoxy-benzylsulfanyl)-3-fluoro-phenyl]-5,6,7,7a-tetrahydro-1H-pyrrolo[1,2-c]imidazole;
2-[2-(Benzo[b]thiophen-3-ylmethylsulfanyl)-phenyl]-1,4,5,6-tetrahydro-pyrimidine;
2-[3-Fluoro-2-(naphthalen-1-ylmethylsulfanyl)-phenyl]-1,4,5,6-tetrahydro-pyrimidine;
2-(Naphthalen-1-ylmethylsulfanyl)-3-(1,4,5,6-tetrahydro-pyrimidin-2-yl)-phenylamine;
2-[2-(5-Bromo-2-methoxy-benzylsulfanyl)-3-chloro-phenyl]-1,4,5,6-tetrahydro-pyrimidine;
2-[2-(2-Methoxy-phenylsulfanylmethyl)-phenyl]-1,4,5,6-tetrahydro-pyrimidine;
1-{2-[2-(5-Bromo-2-methoxy-benzylsulfanyl)-phenyl]-5,6-dihydro-4H-pyrimidin-1-yl}-3-methyl-butan-1-one;
1-{2-[2-(5-Bromo-2-methoxy-benzylsulfanyl)-phenyl]-5,6-dihydro-4H-pyrimidin-1-yl}-2-phenyl-ethanone;

2-[3-(5-Bromo-2-methoxy-benzylsulfanyl)-pyridin-2-yl]-1,4,5,6-tetrahydro-pyrimidine;
N-[2-(5-Bromo-2-methoxy-benzylsulfanyl)-phenyl]-guanidine;
2-[2-(2-Isopropoxy-naphthalen-1-ylmethylsulfanyl)-phenyl]-1,4,5,6-tetrahydro-pyrimidine;
2-[2-(2-Cyclopentyloxy-naphthalen-1-ylmethylsulfanyl)-phenyl]-1,4,5,6-tetrahydro-pyrimidine;
(5-Bromo-2-methoxy-benzyl)-[2-(1,4,5,6-tetrahydro-pyrimidin-2-yl)-phenyl]-amine;
2-[2-(5-Bromo-2-methoxy-benzylsulfanylmethyl)-phenyl]-1,4,5,6-tetrahydro-pyrimidine;
2-[2-(2-Methoxy-naphthalen-1-ylsulfanylmethyl)-pheny]-1,4,5,6-tetrahydro-pyrimidine;
2-[3-(5-Bromo-2-methoxy-benzylsulfanyl)-pyrazin-2-yl]-1,4,5,6-tetrahydro-pyrimidine;
2-[3-Chloro-2-(naphthalen-1-ylsulfanylmethyl)-phenyl]-1,4,5,6-tetrahydro-pyrimidine;
2-[2-(6-Bromo-2-methoxy-naphthalen-1-ylmethylsulfanyl)-phenyl]-1,4,5,6-tetrahydro-pyrimidine;
2-[3-Chloro-2-(2-methoxy-naphthalen-1-ylsulfanylmethyl)-phenyl]-1,4,5,6-tetrahydro-pyrimidine;
2-[2-(5-Bromo-2-methoxy-phenylsulfanylmethyl)-phenyl]-1,4,5,6-tetrahydro-pyrimidine;
2-[2-(5-Bromo-2-methoxy-phenylsulfanylmethyl)-3-chloro-phenyl]-1,4,5,6-tetrahydro-pyrimidine;
2-[1-(2-Naphthalen-1-yl-ethyl)-1H-pyrrol-2-yl]-1,4,5,6-tetrahydro-pyrimidine;
(5-Bromo-2-methoxy-benzyl)-methyl-[2-(1,4,5,6-tetrahydro-pyrimidin-2-yl)-phenyl]-amine;
2-(5-Bromo-2-methoxy-benzylsulfanyl)-benzylamine;
2-[2-(2-Chloro-phenylsulfanylmethyl)-phenyl]-1,4,5,6-tetrahydro-pyrimidine;
2-[2-(2-Bromo-phenylsulfanylmethyl)-phenyl]-1,4,5,6-tetrahydro-pyrimidine;
2-(2-o-Tolylsulfanylmethyl-phenyl)-1,4,5,6-tetrahydro-pyrimidine;
2-[2-(2,5-Dichloro-phenylsulfanylmethyl)-phenyl]-1,4,5,6-tetrahydro-pyrimidine;
2-(3-Amino-propylamino)-6-(5-bromo-2-methoxy-benzylsulfanyl)-benzonitrile;
2-[2-(5-Bromo-2-methoxy-benzylsulfanyl)-benzyl]-1,4,5,6-tetrahydro-pyrimidine;
[2-(5-Bromo-2-methoxy-benzylsulfanyl)-benzyl]-diethyl-amine;
4-[2-(5-Bromo-2-methoxy-benzylsulfanyl)-benzyl]-morpholine;
3'-(5-Bromo-2-methoxy-benzylsulfanyl)-3,4,5,6-tetrahydro-2H-[1,2']bipyrazinyl;
2-(5-Bromo-2-methoxy-benzylsulfanyl)-3-piperazin-1-yl-6,7-dihydro-quinoxaline;
1-[2-(5-Bromo-2-methoxy-benzylsulfanyl)-benzyl]-piperidine;
C-{4-[2-(2-Methoxy-naphthalen-1-ylmethyl sulfanyl)-benzyl]-morpholin-2-yl}-methylamine;
1-[3-(5-Bromo-2-methoxy-benzylsulfanyl)-pyrazin-2-yl]-pyrrolidin-3-ylamine;
1-[3-(5-Bromo-2-methoxy-benzylsulfanyl)-quinoxalin-2-yl]-pyrrolidin-3-ylamine;
1-[2-(2-Methoxy-naphthalen-1-ylmethylsulfanyl)-benzyl]-pyrrolidin-3-ylamine;
C-{4-[3-(5-Bromo-2-methoxy-benzylsulfanyl)-pyrazin-2-yl]-morpholin-3-yl}-methylamine;
1-[3-Fluoro-2-(2-naphthalen-1-yl-ethyl)-benzyl]-piperazine;
1-[2-(5-Bromo-2-methoxy-benzylsulfanyl)-3-chloro-benzyl]-azetidine;
1-[2-(5-Bromo-2-methoxy-benzylsulfanyl)-3-chloro-benzyl]-pyrrolidin-3-ol;
[2-(Naphthalen-1-ylmethylsulfanyl)-phenyl]-carbamic acid 1-aza-bicyclo[2.2.2]oct-3-yl ester;
[2-(2-Methyl-naphthalen-1-ylmethylsulfanyl)-phenyl]-carbamic acid 1-aza-bicyclo[2.2.2]oct-3-yl ester;
[2-(2-Methyl-naphthalen-1-ylmethylsulfanyl)-phenyl]-carbamic acid 2-piperidin-1-yl-ethyl ester;
{1-[2-(5-Bromo-2-methoxy-benzylsulfanyl)-3-chloro-benzyl]-pyrrolidin-2-yl}-methanol;
4-tert-Butyl-N-naphthalen-1-ylmethyl-N-(2-piperidin-1-yl-ethyl)-benzamide;
N,N-Dimethyl-N'-naphthalen-2-ylmethyl-N'-naphthalen-1-ylmethyl-propane-1,3-diamine;
N-(5-Bromo-2-methoxy-benzyl)-N',N'-dimethyl-N-naphthalen-1-ylmethyl-propane-1,3-diamine;
1-Naphthalen-1-ylmethyl-3-phenethyl-1-(2-piperidin-1-yl-ethyl)-thiourea;
3-(4-Dimethylamino-phenyl)-1-(3-dimethylamino-propyl)-1-naphthalen-1-ylmethyl-thiourea;
4-[2-(5-Bromo-2-methoxy-benzylsulfanyl)-3-chloro-benzylamino]-piperidine-1-carboxylic acid ethyl ester;
2-[2-(2-Naphthalen-1-yl-ethyl)-phenyl]-ethylamine;
Naphthalene-2-sulfonic acid (2-dimethylamino-ethyl)-naphthalen-1-ylmethyl-amide;
1-[2-(5-Bromo-2-methoxy-benzylsulfanyl)-3-chloro-benzyl]-2-methoxymethyl-pyrrolidine;
(2-Hexyloxy-phenyl)-carbamic acid 2-piperidin-1-yl-1-piperidin-1-ylmethyl-ethyl ester;
3-[2-(5-Bromo-2-methoxy-benzylsulfanyl)-benzyloxy]-pyrrolidine;
2-[2-(5-Bromo-2-methoxy-benzylsulfanyl)-benzyloxymethyl]-pyrrolidine;
2-[2-(Naphthalen-1-ylsulfanylmethyl)-phenyl]-piperidine;
3-[2-(5-Bromo-2-methoxy-benzylsulfanyl)-benzylamino]-propan-1-ol;
3-[2-(5-Bromo-2-methoxy-benzylsulfanyl)-benzylamino]-3-methyl-butan-1-ol;
1-[2-(5-Bromo-2-methoxy-benzylsulfanyl)-benzyl]-pyrrolidin-3-ol;
{1-[2-(5-Bromo-2-methoxy-benzylsulfanyl)-benzyl]-pyrrolidin-2-yl}-methanol;
{1-[2-(Naphthalen-1-ylsulfanylmethyl)-benzyl]-piperidin-2-yl}-methanol;
2-[2-(Naphthalen-1-ylsulfanylmethyl)-pyrrolidin-1-yl]-ethyl-N-pyrrolidine;
N-pyrrolyl-[1-(2-naphthalen-1-yl-ethyl)-pyrrolidin-2-ylmethyl]-amine;
1-(2-Naphthalen-1-yl-ethyl)-piperidine-2-carboxylic acid methyl ester;
(3-Bromo-benzyl)-(1-ethyl-pyrrolidin-2-ylmethyl)-naphthalen-1-ylmethyl-amine;
3-[2-(5-Bromo-2-methoxy-benzylsulfanyl)-benzyloxy]-piperidine;
(5-Bromo-2-methoxy-benzyl)-(1-ethyl-pyrrolidin-2-ylmethyl)-naphthalen-1-ylmethyl-amine;
(1-Ethyl-pyrrolidin-2-ylmethyl)-naphthalen-2-ylmethyl-naphthalen-1-ylmethyl-amine;
2-[2-(5-Bromo-2-methoxy-benzylsulfanyl)-benzyloxymethyl]-pyrrolidine;
(3-Bromo-benzyl)-(3-imidazol-1-yl-propyl)-naphthalen-1-ylmethyl-amine;
(3-Imidazol-1-yl-propyl)-naphthalen-2-ylmethyl-naphthalen-1-ylmethyl-amine;
[2-(Naphthalen 1-ylmethylsulfanyl)-phenyl]-carbamic acid 2-pipenidin-1-yl-1-piperidin-1-ylmethyl-ethyl ester;

[2-(Naphthalen-1-ylmethylsulfanyl)-phenyl]-carbamic acid 2-dimethylamino-ethyl ester;
1-[2-(Naphthalen-1-ylsulfanylmethyl)-benzyl]-piperazine;
[3-(2-Methyl-piperidin-1-yl)-propyl]-[2-(naphthalen-1-ylsulfanylmethyl)-benzyl]-amine;
1-[3-Chloro-2-(naphthalen-1-ylsulfanylmethyl)-benzyl]-piperazine;
N,N-Dimethyl-N'-(2-naphthalen-1-yl-ethyl)-N'-naphthalen-1-ylmethyl-ethane-1,2-diamine;
{1-[2-(5-Bromo-2-methoxy-benzylsulfanyl)-3-chloro-benzyl]-piperidin-2-yl}-methanol;
1-[2-(2-Naphthalen-1-yl-ethyl)-benzyl]-piperazine;
[3-(2-Methyl-piperidin-1-yl)-propyl]-[2-(2-naphthalen-1-yl-ethyl)-benzyl]-amine;
1-[3-Fluoro-2-(2-naphthalen-1-yl-ethyl)-benzyl]-piperazine;
{1-[3-Chloro-2-(naphthalen-1-ylsulfanylmethyl)-benzyl]-piperidin-2-yl}-methanol;
{1-[2-(5-Bromo-2-methoxy-benzylsulfanyl)-3-chloro-benzyl]-piperidin-2-yl}-methanol;
{1-[2-(2-Naphthalen-1-yl-ethyl)-benzyl]-piperidin-2-yl}-methanol;
[3-(2-Methyl-piperidin-1-yl)-propyl]-[2-(2-naphthalen-1-yl-ethyl)-benzyl]-amine;
1-[2-(2-Naphthalen-1-yl-ethyl)-benzyl]-pyrrolidin-3-ylamine;
1-Phenyl-3-piperazin-1-yl-5,6,7,8-tetrahydro-isoquinoline-4-carbonitrile;
2-[2-(5-Bromo-2-methoxy-benzylsulfanyl)-phenyl]-6-ethyl-1,4,5,6-tetrahydro-pyrimidine;
2-[2-(4-Methoxy-biphenyl-3-ylmethylsulfanyl)-phenyl]-1,4,5,6-tetrahydro-pyrimidine;
2-[2-(2-Methoxy-5-phenylethynyl-benzylsulfanyl)-phenyl]-1,4,5,6-tetrahydro-pyrimidine;
2-[2-(2-Naphthalen-1-yl-ethyl)-phenyl]-1,4,5,6-tetrahydro-pyrimidine;
2-[3-(2-Methoxy-naphthalen-1-ylsulfanylmethyl)-thiophen-2-yl]-1,4,5,6-tetrahydro-pyrimidine;
2-[2-(2,5-Dimethoxy-phenylsulfanylmethyl)-phenyl]-1,4,5,6-tetrahydro-pyrimidine;
2-[2-(4-Methyl-naphthalen-1-ylmethylsulfanyl)-phenyl]-1,4,5,6-tetrahydro-pyrimidine;
2-[2-(5-Bromo-2-methoxy-benzylsulfanyl)-3-fluoro-phenyl]-4,4-dimethyl-4,5-dihydro-1H-imidazole;
2-[2-(5-Bromo-2-methoxy-benzylsulfanyl)-3-fluoro-phenyl]-5,5-dimethyl-1,4,5,6-tetrahydro-pyrimidine;
2-[3-(Naphthalen-1-ylsulfanylmethyl)-thiophen-2-yl]-1,4,5,6-tetrahydro-pyrimidine;
2-{2-[2-(5-Bromo-2-methoxy-phenyl)-ethyl]-phenyl}-1,4,5,6-tetrahydro-pyrimidine;
2-[3-Chloro-2-(2-naphthalen-1-yl-ethyl)-phenyl]-1,4,5,6-tetrahydro-pyrimidine;
2-{2-[2-(5-Bromo-2-methoxy-phenyl)-ethyl]-3-fluoro-phenyl}-1,4,5,6-tetrahydro-pyrimidine;
2-[2-(5-Bromo-2-methoxy-phenylsulfanylmethyl)-3-fluoro-phenyl]-1,4,5,6-tetrahydro-pyrimidine;
2-[2-(Naphthalen-1-ylsulfanylmethyl)-phenyl]-4,5-dihydro-1H-imidazole;
2-[3-Fluoro-2-(naphthalen-1-ylsulfanylmethyl)-phenyl]-1,4,5,6-tetrahydro-pyrimidine;
2-[3-Bromo-2-(naphthalen-1-ylsulfanylmethyl)-phenyl]-1,4,5,6-tetrahydro-pyrimidine;
2-{2-[2-(5-Bromo-2-methoxy-phenyl)-ethyl]-3-chloro-phenyl}-1,4,5,6-tetrahydro-pyrimidine;
2-[2-(2-Methoxy-5-trifluoromethyl-benzylsulfanyl)-phenyl]-1,4,5,6-tetrahydro-pyrimidine;
2-[4-(Naphthalen-1-ylsulfanylmethyl)-thiophen-3-yl]-1,4,5,6-tetrahydro-pyrimidine;
2-[2-(Naphthalen-1-ylsulfanylmethyl)-thiophen-3-yl]-1,4,5,6-tetrahydro-pyrimidine;
2-{2-[2-(5-Bromo-2-methoxy-phenyl)-ethyl]-3-trifluoromethyl-phenyl}-1,4,5,6-tetrahydro-pyrimidine;
2-[2-(2-Naphthalen-1-yl-ethyl)-3-trifluoromethyl-phenyl]-1,4,5,6-tetrahydro-pyrimidine;
2-[2-(6-Fluoro-naphthalen-1-ylmethylsulfanyl)-phenyl]-1,4,5,6-tetrahydro-pyrimidine;
{1-[2-(5-Bromo-2-methoxy-benzylsulfanyl)-benzyl]-piperidin-2-yl}-methanol;
2-[3-Fluoro-2-(2-naphthalen-1-yl-ethyl)-phenyl]-1,4,5,6-tetrahydro-pyrimidine;
[2-(5-Bromo-2-methoxy-benzylsulfanyl)-3-chloro-benzyl]-[3-(2-methyl-piperidin-1-yl)-propyl]-amine;
1-[2-(5-Bromo-2-methoxy-benzylsulfanyl)-3-chloro-benzyl]-pyrrolidin-3-ylamine;
1-[2-(5-Bromo-2-methoxy-benzylsulfanyl)-3-chloro-benzyl]-piperazine;
5,5-Dimethyl-2-[2-(2-naphthalen-1-yl-ethyl)-phenyl]-4,5-dihydro-1H-imidazole;
2-[3-Fluoro-2-(2-naphthalen-1-yl-ethyl)-phenyl]-5,5-dimethyl-4,5-dihydro-1H-imidazole;
2-[2-(5-Bromo-2-methoxy-benzylsulfanyl)-3,5-difluoro-phenyl]-1,4,5,6-tetrahydro-pyrimidine;
2-[2-(5-Bromo-2-methoxy-benzylsulfanyl)-3,5-difluoro-phenyl]-5,5-dimethyl-4,5-dihydro-1H-imidazole;
3-(2-Naphthalen-1-yl-ethyl)-2-(1,4,5,6-tetrahydro-pyrimidin-2-yl)-phenylamine;
Amino-[2-(2-naphthalen-1-yl-ethyl)-phenyl]-acetonitrile;
1-[2-(2-Naphthalen-1-yl-ethyl)-phenyl]-ethane-1,2-diamine;
2-[2-(5-Bromo-2-methoxy-benzylsulfanyl)-phenyl]-4-methyl-4,5-dihydro-1H-imidazole;
2-[2-(5-Bromo-2-methoxy-benzylsulfanyl)-3-fluoro-phenyl]-4-methyl-4,5-dihydro-1H-imidazole;
2-[2-(5-Bromo-2-methoxy-benzylsulfanyl)-3-chloro-phenyl]-4-methyl-4,5-dihydro-1H-imidazole;
2-[2-(5-Bromo-2-methoxy-benzylsulfanyl)-3,4-difluoro-phenyl]-1,4,5,6-tetrahydro-pyrimidine;
2-[3-Fluoro-2-(naphthalen-1-ylsulfanylmethyl)-phenyl]-5,5-dimethyl-4,5-dihydro-1H-imidazole;
2-{2-[2-(5-Bromo-2-methoxy-phenyl)-1-methyl-ethyl]-phenyl}-1,4,5,6-tetrahydro-pyrimidine;
2-[2-(5-Bromo-2-methoxy benzyl sulfanyl)-3-fluoro-4-trifluoromethyl-phenyl]-4,4-dimethyl-4,5-dihydro-1H-imidazole;
2-[2-(5-Bromo-2-methoxy-benzyl sulfanyl)-3-fluoro-4-trifluoromethyl-phenyl]-5,5-dimethyl-1,4,5,6-tetrahydro-pyrimidine;
2-[3-Methoxy-2-(2-naphthalen-1-yl-ethyl)-phenyl]-1,4,5,6-tetrahydro-pyrimidine;
2-[2-(5-Bromo-2-methoxy-benzylsulfanyl)-3-chloro-phenyl]-1,4,5,6-tetrahydro-pyrimidin-5-ol;
2-{2-[2-(5-Bromo-2-methoxy-phenyl)-ethyl]-3-methoxy-phenyl}-1,4,5,6-tetrahydro-pyrimidine;
1-Amino-3-[2-(5-bromo-2-methoxy-phenyl)-7-chloro-benzo[b]thiophen-3-ylamino]-propan-2-ol;
2-[2-(1-Methyl-2-naphthalen-1-yl-ethyl)-phenyl]-1,4,5,6-tetrahydro-pyrimidine;
3-(5-Bromo-2-methoxy-benzylsulfanyl)-2-fluoro-4-(1,4,5,6-tetrahydro-pyrimidin-2-yl)-phenylamine;
2-{2-[2-(5-Bromo-2-methoxy-phenyl)-ethyl]-3-methyl-phenyl}-1,4,5,6-tetrahydro-pyrimidine;
2-[2-(5-Bromo-2-methoxy-benzylsulfanyl)-3-fluoro-phenyl]-1,4,5,6-tetrahydro-pyrimidin-5-ol;

1-Amino-3-[2-(5-bromo-2-methoxy-phenyl)-7-fluoro-benzo[b]thiophen-3-ylamino]-propan-2-ol;
2-[3-Methoxy-2-(naphthalen-1-ylsulfanylmethyl)-phenyl]-1,4,5,6-tetrahydro-pyrimidine;
2-[2-(5-Bromo-2-methoxy-benzylsulfanyl)-3-fluoro-phenyl]-1,4,5,6-tetrahydro-pyrimidin-5-ol;
2-[2-(5-Bromo-2-methoxy-benzylsulfanyl)-5-methoxy-phenyl]-1,4,5,6-tetrahydro-pyrimidine;
2-{2-[2-Chloro-6-(1,4,5,6-tetrahydro-pyrimidin-2-yl)-phenyl]-ethyl}-phenol;
2-[3-Methoxy-2-(naphthalen-1-ylsulfanylmethyl)-phenyl]-1,4,5,6-tetrahydro-pyrimidin-5-ol;
2-{2-[2-(5-Bromo-2-methoxy-phenyl)-ethyl]-3-methyl-phenyl}-5-methyl-4,5-dihydro-1H-imidazole;
2-{2-[2-(5-Bromo-2-methoxy-phenyl)-ethyl]-3-methyl-phenyl}-1,4,5,6-tetrahydro-pyrimidin-5-ol;
2-[2-(5-Bromo-2-methoxy-benzylsulfanyl)-3,4-difluoro-phenyl]-1,4,5,6-tetrahydro-pyrimidin-5-ol;
2-{2-[2-(5-Bromo-2-methoxy-phenyl)-ethyl]-3-chloro-phenyl}-4,4-dimethyl-4,5-dihydro-1H-imidazole;
2-[2-(5-Bromo-2-methoxy-benzylsulfanyl)-3-fluoro-4-methyl-phenyl]-1,4,5,6-tetrahydro-pyrimidine;
4,4-Dimethyl-2-[2-(naphthalen-1-ylmethylsulfanyl)-phenyl]-4,5-dihydro-oxazole;
2-[2-(5-Bromo-2-methoxy-benzylsulfanyl)-4-methoxy-phenyl]-1,4,5,6-tetrahydro-pyrimidine;
2-[5-(5-Bromo-2-methoxy-benzyl)-2-methyl-thiophen-3-yl]-1,4,5,6-tetrahydro-pyrmidine;
2-{2-[2-(5-Bromo-2-methoxy-phenyl)-ethyl]-thiophen-3-yl}-1,4,5,6-tetrahydro-pyrimidine;
2-{2-[2-(5-Bromo-2-methoxy-phenyl)-ethyl]-3-ethoxy-phenyl}-1,4,5,6-tetrahydro-pyrmidine;
2-{2-[2-(5-Bromo-2-methoxy-phenyl)-ethyl]-3-isopropoxy-phenyl}-1,4,5,6-tetrahydro-pyrimidine;
2-{2-[2-(5-Bromo-2-methoxy-phenyl)-ethyl]-3-fluoro-4-methoxy-phenyl}-1,4,5,6-tetrahydro-pyrimidine;
2-{2-[2-(5-Bromo-2-methoxy-phenyl)-ethyl]-3-isopropoxy-phenyl}-1,4,5,6-tetrahydro-pyrimidin-5-ol;
2-{2-[2-(5-Bromo-2-methoxy-phenyl)-ethyl]-3-methoxy-phenyl}-1,4,5,6-tetrahydro-pyrimidin-5-ol;
2-{2-[2-(5-Bromo-2-methoxy-phenyl)-ethyl]-4-methoxy-phenyl}-1,4,5,6-tetrahydro-pyrimidine;
2-{2-[2-(5-Bromo-2-methoxy-phenyl)-ethyl]-3-ethoxy-phenyl}-1,4,5,6-tetrahydro-pyrimidin-5-ol;
2-[2-(5-Bromo-2-methoxy-phenyl)-ethyl]-3-(1,4,5,6-tetrahydro-pyrimidin-2-yl)-benzonitrile;
2-{3-Benzyloxy-2-[2-(5-bromo-2-methoxy-phenyl)-ethyl]-phenyl}-1,4,5,6-tetrahydro-pyrimidine;
2-{2-[2-(5-Bromo-2-methoxy-phenyl)-ethyl]-4-butyl-phenyl}-1,4,5,6-tetrahydro-pyrimidine;
2-{5-[2-(5-Bromo-2-methoxy-phenyl)-ethyl]-2,3-dihydro-benzo[1,4]dioxin-6-yl}-1,4,5,6-tetrahydro-pyrimidine;
2-{5-[2-(5-Bromo-2-methoxy-phenyl)-ethyl]-8-chloro-2,3-dihydro-benzo[1,4]dioxin-6-yl}-1,4,5,6-tetrahydro-pyrimidine;
2-{2-[2-(5-Bromo-2-methoxy-phenyl)-ethyl]-3-ethyl-phenyl}-1,4,5,6-tetrahydro-pyrimidine;
2-{2-[2-(5-Bromo-2-methoxy-phenyl)-ethyl]-3-propyl-phenyl}-1,4,5,6-tetrahydro-pyrimidine;
2-{2-[2-(5-Bromo-2-methoxy-phenyl)-ethyl]-3-butoxy-phenyl}-1,4,5,6-tetrahydro-pyrimidine;
2-{2-[2-(5-Bromo-2-methoxy-phenyl)-ethyl]-3-isobutoxy-phenyl}-1,4,5,6-tetrahydro-pyrimidine;
2-{2-[2-(5-Bromo-2-methoxy-phenyl)-ethyl]-3-butoxy-phenyl}-1,4,5,6-tetrahydro-pyrimidin-5-ol;
2-[2-(5-Bromo-2-methoxy-benzylsulfanyl)-3-fluoro-phenyl]-5-methoxy-1,4,5,6-tetrahydro-pyrimidine;
2-{2-[2-(5-Bromo-2-methoxy-phenyl)-ethyl]-3-chloro-phenyl}-1-methyl-1,4,5,6-tetrahydro-pyrimidine;
2-[2-(5-Bromo-2-methoxy-benzylsulfanyl)-3-fluoro-phenyl]-1-methyl-4,5-dihydro-1H-imidazole;
[2-(5-Bromo-2-methoxy-benzylsulfanyl)-3-fluoro-phenyl]-1-methyl-4,5-dihydro-1H-imidazole;
2-{2-[3-(1,4,5,6-Tetrahydro-pyrimidin-2-yl)-biphenyl-2-yl]-ethyl}-phenol;
2-{2-[2-(5-Bromo-2-methoxy-phenyl)-ethyl]-3-chloro-phenyl}-1-methyl-4,5-dihydro-1H-imidazole;
N-(3-Amino-propyl)-2-[2-(5-bromo-2-methoxy-phenyl)-ethyl]-6-methoxy-benzamide;
N-(3-Amino-propyl)-2-[2-(5-bromo-2-methoxy-phenyl)-ethyl]-6-methyl-benzamide;
2-[2-(5-Bromo-2-methoxy-benzylsulfanyl)-3-fluoro-phenyl]-5,6-dihydro-4H-pyrimidine-1-carboxylic acid 1-acetoxy-2-methyl-propyl ester;
2-[2-(5-Bromo-2-methoxy-benzylsulfanyl)-3-fluoro-phenyl]-5,6-dihydro-4H-pyrimidine-1-carboxylic acid 1-acetoxy-ethyl ester;
3-(5-Bromo-2-methoxy-phenyl)-5-chloro-3,4-dihydro-isoquinolin-1-ylamine;
2-{2-[2-(5-Bromo-2-methoxy-phenyl)-ethyl]-3-(4-methoxy-benzyloxy)-phenyl]-1,4,5,6-tetrahydro-pyrimidine;
2-{2-[2-(5-Bromo-2-methoxy-phenyl)-ethyl]-3-chloro-phenyl}-5-methyl-1,4,5,6-tetrahydro-pyrimidin-5-ol;
2-[(5-Bromo-2-methoxy-phenyl)-(3-piperidin-1-yl-propylamino)-methyl]-3-chloro-6-methyl-phenol;
1-{2-[2-(5-Bromo-2-methoxy-phenyl)-ethyl]-6-methyl-benzyl}-piperazine;
1-{2-[2-(5-Bromo-2-methoxy-phenyl)-ethyl]-6-methyl-benzyl}-4-methyl-piperazine;
1-{2-[2-(5-Bromo-2-methoxy-phenyl)-ethyl]-6-methyl-benzyl}-piperidine;
{2-[2-(5-Bromo-2-methoxy-phenyl)-ethyl]-6-methyl-benzyl}-diethyl-amine;
3-(5-Bromo-2-methoxy-phenyl)-1,2,3,4-tetrahydro-isoquinoline;
1-{2-[2-(5-Bromo-2-methoxy-phenyl)-ethyl]-3-chloro-benzyl}-piperazine;
1-{2-[2-(5-Bromo-2-methoxy-phenyl)-ethyl]-3-chloro-benzyl}-4-methyl-piperazine;
1-{2-[2-(5-Bromo-2-methoxy-phenyl)-ethyl]-3-chloro-benzyl}-piperidine;
{2-[2-(5-Bromo-2-methoxy-phenyl)-ethyl]-3-chloro-benzyl}-diethyl-amine;
2-{2-[2-(5-Bromo-2-methoxy-phenyl)-ethyl]-3-chloro-phenyl}-4,5-dihydro-1H-imidazole;
(1-{2-[2-(5-Bromo-2-methoxy-phenyl)-ethyl]-3-chloro-benzyl}-piperidin-2-yl)-methanol;
2-{2-[2-(5-Bromo-2-methoxy-phenyl)-ethyl]-3-propoxy-phenyl}-1,4,5,6-tetrahydro-pyrimidine;
1-[2-(5-Bromo-2-methoxy-benzylsulfanyl)-benzyl]-4-methyl-piperazine;
1-{2-[2-(5-Bromo-2-methoxy-phenyl)-ethyl]-6-chloro-benzyl}-piperazine;
1-{2-[2-(5-Bromo-2-methoxy-phenyl)-ethyl]-6-chloro-benzyl}-4-methyl-piperazine;
1-{2-[2-(5-Bromo-2-methoxy-phenyl)-ethyl]-6-chloro-benzyl}-piperidine;
{2-[2-(5-Bromo-2-methoxy-phenyl)-ethyl]-6-chloro-benzyl}-diethyl-amine;
1-(5-Bromo-2-methoxy-benzyl)-2-(4-methoxy-benzyl)-2,3-dihydro-1H-isoindole;
2-{2-[2-(5-Bromo-2-methoxy-phenyl)-ethyl]-3-chloro-phenyl}-5,6-dihydro-4H-pyrimidine-1-carboxylic acid 1-acetoxy-ethyl ester;

1-(2-{2-[2-(5-Bromo-2-methoxy-phenyl)-ethyl]-3-chloro-phenyl}-5,6-dihydro-4H-pyrimidin-1-yl)-ethanone;
1-{2-[2-(5-Bromo-2-methoxy-phenyl)-ethyl]-3-fluoro-benzyl}-4-methyl-piperazine;
{2-[2-(5-Bromo-2-methoxy-phenyl)-ethyl]-3-fluoro-benzyl}-diethyl-amine;
1-{2-[2-(5-Bromo-2-methoxy-phenyl)-ethyl]-3-fluoro-benzyl}-piperidine;
(1-{2-[2-(5-Bromo-2-methoxy-phenyl)-ethyl]-3-fluoro-benzyl}-piperidin-2-yl)-methanol;
4-Fluoro-N-{2-[4-(2-methoxy-phenyl)-piperazin-1-yl]-ethyl}-N-pyridin-2-yl-benzamide;
3-(5-Bromo-2-methoxy-phenyl)-2-methyl-1,2,3,4-tetrahydro-isoquinoline;
1-{2-[2-(5-Bromo-2-methoxy-phenyl)-ethyl]-3-chloro-benzyl}-piperazine;
1-{2-[2-(5-Bromo-2-methoxy-phenyl)-ethyl]-3-chloro-benzyl}-4-methyl-piperazine;
1-{2-[2-(5-Bromo-2-methoxy-phenyl)-ethyl]-3-chloro-benzyl}-piperidine;
{2-[2-(5-Bromo-2-methoxy-phenyl)-ethyl]-3-chloro-benzyl}-diethyl-amine;
2-{2-[2-(5-Bromo-2-methoxy-phenyl)-ethyl]-3-chloro-phenyl}-4,5-dihydro-1H-imidazole;
(1-{2-[2-(5-Bromo-2-methoxy-phenyl)-ethyl]-3-chloro-benzyl}-piperidin-2-yl)-methanol;
2-{2-[2-(5-Bromo-2-methoxy-phenyl)-ethyl]-3-propoxy-phenyl}-1,4,5,6-tetrahydro-pyrimidine;
1-[2-(5-Bromo-2-methoxy-benzylsulfanyl)-benzyl]-4-methyl-piperazine;
1-{2-[2-(5-Bromo-2-methoxy-phenyl)-ethyl]-6-chloro-benzyl}-piperazine;
1-{2-[2-(5-Bromo-2-methoxy-phenyl)-ethyl]-6-chloro-benzyl}-4-methyl-piperazine;
1-{2-[2-(5-Bromo-2-methoxy-phenyl)-ethyl]-6-chloro-benzyl}-piperidine;
{2-[2-(5-Bromo-2-methoxy-phenyl)-ethyl]-6-chloro-benzyl}-diethyl-amine;
1-(5-Bromo-2-methoxy-benzyl)-2-(4-methoxy-benzyl)-2,3-dihydro-1H-isoindole;
2-{2-[2-(5-Bromo-2-methoxy-phenyl)-ethyl]-3-chloro-phenyl}-5,6-dihydro-4H-pyrimidine-1-carboxylic acid 1-acetoxy-ethyl ester;
1-(2-{2-[2-(5-Bromo-2-methoxy-phenyl)-ethyl]-3-chloro-phenyl}-5,6-dihydro-4H-pyrimidin-1-yl)-ethanone;
1-{2-[2-(5-Bromo-2-methoxy-phenyl)-ethyl]-3-fluoro-benzyl}-4-methyl-piperazine;
{2-[2-(5-Bromo-2-methoxy-phenyl)-ethyl]-3-fluoro-benzyl}-diethyl-amine;
1-{2-[2-(5-Bromo-2-methoxy-phenyl)-ethyl]-3-fluoro-benzyl}-piperidine;
4-Fluoro-N-{2-[4-(2-methoxy-phenyl)-piperazin-1-yl]-ethyl}-N-pyridin-2-yl-benzamide;
3-(5-Bromo-2-methoxy-phenyl)-2-methyl-1,2,3,4-tetrahydro-isoquinoline;
2-{2-[2-(5-Bromo-2-methoxy-phenyl)-ethyl]-3-chloro-phenyl}-1-ethyl-4,5-dihydro-1H-imidazole;
{2-[3-(5-Bromo-2-methoxy-phenyl)-3,4-dihydro-1H-isoquinolin-2-yl]-ethyl}-diethyl-amine;
1-(2-{2-[2-(5-Bromo-2-methoxy-phenyl)-ethyl]-3-chloro-phenyl}-4,5-dihydro-imidazol-1-yl)-ethanone;
2-{2-[2-(5-Bromo-2-methoxy-phenyl)-ethyl]-3-chloro-phenyl}-4,5-dihydro-imidazole-1-carboxylic acid ethyl ester;
2-{2-[2-(5-Bromo-2-methoxy-phenyl)-ethyl]-3-chloro-phenyl}-4,5-dihydro-imidazole-1-carboxylic acid isobutyl ester;
2-{2-[2-(5-Bromo-2-methoxy-phenyl)-ethyl]-3-chloro-phenyl}-4,5-dihydro-imidazole-1-carboxylic acid tert-butyl ester;
1-(2-{2-[2-(5-Bromo-2-methoxy-phenyl)-ethyl]-3-chloro-phenyl}-4,5-dihydro-imidazol-1-yl)-2,2-dimethyl-propan-1-one;
1-(5-Bromo-2-methoxy-benzyl)-2,3-dihydro-1H-isoindole;
1-(2-Methoxy-benzyl)-2-methyl-2,3-dihydro-1H-isoindole;
2-Methyl-1-naphthalen-1-ylmethyl-2,3-dihydro-1H-isoindole;
1-{2-[3-Chloro-2-(2-naphthalen-1-yl-ethyl)-phenyl]-4,5-dihydro-imidazol-1-yl}-2,2-dimethyl-propan-1-one;
{2-[1-(5-Bromo-2-methoxy-benzyl)-1,3-dihydro-isoindol-2-yl]-ethyl}-diethyl-amine;
2-[3-Chloro-2-(2-naphthalen-1-yl-ethyl)-phenyl]-1-methyl-1,4,5,6-tetrahydro-pyrimidine;
2-[3-Chloro-2-(2-naphthalen-1-yl-ethyl)-phenyl]-5,6-dihydro-4H-pyrimidine-1-carboxylic acid tert-butyl ester;
2-[3-Chloro-2-(2-naphthalen-1-yl-ethyl)-phenyl]-4,5-dihydro-1H-imidazole;
1-{2-[3-Chloro-2-(2-naphthalen-1-yl-ethyl)-phenyl]-4,5-dihydro-imidazol-1-yl}-ethanone;
2-[3-Chloro-2-(2-naphthalen-1-yl-ethyl)-phenyl]-4,5-dihydro-imidazole-1-carboxylic acid isobutyl ester;
2-[3-Chloro-2-(2-naphthalen-1-yl-ethyl)-phenyl]-4,5-dihydro-imidazole-1-carboxylic acid tert-butyl ester;
2-[3-Chloro-2-(2-naphthalen-1-yl-ethyl)-phenyl]-4,5-dihydro-imidazole-1-carboxylic acid ethyl ester;
2-[2-(5-Bromo-2-methoxy-phenyl)-ethyl]-N-(3-formylamino-propyl)-6-methyl-benzamide;
2-[3-Chloro-2-(2-naphthalen-1-yl-ethyl)-phenyl]-1-ethyl-4,5-dihydro-1H-imidazole;
1-(2-{2-[2-(5-Bromo-2-methoxy-phenyl)-ethyl]-3-chloro-phenyl}-5,6-dihydro-4H-pyrimidin-1-yl)-2,2-dimethyl-propan-1-one;
2-{2-[2-(5-Bromo-2-methoxy-phenyl)-ethyl]-thiophen-3-yl}-4,5-dihydro-1H-imidazole;
2-{2-[2-(5-Bromo-2-methoxy-phenyl)-ethyl]-3-chloro-phenyl}-5,6-dihydro-4H-pyrimidine-1-carboxylic acid isobutyl ester;
2-{2-[2-(5-Bromo-2-methoxy-phenyl)-ethyl]-3-chloro-phenyl}-1-isocyanomethyl-4,5-dihydro-1H-imidazole;
2-{2-[2-(5-Bromo-2-methoxy-phenyl)-ethyl]-thiophen-3-yl}-1-methyl-4,5-dihydro-1H-imidazole;
2-{2-[2-(5-Bromo-2-methoxy-phenyl)-ethyl]-thiophen-3-yl}-1-ethyl-4,5-dihydro-1H-imidazole;
3-(5-Bromo-2-methoxy-benzyl)-2-methyl-2,3-dihydro-isoindol-1-one;
4-(2-Methoxy-benzyl)-2-(4-methoxy-benzyl)-1,2,3,4-tetrahydro-isoquinoline;
4-(5-Bromo-2-methoxy-benzyl)-2-(4-methoxy-benzyl)-1,2,3,4-tetrahydro-isoquinoline;
2-{2-[2-(5-Bromo-2-methoxy-phenyl)-ethyl]-3-chloro-phenyl}-1-propyl-4,5-dihydro-1H-imidazole;
2-{2-[2-(5-Bromo-2-methoxy-phenyl)-ethyl]-3-chloro-phenyl}-3a,4,5,6,7,7a-hexahydro-1H-benzoimidazole;
5,5-Dimethyl-2-[2-(naphthalen-1-ylsulfanylmethyl)-phenyl]-4,5-dihydro-1H-imidazole;
2-[2-(5-Bromo-2-methoxy-benzylsulfanyl)-3-chloro-phenyl]-4,4-dimethyl-4,5-dihydro-1H-imidazole;
N-(5-Bromo-2-methoxy-benzyl)-N'-methyl-N-naphthalen-1-ylmethyl-ethane-1,2-diamine;
2-{2-[2-(5-Bromo-2-methoxy-phenyl)-ethyl]-3-chloro-phenyl}-1-ethyl-1,4,5,6-tetrahydro-pyrimidine;
2-[2-(5-Bromo-2-methoxy-phenyl)-ethyl]-3-chloro-N,N,N'-trimethyl-benzamidine;

2-[3-Chloro-2-(2-naphthalen-1-yl-ethyl)-phenyl]-1-methyl-4,5-dihydro-1H-imidazole;
1-Benzyl-2-{2-[2-(5-bromo-2-methoxy-phenyl)-ethyl]-3-chloro-phenyl}-4,5-dihydro-1H-imidazole;
({2-[2-(5-Bromo-2-methoxy-phenyl)-ethyl]-3-chloro-phenyl}-pyrrolidin-1-yl-methylene)-methyl-amine;
2-{2-[2-(5-Bromo-2-methoxy-phenyl)-ethyl]-3-chloro-phenyl}-1-isopropyl-4,5-dihydro-1H-imidazole;
2-{2-[2-(5-Bromo-2-methoxy-phenyl)-ethyl]-3-chloro-phenyl}-1-(2,2,2-trifluoro-ethyl)-4,5-dihydro-1H-imidazole;
2-[2-(5-Bromo-2-methoxy-benzylsulfanyl)-phenyl]-6-ethyl-1,4,5,6-tetrahydro-pyrimidine;
2-(2-Benzylsulfanyl-phenyl)-3a,4,5,6,7,7a-hexahydro-1H-benzoimidazole;
2-[2-(2-Chloro-6-fluoro-benzylsulfanyl)-phenyl]-3a,4,5,6,7,7a-hexahydro-1H-benzoimidazole;
2-[2-(2-Iodo-benzylsulfanyl)-phenyl]-3a,4,5,6,7,7a-hexahydro-1H-benzoimidazole;
2-[2-(2-Methoxy-5-nitro-benzyl sulfanyl)-phenyl]-3a,4,5,6,7,7a-hexahydro-1H-benzoimidazole;
3-[2-(5-Bromo-2-methoxy-benzylsulfanyl)-3-fluoro-phenyl]-1,5,6,7,8,8a-hexahydro-imidazo[1,5-a]pyridine;
2-{2-[2-(5-Bromo-2-methoxy-phenyl)-ethyl]-3-fluoro-phenyl}-4,5-dihydro-1H-imidazole;
2-{2-[2-(5-Bromo-2-methoxy-phenyl)-ethyl]-3-ethoxy-phenyl}-1-ethyl-4,5-dihydro-1H-imidazole;
2-{2-[2-(5-Bromo-2-methoxy-phenyl)-ethyl]-3-ethoxy-phenyl}-4,5-dihydro-1H-imidazole;
2-{2-[2-(5-Bromo-2-methoxy-phenyl)-ethyl]-3-ethoxy-phenyl}-1-methyl-4,5-dihydro-1H-imidazole;
2-{2-[2-(5-Bromo-2-methoxy-phenyl)-ethyl]-3-methoxy-phenyl}-1-methyl-4,5-dihydro-1H-imidazole;
2-{2-[2-(5-Bromo-2-methoxy-phenyl)-ethyl]-3-fluoro-phenyl}-1-ethyl-4,5-dihydro-1H-imidazole;
2-[2-(2-Naphthalen-1-yl-ethyl)-phenyl]-4,5-dihydro-1H-imidazole;
1-Ethyl-2-[2-(2-naphthalen-1-yl-ethyl)-phenyl]-4,5-dihydro-1H-imidazole;
1-Methyl-2-[2-(2-naphthalen-1-yl-ethyl)-phenyl]-4,5-dihydro-1H-imidazole;
2-{2-[2-(5-Bromo-2-methoxy-phenyl)-ethyl]-phenyl}-1-ethyl-4,5-dihydro-1H-imidazole;
2-{2-[2-(5-Bromo-2-methoxy-phenyl)-ethyl]-phenyl}-4,5-dihydro-1H-imidazole;
2-{2-[2-(5-Bromo-2-methoxy-phenyl)-ethyl]-6-methyl-phenyl}-4,5-dihydro-1H-imidazole;
2-{2-[2-(5-Bromo-2-methoxy-phenyl)-ethyl]-phenyl}-1-methyl-4,5-dihydro-1H-imidazole;
3-{2-[2-(5-Bromo-2-methoxy-phenyl)-ethyl]-3-chloro-phenyl}-5,6-dihydro-imidazo[2,1-b]thiazole;
1-{2-[2-(5-Bromo-2-methoxy-phenyl)-ethyl]-3-chloro-phenyl}-2-(4,4-dimethyl-4,5-dihydro-1H-imidazol-2-ylsulfanyl)-ethanone;
3-{2-[2-(5-Bromo-2-methoxy-phenyl)-ethyl]-3-chloro-phenyl}-6,6-dimethyl-5,6-dihydro-imnidazo[2,1-b]thiazole;
{2-[2-(5-Bromo-2-methoxy-phenyl)-ethyl]-3-chloro-benzyl}-(4,5-dihydro-1H-imidazol-2-yl)-amine;
{3-Chloro-2-[2-(2-methoxy-phenyl)-ethyl]-benzyl}-(4,5-dihydro-1H-imidazol-2-yl)-amine;
(2-{2-[2-(5-Bromo-2-methoxy-phenyl)-ethyl]-3-chloro-phenyl}-4,5-dihydro-imidazol-1-yl)-acetic acid;
(2-{2-[2-(5-Bromo-2-methoxy-phenyl)-ethyl]-3-chloro-phenyl}-3a,4,5,6,7,7a-hexahydro-benzoimidazol-1-yl)-acetonitrile;
3-(2-{2-[2-(5-Bromo-2-methoxy-phenyl)-ethyl]-3-chloro-phenyl}-4,5-dihydro-imidazol-1-yl)-propionitrile;
2-(3-Fluoro-2-phenethyl-phenyl)-4,5-dihydro-1H-imidazole;
2-{2-[2-(5-Bromo-2-methoxy-phenyl)-ethyl]-3-chloro-phenyl}-1-propyl-3a,4,5,6,7,7a-hexahydro-1H-benzoimidazole;
3-{2-[2-(5-Bromo-2-methoxy-phenyl)-ethyl]-3-chloro-phenyl}-1,5,6,7,8,8a-hexahydro-imidazo[1,5-a]pyridine;
3-{2-[2-(5-Bromo-2-methoxy-phenyl)-ethyl]-3-chloro-phenyl}-5,6,7,7a-tetrahydro-1H-pyrrolo[1,2-c]imidazole;
3-(2-{2-[2-(5-Bromo-2-methoxy-phenyl)-ethyl]-3-chloro-phenyl}-4,5-dihydro-imidazol-1-yl)-2-methyl-propionitrile;
2-{2-[2-(2-Methyl-naphthalen-1-yl)-ethyl]-phenyl}-3a,4,5,6,7,7a-hexahydro-1H-benzoimidazole;
2-{2-[2-(2-Methyl-naphthalen-1-yl)-ethyl]-phenyl}-4,5-dihydro-1H-imidazole;
2-[2-(2-Naphthalen-1-yl-ethyl)-phenyl]-3a,4,5,6,7,7a-hexahydro-1H-benzoimidazole;
2-{2-[2-(2-Methoxy-naphthalen-1-yl)-ethyl]-phenyl}-4,5-dihydro-1H-imidazole;
2-(1-Isopropyl-4,5-dihydro-1H-imidazol-2-yl)-3-(2-naphthalen-1-yl-ethyl)-pyridine;
2-{2-[2-(5-Bromo-2-methoxy-phenyl)-ethyl]-thiophen-3-yl}-1-propyl-4,5-dihydro-1H-imidazole;
2-{2-[2-(5-Bromo-2-methoxy-phenyl)-ethyl]-thiophen-3-yl}-1-isopropyl-4,5-dihydro-1H-imidazole;
1-{2-[3-Chloro-2-(2-naphthalen-1-yl-ethyl)-phenyl]-4,5-dihydro-imidazol-1-yl}-ethanone;
1-Benzyl-2-{2-[2-(5-bromo-2-methoxy-phenyl)-ethyl]-thiophen-3-yl}-4,5-dihydro-1H-imidazole;
3-(2-{2-[2-(5-Bromo-2-methoxy-phenyl)-ethyl]-thiophen-3-yl}-4,5-dihydro-imidazol-1-yl)-propionitrile;
3-(2-Naphthalen-1-yl-ethyl)-2-(1-propyl-4,5-dihydro-1H-imidazol-2-yl)-pyridine;
2-{2-[2-(2-Methoxy-naphthalen-1-yl)-ethyl]-phenyl}-3a,4,5,6,7,7a-hexahydro-1H-benzoimidazole;
(2-{2-[2-(2-Methoxy-naphthalen-1-yl)-ethyl]-phenyl}-4,5-dihydro-imidazol-1-yl)-acetonitrile;
2-[3-Fluoro-2-(2-naphthalen-1-yl-ethyl)-phenyl]-4,5-dihydro-1H-imidazole;
2-(2-{2-[(tert-Butyl-dimethyl-silanyloxy)-naphthalen-1-yl]-ethyl}-3-fluoro-phenyl)-4,5-dihydro-1H-imidazole;
2-[2-(2-Benzofuran-7-yl-ethyl)-3-fluoro-phenyl]-4,5-dihydro-1H-imidazole;
1-(2,4-Bis-trifluoromethyl-benzyl)-2-{2-[2-(5-bromo-2-methoxy-phenyl)-ethyl]-3-chloro-phenyl}-4,5-dihydro-1H-imidazole;
1-(3,5-Bis-trifluoromethyl-benzyl)-2-{2-[2-(5-bromo-2-methoxy-phenyl)-ethyl]-3-chloro-phenyl}-4,5-dihydro-1H-imidazole;
2-[3-Chloro-2-(2-naphthalen-1-yl-ethyl)-phenyl]-1-propyl-4,5-dihydro-1H-imidazole;
2-[3-Chloro-2-(2-naphthalen-1-yl-ethyl)-phenyl]-1-isopropyl-4,5-dihydro-1H-imidazole;
2-[3-Chloro-2-(2-naphthalen-1-yl-ethyl)-phenyl]-3a,4,5,6,7,7a-hexahydro-1H-benzoimidazole;
{2-[2-(2-Naphthalen-1-yl-ethyl)-phenyl]-4,5-dihydro-imidazol-1-yl}-acetonitrile;
(2-{2-[2-(2-Methyl-naphthalen-1-yl)-ethyl]-phenyl}-4,5-dihydro-imidazol-1-yl)-acetonitrile;
{2-[3-Chloro-2-(2-naphthalen-1-yl-ethyl)-phenyl]-4,5-dihydro-imidazol-1-yl}-acetonitrile;
2-(3-Fluoro-2-{2-[2-(3-methyl-butoxy)-naphthalen-1-yl]-ethyl}-phenyl)-4,5-dihydro-1H-imidazole;
2-{2-[2-(2-Cyclohexylmethoxy-naphthalen-1-yl)-ethyl]-3-fluoro-phenyl}-4,5-dihydro-1H-imidazole;

2-(1-{2-[2-(4,5-Dihydro-1H-imidazol-2-yl)-6-fluoro-phenyl]-ethyl}-naphthalen-2-yloxy)-ethylamine;
[2-(1-{2-[2-(4,5-Dihydro-1H-imidazol-2-yl)-6-fluoro-phenyl]-ethyl}-naphthalen-2-yloxy)-ethyl]-dimethyl-amine;
4-[2-(1-{2-[2-(4,5-Dihydro-1H-imidazol-2-yl)-6-fluoro-phenyl]-ethyl}-naphthalen-2-yloxy)-ethyl]-morpholine;
[3-(1-{2-[2-(4,5-Dihydro-1H-imidazol-2-yl)-6-fluoro-phenyl]-ethyl}-naphthalen-2-yloxy)-propyl]-dimethyl-amine;
2-[2-(2-Benzo[b]thiophen-7-yl-ethyl)-3-fluoro-phenyl]-4,5-dihydro-1H-imidazole;
2-{2-[2-(2,5-Dimethyl-phenyl)-ethyl]-phenyl}-4,5-dihydro-1H-imidazole;
2-{2-[2-(2,5-Dimethoxy-phenyl)-ethyl]-phenyl}-4,5-dihydro-1H-imidazole;
2-[2-(2-Benzofuran-7-yl-ethyl)-phenyl]-4,5-dihydro-1H-imidazole;
2-(2-{2-[2-(5-Bromo-2-methoxy-phenyl)-ethyl]-3-chloro-phenyl}-4,5-dihydro-imidazol-1-yl)-propionitrile;
3-[2-(2-Naphthalen-1-yl-ethyl)-phenyl]-5,6,7,7a-tetrahydro-1H-pyrrolo[1,2-c]imidazole;
3-[3-Chloro-2-(2-naphthalen-1-yl-ethyl)-phenyl]-5,6,7,7a-tetrahydro-1H-pyrrolo[1,2-c]imidazole;
3-[2-(2-Naphthalen-1-yl-ethyl)-phenyl]-1,5,6,7,8,8a-hexahydro-imidazo[1,5-a]pyridine;
3-[3-Chloro-2-(2-naphthalen-1-yl-ethyl)-phenyl]-1,5,6,7,8,8a-hexahydro-imidazo[1,5-a]pyridine;
2-[2-(2-Benzo[1,3]dioxol-4-yl-ethyl)-3-fluoro-phenyl]-4,5-dihydro-1H-imidazole;
3-{2-[2-(5-Bromo-2-methoxy-phenyl)-ethyl]-phenyl}-1,5,6,7,8,8a-hexahydro-imidazo[1,5-a]pyridine;
2-{2-[2-(5-Bromo-2,3-dihydro-benzofuran-7-y)-ethyl]-phenyl}-4,5-dihydro-1H-imidazole;
4,4,4-Trifluoro-3-{2-[2-(2-naphthalen-1-yl-ethyl)-phenyl]-4,5-dihydro-imidazol-1-yl}-butyronitrile;
3-(2-{2-[2-(5-Bromo-2-methoxy-phenyl)-ethyl]-3-chloro-phenyl}-4,5-dihydro-imidazol-1-yl)-3-methoxy-propionitrile;
3-(2-{2-[2-(5-Bromo-2-methoxy-phenyl)-ethyl]-3-chloro-phenyl}-4,5-dihydro-imidazol-1-yl)-butyronitrile;
3-{2-[2-(2-Naphthalen-1-yl-ethyl)-phenyl]-4,5-dihydro-imidazol-1-yl}-pentanenitrile;
3-(2-{2-[2-(5-Bromo-2-methoxy-phenyl)-ethyl]-3-chloro-phenyl}-4,5-dihydro-imidazol-1-yl)-4,4,4-trifluoro-butyronitrile;
3-(2-{2-[2-(5-Bromo-2-methoxy-phenyl)-ethyl]-3-chloro-phenyl}-4,5-dihydro-imidazol-1-yl)-pentanenitrile;
2-[2-(2-Benzo[1,3]dioxol-4-yl-ethyl)-3-chloro-phenyl]-4,5-dihydro-1H-imidazole;
2-[2-(2-Benzo[1,3]dioxol-4-yl-ethyl)-phenyl]-4,5-dihydro-1H-imidazole;
3-Methoxy-3-{2-[2-(2-naphthalen-1-yl-ethyl)-phenyl]-4,5-dihydro-imidazol-1-yl}-propionitrile;
3-[2-(2-Benzo[1,3]dioxol-4-yl-ethyl)-phenyl]-1,5,6,7,8,8a-hexahydro-imidazo[1,5-a]pyridine;
3-[2-(2-Benzo[1,3]dioxol-4-yl-ethyl)-phenyl]-5,6,7,7a-tetrahydro-1H-pyrrolo[1,2-c]imidazole;
3-{2-[2-(5-Bromo-2-methoxy-phenyl)-ethyl]-3-fluoro-phenyl}-1,5,6,7,8,8a-hexahydro-imidazo[1,5-a]pyridine;
3-{2-[2-(5-Bromo-2-methoxy-phenyl)-ethyl]-3-fluoro-phenyl}-5,6,7,7a-tetrahydro-1H-pyrrolo[1,2-c]imidazole;
2-{2-[2-(6-Bromo-benzo[1,3]dioxol-4-yl)-ethyl]-phenyl}-4,5-dihydro-1H-imidazole;
2-{2-[2-(5-Bromo-2-cyclohexylmethoxy-phenyl)-ethyl]-3-chloro-phenyl}-4,5-dihydro-1H-imidazole;
2-{2-[2-(5-Bromo-benzofuran-7-yl)-ethyl]-phenyl}-4,5-dihydro-1H-imidazole;
[2-(4-Bromo-2-{2-[2-chloro-6-(4,5-dihydro-1H-imidazol-2-yl)-phenyl]-ethyl}-phenoxy)-ethyl]-dimethyl-amine;
2-(4-Bromo-2-{2-[2-chloro-6-(4,5-dihydro-1H-imidazol-2-yl)-phenyl]-ethyl}-phenoxy)-ethylamine;
2-{2-[2-(2-Bromo-5-fluoro-phenyl)-ethyl]-phenyl}-4,5-dihydro-1H-imidazole;
2-{2-[2-(5-Bromo-2-fluoro-phenyl)-ethyl]-phenyl}-4,5-dihydro-1H-imidazole;
2-[1-(2-Naphthalen-1-yl-ethyl)-pyrrolidin-2-yl]-4,5-dihydro-1H-imidazole;
2-{2-[2-(5-Chloro-2-fluoro-phenyl)-ethyl]-phenyl}-4,5-dihydro-1H-imidazole;
2-{2-[2-(5-Bromo-2-chloro-phenyl)-ethyl]-phenyl}-4,5-dihydro-1H-imidazole;
2-{2-[2-(2-Chloro-6-fluoro-phenyl)-ethyl]-phenyl}-4,5-dihydro-1H-imidazole;
2-[2-(2-Biphenyl-4-yl-ethyl)-phenyl]-4,5-dihydro-1H-imidazole;
2-{2-[2-(3,5-Dimethoxy-phenyl)-ethyl]-phenyl}-4,5-dihydro-1H-imidazole;
2-[2-(2-Benzo[b]thiophen-4-yl-ethyl)-3-fluoro-phenyl]-4,5-dihydro-1H-imidazole;
2-[2-(2-Benzo[b]thiophen-6-yl-ethyl)-3-fluoro-phenyl]-4,5-dihydro-1H-imidazole;
2-{2-[2-(3-Methoxy-phenyl)-ethyl]-phenyl}-4,5-dihydro-1H-imidazole;
2-{3-Chloro-2-[2-(2-methyl-naphthalen-1-yl)-ethyl]-phenyl}-3a,4,5,6,7,7a-hexahydro-1H-benzoimidazole;
2-{2-[2-(2,3-Dihydro-benzofuran-7-yl)-ethyl]-phenyl}-4,5-dihydro-1H-imidazole;
2-{2-[2-(2-Bromo-5-methoxy-phenyl)-ethyl]-phenyl}-4,5-dihydro-1H-imidazole;
2-{2-[2-(2,5-Difluoro-phenyl)-ethyl]-phenyl}-4,5-dihydro-1H-imidazole;
2-{2-[2-(5-Bromo-benzofuran-7-yl)-ethyl]-3-fluoro-phenyl}-4,5-dihydro-1H-imidazole;
2-{2-[2-(5-Chloro-2-methoxy-phenyl)-ethyl]-phenyl}-4,5-dihydro-1H-imidazole;
2-{2-[2-(5-Fluoro-2-methoxy-phenyl)-ethyl]-phenyl}-4,5-dihydro-1H-imidazole;
2-{2-[2-(2,5-Dibromo-phenyl)-ethyl]-phenyl}-4,5-dihydro-1H-imidazole;
2-{2-[2-(5-Bromo-2-methoxy-phenyl)-ethyl]-phenyl}-4-isopropyl-1-methyl-4,5-dihydro-1H-imidazole;
2-{2-[2-(5-Bromo-2-methoxy-phenyl)-ethyl]-phenyl}-5-ethyl-1-methyl-4,5-dihydro-1H-imidazole;
2-{2-[2-(5-Bromo-2-methoxy-phenyl)-ethyl]-phenyl}-1,4-dimethyl-4,5-dihydro-1H-imidazole;
2-{2-[2-(5-Bromo-2-methoxy-phenyl)-ethyl]-3-fluoro-phenyl}-1-methyl-4,5-dihydro-1H-imidazole;
2-{2-[2-(5-Bromo-2-methoxy-phenyl)-ethyl]-3-fluoro-phenyl}-1-tert-butyl-4,5-dihydro-1H-imidazole;
2-{2-[2-(5-Bromo-2-methoxy-phenyl)-ethyl]-3-fluoro-phenyl}-1-butyl-4,5-dihydro-1H-imidazole;
2-{2-[2-(5-Bromo-2-methoxy-phenyl)-ethyl]-3-fluoro-phenyl}-1-isopropyl-4,5-dihydro-1H-imidazole;
1-[3-(2-{2-[2-(5-Bromo-2-methoxy-phenyl)-ethyl]-3-fluoro-phenyl}-4,5-dihydro-imidazol-1-yl)-propyl]-4-methyl-piperazine;
2-[2-(2-Naphthalen-2-yl-ethyl)-phenyl]-4,5-dihydro-1H-imidazole;
2-{2-[2-(5-Bromo-benzo[b]thiophen-7-yl)-ethyl]-3-fluoro-phenyl}-4,5-dihydro-1H-imidazole;
8-{2-[2-(4,5-Dihydro-1H-imidazol-2-yl)-phenyl]-ethyl}-quinoline;
2-{2-[2-(5-Bromo-2-methoxy-phenyl)-ethyl]-3-fluoro-phenyl}-1-(2-fluoro-ethyl)-4,5-dihydro-1H-imidazole;

2-{2-[2-(5-Bromo-2-methoxy-phenyl)-ethyl]-3-fluoro-phenyl}-1-(2-pyrrolidin-1-yl-ethyl)-4,5-dihydro-1H-imidazole;
2-{2-[2-(5-Bromo-2-methoxy-phenyl)-ethyl]-3-fluoro-phenyl}-1-(3-pyrrolidin-1-yl-propyl)-4,5-dihydro-1H-imidazole;
[3-(2-{2-[2-(5-Bromo-2-methoxy-phenyl)-ethyl]-3-fluoro-phenyl}-4,5-dihydro-imidazol-1-yl)-propyl]-diethyl-amine;
4-[3-(2-{2-[2-(5-Bromo-2-methoxy-phenyl)-ethyl]-3-fluoro-phenyl}-4,5-dihydro-imidazol-1-yl)-propyl]-morpholine;
2-{2-[2-(2,5-Dichloro-phenyl)-ethyl]-phenyl}-4,5-dihydro-1H-imidazole;
2-{2-[2-(5-Bromo-2-methoxy-phenyl)-ethyl]-phenyl}-1,5-dimethyl-4,5-dihydro-1H-imidazole;
2-{2-[2-(2-Bromo-5-chloro-phenyl)-ethyl]-phenyl}-4,5-dihydro-1H-imidazole;
2-{2-[2-(2,5-Dibromo-phenyl)-ethyl]-3-fluoro-phenyl}-4,5-dihydro-1H-imidazole;
2-{2-[2-(2-Bromo-5-chloro-phenyl)-ethyl]-3-fluoro-phenyl}-4,5-dihydro-1H-imidazole;
2-{2-[2-(5-Bromo-2-chloro-phenyl)-ethyl]-3-fluoro-phenyl}-4,5-dihydro-1H-imidazole;
2-{2-[2-(3-Bromo-phenyl)-ethyl]-phenyl}-4,5-dihydro-1H-imidazole;
2-{2-[2-(5-Bromo-2-methoxy-phenyl)-ethyl]-3-fluoro-phenyl}-1-(2,2,2-trifluoro-ethyl)-4,5-dihydro-1H-imidazole;
2-{2-[2-(5-Bromo-2-methoxy-phenyl)-ethyl]-phenyl}-1,4,5-trimethyl-4,5-dihydro-1H-imidazole;
5-Benzyloxymethyl-2-{2-[2-(5-bromo-2-methoxy-phenyl)-ethyl]-phenyl}-1-methyl-4,5-dihydro-1H-imidazole;
2-{2-[2-(5-Bromo-2-methoxy-phenyl)-ethyl]-phenyl}-4-ethyl-1-methyl-4,5-dihydro-1H-imidazole;
2-{2-[2-(5-Bromo-2-methyl-benzofuran-7-yl)-ethyl]-phenyl}-4,5-dihydro-1H-imidazole;
2-{2-[2-(6-Bromo-benzo[1,3]dioxol-4-yl)-ethyl]-3-chloro-phenyl}-4,5-dihydro-1H-imidazole;
2-{2-[2-(6-Bromo-benzo[1,3]dioxol-4-yl)-ethyl]-3-fluoro-phenyl}-4,5-dihydro-1H-imidazole;
2-{2-[2-(5-Bromo-benzo[b]thiophen-7-yl)-ethyl]-phenyl}-4,5-dihydro-1H-imidazole;
2-{2-[2-(5-Bromo-2-methoxy-phenyl)-ethyl]-6-chloro-phenyl}-4,5-dihydro-1H-imidazole;
2-{2-[2-(5-Bromo-2,3-dimethyl-benzofuran-7-yl)-ethyl]-phenyl}-4,5-dihydro-1H-imidazole;
(2-{2-[2-(5-Bromo-2-methoxy-phenyl)-ethyl]-phenyl}-3-methyl-4,5-dihydro-3H-imidazol-4-yl)-methanol;
2-{2-[2-(2,2-Difluoro-benzo[1,3]dioxol-4-yl)-ethyl]-3-fluoro-phenyl}-4,5-dihydro-1H-imidazole;
2-{2-[2-(5-Bromo-2-methoxy-phenyl)-ethyl]-3-fluoro-phenyl}-5,5-dimethyl-4,5-dihydro-1H-imidazole;
2-{2-[2-(2,3,5-Trichloro-phenyl)-ethyl]-phenyl}-4,5-dihydro-1H-imidazole;
2-{2-[2-(3-Bromo-naphthalen-1-yl)-ethyl]-phenyl}-4,5-dihydro-1H-imidazole;
2-{2-[2-(3-Bromo-naphthalen-1-yl)-ethyl]-3-fluoro-phenyl}-4,5-dihydro-1H-imidazole;
2-{2-[2-(5-Bromo-2-methoxy-phenyl)-ethyl]-3-fluoro-phenyl}-5-methyl-4,5-dihydro-1H-imidazole;
4-Chloro-3-{2-[2-(4,5-dihydro-1H-imidazol-2-yl)-6-fluoro-phenyl]-ethyl}-benzonitrile;
2-{2-[2-(5-Bromo-2-trifluoromethoxy-phenyl)-ethyl]-3-fluoro-phenyl}-4,5-dihydro-1H-imidazole;
2-{2-[2-(5-Bromo-2-trifluoromethoxy-phenyl)-ethyl]-phenyl}-4,5-dihydro-1H-imidazole;
2-{2-[2-(5-Bromo-2-trifluoromethoxy-phenyl)-ethyl]-3-chloro-phenyl}-4,5-dihydro-1H-imidazole;
2-{2-[2-(5-Bromo-2-methoxy-phenyl)-ethyl]-6-methoxy-phenyl}-4,5-dihydro-1H-imidazole;
2-{2-[2-(5-Bromo-benzofuran-7-yl)-ethyl]-3-chloro-phenyl}-4,5-dihydro-1H-imidazole;
2-{2-[2-(5-Bromo-2-difluoromethoxy-phenyl)-ethyl]-3-chloro-phenyl}-4,5-dihydro-1H-imidazole;
3-{2-[2-Chloro-6-(4,5-dihydro-1H-imidazol-2-yl)-phenyl]-ethyl}-4-methoxy-benzonitrile;
2-{2-[2-(5-Bromo-benzofuran-7-yl)-ethyl]-3-ethoxy-phenyl}-4,5-dihydro-1H-imidazole;
7-{2-[2-Chloro-6-(4,5-dihydro-1H-imidazol-2-yl)-phenyl]-ethyl}-benzofuran-5-carbonitrile;
2-{2-[2-(8-Bromo-naphthalen-1-yl)-ethyl]-3-chloro-phenyl}-4,5-dihydro-1H-imidazole;
2-{3-Chloro-2-[2-(2-methyl-biphenyl-3-yl)-ethyl]-phenyl}-4,5-dihydro-1H-imidazole;
2-[2-(2-Biphenyl-3-yl-ethyl)-3-chloro-phenyl]-4,5-dihydro-1H-imidazole;
[4-(2-{2-[2-(5-Bromo-2-methoxy-phenyl)-ethyl]-3-chloro-phenyl}-4,5-dihydro-imidazol-1-yl)-pentyl]-diethyl-amine;
2-{2-[2-(4-Bromo-4'-methoxy-biphenyl-2-yl)-ethyl]-3-chloro-phenyl}-4,5-dihydro-1H-imidazole;
2-{2-[2-(4-Bromo-2'-methoxy-biphenyl-2-yl)-ethyl]-3-chloro-phenyl}-4,5-dihydro-1H-imidazole;
2-{2-[2-(4-Bromo-3'-methoxy-biphenyl-2-yl)-ethyl]-3-chloro-phenyl}-4,5-dihydro-1H-imidazole;
2-{2-[2-(6-Bromo-2-methoxy-naphthalen-1-yl)-ethyl]-3-chloro-phenyl}-4,5-dihydro-1H-imidazole;
2-[2-(2-Biphenyl-2-yl-ethyl)-3-chloro-phenyl]-4,5-dihydro-1H-imidazole;
2-{3-Chloro-2-[2-(4-fluoro-naphthalen-1-yl)-ethyl]-phenyl}-4,5-dihydro-1H-imidazole;
2-{2-[2-(4-Bromo-2'-chloro-biphenyl-2-yl)-ethyl]-3-chloro-phenyl}-4,5-dihydro-1H-imidazole;
2-{2-[2-(4-Bromo-3'-chloro-biphenyl-2-yl)-ethyl]-3-chloro-phenyl}-4,5-dihydro-1H-imidazole;
7-{2-[2-(4,5-Dihydro-1H-imidazol-2-yl)-6-fluoro-phenyl]-ethyl}-benzofuran-5-carbonitrile;
2-{2-[2-(4-Bromo-4'-chloro-biphenyl-2-yl)-ethyl]-3-chloro-phenyl}-4,5dihydro-1H-imidazole;
2-{2-[2-(2,5-Dibromo-benzofuran-7-yl)-ethyl]-3-fluoro-phenyl}-4,5-dihydro-1H-imidazole;
2-{3-Fluoro-2-[2-(2-methoxy-5-trifluoromethyl-phenyl)-ethyl]-phenyl}-4,5-dihydro-1H-imidazole;
2-{3-Fluoro-2-[2-(5-phenyl-benzofuran-7-yl)-ethyl]-phenyl}-4,5-dihydro-1H-imidazole;
2-{2-[2-(5-Ethynyl-benzofuran-7-yl)-ethyl]-3-fluoro-phenyl}-4,5-dihydro-1H-imidazole;
2-{3-Fluoro-2-[2-(5-methanesulfonyl-benzofuran-7-yl)-ethyl]-phenyl}-4,5-dihydro-1H-imidazole;
2-{3-Fluoro-2-[2-(5-pyrrol-1-yl-benzofuran-7-yl)-ethyl]-phenyl}-4,5-dihydro-1H-imidazole;
7-{2-[2-Fluoro-6-(1-isopropyl-4,5-dihydro-1H-imidazol-2-yl)-phenyl]-ethyl}-benzofuran-5-carbonitrile;
7-(2-{2-Fluoro-6-[1-(3-pyrrolidin-1-yl-propyl)-4,5-dihydro-1H-imidazol-2-yl]-phenyl}-ethyl)-benzofuran-5-carbonitrile;
7-{2-[2-Fluoro-6-(1-piperidin-4-ylmethyl-4,5-dihydro-1H-imidazol-2-yl)-phenyl]-ethyl}-benzofuran-5-carbonitrile;
4-(2-{2-[2-(5-Bromo-benzofuran-7-yl)-ethyl]-3-fluoro-phenyl}-4,5-dihydro-imidazol-1-ylmethyl)-piperidine;
2-{2-[2-(3-Bromo-naphthalen-1-yl)-ethyl]-3-fluoro-phenyl}-1-(3-pyrrolidin-1-yl-propyl)-4,5-dihydro-1H-imidazole;

2-{2-[2-(5-Bromo-benzofuran-7-yl)-ethyl]-3-fluoro-phenyl}-3a,4,5,6,7,7a-hexahydro-1H-benzoimidazole;
7-{2-[2-Fluoro-6-(3a,4,5,6,7,7a-hexahydro-1H-benzoimidazol-2-yl)-phenyl]-ethyl}-benzofuran-5-carbonitrile;
7-{2-[2-Chloro-6-(3a,4,5,6,7,7a-hexahydro-1H-benzoimidazol-2-yl)-phenyl]-ethyl}-benzofuran-5-carbonitrile;
2-{2-[2-(3-Bromo-naphthalen-1-yl)-ethyl]-3-chloro-phenyl}-3a,4,5,6,7,7a-hexahydro-1H-benzoimidazole;
2-{2-[2-(3-Bromo-naphthalen-1-yl)-ethyl]-3-fluoro-phenyl}-3a,4,5,6,7,7a-hexahydro-1H-benzoimidazole;
2-{2-[2-(5-Bromo-2-methoxy-phenyl)-ethyl]-3-fluoro-phenyl}-3a,4,5,6,7,7a-hexahydro-1H-benzoimidazole;
2-{2-[2-(5-Bromo-2,3-dimethyl-benzofuran-7-yl)-ethyl]-3-fluoro-phenyl}-1-(3-pyrrolidin-1-yl-propyl)-4,5-dihydro-1H-imidazole;
2-{2-[2-(5-Bromo-benzofuran-7-yl)-ethyl]-3-fluoro-phenyl}-1H-imidazole;
2-{2-[2-(5-Bromo-benzofuran-7-yl)-ethyl]-3-fluoro-phenyl}-1-isopropyl-1H-imidazole;
2-{2-[2-(5-Bromo-benzofuran-7-yl)-ethyl]-3-fluoro-phenyl}-1-(3-pyrrolidin-1-yl-propyl)-1H-imidazole;
2-{2-[2-(5-Bromo-3-phenyl-benzofuran-7-yl)-ethyl]-3-fluoro-phenyl}-4,5-dihydro-1H-imidazole;
2-{2-[2-(5-Bromo-3-isopropyl-benzofuran-7-yl)-ethyl]-3-fluoro-phenyl}-4,5-dihydro-1H-imidazole;
2-{2-[2-(5-Bromo-2,3-dimethyl-benzofuran-7-yl)-ethyl]-3-fluoro-phenyl}-4,5-dihydro-1H-imidazole;
2-{2-[2-(3-Bromo-naphthalen-1-yl)-ethyl]-3-fluoro-phenyl}-1-isopropyl-4,5-dihydro-1H-imidazole;
2-{2-[2-(5-Bromo-benzo[b]thiophen-7-yl)-ethyl]-3-fluoro-phenyl}-3a,4,5,6,7,7a-hexahydro-1H-benzoimidazole;
3-{2-[2-Fluoro-6-(3a,4,5,6,7,7a-hexahydro-1H-benzoimidazol-2-yl)-phenyl]-ethyl}-4-methoxy-benzonitrile;
2-{2-[2-(5-Bromo-benzo[b]thiophen-7-yl)-ethyl]-3-fluoro-phenyl}-1-(3-pyrrolidin-1-yl-propyl)-4,5-dihydro-1H-imidazole;
7-(2-{2-Fluoro-6-[1-(3-pyrrolidin-1-yl-propyl)-4,5-dihydro-1H-imidazol-2-yl]-phenyl}-ethyl)-benzo[b]thiophene-5-carbonitrile;
2-{2-[2-(5-Bromo-benzo[b]thiophen-7-yl)-ethyl]-3-chloro-phenyl}-3a,4,5,6,7,7a-hexahydro-1H-benzoimidazole;
3-{2-[2-Chloro-6-(3a,4,5,6,7,7a-hexahydro-1H-benzoimidazol-2-yl)-phenyl]-ethyl}-4-methoxy-benzonitrile;
2-{2-[2-(5-Bromo-benzo[b]thiophen-7-yl)-ethyl]-3-chloro-phenyl}-1-(3-pyrrolidin-1-yl-propyl)-4,5-dihydro-1H-imidazole;
7-(2-{2-Chloro-6-[1-(3-pyrrolidin-1-yl-propyl)-4,5-dihydro-1H-imidazol-2-yl]-phenyl}-ethyl)-benzo[b]thiophene-5-carbonitrile;
7-{2-[2-Chloro-6-(4,5-dihydro-1H-imidazol-2-yl)-phenyl]-ethyl}-benzo[b]thiophene-5-carbonitrile;
7-{2-[2-(4,5-Dihydro-1H-imidazol-2-yl)-6-fluoro-phenyl]-ethyl}-benzo[b]thiophene-5-carbonitrile, and pharmaceutically acceptable salts thereof.

Other compounds of the invention are shown in Table 4.

In one further embodiment, the methods of the invention do not include methods wherein 2-[2-(2,5-dichlorothiophen-3-ylmethylsulfanyl)-phenyl]-1,4,5,6-tetrahydropyrimidine (Compound A); 2[2-(2-chloro-6-fluoro-benzylsulfanyl)-phenyl]-1,4,5,6-tetrahydropyrimidine (Compound B); 1-(6-bromo-2-chloro-quinolin-4-yl)-3-(2-diethylaminoethyl)-urea (Compound AN); 2-[2-(2,6-difluorobenzylsulfanyl)-phenyl]-1,4,5,6-tetrahydropyrimidine (Compound AO); 1-(4-hydroxy-1,3,5-trimethyl-piperadin-4-yl)-ethanone (Compound AR); 4,6-dimethyl-2-piperazin-1-yl-pyrimidine (Compound FP); 2-piperazin-1-yl-pyrimidine (Compound FR); 1-pyridin-2-yl-piperazine (Compound FS); 2-piperazin-1-yl-4-trifluoromethyl pyrimidine (Compound FT); 6-piperazin-1-yl-7-trifluoromethyl-thieno[3,2-b]pyridine-3-carboxylic acid methyl ester (Compound FU); 5-bromo-2-piperazin-1-yl)-pyrimidine (Compound FV); 1-(3-trifluoromethyl-pyridin-2-yl)-piperazine (Compound FW); 1-(5-trifluoromethyl-pyridin-2-yl)-piperazine (Compound FX); piperazine (Compound KY); or (2-Hexyloxy-phenyl)-carbamic acid 2-piperidin-1-yl-1-piperidin-1-ylmethyl-ethyl ester (Compound OQ) are used as MC4-R binding compounds. In another further embodiment, the compounds claimed as MC4-R binding compounds do not include those listed above.

In another embodiment, the methods of the invention do not include methods wherein 2-naphthalen-1-ylmethyl-4,5-dihydro-1H-imidazole (NAPHAZOLINE; Compound AS); 10-[2-(1-methyl-piperadin-2-yl)-ethyl]-2-methylsulfanyl-10H-phenothiazine (THORADIAZINE; THIODIAZINE; Compound AP); (2,6-dichloro-phenyl)-imidazolidin-2-ylidene-amine (CLONIDINE; Compound AY); or 2-benzyl-4,5-dihydro-1H-imidazole (TOLAZOLINE; Compound AZ) are used as MC4-R binding compounds. In another further embodiment, the invention pertain to compounds other than those listed above as MC4-R binding compounds.

In another further embodiment, the methods of the invention do not include 5-(4-chloro-phenyl)-2,5-dihydro-3H-imidazo[2,1-a]-isoindol-5-ol (MASPINDOL; Compound DT) as an MC4-R binding compound. In one embodiment, the compounds of the invention include MC4-R binding compounds other than MASPINDOL.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In an embodiment, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer. Likewise, preferred cycloalkyls have from 4-7 carbon atoms in their ring structure, and more preferably have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids. Examples of halogenated alkyl groups include fluoromethyl, difluoromethyl, trifluoromethyl, chloromethyl, dichloromethyl, trichloromethyl, perfluoromethyl, perchloromethyl, perfluoroethyl, perchloroethyl, etc.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, imidazoline, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, isoindole, indan or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diaryl amino, and alkylaryl amino), acylamino (including alkylcarbonyl amino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, aryl amino, diarylamino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom such as alkyl aminos, alkenyl aminos, dialkyl aminos, aryl aminos, acyl aminos, etc. The term "alkyl amino" includes groups and compounds wherein the nitrogen is bound to at least one additional alkyl group and is included in the term "amino." The term "dialkyl amino" includes groups wherein the nitrogen atom is bound to at least two additional alkyl groups and is included in the term "amino." The term "arylamino" and "diarylamino" include groups wherein the nitrogen is bound to at least one or two aryl groups, respectively, and are included in the term "amino." The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group and is included in the term "amino."

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties which contain a carbon connected with a double bond to an oxygen atom, and tautomeric forms thereof. Examples of moieties which contain a carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties which are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "thiol" includes groups with an —SH group. In certain embodiments, it may also include thioethers, thioalkyls, thioaryls, thiocarbonyls, as described above.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" include moieties with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "heterocycle" or "heterocyclic" includes saturated, unsaturated, aromatic ("heteroaryls" or "heteroaromatic") and polycyclic rings which contain one or more heteroatoms. Examples of heterocycles include, for example, benzodioxazole, benzofuran, benzoimidazole, benzothiazole, benzothiophene, benzoxazole, deazapurine, furan, indole, indolizine, imidazole, isooxazole, isoquinoline, isothiaozole, methylenedioxyphenyl, napthridine, oxazole, purine, pyrazine, pyrazole, pyridazine, pyridine, pyrimidine, pyrrole, quinoline, tetrazole, thiazole, thiophene, and triazole. Other heterocycles include morpholine, piprazine, piperidine, thiomorpholine, and thioazolidine. The heterocycles may be substituted or unsubstituted. Examples of substituents include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

In a further embodiment, the compound is an antagonist of the MC4-R. In another embodiment, the compound is an agonist of the MC4-R. Compounds which are agonists of MC4-R can be identified using the cAMP assay given in Example 7.

The term "administering" includes routes of administration which allow the MC4-R binding compound to perform its intended function, e.g. interacting with MC4-Rs and/or treating a MC4-R associated state. Examples of routes of administration which can be used include parental injection (e.g., subcutaneous, intravenous, and intramuscular), intraperitoneal injection, oral, inhalation, and transdermal. The injection can be bolus injections or can be continuous infusion. Depending on the route of administration, the MC4-R binding compound can be coated with or disposed in a selected material to protect it from natural conditions which may detrimentally effect its ability to perform its intended function. The MC4-R binding compound can be administered alone or with a pharmaceutically acceptable carrier. Further, the MC4-R binding compound can be administered as a mixture of MC4-R binding compounds, which also can be coadministered with a pharmaceutically acceptable carrier. The MC4-R binding compound can be administered prior to the onset of a MC4-R associated state, or after the onset of a MC4-R associated state. The MC4-R binding compound also can be administered as a prodrug which is converted to another form in vivo.

In one embodiment of the invention, the invention includes methods of treating an MC4-R associated state by administering the MC4-R binding compound of the invention in combination with art recognized compounds, e.g., therapeutic agents. For example, a patient suffering from cachexia resulting from HIV, may be treated using both the MC4-R binding compounds of the invention in combination with art recognized compounds for treating the cachexia or HIV itself. The term "combination with" includes both simultaneous administration as well as administration of the MC4-R binding compound before the art recognized compound or after the compound. The period between administrations of the MC4-R binding compound and the other agent may be any length of time which allows the compositions to perform their intended function, e.g., the interval may be between few minutes, an hour, more than one hour, etc. In addition, the MC4-R binding compounds may also be administered in combination with other MC4-R binding compounds of the invention.

The invention also features a pharmaceutical composition for the treatment of a MC4-R associated state in a mammal. The pharmaceutical composition includes a pharmaceutically acceptable carrier and an effective amount of an MC4-R binding compound of the formula (I):

$$B-Z-E \quad\quad (I)$$

wherein B is an anchor moiety, Z is a central moiety, and E is a MC4-R interacting moiety. In other embodiments, the pharmaceutical compositions of the invention include MC4-R binding compounds of formulae II, III, IV, V, VI, VII, VIII, IX, XVII, X, and/or XI. Pharmaceutical compositions comprising pharmaceutically acceptable salts of at least one MC4-R binding compound are also included.

The language "effective amount" of the compound is that amount necessary or sufficient to treat or prevent a MC4-R associated state, e.g. prevent the various morphological and somatic symptoms of a MC4-R associated state. The effective amount can vary depending on such factors as the size and weight of the subject, the type of illness, or the particular MC4-R binding compound. For example, the choice of the MC4-R binding compound can affect what constitutes an "effective amount". One of ordinary skill in the art would be able to study the aforementioned factors and make the determination regarding the effective amount of the MC4-R binding compound without undue experimentation. An in vivo assay as described in Example 6 below or an assay similar thereto (e.g., differing in choice of cell line or type of illness) also can be used to determine an "effective amount" of a MC4-R binding compound. The ordinarily skilled artisan would select an appropriate amount of a MC4-R binding compound for use in the aforementioned in vivo assay. Advantageously, the effective amount is effective to treat a disorder associated with pigmentation, bones (e.g., osteoporosis, osteogenesis imperfecta (brittle bone disease), hypophosphatasia, Paget's disease, fibrous dysplasia, osteopetrosis, myeloma bone disease, bone formation, bone remodeling, bone healing, or the depletion of calcium in bone, such as that which is related to primary hyperparathyroidism) or feeding behavior and body weight disorders or diseases associated with weight loss and wasting (e.g., cachexia (e.g., chronic disease associated cachexia including cancer cachexia, AIDS cachexia, CHF cachexia, etc.), anorexia, catabolic wasting, aging associated involuntary weight loss, and sarcopenia.

The regimen of administration can affect what constitutes an effective amount. The MC4-R binding compound can be administered to the subject either prior to or after the onset of a MC4-R associated state. Further, several divided dosages, as well as staggered dosages, can be administered daily or sequentially, or the dose can be continuously infused, or can be a bolus injection. Further, the dosages of the MC4-R binding compound(s) can be proportionally increased or decreased as indicated by the exigencies of the therapeutic or prophylactic situation.

The term "treated," "treating" or "treatment" includes the diminishment or alleviation of at least one symptom associated or caused by the state, disorder or disease being treated. For example, treatment can be diminishment of one or several symptoms of a disorder or complete eradication of a disorder.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preserving agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats an MC4-R associated state.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances includes relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.) A preferred ester group is an acetomethoxy ester group. Preferably, the amount of the MC4-R binding compound is effective to treat a pigmentation, bone, pain, or weight homeostasis disorder (e.g., disorders or diseases associated with weight loss and wasting (e.g., cachexia anorexia, catabolic wasting, aging associated involuntary weight loss, sarcopenia).

The invention also pertains to packaged MC4-R binding compounds. The packaged MC4-R binding compounds include, an MC4-R binding compound (e.g., of formulae I, II, III, IV, V, VI, VII, VIII, IX, XVII, X, and/or XI), a container, and directions for using said MC4-R binding compound to treat an MC4-R associated state, e.g., weight loss, etc.

Examples of MC4-R binding compounds for inclusion in pharmaceutical compositions include, for example, 2-[2-(4-benzyloxy-benzylsulfanyl)-phenyl]-1,4,5,6-tetrahydro-pyrimidine;
2-[2-(2-iodo-benzylsulfanyl)-phenyl]-1,4,5,6-tetrahydro-pyrimidine;
2-[2-(2-methoxy-5-nitro-benzylsulfanyl)-phenyl]-1,4,5,6-tetrahydro-pyrimidine;
2-[2-(naphthalen-1-ylmethylsulfanyl)-phenyl]-1,4,5,6-tetrahydro-pyrimidine;
2-[2-(3-chloro-benzylsulfanyl)-phenyl]-1,4,5,6-tetrahydro-pyrimidine;
2-[2-(2,5-dimethoxy-benzylsulfanyl)-phenyl]-1,4,5,6-tetrahydro-pyrimidine;
2-[2-(3-bromo-benzylsulfanyl)-phenyl]-1,4,5,6-tetrahydro-pyrimidine;
2-[2-(2-iodo-benzylsulfanyl)-phenyl]-4,5-dihydro-1H-imidazole;
2-[2-(2-methoxy-5-nitro-benzylsulfanyl)-phenyl]-4,5-dihydro-1H-imidazole;
2-[2-(2-methoxy-5-nitro-benzyloxy)-phenyl]-1,4,5,6-tetrahydropyrimidine;
2-[2-(2-bromo-benzylsulfanyl)-phenyl]-1,4,5,6-tetrahydro-pyrimidine;
2-[2-(3-iodo-benzylsulfanyl)-phenyl]-1,4,5,6-tetrahydro-pyrimidine;
2-[2-(2-methoxy-5-nitro-benzylsulfanyl)-phenyl]-3a,4,5,6,7,7a-hexahydro-1H-benzoimidazole;
2-{2-[2-(2-methoxy-naphthalen-1-yl)-ethyl]-phenyl}-1,4,5,6-tetrahydropyrimidine;
2-[2-(5-bromo-2-methoxy-benzylsulfanyl)-phenyl]-1,4,5,6,-tetrahydropyrimidine;
2-{2-[2-(2-methyl-naphthalen-1-yl)-ethyl]-phenyl}-1,4,5,6-tetrahydropyrimidine;
2-{2-[2-(2,3-dihydro-benzo[1,4]dioxin-5-yl)-ethyl]-phenyl}-1,4,5,6-tetrahydropyrimidine;
2-[2-(2-methoxy-napthalen-1-ylmethylsulfanyl)-phenyl]-1,4,5,6-tetrahydropyrimidine;
2-(2-Benzylsulfanyl-phenyl)-1,4,5,6-tetrahydro-pyrimidine;
2-(2-Pentadecylsulfanyl-phenyl)-1,4,5,6-tetrahydro-pyrimidine;
2-(2-Cyclohexylmethylsulfanyl-phenyl)-1,4,5,6-tetrahydro-pyrimidine;
2-[2-(2-Methyl-benzylsulfanyl)-phenyl]-1,4,5,6-tetrahydro-pyrimidine;
2-[2-(3-Nitro-benzylsulfanyl)-phenyl]-1,4,5,6-tetrahydro-pyrimidine;
2-[2-(3,5-Dimethoxy-benzylsulfanyl)-phenyl]-1,4,5,6-tetrahydro-pyrimidine;
2-[2-(4-Fluoro-benzylsulfanyl)-phenyl]-1,4,5,6-tetrahydro-pyrimidine;
2-[2-(2-Chloro-benzylsulfanyl)-phenyl]-1,4,5,6-tetrahydro-pyrimidine;
2-[2-(2-Fluoro-benzylsulfanyl)-phenyl]-1,4,5,6-tetrahydro-pyrimidine;
2-[2-(2,4-Bis-trifluoromethyl-benzylsulfanyl)-phenyl]-1,4,5,6-tetrahydro-pyrimidine;
2-[2-(3-Methoxy-benzylsulfanyl)-phenyl]-1,4,5,6-tetrahydro-pyrimidine;
2-[2-(3,5-Bis-trifluoromethyl-benzylsulfanyl)-phenyl]-1,4,5,6-tetrahydro-pyrimidine;
2-[2-(2-Methoxy-5-nitro-benzyloxy)-phenyl]-1,4,5,6-tetrahydro-pyrimidine;
2-[2-(2-Chloro-6-fluoro-benzylsulfanyl)-phenyl]-4,5-dihydro-1H-imidazole;
2-(2-Benzylsulfanyl-phenyl)-4,5-dihydro-1H-imidazole;
2-[2-(2,6-Difluoro-benzylsulfanyl)-phenyl]-1,4,5,6-tetrahydro-pyrimidine;
2-[2-(Naphthalen-1-ylmethoxy)-phenyl]-1,4,5,6-tetrahydro-pyrimidine;
2-[2-(2-Methyl-naphthalen-1-ylmethylsulfanyl)-phenyl]-1,4,5,6-tetrahydro-pyrimidine;
1-{2-[2-(2-Chloro-6-fluoro-benzylsulfanyl)-phenyl]-5,6-dihydro-4H-pyrmidin-1-yl}-ethanone;
2-[2-(2-Chloro-6-fluoro-benzylsulfanyl)-phenyl]-3a,4,5,6,7,7a-hexahydro-1H-benzoimidazole;
2-[2-(2-Iodo-benzylsulfanyl)-phenyl]-3a,4,5,6,7,7a-hexahydro-1H-benzoimidazole;
2-[2-(2,5-Dimethyl-benzylsulfanyl)-phenyl]-1,4,5,6-tetrahydro-pyrimidine;
4-[2-(1,4,5,6-Tetrahydro-pyrimidin-2-yl)-phenylsulfanylmethyl]-quinoline;
2-[2-(2-Methoxy-5-nitro-benzylsulfanyl)-pyridin-3-yl]-1,4,5,6-tetrahydro-pyrimidine;
2-[2-(2-Methoxy-benzylsulfanyl)-phenyl]-1,4,5,6-tetrahydro-pyrimidine;
2-[2-(2-Cyclopentyloxy-benzylsulfanyl)-phenyl]-1,4,5,6-tetrahydro-pyrimidine;
2-[2-(2,3-Dihydro-benzo[1,4]dioxin-5-ylmethylsulfanyl)-phenyl]-1,4,5,6-tetrahydro-pyrimidine;
2-[2-(6-Methoxy-2,3-dihydro-benzo[1,4]dioxin-5-ylmethylsulfanyl)-phenyl]-1,4,5,6-tetrahydro-pyrimidine;

2-[2-(5-fluoro-2-methoxy-benzylsulfanyl)-phenyl]-4,5-di-hydro-1H-imidazole;
1-Methyl-2-[2-(naphthalen-1-ylmethylsulfanyl)-phenyl]-1,4,5,6-tetrahydro-pyrimidine;
2-[2-(5-Bromo-2-methoxy-benzylsulfanyl)-phenyl]-4,5-di-hydro-1H-imidazole;
2-[2-(5-Bromo-2-methoxy-benzyloxy)-phenyl]-1,4,5,6-tetrahydro-pyrimidine;
2-[2-(Naphthalen-1-yloxymethyl)-phenyl]-1,4,5,6-tetrahydro-pyrimidine;
2-[2-(5-Bromo-2-methoxy-benzylsulfanyl)-phenyl]-5,5-dimethyl-1,4,5,6-tetrahydro-pyrimidine;
2-[2-(5-Bromo-2-methoxy-benzylsulfanyl)-phenyl]-5,5-dimethyl-4,5-dihydro-1H-imidazole;
2-[2-(2,6-Dimethoxy-benzylsulfanyl)-phenyl]-1,4,5,6-tetrahydro-pyrimidine;
2-[2-(2-Bromo-6-methoxy-benzylsulfanyl)-phenyl]-1,4,5,6-tetrahydro-pyrimidine;
2-[5-Bromo-2-(5-bromo-2-methoxy-benzylsulfanyl)-phenyl]-4,5-dihydro-1H-imidazole;
2-[5-Bromo-2-(5-bromo-2-methoxy-benzylsulfanyl)-phenyl]-1,4,5,6-tetrahydro-pyrimidine;
2-[4-Bromo-2-(5-bromo-2-methoxy-benzylsulfanyl)-phenyl]-1,4,5,6-tetrahydro-pyrimidine;
2-[2-(2-Bromo-5-methoxy-benzylsulfanyl)-phenyl]-1,4,5,6-tetrahydro-pyrimidine;
2-[2-(5-Bromo-2-methoxy-benzylsulfanyl)-5-methyl-phenyl]-1,4,5,6-tetrahydro-pyrimidine;
2-[2-(Biphenyl-3-ylmethylsulfanyl)-phenyl]-1,4,5,6-tetrahydro-pyrimidine;
2-[2-(5-Chloro-2-methoxy-benzylsulfanyl)-phenyl]-1,4,5,6-tetrahydro-pyrimidine;
2-[2-(2-Methoxy-5-thiophen-3-yl-benzylsulfanyl)-phenyl]-1,4,5,6-tetrahydro-pyrimidine;
2-[2-(Biphenyl-2-ylmethylsulfanyl)-phenyl]-1,4,5,6-tetrahydro-pyrimidine;
2-[2-(5-Iodo-2-methoxy-benzylsulfanyl)-phenyl]-1,4,5,6-tetrahydro-pyrimidine;
2-[2-(5-Bromo-2-methoxy-benzylsulfanyl)-5-fluoro-phenyl]-1,4,5,6-tetrahydro-pyrimidine;
2-[2-(5-Bromo-2-methoxy-benzylsulfanyl)-3-fluoro-phenyl]-1,4,5,6-tetrahydro-pyrimidine;
2-[2-(4,4'-Dimethoxy-biphenyl-3-ylmethylsulfanyl)-phenyl]-1,4,5,6-tetrahydro-pyrimidine;
2-[2-(9H-Fluoren-9-ylsulfanyl)-phenyl]-1,4,5,6-tetrahydro-pyrimidine;
2-[2-(3'-Chloro-4'-fluoro-4-methoxy-biphenyl-3-ylmethylsulfanyl)-phenyl]-1,4,5,6-tetrahydro-pyrimidine;
2-[2-(1-Naphthalen-1-yl-ethylsulfanyl)-phenyl]-1,4,5,6-tetrahydro-pyrimidine;
2-[2-(5-Bromo-2-methoxy-benzylsulfanyl)-5-fluoro-phenyl]-4,5-dihydro-1H-imidazole;
2-(2-Benzhydrylsulfanyl-phenyl)-1,4,5,6-tetrahydro-pyrimidine;
2-[2-(2'-Fluoro-4''-methoxy-[1,1';4',1'']terphenyl-3''-ylmethylsulfanyl)-phenyl]-1,4,5,6-tetrahydro-pyrimidine;
2-(5-Bromo-2-methoxy-benzylsulfanyl)-benzamidine;
2-[4-(Naphthalen-1-ylmethylsulfanyl)-phenyl]-1,4,5,6-tetrahydro-pyrimidine;
2-[2-(5-Ethynyl-2-methoxy-benzylsulfanyl)-phenyl]-1,4,5,6-tetrahydro-pyrimidine;
2-[2-(5-Bromo-2-methoxy-benzylsulfanyl)-benzyl]-1,4,5,6-tetrahydro-pyrimidine;
2-[2-(5-Bromo-2-cyclopentyloxy-benzylsulfanyl)-phenyl]-1,4,5,6-tetrahydro-pyrimidine;
2-[2-(5-Bromo-2-ethoxy-benzylsulfanyl)-phenyl]-1,4,5,6-tetrahydro-pyrimidine;
2-[2-(5-Bromo-2-propoxy-benzylsulfanyl)-phenyl]-1,4,5,6-tetrahydro-pyrimidine;
[2-(5-Bromo-2-methoxy-benzylsulfanyl)-benzyl]-diethyl-amine;
1-[2-(5-Bromo-2-methoxy-benzylsulfanyl)-benzyl]-piperazine;
C-{4-[3-(5-Bromo-2-methoxy-benzylsulfanyl)-quinoxalin-2-yl]-morpholin-2-yl}-methylamine;
2-[2-(2-Methoxy-5-methyl-benzylsulfanyl)-phenyl]-1,4,5,6-tetrahydro-pyrimidine;
2-[2-(5-Bromo-2-methoxy-benzyloxymethyl)-phenyl]-1,4,5,6-tetrahydro-pyrimidine;
[2-(5-Bromo-2-methoxy-benzylsulfanyl)-benzyl]-dimethyl-amine;
2-[2-(5-Bromo-2-isopropoxy-benzylsulfanyl)-phenyl]-1,4,5,6-tetrahydro-pyrimidine;
2-[2-(2-Ethoxy-naphthalen-1-ylmethylsulfanyl)-phenyl]-1,4,5,6-tetrahydro-pyrimidine;
2-[2-(2-Propoxy-naphthalen-1-ylmethylsulfanyl)-phenyl]-1,4,5,6-tetrahydro-pyrimidine;
4-Methoxy-3-[2-(1,4,5,6-tetrahydro-pyrimidin-2-yl)-phenylsulfanylmethyl]-benzonitrile;
1-{4-Methoxy-3-[2-(1,4,5,6-tetrahydro-pyrimidin-2-yl)-phenylsulfanylmethyl]-phenyl}-ethanone;
2-[2-(Naphthalen-1-ylsulfanylmethyl)-phenyl]-1,4,5,6-tetrahydro-pyrimidine;
1-[2-(5-Bromo-2-methoxy-benzylsulfanyl)-benzyl]-piperidine;
C-{4-[2-(2-Methoxy-naphthalen-1-ylmethylsulfanyl)-benzyl]-morpholin-2-yl}-methylamine;
1-[2-(5-Bromo-2-methoxy-benzylsulfanyl)-benzyl]-pyrrolidin-3-ylamine;
1-[2-(2-Methoxy-naphthalen-1-ylmethylsulfanyl)-benzyl]-pyrrolidin-3-ylamine;
3-[2-(5-Bromo-2-methoxy-benzylsulfanyl)-3-fluoro-phenyl]-1,5,6,7,8,8a-hexahydro-imidazo[1,5-a]pyridine;
3-[2-(5-Bromo-2-methoxy-benzylsulfanyl)-3-fluoro-phenyl]-5,6,7,7a-tetrahydro-1H-pyrrolo[1,2-c]imidazole;
2-[2-(Benzo[b]thiophen-3-ylmethylsulfanyl)-phenyl]-1,4,5,6-tetrahydro-pyrimidine;
2-[3-Fluoro-2-(naphthalen-1-ylmethylsulfanyl)-phenyl]-1,4,5,6-tetrahydro-pyrimidine;
2-(Naphthalen-1-ylmethylsulfanyl)-3-(1,4,5,6-tetrahydro-pyrimidin-2-yl)-phenylamine;
2-[2-(5-Bromo-2-methoxy-benzylsulfanyl)-3-chloro-phenyl]-1,4,5,6-tetrahydro-pyrimidine;
2-[2-(2-Methoxy-phenylsulfanylmethyl)-phenyl]-1,4,5,6-tetrahydro-pyrimidine;
1-{2-[2-(5-Bromo-2-methoxy-benzylsulfanyl)-phenyl]-5,6-dihydro-4H-pyrimidin-1-yl}-3-methyl-butan-1-one;
1-{2-[2-(5-Bromo-2-methoxy-benzylsulfanyl)-phenyl]-5,6-dihydro-4H-pyrimidin-1-yl}-2-phenyl-ethanone;
2-[3-(5-Bromo-2-methoxy-benzylsulfanyl)-pyridin-2-yl]-1,4,5,6-tetrahydro-pyrimidine;
N-[2-(5-Bromo-2-methoxy-benzylsulfanyl)-phenyl]-guanidine;
2-[2-(2-Isopropoxy-naphthalen-1-ylmethylsulfanyl)-phenyl]-1,4,5,6-tetrahydro-pyrimidine;
2-[2-(2-Cyclopentyloxy-naphthalen-1-ylmethylsulfanyl)-phenyl]-1,4,5,6-tetrahydro-pyrimidine;
(5-Bromo-2-methoxy-benzyl)-[2-(1,4,5,6-tetrahydro-pyrimidin-2-yl)-phenyl]-amine;
2-[2-(5-Bromo-2-methoxy-benzylsulfanylmethyl)-phenyl]-1,4,5,6-tetrahydro-pyrimidine;
2-[2-(2-Methoxy-naphthalen-1-ylsulfanylmethyl)-phenyl]-1,4,5,6-tetrahydro-pyrimidine;

2-[3-(5-Bromo-2-methoxy-benzylsulfanyl)-pyrazin-2-yl]-1,4,5,6-tetrahydro-pyrimidine;
2-[3-Chloro-2-(naphthalen-1-ylsulfanylmethyl)-phenyl]-1,4,5,6-tetrahydro-pyrimidine;
2-[2-(6-Bromo-2-methoxy-naphthalen-1-ylmethylsulfanyl)-phenyl]-1,4,5,6-tetrahydro-pyrimidine;
2-[3-Chloro-2-(2-methoxy-naphthalen-1-ylsulfanylmethyl)-phenyl]-1,4,5,6-tetrahydro-pyrimidine;
2-[2-(5-Bromo-2-methoxy-phenylsulfanylmethyl)-phenyl]-1,4,5,6-tetrahydro-pyrimidine;
2-[2-(5-Bromo-2-methoxy-phenylsulfanylmethyl)-3-chloro-phenyl]-1,4,5,6-tetrahydro-pyrimidine;
2-[1-(2-Naphthalen-1-yl-ethyl)-1H-pyrrol-2-yl]-1,4,5,6-tetrahydro-pyrimidine;
(5-Bromo-2-methoxy-benzyl)-methyl-[2-(1,4,5,6-tetrahydro-pyrimidin-2-yl)-phenyl]-amine;
2-(5-Bromo-2-methoxy-benzylsulfanyl)-benzylamine;
2-[2-(2-Chloro-phenylsulfanylmethyl)-phenyl]-1,4,5,6-tetrahydro-pyrimidine;
2-[2-(2-Bromo-phenylsulfanylmethyl)-phenyl]-1,4,5,6-tetrahydro-pyrimidine;
2-(2-o-Tolylsulfanylmethyl-phenyl)-1,4,5,6-tetrahydro-pyrimidine;
2-[2-(2,5-Dichloro-phenylsulfanylmethyl)-phenyl]-1,4,5,6-tetrahydro-pyrimidine;
2-(3-Amino-propylamino)-6-(5-bromo-2-methoxy-benzylsulfanyl)-benzonitrile;
2-[2-(5-Bromo-2-methoxy-benzylsulfanyl)-benzyl]-1,4,5,6-tetrahydro-pyrimidine;
[2-(5-Bromo-2-methoxy-benzylsulfanyl)-benzyl]-diethyl-amine;
4-[2-(5-Bromo-2-methoxy-benzylsulfanyl)-benzyl]-morpholine;
3'-(5-Bromo-2-methoxy-benzylsulfanyl)-3,4,5,6-tetrahydro-2H-[1,2']bipyrazinyl;
2-(5-Bromo-2-methoxy-benzylsulfanyl)-3-piperazin-1-yl-6,7-dihydro-quinoxaline;
1-[2-(5-Bromo-2-methoxy-benzylsulfanyl)-benzyl]-piperidine;
C-{4-[2-(2-Methoxy-naphthalen-1-ylmethylsulfanyl)-benzyl]-morpholin-2-yl}-methylamine;
1-[3-(5-Bromo-2-methoxy-benzylsulfanyl)-pyrazin-2-yl]-pyrrolidin-3-ylamine;
1-[3-(5-Bromo-2-methoxy-benzylsulfanyl)-quinoxalin-2-yl]-pyrrolidin-3-ylamine;
1-[2-(2-Methoxy-naphthalen-1-ylmethylsulfanyl)-benzyl]-pyrrolidin-3-ylamine;
C-{4-[3-(5-Bromo-2-methoxy-benzylsulfanyl)-pyrazin-2-yl]-morpholin-3-yl}-methylamine;
1-[3-Fluoro-2-(2-naphthalen-1-yl-ethyl)-benzyl]-piperazine;
1-[2-(5-Bromo-2-methoxy-benzylsulfanyl)-3-chloro-benzyl]-azetidine;
1-[2-(5-Bromo-2-methoxy-benzylsulfanyl)-3-chloro-benzyl]-pyrrolidin-3-ol;
[2-(Naphthalen-1-ylmethylsulfanyl)-phenyl]-carbamic acid 1-aza-bicyclo[2.2.2]oct-3-yl ester;
[2-(2-Methyl-naphthalen-1-ylmethylsulfanyl)-phenyl]-carbamic acid 1-aza-bicyclo[2.2.2]oct-3-yl ester;
[2-(2-Methyl-naphthalen-1-ylmethylsulfanyl)-phenyl]-carbamic acid 2-piperidin-1-yl-ethyl ester;
{1-[2-(5-Bromo-2-methoxy-benzylsulfanyl)-3-chloro-benzyl]-pyrrolidin-2-yl}-methanol;
4-tert-Butyl-N-naphthalen-1-ylmethyl-N-(2-piperidin-1-yl-ethyl)-benzamide;
N,N-Dimethyl-N'-naphthalen-2-ylmethyl-N'-naphthalen-1-ylmethyl-propane-1,3-diamine;
N-(5-Bromo-2-methoxy-benzyl)-N',N'-dimethyl-N-naphthalen-1-ylmethyl-propane-1,3-diamine;
1-Naphthalen-1-ylmethyl-3-phenethyl-1-(2-piperidin-1-yl-ethyl)-thiourea;
3-(4-Dimethylamino-phenyl)-1-(3-dimethylamino-propyl)-1-naphthalen-1-ylmethyl-thiourea;
4-[2-(5-Bromo-2-methoxy-benzylsulfanyl)-3-chloro-benzylamino]-piperidine-1-carboxylic acid ethyl ester;
2-[2-(2-Naphthalen-1-yl-ethyl)-phenyl]-ethylamine;
Naphthalene-2-sulfonic acid (2-dimethylamino-ethyl)-naphthalen-1-ylmethyl-amide;
1-[2-(5-Bromo-2-methoxy-benzylsulfanyl)-3-chloro-benzyl]-2-methoxymethyl-pyrrolidine;
(2-Hexyloxy-phenyl)-carbamic acid 2-piperidin-1-yl-1-piperidin-1-ylmethyl-ethyl ester;
3-[2-(5-Bromo-2-methoxy-benzylsulfanyl)-benzyloxy]-pyrrolidine;
2-[2-(5-Bromo-2-methoxy-benzylsulfanyl)-benzyloxymethyl]-pyrrolidine;
2-[2-(Naphthalen-1-ylsulfanylmethyl)-phenyl]-piperidine;
3-[2-(5-Bromo-2-methoxy-benzylsulfanyl)-benzylamino]-propan-1-ol;
3-[2-(5-Bromo-2-methoxy-benzylsulfanyl)-benzylamino]-3-methyl-butan-1-ol;
1-[2-(5-Bromo-2-methoxy-benzylsulfanyl)-benzyl]-pyrrolidin-3-ol;
{1-[2-(5-Bromo-2-methoxy-benzylsulfanyl)-benzyl]-pyrrolidin-2-yl}-methanol;
{1-[2-(Naphthalen-1-ylsulfanylmethyl)-benzyl]-piperidin-2-yl}-methanol;
2-[2-(Naphthalen-1-ylsulfanylmethyl)-pyrrolidin-1-yl]-ethyl-N-pyrrolidine;
N-pyrrolyl-[1-(2-naphthalen-1-yl-ethyl)-pyrrolidin-2-ylmethyl]-amine;
1-(2-Naphthalen-1-yl-ethyl)-piperidine-2-carboxylic acid methyl ester;
(3-Bromo-benzyl)-(1-ethyl-pyrrolidin-2-ylmethyl)-naphthalen-1-ylmethyl-amine;
3-[2-(5-Bromo-2-methoxy-benzylsulfanyl)-benzyloxy]-piperidine;
(5-Bromo-2-methoxy-benzyl)-(1-ethyl-pyrrolidin-2-ylmethyl)-naphthalen-1-ylmethyl-amine;
(1-Ethyl-pyrrolidin-2-ylmethyl)-naphthalen-2-ylmethyl-naphthalen-1-ylmethyl-amine;
2-[2-(5-Bromo-2-methoxy-benzylsulfanyl)-benzyloxymethyl]-pyrrolidine;
(3-Bromo-benzyl)-(3-imidazol-1-yl-propyl)-naphthalen-1-ylmethyl-amine;
(3-Imidazol-1-yl-propyl)-naphthalen-2-ylmethyl-naphthalen-1-ylmethyl-amine;
[2-(Naphthalen 1-ylmethylsulfanyl)-phenyl]-carbamic acid 2-pipenidin-1-yl-1-piperidin-1-ylmethyl-ethyl ester;
[2-(Naphthalen-1-ylmethylsulfanyl)-phenyl]-carbamic acid 2-dimethylamino-ethyl ester;
1-[2-(Naphthalen-1-ylsulfanylmethyl)-benzyl]-piperazine;
[3-(2-Methyl-piperidin-1-yl)-propyl]-[2-(naphthalen-1-ylsulfanylmethyl)-benzyl]-amine;
1-[3-Chloro-2-(naphthalen-1-ylsulfanylmethyl)-benzyl]-piperazine;
N,N-Dimethyl-N'-(2-naphthalen-1-yl-ethyl)-N'-naphthalen-1-ylmethyl-ethane-1,2-diamine;
{1-[2-(5-Bromo-2-methoxy-benzylsulfanyl)-3-chloro-benzyl]-piperidin-2-yl}-methanol;
1-[2-(2-Naphthalen-1-yl-ethyl)-benzyl]-piperazine;
[3-(2-Methyl-piperidin-1-yl)-propyl]-[2-(2-naphthalen-1-yl-ethyl)-benzyl]-amine;

1-[3-Fluoro-2-(2-naphthalen-1-yl-ethyl)-benzyl]-piperazine;
{1-[3-Chloro-2-(naphthalen-1-ylsulfanylmethyl)-benzyl]-piperidin-2-yl}-methanol;
{1-[2-(5-Bromo-2-methoxy-benzylsulfanyl)-3-chloro-benzyl]-piperidin-2-yl}-methanol;
{1-[2-(2-Naphthalen-1-yl-ethyl)-benzyl]-piperidin-2-yl}-methanol;
[3-(2-Methyl-piperidin-1-yl)-propyl]-[2-(2-naphthalen-1-yl-ethyl)-benzyl]-amine;
1-[2-(2-Naphthalen-1-yl-ethyl)-benzyl]-pyrrolidin-3-ylamine;
1-Phenyl-3-piperazin-1-yl-5,6,7,8-tetrahydro-isoquinoline-4-carbonitrile;
2-[2-(5-Bromo-2-methoxy-benzylsulfan yl)-phenyl]-6-ethyl-1,4,5,6-tetrahydro-pyrimidine;
2-[2-(4-Methoxy-biphenyl-3-ylmethylsulfanyl)-phenyl]-1,4,5,6-tetrahydro-pyrimidine;
2-[2-(2-Methoxy-5-phenylethynyl-benzylsulfanyl)-phenyl]-1,4,5,6-tetrahydro-pyrimidine;
2-[2-(2-Naphthalen-1-yl-ethyl)-phenyl]-1,4,5,6-tetrahydro-pyrimidine;
2-[3-(2-Methoxy-naphthalen-1-ylsulfanylmethyl)-thiophen-2-yl]-1,4,5,6-tetrahydro-pyrimidine;
2-[2-(2,5-Dimethoxy-phenylsulfanylmethyl)-phenyl]-1,4,5,6-tetrahydro-pyrimidine;
2-[2-(4-Methyl-naphthalen-1-ylmethylsulfanyl)-phenyl]-1,4,5,6-tetrahydro-pyrimidine;
2-[2-(5-Bromo-2-methoxy-benzylsulfanyl)-3-fluoro-phenyl]-4,4-dimethyl-4,5-dihydro-1H-imidazole;
2-[2-(5-Bromo-2-methoxy-benzylsulfanyl)-3-fluoro-phenyl]-5,5-dimethyl-1,4,5,6-tetrahydro-pyrimidine;
2-[3-(Naphthalen-1-ylsulfanylmethyl)-thiophen-2-yl]-1,4,5,6-tetrahydro-pyrimidine;
2-{2-[2-(5-Bromo-2-methoxy-phenyl)-ethyl]-phenyl}-1,4,5,6-tetrahydro-pyrimidine;
2-[3-Chloro-2-(2-naphthalen-1-yl-ethyl)-phenyl]-1,4,5,6-tetrahydro-pyrimidine;
2-{2-[2-(5-Bromo-2-methoxy-phenyl)-ethyl]-3-fluoro-phenyl}-1,4,5,6-tetrahydro-pyrimidine;
2-[2-(5-Bromo-2-methoxy-phenylsulfanylmethyl)-3-fluoro-phenyl]-1,4,5,6-tetrahydro-pyrimidine;
2-[2-(Naphthalen-1-ylsulfanylmethyl)-phenyl]-4,5-dihydro-1H-imidazole;
2-[3-Fluoro-2-(naphthalen-1-ylsulfanylmethyl)-phenyl]-1,4,5,6-tetrahydro-pyrimidine;
2-[3-Bromo-2-(naphthalen-1-ylsulfanylmethyl)-phenyl]-1,4,5,6-tetrahydro-pyrimidine;
2-{2-[2-(5-Bromo-2-methoxy-phenyl)-ethyl]-3-chloro-phenyl}-1,4,5,6-tetrahydro-pyrimidine;
2-[2-(2-Methoxy-5-trifluoromethyl-benzylsulfanyl)-phenyl]-1,4,5,6-tetrahydro-pyrimidine;
2-[4-(Naphthalen-1-ylsulfanylmethyl)-thiophen-3-yl]-1,4,5,6-tetrahydro-pyrimidine;
2-[2-(Naphthalen-1-ylsulfanylmethyl)-thiophen-3-yl]-1,4,5,6-tetrahydro-pyrimidine;
2-{2-[2-(5-Bromo-2-methoxy-phenyl)-ethyl]-3-trifluoromethyl-phenyl}-1,4,5,6-tetrahydro-pyrimidine;
2-[2-(2-Naphthalen-1-yl-ethyl)-3-trifluoromethyl-phenyl]-1,4,5,6-tetrahydro-pyrimidine;
2-[2-(6-Fluoro-naphthalen-1-ylmethylsulfanyl)-phenyl]-1,4,5,6-tetrahydro-pyrimidine;
{1-[2-(5-Bromo-2-methoxy-benzylsulfanyl)-benzyl]-piperidin-2-yl}-methanol;
2-[3-Fluoro-2-(2-naphthalen-1-yl-ethyl)-phenyl]-1,4,5,6-tetrahydro-pyrimidine;
[2-(5-Bromo-2-methoxy-benzylsulfanyl)-3-chloro-benzyl]-[3-(2-methyl-piperidin-1-yl)-propyl]-amine;
1-[2-(-Bromo-2-methoxy-benzylsulfanyl)-3-chloro-benzyl]-pyrrolidin-3-ylamine;
1-[2-(5-Bromo-2-methoxy-benzylsulfanyl)-3-chloro-benzyl]-piperazine;
5,5-Dimethyl-2-[2-(2-naphthalen-1-yl-ethyl)-phenyl]-4,5-dihydro-1H-imidazole;
2-[3-Fluoro-2-(2-naphthalen-1-yl-ethyl)-phenyl]-5,5-dimethyl-4,5-dihydro-1H-imidazole;
2-[2-(5-Bromo-2-methoxy-benzylsulfanyl)-3,5-difluoro-phenyl]-1,4,5,6-tetrahydro-pyrimidine;
2-[2-(5-Bromo-2-methoxy-benzylsulfanyl)-3,5-difluoro-phenyl]-5,5-dimethyl-4,5-dihydro-1H-imidazole;
3-(2-Naphthalen-1-yl-ethyl)-2-(1,4,5,6-tetrahydro-pyrimidin-2-yl)-phenylamine;
Amino-[2-(2-naphthalen-1-yl-ethyl)-phenyl]-acetonitrile;
1-[2-(2-Naphthalen-1-yl-ethyl)-phenyl]-ethane-1,2-diamine;
2-[2-(5-Bromo-2-methoxy-benzylsulfanyl)-phenyl]-4-methyl-4,5-dihydro-1H-imidazole;
2-[2-(5-Bromo-2-methoxy-benzylsulfanyl)-3-fluoro-phenyl]-4-methyl-4,5-dihydro-1H-imidazole;
2-[2-(5-Bromo-2-methoxy-benzylsulfanyl)-3-chloro-phenyl]-4-methyl-4,5-dihydro-1H-imidazole;
2-[2-(5-Bromo-2-methoxy-benzylsulfanyl)-3,4-difluoro-phenyl]-1,4,5,6-tetrahydro-pyrimidine;
2-[3-Fluoro-2-(naphthalen-1-ylsulfanylmethyl)-phenyl]-5,5-dimethyl-4,5-dihydro-1H-imidazole;
2-{2-[2-(5-Bromo-2-methoxy-phenyl)-1-methyl-ethyl]-phenyl}-1,4,5,6-tetrahydro-pyrimidine;
2-[2-(5-Bromo-2-methoxy benzyl sulfanyl)-3-fluoro-4-trifluoromethyl-phenyl]-4,4-dimethyl-4,5-dihydro-1H-imidazole;
2-[2-(5-Bromo-2-methoxy-benzyl sulfanyl)-3-fluoro-4-trifluoromethyl-phenyl]-5,5-dimethyl-1,4,5,6-tetrahydro-pyrimidine;
2-[3-Methoxy-2-(2-naphthalen-1-yl-ethyl)-phenyl]-1,4,5,6-tetrahydro-pyrimidine;
2-[2-(5-Bromo-2-methoxy-benzylsulfanyl)-3-chloro-phenyl]-1,4,5,6-tetrahydro-pyrimidin-5-ol;
2-{2-[2-(5-Bromo-2-methoxy-phenyl)-ethyl]-3-methoxy-phenyl}-1,4,5,6-tetrahydro-pyrimidine;
1-Amino-3-[2-(5-bromo-2-methoxy-phenyl)-7-chloro-benzo[b]thiophen-3-ylamino]-propan-2-ol;
2-[2-(1-Methyl-2-naphthalen-1-yl-ethyl)-phenyl]-1,4,5,6-tetrahydro-pyrimidine;
3-(5-Bromo-2-methoxy-benzylsulfanyl)-2-fluoro-4-(1,4,5,6-tetrahydro-pyrimidin-2-yl)-phenylamine;
2-{2-[2-(5-Bromo-2-methoxy-phenyl)-ethyl]-3-methyl-phenyl}-1,4,5,6-tetrahydro-pyrimidine;
2-[2-(5-Bromo-2-methoxy-benzylsulfanyl)-3-fluoro-phenyl]-1,4,5,6-tetrahydro-pyrimidin-5-ol;
1-Amino-3-[2-(5-bromo-2-methoxy-phenyl)-7-fluoro-benzo[b]thiophen-3-ylamino]-propan-2-ol;
2-[3-Methoxy-2-(naphthalen-1-ylsulfanylmeth yl)-phenyl]-1,4,5,6-tetrahydro-pyrimidine;
2-[2-(5-Bromo-2-methoxy-benzylsulfanyl)-3-fluoro-phenyl]-1,4,5,6-tetrahydro-pyrimidin-5-ol;
2-[2-(5-Bromo-2-methoxy-benzylsulfanyl)-5-methoxy-phenyl]-1,4,5,6-tetrahydro-pyrimidine;
2-{2-[2-Chloro-6-(1,4,5,6-tetrahydro-pyrimidin-2-yl)-phenyl]-ethyl}-phenol;
2-[3-Methoxy-2-(naphthalen-1-ylsulfanylmethyl)-phenyl]-1,4,5,6-tetrahydro-pyrimidin-5-ol;
2-{2-[2-(5-Bromo-2-methoxy-phenyl)-ethyl]-3-methyl-phenyl}-5-methyl-4,5dihydro-1H-imidazole;

2-{2-[2-(5-Bromo-2-methoxy-phenyl)-ethyl]-3-methyl-phenyl}-1,4,5,6-tetrahydro-pyrimidin-5-ol;
2-[2-(5-Bromo-2-methoxy-benzylsulfanyl)-3,4-difluoro-phenyl]-1,4,5,6-tetrahydro-pyrimidin-5-ol;
2-{2-[2-(5-Bromo-2-methoxy-phenyl)-ethyl]-3-chloro-phenyl}-4,4-dimethyl-4,5-dihydro-1H-imidazole;
2-[2-(5-Bromo-2-methoxy-benzylsulfanyl)-3-fluoro-4-methyl-phenyl]-1,4,5,6-tetrahydro-pyrimidine;
4,4-Dimethyl-2-[2-(naphthalen-1-ylmethylsulfanyl)-phenyl]-4,5-dihydro-oxazole;
2-[2-(5-Bromo-2-methoxy-benzylsulfanyl)-4-methoxy-phenyl]-1,4,5,6-tetrahydro-pyrimidine;
2-[5-(5-Bromo-2-methoxy-benzyl)-2-methyl-thiophen-3-yl]-1,4,5,6-tetrahydro-pyrmidine;
2-{2-[2-(5-Bromo-2-methoxy-phenyl)-ethyl]-thiophen-3-yl}-1,4,5,6-tetrahydro-pyrimidine;
2-{2-[2-(5-Bromo-2-methoxy-phenyl)-ethyl]-3-ethoxy-phenyl}-1,4,5,6-tetrahydro-pyrmidine;
2-{2-[2-(5-Bromo-2-methoxy-phenyl)-ethyl]-3-isopropoxy-phenyl}-1,4,5,6-tetrahydro-pyrimidine;
2-{2-[2-(5-Bromo-2-methoxy-phenyl)-ethyl]-3-fluoro-4-methoxy-phenyl}-1,4,5,6-tetrahydro-pyrimidine;
2-{2-[2-(5-Bromo-2-methoxy-phenyl)-ethyl]-3-isopropoxy-phenyl}-1,4,5,6-tetrahydro-pyrimidin-5-ol;
2-{2-[2-(5-Bromo-2-methoxy-phenyl)-ethyl]-3-methoxy-phenyl}-1,4,5,6-tetrahydro-pyrimidin-5-ol;
2-{2-[2-(5-Bromo-2-methoxy-phenyl)-ethyl]-4-methoxy-phenyl}-1,4,5,6-tetrahydro-pyrimidine;
2-{2-[2-(5-Bromo-2-methoxy-phenyl)-ethyl]-3-ethoxy-phenyl}-1,4,5,6-tetrahydro-pyrimidin-5-ol;
2-[2-(5-Bromo-2-methoxy-phenyl)-ethyl]-3-(1,4,5,6-tetrahydro-pyrimidin-2-yl)-benzonitrile;
2-{3-Benzyloxy-2-[2-(5-bromo-2-methoxy-phenyl)-ethyl]-phenyl}-1,4,5,6-tetrahydro-pyrimidine;
2-{2-[2-(5-Bromo-2-methoxy-phenyl)-ethyl]-4-butyl-phenyl}-1,4,5,6-tetrahydro-pyrimidine;
2-{5-[2-(5-Bromo-2-methoxy-phenyl)-ethyl]-2,3-dihydro-benzo[1,4]dioxin-6-yl}-1,4,5,6-tetrahydro-pyrimidine;
2-{5-[2-(5-Bromo-2-methoxy-phenyl)-ethyl]-8-chloro-2,3-dihydro-benzo[1,4]dioxin-6-yl}-1,4,5,6-tetrahydro-pyrimidine;
2-{2-[2-(5-Bromo-2-methoxy-phenyl)-ethyl]-3-ethyl-phenyl}-1,4,5,6-tetrahydro-pyrimidine;
2-[2-(5-Bromo-2-methoxy-phenyl)-ethyl]-3-propyl-phenyl}-1,4,5,6-tetrahydro-pyrimidine;
2-{2-[2-(5-Bromo-2-methoxy-phenyl)-ethyl]-3-butoxy-phenyl}-1,4,5,6-tetrahydro-pyrimidine;
2-{2-[2-(5-Bromo-2-methoxy-phenyl)-ethyl]-3-isobutoxy-phenyl}-1,4,5,6-tetrahydro-pyrimidine;
2-{2-[2-(5-Bromo-2-methoxy-phenyl)-ethyl]-3-butoxy-phenyl}-1,4,5,6-tetrahydro-pyrimidin-5-ol;
2-[2-(5-Bromo-2-methoxy-benzylsulfanyl)-3-fluoro-phenyl]-5-methoxy-1,4,5,6-tetrahydro-pyrimidine;
2-{2-[2-(5-Bromo-2-methoxy-phenyl)-ethyl]-3-chloro-phenyl}-1-methyl-1,4,5,6-tetrahydro-pyrimidine;
2-[2-(5-Bromo-2-methoxy-benzylsulfanyl)-3-fluoro-phenyl]-1-methyl-4,5-dihydro-1H-imidazole;
[2-(5-Bromo-2-methoxy-benzylsulfanyl)-3-fluoro-phenyl]-1-methyl-4,5-dihydro-1H-imidazole;
2-{2-[3-(1,4,5,6-Tetrahydro-pyrimidin-2-yl)-biphenyl-2-yl]-ethyl}-phenol;
2-{2-[2-(5-Bromo-2-methoxy-phenyl)-ethyl]-3-chloro-phenyl}-1-methyl-4,5-dihydro-1H-imidazole;
N-(3-Amino-propyl)-2-[2-(5-bromo-2-methoxy-phenyl)-ethyl]-6-methoxy-benzamide;
N-(3-Amino-propyl)-2-[2-(5-bromo-2-methoxy-phenyl)-ethyl]-6-methyl-benzamide;
2-[2-(5-Bromo-2-methoxy-benzylsulfanyl)-3-fluoro-phenyl]-5,6-dihydro-4H-pyrimidine-1-carboxylic acid 1-acetoxy-2-methyl-propyl ester;
2-[2-(5-Bromo-2-methoxy-benzylsulfanyl)-3-fluoro-phenyl]-5,6-dihydro-4H-pyrimidine-1-carboxylic acid 1-acetoxy-ethyl ester;
3-(5-Bromo-2-methoxy-phenyl)-5-chloro-3,4-dihydro-isoquinolin-1-ylamine;
2-[2-[2-(5-Bromo-2-methoxy-phenyl)-ethyl]-3-(4-methoxy-benzyloxy)-phenyl]-1,4,5,6-tetrahydro-pyrimidine;
2-{2-[2-(5-Bromo-2-methoxy-phenyl)-ethyl]-3-chloro-phenyl}-5-methyl-1,4,5,6-tetrahydro-pyrimidin-5-ol;
2-[(5-Bromo-2-methoxy-phenyl)-(3-piperidin-1-yl-propylamino)-methyl]-3-chloro-6-methyl-phenol;
1-{2-[2-(5-Bromo-2-methoxy-phenyl)-ethyl]-6-methyl-benzyl}-piperazine;
1-{2-[2-(5-Bromo-2-methoxy-phenyl)-ethyl]-6-methyl-benzyl}-4-methyl-piperazine;
1-{2-[2-(5-Bromo-2-methoxy-phenyl)-ethyl]-6-methyl-benzyl}-piperidine;
{2-[2-(5-Bromo-2-methoxy-phenyl)-ethyl]-6-methyl-benzyl}-diethyl-amine;
3-(5-Bromo-2-methoxy-phenyl)-1,2,3,4-tetrahydro-isoquinoline;
1-{2-[2-(5-Bromo-2-methoxy-phenyl)-ethyl]-3-chloro-benzyl}-piperazine;
1-{2-[2-(5-Bromo-2-methoxy-phenyl)-ethyl]-3-chloro-benzyl}-4-methyl-piperazine;
1-{2-[2-(5-Bromo-2-methoxy-phenyl)-ethyl]-3-chloro-benzyl}-piperidine;
{2-[2-(5-Bromo-2-methoxy-phenyl)-ethyl]-3-chloro-benzyl}-diethyl-amine;
2-{2-[2-(5-Bromo-2-methoxy-phenyl)-ethyl]-3-chloro-phenyl}-4,5-dihydro-1H-imidazole;
(1-{2-[2-(5-Bromo-2-methoxy-phenyl)-ethyl]-3-chloro-benzyl}-piperidin-2-yl)-methanol;
2-{2-[2-(5-Bromo-2-methoxy-phenyl)-ethyl]-3-propoxy-phenyl}-1,4,5,6-tetrahydro-pyrimidine;
1-[2-(5-Bromo-2-methoxy-benzylsulfanyl)-benzyl]-4-methyl-piperazine;
1-{2-[2-(5-Bromo-2-methoxy-phenyl)-ethyl]-6-chloro-benzyl}-piperazine;
1-{2-[2-(5-Bromo-2-methoxy-phenyl)-ethyl]-6-chloro-benzyl}-4-methyl-piperazine;
1-{2-[2-(5-Bromo-2-methoxy-phenyl)-ethyl]-6-chloro-benzyl}-piperidine;
{2-[2-(5-Bromo-2-methoxy-phenyl)-ethyl]-6-chloro-benzyl}-diethyl-amine;
1-(5-Bromo-2-methoxy-benzyl)-2-(4-methoxy-benzyl)-2,3-dihydro-1H-isoindole;
2-{2-[2-(5-Bromo-2-methoxy-phenyl)-ethyl]-3-chloro-phenyl}-5,6-dihydro-4H-pyrimidine-1-carboxylic acid 1-acetoxy-ethyl ester;
1-(2-{2-[2-(5-Bromo-2-methoxy-phenyl)-ethyl]-3-chloro-phenyl}-5,6-dihydro-4H-pyrimidin-1-yl)-ethanone;
1-{2-[2-(5-Bromo-2-methoxy-phenyl)-ethyl]-3-fluoro-benzyl}-4-methyl-piperazine;
{2-[2-(5-Bromo-2-methoxy-phenyl)-ethyl]-3-fluoro-benzyl}-diethyl-amine;
1-{2-[2-(5-Bromo-2-methoxy-phenyl)-ethyl]-3-fluoro-benzyl}-piperidine;
(1-{2-[2-(5-Bromo-2-methoxy-phenyl)-ethyl]-3-fluoro-benzyl}-piperidin-2-yl)-methanol;
4-Fluoro-N-{2-[4-(2-methoxy-phenyl)-piperazin-1-yl]-ethyl}-N-pyridin-2-yl-benzamide;
3-(5-Bromo-2-methoxy-phenyl)-2-methyl-1,2,3,4-tetrahydro-isoquinoline;

1-{2-[2-(5-Bromo-2-methoxy-phenyl)-ethyl]-3-chloro-benzyl}-piperazine;
1-{2-[2-(5-Bromo-2-methoxy-phenyl)-ethyl]-3-chloro-benzyl}-4-methyl-piperazine;
1-{2-[2-(5-Bromo-2-methoxy-phenyl)-ethyl]-3-chloro-benzyl}-piperidine;
{2-[2-(5-Bromo-2-methoxy-phenyl)-ethyl]-3-chloro-benzyl}-diethyl-amine;
2-{2-[2-(5-Bromo-2-methoxy-phenyl)-ethyl]-3-chloro-phenyl}-4,5-dihydro-1H-imidazole;
(1-{2-[2-(5-Bromo-2-methoxy-phenyl)-ethyl]-3-chloro-benzyl}-piperidin-2-yl)-methanol;
2-{2-[2-(5-Bromo-2-methoxy-phenyl)-ethyl]-3-propoxy-phenyl}-1,4,5,6-tetrahydro-pyrimidine;
1-[2-(5-Bromo-2-methoxy-benzylsulfanyl)-benzyl]-4-methyl-piperazine;
1-{2-[2-(5-Bromo-2-methoxy-phenyl)-ethyl]-6-chloro-benzyl}-piperazine;
1-{2-[2-(5-Bromo-2-methoxy-phenyl)-ethyl]-6-chloro-benzyl}-4-methyl-piperazine;
1-{2-[2-(5-Bromo-2-methoxy-phenyl)-ethyl]-6-chloro-benzyl}-piperidine;
{2-[2-(5-Bromo-2-methoxy-phenyl)-ethyl]-6-chloro-benzyl}-diethyl-amine;
1-(5-Bromo-2-methoxy-benzyl)-2-(4-methoxy-benzyl)-2,3-dihydro-1H-isoindole;
2-{2-[2-(5-Bromo-2-methoxy-phenyl)-ethyl]-3-chloro-phenyl}-5,6-dihydro-4H-pyrimidine-1-carboxylic acid 1-acetoxy-ethyl ester;
1-(2-{2-[2-(5-Bromo-2-methoxy-phenyl)-ethyl]-3-chloro-phenyl}-5,6-dihydro-4H-pyrimidin-1-yl)-ethanone;
1-{2-[2-(5-Bromo-2-methoxy-phenyl)-ethyl]-3-fluoro-benzyl}-4-methyl-piperazine;
{2-[2-(5-Bromo-2-methoxy-phenyl)-ethyl]-3-fluoro-benzyl}-diethyl-amine;
1-{2-[2-(5-Bromo-2-methoxy-phenyl)-ethyl]-3-fluoro-benzyl}-piperidine;
4-Fluoro-N-{2-[4-(2-methoxy-phenyl)-piperazin-1-yl]-ethyl}-N-pyridin-2-yl-benzamide;
3-(5-Bromo-2-methoxy-phenyl)-2-methyl-1,2,3,4-tetrahydro-isoquinoline;
2-{2-[2-(5-Bromo-2-methoxy-phenyl)-ethyl]-3-chloro-phenyl}-1-ethyl-4,5-dihydro-1H-imidazole;
{2-[3-(5-Bromo-2-methoxy-phenyl)-3,4-dihydro-1H-isoquinolin-2-yl]-ethyl}-diethyl-amine;
1-(2-{2-[2-(5-Bromo-2-methoxy-phenyl)-ethyl]-3-chloro-phenyl}-4,5-dihydro-imidazol-1-yl)-ethanone;
2-{2-[2-(5-Bromo-2-methoxy-phenyl)-ethyl]-3-chloro-phenyl}-4,5-dihydro-imidazole-1-carboxylic acid ethyl ester;
2-{2-[2-(5-Bromo-2-methoxy-phenyl)-ethyl]-3-chloro-phenyl}-4,5-dihydro-imidazole-1-carboxylic acid isobutyl ester;
2-{2-[2-(5-Bromo-2-methoxy-phenyl)-ethyl]-3-chloro-phenyl}-4,5-dihydro-imidazole-1-carboxylic acid tert-butyl ester;
1-(2-{2-[2-(5-Bromo-2-methoxy-phenyl)-ethyl]-3-chloro-phenyl}-4,5-dihydro-imidazol-1-yl)-2,2-dimethyl-propan-1-one;
1-(5-Bromo-2-methoxy-benzyl)-2,3-dihydro-1H-isoindole;
1-(2-Methoxy-benzyl)-2-methyl-2,3-dihydro-1H-isoindole;
2-Methyl-1-naphthalen-1-ylmethyl-2,3-dihydro-1H-isoindole;
1-{2-[3-Chloro-2-(2-naphthalen-1-yl-ethyl)-phenyl]-4,5-dihydro-imidazol-1-yl}-2,2-dimethyl-propan-1-one;
{2-[1-(5-Bromo-2-methoxy-benzyl)-1,3-dihydro-isoindol-2-yl]-ethyl}-diethyl-amine;
2-[3-Chloro-2-(2-naphthalen-1-yl-ethyl)-phenyl]-1-methyl-1,4,5,6-tetrahydro-pyrimidine;
2-[3-Chloro-2-(2-naphthalen-1-yl-ethyl)-phenyl]-5,6-dihydro-4H-pyrimidine-1-carboxylic acid tert-butyl ester;
2-[3-Chloro-2-(2-naphthalen-1-yl-ethyl)-phenyl]-4,5-dihydro-1H-imidazole;
1-{2-[3-Chloro-2-(2-naphthalen-1-yl-ethyl)-phenyl]-4,5-dihydro-imidazol-1-yl}-ethanone;
2-[3-Chloro-2-(2-naphthalen-1-yl-ethyl)-phenyl]-4,5-dihydro-imidazole-1-carboxylic acid isobutyl ester;
2-[3-Chloro-2-(2-naphthalen-1-yl-ethyl)-phenyl]-4,5-dihydro-imidazole-1-carboxylic acid tert-butyl ester;
2-[3-Chloro-2-(2-naphthalen-1-yl-ethyl)-phenyl]-4,5-dihydro-imidazole-1-carboxylic acid ethyl ester;
2-[2-(5-Bromo-2-methoxy-phenyl)-ethyl]-N-(3-formylamino-propyl)-6-methyl-benzamide;
2-[3-Chloro-2-(2-naphthalen-1-yl-ethyl)-phenyl]-1-ethyl-4,5-dihydro-1H-imidazole;
1-(2-{2-[2-(5-Bromo-2-methoxy-phenyl)-ethyl]-3-chloro-phenyl}-5,6-dihydro-4H-pyrimidin-1-yl)-2,2-dimethyl-propan-1-one;
2-{2-[2-(5-Bromo-2-methoxy-phenyl)-ethyl]-thiophen-3-yl}-4,5-dihydro-1H-imidazole;
2-{2-[2-(5-Bromo-2-methoxy-phenyl)-ethyl]-3-chloro-phenyl}-5,6-dihydro-4H-pyrimidine-1-carboxylic acid isobutyl ester;
2-{2-[2-(5-Bromo-2-methoxy-phenyl)-ethyl]-3-chloro-phenyl}-1-isocyanomethyl-4,5-dihydro-1H-imidazole;
2-{2-[2-(5-Bromo-2-methoxy-phenyl)-ethyl]-thiophen-3-yl}-1-methyl-4,5-dihydro-1H-imidazole;
2-{2-[2-(5-Bromo-2-methoxy-phenyl)-ethyl]-thiophen-3-yl}-1-ethyl-4,5-dihydro-1H-imidazole;
3-(5-Bromo-2-methoxy-benzyl)-2-methyl-2,3-dihydro-isoindol-1-one;
4-(2-Methoxy-benzyl)-2-(4-methoxy-benzyl)-1,2,3,4-tetrahydro-isoquinoline;
4-(5-Bromo-2-methoxy-benzyl)-2-(4-methoxy-benzyl)-1,2,3,4-tetrahydro-isoquinoline;
2-{2-[2-(5-Bromo-2-methoxy-phenyl)-ethyl]-3-chloro-phenyl}-1-propyl-4,5-dihydro-1H-imidazole;
2-{2-[2-(5-Bromo-2-methoxy-phenyl)-ethyl]-3-chloro-phenyl}-3a,4,5,6,7,7a-hexahydro-1H-benzoimidazole;
5,5-Dimethyl-2-[2-(naphthalen-1-ylsulfanylmethyl)-phenyl]-4,5-dihydro-1H-imidazole;
2-[2-(5-Bromo-2-methoxy-benzylsulfanyl)-3-chloro-phenyl]-4,4-dimethyl-4,5-dihydro-1H-imidazole;
N-(5-Bromo-2-methoxy-benzyl)-N'-methyl-N-naphthalen-1-ylmethyl-ethane-1,2-diamine;
2-{2-[2-(5-Bromo-2-methoxy-phenyl)-ethyl]-3-chloro-phenyl}-1-ethyl-1,4,5,6-tetrahydro-pyrimidine;
2-[2-(5-Bromo-2-methoxy-phenyl)-ethyl]-3-chloro-N,N,N'-trimethyl-benzamidine;
2-[3-Chloro-2-(2-naphthalen-1-yl-ethyl)-phenyl]-1-methyl-4,5-dihydro-1H-imidazole;
1-Benzyl-2-{2-[2-(5-bromo-2-methoxy-phenyl)-ethyl]-3-chloro-phenyl}-4,5-dihydro-1H-imidazole;
({2-[2-(5-Bromo-2-methoxy-phenyl)-ethyl]-3-chloro-phenyl}-pyrrolidin-1-yl-methylene)-methyl-amine;
2-{2-[2-(5-Bromo-2-methoxy-phenyl)-ethyl]-3-chloro-phenyl}-1-isopropyl-4,5-dihydro-1H-imidazole;
2-{2-[2-(5-Bromo-2-methoxy-phenyl)-ethyl]-3-chloro-phenyl}-1-(2,2,2-trifluoro-ethyl)-4,5-dihydro-1H-imidazole;
2-[2-(5-Bromo-2-methoxy-benzylsulfanyl)-phenyl]-6-ethyl-1,4,5,6-tetrahydro-pyrimidine;
2-(2-Benzylsulfanyl-phenyl)-3a,4,5,6,7,7a-hexahydro-1H-benzoimidazole;

2-[2-(2-Chloro-6-fluoro-benzylsulfanyl)-phenyl]-3a,4,5,6,7,7a-hexahydro-1H-benzoimidazole;
2-[2-(2-Iodo-benzylsulfanyl)-phenyl]-3a,4,5,6,7,7a-hexahydro-1H-benzoimidazole;
2-[2-(2-Methoxy-5-nitro-benzyl sulfanyl)-phenyl]-3 a,4,5,6,7,7a-hexahydro-1H-benzoimidazole;
3-[2-(5-Bromo-2-methoxy-benzylsulfanyl)-3-fluoro-phenyl]-1,5,6,7,8,8a-hexahydro-imidazo[1,5-a]pyridine;
2-{2-[2-(5-Bromo-2-methoxy-phenyl)-ethyl]-3-fluoro-phenyl}-4,5-dihydro-1H-imidazole;
2-{2-[2-(5-Bromo-2-methoxy-phenyl)-ethyl]-3-ethoxy-phenyl}-1-ethyl-4,5-dihydro-1H-imidazole;
2-{2-[2-(5-Bromo-2-methoxy-phenyl)-ethyl]-3-ethoxy-phenyl}-4,5-dihydro-1H-imidazole;
2-{2-[2-(5-Bromo-2-methoxy-phenyl)-ethyl]-3-ethoxy-phenyl}-1-methyl-4,5-dihydro-1H-imidazole;
2-{2-[2-(5-Bromo-2-methoxy-phenyl)-ethyl]-3-methoxy-phenyl}-1-methyl-4,5-dihydro-1H-imidazole;
2-{2-[2-(5-Bromo-2-methoxy-phenyl)-ethyl]-3-fluoro-phenyl}-1-ethyl-4,5-dihydro-1H-imidazole;
2-[2-(2-Naphthalen-1-yl-ethyl)-phenyl]-4,5-dihydro-1H-imidazole;
1-Ethyl-2-[2-(2-naphthalen-1-yl-ethyl)-phenyl]-4,5-dihydro-1H-imidazole;
1-Methyl-2-[2-(2-naphthalen-1-yl-ethyl)-phenyl]-4,5-dihydro-1H-imidazole;
2-{2-[2-(5-Bromo-2-methoxy-phenyl)-ethyl]-phenyl}-1-ethyl-4,5-dihydro-1H-imidazole;
2-{2-[2-(5-Bromo-2-methoxy-phenyl)-ethyl]-phenyl}-4,5-dihydro-1H-imidazole;
2-{2-[2-(5-Bromo-2-methoxy-phenyl)-ethyl]-6-methyl-phenyl}-4,5-dihydro-1H-imidazole;
2-{2-[2-(5-Bromo-2-methoxy-phenyl)-ethyl]-phenyl}-1-methyl-4,5-dihydro-1H-imidazole;
3-{2-[2-(5-Bromo-2-methoxy-phenyl)-ethyl]-3-chloro-phenyl}-5,6-dihydro-imidazo[2,1-b]thiazole;
1-{2-[2-(5-Bromo-2-methoxy-phenyl)-ethyl]-3-chloro-phenyl}-2-(4,4-dimethyl-4,5-dihydro-1H-imidazol-2-ylsulfanyl)-ethanone;
3-{2-[2-(5-Bromo-2-methoxy-phenyl)-ethyl]-3-chloro-phenyl}-6,6-dimethyl-5,6-dihydro-imnidazo[2, 1-b]thiazole;
{2-[2-(5-Bromo-2-methoxy-phenyl)-ethyl]-3-chloro-benzyl}-(4,5-dihydro-1H-imidazol-2-yl)-amine;
{3-Chloro-2-[2-(2-methoxy-phenyl)-ethyl]-benzyl}-(4,5-dihydro-1H-imidazol-2-yl)-amine;
(2-{2-[2-(5-Bromo-2-methoxy-phenyl)-ethyl]-3-chloro-phenyl}-4,5-dihydro-imidazol-1-yl)-acetic acid;
(2-{2-[2-(5-Bromo-2-methoxy-phenyl)-ethyl]-3-chloro-phenyl}-3a,4,5,6,7,7a-hexahydro-benzoimidazol-1-yl)-acetonitrile;
3-(2-{2-[2-(5-Bromo-2-methoxy-phenyl)-ethyl]-3-chloro-phenyl}-4,5-dihydro-imidazol-1-yl)-propionitrile;
2-(3-Fluoro-2-phenethyl-phenyl)-4,5-dihydro-1H-imidazole;
2-{2-[2-(5-Bromo-2-methoxy-phenyl)-ethyl]-3-chloro-phenyl}-1-propyl-3a,4,5,6,7,7a-hexahydro-1H-benzoimidazole;
3-{2-[2-(5-Bromo-2-methoxy-phenyl)-ethyl]-phenyl}-1,5,6,7,8,8a-hexahydro-imidazo[1,5-a]pyridine;
3-{2-[2-(5-Bromo-2-methoxy-phenyl)-ethyl]-3-chloro-phenyl}-5,6,7,7a-tetrahydro-1H-pyrrolo[1,2-c]imidazole;
3-(2-{2-[2-(5-Bromo-2-methoxy-phenyl)-ethyl]-3-chloro-phenyl}-4,5-dihydro-imidazol-1-yl)-2-methyl-propionitrile;
2-{2-[2-(2-Methyl-naphthalen-1-yl)-ethyl]-phenyl}-3a,4,5,6,7,7a-hexahydro-1H-benzoimidazole;
2-{2-[2-(2-Methyl-naphthalen-1-yl)-ethyl]-phenyl}-4,5-dihydro-1H-imidazole;
2-[2-(2-Naphthalen-1-yl-ethyl)-phenyl]-3a,4,5,6,7,7a-hexahydro-1H-benzoimidazole;
2-{2-[2-(2-Methoxy-naphthalen-1-yl)-ethyl]-phenyl}-4,5-dihydro-1H-imidazole;
2-(1-Isopropyl-4,5-dihydro-1H-imidazol-2-yl)-3-(2-naphthalen-1-yl-ethyl)-pyridine;
2-{2-[2-(5-Bromo-2-methoxy-phenyl)-ethyl]-thiophen-3-yl}-1-propyl-4,5-dihydro-1H-imidazole;
2-{2-[2-(5-Bromo-2-methoxy-phenyl)-ethyl]-thiophen-3-yl}-1-isopropyl-4,5-dihydro-1H-imidazole;
1-{2-[3-Chloro-2-(2-naphthalen-1-yl-ethyl)-phenyl]-4,5-dihydro-imidazol-1-yl}-ethanone;
1-Benzyl-2-{2-[2-(5-bromo-2-methoxy-phenyl)-ethyl]-thiophen-3-yl}-4,5-dihydro-1H-imidazole;
3-(2-{2-[2-(5-Bromo-2-methoxy-phenyl)-ethyl]-thiophen-3-yl}-4,5-dihydro-imidazol-1-yl)-propionitrile;
3-(2-Naphthalen-1-yl-ethyl)-2-(1-propyl-4,5-dihydro-1H-imidazol-2-yl)-pyridine;
2-{2-[2-(2-Methoxy-naphthalen-1-yl)-ethyl]-phenyl}-3a,4,5,6,7,7a-hexahydro-1H-benzoimidazole;
(2-{2-[2-(2-Methoxy-naphthalen-1-yl)-ethyl]-phenyl}-4,5-dihydro-imidazol-1-yl)-acetonitrile;
2-[3-Fluoro-2-(2-naphthalen-1-yl-ethyl)-phenyl]-4,5-dihydro-1H-imidazole;
2-(2-{2-[2-(tert-Butyl-dimethyl-silanyloxy)-naphthalen-1-yl]-ethyl}-3-fluoro-phenyl)-4,5-dihydro-1H-imidazole;
2-[2-(2-Benzofuran-7-yl-ethyl)-3-fluoro-phenyl]-4,5-dihydro-1H-imidazole;
1-(2,4-Bis-trifluoromethyl-benzyl)-2-{2-[2-(5-bromo-2-methoxy-phenyl)-ethyl]-3-chloro-phenyl}-4,5-dihydro-1H-imidazole;
1-(3,5-Bis-trifluoromethyl-benzyl)-2-{2-[2-(5-bromo-2-methoxy-phenyl)-ethyl]-3-chloro-phenyl}-4,5-dihydro-1H-imidazole;
2-[3-Chloro-2-(2-naphthalen-1-yl-ethyl)-phenyl]-1-propyl-4,5-dihydro-1H-imidazole;
2-[3-Chloro-2-(2-naphthalen-1-yl-ethyl)-phenyl]-1-isopropyl-4,5-dihydro-1H-imidazole;
2-[3-Chloro-2-(2-naphthalen-1-yl-ethyl)-phenyl]-3a,4,5,6,7,7a-hexahydro-1H-benzoimidazole;
{2-[2-(2-Naphthalen-1-yl-ethyl)-phenyl]-4,5-dihydro-imidazol-1-yl}-acetonitrile;
(2-{2-[2-(2-Methyl-naphthalen-1-yl)-ethyl]-phenyl}-4,5-dihydro-imidazol-1-yl)-acetonitrile;
{2-[3-Chloro-2-(2-naphthalen-1-yl-ethyl)-phenyl]-4,5-dihydro-imidazol-1-yl}-acetonitrile;
2-(3-Fluoro-2-{2-[2-(3-methyl-butoxy)-naphthalen-1-yl]-ethyl}-phenyl)-4,5-dihydro-1H-imidazole;
2-{2-[2-(2-Cyclohexylmethoxy-naphthalen-1-yl)-ethyl]-3-fluoro-phenyl}-4,5-dihydro-1H-imidazole;
2-(1-{2-[2-(4,5-Dihydro-1H-imidazol-2-yl)-6-fluoro-phenyl]-ethyl}-naphthalen-2-yloxy)-ethylamine;
[2-(1-{2-[2-(4,5-Dihydro-1H-imidazol-2-yl)-6-fluoro-phenyl]-ethyl}-naphthalen-2-yloxy)-ethyl]-dimethyl-amine;
4-[2-(1-{2-[2-(4,5-Dihydro-1H-imidazol-2-yl)-6-fluoro-phenyl]-ethyl}-naphthalen-2-yloxy)-ethyl]-morpholine;
[3-(1-{2-[2-(4,5-Dihydro-1H-imidazol-2-yl)-6-fluoro-phenyl]-ethyl}-naphthalen-2-yloxy)-propyl]-dimethyl-amine;
2-[2-(2-Benzo[b]thiophen-7-yl-ethyl)-3-fluoro-phenyl]-4,5-dihydro-1H-imidazole;
2-{2-[2-(2,5-Dimethyl-phenyl)-ethyl]-phenyl}-4,5-dihydro-1H-imidazole;
2-{2-[2-(2,5-Dimethoxy-phenyl)-ethyl]-phenyl}-4,5-dihydro-1H-imidazole;

2-[2-(2-Benzofuran-7-yl-ethyl)-phenyl]-4,5-dihydro-1H-imidazole;
2-(2-{2-[2-(5-Bromo-2-methoxy-phenyl)-ethyl]-3-chloro-phenyl}-4,5-dihydro-imidazol-1-yl)-propionitrile;
3-[2-(2-Naphthalen-1-yl-ethyl)-phenyl]-5,6,7,7a-tetrahydro-1H-pyrrolo[1,2-c]imidazole;
3-[3-Chloro-2-(2-naphthalen-1-yl-ethyl)-phenyl]-5,6,7,7a-tetrahydro-1H-pyrrolo[1,2-c]imidazole;
3-[2-(2-Naphthalen-1-yl-ethyl)-phenyl]-1,5,6,7,8,8a-hexahydro-imidazo[1,5-a]pyridine;
3-[3-Chloro-2-(2-naphthalen-1-yl-ethyl)-phenyl]-1,5,6,7,8,8a-hexahydro-imidazo[1,5-a]pyridine;
2-[2-(2-Benzo[1,3]dioxol-4-yl-ethyl)-3-fluoro-phenyl]-4,5-dihydro-1H-imidazole;
3-{2-[2-(5-Bromo-2-methoxy-phenyl)-ethyl]-phenyl}-1,5,6,7,8,8a-hexahydro-imidazo[1,5-a]pyridine;
2-{2-[2-(5-Bromo-2,3-dihydro-benzofuran-7-y)-ethyl]-phenyl}-4,5-dihydro-1H-imidazole;
4,4,4-Trifluoro-3-{2-[2-(2-naphthalen-1-yl-ethyl)-phenyl]-4,5-dihydro-imidazol-1-yl}-butyronitrile;
3-(2-{2-[2-(5-Bromo-2-methoxy-phenyl)-ethyl]-3-chloro-phenyl}-4,5-dihydro-imidazol-1-yl)-3-methoxy-propionitrile;
3-(2-{2-[2-(5-Bromo-2-methoxy-phenyl)-ethyl]-3-chloro-phenyl}-4,5-dihydro-imidazol-1-yl)-butyronitrile;
3-{2-[2-(2-Naphthalen-1-yl-ethyl)-phenyl]-4,5-dihydro-imidazol-1-yl}-pentanenitrile;
3-(2-{2-[2-(5-Bromo-2-methoxy-phenyl)-ethyl]-3-chloro-phenyl}-4,5-dihydro-imidazol-1-yl)-4,4,4-trifluoro-butyronitrile;
3-(2-{2-[2-(5-Bromo-2-methoxy-phenyl)-ethyl]-3-chloro-phenyl}-4,5-dihydro-imidazol-1-yl)-pentanenitrile;
2-[2-(2-Benzo[1,3]dioxol-4-yl-ethyl)-3-chloro-phenyl]-4,5-dihydro-1H-imidazole;
2-[2-(2-Benzo[1,3]dioxol-4-yl-ethyl)-phenyl]-4,5-dihydro-1H-imidazole;
3-Methoxy-3-{2-[2-(2-naphthalen-1-yl-ethyl)-phenyl]-4,5-dihydro-imidazol-1-yl}-propionitrile;
3-[2-(2-Benzo[1,3]dioxol-4-yl-ethyl)-phenyl]-1,5,6,7,8,8a-hexahydro-imidazo[1,5-a]pyridine;
3-[2-(2-Benzo[1,3]dioxol-4-yl-ethyl)-phenyl]-5,6,7,7a-tetrahydro-1H-pyrrolo[1,2-c]imidazole;
3-{2-[2-(5-Bromo-2-methoxy-phenyl)-ethyl]-3-fluoro-phenyl}-1,5,6,7,8,8a-hexahydro-imidazo[1,5-a]pyridine;
3-{2-[2-(5-Bromo-2-methoxy-phenyl)-ethyl]-3-fluoro-phenyl}-5,6,7,7a-tetrahydro-1H-pyrrolo[1,2-c]imidazole;
2-{2-[2-(6-Bromo-benzo[1,3]dioxol-4-yl)-ethyl]-phenyl}-4,5-dihydro-1H-imidazole;
2-{2-[2-(5-Bromo-2-cyclohexylmethoxy-phenyl)-ethyl]-3-chloro-phenyl]-4,5-dihydro-1H-imidazole;
2-{2-[2-(5-Bromo-benzofuran-7-yl)-ethyl]-phenyl}-4,5-dihydro-1H-imidazole;
[2-(4-Bromo-2-{2-[2-chloro-6-(4,5-dihydro-1H-imidazol-2-yl)-phenyl]-ethyl}-phenoxy)-ethyl]-dimethyl-amine;
2-(4-Bromo-2-{2-[2-chloro-6-(4,5-dihydro-1H-imidazol-2-yl)-phenyl]-ethyl}-phenoxy)-ethylamine;
2-{2-[2-(2-Bromo-5-fluoro-phenyl)-ethyl]-phenyl}-4,5-dihydro-1H-imidazole;
2-{2-[2-(5-Bromo-2-fluoro-phenyl)-ethyl]-phenyl}-4,5-dihydro-1H-imidazole;
2-[1-(2-Naphthalen-1-yl-ethyl)-pyrrolidin-2-yl]-4,5-dihydro-1H-imidazole;
2-{2-[2-(5-Chloro-2-fluoro-phenyl)-ethyl]-phenyl}-4,5-dihydro-1H-imidazole;
2-{2-[2-(5-Bromo-2-chloro-phenyl)-ethyl]-phenyl}-4,5-dihydro-1H-imidazole;
2-{2-[2-(2-Chloro-6-fluoro-phenyl)-ethyl]-phenyl}-4,5-dihydro-1H-imidazole;
2-[2-(2-Biphenyl-4-yl-ethyl)-phenyl]-4,5-dihydro-1H-imidazole;
2-{2-[2-(3,5-Dimethoxy-phenyl)-ethyl]-phenyl}-4,5-dihydro-1H-imidazole;
2-[2-(2-Benzo[b]thiophen-4-yl-ethyl)-3-fluoro-phenyl]-4,5-dihydro-1H-imidazole;
2-[2-(2-Benzo[b]thiophen-6-yl-ethyl)-3-fluoro-phenyl]-4,5-dihydro-1H-imidazole;
2-{2-[2-(3-Methoxy-phenyl)-ethyl]-phenyl}-4,5-dihydro-1H-imidazole;
2-{3-Chloro-2-[2-(2-methyl-naphthalen-1-yl)-ethyl]-phenyl}-3a,4,5,6,7,7a-hexahydro-1H-benzoimidazole;
2-{2-[2-(2,3-Dihydro-benzofuran-7-yl)-ethyl]-phenyl}-4,5-dihydro-1H-imidazole;
2-{2-[2-(2-Bromo-5-methoxy-phenyl)-ethyl]-phenyl}-4,5-dihydro-1H-imidazole;
2-{2-[2-(2,5-Difluoro-phenyl)-ethyl]-phenyl}-4,5-dihydro-1H-imidazole;
2-{2-[2-(5-Bromo-benzofuran-7-yl)-ethyl]-3-fluoro-phenyl}-4,5-dihydro-1H-imidazole;
2-{2-[2-(5-Chloro-2-methoxy-phenyl)-ethyl]-phenyl}-4,5-dihydro-1H-imidazole;
2-{2-[2-(5-Fluoro-2-methoxy-phenyl)-ethyl]-phenyl}-4,5-dihydro-1H-imidazole;
2-{2-[2-(2,5-Dibromo-phenyl)-ethyl]-phenyl}-4,5-dihydro-1H-imidazole;
2-{2-[2-(5-Bromo-2-methoxy-phenyl)-ethyl]-phenyl}-4-isopropyl-1-methyl-4,5-dihydro-1H-imidazole;
2-{2-[2-(5-Bromo-2-methoxy-phenyl)-ethyl]-phenyl}-5-ethyl-1-methyl-4,5-dihydro-1H-imidazole;
2-{2-[2-(5-Bromo-2-methoxy-phenyl)-ethyl]-phenyl}-1,4-dimethyl-4,5-dihydro-1H-imidazole;
2-{2-[2-(5-Bromo-2-methoxy-phenyl)-ethyl]-3-fluoro-phenyl}-1-methyl-4,5-dihydro-1H-imidazole;
2-{2-[2-(5-Bromo-2-methoxy-phenyl)-ethyl]-3-fluoro-phenyl}-1-tert-butyl-4,5-dihydro-1H-imidazole;
2-{2-[2-(5-Bromo-2-methoxy-phenyl)-ethyl]-3-fluoro-phenyl}-1-butyl-4,5-dihydro-1H-imidazole;
2-{2-[2-(5-Bromo-2-methoxy-phenyl)-ethyl]-3-fluoro-phenyl}-1-isopropyl-4,5-dihydro-1H-imidazole;
1-[3-(2-{2-[2-(5-Bromo-2-methoxy-phenyl)-ethyl]-3-fluoro-phenyl}-4,5-dihydro-imidazol-1-yl)-propyl]-4-methyl-piperazine;
2-[2-(2-Naphthalen-2-yl-ethyl)-phenyl]-4,5-dihydro-1H-imidazole;
2-{2-[2-(5-Bromo-benzo[b]thiophen-7-yl)-ethyl]-3-fluoro-phenyl}-4,5-dihydro-1H-imidazole;
8-{2-[2-(4,5-Dihydro-1H-imidazol-2-yl)-phenyl]-ethyl}-quinoline;
2-{2-[2-(5-Bromo-2-methoxy-phenyl)-ethyl]-3-fluoro-phenyl}-1-(2-fluoro-ethyl)-4,5-dihydro-1H-imidazole;
2-{2-[2-(5-Bromo-2-methoxy-phenyl)-ethyl]-3-fluoro-phenyl}-1-(2-pyrrolidin-1-yl-ethyl)-4,5-dihydro-1H-imidazole;
2-{2-[2-(5-Bromo-2-methoxy-phenyl)-ethyl]-3-fluoro-phenyl}-1-(3-pyrrolidin-1-yl-propyl)-4,5-dihydro-1H-imidazole;
[3-(2-{2-[2-(5-Bromo-2-methoxy-phenyl)-ethyl]-3-fluoro-phenyl}-4,5-dihydro-imidazol-1-yl)-propyl]-diethyl-amine;
4-[3-(2-{2-[2-(5-Bromo-2-methoxy-phenyl)-ethyl]-3-fluoro-phenyl}-4,5-dihydro-imidazol-1-yl)-propyl]-morpholine;
2-{2-[2-(2,5-Dichloro-phenyl)-ethyl]-phenyl}-4,5-dihydro-1H-imidazole;

2-{2-[2-(5-Bromo-2-methoxy-phenyl)-ethyl]-phenyl}-1,5-dimethyl-4,5-dihydro-1H-imidazole;
2-{2-[2-(2-Bromo-5-chloro-phenyl)-ethyl]-phenyl}-4,5-dihydro-1H-imidazole;
2-{2-[2-(2,5-Dibromo-phenyl)-ethyl]-3-fluoro-phenyl}-4,5-dihydro-1H-imidazole;
2-{2-[2-(2-Bromo-5-chloro-phenyl)-ethyl]-3-fluoro-phenyl}-4,5-dihydro-1H-imidazole;
2-{2-[2-(5-Bromo-2-chloro-phenyl)-ethyl]-3-fluoro-phenyl}-4,5-dihydro-1H-imidazole;
2-{2-[2-(3-Bromo-phenyl)-ethyl]-phenyl}-4,5-dihydro-1H-imidazole;
2-{2-[2-(5-Bromo-2-methoxy-phenyl)-ethyl]-3-fluoro-phenyl}-1-(2,2,2-trifluoro-ethyl)-4,5-dihydro-1H-imidazole;
2-{2-[2-(5-Bromo-2-methoxy-phenyl)-ethyl]-phenyl}-1,4,5-trimethyl-4,5-dihydro-1H-imidazole;
5-Benzyloxymethyl-2-{2-[2-(5-bromo-2-methoxy-phenyl)-ethyl]-phenyl}-1-methyl-4,5-dihydro-1H-imidazole;
2-{2-[2-(5-Bromo-2-methoxy-phenyl)-ethyl]-phenyl}-4-ethyl-1-methyl-4,5-dihydro-1H-imidazole;
2-{2-[2-(5-Bromo-2-methyl-benzofuran-7-yl)-ethyl]-phenyl}-4,5-dihydro-1H-imidazole;
2-{2-[2-(6-Bromo-benzo[1,3]dioxol-4-yl)-ethyl]-3-chloro-phenyl}-4,5-dihydro-1H-imidazole;
2-{2-[2-(6-Bromo-benzo[1,3]dioxol-4-yl)-ethyl]-3-fluoro-phenyl}-4,5-dihydro-1H-imidazole;
2-{2-[2-(5-Bromo-benzo[b]thiophen-7-yl)-ethyl]-phenyl}-4,5-dihydro-1H-imidazole;
2-{2-[2-(5-Bromo-2-methoxy-phenyl)-ethyl]-6-chloro-phenyl}-4,5-dihydro-1H-imidazole;
2-{2-[2-(5-Bromo-2,3-dimethyl-benzofuran-7-yl)-ethyl]-phenyl}-4,5-dihydro-1H-imidazole;
(2-{2-[2-(5-Bromo-2-methoxy-phenyl)-ethyl]-phenyl}-3-methyl-4,5-dihydro-3H-imidazol-4-yl)-methanol;
2-{2-[2-(2,2-Difluoro-benzo[1,3]dioxol-4-yl)-ethyl]-3-fluoro-phenyl}-4,5-dihydro-1H-imidazole;
2-{2-[2-(5-Bromo-2-methoxy-phenyl)-ethyl]-3-fluoro-phenyl}-5,5-dimethyl-4,5-dihydro-1H-imidazole;
2-{2-[2-(2,3,5-Trichloro-phenyl)-ethyl]-phenyl}-4,5-dihydro-1H-imidazole;
2-{2-[2-(3-Bromo-naphthalen-1-yl)-ethyl]-phenyl}-4,5-dihydro-1H-imidazole;
2-{2-[2-(3-Bromo-naphthalen-1-yl)-ethyl]-3-fluoro-phenyl}-4,5-dihydro-1H-imidazole;
2-{2-[2-(5-Bromo-2-methoxy-phenyl)-ethyl]-3-fluoro-phenyl}-5-methyl-4,5-dihydro-1H-imidazole;
4-Chloro-3-{2-[2-(4,5-dihydro-1H-imidazol-2-yl)-6-fluoro-phenyl]-ethyl}-benzonitrile;
2-{2-[2-(5-Bromo-2-trifluoromethoxy-phenyl)-ethyl]-3-fluoro-phenyl}-4,5-dihydro-1H-imidazole;
2-{2-[2-(5-Bromo-2-trifluoromethoxy-phenyl)-ethyl]-phenyl}-4,5-dihydro-1H-imidazole;
2-{2-[2-(5-Bromo-2-trifluoromethoxy-phenyl)-ethyl]-3-chloro-phenyl}-4,5-dihydro-1H-imidazole;
2-{2-[2-(5-Bromo-2-methoxy-phenyl)-ethyl]-6-methoxy-phenyl}-4,5-dihydro-1H-imidazole;
2-{2-[2-(5-Bromo-benzofuran-7-yl)-ethyl]-3-chloro-phenyl}-4,5-dihydro-1H-imidazole;
2-{2-[2-(5-Bromo-2-difluoromethoxy-phenyl)-ethyl]-3-chloro-phenyl}-4,5-dihydro-1H-imidazole;
3-{2-[2-Chloro-6-(4,5-dihydro-1H-imidazol-2-yl)-phenyl]-ethyl}-4-methoxy-benzonitrile;
2-{2-[2-(5-Bromo-benzofuran-7-yl)-ethyl]-3-ethoxy-phenyl}-4,5-dihydro-1H-imidazole;
7-{2-[2-Chloro-6-(4,5-dihydro-1H-imidazol-2-yl)-phenyl]-ethyl}-benzofuran-5-carbonitrile;
2-{2-[2-(8-Bromo-naphthalen-1-yl)-ethyl]-3-chloro-phenyl}-4,5-dihydro-1H-imidazole;
2-{3-Chloro-2-[2-(2-methyl-biphenyl-3-yl)-ethyl]-phenyl}-4,5-dihydro-1H-imidazole;
2-[2-(2-Biphenyl-3-yl-ethyl)-3-chloro-phenyl]-4,5-dihydro-1H-imidazole;
[4-(2-{2-[2-(5-Bromo-2-methoxy-phenyl)-ethyl]-3-chloro-phenyl}-4,5-dihydro-imidazol-1-yl)-pentyl]-diethyl-amine;
2-{2-[2-(4-Bromo-4'-methoxy-biphenyl-2-yl)-ethyl]-3-chloro-phenyl}-4,5-dihydro-1H-imidazole;
2-{2-[2-(4-Bromo-2'-methoxy-biphenyl-2-yl)-ethyl]-3-chloro-phenyl}-4,5-dihydro-1H-imidazole;
2-{2-[2-(4-Bromo-3'-methoxy-biphenyl-2-yl)-ethyl]-3-chloro-phenyl}-4,5-dihydro-1H-imidazole;
2-{2-[2-(6-Bromo-2-methoxy-naphthalen-1-yl)-ethyl]-3-chloro-phenyl}-4,5-dihydro-1H-imidazole;
2-[2-(2-Biphenyl-2-yl-ethyl)-3-chloro-phenyl]-4,5-dihydro-1H-imidazole;
2-{3-Chloro-2-[2-(4-fluoro-naphthalen-1-yl)-ethyl]-phenyl}-4,5-dihydro-1H-imidazole;
2-{2-[2-(4-Bromo-2'-chloro-biphenyl-2-yl)-ethyl]-3-chloro-phenyl}-4,5-dihydro-1H-imidazole;
2-{2-[2-(4-Bromo-3'-chloro-biphenyl-2-yl)-ethyl]-3-chloro-phenyl}-4,5-dihydro-1H-imidazole;
7-{2-[2-(4,5-Dihydro-1H-imidazol-2-yl)-6-fluoro-phenyl]-ethyl}-benzofuran-5-carbonitrile;
2-{2-[2-(4-Bromo-4'-chloro-biphenyl-2-yl)-ethyl]-3-chloro-phenyl}-4,5dihydro-1H-imidazole;
2-{2-[2-(2,5-Dibromo-benzofuran-7-yl)-ethyl]-3-fluoro-phenyl}-4,5-dihydro-1H-imidazole;
2-{3-Fluoro-2-[2-(2-methoxy-5-trifluoromethyl-phenyl)-ethyl]-phenyl}-4,5-dihydro-1H-imidazole;
2-{3-Fluoro-2-[2-(5-phenyl-benzofuran-7-yl)-ethyl]-phenyl}-4,5-dihydro-1H-imidazole;
2-{2-[2-(5-Ethynyl-benzofuran-7-yl)-ethyl]-3-fluoro-phenyl}-4,5-dihydro-1H-imidazole;
2-{3-Fluoro-2-[2-(5-methanesulfonyl-benzofuran-7-yl)-ethyl]-phenyl}-4,5-dihydro-1H-imidazole;
2-{3-Fluoro-2-[2-(5-pyrrol-1-yl-benzofuran-7-yl)-ethyl]-phenyl}-4,5-dihydro-1H-imidazole;
7-{2-[2-Fluoro-6-(1-isopropyl-4,5-dihydro-1H-imidazol-2-yl)-phenyl]-ethyl}-benzofuran-5-carbonitrile;
7-(2-{2-Fluoro-6-[1-(3-pyrrolidin-1-yl-propyl)-4,5-dihydro-1H-imidazol-2-yl]-phenyl}-ethyl)-benzofuran-5-carbonitrile;
7-{2-[2-Fluoro-6-(1-piperidin-4-ylmethyl-4,5-dihydro-1H-imidazol-2-yl)-phenyl]-ethyl}-benzofuran-5-carbonitrile;
4-(2-{2-[2-(5-Bromo-benzofuran-7-yl)-ethyl]-3-fluoro-phenyl}-4,5-dihydro-imidazol-1-ylmethyl)-piperidine;
2-{2-[2-(3-Bromo-naphthalen-1-yl)-ethyl]-3-fluoro-phenyl}-1-(3-pyrrolidin-1-yl-propyl)-4,5-dihydro-1H-imidazole;
2-{2-[2-(5-Bromo-benzofuran-7-yl)-ethyl]-3-fluoro-phenyl}-3a,4,5,6,7,7a-hexahydro-1H-benzoimidazole;
7-{2-[2-Fluoro-6-(3a,4,5,6,7,7a-hexahydro-1H-benzoimidazol-2-yl)-phenyl]-ethyl}-benzofuran-5-carbonitrile;
7-{2-[2-Chloro-6-(3a,4,5,6,7,7a-hexahydro-1H-benzoimidazol-2-yl)-phenyl]-ethyl}-benzofuran-5-carbonitrile;
2-{2-[2-(3-Bromo-naphthalen-1-yl)-ethyl]-3-chloro-phenyl}-3a,4,5,6,7,7a-hexahydro-1H-benzoimidazole;
2-{2-[2-(3-Bromo-naphthalen-1-yl)-ethyl]-3-fluoro-phenyl}-3a,4,5,6,7,7a-hexahydro-1H-benzoimidazole;
2-{2-[2-(5-Bromo-2-methoxy-phenyl)-ethyl]-3-fluoro-phenyl}-3a,4,5,6,7,7a-hexahydro-1H-benzoimidazole;

2-{2-[2-(5-Bromo-2,3-dimethyl-benzofuran-7-yl)-ethyl]-3-fluoro-phenyl}-1-(3-pyrrolidin-1-yl-propyl)-4,5-dihydro-1H-imidazole;

2-{2-[2-(5-Bromo-benzofuran-7-yl)-ethyl]-3-fluoro-phenyl}-1H-imidazole;

2-{2-[2-(5-Bromo-benzofuran-7-yl)-ethyl]-3-fluoro-phenyl}-1-isopropyl-1H-imidazole;

2-{2-[2-(5-Bromo-benzofuran-7-yl)-ethyl]-3-fluoro-phenyl}-1-(3-pyrrolidin-1-yl-propyl)-1H-imidazole;

2-{2-[2-(5-Bromo-3-phenyl-benzofuran-7-yl)-ethyl]-3-fluoro-phenyl}-4,5-dihydro-1H-imidazole;

2-{2-[2-(5-Bromo-3-isopropyl-benzofuran-7-yl)-ethyl]-3-fluoro-phenyl}-4,5-dihydro-1H-imidazole;

2-{2-[2-(5-Bromo-2,3-dimethyl-benzofuran-7-yl)-ethyl]-3-fluoro-phenyl}-4,5-dihydro-1H-imidazole;

2-{2-[2-(3-Bromo-naphthalen-1-yl)-ethyl]-3-fluoro-phenyl}-1-isopropyl-4,5-dihydro-1H-imidazole;

2-{2-[2-(5-Bromo-benzo[b]thiophen-7-yl)-ethyl]-3-fluoro-phenyl}-3a,4,5,6,7,7a-hexahydro-1H-benzoimidazole;

3-{2-[2-Fluoro-6-(3a,4,5,6,7,7a-hexahydro-1H-benzoimidazol-2-yl)-phenyl]-ethyl}-4-methoxy-benzonitrile;

2-{2-[2-(5-Bromo-benzo[b]thiophen-7-yl)-ethyl]-3-fluoro-phenyl}-1-(3-pyrrolidin-1-yl-propyl)-4,5-dihydro-1H-imidazole;

7-(2-{2-Fluoro-6-[1-(3-pyrrolidin-1-yl-propyl)-4,5-dihydro-1H-imidazol-2-yl]-phenyl}-ethyl)-benzo[b]thiophene-5-carbonitrile;

2-{2-[2-(5-Bromo-benzo[b]thiophen-7-yl)-ethyl]-3-chloro-phenyl}-3a,4,5,6,7,7a-hexahydro-1H-benzoimidazole;

3-{2-[2-Chloro-6-(3a,4,5,6,7,7a-hexahydro-1H-benzoimidazol-2-yl)-phenyl]-ethyl}-4-methoxy-benzonitrile;

2-{2-[2-(5-Bromo-benzo[b]thiophen-7-yl)-ethyl]-3-chloro-phenyl}-1-(3-pyrrolidin-1-yl-propyl)-4,5-dihydro-1H-imidazole;

7-(2-{2-Chloro-6-[1-(3-pyrrolidin-1-yl-propyl)-4,5-dihydro-1H-imidazol-2-yl]-phenyl}-ethyl)-benzo[b]thiophene-5-carbonitrile;

7-{2-[2-Chloro-6-(4,5-dihydro-1H-imidazol-2-yl)-phenyl]-ethyl}-benzo[b]thiophene-5-carbonitrile;

7-{2-[2-(4,5-Dihydro-1H-imidazol-2-yl)-6-fluoro-phenyl]-ethyl}-benzo[b]thiophene-5-carbonitrile, and pharmaceutically acceptable salts thereof. Also included are compositions containing the compounds listed in Table 4.

In a further embodiment, the pharmaceutical compositions of the invention include compositions wherein the MC4-R binding compound is not 5-(4-chloro-phenyl)-2,5-dihydro-3H-imidazo[2,1-a]-isoindol-5-ol (MASPINDOL; Compound DT).

In another embodiment, the pharmaceutical compositions of the invention include compositions wherein the MC4-R binding compound is not 2-naphthalen-1-ylmethyl-4,5-dihydro-1H-imidazole (NAPHAZOLINE; Compound AS); 10-[2-(1-methyl-piperadin-2-yl)-ethyl]-2-methylsulfanyl-10H-phenothiazine (THORADIAZINE; THIODIAZINE; Compound AP); (2,6-dichloro-phenyl)-imidazolidin-2-ylidene-amine (CLONIDINE; Compound AY); or 2-benzyl-4,5-dihydro-1H-imidazole (TOLAZOLINE; Compound AZ).

In another further embodiment, the pharmaceutical compositions of the invention includes compositions wherein the MC4-R binding compound is not 2-[2-(2,5-dichlorothiophen-3-ylmethylsulfanyl)-phenyl]-1,4,5,6-tetrahydropyrimidine (Compound A); 2[2-(2-chloro-6-fluoro-benzylsulfanyl)-phenyl]-1,4,5,6-tetrahydropyrimidine (Compound B); 1-(6-bromo-2-chloro-quinolin-4-yl)-3-(2-diethylamino-ethyl)-urea (Compound AN); 2-[2-(2,6-difluorobenzylsulfanyl)-phenyl]-1,4,5,6-tetrahydropyrimidine (Compound AO); 1-(4-hydroxy-1,3,5-trimethyl-piperadin-4-yl)-ethanone (Compound AR); 4,6-dimethyl-2-piperazin-1-yl-pyrimidine (Compound FP); 2-piperazin-1-yl-pyrimidine (Compound FR); 1-pyridin-2-yl-piperazine (Compound FS); 2-piperazin-1-yl-4-trifluoromethyl pyrimidine (Compound FT); 6-piperazin-1-yl-7-trifluoromethyl-thieno[3,2-b]pyridine-3-carboxylic acid methyl ester (Compound FU); 5-bromo-2-piperazin-1-yl)-pyrimidine (Compound FV); 1-(3-trifluoromethyl-pyridin-2-yl)-piperazine (Compound FW); 1-(5-trifluoromethyl-pyridin-2-yl)-piperazine (Compound FX); piperazine (Compound KY); or (2-Hexyloxyphenyl)-carbamic acid 2-piperidin-1-yl-1-piperidin-1-ylmethyl-ethyl ester (Compound OQ).

The compounds of the present invention can be synthesized using standard methods of chemical synthesis and/or can be synthesized using schemes described herein. Synthesis of specific compounds is discussed in detail in the Example sections below. Examples of syntheses of several classes of compounds of the invention are outlined in the schemes below.

Scheme 1 depicts a method of synthesizing thiomethylene or hydroxymethylene compound of the invention.

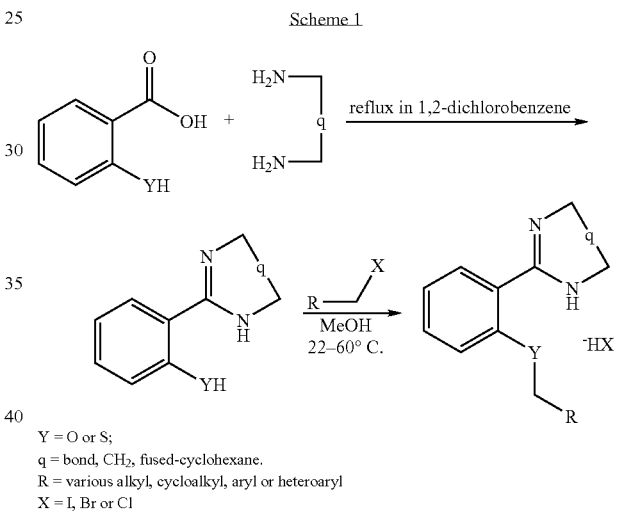

Scheme 1

Y = O or S;
q = bond, $CH_2$, fused-cyclohexane.
R = various alkyl, cycloalkyl, aryl or heteroaryl
X = I, Br or Cl 2-hydroxy or 2-mercapto benzoic acid is heated with the diamine in refluxing 1,2-dichlorobenzene to form the corresponding heterocyclic compound. The desired thioether or ether is formed by treating the thiol or alcohol with a corresponding halogenated compound.

Scheme 2 depicts a general preparation of ethanyl-linked compounds of the invention.

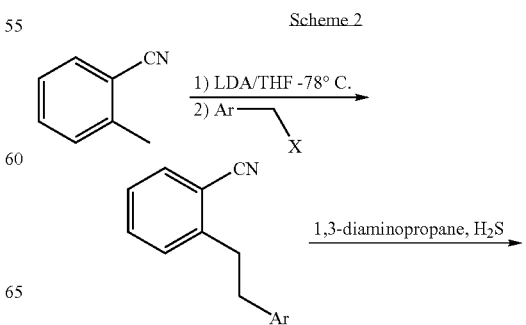

Scheme 2

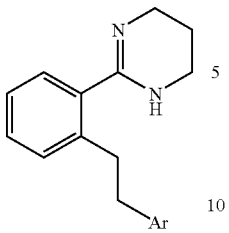

Scheme 2 shows a method of synthesizing ethanyl linked compounds by treating α-tolunitrile with a lithium base in THF at −78° C. A halogenated alkylaryl compound is then added to form the ethanyl linkage. To form the heterocycle, hydrogen sulfide gas is bubbled through a solution of the nitrile and 1,3 diaminopropane. After formation, the product can then be obtained and purified using standard techniques.

Scheme 3 depicts a method of preparing methylenethio linked compounds of the invention.

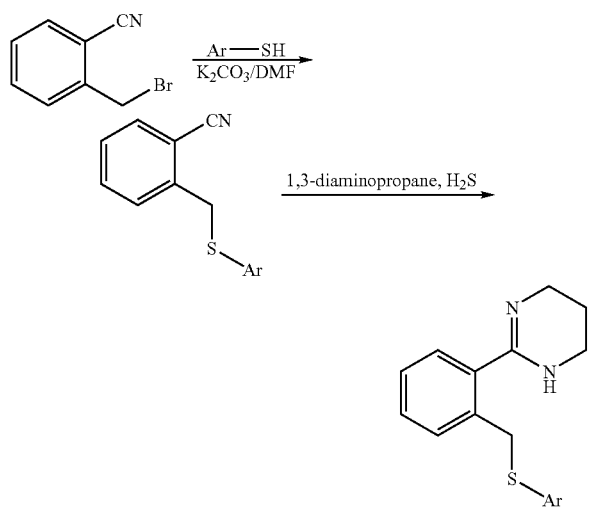

As depicted in Scheme 3, the methylenethio compounds of the invention can be prepared by adding anhydrous $K_2CO_3$ to a thiophenol compound (Ar—SH) in DMF. The solution is then stirred and bromomethyl-benzonitrile is subsequently added. The thioether is then converted to the heterocyclic compound by bubbling hydrogen sulfide through a solution of the thioether and 1,3 diaminopropane. After formation, the product can then be obtained and purified using standard techniques.

Scheme 4

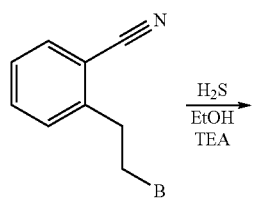

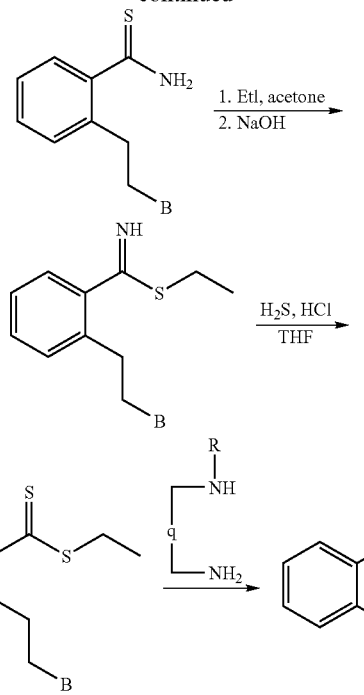

As depicted in Scheme 4, cyclic amidines of the invention can be prepared by reacting 2-substituted benzonitrile with hydrogen sulfide to form a thiobenzamide. The resulting thiobenzamide is then treated with iodoethane to give a thiobenzimidic acid ethyl ester. In the presence of hydrochloric acid, the thiobenzimidic acid ethyl ester is suspended in tetrahydrofuran and treated with hydrogen sulfide. The resulting dithiobenzoic acid ethyl ester is then heated with various diamines, in the presence or absence of an added catalyst such as silver trifluoroacetate, to give cyclic amidines.

The invention is further illustrated by the following examples which in no way should be construed as being further limiting. The contents of all references, pending patent applications and published patent applications, cited throughout this application are hereby incorporated by reference. It should be understood that the animal models used throughout the examples are accepted animal models and that the demonstration of efficacy in these animal models is predictive of efficacy in humans.

EXEMPLIFICATION OF THE INVENTION

Example 1

Synthesis of Intermediate Compounds

Synthesis of 2-(4,5-Dihydro-1H-imidazol-2-yl)-benzenethiol:

21.6 mL (0.323 mol) of ethylenediamine was added to a suspension of 20.0 g (0.112 mol) of thiosalicylic acid in 200 mL of 1,2-dichlorobenzene, and refluxed under nitrogen for 4 h then cooled to ca. 60° C. and 50 mL of methanol was added. The solution was allowed to stand at 22° C. overnight and the resulting yellow crystalline solid was collected and washed with ether to give 10.6 g of pure product.

Synthesis of 2-(2-Naphthalen-1-yl-ethyl)-benzonitrile:

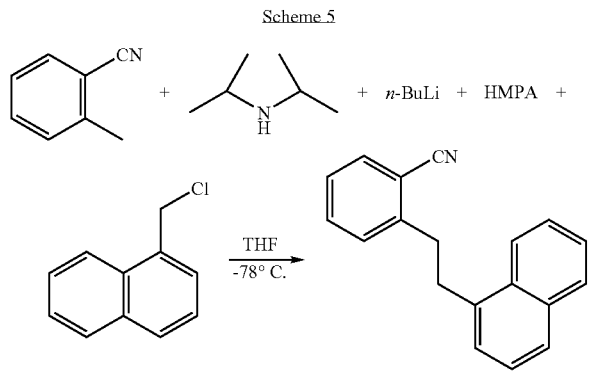

5.6 mL (9.0 mmol) of n-butyllithium, 1.6 M in hexanes, was added to a solution of 1.26 mL (911 mg, 9.00 mmol) of diisopropylamine in 50 mL of THF (tetrahydrofuran) was cooled to −78° C. under nitrogen and via syringe. The mixture was stirred at −78° C. for 1 hour and a solution of 353 mg (3.00 mmol) of α-tolunitrile in 10 mL of THF was added. The solution was stirred at −78° C. for one additional hour and a solution of 1.57 mL (9.00 mmol) of HMPA and 583 mg (3.30 mmol) of 1-chloromethylnaphthalene in 10 mL of THF was added dropwise. After stirring for one additional hour at −78° C., the reaction was quenched with water and extracted with Et$_2$O (diethyl ether) (2×30 mL). The organic layer was washed with aqueous 1 N HCl (30 mL), water (3×30 mL), brine (30 mL) and dried (Na$_2$SO$_4$). The solvent was evaporated to give 735 mg of crude product which is used directly next steps.

Synthesis of 2-(5-Bromo-2-methoxy-phenylsulfanylmethyl)-benzonitrile:

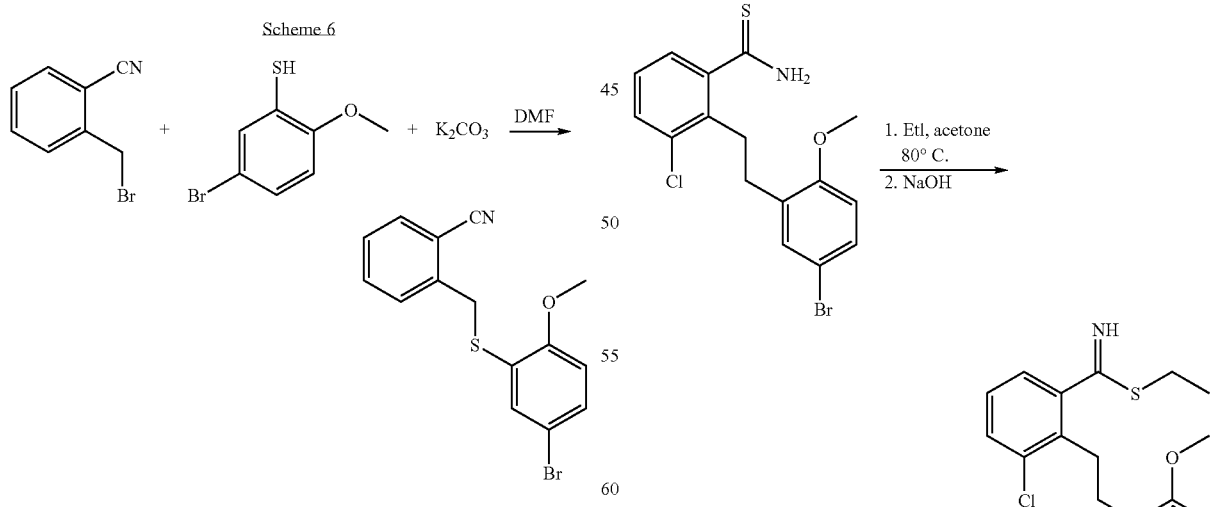

As depicted in Scheme 6, 162 mg (1.18 mmol) of anhydrous K$_2$CO$_3$ was added to a solution of 104 mg (0.470 mmol) of 2-methoxy-5-bromo-thiophenol in 5 mL of DMF, stirred for 15 minutes at 22° C. and 103 mg (0.520 mmol) of 2-bromomethyl-benzonitrile was added, then the reaction was capped and heated to 40° C. for 12 hours. The mixture was subsequently diluted with 5 mL of water, extracted with ethyl acetate (2×10 mL), and the organic extracts washed with water (3×10 mL), brine (2×10 mL), and dried (Na$_2$SO$_4$). The solvent was evaporated and the product was purified on silica gel (eluting with 9:1 of hexane/ethyl acetate) to afford 102 mg of the product as a colorless oil.

Synthesis of 9,2-[2-(5-Bromo-2-methoxy-phenyl)-ethyl]-3-chloro-thiobenzamide:

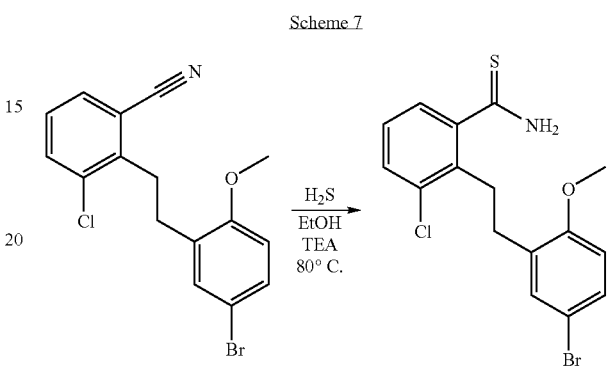

As shown in Scheme 7, hydrogen sulfide gas was bubbled into a solution of 2.75 g (7.8 mmol) of 2-[2-(5-Bromo-2-methoxy-phenyl)-ethyl]-3-chloro-benzonitrile in 20 mL of ethanol and triethylamine (5:4 v/v) for 10 minutes, and the solution then heated to 80° C. in a sealed pressure tube for 5 hours. The reaction mixture was diluted with water and extracted with ethyl acetate twice; organic extracts were washed with brine, dried (MgSO$_4$), filtered and evaporated to give 3.0 g of crude product which was used directly.

Synthesis of 2-[2-(5-Bromo-2-methoxy-phenyl)-ethyl]-3-chloro-thiobenzimidic acid: ethyl ester 6 mL (75 mmol) of iodoethane was added to a solution of 3.0 g (7.8 mmol) of 2-[2-(5-Bromo-2-methoxy-phenyl)-ethyl]-3-chloro-thiobenzamide in 50 mL of acetone (Scheme 8), heated to 80° C. for 2 hours and then stirred at room temperature overnight. A white solid precipitated and was filtered to give 3.23 g of the iodide salt. The salt was neutralized by partitioning between CH$_2$Cl$_2$ and 1 N aqueous sodium hydroxide. After drying (MgSO$_4$) and evaporation of the organic layer, 2.8 g of crude powder was obtained which was used directly.

Synthesis of 2-[2-(5-Bromo-2-methoxy-phenyl)-ethyl]-3-chloro-dithiobenzoic acid:

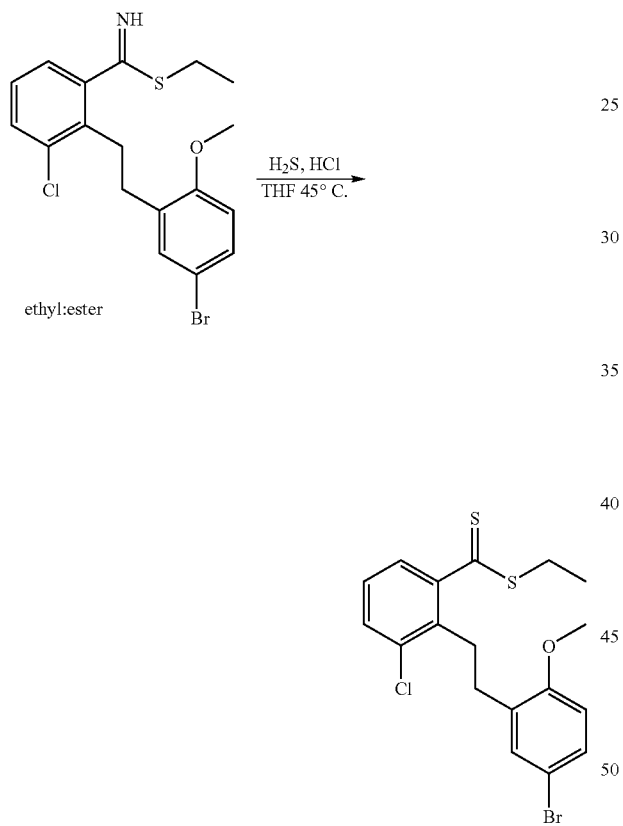

As shown in Scheme 9, hydrogen sulfide gas (2 mL) was condensed into a cooled (−78° C.) solution of 2.8 grams (6.8 mmol) of 2-[2-(5-Bromo-2-methoxy-phenyl)-ethyl]-3-chloro-thiobenzimidic acid ethyl ester and 13.6 mL (13.6 mmol) of 1.0 M HCl/ether in 100 mL of tetrahydrofuran. The reaction was heated to 45° C. and stirred overnight in a sealed tube. The reaction mixture was diluted with water and extracted with methylene chloride once, organic layer was washed with brine, dried (MgSO$_4$), filtered and evaporated to give a crude orange oil. The oil was partially purified by chromatography through a short column of silica gel (eluting with 5:95 ethyl acetate/hexanes) which resulted in 1.8 g of an orange powder which was used directly.

Synthesis of 5-bromo-7-bromomethyl-benzo[b]thiophene:

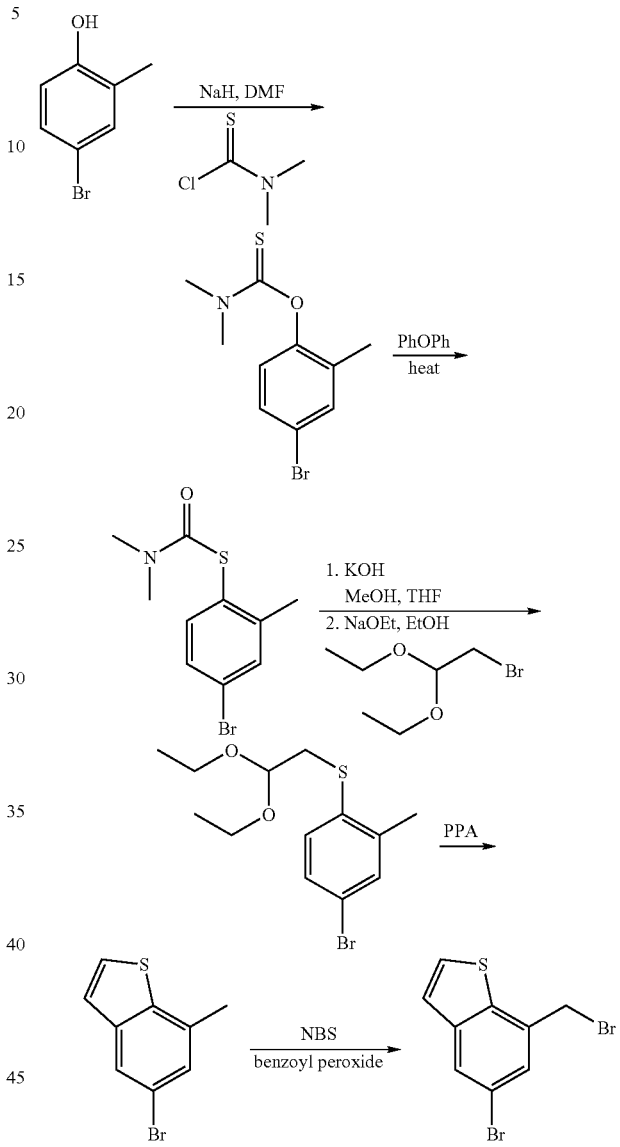

A suspension of NaH (washed with hexane) (9.4 g, 1.1 equiv) in DMF (1 L) at 0° C. was degassed with nitrogen. To this slurry was added a solution of 4-bromo-2-methyl phenol (40 g, 1.0 equiv) in DMF (35 mL) was added dropwise, and the mixture was allowed to stir at 0° C. for 30 min (hydrogen evolution ceased) before the addition of a solution of the carbamoyl choloride (29 g, 1.1 equiv), then allowed to warm to room temperature overnight and the reaction was quenched by the addition of water. The solution was extracted with EtOAc, the organic phase washed with water and brine, dried over Na$_2$SO$_4$, filtered and concentrated. The resulting residue was triturated with hexane to give dimethyl-thiocarbamic acid O-(4-bromo-2-methylphenyl) ester (50.3 g, 86%). The thiocarbamic acid O-ester (48.2 g) was heated in diphenylether (100 mL) at 230° C. for 10 hr, then cooled to room temperature, the mixture was filtered through SiO$_2$ (hexane), concentrated, and filtered a second time to give dimethyl-thiocarbamic acid S-(4-bromo-2-methylphenyl) ester (34.7 g, 72%).

To a solution of the thiocarbamic acid S-ester (34.7 g) in THF (500 mL) under an atmosphere of nitrogen was added a solution of KOH (17.8 g, 2.5 equiv) in MeOH (90 mL), the solution allowed to stir at room temperature for 5 hr and quenched by the addition of 1N HCl, extracted with EtOAc and the organic phase was washed with brine, dried over $Na_2SO_4$, filtered and concentrated to give 4-bromo-2-methyl benzenethiol which was used immediately. The thiol was added dropwise to a solution of sodium ethoxide (10.3 g, 1.2 equiv) in EtOH (600 mL), allowed to stir for 30 min before the dropwise addition of 2-bromo-1,1-diethoxyethane (23 mL, 1.2 equiv). The reaction mixture was heated at reflux for 4 hr, allowed to cool and stir at room temperature overnight, then quenched by the addition of water and concentrated. Water and EtOAc were added, the phases separated, and the aqueous phase was further extracted with EtOAc. The organic phase was dried over $Na_2SO_4$, filtered and concentrated. The crude product was purified by column chromatography ($SiO_2$, 5% EtOAC in hexanes) to give 4-bromo-1-(2,2-diethoxyethylsulfanyl)-2-methylbenzene (38.4 g, 88% for 2 steps).

To the acetal (35.4 g) in toluene (550 mL) was added PPA (18 mL) at 100° C. The mixture was heated at 120° C. for 30 min, cooled to 90° C. and the toluene was decanted. Water was added and the mixture stirred vigorously at 90° C., and toluene was again decanted. This procedure was repeated two additional times and then the organic phase was diluted with EtOAc, washed with brine, dried over $Na_2SO_4$, filtered and concentrated. The crude product was filtered through $SiO_2$ (hexane). Concentration gave 5-bromo-7-methyl-benzo[b]thiophene (10.4 g, 41%).

The thiophene (10.16 g, 1.0 equiv), NBS (8.76 g, 1.1 equiv), and benzoyl peroxide (0.54 g, 0.05 equiv) were dissolved in $CCl_4$, heated to reflux under UV irradiation for 2 hr and then cooled to 0° C. and filtered. The filtrate was evaporated. Repeated trituration with hexane gave 5-bromo-7-bromomethyl-benzo[b]thiophene (7.0 g). Concentration of the hexane gave an oil which was purified by column chromatography ($SiO_2$, hexane) to give additional product (total yield 9.96 g, 86%).

Synthesis of 4-bromo-2-bromomethyl-3'-chloro-biphenyl:

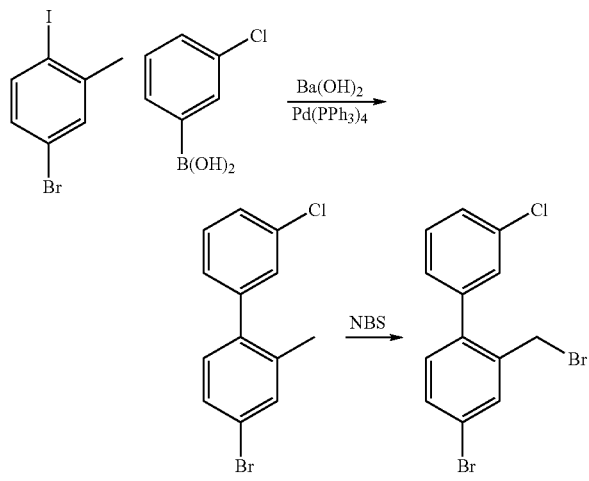

Barium hydroxide monohydrate (2.27 g, 2.0 equiv), 4-bromo-1-iodo-2-methylbenzene (0.94 mL, 1.1 equiv), 3-chlorophenyl boronic acid (0.94 g, 1.0 equiv), and palladium tetrakis(triphenylphosphine) (0.14 g, 0.02 equiv) were combined and stirred in dioxane (15 mL) and water (5 mL), heated at reflux for 2 hr and then allowed to cool to room temperature. The solution was concentrated and the residue dissolved in $CH_2Cl_2$, washed with water and brine and then dried over $Na_2SO_4$, filtered and concentrated. The residue was purified by column chromatography ($SiO_2$, hexane) to give 4-bromo-3'-chloro-2-methyl biphenyl (0.33 g, 21%).

The biphenyl (0.235 mg, 1.0 equiv) was dissolved in $CCl_4$ (5 mL), NBS added, and the solution was irradiated until starting material was consumed. The mixture was allowed to cool to room temperature and then filtered through celite. The filtrate was concentrated and the residue purified by column chromatography ($SiO_2$, hexane) to give the desired product (0.258 g, 60%).

Synthesis of 4-bromo-2-bromomethyl-1-trifluoromethoxybenzene:

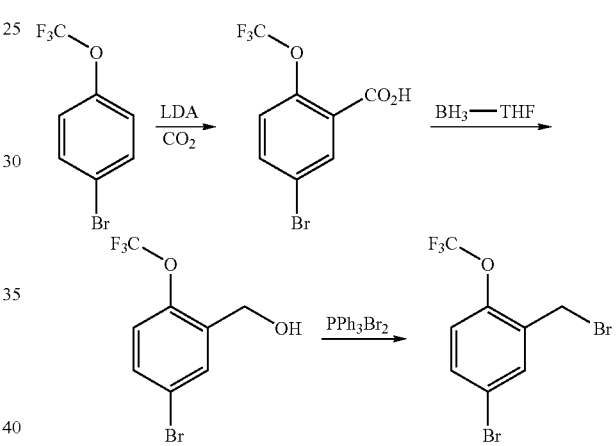

LDA was prepared by the dropwise addition of n-BuLi (2.5 M in hexanes, 9.96 mL, 1.2 equiv) to a solution of DIPEA (3.49 mL, 1.2 equiv) in THF (40 mL) at 0° C. under an atmosphere of nitrogen. The solution was allowed to stir for 30 min at 0° C. and then cooled to −100° C. and 1-bromo-4-trifluoromethoxybenzene (5.0 g, 1.0 equiv) was added dropwise. The reaction mixture was allowed to stir at −100° C. for 1.5 hr, carbon dioxide gas was bubbled through the solution for 45 min, and allowed to warm to −60° C. during this time. The reaction was then allowed to warm to room temperature and stirred for 18 hrs. The solvents were evaporated and the residue was dissolved in 1N NaOH (50 mL) and then washed with $Et_2O$ (2×). The aqueous phase was acidified to pH=1 by the addition of conc. HCl and then extracted with $Et_2O$. The organic phase was dried over $Na_2SO_4$, filtered, and concentrated. The residue was purified by filtering through $SiO_2$ (94:5:1 $CH_2Cl_2$:MeOH:AcOH) to give the carboxylic acid (2.2 g, 37%).

To a solution of 5-bromo-2-trifluoromethoxy benzoic acid (2.2 g, 1.0 equiv) in THF (80 mL) at 0° C. under an atmosphere of nitrogen was added dropwise a solution of borane-THF (1.0 M in THF, 19.3 mL, 2.5 equiv). The solution was heated at 70° C. for 18 hr and then allowed to cool to room temperature and concentrated. The residue was dissolved in methanol and the solvent evaporated (2×). The crude product was purified by column chromatography (SiO$_2$, 20% EtOAc in hexane) to give the desired benzylic alcohol (1.45 g, 69%).

To a suspension of PPh$_3$Br$_2$ (1.91 g, 1.2 equiv) in CCl$_4$ (40 mL) at 0° C. was added dropwise a solution of (5-bromo-2-trifluoromethoxyphenyl)-methanol (1.02 g, 1.0 equiv) in CCl$_4$ (5 mL). The reaction mixture was allowed to warm to room temperature, stirred for 2 hr, and then concentrated. Hexane was added to the residue and the suspension was filtered through SiO$_2$ (hexane) to give the desired benzylic bromide (1.0 g, 80%).

Synthesis of 2-bromomethyl-1-methoxy-4-trifluoromethyl-benzene:

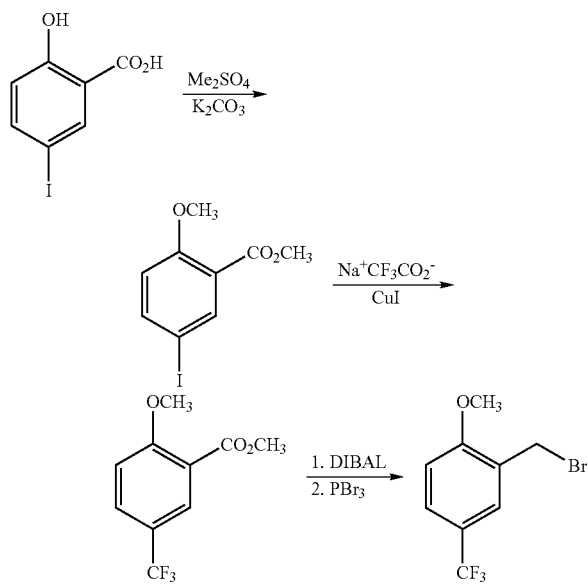

Scheme 13

A heterogeneous slurry of 5-iodosalicylic acid (5.28 g, 1.0 equiv), dimethylsulfate (5.5 g, 2.2 equiv) and potassium carbonate (12.2 g, 4.4 equiv) in acetone (40 mL) was allowed to reflux under an atmosphere of nitrogen overnight. After cooling to room temperature, the reaction contents were slowly poured into stirring water (250 mL). The mixture was acidified to pH<5 (conc. HCl) and allowed to stir for 30 min. The precipitated solid was filtered, washed with water, and air-dried. The crude product was purified by column chromatography (SiO$_2$, 15% EtOAc in hexane) to yield the desired methyl ether (5.3 g, 91%).

A mixture of methyl 5-iodo-2-methoxybenzoate (1.46 g, 1.0 equiv), sodium trifluoroacetate (2.72 g, 4.0 equiv) and copper(I) iodide (3.3 g, 3.1 equiv) in toluene (15 mL) was allowed to reflux for 2 hr to azeotrope water. Upon removal of water, dry DMF (15 mL) was added dropwise via addition funnel while the reaction temperature was raised. Toluene was removed by distillation until the internal reaction temperature reached 140° C. The solution was held at this temperature for 1 hr and then the temperature was raised to 150° C. for 5 hr. The reaction mixture was then allowed to cool to room temperature and stir overnight before being quenched by pouring into stirring water (100 mL). The solution was extracted with EtOAc (2×50 mL) and the organic phase was washed with brine (25 mL), dried over Na$_2$SO$_4$, filtered and concentrated. Purification of the residue by column chromatography (SiO$_2$, 15% EtOAc in hexane) gave the desired ester (0.4 g, 33%).

To a solution of DIBAL (1.0 M in CH$_2$Cl$_2$, 16 mL, 2.0 equiv) in CH$_2$Cl$_2$ (10 mL) at 0° C. was added a solution of methyl 5-trifluoromethyl-2-methoxy benzoate (1.7 g, 1.0 equiv) in CH$_2$Cl$_2$ (7.5 mL). The reaction mixture was allowed to stir for 3 hr at 0° C. and then at room temperature overnight. After recooling to −15° C., the reaction was quenched by the slow addition of 1N HCl (20 mL). The resulting mixture was allowed to stir at room temperature for 1 hr and then was extracted with CH$_2$Cl$_2$. The organic phase was washed with brine, dried over Na$_2$SO$_4$, filtered and concentrated to give the desired alcohol (1.46 g, 98%) which was used without further purification.

To a stirring solution of 5'-trifluoromethyl-2'-methoxybenzyl alcohol (1.4 g, 1.0 equiv) in toluene (10 mL) at 0° C. under a an atmposhere of nitrogen was added PBr$_3$ (2.27 g, 1.2 equiv). The resulting solution was allowed to stir at 0° C. for 30 min and then at room temperature overnight. After recooling to 0° C., water (10 mL) was added dropwise. The solution was allowed to stir at 0° C. for 5 min, then at room temperature for 3 hr. The mixture was extracted with EtOAc (2×25 mL) and the organic phases were combined, washed with saturated aqueous NaHCO$_3$ (25 mL) and brine (25 mL), dried over Na$_2$SO$_4$, filtered and concentrated to give the desired benzyl bromide (1.57 g, 87%).

Synthesis of 5-bromo-7-bromomethyl-2-methyl-benzofuran:

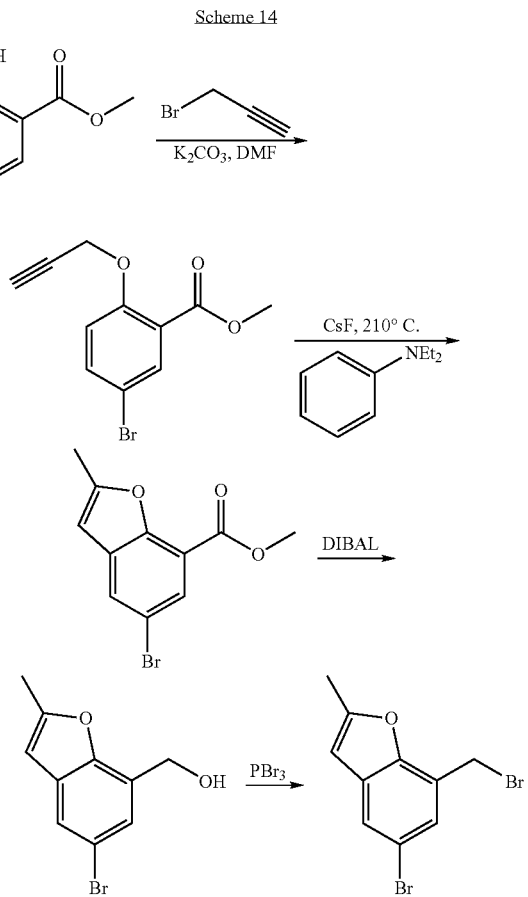

Scheme 14

To a solution of 5-bromo-2-hydroxy-benzoic acid methyl ester (2.5 g, 1.0 equiv) in DMF (20 mL) was added $K_2CO_3$ (4.5 g, 3.0 equiv) and then propargyl bromide (2.3 mL, 1.4 equiv). The resulting solution was allowed to stir at room temperature for 16 hr and then diluted with water and extracted with $Et_2O$. The organic phase was washed with 5% NaOH and brine and then dried over $Na_2SO_4$, filtered and concentrated. The residue was purified by column chromatography ($SiO_2$, hexane/acetone) to give the desired phenyl ether (2.1 g, 70%).

The phenyl ether (2.1 g, 1.0 equiv) was dissolved in diethylaniline (20 mL) and to this solution was added CsF (1.7 g, 1.5 equiv). After heating at 210° C. for 16 hr, the solution was allowed to cool to room temperature and diluted with $Et_2O$. The mixture was filtered through celite and the organic phase was washed with saturated aqueous $NaHCO_3$ and water, dried over $Na_2SO_4$, filtered and concentrated. Purification of the residue by column chromatography ($SiO_2$, hexane/acetone) to gave the desired benzofuran (1.1 g, 50%).

DIBAL (1.0 M in $CH_2Cl_2$, 4.1 mL, 2.5 equiv) was added to a stirred solution of the methyl ester (0.4 g, 1.0 equiv) in $CH_2Cl_2$ (7 mL) at −10° C. The reaction mixture was allowed to warm to room temperature while vigorously stirring and then quenched by the addition of saturated aqueous potassium sodium tartrate. The solution was extracted with $CH_2Cl_2$, dried over $Na_2SO_4$, filtered and concentrated. Purification of the residue by column chromatography ($SiO_2$, hexane/acetone) gave the desired alcohol (0.3 g, 76%).

To a solution of the alcohol (0.8 g, 1.0 equiv) in toluene (14 mL) at 0° C. was added $PBr_3$ (0.4 mL, 1.1 equiv). The resulting solution was allowed to warm to room temperature. After recooling to 0° C., the reaction was quenched by the slow addition of water. The solution was extracted with $CH_2Cl_2$ and the organic phase was dried over $Na_2SO_4$ filtered, and concentrated. Purification of the residue by column chromatography ($SiO_2$, hexane/acetone) gave the desired bromide (0.6 g, 56%).

Synthesis of 5-bromo-7-bromomethyl-2,3-dimethyl-benzofuran:

Scheme 15

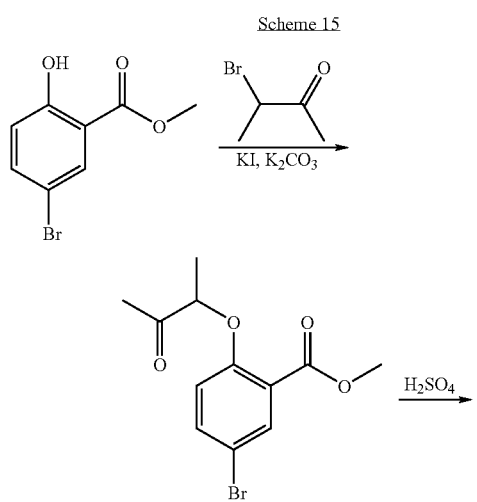

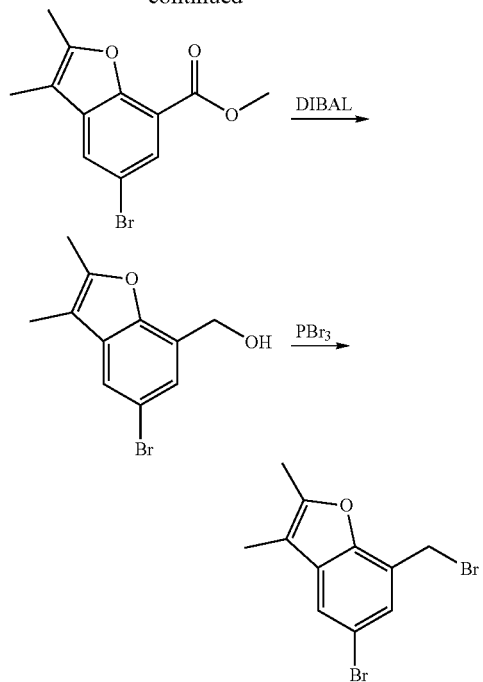

To a solution of 5-bromo-2-hydroxy-benzoic acid methyl ester (5.0 g, 1.0 equiv) in DMF (40 mL) at room temperature was added 3-bromo-butan-2-one (4.0 g, 1.4 equiv), $K_2CO_3$ (9.0 g, 3 equiv), and KI (11.0 g, 3.0 equiv). The reaction mixture was allowed to stir at room temperature for 16 hr and then quenched by the addition of water. The solution was extracted with EtOAc and the organic phase was dried over $Na_2SO_4$, filtered and concentrated. Purification of the residue by column chromatography ($SiO_2$, hexane/acetone) gave the desired ether (5.5 g, 85%).

The ether (1.0 g) was dissolved in $H_2SO_4$ (1.5 mL) and stirred at room temperature for 16 hr. The reaction mixture was diluted with MeOH and water and then extracted with EtOAc. The organic phase was dried over $Na_2SO_4$, filtered and concentrated. The residue was purified by column chromatography ($SiO_2$, hexane/acetone) to give the desired benzofuran (0.2 g, 20%).

A solution of the methyl ester (1.0 g, 1.0 equiv) in $CH_2Cl_2$ (7 mL) was cooled to −10° C. and treated with DIBAL (1.0 M in $CH_2Cl_2$, 12 mL, 3.25 equiv). The reaction mixture was allowed to warm to room temperature, quenched by the addition of saturated aqueous potassium sodium tartrate, and extracted with $CH_2Cl_2$. The organic phase was dried over $Na_2SO_4$, filtered, and concentrated. Purification of the residue by column chromatography ($SiO_2$, hexane/acetone) gave the desired alcohol (0.9 g, 97%).

To a solution of the alcohol (0.9 g, 1.0 equiv) in toluene (14 mL) at 0° C. was added $PBr_3$ (0.4 mL, 1.1 equiv). The resulting solution was allowed to warm to room temperature. After recooling to 0° C., the reaction was quenched by the slow addition of water. The solution was extracted with $CH_2Cl_2$, and the organic phase was dried over $Na_2SO_4$ filtered, and concentrated. Purification of the residue by column chromatography ($SiO_2$, hexane/acetone) gave the desired bromide (1.1 g, 100%).

Synthesis of 6-bromo-4-bromomethyl-benzo[1,3]dioxole:

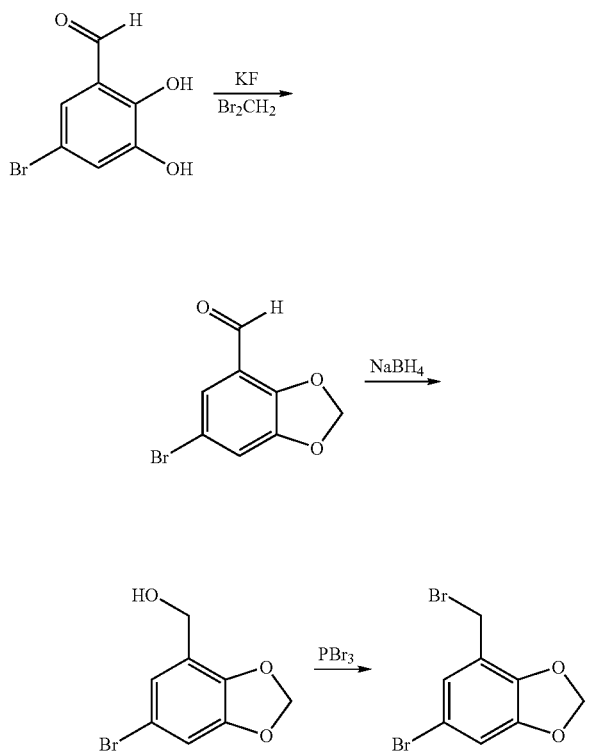

To a mixture of potassium fluoride (0.24 g, 9.0 equiv) and 5-bromo-2,3-dihydroxy-benzaldehyde (0.10 g, 1.0 equiv) in DMF (5 ml) under an inert atmosphere was added dibromomethane (0.03 mL, 1.0 equiv). The reaction mixture was heated at 140° C. for 3 hr and then allowed to cool to room temperature and quenched by the addition of water. The solution was extracted with diethyl ether and the organic phase was washed with 1N NaOH and brine, and dried over $Na_2SO_4$, filtered, and concentrated to give the desired aldehyde (0.06 g, 57%) which was used without further purification.

Sodium borohydride (0.018 g, 1.1 equiv) was slowly added to a solution of the aldehyde (0.10 g, 1.0 equiv) in MeOH (5 mL) at 0° C. After 20 min, the reaction was quenched by the addition of 1N NaOH and concentrated. The residue was diluted with water and extracted with EtOAc. The organic phase was washed with brine, dried over $Na_2SO_4$, filtered, and concentrated to give the desired alcohol (0.08 g, 81%) which was used without further purification.

A solution of the alcohol (0.62 g, 1.0 equiv) in $Et_2O$ (5 mL) was cooled to 0° C. under an inert atmosphere. To this cooled solution was added $PBr_3$ (0.25 mL, 1.0 equiv) dropwise. After 20 min, the reaction contents were poured onto ice and diluted with 1N NaOH. The solution was extracted with EtOAc and the organic phase was washed with brine, dried over $Na_2SO_4$, filtered, and concentrated to give the desired alcohol. Purification of the residue by filtration through $SiO_2$ (EtOAc) gave the desired bromide (0.42 g, 53%).

Synthesis of tert-butyl-(1-chloromethyl-naphthalen-2-yloxy)-dimethyl-silane:

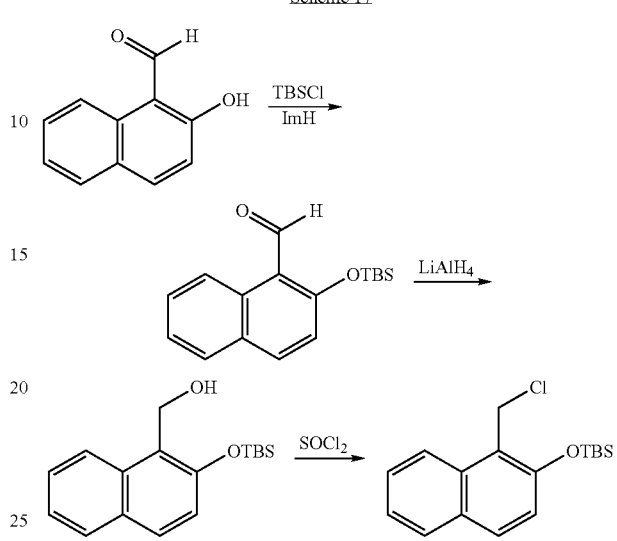

To a solution of 2-hydroxy-naphthalene-1-carbaldehyde (3.0 g, 1.0 equiv) in DMF under an inert atmosphere was added imidazole (1.31 g, 1.1 equiv) and tert-butyl-chlorodimethyl-silane (2.88 g, 1.1 equiv). The reaction mixture was allowed to stir at room temperature for 20 min and was then quenched by the addition of water. The solution was extracted with EtOAc, washed with brine, dried over $Na_2SO_4$, filtered, and concentrated to give the protected alcohol which was used without further purification.

To a solution of the aldehyde (3.3 g, 2.0 equiv) in THF at 0° C. under an inert atmosphere was added LiAlH4 (0.22 g, 1.0 equiv). The reaction mixture was allowed to stir for 45 min and then quenched by the addition of water and allowed to stir overnight at room temperature. The crude mixture was filtered through $SiO_2$ (EtOAc) and the filtrate was washed with brine, dried over $Na_2SO_4$, filtered, and concentrated. The residue was used directly without purification.

Thionyl chloride (0.34 g, 1.5 equiv) was added dropwise to a solution of the alcohol (0.50 g, 1.0 equiv) in $CH_2Cl_2$. The solution was allowed to stir for 20 min at room temperature and then concentrated. Purification of the residue by column chromatography ($SiO_2$, hexane) gave the desired chloride (0.40 g, 68%).

Synthesis of 2-(2-naphthalene-1-yl-ethyl)-benzonitrile:

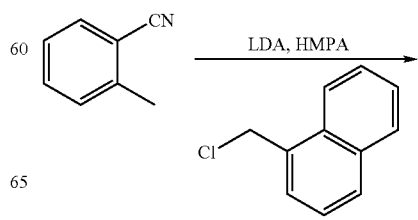

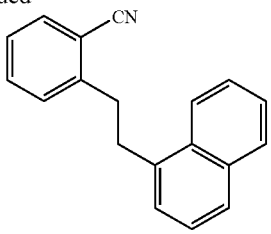

A solution of the nitrile (2 mL, 1.0 equiv) and HMPA (3.3 mL, 1.1 equiv) in THF (50 mL) was cooled to −78° C. under an atmosphere of argon. To this solution was added LDA (2 M in THF, 9.4 mL, 1.1 equiv). The dark red solution was allowed to stir for 15 min and then 1-chloromethylnaphthalene (3.3 g, 1.1 equiv) was added. The reaction was quenched after 1.5 hr by the addition of saturated aqueous NH₄Cl. The mixture was diluted with EtOAc and water, the organic and aqueous phases separated, and the organic phase further washed with brine, dried over Na₂SO₄, filtered, and concentrated. The residue was purified by column chromatography (SiO₂, 10% EtOAc in hexane) to give the desired product (2.06 g, 47%).

A similar procedure can be used to couple a variety of bromomethyl- or chloromethyl-aryls to substituted or unsubstituted tolunitriles.

Synthesis of 2-[2-(5-bromo-2-difluoromethoxyphenyl)-ethyl]-3-chlorobenzonitrile:

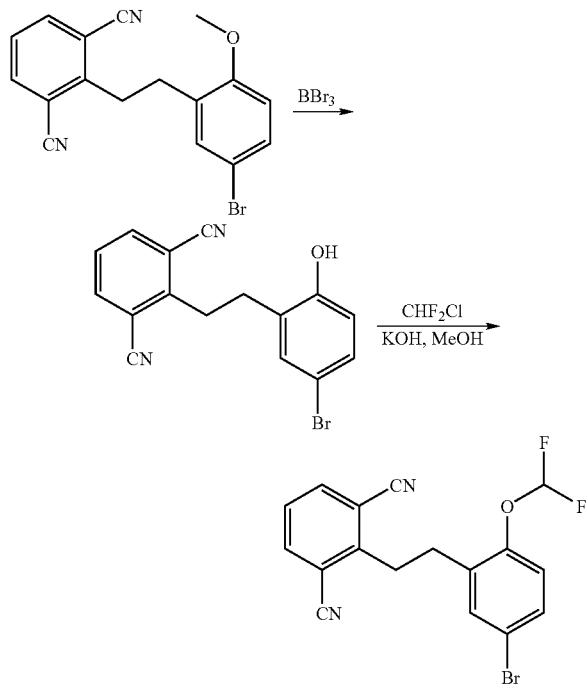

Scheme 19

A solution of 2-[2-(5-bromo-2-methoxyphenyl)-ethyl]-3-chlorobenzonitrile (0.187 g, 1.0 equiv) in CH₂Cl₂ (2.5 mL) was allowed to stir under an atmosphere of argon at −78° C. To this solution was added boron tribromide (1.0 M in CH₂Cl₂, 2.65 mL, 5.0 equiv). After 15 min at −78° C., the solution was allowed to warm to room temperature and stir overnight. The reaction was quenched by the addition of water and the solution was extracted with EtOAc. The organic phase was dried over Na₂SO₄, filtered and concentrated. The residue was purified by column chromotagraphy (SiO₂, 20% EtOAc in hexane) to give 2-[2-(5-bromo-2-hydroxyphenyl)-ethyl]-3-chlorobenzonitrile (0.144 g, 81%).

To a solution of the phenol (0.144 g, 1.0 equiv) in isopropanol (8 mL) at room temperature was added KOH (85%, 0.284 g, 10.0 equiv). Chlorodifluoromethane was bubbled through the heterogeneous mixture for approximately 3 minutes at room temperature and then for 3 minutes while heating at 65° C. After 1 hour at 65° C., the reaction mixture was allowed to cool to room temperature and diluted with EtOAc. The solution was washed with 1N HCl and then dried over Na₂SO₄, filtered and concentrated to give the desired product in quantitative yield.

Synthesis of 3-(2-naphthalen-1yl-ethyl)-pyridine-2-carbonitrile:

Scheme 20

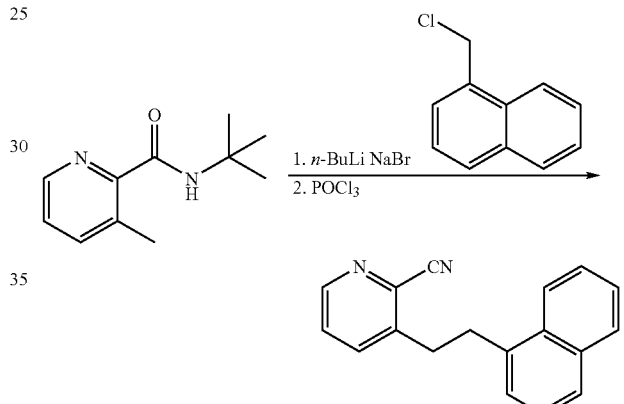

To a solution of the amide (4.02 g, 1.0 equiv) in TBF (80 mL) under an atmosphere of argon at −40° C. was added n-BuLi (2.5 M in hexane, 17.2 mL, 2.05 equiv) and then NaBr (0.22 g, 0.1 equiv). The solution was allowed to stir for 30 min before the addition of a solution of 1-chloromethylnaphthalene (4.06 g, 1.1 equiv) in THF (15 mL). The reaction was quenched after 1.5 hr by the addition of water and then allowed to warm to room tempearature and extracted with EtOAc. The organic phase was dried over Na₂SO₄, filtered and concentrated to give the desired product in quantitative yield which was used directly in the next step.

The amide (3.6 g, 1.0 equiv) was dissolved in POCl₃ (10 mL, 10.0 equiv). The solution was heated at reflux for 2 hours and then was allowed to cool to room temperature and basified with 6N NaOH to pH=8. The basic solution was allowed to stir at room temperature for 1.5 hours and then diluted with Et₂O. After separation of aqueous and organic phases, the organic phase was further extracted with Et₂O. The organic phase was washed with water and brine, dried over Na₂SO₄, filtered and concentrated. The residue was purified by column chromatography (SiO₂, 40% EtOAc in hexane) to give the desired product (1.6 g, 57%).

Synthesis of 2-[2-(5-bromo-2-methoxyphenyl)-ethyl]-3-fluoro benzoic acid:

Scheme 21

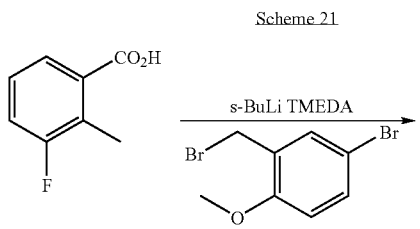

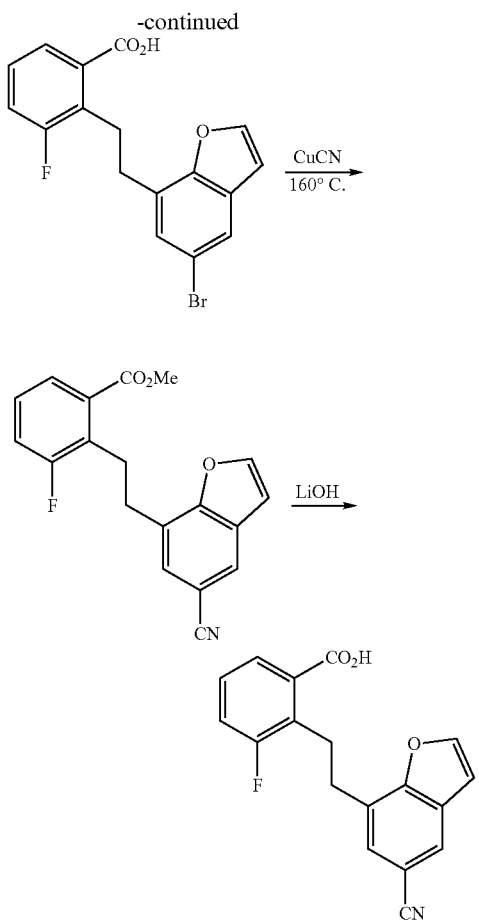

A solution of 3-fluoro-2-methylbenzoic acid (5.0 g, 1.0 equiv) in THF (175 mL) was cooled to −78° C. under an atmosphere of argon. TMEDA (9.86 mL, 2.0 equiv) was added via syringe. s-BuLi (1.4 M in cyclohexane, 49 mL, 2.1 equiv) was added dropwise via addition funnel over 30 min. After stirring for 2.5 hr, the bromide (13.7 g, 1.5 equiv) in THF (25 mL) was added dropwise. Upon completion of the addition, the solution was allowed to stir and warm to room temperature overnight. The reaction was quenched by the addition of water and then diluted with hexanes. The aqueous and organic phases were separated and the organic phase was washed with water. The aqueous phase was acidified to pH=1 with 1N HCl and then extracted with EtOAc. The resulting organic solution was dried over $Na_2SO_4$, filtered and concentrated. The residue was rinsed with dichloromethane, filtered, and dried to give the desired product (7.6 g, 66%).

A similar procedure can be used to couple a variety of bromomethyl- or chloromethyl-aryls to substituted or unsubstituted aryl carboxylic acids.

Synthesis of 2-[2-(5-cyano-benzofuran-7-yl)-ethyl]-3-fluoro-benzoic acid:

Scheme 22

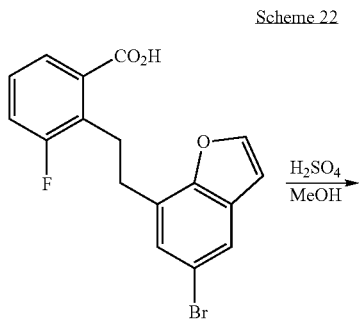

To a solution of 2-[2-(5-bromo-benzofuran-7-yl)-ethyl]-3-fluoro-benzoic acid (1.5 g) in MeOH (5 mL) was added of conc. $H_2SO_4$ (0.2 mL). The resulting reaction mixture was heated at reflux for 16 hr and then cooled to room temperature, quenched with saturated aqueous $NaHCO_3$ (10 mL) and extracted with EtOAc (3×25 mL). The organic phase was dried over $MgSO_4$, filtered, and concentrated. The residue was purified by column chromatography ($SiO_2$, EtOAc/hexane) to give the desired methyl ester (1.5 g, 95%).

To a solution of 2-[2-(5-bromo-benzofuran-7-yl)-ethyl]-3-fluoro-benzoic acid methyl ester (1.5 g, 1.0 equiv) in DMF (16 mL) was added CuCN (0.7 g, 2.0 equiv). The resulting reaction mixture was allowed to heat for 16 hr before additional CuCN (0.7 g, 2.0 equiv) was added. After heating for 6 hr, the reaction mixture was allowed to cool to room temperature, diluted with EtOAc and filtered through celite. The filtrate was washed with saturated aqueous $NaHCO_3$ and water and then dried over $MgSO_4$, filtered, and concentrated. Purification of the residue by column chromatography ($SiO_2$, EtOAc/hexane) gave the desired nitrile (0.6 g, 50%).

To a solution of the methyl ester (0.5 g, 1.0 equiv) in THF (4 mL) and $H_2O$ (2 mL) was added LiOH (0.1 g, 2.0 equiv). The mixture was allowed to stir at room temperature for 16 hr and then the reaction mixture was diluted with $H_2O$ and washed with hexane. The aqueous phase was acidified with 1N HCl and extracted with EtOAc. The resulting organic phase was dried over $Na_2SO_4$, filtered, and concentrated to give the desired acid (0.4 g, 93%) which was used without further purification.

Example 2

Synthesis of Compounds B, HO, and IZ

Synthesis of Compound B

2-[2-(2-Chloro-6-fluoro-benzylsulfanyl)-phenyl]-1,4,5,6-tetrahydro-pyrimidine; hydrochloride (Compound B). To a solution of 750 mg (3.90 mmol) of 2-(1,4,5,6-Tetrahydro-pyrimidin-2-yl)-benzenethiol was added 1.04 g (5.81 mmol) of 1-Chloro-2-chloromethyl-3-fluoro-benzene. The solution was stirred overnight at 22° C. and 2-3 mL of ether was added to induce crystallization. The crystals were collected and washed with ether to give 1.34 g of product.

NMR Data for Compound B $^1$H NMR (300 MHz, CD$_3$OD) δ 2.01-2.09 (2H, m), 3.49 (4H, br t, J=5.8 Hz), 4.28 (2H, s), 7.01-7.07 (1H, m), 7.22-7.33 (2H, m), 7.48 (2H, m), 7.56-7.64 (1H, m), 7.75 (1H, d, J=7.8 Hz)

Synthesis of Compound HO:

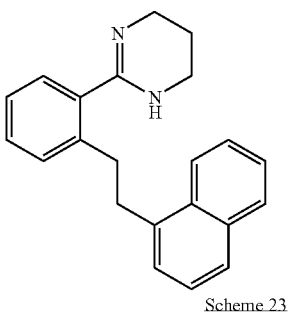

Compound HO

Scheme 23

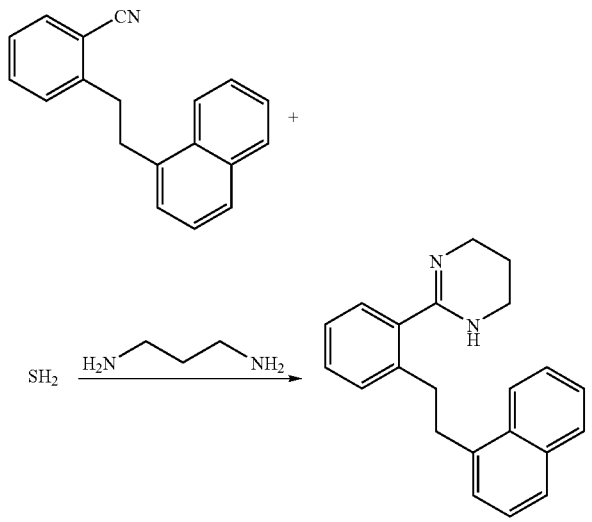

2-[2-(2-Naphthalen-1-yl-ethyl)-phenyl]-1,4,5,6-tetrahydro-pyrimidine (Compound HO). Hydrogen sulfide gas was bubbled through a solution of 735 mg of crude 2-(2-Naphthalen-1-yl-ethyl)-benzonitrile in 5 mL of 1,3-diaminopropane for 5 minutes, as depicted in Scheme 23. The reaction was capped and heated to 80° C. for 72 hours. The reaction mixture was then diluted with 5 mL of water and extracted with ethyl acetate (2×10 mL). The organic extracts were washed with water (3×10 mL), brine (2×10 mL), dried (Na$_2$SO$_4$) and the solvent was evaporated. The residue was purified on silica gel (eluting with 90:10:1:1 of dichloromethane/methanol/water/formic acid) to afford 310 mg of the formate salt of the product as a colorless oil.

NMR Data for Compound HO:

$^1$H NMR (300 MHz, CDCl$_3$) δ 1.35-1.50 (2H, m), 2.80-2.95 (4H, m), 3.03 (2H, t, J=6.8), 3.30 (2H, t, J=6.8), 6.77 (1H, d, J=6.9), 7.03-7.30 (3H, m), 7.30-7.57 (4H, m), 7.67 (1H, d, J=8.1), 7.80-7.90 (1H, m), 7.94-8.03 (1H, m), 8.06 (2H, brs, formate salt).

Synthesis of Compound IZ:

Compound IZ

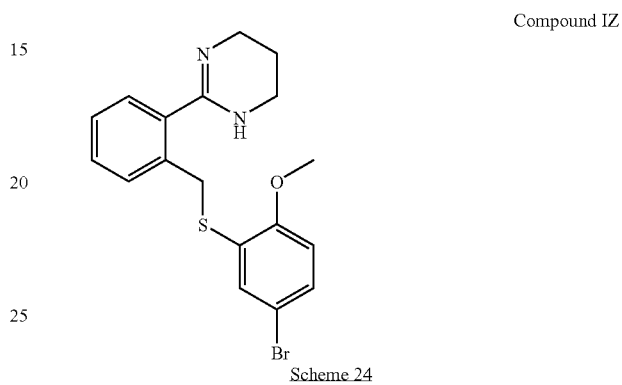

Scheme 24

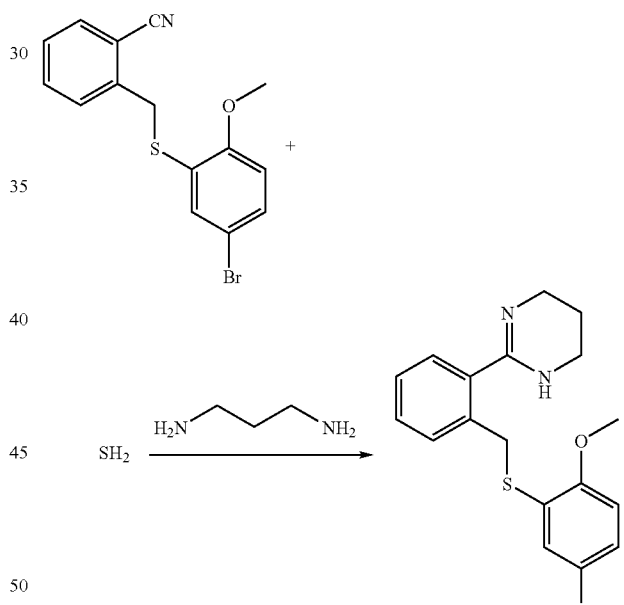

2-[2-(5-Bromo-2-methoxy-phenylsulfanylmethyl)-phenyl]-1,4,5-6-tetrahydro-pyrimidine. (Compound IZ) Compound DV was obtained from 2-(5-Bromo-2-methoxy-phenylsulfanylmethyl)-benzonitrile, 1,3-propanediamine and hydrogen sulfide in 73% yield by a procedure analogous to that used for the preparation of 2-[2-(2-Naphthalen-1-yl-ethyl)-phenyl]-1,4,5,6-tetrahydro-pyrimidine described above. Following chromatography, the material was converted to the hydrochloride salt and recrystallized from methanol/ether.

NMR Data for Compound IZ $^1$H NMR (300 MHz, DMSO-d$_6$) δ 1.95-2.10 (2H, m), 3.45-3.55 (4H, m), 3.86 (3H, s), 4.40 (2H, s), 6.97-7.04 (1H, m), 7.36-7.65 (6H, m), 10.03 (2H, s, hydrochloride salt).

Synthesis of Compound UZ:

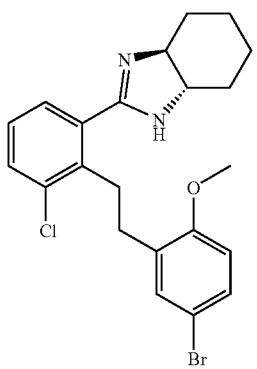
Compound UZ

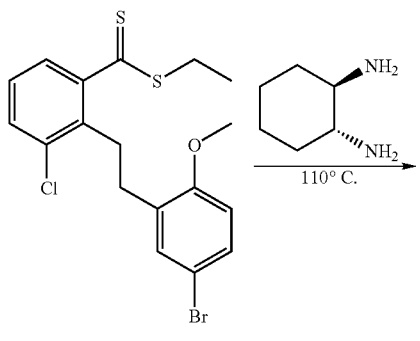
Scheme 25

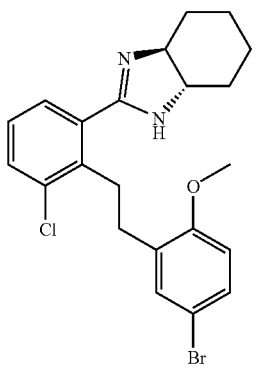

2-{2[2-(5-Bromo-2-methoxy-phenyl)-ethyl]-3-chlorophenyl}-3a,4,5,6,7,7a-hexahydro-1H-benzoimidazole (Compound UZ). As shown in Scheme 25, a solution of 187 mg (0.43 mmol) of 2-[2-(5-Bromo-2-methoxy-phenyl)-ethyl]-3-chloro-dithiobenzoic acid ethyl ester in 2.5 mL of trans-1,2 diaminocyclohexane was heated to 110° C. in a sealed pressure tube for 12 hours. The reaction mixture was diluted with water and extracted with methylene chloride twice. The organic extracts were washed with brine, dried (MgSO$_4$) and evaporated. The residue was chromatographed on silica gel (eluting with 95:5 CH$_2$Cl$_2$/methanol) to give a yellow oil. The oil was treated with methanolic HCl and evaporated to yield 34 mg of product as a pure hydrochloride salt.

NMR Data for Compound UZ $^1$H NMR (300 MHz, CD$_3$OD) δ 1.41-1.58 (2 H, br m), 1.64-1.80 (2 H, br m), 1.98 (2 H, br m), 2.30 (2 H, br m), 2.78-2.97 (2 H, m), 3.08 (1 H, m), 3.22-3.36 (1 H, m), 3.61 (2 H, m), 3.59(3 H, s), 6.81 (1H, d, J=8.7 Hz), 7.21 (H, m), 7.34(1 H, dd, J=2.5, 8.6 Hz), 7.42 (2 H, m), 7.75 (1 H, dd, J=2.3, 7.0 Hz).

Example 3

Synthesis of Compounds TB, AAP, ZF, ZO, ABB, ABC, and ZM

Synthesis of 2-{2-[2-(5-bromo-2-methoxyphenyl)-ethyl]-3-chlorophenyl}-4,5-dihydro-1H-imidazole (Compound TB)

Scheme 26

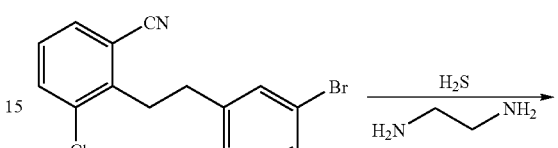

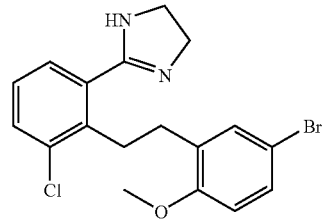

2-[2-(5-bromo-2-hydroxyphenyl)-ethyl]-3-chlorobenzonitrile (2.08 g, 1.0 equiv) was stirred in ethylene diamine (3 mL, 4.0 equiv) at room temperature. Hydrogen sulfide was bubbled through the solution for approximately 5 minutes. The mixture was heated in a sealed tube at 100° C. for 18 hr. After cooling to room temperature, the residue was dissolved in water and the solution extracted with EtOAc. The organic phase was dried over Na$_2$SO$_4$, filtered and concentrated to give the desired product (1.61 g, 69%).

Synthesis of 2-{2-[2-(5-bromo-2-methoxyphenyl)-ethyl]-3-fluorophenyl}-1-isopropyl-4,5-dihydro-1H-imidazole (Compound AAP):

Scheme 27

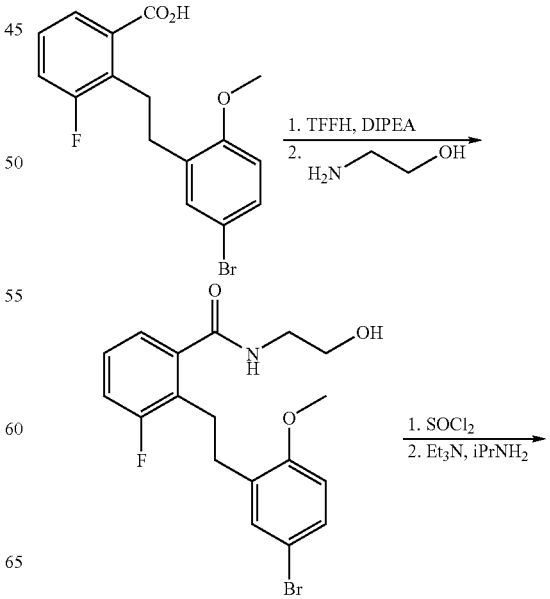

-continued

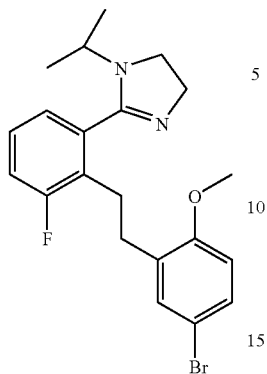

To a solution of the carboxylic acid (1.1 g, 1.0 equiv) and DIPEA (1.16 mL, 2.2 equiv) in DMF (15 mL) was added fluoro-N,N,N'-tetramethylformamidinium hexafluorophosphate (TFFH, 0.88 g, 1.1 equiv). The mixture was allowed to stir at room temperature for 1 hr before the addition of ethanolamine (0.37 mL, 2.0 equiv). The solution was allowed to stir at room temperature overnight and then quenched by the addition of water. The solution was extracted with EtOAc, dried over $Na_2SO_4$, filtered and concentrated. Purification of the residue by column chromatography ($SiO_2$, 50-100% EtOAc in hexane) gave the desired hydroxy amide (1.1 g, 100%).

A solution of the hydroxy amide (0.51 g, 1.0 equiv) in thionyl chloride (2.2 mL, 20 equiv) was heated at reflux for 4 hr and then allowed to cool to room temperature and concentrated. The residue was dissolved in chloroform (2 mL) and stirred under an atmosphere of nitrogen. To this solution was added triethylamine (0.43 mL, 2.0 equiv) and isopropylamine (0.26 mL, 2.0 equiv). The reaction mixture was allowed to stir overnight at room temperature and then quenched by the addition of 1N NaOH. EtOAc was added to the solution and the aqueous and organic phases separated. The organic phase was washed with 1N NaOH and brine, dried over $MgSO_4$, filtered and concentrated. The residue was purified by column chromatography ($SiO_2$, 89:10:1 $CH_2Cl_2$:MeOH:$NH_4OH$) to give the desired product (0.27 g, 51%).

Synthesis of 3-(2-{2-[2-(5-bromo-2-methoxyphenyl)-ethyl]-3-chlorophenyl}-4,5-dihydroimidazol-1-yl)-propionitrile (Compound ZF):

-continued

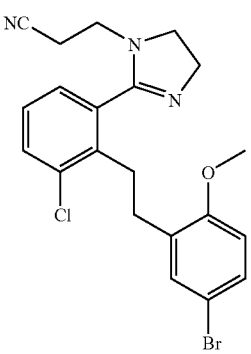

To a stirring slurry of the amidine (0.1 g, 1.0 equiv) and basic dowex (0.2 g, 8 wt %/mmol) in EtOH (0.85 mL) was added freshly distilled acrylonitrile (0.033 mL, 2.0 equiv). The mixture was heated at 60° C. in a sealed tube for 5.5 hr and then allowed to cool to room temperature. The slurry was filtered and the solid rinsed with EtOH. The filtrate was concentrated and the residue purified by column chromatography ($SiO_2$, 90:10:1:1 $CH_2Cl_2$:MeOH:$H_2O$:HCOOH) to give the desired product (0.049 g, 43%).

Synthesis of 2-{2-[2-(5-bromo-2-methoxyphenyl)-ethyl]-3-chlorobenzyl}-(4,5-dihydro-1H-imidazol-2-yl)-amine (Compound ZP):

Scheme 29

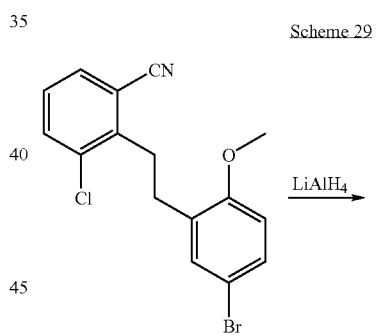

Scheme 28

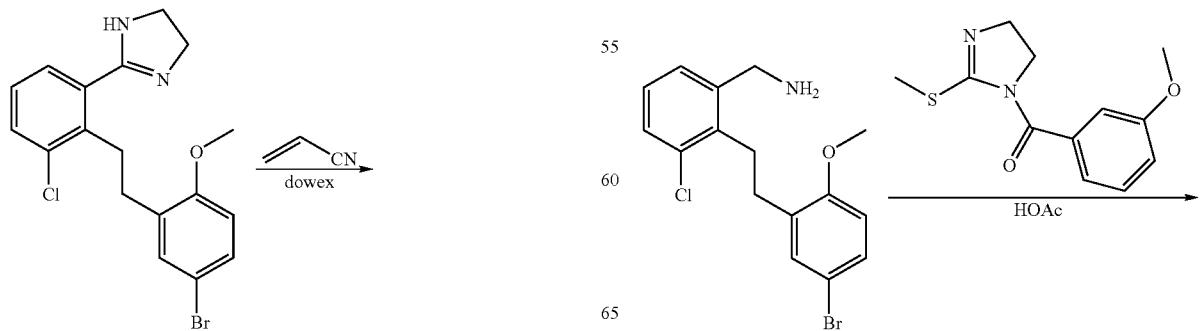

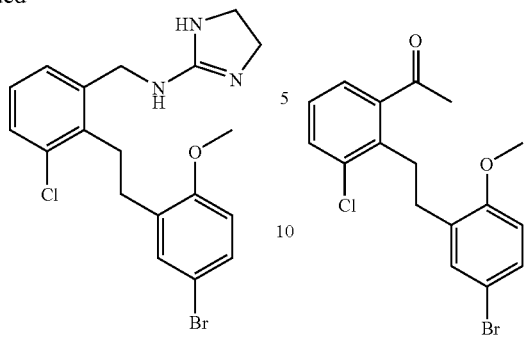

The benzonitrile (1.0 g, 1.0 equiv) was dissolved in THF (5 mL) and cooled to −78° C. under an atmosphere of argon. To this cooled solution was added LiAlH$_4$ (1.0 M 20 in THF, 3.7 mL, 1.3 equiv) dropwise. The reaction mixture was allowed to stir while warming to room temperature over 30 minutes. The reaction contents were poured onto ice and the resulting solution was basified by the addition of 6N NaOH. The mixture was extracted with ether and then the organic phase was dried over Na$_2$SO$_4$, filtered, and concentrated. The residue was purified by column chromatography (SiO$_2$, CH$_2$Cl$_2$/MeOH gradient) to give the desired benzyl amine (0.6 g, 60%).

To a solution of 2-methylsulfanyl-4,5-dihydro-1H-imidazole hydroiodide (1.22 g, 1.0 equiv) in CH$_2$Cl$_2$ (25 mL) under an atmosphere of argon at 0° C. was added triethylamine (1.5 mL, 2.2 equiv) and then 3-methoxybenzoyl chloride (0.78 mL, 1.1 equiv) dropwise. The reaction mixture was allowed to warm to room temperature and stir for 24 hr. After concentration, the resulting residue was diluted with EtOAc (50 mL) and hexane (50 mL). The mixture was filtered and then the filtrate concentrated and dried under vacuum to give a quantitative yield of (3-methoxyphenyl)-(2-methylsulfanyl-4,5-dihydroimidazol-1-yl)-methanone which was used directly in the next step.

A solution of the benzyl amine (0.252 g, 1.0 equiv) and the thiomethylimidazole (0.178 g, 1.0 equiv) in MeOH (4 mL) and HOAc (1 mL) was heated at 60° C. for 2 days. The solution was allowed to cool to room temperature and then concentrated. The residue was partitioned between CH$_2$Cl$_2$ and saturated aqueous NaHCO$_3$ and the organic phase was separated, dried over Na$_2$SO$_4$, filtered, and concentrated. The crude product was purified by column chromatography (SiO$_2$, CH$_2$Cl$_2$:MeOH:NH$_3$ 40:10:2) to give the desired product.

Synthesis of 3-{2-[2-(5-bromo-2-methoxyphenyl)-ethyl]-3-chlorophenyl}-(5,6-dihydroimidazo[2,1-b]thiazole (Compound ZQ):

Scheme 30

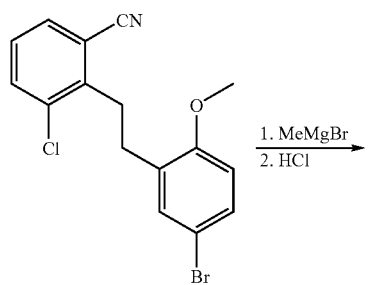

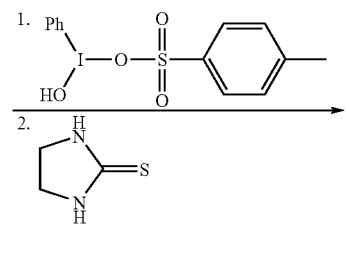

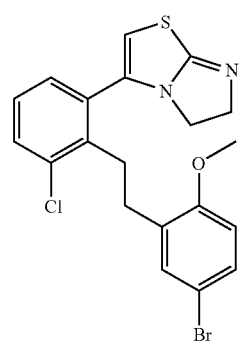

To a solution of methylmagnesium bromide (3.0 M in diethyl ether, 2.85 mL, 3.0 equiv) in THF (6 mL) under an atmosphere of argon at room temperature was added a solution of the nitrile (1.0 g, 1.0 equiv) in THF (6 mL). The resulting solution was allowed to stir at 60° C. for 16 hr and then allowed to cool to room temperature. The reaction mixture was poured into a mixture of diethyl ether (100 mL) and 1N aqueous HCl (100 mL). The aqueous phase was separated, transferred to a round-bottomed flask, and heated at reflux for 1 hr. After cooling to room temperature, the solution was extracted with diethyl ether (3×50 mL). The organic phase was washed with saturated aqueous NaHCO$_3$ (50 mL) and brine (50 mL), dried over MgSO$_4$, filtered, and concentrated. The residue was purified by column chromatography (SiO$_2$, 15% EtOAc in hexanes) to give the desired methyl ketone (0.85 g, 81%).

To a solution of the methyl ketone (0.78 g, 1.0 equiv) in acetonitrile (12 mL) under an atmosphere of argon at room temperature was added [hydroxyl(tosyloxy)iodo]benzene (0.83 g, 1 equiv). The solution was heated at reflux for 4 hr and then the solvent was evaporated. The residue was dissolved in ethanol (20 mL) and to this was added 2-imidazolidinethione (0.22 g, 1 equiv). The solution was heated at reflux for 4 hr and then allowed to cool to room temperature. The solvent was evaporated and the residue was diluted with EtOAc and then washed with saturated aqueous NaHCO$_3$ and brine. The aqueous phase was dried over MgSO$_4$, filtered, and concentrated. The residue was purified by column chromatography (SiO$_2$, 30% EtOAc in hexanes) to give the desired heterocycle (0.40 g, 42%).

Synthesis of 2-{2-[2-(5-bromo-2-methoxyphenyl)-ethyl]-3-chlorophenyl}-4,5-dihydro-imidazol-1-yl)-acetic acid (Compound ABB):

Scheme 31

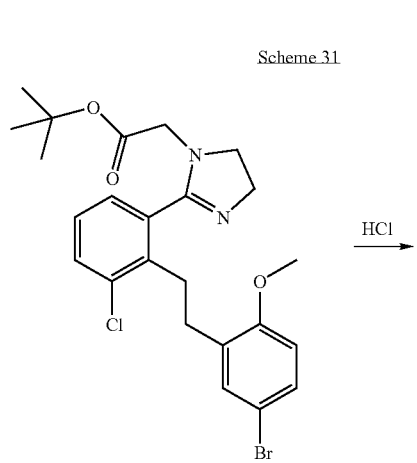

A solution of the t-butyl ester (0.046 g, 1.0 equiv) was stirred in a solution of HCl in dioxane (4N, 0.7 mL) at room temperature overnight. Concentration of the solvent and purification by column chromatography (SiO$_2$, 90:10:1:1 CH$_2$Cl$_2$:MeOH:H$_2$O:HCOOH) gave the desired carboxylic acid (0.016 g, 50%).

Synthesis of (2-{2-[2-(5-Bromo-2-methoxy-phenyl)-ethyl]-phenyl}-3-methyl-4,5-dihydro-3H-imidazol-4-yl)-methanol (Compound ABC):

Scheme 32

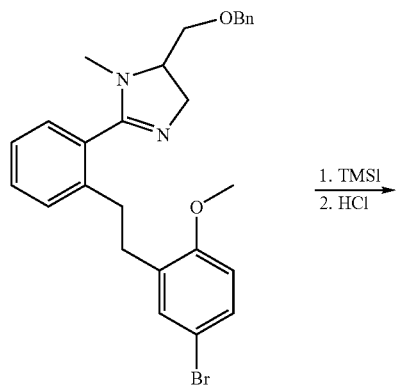

-continued

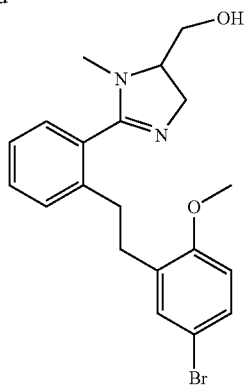

To a solution of the imidazoline (0.11 g, 1.0 equiv) in CH$_2$Cl$_2$ under an atmosphere of nitrogen was added iodotrimethylsilane (0.5 mL, 15 equiv). After 42.5 hours, additional iodotrimethylsilane (0.5 mL, 15 equiv) was added. After 67 hours total reaction time, the solution was concentrated under nitrogen and the residue was diluted with CH$_2$Cl$_2$. The solution was washed with saturated aqueous NaHCO$_3$ and brine before being dried over MgSO$_4$, filtered and concentrated. The residue was purified by RP HPLC and the resulting product was converted to the hydrochloride salt (6 mg, 6%).

Synthesis of [2-(1-[2-(4,5-dihydro-1H-imidazol-2-yl)-6-fluoro-phenyl]-ethyl]-naphthalen-2-yloxy)-ethyl]-dimethylamine (Compound ZM):

Scheme 33

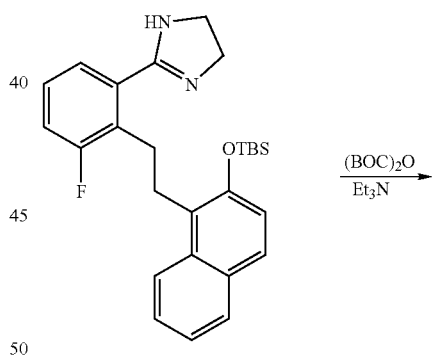

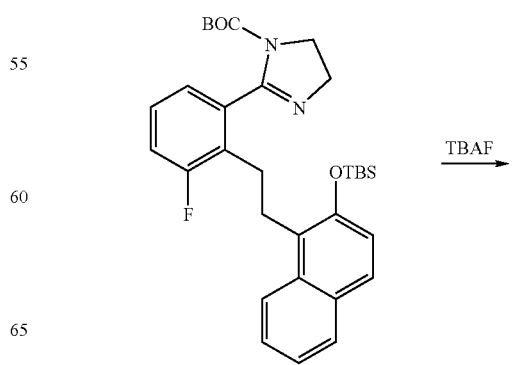

-continued

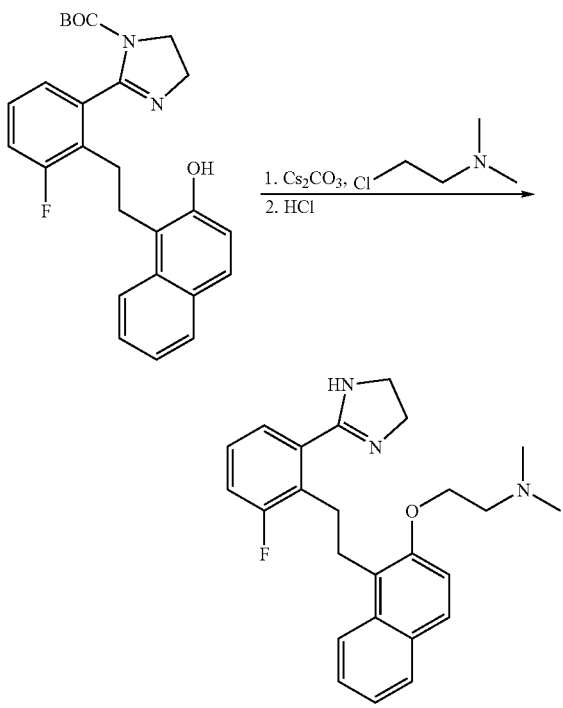

To a solution of the amidine (1.62 g, 1.0 equiv) in CH$_2$Cl$_2$ at 0° C. were added triethylamine (1.0 mL, 2.0 equiv) and di-tert-butyl-dicarbonate (0.95 g, 1.2 equiv). The reaction mixture was allowed to warm to room temperature and stir for 2 hr. The reaction was quenched by the addition of water and the solution was extracted with EtOAc. The organic phase was washed with brine, dried over Na$_2$SO$_4$, filtered, and concentrated. Purification of the residue by column chromatography (SiO$_2$, 99:1 CH$_2$Cl$_2$:1% NH$_3$ in MeOH) gave the desired product (1.5 g, 76%).

TBAF (1.0 M in THF, 5.5 mL, 1.5 equiv) was added to a solution of the protected alcohol (2.0 g, 1.0 equiv) in THF. The solution was allowed to stir for 30 min and was then quenched by the addition of water. The solution was extracted with EtOAc. The organic phase was washed with 1N HCl and brine, dried over Na$_2$SO$_4$, filtered, and concentrated. Purification of the residue by column chromatography (SiO$_2$, 99:1 CH$_2$Cl$_2$:1% NH$_3$ in MeOH) gave the desired product (0.90 g, 58%).

A heterogeneous mixture of the naphthol (0.097 g, 1.0 equiv) and cesium carbonate 0.18 g, 2.5 equiv) was heated at 60° C. for 20 min before the addition of dimethylamino ethyl chloride (0.034 g, 1.1 equiv). The reaction mixture was allowed to cool to room temperature and stir overnight. The reaction was quenched by the addition of water and the solution was extracted with EtOAc. The organic phase was washed with brine, s were combined, washed with brine, dried over Na$_2$SO$_4$, filtered, and concentrated. Purification of the residue by column chromatography (SiO$_2$, 99:1 CH$_2$Cl$_2$:1% NH$_3$ in MeOH) gave the protected amidine. Deprotection and salt formation with 4M HCl in dioxane at 60° C. gave the desired product as its bishydrochloride salt (0.011 g, 11%).

TABLE 1

Physical Data of Selected MC4-R Binding Compounds

| ID | Name | Molecular Formula | Exact Mass (free Base) | ES-LRMS found (M + H) | Melt Point (° C.) |
|---|---|---|---|---|---|
| I | 2-[2-(4-Benzyloxy-benzylsulfanyl)-phenyl]-1,4,5,6-tetrahydro-pyrimidine; hydrochloride | C$_{24}$H$_{24}$N$_2$OS HCl | 388.16 | 389.6 | 178-179 |
| M | 2-[2-(2-Iodo-benzylsulfanyl)-phenyl]-1,4,5,6-tetrahydro-pyrimidine; hydrochloride | C$_{17}$H$_{17}$IN$_2$S HCl | 408.02 | 409 | 207-209 |
| N | 2-[2-(2-Methoxy-5-nitro-benzylsulfanyl)-phenyl]-1,4,5,6-tetrahydro-pyrimidine; hydrobromide | C$_{18}$H$_{19}$N$_3$O$_3$S HBr | 357.11 | 358.1 | 239-241 |
| O | 2-[2-(Naphthalen-1-ylmethylsulfanyl)-phenyl]-1,4,5,6-tetrahydro-pyrimidine; hydrochloride | C$_{21}$H$_{20}$N$_2$S HCl | 332.13 | 333.1 | 207-208 |
| Q | 2-[2-(3-Chloro-benzylsulfanyl)-phenyl]-1,4,5,6-tetrahydro-pyrimidine; hydrobromide | C$_{17}$H$_{17}$ClN$_2$S HBr | 316.08 | 317 | 224-225.5 |
| AI | 2-[2-(2,5-Dimethoxy-benzylsulfanyl)-phenyl]-1,4,5,6-tetrahydro-pyrimidine; hydrochloride | C$_{19}$H$_{22}$N$_2$O$_2$S HCl | 342.14 | 343.2 | 201-202 |
| Z | 2-[2-(3-Bromo-benzylsulfanyl)-phenyl]-1,4,5,6-tetrahydro-pyrimidine; hydrobromide | C$_{17}$H$_{17}$BrN$_2$S HBr | 360.03 | 361 | 210-211 |
| B | 2-[2-(2-Chloro-6-fluoro-benzylsulfanyl)-phenyl]-1,4,5,6-tetrahydro-pyrimidine; hydrochloride | C$_{17}$H$_{16}$ClFN$_2$S HCl | 334.07 | 335 | 232-233 |
| AE | 2-[2-(2-Iodo-benzylsulfanyl)-phenyl]-4,5-dihydro-1H-imidazole; hydrochloride | C$_{16}$H$_{15}$IN$_2$S HCl | 394 | 394.9 | 184-185 |
| AF | 2-[2-(2-Methoxy-5-nitro-benzylsulfanyl)-phenyl]-4,5-dihydro-1H-imidazole; hydrobromide | C$_{17}$H$_{17}$N$_3$O$_3$ HBr | 343.1 | 344.1 | 253-254 |

TABLE 1-continued

Physical Data of Selected MC4-R Binding Compounds

| ID | Name | Molecular Formula | Exact Mass (free Base) | ES-LRMS found (M + H) | Melt Point (° C.) |
|---|---|---|---|---|---|
| Y | 2-[2-(2-Methoxy-5-nitro-benzyloxy)-phenyl]-1,4,5,6-tetrahydro-pyrimidine; hydrochloride | $C_{18}H_{19}N_3O_4$ HCl | 341.14 | 342.1 | 220-221 |
| AA | 2-[2-(2-Bromo-benzylsulfanyl)-phenyl]-1,4,5,6-tetrahydro-pyrimidine; hydrobromide | $C_{17}H_{17}BrN_2S$ HBr | 360.03 | 361.0 (rel. int. = 96) | 177-179 |
| P | 2-[2-(3-Iodo-benzylsulfanyl)-phenyl]-1,4,5,6-tetrahydro-pyrimidine; hydrobromide | $C_{17}H_{17}IN_2S$ HBr | 408.02 | 409 | 183-185 |
| AG | 2-[2-(2-Methoxy-5-nitro-benzylsulfanyl)-phenyl]-3a,4,5,6,7,7a-hexahydro-1H-benzoimidazole; hydrobromide | $C_{21}H_{23}N_3O_3S$ HBr | 397.15 | 398.1 | >240 |
| AL | 2-[2-(2-Methoxy-napthalen-1-ylmethylsulfanyl)-phenyl]-1,4,5,6-tetrahydropyrimidine; hydrochloride | $C_{22}H_{22}N_2OS$ HCl | 362.1 | 363 | |
| AM | 2-[2-(5-bromo-2-methoxy-benzylsulfanyl)-phenyl]-1,4,5,6-tetrahydropyrimidine; hydrochloride | $C_{18}H_{19}BrN_2OS$ HCl | 390 | 390.9 | |

The compounds given in Table 1, were made using procedures similar to that used for Compound IZ. The ES-LRMS values each had a relative intensity of 100.

The compounds given in Table 6, were made using general procedures similar to those used for Compounds TB, AAP, ZF, ZP, ZQ, ABB, ABC, ZM. For example:

a similar procedure can be used to couple a variety of halomethylaryls to substituted or unsubstituted aryl carbonitriles as that used in scheme 5 or 18 above;

a similar procedure can be used to couple a variety of bromomethyl- or chloromethyl-aryls to substituted or unsubstituted aryl carboxylic acids as that used in scheme 21 above, a variety of substituted ethylenediamines can be synthesized using a similar procedure to that of scheme 26;

by utilizing ethanolamines containing substituents on either or both carbons in the first step and other primary amines in the second step, a variety of amidines can be prepared using a similar procedure to that of scheme 27;

amidines can be synthesized using substituted acrylonitriles in a similar procedure to that of scheme 28;

substituted thiazoles can be prepared using a similar procedure to scheme 30 with a substituted imidazolidinethione; and other analogs can be prepared by the general procedure of scheme 33 using a variety of alkylchlorides in the final step.

Similar synthetic methods are designated according to the schemes depicted in examples above.

TABLE 6

Physical Data of Selected MC4-R Binding Compounds

| ID | Chemical Name | Mol Weight | LCMS m/z observed | Synthetic Methods |
|---|---|---|---|---|
| PZ | 5,5-Dimethyl-2-[2-(2-naphthalen-1-yl-ethyl)-phenyl]-4,5-dihydro-1H-imidazole | 328.4564 | 329 | 18, 26 |
| QA | 2-[3-Fluoro-2-(2-naphthalen-1-yl-ethyl)-phenyl]-5,5-dimethyl-4,5-dihydro-1H-imidazole | 346.4469 | 347 | 18, 26 |
| RD | 2-{2-[2-(5-Bromo-2-methoxy-phenyl)-ethyl]-3-methyl-phenyl}-5-methyl-4,5-dihydro-1H-imidazole | 387.3195 | 387.16 | 18, 26 |
| RG | 2-{2-[2-(5-Bromo-2-methoxy-phenyl)-ethyl]-3-chloro-phenyl}-4,4-dimethyl-4,5-dihydro-1H-imidazole | 421.7637 | 421.21 | 18, 26 |
| SJ | 2-{2-[2-(5-Bromo-2-methoxy-phenyl)-ethyl]-3-chloro-phenyl}-1-methyl-4,5-dihydro-1H-imidazole | 407.7374 | N/A | 18, 26 |
| TB | 2-{2-[2-(5-Bromo-2-methoxy-phenyl)-ethyl]-3-chloro-phenyl}-4,5-dihydro-1H-imidazole | 393.7105 | 394.66 | 18, 26 |
| TS | 2-{2-[2-(5-Bromo-2-methoxy-phenyl)-ethyl]-3-chloro-phenyl}-1-ethyl-4,5-dihydro-1H-imidazole | 421.7643 | 421 | 18, 26 |
| UH | 2-[3-Chloro-2-(2-naphthalen-1-yl-ethyl)-phenyl]-4,5-dihydro-1H-imidazole | 334.848 | 335.06 | 18, 26 |
| US | 2-{2-[2-(5-Bromo-2-methoxy-phenyl)-ethyl]-thiophen-3-yl}-1-methyl-4,5-dihydro-1H-imidazole | 379.3207 | 378.82 | 18, 26 |
| UZ | 2-{2-[2-(5-Bromo-2-methoxy-phenyl)-ethyl]-3-chloro-phenyl}-3a,4,5,6,7,7a-hexahydro-1H-benzoimidazole | 447.8021 | 446.95 | 7, 8, 9, 25, 21, 27 |
| VF | 2-[3-Chloro-2-(2-naphthalen-1-yl-ethyl)-phenyl]-1-methyl-4,5-dihydro-1H-imidazole | 348.8749 | 349.06 | 18, 26 |
| WL | 2-[2-(2-Benzofuran-7-yl-ethyl)-phenyl]-4,5-dihydro-1H-imidazole | 290.3648 | 291.1 | 18, 26 |

TABLE 6-continued

Physical Data of Selected MC4-R Binding Compounds

| ID | Chemical Name | Mol Weight | LCMS m/z observed | Synthetic Methods |
|---|---|---|---|---|
| WM | 2-[2-(2-Naphthalen-1-yl-ethyl)-phenyl]-4,5-dihydro-1H-imidazole | 300.433 | 301.12 | 18, 26 |
| WN | 2-[2-(2-Benzofuran-7-yl-ethyl)-3-fluoro-phenyl]-4,5-dihydro-1H-imidazole | 308.3553 | 309.09 | 18, 26 |
| WO | 1-Methyl-2-[2-(2-naphthalen-1-yl-ethyl)-phenyl]-4,5-dihydro-1H-imidazole | 314.4302 | 315.25 | 18, 26 |
| WP | 2-{2-[2-(2-Methyl-naphthalen-1-yl)-ethyl]-phenyl}-4,5-dihydro-1H-imidazole | 314.4302 | 315.16 | 18, 26 |
| WQ | 2-{2-[2-(5-Chloro-2-methoxy-phenyl)-ethyl]-phenyl}-4,5-dihydro-1H-imidazole | 314.8411 | 315.19 | 18, 26 |
| WR | 2-[3-Fluoro-2-(2-naphthalen-1-yl-ethyl)-phenyl]-4,5-dihydro-1H-imidazole | 318.3937 | 319.13 | 18, 26 |
| WS | 2-{2-[2-(2,5-Dichloro-phenyl)-ethyl]-phenyl}-4,5-dihydro-1H-imidazole | 319.2329 | 319.01 | 18, 26 |
| WT | 2-[2-(2-Benzo[b]thiophen-4-yl-ethyl)-3-fluoro-phenyl]-4,5-dihydro-1H-imidazole | 324.4219 | 325.12 | 18, 26 |
| WU | 1-Ethyl-2-[2-(2-naphthalen-1-yl-ethyl)-phenyl]-4,5-dihydro-1H-imidazole | 328.457 | 329 | 18, 26 |
| WV | 2-[2-(2-Benzo[1,3]dioxol-4-yl-ethyl)-3-chloro-phenyl]-4,5-dihydro-1H-imidazole | 328.798 | 329.11 | 18, 26 |
| WX | 2-{2-[2-(2-Methoxy-naphthalen-1-yl)-ethyl]-phenyl}-4,5-dihydro-1H-imidazole | 330.4296 | 331.11 | 18, 26 |
| WY | 2-{3-Chloro-2-[2-(4-fluoro-naphthalen-1-yl)-ethyl]-phenyl}-4,5-dihydro-1H-imidazole | 352.8385 | 353.15 | 18, 26 |
| WZ | 2-{2-[2-(2,3,5-Trichloro-phenyl)-ethyl]-phenyl}-4,5-dihydro-1H-imidazole | 353.6777 | 353.05 | 18, 26 |
| XA | 3-[2-(2-Naphthalen-1-yl-ethyl)-phenyl]-1,5,6,7,8,8a-hexahydro-imidazo[1,5-a]pyridine | 354.4949 | 355.15 | 18, 26 |
| XB | 2-{2-[2-(5-Bromo-2-methoxy-phenyl)-ethyl]-phenyl}-4,5-dihydro-1H-imidazole | 359.2657 | 359.98 | 18, 26 |
| XC | 2-{2-[2-(2-Bromo-5-chloro-phenyl)-ethyl]-phenyl}-4,5-dihydro-1H-imidazole | 363.6842 | N/A | 18, 26 |
| XD | 2-{2-[2-(5-Bromo-2-chloro-phenyl)-ethyl]-phenyl}-4,5-dihydro-1H-imidazole | 363.6842 | 363.73 | 18, 26 |
| XE | 2-{3-Fluoro-2-[2-(2-methoxy-5-trifluoromethyl-phenyl)-ethyl]-phenyl}-4,5-dihydro-1H-imidazole | 366.3584 | 367.27 | 18, 26 |
| XF | 2-{2-[2-(2-Methyl-naphthalen-1-yl)-ethyl]-phenyl}-3a,4,5,6,7,7a-hexahydro-1H-benzoimidazole | 368.5218 | 369.09 | 18, 26 |
| XG | 2-{2-[2-(5-Bromo-benzofuran-7-yl)-ethyl]-phenyl}-4,5-dihydro-1H-imidazole | 369.2609 | 369.07 | 18, 26 |
| XH | 2-{2-[2-(5-Bromo-2,3-dihydro-benzofuran-7-yl)-ethyl]-phenyl}-4,5-dihydro-1H-imidazole | 371.2767 | 372.99 | 18, 26 |
| XJ | 2-{2-[2-(6-Bromo-benzo[1,3]dioxol-4-yl)-ethyl]-phenyl}-4,5-dihydro-1H-imidazole | 373.2493 | 373.11 | 18, 26 |
| XK | 2-{2-[2-(5-Bromo-2-methoxy-phenyl)-ethyl]-phenyl}-1-methyl-4,5-dihydro-1H-imidazole | 373.2926 | 375.97 | 18, 26 |
| XL | 3-[3-Chloro-2-(2-naphthalen-1-yl-ethyl)-phenyl]-5,6,7,7a-tetrahydro-1H-pyrrolo[1,2-c]imidazole | 374.9128 | 375.09 | 18, 26 |
| XM | 2-{2-[2-(5-Bromo-2-methoxy-phenyl)-ethyl]-3-fluoro-phenyl}-4,5-dihydro-1H-imidazole | 377.2562 | 377.11 | 18, 26 |
| XN | 2-{2-[2-(3-Bromo-naphthalen-1-yl)-ethyl]-phenyl}-4,5-dihydro-1H-imidazole | 379.2993 | 378.82 | 18, 26 |
| XO | 2-{2-[2-(2-Bromo-5-chloro-phenyl)-ethyl]-3-fluoro-phenyl}-4,5-dihydro-1H-imidazole | 381.6747 | 380.93 | 18, 26 |
| XP | 2-{2-[2-(5-Bromo-2-chloro-phenyl)-ethyl]-3-fluoro-phenyl}-4,5-dihydro-1H-imidazole | 381.6747 | 380.93 | 18, 26 |
| XQ | 2-{2-[2-(5-Bromo-2-methyl-benzofuran-7-yl)-ethyl]-phenyl}-4,5-dihydro-1H-imidazole | 383.2877 | 383.09 | 18, 26 |
| XR | 2-{2-[2-(2-Methoxy-naphthalen-1-yl)-ethyl]-phenyl}-3a,4,5,6,7,7a-hexahydro-1H-benzoimidazole | 384.5212 | 385.22 | 18, 26 |
| XS | 2-{2-[2-(5-Bromo-benzo[b]thiophen-7-yl)-ethyl]-phenyl}-4,5-dihydro-1H-imidazole | 385.3275 | 385.14 | 18, 26 |
| XT | 2-{2-[2-(5-Bromo-benzofuran-7-yl)-ethyl]-3-fluoro-phenyl}-4,5-dihydro-1H-imidazole | 387.2513 | 388.98 | 18, 26 |
| XU | 2-{2-[2-(5-Bromo-2-methoxy-phenyl)-ethyl]-phenyl}-1-ethyl-4,5-dihydro-1H-imidazole | 387.3195 | 388.99 | 18, 26 |
| XW | 2-[3-Chloro-2-(2-naphthalen-1-yl-ethyl)-phenyl]-3a,4,5,6,7,7a-hexahydro-1H-benzoimidazole | 388.9397 | 389.13 | 18, 26 |
| XY | 3-[3-Chloro-2-(2-naphthalen-1-yl-ethyl)-phenyl]-1,5,6,7,8,8a-hexahydro-imidazo[1,5-a]pyridine | 388.9397 | 389.11 | 18, 26 |
| XZ | 2-{2-[2-(6-Bromo-benzo[1,3]dioxol-4-yl)-ethyl]-3-fluoro-phenyl}-4,5-dihydro-1H-imidazole | 391.2397 | 392.91 | 18, 26 |
| YA | 2-{2-[2-(5-Bromo-2-methoxy-phenyl)-ethyl]-3-fluoro-phenyl}-1-methyl-4,5-dihydro-1H-imidazole | 391.2831 | 391.26 | 18, 26 |
| YB | 2-{2-[2-(3-Bromo-naphthalen-1-yl)-ethyl]-3-fluoro-phenyl}-4,5-dihydro-1H-imidazole | 397.2898 | 396.77 | 18, 26 |
| YC | 2-{2-[2-(5-Bromo-2,3-dimethyl-benzofuran-7-yl)-ethyl]-phenyl}-4,5-dihydro-1H-imidazole | 397.3146 | 397.07 | 18, 26 |
| YD | 2-{2-[2-(5-Bromo-benzo[b]thiophen-7-yl)-ethyl]- | 403.3179 | 402.96 | 18, 26 |

TABLE 6-continued

Physical Data of Selected MC4-R Binding Compounds

| ID | Chemical Name | Mol Weight | LCMS m/z observed | Synthetic Methods |
|---|---|---|---|---|
| | 3-fluoro-phenyl}-4,5-dihydro-1H-imidazole | | | |
| YE | 2-{2-[2-(5-Bromo-2-methoxy-phenyl)-ethyl]-3-ethoxy-phenyl}-4,5-dihydro-1H-imidazole | 403.3189 | 403.1 | 18, 26 |
| YF | 2-{2-[2-(5-Bromo-2-methoxy-phenyl)-ethyl]-3-methoxy-phenyl}-1-methyl-4,5-dihydro-1H-imidazole | 403.3189 | 404.93 | 18, 26 |
| YG | 2-{2-[2-(5-Bromo-benzofuran-7-yl)-ethyl]-3-chloro-phenyl}-4,5-dihydro-1H-imidazole | 403.7056 | 404.96 | 18, 26 |
| YH | 2-{2-[2-(5-Bromo-2-methoxy-phenyl)-ethyl]-3-fluoro-phenyl}-1-ethyl-4,5-dihydro-1H-imidazole | 405.31 | N/A | 18, 26 |
| YI | 2-{2-[2-(5-Bromo-2-methoxy-phenyl)-ethyl]-3-fluoro-phenyl}-5,5-dimethyl-4,5-dihydro-1H-imidazole | 405.31 | 405.18 | 18, 26 |
| YJ | 2-{2-[2-(6-Bromo-benzo[1,3]dioxol-4-yl)-ethyl]-3-chloro-phenyl}-4,5-dihydro-1H-imidazole | 407.694 | 406.95 | 18, 26 |
| YK | 2-{2-[2-(2,5-Dibromo-phenyl)-ethyl]-phenyl}-4,5-dihydro-1H-imidazole | 408.1355 | 407.07 | 18, 26 |
| YL | 2-{2-[2-(5-Bromo-benzofuran-7-yl)-ethyl]-3-ethoxy-phenyl}-4,5-dihydro-1H-imidazole | 413.314 | 415.1 | 18, 26 |
| YM | 3-{2-[2-(5-Bromo-2-methoxy-phenyl)-ethyl]-phenyl}-1,5,6,7,8,8a-hexahydro-imidazo[1,5-a]pyridine | 413.3547 | 415.1 | 18, 26 |
| YN | 2-{2-[2-(3-Bromo-naphthalen-1-yl)-ethyl]-3-chloro-phenyl}-4,5-dihydro-1H-imidazole | 413.7441 | 412.69 | 18, 26 |
| YO | 2-{2-[2-(8-Bromo-naphthalen-1-yl)-ethyl]-3-chloro-phenyl}-4,5-dihydro-1H-imidazole | 413.7441 | 413.38 | 18, 26 |
| YP | 2-{2-[2-(5-Bromo-2-methoxy-phenyl)-ethyl]-3-ethoxy-phenyl}-1-methyl-4,5-dihydro-1H-imidazole | 417.3458 | 418.93 | 18, 26 |
| YQ | 2-{2-[2-(2,5-Dibromo-phenyl)-ethyl]-3-fluoro-phenyl}-4,5-dihydro-1H-imidazole | 426.126 | 424.92 | 18, 26 |
| YR | 2-{2-[2-(5-Bromo-2-trifluoromethoxy-phenyl)-ethyl]-3-fluoro-phenyl}-4,5-dihydro-1H-imidazole | 431.2276 | 430.76 | 18, 26 |
| YS | 2-{2-[2-(5-Bromo-2-trifluoromethoxy-phenyl)-ethyl]-phenyl}-4,5-dihydro-1H-imidazole | 431.2371 | 412.73 | 18, 26 |
| YT | 3-{2-[2-(5-Bromo-2-methoxy-phenyl)-ethyl]-3-fluoro-phenyl}-1,5,6,7,8,8a-hexahydro-imidazo[1,5-a]pyridine | 431.3478 | 431.1 | 18, 26 |
| YU | 2-{2-[2-(5-Bromo-2-methoxy-phenyl)-ethyl]-3-ethoxy-phenyl}-1-ethyl-4,5-dihydro-1H-imidazole | 431.3727 | 430.97 | 18, 26 |
| YV | 3-{2-[2-(5-Bromo-2-methoxy-phenyl)-ethyl]-3-chloro-phenyl}-5,6,7,7a-tetrahydro-1H-pyrrolo[1,2-c]imidazole | 433.7753 | 432.88 | 18, 26 |
| YW | 2-{2-[2-(6-Bromo-2-methoxy-naphthalen-1-yl)-ethyl]-3-chloro-phenyl}-4,5-dihydro-1H-imidazole | 443.7704 | 443.54 | 18, 26 |
| YX | 2-{2-[2-(5-Bromo-2-trifluoromethoxy-phenyl)-ethyl]-3-chloro-phenyl}-4,5-dihydro-1H-imidazole | 447.6819 | 446.75 | 18, 26 |
| YY | 2-{2-[2-(5-Bromo-2-methoxy-phenyl)-ethyl]-3-chloro-phenyl}-3a,4,5,6,7,7a-hexahydro-1H-benzoimidazole | 447.8021 | 449.12 | 18, 26 |
| YZ | 3-{2-[2-(5-Bromo-2-methoxy-phenyl)-ethyl]-3-chloro-phenyl}-1,5,6,7,8,8a-hexahydro-imidazo[1,5-a]pyridine | 447.8021 | 446.87 | 18, 26 |
| ZA | 2-{2-[2-(2,5-Dibromo-benzofuran-7-yl)-ethyl]-3-fluoro-phenyl}-4,5-dihydro-1H-imidazole | 466.1474 | 466.99 | 18, 26 |
| ZB | 2-{2-[2-(5-Bromo-2-methoxy-phenyl)-ethyl]-3-chloro-phenyl}-1-phenyl-4,5-dihydro-1H-imidazole | 469.8083 | 468.92 | 18, 26 |
| ZC | 2-{2-[2-(4-Bromo-3'-chloro-biphenyl-2-yl)-ethyl]-3-chloro-phenyl}-4,5-dihydro-1H-imidazole | 474.2267 | 473.68 | 18, 26 |
| ZD | 3-{2-[2-(2-Naphthalen-1-yl-ethyl)-phenyl]-4,5-dihydro-imidazol-1-yl}-pentanenitrile | 381.5206 | 382.37 | 18, 26, 28 |
| ZE | 3-Methoxy-3-{2-[2-(2-naphthalen-1-yl-ethyl)-phenyl]-4,5-dihydro-imidazol-1-yl}-propionitrile | 383.4931 | 384.11 | 18, 26, 28 |
| ZF | 3-(2-{2-[2-(5-Bromo-2-methoxy-phenyl)-ethyl]-3-chloro-phenyl}-4,5-dihydro-imidazol-1-yl)-propionitrile | 446.7741 | 446.02 | 18, 26, 28 |
| ZG | 3-(2-{2-[2-(5-Bromo-2-methoxy-phenyl)-ethyl]-3-chloro-phenyl}-4,5-dihydro-imidazol-1-yl)-2-methyl-propionitrile | 460.8009 | 460.06 | 18, 26, 28 |
| ZH | 3-(2-{2-[2-(5-Bromo-2-methoxy-phenyl)-ethyl]-3-chloro-phenyl}-4,5-dihydro-imidazol-1-yl)-butyronitrile | 460.8009 | 459.99 | 18, 26, 28 |
| ZI | 3-(2-{2-[2-(5-Bromo-2-methoxy-phenyl)-ethyl]-3-chloro-phenyl}-4,5-dihydro-imidazol-1-yl)-pentanenitrile | 474.8278 | 474 | 18, 26, 28 |
| ZJ | 3-(2-{2-[2-(5-Bromo-2-methoxy-phenyl)-ethyl]-3-chloro-phenyl}-4,5-dihydro-imidazol-1-yl)-3-methoxy-propionitrile | 476.8003 | 475.97 | 18, 26, 28 |
| ZK | 2-(1-{2-[2-(4,5-Dihydro-1H-imidazol-2-yl)-6-fluoro-phenyl]-ethyl}-naphthalen-2-yloxy)-ethylamine | 377.4616 | N/A | 18, 26, 33 |
| ZL | 2-(3-Fluoro-2-{2-[2-(3-methyl-butoxy)-naphthalen-1-yl]-ethyl}-phenyl)-4,5-dihydro-1H-imidazole | 404.5275 | 405.16 | 18, 26, 33 |
| ZM | [2-(1-{2-[2-(4,5-Dihydro-1H-imidazol-2-yl)-6-fluoro-phenyl]-ethyl}-naphthalen-2-yloxy)-ethyl]-dimethyl-amine | 405.5153 | 406.14 | 18, 26, 33 |
| ZN | [3-(1-{2-[2-(4,5-Dihydro-1H-imidazol-2-yl)-6-fluoro- | 419.5422 | N/A | 18, 26, 33 |

TABLE 6-continued

Physical Data of Selected MC4-R Binding Compounds

| ID | Chemical Name | Mol Weight | LCMS m/z observed | Synthetic Methods |
|---|---|---|---|---|
| | phenyl]-ethyl}-naphthalen-2-yloxy)-propyl]-dimethyl-amine | | | |
| ZO | 4-[2-[1-{2-[2-(4,5-Dihydro-1H-imidazol-2-yl)-6-fluoro-phenyl]-ethyl}-naphthalen-2-yloxy)-ethyl]-morpholine | 447.5526 | N/A | 18, 26, 33 |
| ZP | {2-[2-(5-Bromo-2-methoxy-phenyl)-ethyl]-3-chloro-benzyl}-(4,5-dihydro-1H-imidazol-2-yl)-amine | 422.7521 | 422 | 18, 29 |
| ZQ | 3-{2-[2-(5-Bromo-2-methoxy-phenyl)-ethyl]-3-chloro-phenyl}-5,6-dihydro-imidazo[2,1-b]thiazole | 449.7985 | 449.25 | 18, 30 |
| ZR | 3-{2-[2-(5-Bromo-2-methoxy-phenyl)-ethyl]-3-chloro-phenyl}-6,6-dimethyl-5,6-dihydro-imidazo[2,1-b]thiazole | 477.8523 | 477.27 | 18, 30 |
| ZS | 2-{2-[2-(5-Bromo-2-difluoromethoxy-phenyl)-ethyl]-3-chloro-phenyl}-4,5-dihydro-1H-imidazole | 429.6914 | 431.01 | 19, 26 |
| ZT | 2-(4,5-Dihydro-1H-imidazol-2-yl)-3-(2-naphthalen-1-yl-ethyl)-pyridine | 301.3911 | 302.16 | 20, 26 |
| UR | (2-{2-[2-(5-Bromo-2-methoxy-phenyl)-ethyl]-3-chloro-phenyl}-4,5-dihydro-imidazol-1-yl)-acetonitrile | 432.7472 | 432.03 | 21, 27 |
| UY | 2-{2-[2-(5-Bromo-2-methoxy-phenyl)-ethyl]-3-chloro-phenyl}-1-propyl-4,5-dihydro-1H-imidazole | 435.7911 | 434.73 | 21, 27 |
| VG | 1-Benzyl-2-{2-[2-(5-bromo-2-methoxy-phenyl)-ethyl]-3-chloro-phenyl}-4,5-dihydro-1H-imidazole | 483.8351 | 484.91 | 21, 27 |
| VI | 2-{2-[2-(5-Bromo-2-methoxy-phenyl)-ethyl]-3-chloro-phenyl}-1-isopropyl-4,5-dihydro-1H-imidazole | 435.7911 | 435.55 | 21, 27 |
| VJ | 2-{2-[2-(5-Bromo-2-methoxy-phenyl)-ethyl]-3-chloro-phenyl}-1-(2,2,2-trifluoro-ethyl)-4,5-dihydro-1H-imidazole | 475.7356 | 475 | 21, 27 |
| ZU | 4-Chloro-3-{2-[2-(4,5-dihydro-1H-imidazol-2-yl)-6-fluoro-phenyl]-ethyl}-benzonitrile | 327.7884 | 327.76 | 21, 27 |
| ZV | 7-{2-[2-(4,5-Dihydro-1H-imidazol-2-yl)-6-fluoro-phenyl]-ethyl}-benzofuran-5-carbonitrile | 333.3651 | 334.15 | 21, 27 |
| ZW | 3-{2-[2-Chloro-6-(4,5-dihydro-1H-imidazol-2-yl)-phenyl]-ethyl}-4-methoxy-benzonitrile | 339.8242 | 340.55 | 21, 27 |
| ZX | 2-(1-Isopropyl-4,5-dihydro-1H-imidazol-2-yl)-3-(2-naphthalen-1-yl-ethyl)-pyridine | 343.4717 | 344.24 | 21, 27 |
| ZY | 7-{2-[2-Chloro-6-(4,5-dihydro-1H-imidazol-2-yl)-phenyl]-ethyl}-benzofuran-5-carbonitrile | 349.8194 | 350.13 | 21, 27 |
| ZZ | (2-{2-[2-(2-Methyl-naphthalen-1-yl)-ethyl]-phenyl}-4,5-dihydro-imidazol-1-yl)-acetonitrile | 353.4668 | 354.18 | 21, 27 |
| AAA | (2-{2-[2-(2-Methoxy-naphthalen-1-yl)-ethyl]-phenyl}-4,5-dihydro-imidazol-1-yl)-acetonitrile | 369.4662 | 370.18 | 21, 27 |
| AAB | 2-{2-[2-(5-Bromo-2-methoxy-phenyl)-ethyl]-6-methyl-phenyl}-4,5-dihydro-1H-imidazole | 373.2926 | 375.14 | 21, 27 |
| AAC | {2-[3-Chloro-2-(2-naphthalen-1-yl-ethyl)-phenyl]-4,5-dihydro-imidazol-1-yl}-acetonitrile | 373.8847 | 373.79 | 21, 27 |
| AAD | 2-[3-Chloro-2-(2-naphthalen-1-yl-ethyl)-phenyl]-1-propyl-4,5-dihydro-1H-imidazole | 376.9287 | 377.2 | 21, 27 |
| AAE | 2-{2-[2-(5-Bromo-2-methoxy-phenyl)-ethyl]-phenyl}-1,5-dimethyl-4,5-dihydro-1H-imidazole | 387.3195 | 387.25 | 21, 27 |
| AAF | 2-{2-[2-(5-Bromo-2-methoxy-phenyl)-ethyl]-phenyl}-1,4-dimethyl-4,5-dihydro-1H-imidazole | 387.3195 | 387.16 | 21, 27 |
| AAG | 2-{2-[2-(5-Bromo-2-methoxy-phenyl)-ethyl]-6-methoxy-phenyl}-4,5-dihydro-1H-imidazole | 389.292 | 388.79 | 21, 27 |
| AAH | 2-{2-[2-(5-Bromo-2-methoxy-phenyl)-ethyl]-3-fluoro-phenyl}-5-methyl-4,5-dihydro-1H-imidazole | 391.2831 | 393.03 | 21, 27 |
| AAI | 2-{2-[2-(5-Bromo-2-methoxy-phenyl)-ethyl]-phenyl}-5-ethyl-1-methyl-4,5-dihydro-1H-imidazole | 401.3464 | 401.25 | 21, 27 |
| AAJ | 2-{2-[2-(5-Bromo-2-methoxy-phenyl)-ethyl]-phenyl}-1,4,5-trimethyl-4,5-dihydro-1H-imidazole | 401.3464 | 401.21 | 21, 27 |
| AAK | 2-{2-[2-(5-Bromo-2-methoxy-phenyl)-ethyl]-phenyl}-4-ethyl-1-methyl-4,5-dihydro-1H-imidazole | 401.3464 | 401.23 | 21, 27 |
| AAL | 2-{2-[2-(5-Bromo-2-methoxy-phenyl)-ethyl]-thiophen-3-yl}-1-propyl-4,5-dihydro-1H-imidazole | 407.3745 | 409.05 | 21, 27 |
| AAM | 2-{2-[2-(5-Bromo-2-methoxy-phenyl)-ethyl]-thiophen-3-yl}-1-isopropyl-4,5-dihydro-1H-imidazole | 407.3745 | 409.05 | 21, 27 |
| AAN | 2-{2-[2-(5-Bromo-2-methoxy-phenyl)-ethyl]-phenyl}-4-isopropyl-1-methyl-4,5-dihydro-1H-imidazole | 415.3733 | 415.3 | 21, 27 |
| AAO | 3-(2-{2-[2-(5-Bromo-2-methoxy-phenyl)-ethyl]-thiophen-3-yl}-4,5-dihydro-imidazol-1-yl)-propionitrile | 418.3574 | 420.06 | 21, 27 |
| AAP | 2-{2-[2-(5-Bromo-2-methoxy-phenyl)-ethyl]-3-fluoro-phenyl}-1-isopropyl-4,5-dihydro-1H-imidazole | 419.3368 | 419.17 | 21, 27 |
| AAQ | 2-{2-[2-(5-Bromo-2-methoxy-phenyl)-ethyl]-3-fluoro-phenyl}-1-(2-fluoro-ethyl)-4,5-dihydro-1H-imidazole | 423.3004 | 423.25 | 21, 27 |
| AAR | 2-{2-[2-(5-Bromo-2-methoxy-phenyl)-ethyl]-3-fluoro-phenyl}-1-butyl-4,5-dihydro-1H-imidazole | 433.3637 | 433.29 | 21, 27 |
| AAS | 2-(2-{2-[2-(5-Bromo-2-methoxy-phenyl)-ethyl]-3- | 446.7741 | 447.87 | 21, 27 |

TABLE 6-continued

Physical Data of Selected MC4-R Binding Compounds

| ID | Chemical Name | Mol Weight | LCMS m/z observed | Synthetic Methods |
|---|---|---|---|---|
| | chloro-phenyl}-4,5-dihydro-imidazol-1-yl)-propionitrile | | | |
| AAT | 2-{2-[2-(5-Bromo-2-methoxy-phenyl)-ethyl]-3-fluoro-phenyl}-1-(2,2,2-trifluoro-ethyl)-4,5-dihydro-1H-imidazole | 459.2814 | 459.13 | 21, 27 |
| AAU | 2-{2-[2-(5-Bromo-2-methoxy-phenyl)-ethyl]-3-fluoro-phenyl}-1-(2-pyrrolidin-1-yl-ethyl)-4,5-dihydro-1H-imidazole | 474.4163 | 474.29 | 21, 27 |
| AAV | 2-{2-[2-(5-Bromo-2-methoxy-phenyl)-ethyl]-3-fluoro-phenyl}-1-(3-pyrrolidin-1-yl-propyl)-4,5-dihydro-1H-imidazole | 488.4432 | 488.35 | 21, 27 |
| AAW | 2-{2-[2-(5-Bromo-2-methoxy-phenyl)-ethyl]-3-chloro-phenyl}-1-propyl-3a,4,5,6,7,7a-hexahydro-1H-benzoimidazole | 489.8828 | 491.09 | 21, 27 |
| AAX | [3-(2-{2-[2-(5-Bromo-2-methoxy-phenyl)-ethyl]-3-fluoro-phenyl}-4,5-dihydro-imidazol-1-yl)-propyl]-diethyl-amine | 490.459 | 490.32 | 21, 27 |
| AAY | 4-[3-(2-{2-[2-(5-Bromo-2-methoxy-phenyl)-ethyl]-3-fluoro-phenyl}-4,5-dihydro-imidazol-1-yl)-propyl]-morpholine | 504.4426 | 504.37 | 21, 27 |
| AAZ | 1-[3-(2-{2-[2-(5-Bromo-2-methoxy-phenyl)-ethyl]-3-fluoro-phenyl}-4,5-dihydro-imidazol-1-yl)-propyl]-4-methyl-piperazine | 517.4847 | 517.38 | 21, 27 |
| ABA | [4-(2-{2-[2-(5-Bromo-2-methoxy-phenyl)-ethyl]-3-chloro-phenyl}-4,5-dihydro-imidazol-1-yl)-pentyl]-diethyl-amine | 534.9671 | 534.13 | 21, 27 |
| ABB | (2-{2-[2-(5-Bromo-2-methoxy-phenyl)-ethyl]-3-chloro-phenyl}-4,5-dihydro-imidazol-1-yl)-acetic acid | 451.7472 | 453.03 | 21, 27, 32 |
| ABC | (2-{2-[2-(5-Bromo-2-methoxy-phenyl)-ethyl]-phenyl}-3-methyl-4,5-dihydro-3H-imidazol-4-yl)-methanol | 403.3189 | 403.15 | 21, 27, 32 |
| ABD | 2-{2-[2-(5-Bromo-2-methoxy-phenyl)-ethyl]-6-chloro-phenyl}-4,5-dihydro-1H-imidazole | 393.7105 | 392.93 | 21, 27, 33 |

Example 4

Scincillation Proximity Assay (SPA)

High-Throughput Receptor Binding Screening for MC4-R Binding Compounds

A. Preparation of Membranes from MC4-R Cells

A crude preparation of plasma membranes, of sufficient purity for use in the scintillation proximity assay (SPA), was prepared using the following protocol (Maeda et al. (1983) *Biochem. Biophys. Acta* 731:115-120).

MC4-R cells were stable recombinant K293 cells overexpressing the MC4-R. The cells were routinely cultured and passaged in a growth medium composed of DMEM base medium: 10% fetal bovine serum (FBS), 1× Glutamine, and 0.5 mg/ml G418. Terminal cultures (i.e., those which will be processed to produce plasma membranes) were grown in identical media, with the exception that the media contained 0.2 mg/ml G418.

At 4° C., harvested cells were pelleted and immediately washed with 25 mL of PBS. The washed cells were resuspended in two volumes of STM buffer (0.25 M sucrose, 5 mM Tris, 1 mM $MgCl_2$, pH 7.5), containing Boehringer Complete™ protease inhibitors. Cell breakage was accomplished using a Dounce homogenizer. After 20-30 strokes, nuclei and unbroken cells were pelleted by centrifugation at 1100 rpm for 5 minutes. The supernatant was saved and the pellet was resuspended in 1 volume of STM/protease inhibitors, and then a further lysis step was carried out by the Dounce homogenizer (10-20 strokes). This material was then combined with the first supernatant. 11.25 mL of the homogenate was gently layered on top of 27.25 mL f 42% (w/w) sucrose (5 mM Tris, 1 mM $MgCl_2$, pH 7.5). After spinning at 28,000 rpm (ultracentrifuge, SW-28 rotor) for 90 minutes, membranes were collected at the interface with a transfer pipette.

The membrane suspension obtained from the sucrose interface was collected and diluted with 5 mM Tris and 1 mM $MgCl_2$. Membranes were collected by a further round of centrifugation at 33,000 rpm for 30 minutes (SW-41 Ti rotor). The pellet of membranes was subsequently resuspended in a small (0.5 mL) volume of STM, using a 2 mL Dounce homogenizer, and immediately frozen. The resulting membranes were stable to both freeze-thaw cycles and temperatures around 4° C. for at least 6 hours.

B. High-throughput Screen

A scincillation proximity assay (SPA) format ligand binding assay was used. The membranes from the MC4-R mammalian cells (K293 expressing MC4-R) were bound to wheat germ agglutinin (WGA) coated SPA beads. The membrane coated SPA beads were added to screening plates, which contained the test compounds pre-dissolved in 30 µL of 10% DMSO. After pre-equilibration of the receptor coated beads with the test compounds (1 hour), 2 nM of radioactive ligand ([$^{125}$I]NDP-α-MSH) was added. Since the binding of the radioactive ligand to the receptor causes the scincillation of the beads, blockage of the binding of the radioactive ligand by a small molecule causes a reduction in scincillation.

1. Pre-Binding of the MC4R Membranes to the WGA-SPA Beads

The membranes were mixed with the SPA beads to make a 2× stock of membrane and beads.

For a twenty plate batch of screening plates, the components were mixed in proportions given in Table 2. The membranes and beads were stirred with a magnetic stir bar at room temperature for 1-2 hours to allow binding.

TABLE 2

| Component | Volume | Final Concentration in Assay |
|---|---|---|
| 4 mg/ml WGA-SPA Beads | 14.4 mL | 25 µg/well |
| MC4R crude plasma membranes* | 600 µL* | 5 µg/well |
| SPA Binding Buffer | 100 mL | N/A |

*the exact amount of membranes used varies with the quality of the membrane preparation and must be checked for each new batch.

2. Binding Assay

The following assay was performed with automation using a Titertec MultiDrop with plate stacker.

30 µL of 10% DMSO was added per well to the dried compound film in an OptiPlate. Then, 5 µL of cold NDP-α-MSH was added to the control wells. Subsequently, 50 µl per well of 2× membranes and beads were added and pre-equilibrated with the compounds for 1 hour.

Binding was initiated by adding 20 µL of radioactive ligand (a 20 nM solution of [$^{125}$I]-NDP-α-MSH) to each test well. The plates were incubated overnight at room temperature and read the following morning.

The reagents and amounts are summarized below in Table 3.

TABLE 3

| | Volume (µL) | | | |
|---|---|---|---|---|
| Reagent | Max (100%) | Min (0%) | 50% | Test |
| 20% DMSO | 30 | 30 | 30 | 30 |
| 2X membranes + beads | 60 | 0 | 60 | 60 |
| 2 nM [$^{125}$I]-NDP-α-MSH in binding buffer | 20 | 20 | 20 | 20 |
| NDP-α-MSH (5 µM in H$_2$O) | 5 | 0 | 0 | 0 |
| NDP-α-MSH (20 nM in H$_2$O) | 0 | 0 | 5 | 0 |
| Test Compound* | 0 | 0 | 0 | 5 µM |

*Test compound stock diluted in BuOH 1:10, 25 µL dried in assay plate in hood prior to addition of assay buffer. Well contained 0.5 nmol of each test compound (20/well) in 2.5 µL 100% DMSO.

Potency of inhibitors was quantified with respect to positive (100% inhibition) and negative (no inhibitor; 0% inhibition) controls. The following formula was used:

% Inhibition={1−[cpm−(positive control)]/[(negative control)−(positive control)]}*100%

Results from the SPA, are summarized in Table 4. In Table 4, * indicates good inhibition of the MC4-R,  indicates very good inhibition of the MC4-R, and * indicates exemplary inhibition of the MC4-R.

Compounds which were found to be not active as MC4-R binding compounds, using the SPA assay described herein, are depicted in Table 5.

In an embodiment, the present invention pertains to the compounds and methods described herein provided that the compound is not selected from the group consisting of those depicted in Table 5.

TABLE 4

| ID | CHEMICAL NAME | Mol Weight (Tot) | Structure | MC4-R Binding |
|---|---|---|---|---|
| A | 2-[2-(2,5-Dichloro-thiophen-3-ylmethylsulfanyl)-phenyl]-1,4,5,6-tetrahydro-pyrimidine; HCl | 393.7877 | 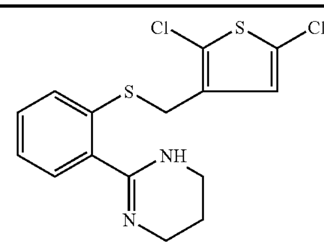 | ** |
| B | 2-[2-(2-Chloro-6-fluoro-benzylsulfanyl)-phenyl]-1,4,5,6-tetrahydro-pyrimidine; HCl | 415.7566 | 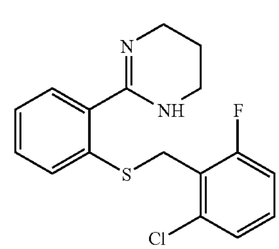 | ** |

TABLE 4-continued

| ID | CHEMICAL NAME | Mol Weight (Tot) | Structure | MC4-R Binding |
|---|---|---|---|---|
| D | 2-(2-Benzylsulfanyl-phenyl)-1,4,5,6-tetrahydro-pyrimidine; HBr | 363.3214 | 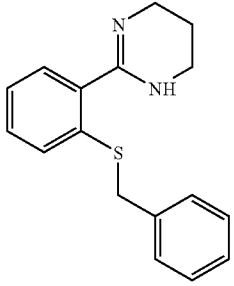 | * |
| E | 2-(2-Pentadecylsulfanyl-phenyl)-1,4,5,6-tetrahydro-pyrimidine; HBr | 483.6 | 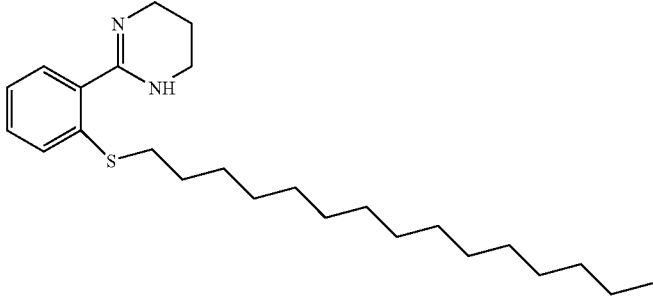 | * |
| F | 2-(2-Cyclohexylmethylsulfanyl-phenyl)-1,4,5,6-tetrahydro-pyrimidine; HBr | 369.369 | 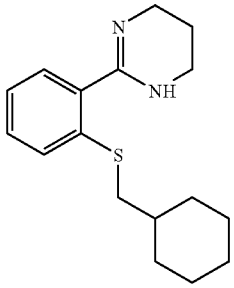 | * |
| G | 2-[2-(2-Methyl-benzylsulfanyl)-phenyl]-1,4,5,6-tetrahydro-pyrimidine; HBr | 377.3483 | 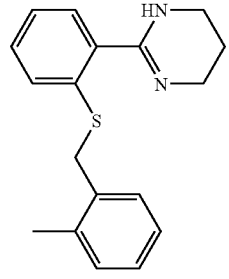 | * |
| H | 2-[2-(3-Nitro-benzylsulfanyl)-phenyl]-1,4,5,6-tetrahydro-pyrimidine; HBr | 408.319 | 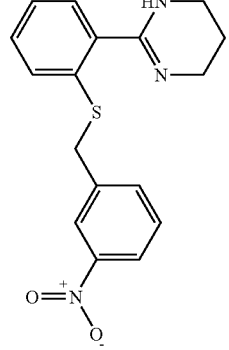 | * |

TABLE 4-continued

| ID | CHEMICAL NAME | Mol Weight (Tot) | Structure | MC4-R Binding |
|----|---------------|------------------|-----------|---------------|
| I | 2-[2-(4-Benzyloxy-benzylsulfanyl)-phenyl]-1,4,5,6-tetrahydro-pyrimidine; HCl | 424.9934 | 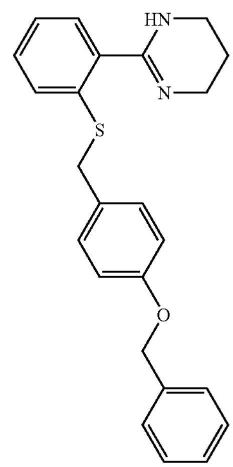 | ** |
| M | 2-[2-(2-Iodo-benzylsulfanyl)-phenyl]-1,4,5,6-tetrahydro-pyrimidine; HCl | 444.7659 | 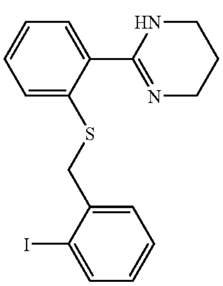 | ** |
| N | 2-[2-(2-Methoxy-5-nitro-benzylsulfanyl)-phenyl]-1,4,5,6-tetrahydro-pyrimidine; HBr | 438.3453 | 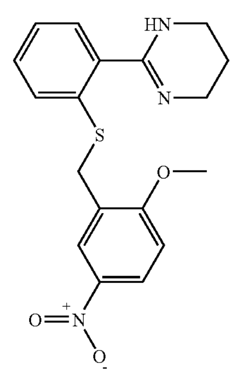 | *** |
| O | 2-[2-(Naphthalen-1-ylmethylsulfanyl)-phenyl]-1,4,5,6-tetrahydro-pyrimidine; HCl | 368.9293 | 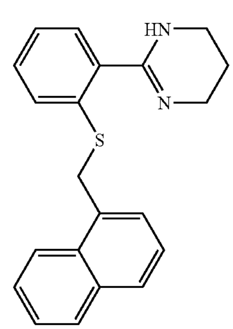 | *** |

TABLE 4-continued

| ID | CHEMICAL NAME | Mol Weight (Tot) | Structure | MC4-R Binding |
|---|---|---|---|---|
| P | 2-[2-(3-Iodo-benzylsulfanyl)-phenyl]-1,4,5,6-tetrahydro-pyrimidine; HBr | 489.2179 | 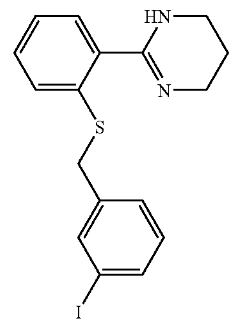 | ** |
| Q | 2-[2-(3-Chloro-benzylsulfanyl)-phenyl]-1,4,5,6-tetrahydro-pyrimidine | 397.7662 | 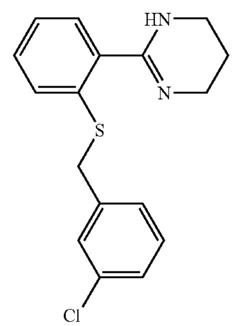 | * |
| R | 2-[2-(3,5-Dimethoxy-benzylsulfanyl)-phenyl]-1,4,5,6-tetrahydro-pyrimidine; HCl | 378.922 | 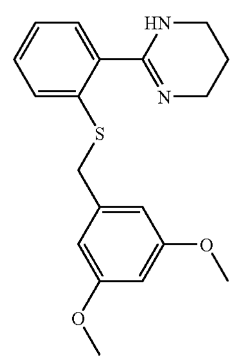 | ** |
| S | 2-[2-(4-Fluoro-benzylsulfanyl)-phenyl]-1,4,5,6-tetrahydro-pyrimidine; HBr | 381.3119 | 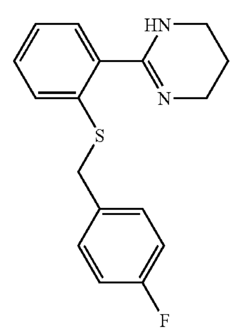 | * |

TABLE 4-continued

| ID | CHEMICAL NAME | Mol Weight (Tot) | Structure | MC4-R Binding |
|----|---------------|------------------|-----------|---------------|
| T | 2-[2-(2-Chloro-benzylsulfanyl)-phenyl]-1,4,5,6-tetrahydro-pyrimidine | 397.7662 | 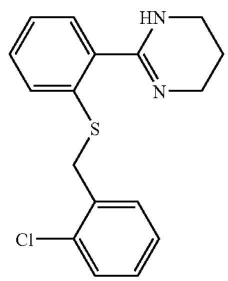 | * |
| U | 2-[2-(2-Fluoro-benzylsulfanyl)-phenyl]-1,4,5,6-tetrahydro-pyrimidine; HBr | 381.3119 | 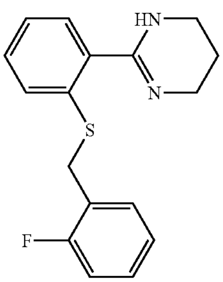 | * |
| V | 2-[2-(2,4-Bis-trifluoromethyl-benzylsulfanyl)-phenyl]-1,4,5,6-tetrahydro-pyrimidine; HBr | 499.3179 | 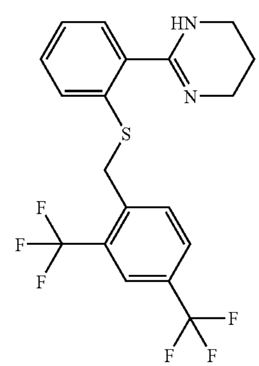 | * |
| W | 2-[2-(3-Methoxy-benzylsulfanyl)-phenyl]-1,4,5,6-tetrahydro-pyrimidine; HCl | 348.8957 | 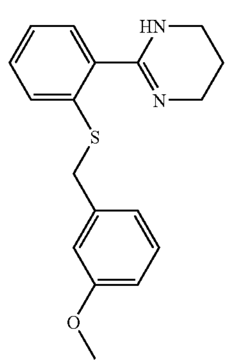 | * |

TABLE 4-continued

| ID | CHEMICAL NAME | Mol Weight (Tot) | Structure | MC4-R Binding |
|---|---|---|---|---|
| X | 2-[2-(3,5-Bis-trifluoromethyl-benzylsulfanyl)-phenyl]-1,4,5,6-tetrahydro-pyrimidine; HCl | 454.8659 | 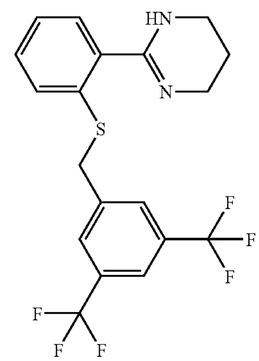 | * |
| Y | 2-[2-(2-Methoxy-5-nitro-benzyloxy)-phenyl]-1,4,5,6-tetrahydro-pyrimidine; HCl | 377.8267 | 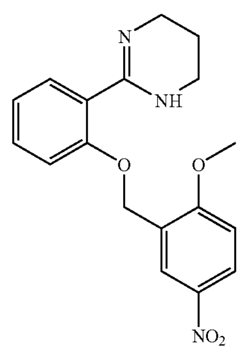 | ** |
| Z | 2-[2-(3-Bromo-benzylsulfanyl)-phenyl]-1,4,5,6-tetrahydro-pyrimidine; HBr | 442.2175 | 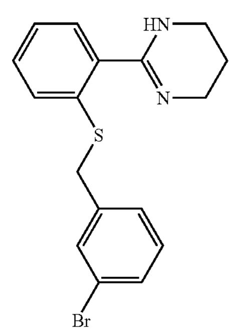 | ** |
| AA | 2-[2-(2-Bromo-benzylsulfanyl)-phenyl]-1,4,5,6-tetrahydro-pyrimidine | 442.2175 | 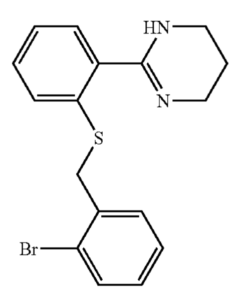 | ** |

TABLE 4-continued

| ID | CHEMICAL NAME | Mol Weight (Tot) | Structure | MC4-R Binding |
|---|---|---|---|---|
| AB | 2-[2-(2-Chloro-6-fluoro-benzylsulfanyl)-phenyl]-4,5-dihydro-1H-imidazole | 357.2777 | 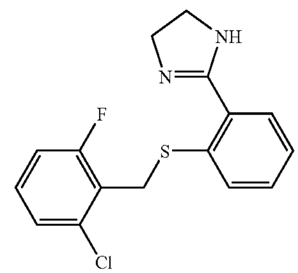 | * |
| AC | 2-(2-Benzylsulfanyl-phenyl)-4,5-dihydro-1H-imidazole; HCl | 304.8425 | 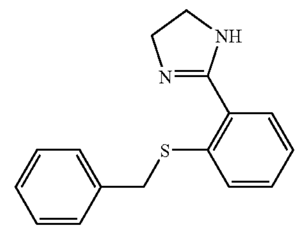 | * |
| AE | 2-[2-(2-Iodo-benzylsulfanyl)-phenyl]-4,5-dihydro-1H-imidazole; HCl | 430.7391 | 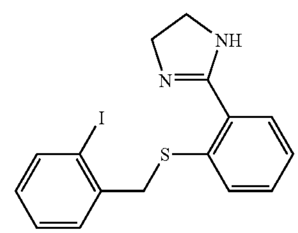 | ** |
| AF | 2-[2-(2-Methoxy-5-nitro-benzylsulfanyl)-phenyl]-4,5-dihydro-1H-imidazole; HBr | 424.3184 | 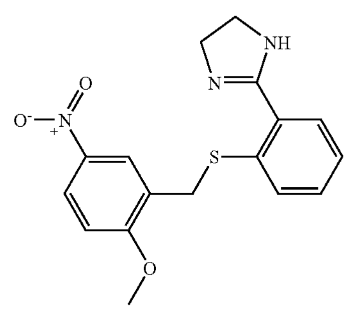 | ** |
| AG | 2-[2-(2-Methoxy-5-nitro-benzylsulfanyl)-phenyl]-3a,4,5,6,7,7a-hexahydro-1H-benzoimidazole; HBr | 478.41 | 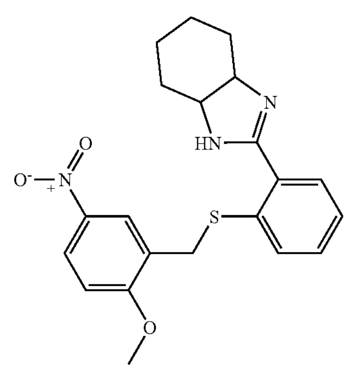 | *** |

TABLE 4-continued

| ID | CHEMICAL NAME | Mol Weight (Tot) | Structure | MC4-R Binding |
|---|---|---|---|---|
| AH | 2-[2-(Naphthalen-1-ylmethoxy)-phenyl]-1,4,5,6-tetrahydro-pyrimidine; Formate | 362.4327 | 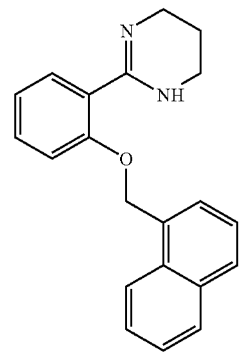 | ** |
| AI | 2-[2-(2,5-Dimethoxy-benzylsulfanyl)-phenyl]-1,4,5,6-tetrahydro-pyrimidine; HCl | 378.922 | 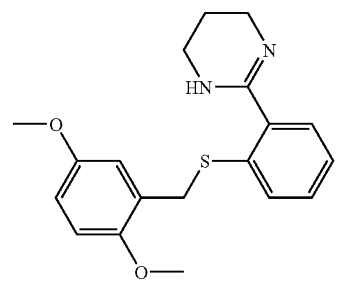 | ** |
| AJ | 2-[2-(2-Methyl-naphthalen-1-ylmethylsulfanyl)-phenyl]-1,4,5,6-tetrahydro-pyrimidine | 346.4962 | 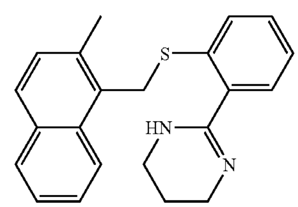 | *** |
| AK | 1-{2-[2-(2-Chloro-6-fluoro-benzylsulfanyl)-phenyl]-5,6-dihydro-4H-pyrimidin-1-yl}-ethanone | 376.8819 | 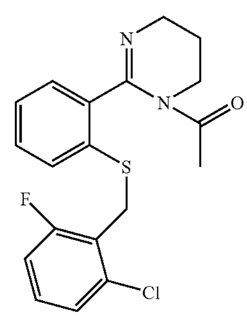 | ** |
| AL | 2-[2-(2-Methoxy-naphthalen-1-ylmethylsulfanyl)-phenyl]-1,4,5,6-tetrahydro-pyrimidine; HCl | 398.9556 | 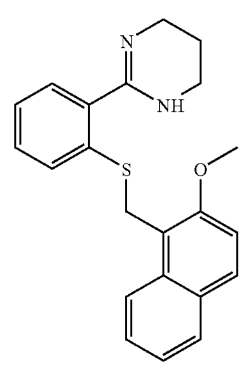 | *** |

TABLE 4-continued

| ID | CHEMICAL NAME | Mol Weight (Tot) | Structure | MC4-R Binding |
|---|---|---|---|---|
| AM | 2-[2-(5-Bromo-2-methoxy-benzylsulfanyl)-phenyl]-1,4,5,6-tetrahydro-pyrimidine; HCl | 427.7917 | 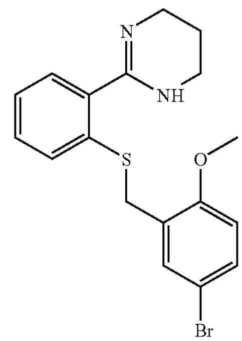 | *** |
| AN | 1-(6-Bromo-2-chloro-quinolin-4-yl)-3-(2-diethylamino-ethyl)-urea | 399.7179 | 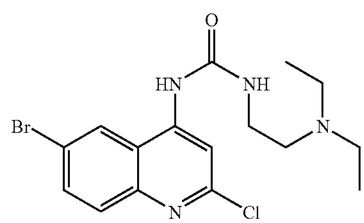 | * |
| AO | 2-[2-(2,6-Difluoro-benzylsulfanyl-phenyl]-1,4,5,6-tetrahydro-pyrimidine; HBr | 480.2143 | 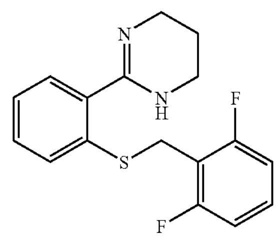 | * |
| AP | 10-[2-(1-Methyl-piperidin-2-yl)-ethyl]-2-methylsulfanyl-10H-phenothiazine; HCl | 407.0429 | 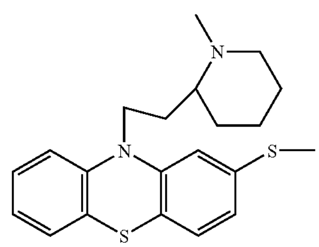 | * |
| AQ | 4-(3,5-Bis-trifluoromethyl-phenyl)-1,4,6,7-tetrahydro-imidazo[4,5-c]pyridine-5-carbothioic acid (3-diethylamino-propyl)-amide | 507.5465 | 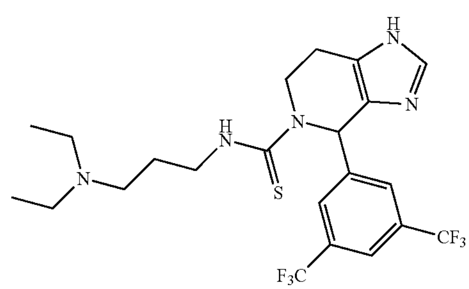 | * |
| AR | 1-(4-Hydroxy-1,3,5-trimethyl-piperidin-4-yl)-ethanone | 185.2664 | 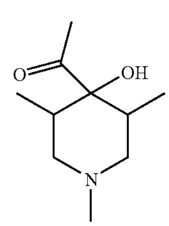 | ** |

TABLE 4-continued

| ID | CHEMICAL NAME | Mol Weight (Tot) | Structure | MC4-R Binding |
|---|---|---|---|---|
| AS | 2-Naphthalen-1-ylmethyl-4,5-dihydro-1H-imidazole; HCl | 246.7386 | 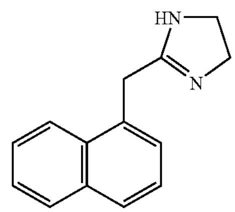 | * |
| AT | 1-(3-Diethylamino-propyl)-3-{1-[5-(2-methyl-5-trifluoromethyl-2H-pyrazol-3-yl)-thiophene-2-sulfonyl]-pyrrolidin-3-yl}-thiourea | 552.7096 | 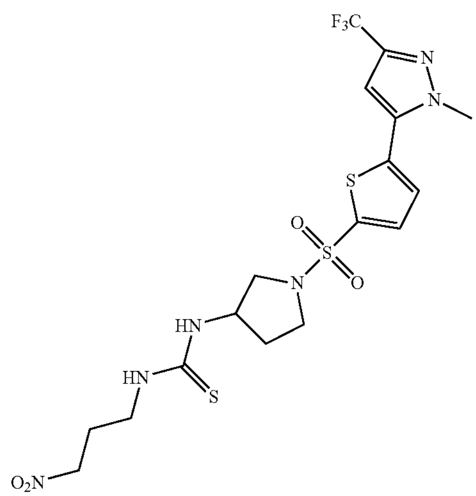 | * |
| AU | N-[2-Cyclopropyl-3-(1,1,3,3-tetramethyl-butylamino)-imidazo[1,2-a]pyridin-8-yl]-acetamide | 342.4846 | 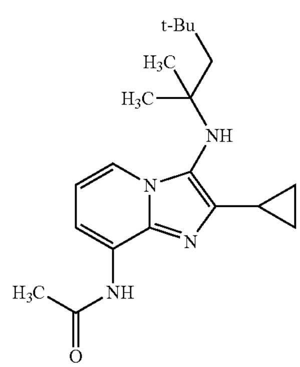 | * |
| AV | (2-Isopropyl-imidazo[1,2-a]pyridin-3-yl)-(1,1,3,3-tetramethyl-butyl)-amine | 342.4846 | 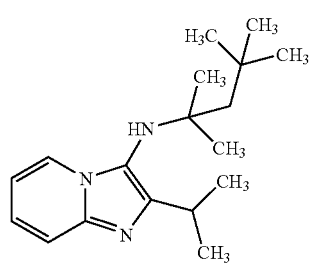 | * |

TABLE 4-continued

| ID | CHEMICAL NAME | Mol Weight (Tot) | Structure | MC4-R Binding |
|---|---|---|---|---|
| AW | (2-Isopropyl-imidazo[1,2-a]pyridin-3-yl)-(1,1,3,3-tetramethyl-butyl)-amine | 287.4485 | 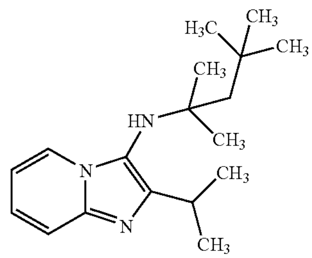 | * |
| AX | 1-(4-Phenyl-5'-trifluoromethyl-3,4,5,6-tetrahydro-2H-[1,2']-bipyridinyl-4-ylmethyl)-3-(2-piperidin-1-yl-ethyl)-thiourea | 505.6509 | 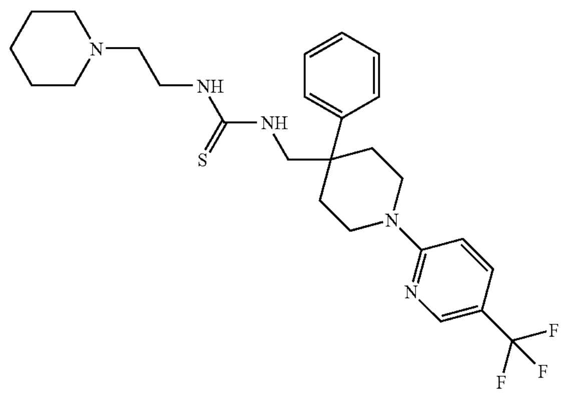 | * |
| AY | (2,6-Dichloro-phenyl)-imidazolidin-2-ylidene-amine; HCl | 266.5561 | 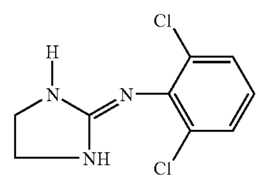 | * |
| AZ | 2-Benzyl-4,5-dihydro-1H-imidazole | 160.2188 | 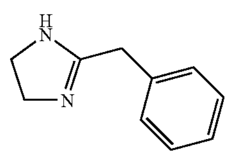 | * |
| BA | 1-(4-Phenyl-5'-trifluoromethyl-3,4,5,6-tetrahydro-2H-[1,2']bipyridinyl-4-ylmethyl)-3-(2-piperidin-1-yl-ethyl)-urea | 489.5843 | 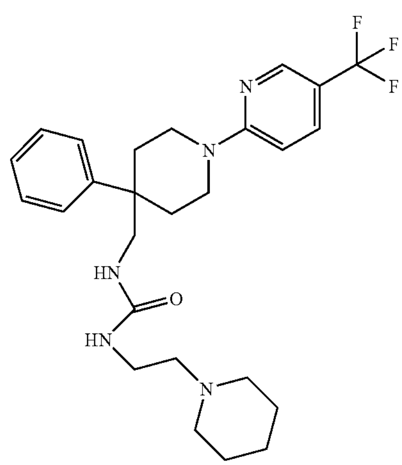 | * |

TABLE 4-continued

| ID | CHEMICAL NAME | Mol Weight (Tot) | Structure | MC4-R Binding |
|----|---------------|------------------|-----------|---------------|
| BB | 2-(2-Methylsulfanyl-phenyl)-1,4,5,6-tetrahydro-pyrimidine | 334.2216 | 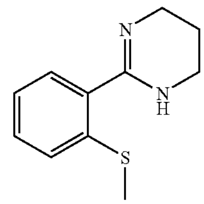 | * |
| BZ | 2-(1,4,5,6-Tetrahydro-pyrimidin-2-yl)-benzenethiol | 192.2848 | 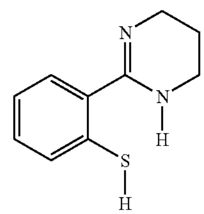 | * |
| BD | 2-[2-(4-Nitro-benzylsulfanyl)-phenyl]-1,4,5,6-tetrahydro-pyrimidine | 408.319 | 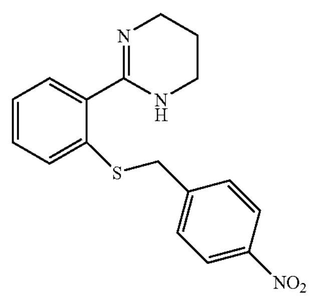 | * |
| BE | 2-{3-[2-(1,4,5,6-Tetrahydro-pyrimidin-2-yl)-phenylsulfanyl]-propyl}-isoindole-1,3-dione; HBr | 460.3948 | 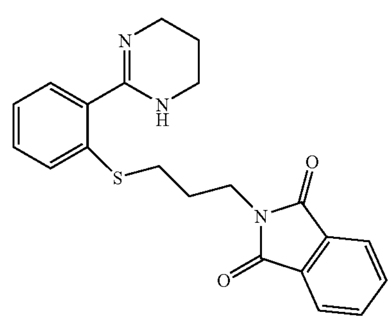 | * |
| BF | 2-[2-(3-Phenyl-propylsulfanyl)-phenyl]-1,4,5,6-tetrahydro-pyrimidine; HBr | 391.3752 | 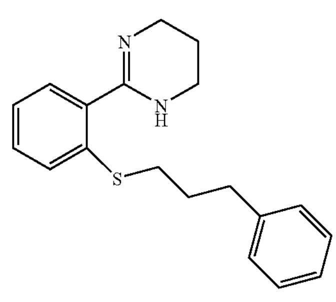 | * |

TABLE 4-continued

| ID | CHEMICAL NAME | Mol Weight (Tot) | Structure | MC4-R Binding |
|---|---|---|---|---|
| BG | 2-[2-(4-Trifluoromethyl-benzylsulfanyl)-phenyl]-1,4,5,6-tetrahydro-pyrimidine; HBr | 431.3197 | 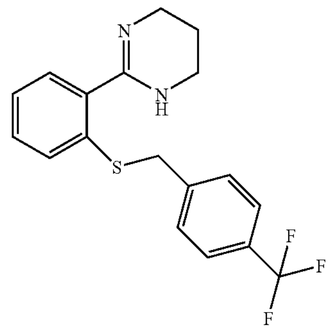 | * |
| BH | 4-Piperazin-1-yl-2-trifluoromethyl-quinoline | 281.2806 | 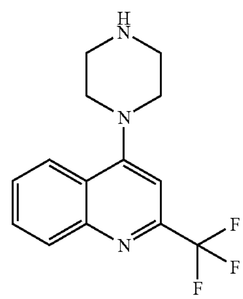 | * |
| BI | 3-Nitro-benzamidine; HCl | 201.6116 | 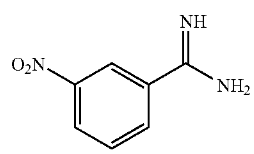 | * |
| BJ | 4-Carbamimidoyl-benzamide | 163.1791 | 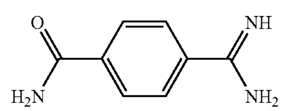 | * |
| BK | 2-Phenyl-4,5-dihydro-1H-imidazole | 146.1919 | 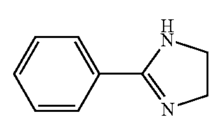 | * |
| BL | 2-(3-Benzylsulfanyl-phenyl)-1,4,5,6-tetrahydro-pyrimidine | 282.4094 | 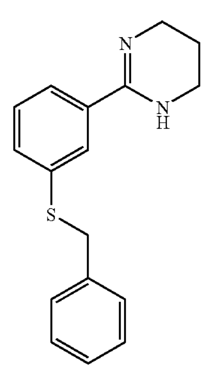 | * |

TABLE 4-continued

| ID | CHEMICAL NAME | Mol Weight (Tot) | Structure | MC4-R Binding |
|----|---------------|------------------|-----------|---------------|
| BM | 2-[2-(4-tert-Butyl-benzylsulfanyl)-phenyl]-1,4,5,6-tetrahydro-pyrimidine; HBr | 419.4289 | 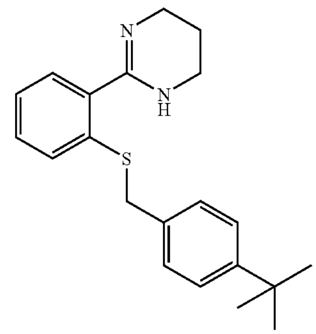 | * |
| BN | 2,2-Diphenyl-4-[2-(1,4,5,6-tetrahydro-pyrimidin-2-yl)-phenylsulfanyl]-butyronitrile; HBr | 492.4827 | 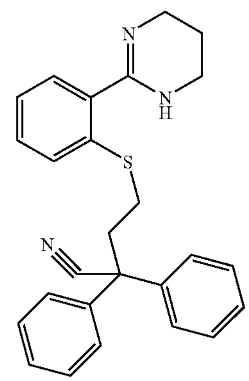 | * |
| BO | 2-[2-(3,4-Dimethyl-benzylsulfanyl)-phenyl]-1,4,5,6-tetrahydro-pyrimidine; HCl | 346.9232 | 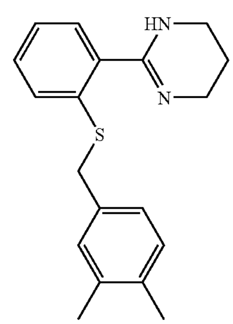 | * |
| BQ | 3-[2-(1,4,5,6-Tetrahydro-pyrimidin-2-yl)-phenylsulfanyl-methyl]-benzonitrile; HBr | 388.3312 | 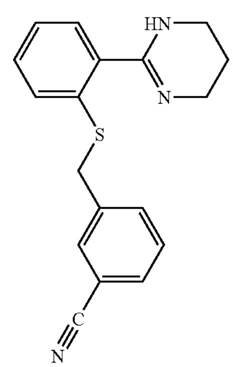 | * |

TABLE 4-continued

| ID | CHEMICAL NAME | Mol Weight (Tot) | Structure | MC4-R Binding |
|----|---------------|------------------|-----------|---------------|
| BR | 2-[2-(4-Bromo-benzylsulfanyl)-phenyl]-1,4,5,6-tetrahydro-pyrimidine; HBr | 442.2175 | 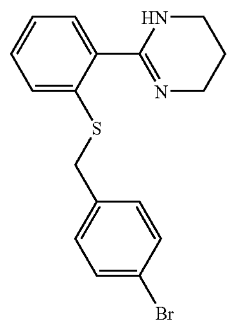 | * |
| BS | 2-[2-(2,6-Dichloro-benzylsulfanyl)-phenyl]-1,4,5,6-tetrahydro-pyrimidine; HBr | 432.2109 | 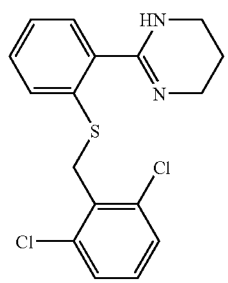 | * |
| BT | 2-[2-(Naphthalen-2-ylmethylsulfanyl)-phenyl]-1,4,5,6-tetrahydro-pyrimidine; HBr | 413.3813 | 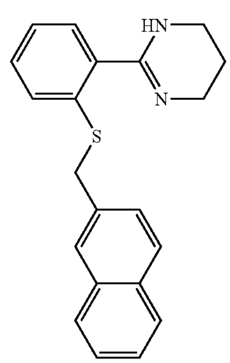 | * |
| BU | 2-[2-(4-Fluoro-benzylsulfanyl)-phenyl]-1,4,5,6-tetrahydro-pyrimidine; HBr | 381.3119 | 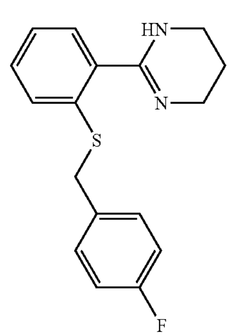 | * |

TABLE 4-continued

| ID | CHEMICAL NAME | Mol Weight (Tot) | Structure | MC4-R Binding |
|---|---|---|---|---|
| BV | 2-[2-(Biphenyl-4-ylmethylsulfanyl)-phenyl]-1,4,5,6-tetrahydro-pyrimidine; HCl | 394.9672 | 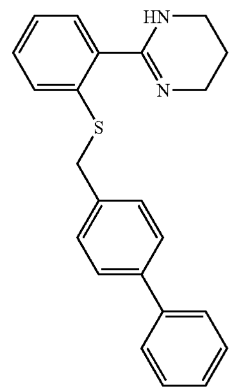 | * |
| BW | 2-[2-(2,4-Bis-trifluoromethyl-benzylsulfanyl)-phenyl]-1,4,5,6-tetrahydro-pyrimidine; HBr | 499.3179 | 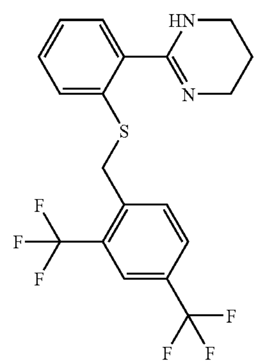 | * |
| BX | 2-[2-(1,4,5,6-Tetrahydro-pyrimidin-2-yl)-phenylsulfanyl-methyl]-benzonitrile; HBr | 388.3312 | 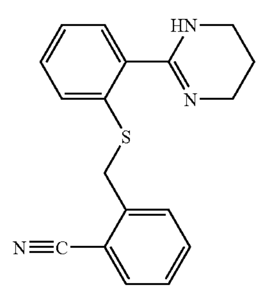 | * |
| BY | 4-[2-(1,4,5,6-Tetrahydro-pyrimidin-2-yl)-phenylsulfanyl-methyl]-benzonitrile; HBr | 388.3312 | 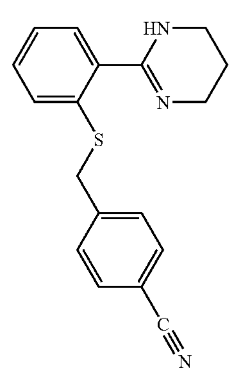 | * |

TABLE 4-continued

| ID | CHEMICAL NAME | Mol Weight (Tot) | Structure | MC4-R Binding |
|---|---|---|---|---|
| BZ | 2-[2-(4-Methoxy-benzylsulfanyl)-phenyl]-1,4,5,6-tetrahydro-pyrimidine; HCl | 348.8957 | 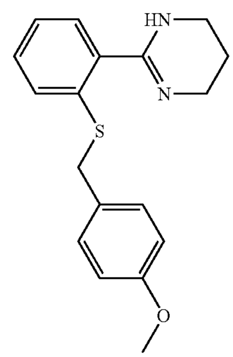 | * |
| CA | Benzamidine; HCl | 156.614 | 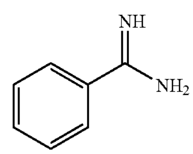 | * |
| CB | 3,5-Bis-trifluoromethyl-benzamidine; HCl | 292.6105 | 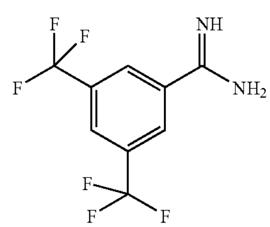 | * |
| CC | 2-(2-Benzylsulfanyl-phenyl)-4,5-dihydro-1H-imidazole; HCl | 304.8425 | 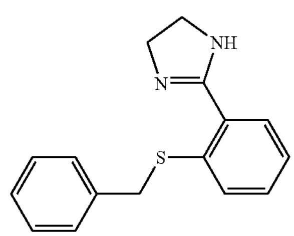 | * |
| CD | (2-Butoxy-phenyl)-carbamic acid 2-piperidin-1-yl-1-piperidin-1-ylmethyl-ethyl ester; Formate | 463.6221 | 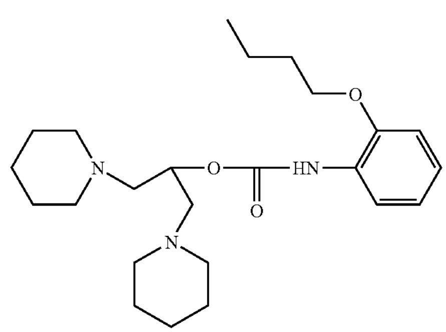 | ** |

TABLE 4-continued

| ID | CHEMICAL NAME | Mol Weight (Tot) | Structure | MC4-R Binding |
|----|---------------|------------------|-----------|---------------|
| CE | (2-Pentyloxy-phenyl)-carbamic acid 2-piperidin-1-yl-1-piperidin-1-ylmethyl-ethyl ester; Formate | 477.649 | 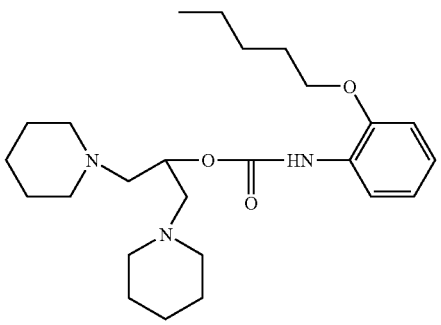 | ** |
| CF | 2-(2-Bromo-phenyl)-4,5-dihydro-1H-imidazole; HCl | 261.5479 | 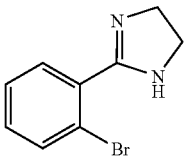 | * |
| CJ | 4-Phenyl-2-piperazin-1-yl-6-p-tolyl-pyrimidine | 330.4326 | 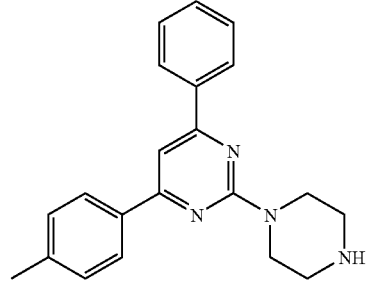 | * |
| CK | N-Benzyl-N-(3-chloro-benzyl)-N',N'-dimethyl-ethane-1,2-diamine | 302.8468 | 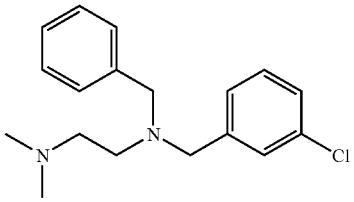 | * |
| CL | N-Benzyl-N-(4-bromo-benzyl)-N',N'-dimethyl-ethane-1,2-diamine | 347.2981 | 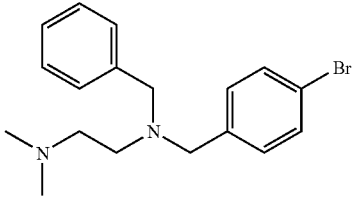 | * |
| CM | N-Benzyl-N-(3,4-dichloro-benzyl)-N',N'-dimethyl-ethane-1,2-diamine | 337.2916 | 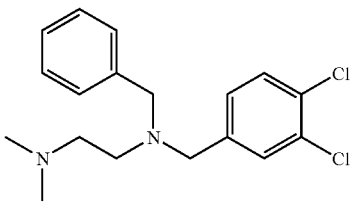 | * |

TABLE 4-continued

| ID | CHEMICAL NAME | Mol Weight (Tot) | Structure | MC4-R Binding |
|---|---|---|---|---|
| CO | 7-Chloro-4,8-dimethyl-2-piperazin-1-yl-quinoline; Oxalate | 365.8208 | 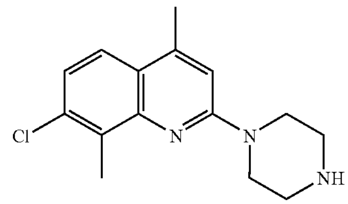 | * |
| CP | 7-Chloro-4,8-dimethyl-2-piperazin-1-yl-quinoline | 275.7808 | 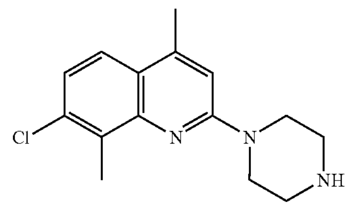 | * |
| CQ | 7-Chloro-4,8-dimethyl-2-piperazin-1-yl-quinoline; Formate | 321.8108 | 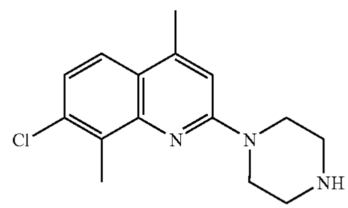 | * |
| CS | 2,7-Dichloro-4,8-dimethyl-quinoline | 226.1046 | 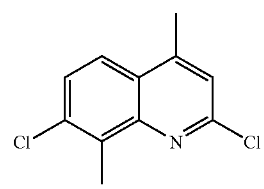 | * |
| CT | 2-(2-Benzylsulfanylphenyl)-3a,4,5,6,7,7a-hexahydro-1H-benzoimidazole; HCl | 358.9342 | 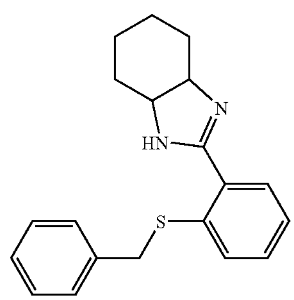 | * |
| CU | 2-[2-(2-Chloro-6-fluoro-benzylsulfanyl)-phenyl]-3a,4,5,6,7,7a-hexahydro-1H-benzoimidazole; HCl | 411.3694 | 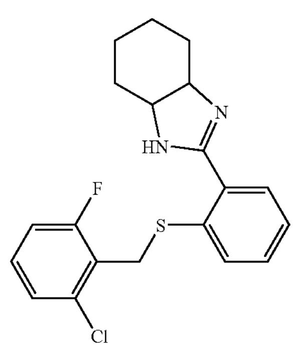 | ** |

TABLE 4-continued

| ID | CHEMICAL NAME | Mol Weight (Tot) | Structure | MC4-R Binding |
|---|---|---|---|---|
| CV | 2-[2-(2-Iodo-benzylsulfanyl)-phenyl]-3a,4,5,6,7,7a-hexahydro-1H-benzoimidazole; HCl | 484.8307 | 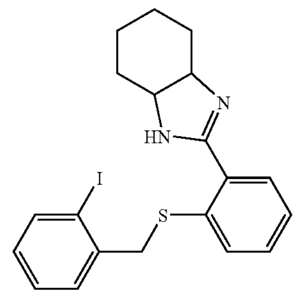 | ** |
| CY | 1-Phenyl-3-piperazin-1-yl-5,6,7,8-tetrahydro-isoquinoline-4-carbonitrile | 318.4216 | 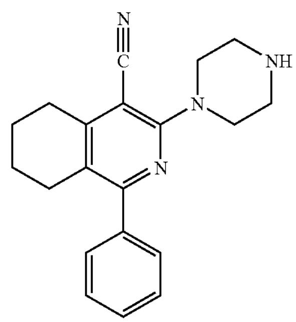 | ** |
| CZ | 2-[2-(Pyridin-3-ylmethylsulfanyl)-phenyl]-1,4,5,6-tetrahydro-pyrimidine | 283.3972 | 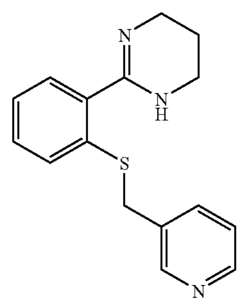 | * |
| DA | 1-Pyridin-3-ylmethyl-2-[2-(pyridin-3-ylmethylsulfanyl)-phenyl]-1,4,5,6-tetrahydro-pyrimidine | 374.5096 | 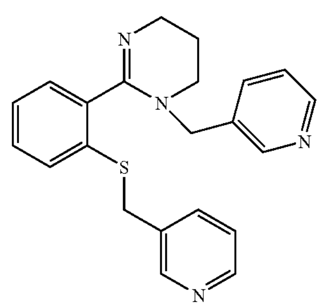 | * |
| DB | 2-[2-(2-Ethoxy-ethylsulfanyl)-phenyl]-1,4,5,6-tetrahydro-pyrimidine; HBr | 345.3037 | 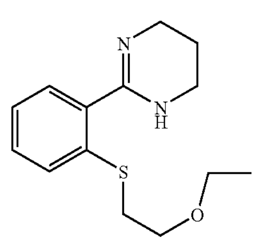 | * |

TABLE 4-continued

| ID | CHEMICAL NAME | Mol Weight (Tot) | Structure | MC4-R Binding |
|----|---------------|------------------|-----------|---------------|
| DC | 2-[2-(2,5-Dimethyl-benzylsulfanyl)-phenyl]-1,4,5,6-tetrahydro-pyrimidine; HCl | 346.9232 | 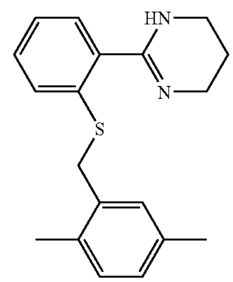 | ** |
| DD | 2-[2-(2-Benzenesulfonylmethyl-benzylsulfanyl)-phenyl]-1,4,5,6-tetrahydro-pyrimidine; HBr | 517.5108 | 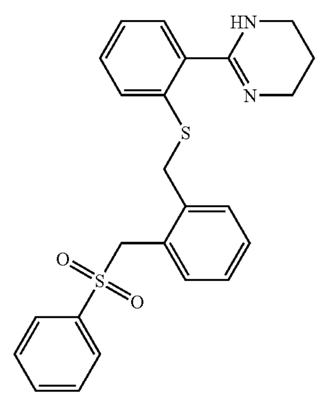 | * |
| DE | 4-[2-(1,4,5,6-Tetrahydro-pyrimidin-2-yl)-phenylsulfanylmethyl]-quinoline; HBr | 414.3691 | 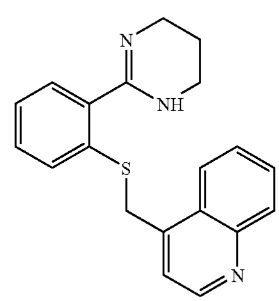 | ** |
| DF | 2-[2-(2-Methoxy-5-nitro-benzylsulfanyl)-pyridin-3-yl]-1,4,5,6-tetrahydro-pyrimidine; HBr | 439.3331 | 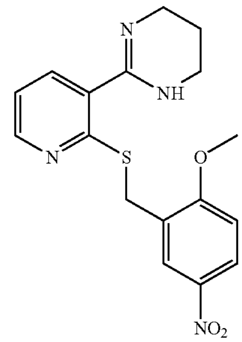 | ** |

TABLE 4-continued

| ID | CHEMICAL NAME | Mol Weight (Tot) | Structure | MC4-R Binding |
|----|---------------|------------------|-----------|---------------|
| DG | 2-[2-(2-Methoxy-benzylsulfanyl)-phenyl]-1,4,5,6-tetrahydro-pyrimidine; HCl | 348.8957 | 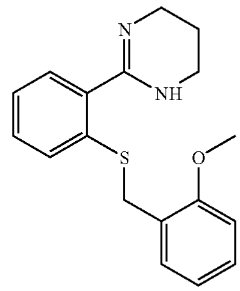 | ** |
| DH | 2-[2-(2-Cyclopentyloxy-benzylsulfanyl)-phenyl]-1,4,5,6-tetrahydro-pyrimidine; HBr | 447.4393 | 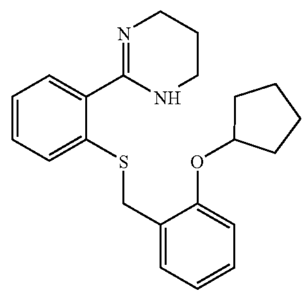 | ** |
| DI | 2-Biphenyl-2-yl-1,4,5,6-tetrahydro-pyrimidine; Formate | 282.3465 | 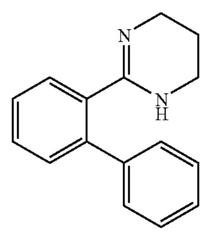 | * |
| DJ | 2-[2-(2,3-Dimethoxy-benzylsulfanyl)-phenyl]-1,4,5,6-tetrahydro-pyrimidine; HBr | 423.374 | 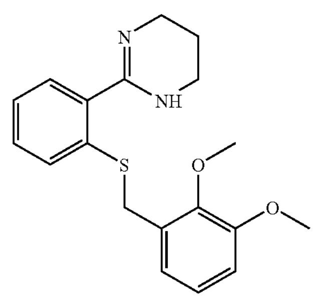 | * |
| DK | 2-[2-(2,3-Dihydro-benzo[1,4]dioxin-5-ylmethylsulfanyl)-phenyl]-1,4,5,6-tetrahydro-pyrimidine; HBr | 421.3581 | 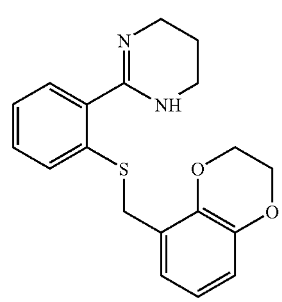 | ** |

TABLE 4-continued

| ID | CHEMICAL NAME | Mol Weight (Tot) | Structure | MC4-R Binding |
|---|---|---|---|---|
| DL | 2-[2-(-6-Methoxy-2,3-dihydro-benzo[1,4]dioxin-5-ylmethylsulfanyl)-phenyl]-1,4,5,6-tetrahydro-pyrimidine | 451.3844 | 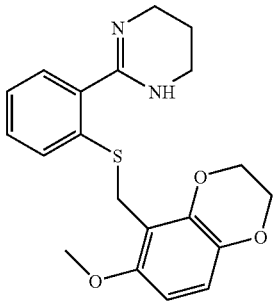 | *** |
| DM | 2-[2-(5-fluoro-2-methoxy-benzylsulfanyl)-phenyl]-4,5-dihydro-1H-imidazole; HCl | 411.3381 | 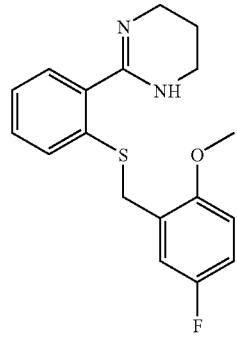 | ** |
| DN | 1-Methyl-2-[2-(naphthalen-1-ylmethyl-sulfanyl)-phenyl]-1,4,5,6-tetrahydro-pyrimidine; formate | 392.5262 | 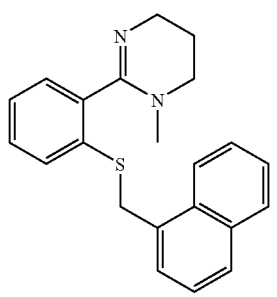 | ** |
| DO | 1-Methyl-2-[2-(naphthalen-1-ylmethyl-sulfanyl)-phenyl]-4,5-dihydro-1H-imidazole | 332.4693 | 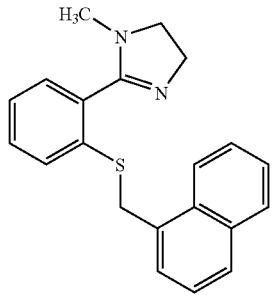 | *** |

TABLE 4-continued

| ID | CHEMICAL NAME | Mol Weight (Tot) | Structure | MC4-R Binding |
|---|---|---|---|---|
| DP | 2-[2-(5-Bromo-2-methoxy-benzylsulfanyl)-phenyl]-4,5-dihydro-1H-imidazole; HCl | 413.7649 | 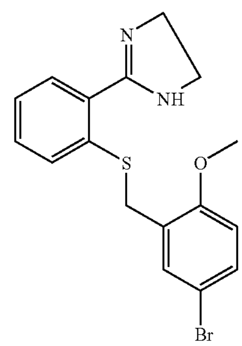 | *** |
| DQ | 2-[2-(5-Bromo-2-methoxy-benzyloxy)-phenyl]-1,4,5,6-tetrahydro-pyrimidine; HCl | 411.7251 | 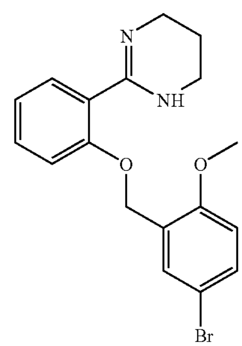 | *** |
| DR | 2-[2-(Naphthalen-1-yloxymethyl)-phenyl]-1,4,5,6-tetrahydro-pyrimidine | 316.4027 | 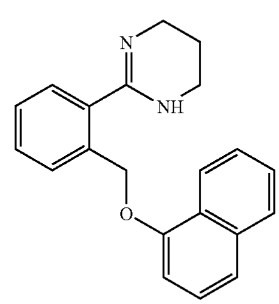 | ** |
| DS | 2-(2-Phenoxy-phenyl)-1,4,5,6-tetrahydro-pyrimidine; HCl | 288.7759 | 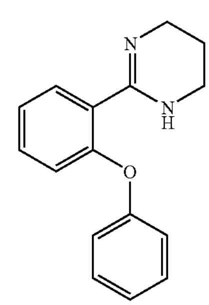 | * |

TABLE 4-continued

| ID | CHEMICAL NAME | Mol Weight (Tot) | Structure | MC4-R Binding |
|---|---|---|---|---|
| DT | 5-(4-Chloro-phenyl)-2,5-dihydro-3H-imidazo[2,1-a]isoindol-5-ol | 284.7448 | 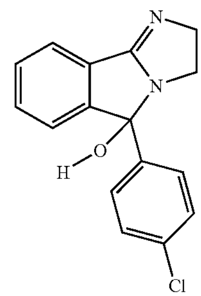 | * |
| DU | 2-[2-(2-Methoxy-phenoxymethyl)-phenyl]-1,4,5,6-tetrahydro-pyrimidine; HCl | 332.8291 | 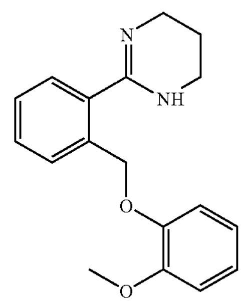 | * |
| DV | 2-[2-(2,6-Dimethoxy-phenoxymethyl)-phenyl]-1,4,5,6-tetrahydro-pyrimidine | 326.3954 | 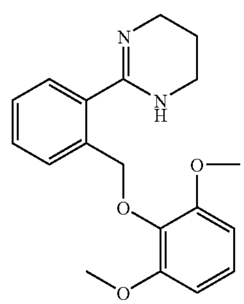 | * |
| DW | 2-[2-(5-Bromo-2-methoxy-benzylsulfanyl)-phenyl]-5,5-dimethyl-1,4,5,6-tetrahydro-pyrimidine | 419.3855 | 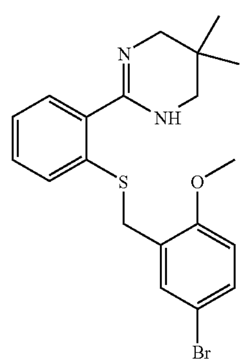 | *** |
| DX | 2-[2-(2-Methoxy-phenoxy)-phenyl]-1,4,5,6-tetrahydro-pyrimidine; Formate | 328.3722 | 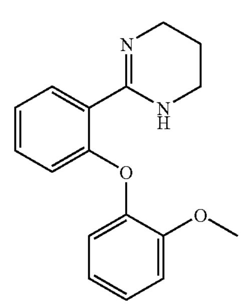 | * |

TABLE 4-continued

| ID | CHEMICAL NAME | Mol Weight (Tot) | Structure | MC4-R Binding |
|---|---|---|---|---|
| DY | 2-[2-(5-Bromo-2-methoxy-benzylsulfanyl)-phenyl]-5,5-dimethyl-4,5-dihydro-1H-imidazole | 405.3586 | 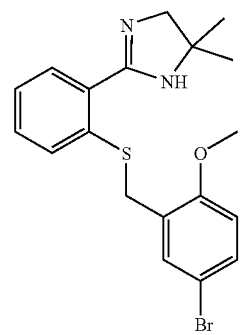 | *** |
| DZ | 2-[2-(5-Bromo-2-methoxy-benzylsulfanyl)-5-trifluoromethyl-phenyl]-1,4,5,6-tetrahydro-pyrimidine | 459.33 | 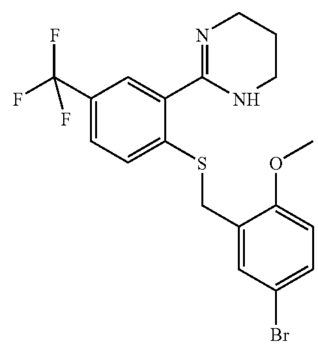 | * |
| EA | 2-[2-(2,6-Dimethoxy-benzylsulfanyl)-phenyl]-1,4,5,6-tetrahydro-pyrimidine; HCl | 378.922 | 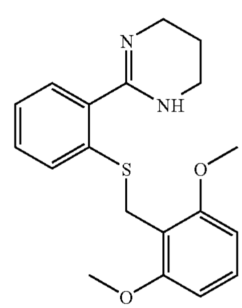 | *** |
| EB | 2-[2-(5-Bromo-2-methoxy-benzylsulfanyl)-phenyl]-6-ethyl-1,4,5,6-tetrahydro-pyrimidine | 419.3855 | 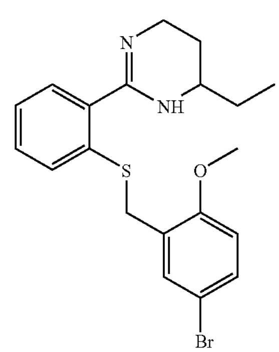 | *** |

TABLE 4-continued

| ID | CHEMICAL NAME | Mol Weight (Tot) | Structure | MC4-R Binding |
|---|---|---|---|---|
| EC | 2-(5-Bromo-2-methoxy-benzylsulfanyl)-benzonitrile | 334.2364 | 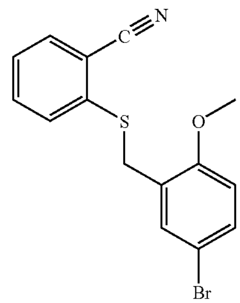 | * |
| ED | 2-[2-(2-Bromo-6-methoxy-benzylsulfanyl)-phenyl]-1,4,5,6-tetrahydro-pyrimidine; HBr | 472.2437 | 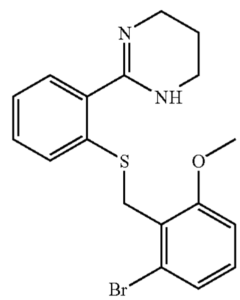 | *** |
| EF | 2-[5-Bromo-2-(5-bromo-2-methoxy-benzylsulfanyl)-phenyl]-4,5-dihydro-1H-imidazole; Formate | 502.2309 | 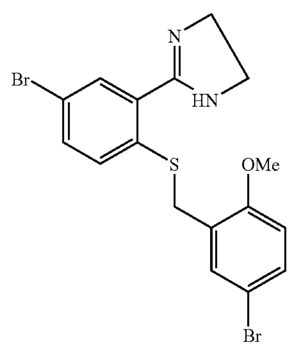 | *** |
| EJ | 9-Benzylidene-1,2,3,9-tetrahydro-4,9a-diaza-fluorene; Formate | 306.3685 | 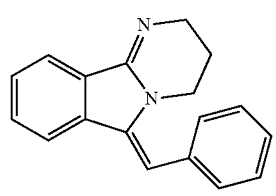 | * |
| EK | 2-[2-(Biphenyl-3-yloxy)-phenyl]-4,5-dihydro-1H-imidazole | 314.3868 | 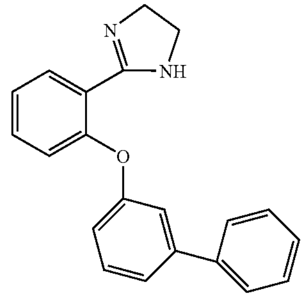 | * |

TABLE 4-continued

| ID | CHEMICAL NAME | Mol Weight (Tot) | Structure | MC4-R Binding |
|---|---|---|---|---|
| EL | 2-[2-(4-Chloro-phenoxy)-phenyl]-4,5-dihydro-1H-imidazole | 272.7338 | 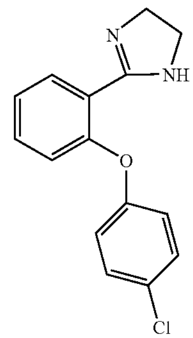 | * |
| EM | 2-[5-Bromo-2-(5-bromo-2-methoxy-benzylsulfanyl)-phenyl]-1,4,5,6-tetrahydro-pyrimidine; Formate | 516.2578 | 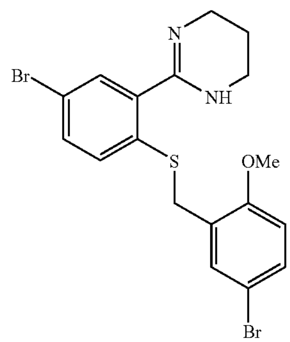 | *** |
| EN | 2-[2-(Naphthalen-2-yloxy)-phenyl]-4,5-dihydro-1H-imidazole; Formate | 334.3789 | 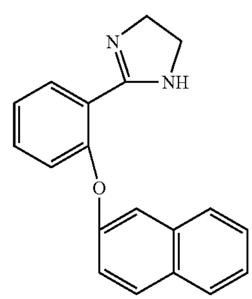 | * |
| EO | 2-[4-Bromo-2-(5-bromo-2-methoxy-benzylsulfanyl)-phenyl]-1,4,5,6-tetrahydro-pyrimidine | 470.2278 | 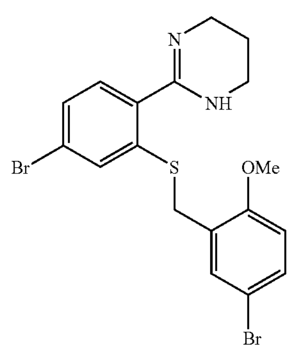 | ** |

TABLE 4-continued

| ID | CHEMICAL NAME | Mol Weight (Tot) | Structure | MC4-R Binding |
|----|---------------|------------------|-----------|---------------|
| EP | 2-[2-(2-Bromo-5-methoxy-benzylsulfanyl)-phenyl]-1,4,5,6-tetrahydro-pyrimidine; HBr | 472.2437 | 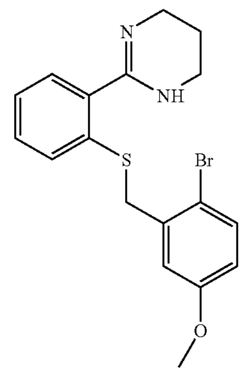 | *** |
| EQ | 2-[2-(5-Bromo-2-methoxy-benzylsulfanyl)-5-methyl-phenyl]-1,4,5,6-tetrahydro-pyrimidine | 405.3586 | 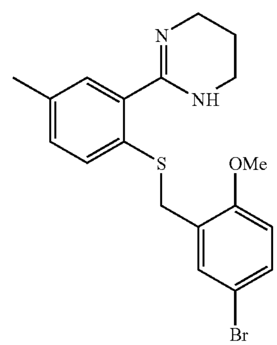 | *** |
| ER | 2-[2-(Naphthalen-1-yloxy)-phenyl]-4,5-dihydro-1H-imidazole; formate | 334.3789 | 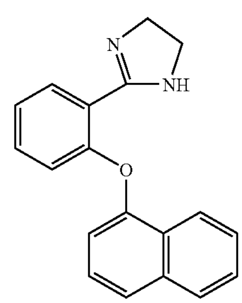 | * |
| ES | 2-[2-(Naphthalen-1-yloxy)-phenyl]-1,4,5,6-tetrahydro-pyrimidine; Formate | 348.4058 | 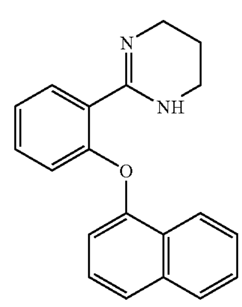 | * |

TABLE 4-continued
| ID | CHEMICAL NAME | Mol Weight (Tot) | Structure | MC4-R Binding |
|---|---|---|---|---|
| ET | 2-[2-(Biphenyl-3-ylmethylsulfanyl)-phenyl]-1,4,5,6-tetrahydro-pyrimidine; HBr | 439.4192 | 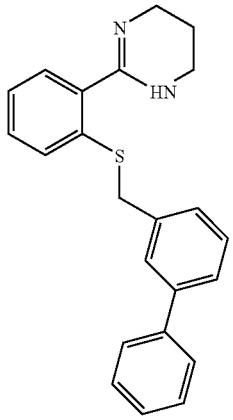 | ** |
| EU | 2-[2-(Naphthalen-2-yloxy)-phenyl]-1,4,5,6-tetrahydro-pyrimidine; Formate | 348.4058 | 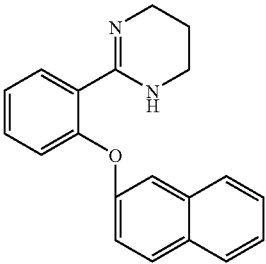 | * |
| EV | 2-[2-(5-Bromo-2-methoxy-phenylmethanesulfinyl)-phenyl]-1,4,5,6-tetrahydro-pyrimidine | 407.3311 | 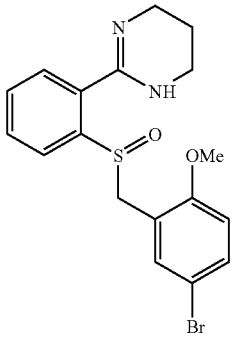 | * |
| EW | 2-[2-(5-Chloro-2-methoxy-benzylsulfanyl)-phenyl]-1,4,5,6-tetrahydro-pyrimidine; HCl | 383.3404 | 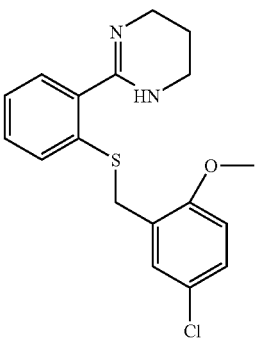 | *** |

TABLE 4-continued

| ID | CHEMICAL NAME | Mol Weight (Tot) | Structure | MC4-R Binding |
|---|---|---|---|---|
| EX | 2-[2-(2-Methoxy-5-thiophen-3-yl-benzylsulfanyl)-phenyl]-1,4,5,6-tetrahydro-pyrimidine; HCl | 431.0216 | 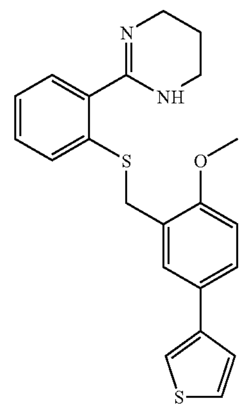 | *** |
| EY | 2-[2-(Biphenyl-2-ylmethylsulfanyl)-phenyl]-1,4,5,6-tetrahydro-pyrimidine; Formate | 404.5372 | 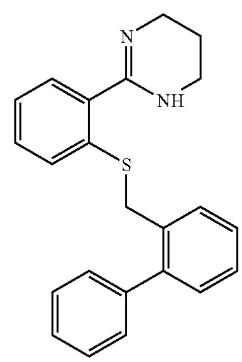 | ** |
| EZ | 2-[2-(5-Iodo-2-methoxy-benzylsulfanyl)-phenyl]-1,4,5,6-tetrahydro-pyrimidine; Formate | 484.3622 | 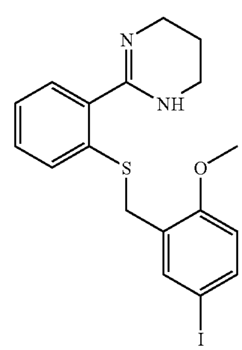 | *** |
| FA | 2-[2-(5-Bromo-2-methoxy-benzylsulfanyl)-5-fluoro-phenyl]-1,4,5,6-tetrahydro-pyrimidine | 409.3222 | 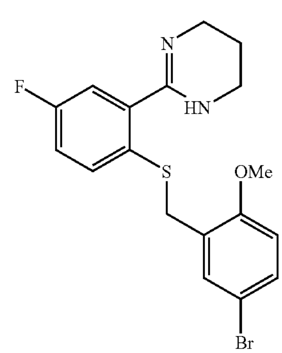 | *** |

TABLE 4-continued

| ID | CHEMICAL NAME | Mol Weight (Tot) | Structure | MC4-R Binding |
|---|---|---|---|---|
| FB | 2-[2-(5-Bromo-2-methoxy-benzylsulfanyl)-3-fluoro-phenyl]-1,4,5,6-tetrahydro-pyrimidine | 409.3222 | 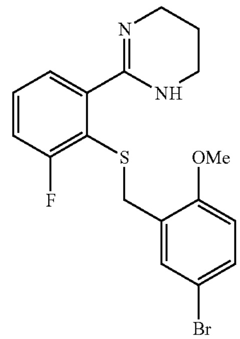 | *** |
| FC | 2-[2-(4,4'-Dimethoxy-biphenyl-3-ylmethylsulfanyl)-phenyl]-1,4,5,6-tetrahydro-pyrimidine; HBr | 499.4717 | 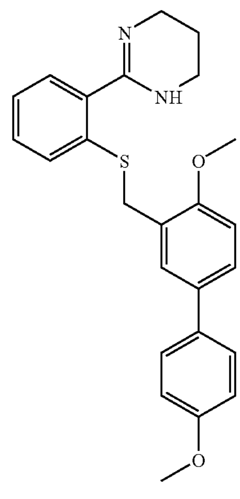 | ** |
| FD | 2-[2-(9H-Fluoren-9-ylsulfanyl)-phenyl]-1,4,5,6-tetrahydro-pyrimidine; HBr | 437.4033 | 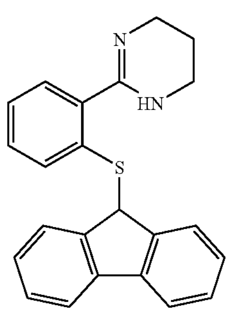 | ** |

TABLE 4-continued

| ID | CHEMICAL NAME | Mol Weight (Tot) | Structure | MC4-R Binding |
|---|---|---|---|---|
| FE | 2-[2-(3'-Chloro-4'-fluoro-4-methoxy-biphenyl-3-ylmethylsulfanyl)-phenyl]-1,4,5,6-tetrahydro-pyrimidine; Formate | 486.9987 | 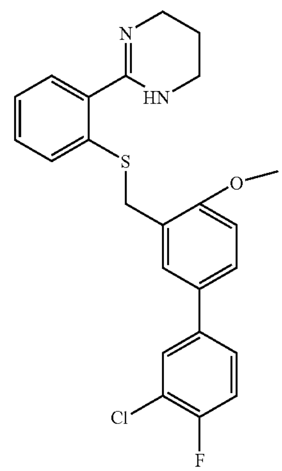 | ** |
| FF | 2-[2-(1-Naphthalen-1-yl-ethylsulfanyl)-phenyl]-1,4,5,6-tetrahydro-pyrimidine; HCl | 382.9562 | 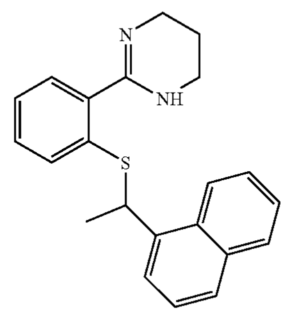 | *** |
| FG | 2-[2-(4-Methoxy-biphenyl-3-ylmethylsulfanyl)-phenyl]-1,4,5,6-tetrahydro-pyrimidine; Formate | 434.5634 | 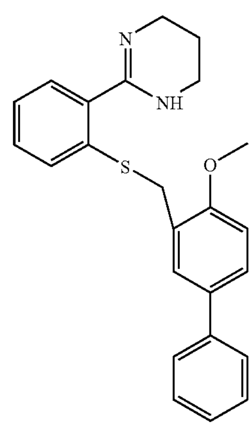 | *** |
| FH | 2-[2-(5-Bromo-2-methoxy-benzylsulfanyl)-5-fluoro-phenyl]-4,5-dihydro-1H-imidazole; Formate | 441.3253 | 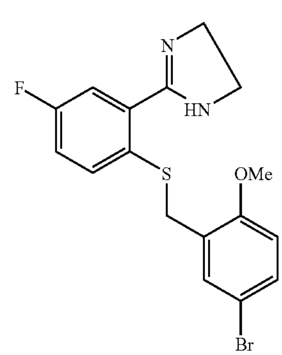 | *** |

TABLE 4-continued

| ID | CHEMICAL NAME | Mol Weight (Tot) | Structure | MC4-R Binding |
|----|---------------|------------------|-----------|---------------|
| FI | 2-(2-Benzhydrylsulfanyl-phenyl)-1,4,5,6-tetrahydro-pyrimidine; Formate | 404.5372 | 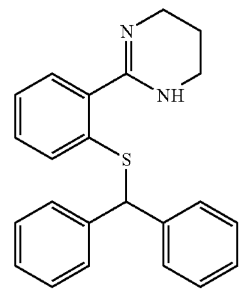 | *** |
| FJ | 2-(3-Amino-propylamino)-6-(5-bromo-2-methoxy-benzylsulfanyl)-benzonitrile; Formate | 452.3764 | 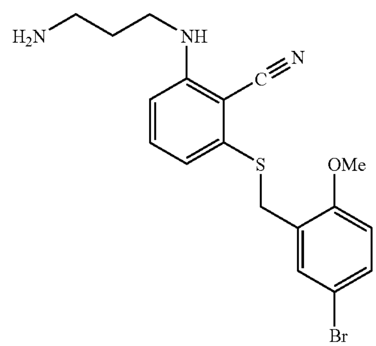 | * |
| FK | 2-[2-(2'-Fluoro-4''-methoxy[1,1',4',1'']terphenyl-3''-ylmethylsulfanyl)-phenyl]-1,4,5,6-tetrahydro-pyrimidine; formate | 528.6517 | 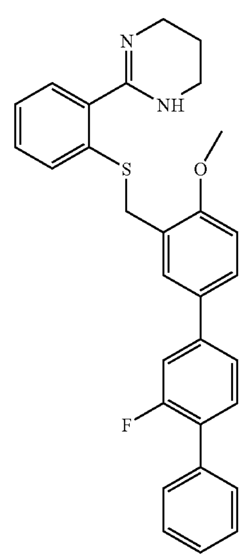 | ** |

TABLE 4-continued

| ID | CHEMICAL NAME | Mol Weight (Tot) | Structure | MC4-R Binding |
|---|---|---|---|---|
| FL | 2-[2-(2-Methoxy-5-phenylethynyl-benzylsulfanyl)-phenyl]-1,4,5,6-tetrahydro-pyrimidine; Formate | 458.5854 | 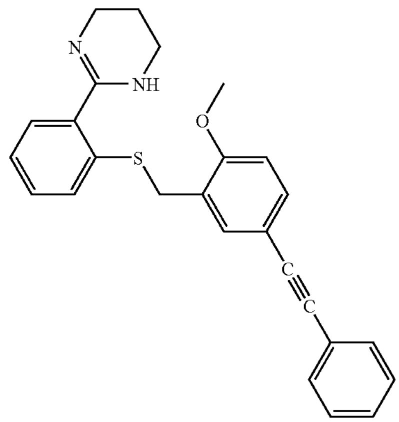 | ** |
| FM | 2-[3-(Naphthalen-1-ylmethylsulfanyl)-phenyl]-1,4,5,6-tetrahydro-pyrimidine; Formate | 378.4993 | 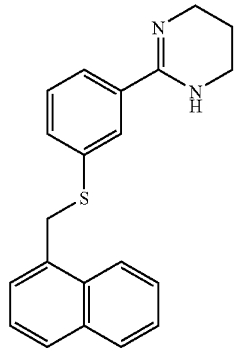 | * |
| FN | 4-Methoxy-N-[4-methyl-2-(1,4,5,6-tetrahydro-pyrimidin-2-yl)-phenyl]-benzamide; Formate | 369.4248 | 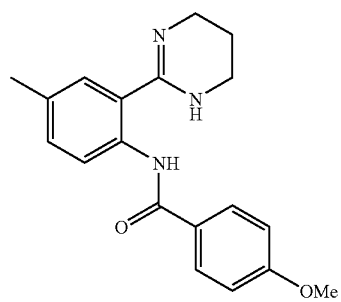 | * |
| FO | 2-(5-Bromo-2-methoxy-benzylsulfanyl)-benzamidine; formate | 397.297 | 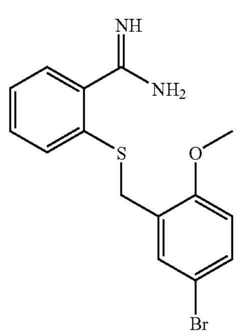 | ** |

TABLE 4-continued

| ID | CHEMICAL NAME | Mol Weight (Tot) | Structure | MC4-R Binding |
|---|---|---|---|---|
| FP | 4,6-Dimethyl-2-piperazin-1-yl-pyrimidine | 192.264 | 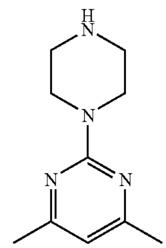 | * |
| FQ | 8-Isopropyl-3,3-dimethyl-6-piperazin-1-yl-3,4-dihydro-1H-pyrano[3,4-c]pyridine-5-carbonitrile | 314.4308 | 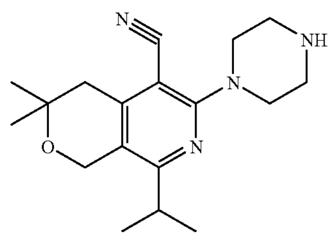 | * |
| FR | 2-Piperazin-1-yl-pyrimidine | 164.2102 | 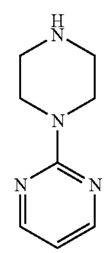 | * |
| FS | 1-Pyridin-2-yl-piperazine | 163.2224 | 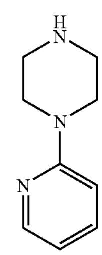 | * |
| FT | 2-Piperazin-1-yl-4-trifluoromethyl-pyrimidine | 232.2085 | 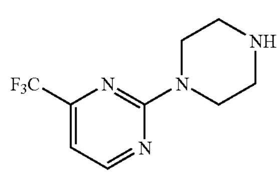 | * |
| FU | 5-Piperazin-1-yl-7-trifluoromethyl-thieno[3,2-b]pyridine-3-carboxylic acid methyl ester | 345.3454 | 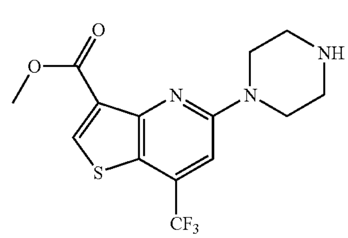 | * |

TABLE 4-continued

| ID | CHEMICAL NAME | Mol Weight (Tot) | Structure | MC4-R Binding |
|---|---|---|---|---|
| FV | 5-Bromo-2-piperazin-1-yl-pyrimidine | 243.1063 | 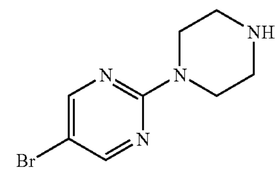 | * |
| FW | 1-(3-Trifluoromethyl-pyridin-2-yl)-piperazine | 231.2207 | 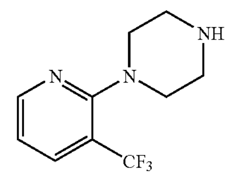 | * |
| FX | 1-(5-Trifluoromethyl-pyridin-2-yl)-piperazine | 231.2207 | 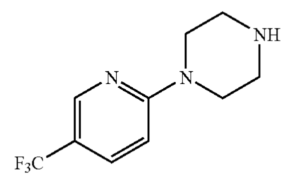 | * |
| FY | Benzyl-[2-(1,4,5,6-tetrahydro-pyrimidin-2-yl)-phenyl]-amine | 265.3581 | 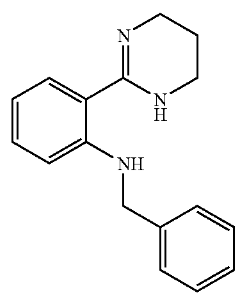 | * |
| FZ | 2-[4-(Naphthalen-1-ylmethylsulfanyl)-phenyl]-1,4,5,6-tetrahydro-pyrimidine; Formate | 378.4993 | 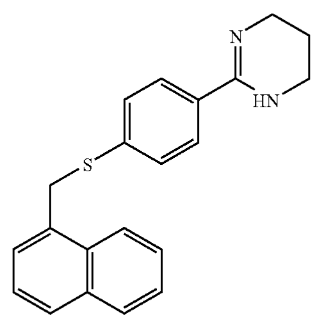 | ** |
| GA | 2-[2-(5-Ethynyl-2-methoxy-benzylsulfanyl)-phenyl]-1,4,5,6-tetrahydro-pyrimidine; HCl | 372.9177 | 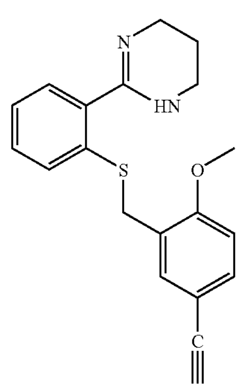 | *** |

TABLE 4-continued

| ID | CHEMICAL NAME | Mol Weight (Tot) | Structure | MC4-R Binding |
|---|---|---|---|---|
| GB | 2-[2-(5-Bromo-2-methoxy-benzylsulfanyl)-benzyl]-1,4,5,6-tetrahydro-pyrimidine; HCl | 441.8186 | 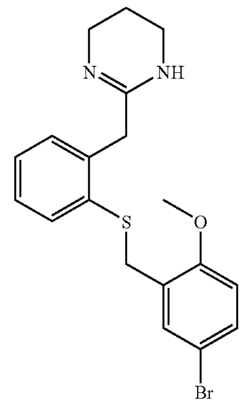 | ** |
| GC | 2-[2-(5-tert-Butyl-2-methoxy-benzylsulfanyl)-phenyl]-1,4,5,6-tetrahydro-pyrimidine; HCl | 405.0032 | 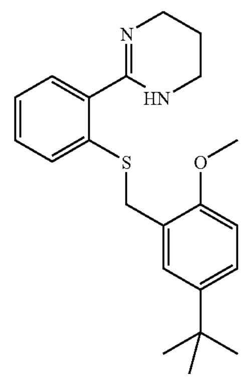 | * |
| GD | 2-[2-(5-Bromo-2-cyclopentyloxy-benzylsulfanyl)-phenyl]-1,4,5,6-tetrahydro-pyrimidine; Formate | 491.4534 | 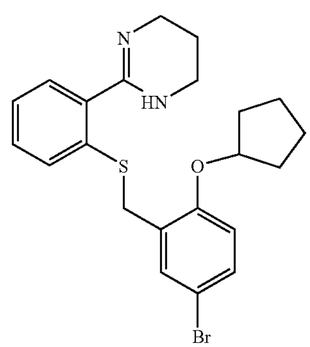 | *** |
| GE | 2-[2-(5-Bromo-2-ethoxy-benzylsulfanyl-phenyl]-1,4,5,6-tetrahydro-pyrimidine; HCl | 441.8186 | 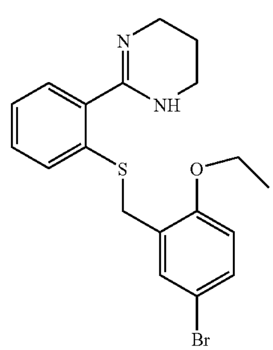 | *** |

TABLE 4-continued

| ID | CHEMICAL NAME | Mol Weight (Tot) | Structure | MC4-R Binding |
|---|---|---|---|---|
| GF | 2-[2-(5-Bromo-2-propoxy-benzylsulfanyl)-phenyl]-1,4,5,6-tetrahydro-pyrimidine; HCl | 455.8455 | 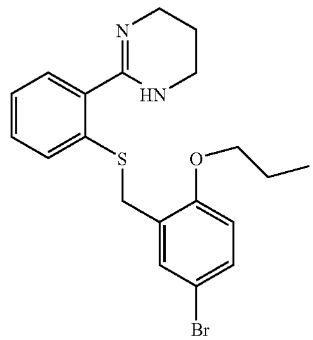 | *** |
| GG | [2-(5-Bromo-2-methoxy-benzylsulfanyl)-benzyl]-diethyl-amine; HCl | 430.8357 | 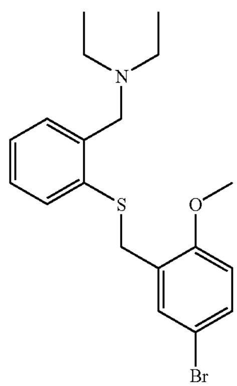 | ** |
| GH | 4-[2-(5-Bromo-2-methoxy-benzylsulfanyl)-benzyl]-morpholine; HCl | 444.8192 | 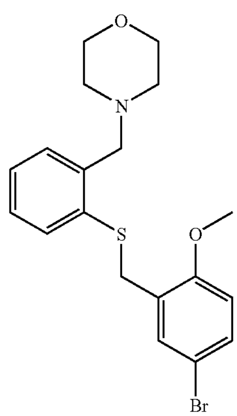 | * |
| GI | 1-[2-(5-Bromo-2-methoxy-benzylsulfanyl)-benzyl]-piperazine; Oxalate | 497.4145 | 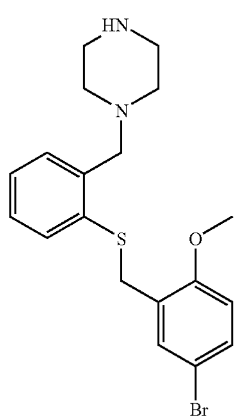 | ** |

TABLE 4-continued

| ID | CHEMICAL NAME | Mol Weight (Tot) | Structure | MC4-R Binding |
|----|---------------|------------------|-----------|---------------|
| GK | {1-[2-(5-Bromo-2-methoxy-benzylsulfanyl)-benzyl]-pyrrolidin-3-yl}-carbamic acid tert-butyl ester | 507.4918 | 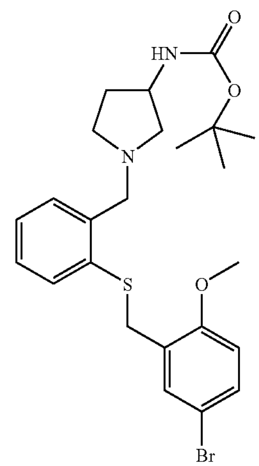 | * |
| GL | 3'-(5-Bromo-2-methoxy-benzylsulfanyl)-3,4,5,6-tetrahydro-2H-[1,2']bipyrazinyl | 395.3232 | 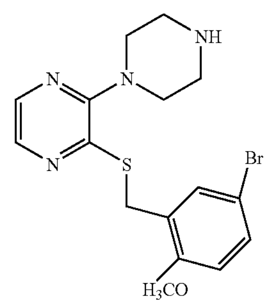 | * |
| GM | C-{4-[3-(5-Bromo-2-methoxy-benzylsulfanyl)-quinoxalin-2-yl]-morpholin-2-yl}-methylamine; 2HCl | 548.3308 | 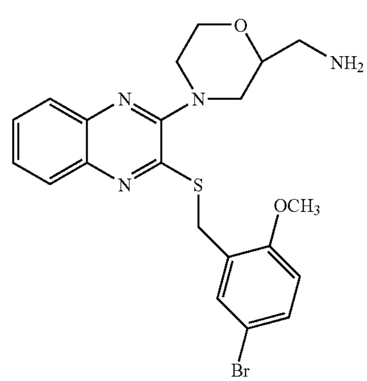 | ** |
| GN | 2-(5-Bromo-2-methoxy-benzylsulfanyl)-3-piperazin-1-yl-quinoxaline; Formate | 491.4131 | 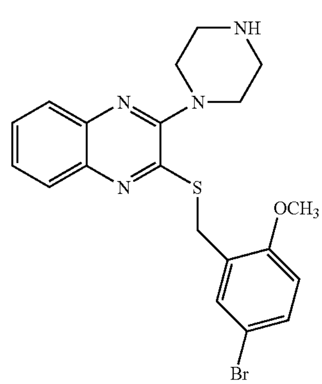 | * |

TABLE 4-continued

| ID | CHEMICAL NAME | Mol Weight (Tot) | Structure | MC4-R Binding |
|---|---|---|---|---|
| GO | 2-[2-(2-Methoxy-5-methyl-benzylsulfanyl)-phenyl]-1,4,5,6-tetrahydro-pyrimidine; HCl | 362.9226 | 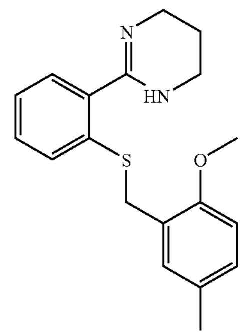 | *** |
| GP | 2-[2-(5-Bromo-2-methoxy-benzyloxymethyl)-phenyl]-1,4,5,6-tetrahydro-pyrimidine; HCl | 425.752 | 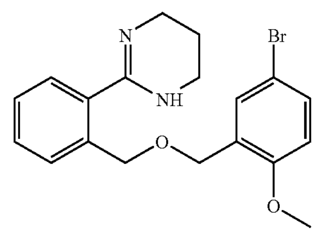 | *** |
| GQ | 2-{2-[5-(3,3-Dimethyl-but-1-ynyl)-2-methoxy-benzylsulfanyl]-phenyl}-1,4,5,6-tetrahydro-pyrimidine; HCl | 429.0252 | 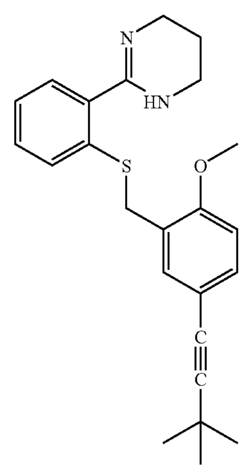 | * |
| GR | 3-Benzylidene-2-(2-methylamino-ethyl)-2,3-dihydro-isoindol-1-one | 278.3538 | 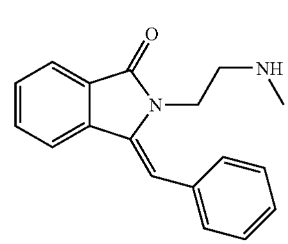 | * |

TABLE 4-continued

| ID | CHEMICAL NAME | Mol Weight (Tot) | Structure | MC4-R Binding |
|----|---------------|------------------|-----------|---------------|
| GS | 2-[2-(2-Naphthalen-1-yl-ethylsulfanyl)-phenyl]-1,4,5,6-tetrahydro-pyrimidine | 346.4962 | 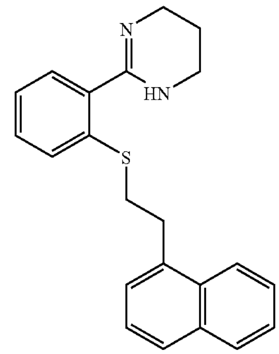 | * |
| GU | [2-(5-Bromo-2-methoxy-benzylsulfanyl)-benzyl]-dimethyl-amine; HCl | 402.7819 | 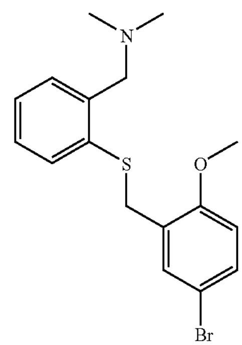 | ** |
| GV | 2-[2-(5-Bromo-2-isopropoxy-benzylsulfanyl)-phenyl]-1,4,5,6-tetrahydro-pyrimidine; HCl | 455.8455 | 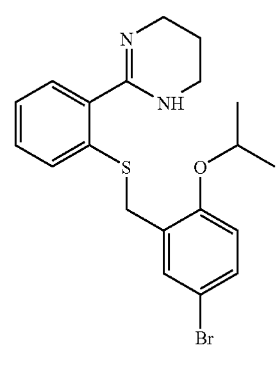 | *** |
| GW | 2-[2-(2-Ethoxy-naphthalen-1-ylmethylsulfanyl)-phenyl]-1,4,5,6-tetrahydro-pyrimidine; HCl | 412.9824 | 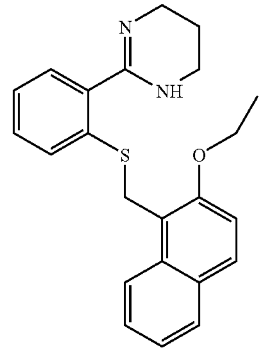 | *** |

TABLE 4-continued

| ID | CHEMICAL NAME | Mol Weight (Tot) | Structure | MC4-R Binding |
|---|---|---|---|---|
| GX | 2-[2-(2-Propoxy-naphthalen-1-ylmethylsulfanyl)-phenyl]-1,4,5,6-tetrahydro-pyrimidine; HCl | 427.0093 | 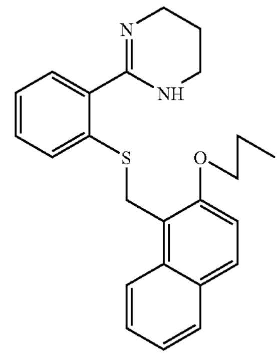 | *** |
| GY | 4-Methoxy-3-[2-(1,4,5,6-tetrahydro-pyrimidin-2-yl)-phenylsulfanylmethyl]-benzonitrile; HCl | 373.9055 | 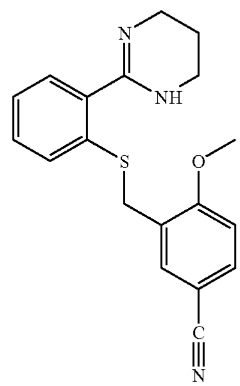 | *** |
| GZ | 1-{4-Methoxy-3-[2-(1,4,5,6-tetrahydro-pyrimidin-2-yl)-phenylsulfanylmethyl]-phenyl}-ethanone; Formate | 400.503 | 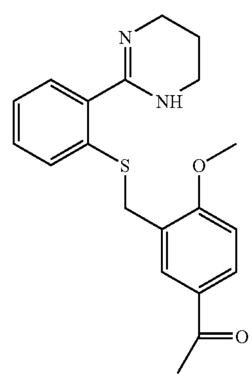 | ** |
| HA | {1-[2-(2-Methoxy-naphthalen-1-ylmethylsulfanyl)-benzyl]-pyrrolidin-3-yl}-carbamic acid tert-butyl ester | 478.6556 | 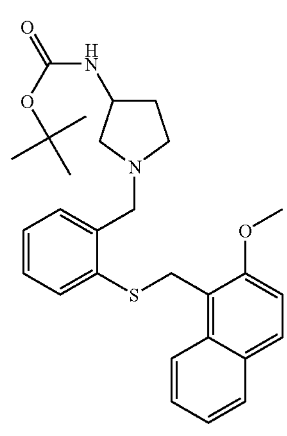 | * |

TABLE 4-continued

| ID | CHEMICAL NAME | Mol Weight (Tot) | Structure | MC4-R Binding |
|----|---------------|------------------|-----------|---------------|
| HB | 2-[2-(Naphthalen-1-ylsulfanylmethyl)-phenyl]-1,4,5,6-tetrahydro-pyrimidine; HCl | 368.9293 | 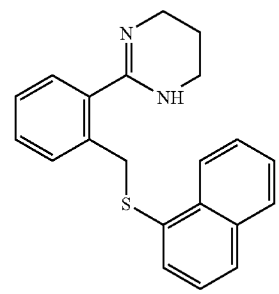 | *** |
| HC | 2-(2-Phenethyl-phenyl)-1,4,5,6-tetrahydro-pyrimidine; Formate | 310.4003 | 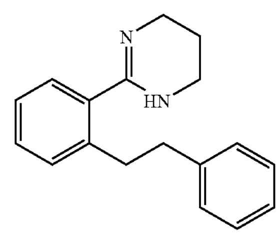 | * |
| HD | 1-[2-(5-Bromo-2-methoxy-benzylsulfanyl)-benzyl]-piperidine; Formate | 452.4167 | 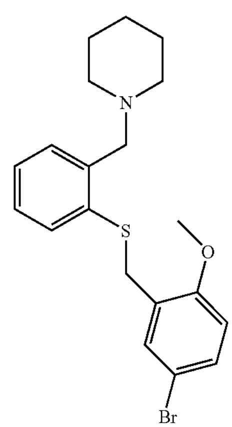 | ** |
| HE | {4-[2-(2-Methoxy-naphthalen-1-ylmethylsulfanyl)-benzyl]-morpholin-2-ylmethyl}-carbamic acid tert-butyl ester | 508.6819 | 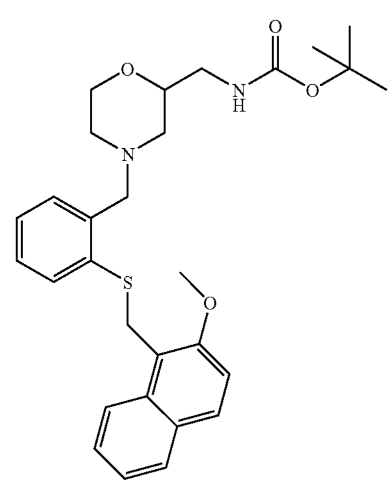 | * |

TABLE 4-continued

| ID | CHEMICAL NAME | Mol Weight (Tot) | Structure | MC4-R Binding |
|----|---------------|------------------|-----------|---------------|
| HF | C-{4-[2-(2-Methoxy-naphthalen-1-ylmethylsulfanyl)-benzyl]-morpholin-2-yl}-methylamine; 2HCl | 481.486 | 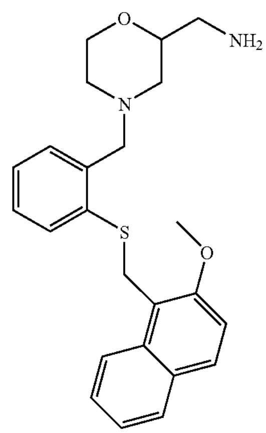 | ** |
| HG | 1-[2-(5-Bromo-2-methoxy-benzylsulfanyl)-benzyl]-pyrrolidin-3-ylamine; 2HCl | 480.2959 | 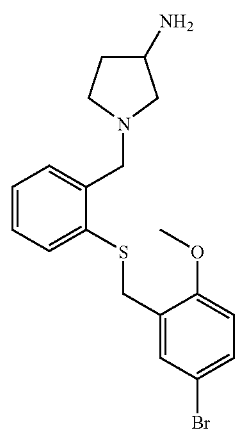 | ** |
| HH | 2-[2-(Naphthalen-1-ylmethylsulfanyl)-phenyl]-1H-imidazole | 316.4265 | 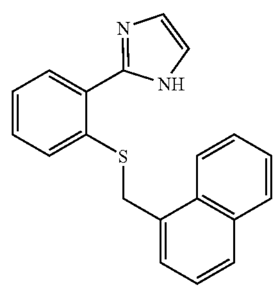 | * |
| HI | 2-[2-(1-Benzyl-1H-imidazol-2-ylmethylsulfanyl)-phenyl]-1,4,5,6-tetrahydro-pyrimidine | 362.4986 | 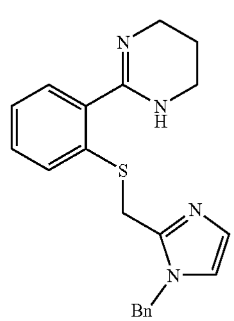 | * |

TABLE 4-continued

| ID | CHEMICAL NAME | Mol Weight (Tot) | Structure | MC4-R Binding |
|---|---|---|---|---|
| HJ | 1-[3-(5-Bromo-2-methoxy-benzylsulfanyl)-pyrazin-2-yl]-pyrrolidin-3-ylamine; 2HCl | 468.2446 | 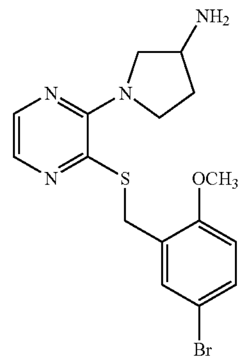 | * |
| HK | 1-[3-(5-Bromo-2-methoxy-benzylsulfanyl)-quinoxalin-2-yl]-pyrrolidin-3-ylamine; 2HCl | 518.3045 | 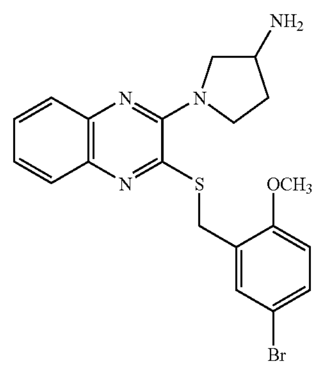 | * |
| HL | 1-[2-(2-Methoxy-naphthalen-1-ylmethylsulfanyl)-benzyl]-pyrrolidin-3-ylamine; HCl | 414.9983 | 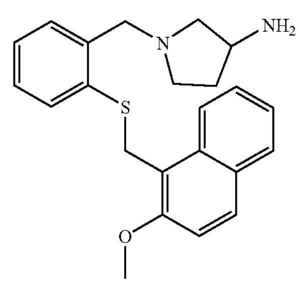 | ** |
| HM | 1-(5-Bromo-2-methoxy-benzyl)-2-phenyl-piperidine | 360.2938 | 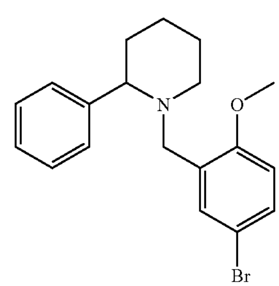 | * |

TABLE 4-continued

| ID | CHEMICAL NAME | Mol Weight (Tot) | Structure | MC4-R Binding |
|---|---|---|---|---|
| HN | 9-Benzyl-2,3,9,10-tetrahydro-1H-4,9,10a-triaza-phenanthrene; Formate | 323.3991 | 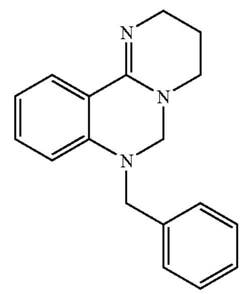 | * |
| HO | 2-[2-(2-Naphthalen-1-yl-ethyl)-phenyl]-1,4,5,6-tetrahydro-pyrimidine; Formate | 360.4602 | 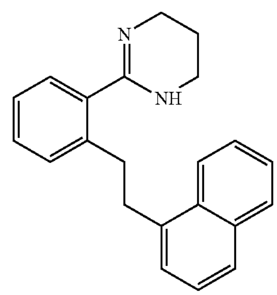 | *** |
| HP | 3-[2-(5-Bromo-2-methoxy-benzylsulfanyl)-3-fluoro-phenyl]-1,5,6,7,8,8a-hexahydro-imidazo[1,5-a]pyridine; HCl | 485.847 | 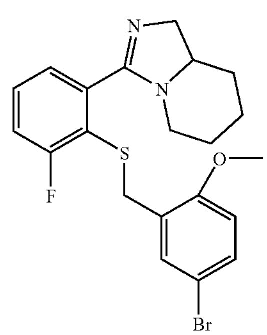 | *** |
| HQ | 3-[2-(5-Bromo-2-methoxy-benzylsulfanyl)-3-fluoro-phenyl]-5,6,7,7a-tetrahydro-1H-pyrrolo[1,2-c]imidazole; Formate | 481.3901 | 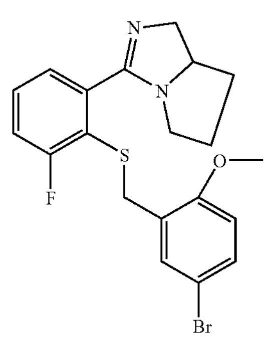 | *** |

TABLE 4-continued

| ID | CHEMICAL NAME | Mol Weight (Tot) | Structure | MC4-R Binding |
|---|---|---|---|---|
| HR | 2-[2-(Benzo[b]thiophen-3-ylmethylsulfanyl)-phenyl]-1,4,5,6-tetrahydro-pyrimidine; HBr | 419.4094 | 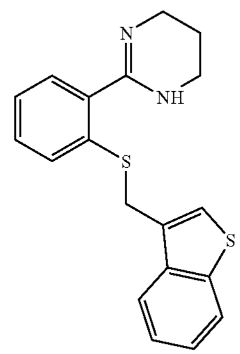 | *** |
| HS | 2-[3-Fluoro-2-(naphthalen-1-ylmethylsulfanyl)-phenyl]-1,4,5,6-tetrahydro-pyrimidine; Formate | 396.4897 | 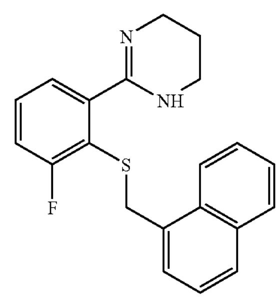 | *** |
| HT | 2-(Naphthalen-1-ylmethylsulfanyl)-3-(1,4,5,6-tetrahydro-pyrimidin-2-yl)-phenylamine; Formate | 393.514 | 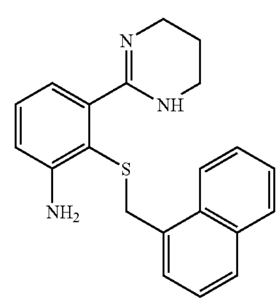 | ** |
| HU | 2-[2-(5-Bromo-2-methoxy-benzylsulfanyl)-3-chloro-phenyl]-1,4,5,6-tetrahydro-pyrimidine | 471.8065 | 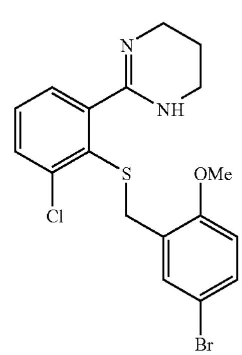 | *** |

TABLE 4-continued

| ID | CHEMICAL NAME | Mol Weight (Tot) | Structure | MC4-R Binding |
|---|---|---|---|---|
| HV | C-{4-[3-(5-Bromo-2-methoxy-benzylsulfanyl)-pyrazin-2-yl]-morpholin-2-yl}-methylamine; Formate | 471.3795 | 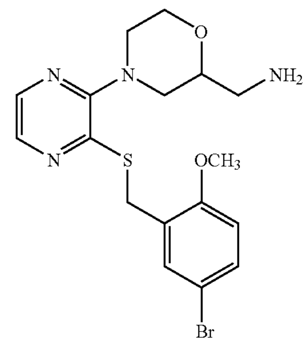 | * |
| HW | Benzyl-methyl-[2-(1,4,5,6-tetrahydro-pyrimidin-2-yl)-phenyl]-amine; Formate | 325.415 | 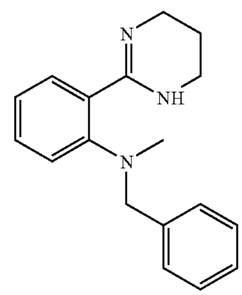 | * |
| HX | 2-[2-(2-Methoxy-phenylsulfanylmethyl)-phenyl]-1,4,5,6-tetrahydro-pyrimidine; HCl | 348.8957 | 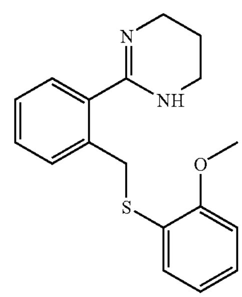 | ** |
| HY | 1-{2-[2-(5-Bromo-2-methoxy-benzylsulfanyl)-phenyl]-5,6-dihydro-4H-pyrimidin-1-yl}-3-methyl-butan-1-one | 475.4497 | 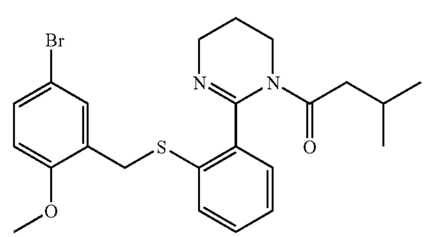 | ** |
| HZ | 2-[2-(5-Bromo-2-methoxy-benzylsulfanyl)-phenyl]-5,6-dihydro-4H-pyrimidine-1-carboxylic acid benzyl | 525.4662 | 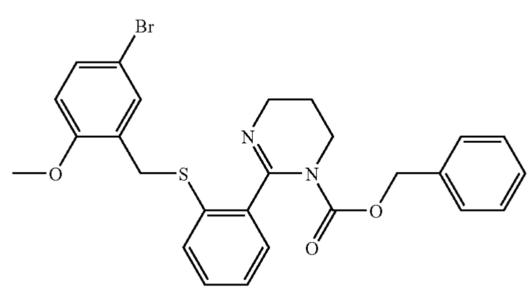 | ** |

TABLE 4-continued

| ID | CHEMICAL NAME | Mol Weight (Tot) | Structure | MC4-R Binding |
|---|---|---|---|---|
| IA | 1-{2-[2-(5-Bromo-2-methoxy-benzylsulfanyl)-phenyl]-5,6-dihydro-4H-pyrimidin-1-yl}-2-phenyl-ethanone | 509.4668 | 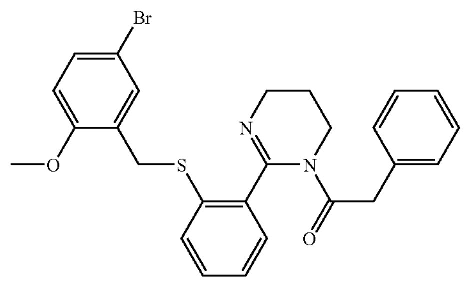 | *** |
| IB | 2-[2-(5-Bromo-2-methoxy-benzylsulfanyl)-phenyl]-1-methanesulfonyl-1,4,5,6-tetrahydro-pyrimidine | 469.4234 | 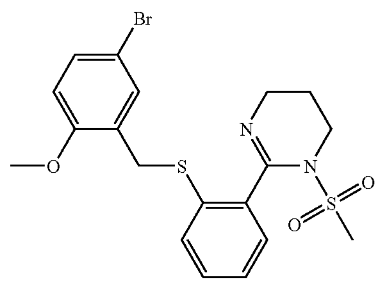 | * |
| IC | 2-(5-Bromo-2-methoxy-benzylsulfanyl)-phenylamine | 324.2413 | 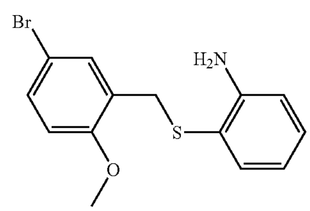 | * |
| ID | 2-o-Tolyl-1,4,5,6-tetrahydro-pyrimidine | 174.2456 | 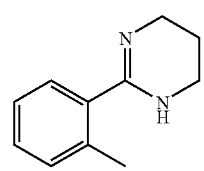 | * |
| IE | 2-[3-(5-Bromo-2-methoxy-benzylsulfanyl)-pyridin-2-yl]-1,4,5,6-tetrahydro-pyrimidine | 392.3195 | 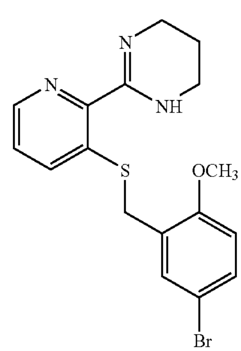 | *** |

TABLE 4-continued

| ID | CHEMICAL NAME | Mol Weight (Tot) | Structure | MC4-R Binding |
|---|---|---|---|---|
| IF | 5-[2-(5-Bromo-2-methoxy-benzylsulfanyl)-phenyl]-[1,3,4]oxadiazol-2-ylamine | 392.2762 | 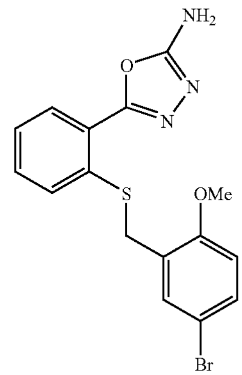 | * |
| IJ | 2-(5-Bromo-2-methoxy-benzylsulfanyl)-benzoic acid hydrazide | 367.2664 | 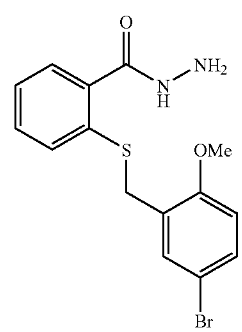 | * |
| IK | N-[2-(5-Bromo-2-methoxy-benzylsulfanyl)-phenyl]-guanidine | 366.2817 | 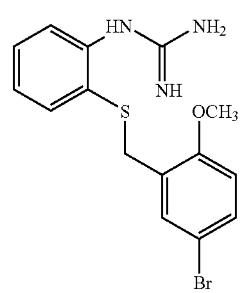 | ** |
| IL | 2-[2-(2-Isopropoxy-naphthalen-1-ylmethylsulfanyl)-phenyl]-1,4,5,6-tetrahydro-pyrimidine; Formate | 436.5793 | 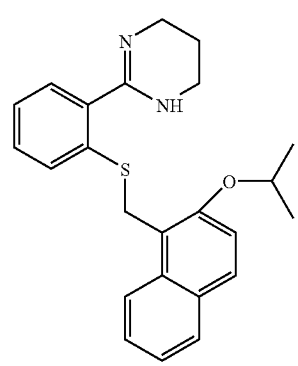 | ** |

TABLE 4-continued

| ID | CHEMICAL NAME | Mol Weight (Tot) | Structure | MC4-R Binding |
|---|---|---|---|---|
| IM | 2-[2-(2-Cyclopentyloxy-naphthalen-1-ylmethylsulfanyl)-phenyl]-1,4,5,6-tetrahydro-pyrimidine; HCl | 453.0472 | 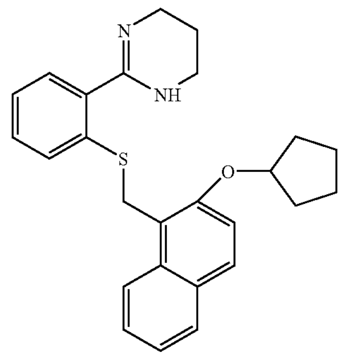 | ** |
| IN | (5-Bromo-2-methoxy-benzyl)-[2-(1,4,5,6-tetrahydro-pyrimidin-2-yl)-phenyl]-amine | 374.2804 | 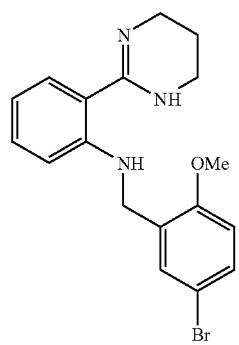 | ** |
| IO | 2-[2-(5-Bromo-2-methoxy-benzylsulfanylmethyl)-phenyl]-1,4,5,6-tetrahydro-pyrimidine; Formate | 451.3886 | 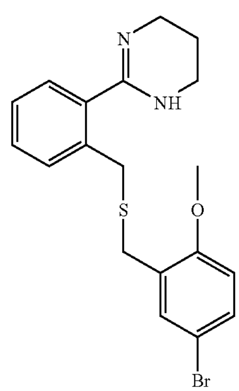 | *** |
| IP | 2-[2-(2-Methoxy-naphthalen-1-ylsulfanylmethyl)-phenyl]-1,4,5,6-tetrahydro-pyrimidine; HCl | 398.9556 | 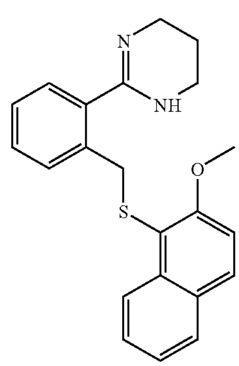 | *** |

TABLE 4-continued

| ID | CHEMICAL NAME | Mol Weight (Tot) | Structure | MC4-R Binding |
|---|---|---|---|---|
| IQ | 2-[3-(5-Bromo-2-methoxy-benzylsulfanyl)-pyrazin-2-yl]-1,4,5,6-tetrahydro-pyrimidine | 393.3073 | 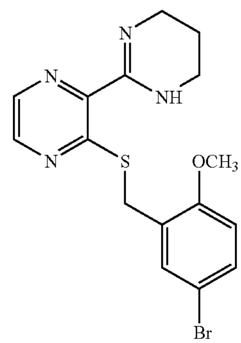 | ** |
| IR | 2-[3-Chloro-2-(naphthalen-1-ylsulfanylmethyl)-phenyl]-1,4,5,6-tetrahydro-pyrimidine; HCl | 403.374 | 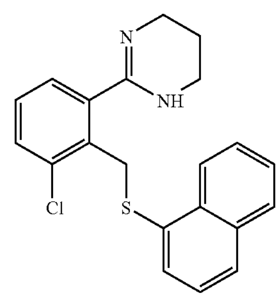 | *** |
| IS | 2-[2-(6-Bromo-2-methoxy-naphthalen-1-ylmethylsulfanyl)-phenyl]-1,4,5,6-tetrahydro-pyrimidine; HCl | 477.8516 | 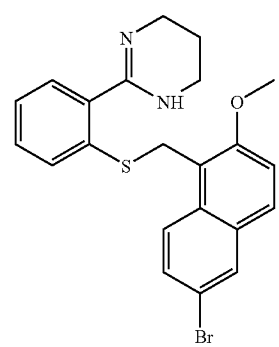 | *** |
| IT | 9-(5-Bromo-2-methoxy-benzyl)-2,3,9,10-tetrahydro-1H-4,9,10a-triaza-phenanthrene; Formate | 432.3214 | 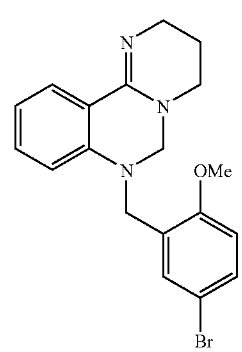 | * |

TABLE 4-continued

| ID | CHEMICAL NAME | Mol Weight (Tot) | Structure | MC4-R Binding |
|----|---------------|------------------|-----------|---------------|
| IU | 2-[3-Chloro-2-(2-methoxy-naphthalen-1-ylsulfanylmethyl)-phenyl]-1,4,5,6-tetrahydro-pyrimidine | 396.9403 | 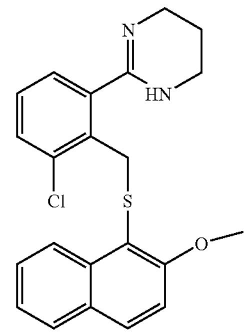 | *** |
| IV | 2-[2-(2,7-Dimethoxy-naphthalen-1-ylmethylsulfanyl)-phenyl]-1,4,5,6-tetrahydro-pyrimidine; Formate | 438.5518 | 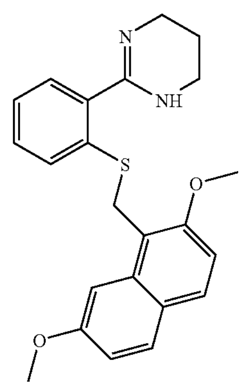 | * |
| IW | 2-Piperazin-1-yl-pyridine-3-sulfonic acid ethylamide | 270.3557 | 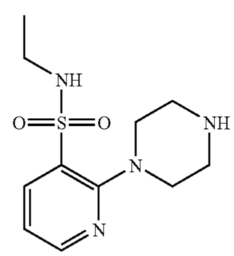 | * |
| IX | 7-Methoxy-3-(4-nitro-phenyl)-2-piperazin-1-yl-quinoline | 364.404 | 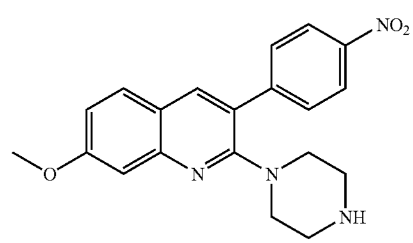 | * |
| IY | 4-Methyl-2-piperazin-1-yl-quinoline | 227.3092 | 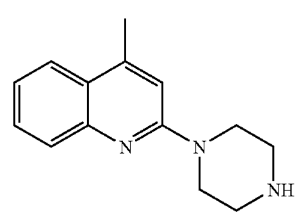 | * |

TABLE 4-continued

| ID | CHEMICAL NAME | Mol Weight (Tot) | Structure | MC4-R Binding |
|---|---|---|---|---|
| IZ | 2-[2-(5-Bromo-2-methoxy-phenylsulfanylmethyl)-phenyl]-1,4,5,6-tetrahydro-pyrimidine; HCl | 427.7917 | 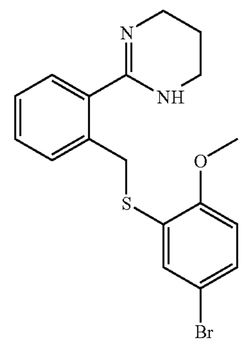 | *** |
| JA | 2-[2-(5-Bromo-2-methoxy-phenylsulfanylmethyl)-3-chloro-phenyl]-1,4,5,6-tetrahydro-pyrimidine; HCl | 462.2365 | 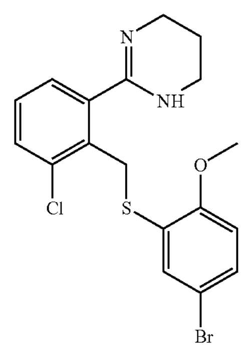 | *** |
| JB | 3-(5-Bromo-2-methoxy-benzylsulfanyl)-2-(1,4,5,6-tetrahydro-pyrimidin-2-yl)-quinoline | 442.3794 | 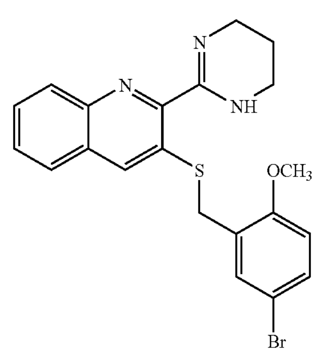 | * |
| JC | 2-[1-(2-Naphthalen-1-yl-ethyl)-1H-pyrrol-2-yl]-1,4,5,6-tetrahydro-pyrimidine | 303.407 | 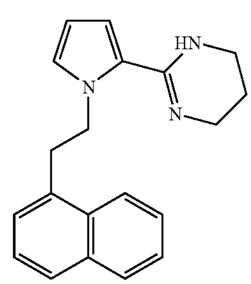 | ** |

TABLE 4-continued

| ID | CHEMICAL NAME | Mol Weight (Tot) | Structure | MC4-R Binding |
|---|---|---|---|---|
| JD | (5-Bromo-2-methoxy-benzyl)-methyl-[2-(1,4,5,6-tetrahydro-pyrimidin-2-yl)-phenyl]-amine | 388.3073 | 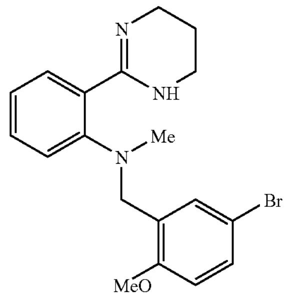 | ** |
| JE | [2-(5-Bromo-2-methoxy-benzylsulfanyl)-phenyl]-methyl-amine | 338.2682 | 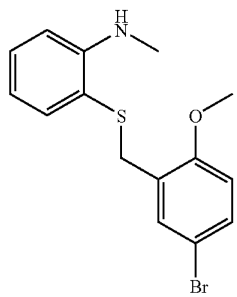 | * |
| JF | 2-(5-Bromo-2-methoxy-benzylsulfanyl)-benzylamine; HCl | 374.7282 | 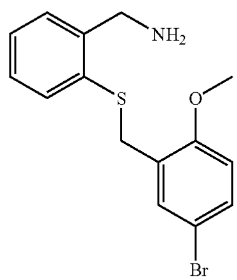 | ** |
| JK | 2-[2-(2-Chloro-phenylsulfanylmethyl)-phenyl]-1,4,5,6-tetrahydro-pyrimidine; HCl | 353.3142 | 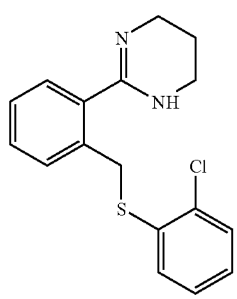 | ** |
| JL | 2-[2-(2-Bromo-phenylsulfanylmethyl)-phenyl]-1,4,5,6-tetrahydro-pyrimidine; HCl | 397.7655 | 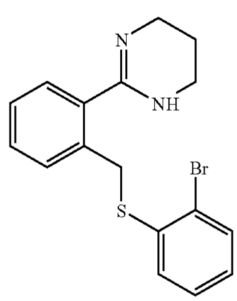 | ** |

TABLE 4-continued

| ID | CHEMICAL NAME | Mol Weight (Tot) | Structure | MC4-R Binding |
|---|---|---|---|---|
| JM | 2-(2-o-Tolylsulfanylmethyl-phenyl)-1,4,5,6-tetrahydro-pyrimidine; HCl | 332.8963 | 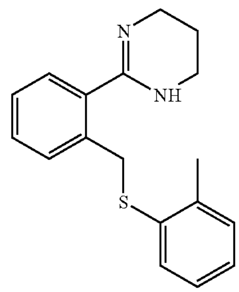 | ** |
| JN | 2-[2-(2,5-Dichloro-phenylsulfanylmethyl)-phenyl]-1,4,5,6-tetrahydro-pyrimidine; HCl | 387.7589 | 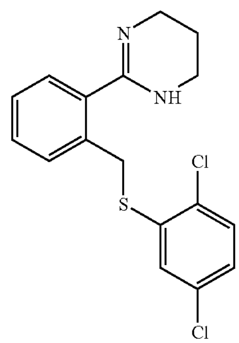 | *** |
| JO | 2-[3-(3-Chloro-benzylsulfanyl)-5-methyl-isothiazol-4-yl]-1,4,5,6-tetrahydro-pyrimidine; Formate | 383.927 | 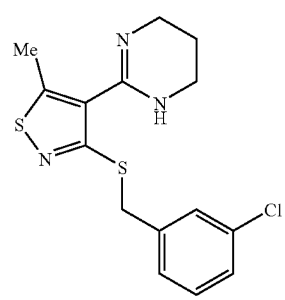 | * |
| JP | N-(4-Methyl-quinazolin-2-yl)-guanidine; HCl | 237.691 | 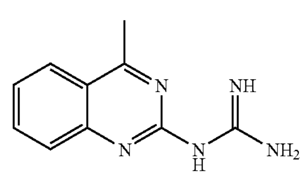 | * |
| JQ | N-(1-Methyl-benzo[f]-quinazolin-3-yl)-guanidine; HCl | 287.7509 | 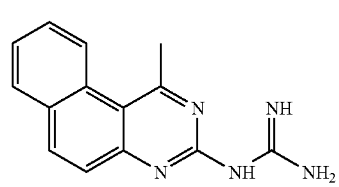 | * |

TABLE 4-continued

| ID | CHEMICAL NAME | Mol Weight (Tot) | Structure | MC4-R Binding |
|---|---|---|---|---|
| JR | 2-[3-(2-Methoxy-naphthalen-1-ylsulfanylmethyl)-thiophen-2-yl]-1,4,5,6-tetrahydro-pyrimidine; Formate | 414.5537 | 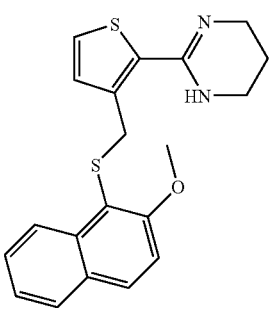 | ** |
| JS | 2-[2-(2,5-Dimethoxy-phenylsulfanylmethyl)-phenyl]-1,4,5,6-tetrahydro-pyrimidine | 342.462 | 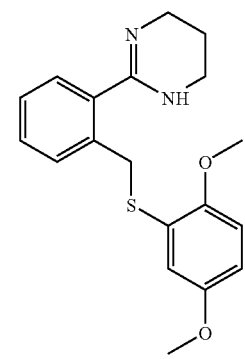 | ** |
| JT | 2-[2-(4-Methyl-naphthalen-1-ylmethylsulfanyl)-phenyl]-1,4,5,6-tetrahydro-pyrimidine; HCl | 382.9562 | 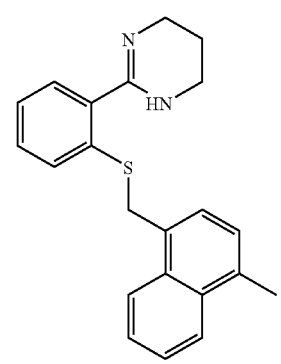 | *** |
| JU | 2-[2-(5-Bromo-2-methoxy-benzylsulfanyl)-3-fluoro-phenyl]-4,4-dimethyl-4,5-dihydro-1H-imidazole; HCl | 459.8091 | 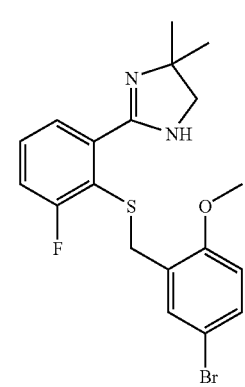 | *** |

TABLE 4-continued

| ID | CHEMICAL NAME | Mol Weight (Tot) | Structure | MC4-R Binding |
|---|---|---|---|---|
| JV | 2-[2-(5-Bromo-2-methoxy-benzylsulfanyl)-3-fluoro-phenyl]-5,5-dimethyl-1,4,5,6-tetrahydro-pyrimidine; HCl | 473.836 | 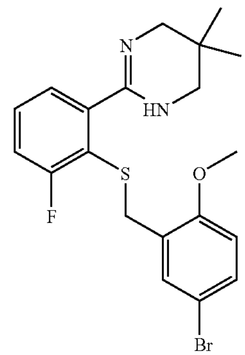 | *** |
| JW | Methyl-naphthalen-1-yl-[2-(1,4,5,6-tetrahydro-pyrimidin-2-yl)-benzyl]-amine; Formate | 375.4748 | 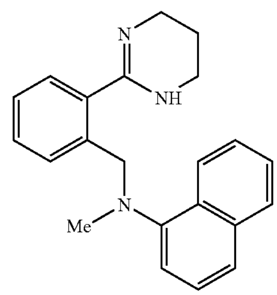 | * |
| JX | Methyl-[2-(1,4,5,6-tetrahydro-pyrimidin-2-yl)-phenyl]-amine | 189.2603 | 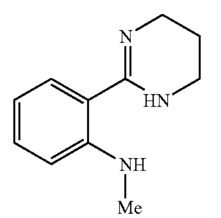 | * |
| JY | 2-(5-Bromo-2-methoxy-benzylsulfanyl)-3-(1,4,5,6-tetrahydro-pyrimidin-2-yl)-quinoxaline | 443.3672 | 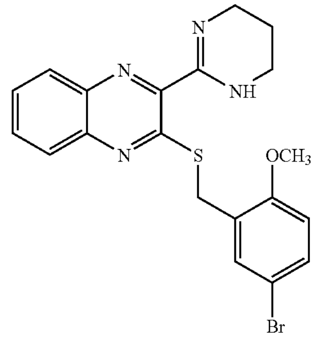 | * |
| JZ | 2-[3-(Naphthalen-1-ylsulfanylmethyl)-thiophen-2-yl]-1,4,5,6-tetrahydro-pyrimidine; Formate | 384.5274 | 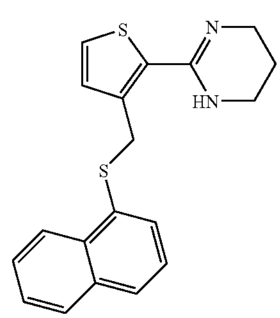 | *** |

TABLE 4-continued

| ID | CHEMICAL NAME | Mol Weight (Tot) | Structure | MC4-R Binding |
|---|---|---|---|---|
| KA | 2-[6-(2-Naphthalen-1-yl-ethoxy)-pyridin-2-yl]-1,4,5,6-tetrahydro-pyrimidine; Formate | 377.4474 | 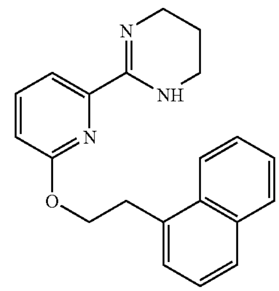 | * |
| KB | 2-{2-[2-(5-Bromo-2-methoxy-phenyl)-ethyl]-phenyl}-1,4,5,6-tetrahydro-pyrimidine | 373.2926 | 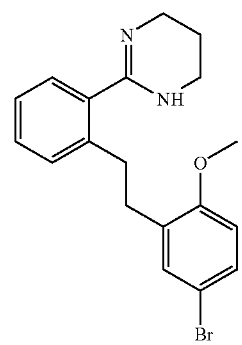 | *** |
| KC | 10-(5-Bromo-2-methoxy-phenyl)-9-methyl-2,3,9,10-tetrahydro-1H-4,9,10a-triaza-phenanthrene; Formate | 432.3214 | 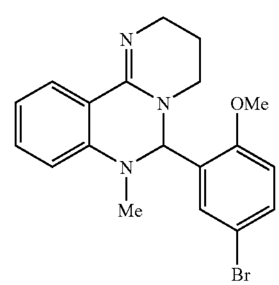 | * |
| KD | 2-Morpholin-4-ylmethyl-quinazolin-4-ol | 245.2811 | 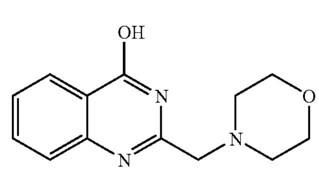 | * |
| KE | N,N-Dimethyl-N'-(4-phenyl-quinazolin-2-yl)-ethane-1,2-diamine | 292.3838 | 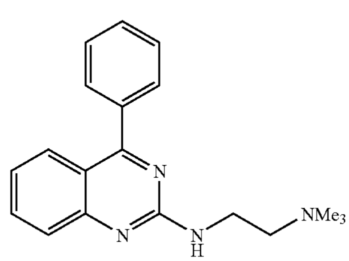 | * |

TABLE 4-continued
| ID | CHEMICAL NAME | Mol Weight (Tot) | Structure | MC4-R Binding |
|----|---------------|------------------|-----------|---------------|
| KF | 4-Phenyl-2-piperazin-1-yl-quinazoline | 290.3679 | 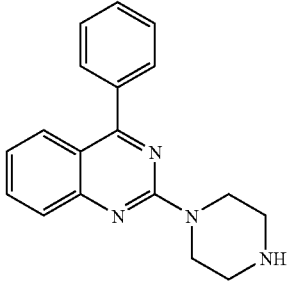 | * |
| KG | 2-[3-Chloro-2-(2-naphthalen-1-yl-ethyl)-phenyl]-1,4,5,6-tetrahydro-pyrimidine; HCl | 385.3349 | 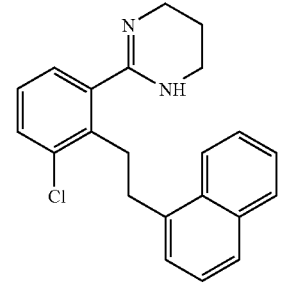 | *** |
| KH | 2-{2-[2-(5-Bromo-2-methoxy-phenyl)-ethyl]-3-fluoro-phenyl)-1,4,5,6-tetrahydro-pyrimidine; HCl | 427.7431 | 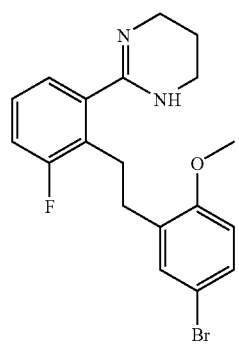 | *** |
| KI | 1-(2-Naphthalen-1-yl-ethyl)-6-(1,4,5,6-tetrahydro-pyrimidin-2-yl)-1H-pyridin-2-one; Formate | 377.4474 | 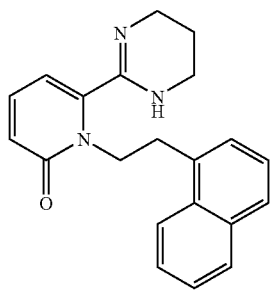 | * |

TABLE 4-continued

| ID | CHEMICAL NAME | Mol Weight (Tot) | Structure | MC4-R Binding |
|---|---|---|---|---|
| KJ | 2-[2-(5-Bromo-2-methoxy-phenylsulfanylmethyl)-3-fluoro-phenyl]-1,4,5,6-tetrahydro-pyrimidine; HCl | 445.7822 | 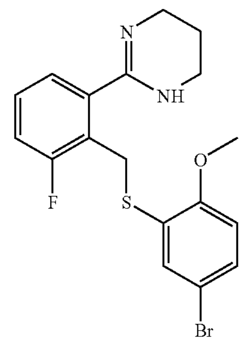 | *** |
| KK | 2-[2-(Naphthalen-1-ylsulfanylmethyl)-phenyl]-4,5-dihydro-1H-imidazole; HCl | 354.9024 | 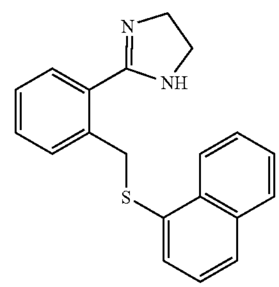 | *** |
| KL | 2-[3-Fluoro-2-(naphthalen-1-ylsulfanylmethyl)-phenyl]-1,4,5,6-tetrahydro-pyrimidine; HCl | 386.9197 | 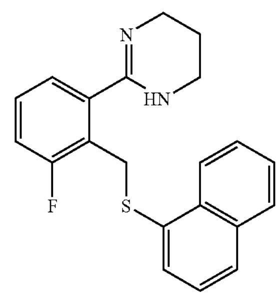 | *** |
| KM | 2-[3-Bromo-2-(naphthalen-1-ylsulfanylmethyl)-phenyl]-1,4,5,6-tetrahydro-pyrimidine; HCl | 447.8253 | 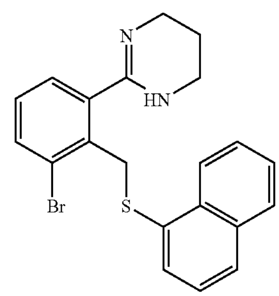 | *** |
| KN | 2-{2-[2-(5-Bromo-2-methoxy-phenyl)-ethyl]-3-chloro-phenyl}-1,4,5,6-tetrahydro-pyrimidine; HCl | 444.1974 | 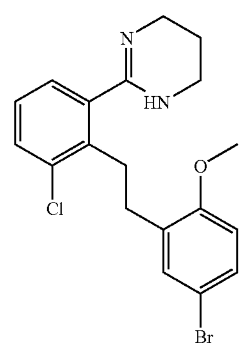 | *** |

TABLE 4-continued

| ID | CHEMICAL NAME | Mol Weight (Tot) | Structure | MC4-R Binding |
|---|---|---|---|---|
| KO | 6-Benzylsulfanyl-5-(1,4,5,6-tetrahydro-pyrimidin-2-yl)-imidazo[2,1-b]thiazole; Formate | 374.492 | 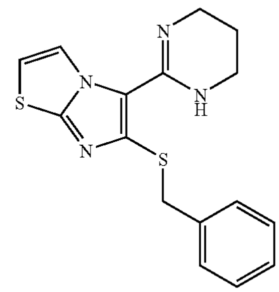 | * |
| KP | 2-[3-(5-Bromo-2-methoxy-phenylsulfanyl)-propyl]-1,4,5,6-tetrahydro-pyrimidine; Formate | 389.3177 | 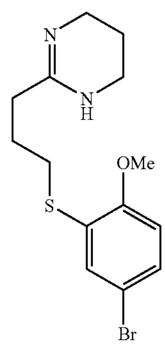 | * |
| KQ | 2-[2-(2-Methoxy-5-trifluoromethyl-benzylsulfanyl)-phenyl]-1,4,5,6-tetrahydro-pyrimidine | 380.4339 | 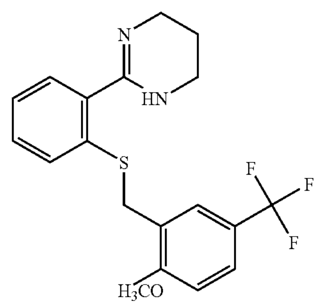 | *** |
| KR | 9-Methyl-10-naphthalen-1-yl-2,3,9,10-tetrahydro-1H-4,9,10a-triaza-phenanthrene; Formate | 373.459 | 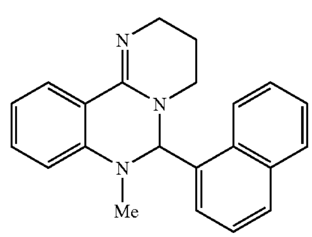 | * |
| KS | 7-Chloro-4,8-dimethyl-1H-quinolin-2-one | 207.6592 | 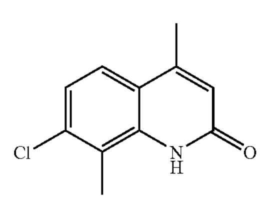 | * |

TABLE 4-continued

| ID | CHEMICAL NAME | Mol Weight (Tot) | Structure | MC4-R Binding |
|---|---|---|---|---|
| KT | 7-Chloro-4-methyl-2-piperazin-1-yl-quinoline | 261.754 | 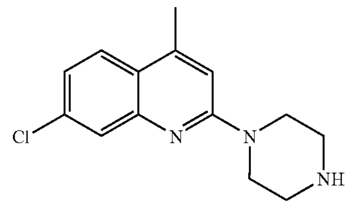 | * |
| KU | 4,8-Dimethyl-2-piperazin-1-yl-quinoline | 241.3361 | 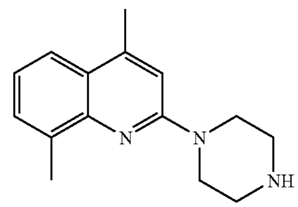 | * |
| KV | 2-[4-(Naphthalen-1-ylsulfanylmethyl)-thiophen-3-yl]-1,4,5,6-tetrahydro-pyrimidine; HCl | 374.9574 | 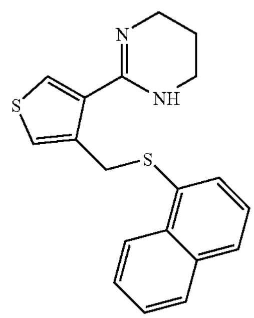 | ** |
| KW | 2-[2-(Naphthalen-1-ylsulfanylmethyl)-thiophen-3-yl]-1,4,5,6-tetrahydro-pyrimidine; HCl | 374.9574 | 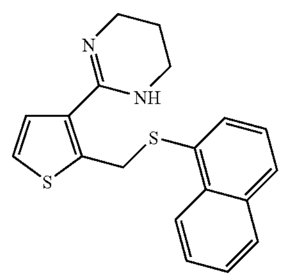 | *** |
| KX | 6-(2-Methoxy-phenyl)-3,4-dihydro-2H-pyrimido[2,1-a]isoquinoline; Formate | 336.3948 | 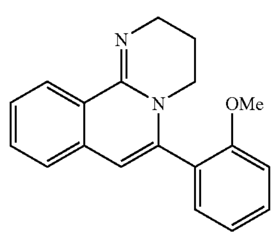 | * |
| KY | Piperazine | 86.1369 | 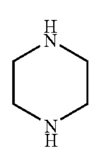 | * |

TABLE 4-continued

| ID | CHEMICAL NAME | Mol Weight (Tot) | Structure | MC4-R Binding |
|---|---|---|---|---|
| KZ | 2-[2-(4-Fluoro-naphthalen-1-ylmethylsulfanyl)-phenyl]-1,4,5,6-tetrahydro-pyrimidine; HBr | 431.3717 | 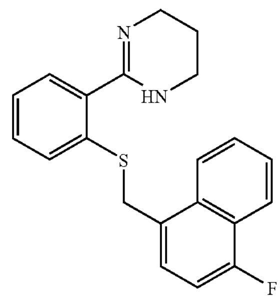 | *** |
| LA | 7-Ethyl-4-methyl-2-piperazin-1-yl-quinoline | 255.363 | 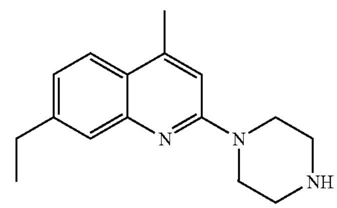 | * |
| LB | 6-Ethyl-4-methyl-2-piperazin-1-yl-quinoline | 255.363 | 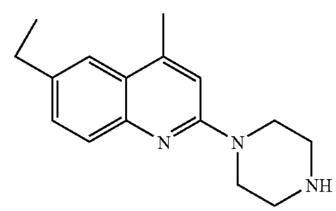 | * |
| LC | 5,8-Dimethoxy-4-methyl-2-piperazin-1-yl-quinoline | 287.3618 | 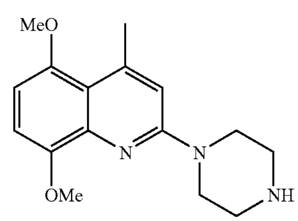 | * |
| LD | 2-{2-[2-(5-Bromo-2-methoxy-phenyl)-ethyl]-3-trifluoromethyl-phenyl}-1,4,5,6-tetrahydro-pyrimidine; Parent | 441.2909 | 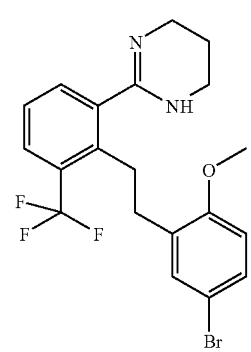 | *** |

TABLE 4-continued

| ID | CHEMICAL NAME | Mol Weight (Tot) | Structure | MC4-R Binding |
|---|---|---|---|---|
| LE | 2-[2-(2-Naphthalen-1-yl-ethyl)-3-trifluoromethyl-phenyl]-1,4,5,6-tetrahydro-pyrimidine; HCl | 418.8884 | 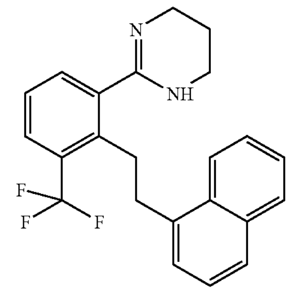 | *** |
| LF | 2-[4-Benzyloxy-2-(5-bromo-2-methoxy-benzylsulfanyl)-phenyl]-1,4,5,6-tetrahydro-pyrimidine; Formate | 543.4858 | 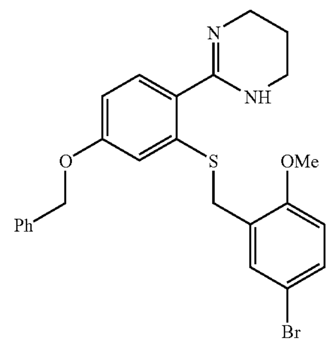 | ** |
| LG | [3-(5-Bromo-2-methoxy-benzylsulfanyl)-quinoxalin-2-yl]-(3-pyrrolidin-1-yl-propyl)-amine; formate | 533.4937 | 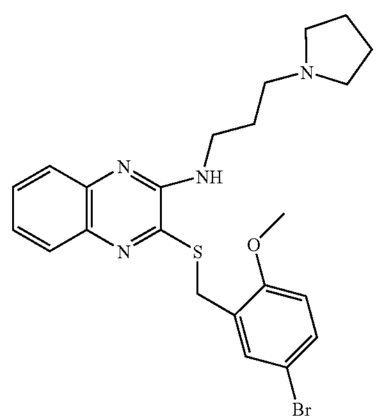 | * |
| LH | Naphthalen-1-ylmethyl-[2-(1,4,5,6-tetrahydro-pyrimidin-2-yl)-phenyl]-amine; Formate | 361.448 | 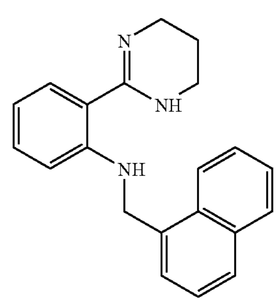 | * |

TABLE 4-continued

| ID | CHEMICAL NAME | Mol Weight (Tot) | Structure | MC4-R Binding |
|----|---------------|------------------|-----------|---------------|
| LI | [3-(5-Bromo-2-methoxy-benzylsulfanyl)-quinoxalin-2-yl]-[2-(1-methyl-pyrrolidin-2-yl)-ethyl]-amine; Formate | 533.4937 | 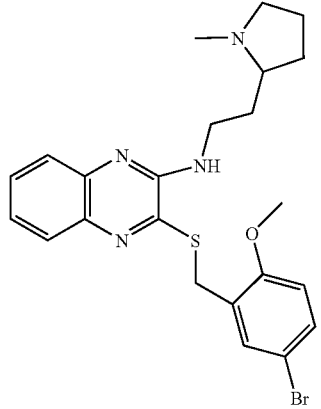 | * |
| LJ | [3-(5-Bromo-2-methoxy-benzylsulfanyl)-quinoxalin-2-yl]-[3-(2-methyl-piperidin-1-yl)-propyl]-amine; Formate | 561.5475 | 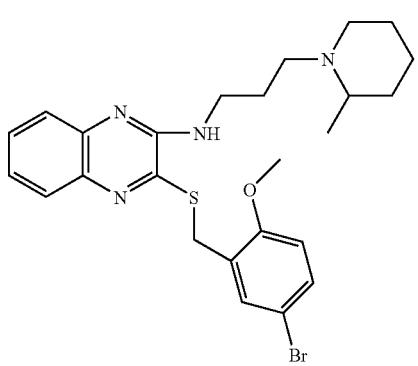 | * |
| LK | [3-(5-Bromo-2-methoxy-benzylsulfanyl)-quinoxalin-2-yl]-piperidin-4-ylmethyl-amine; Formate | 519.4669 | 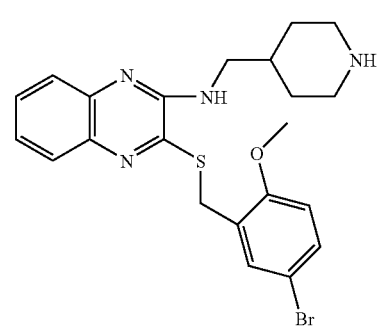 | * |
| LM | 2-[1,4']Bipiperidinyl-1'-yl-3-(5-bromo-2-methoxy-benzylsulfanyl)-quinoxaline; Formate | 573.5585 | 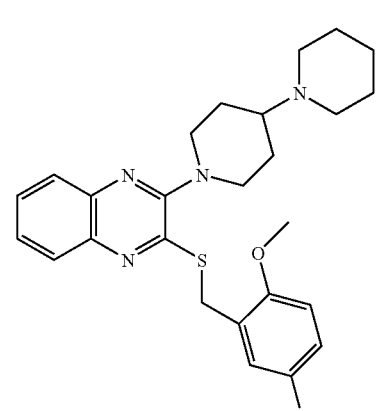 | * |

TABLE 4-continued

| ID | CHEMICAL NAME | Mol Weight (Tot) | Structure | MC4-R Binding |
|----|---------------|------------------|-----------|---------------|
| LN | N1-[3-(5-Bromo-2-methoxy-benzylsulfanyl)-quinoxalin-2-yl]-propane-1,3-diamine; 2HCl | 506.2935 | 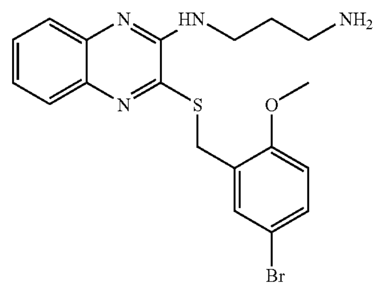 | * |
| LO | 2-[1,4']Bipiperidinyl-1'-yl-3-(5-bromo-2-methoxy-benzylsulfanyl)-quinoxaline; Formate | 581.5377 | 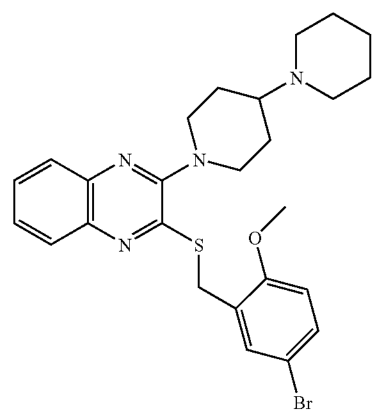 | * |
| LP | 2-(5-Bromo-2-methoxy-benzylsulfanyl)-3-[4-(3-morpholin-4-yl-propyl)-piperazin-1-yl]-quinoxaline; Formate | 618.5995 | 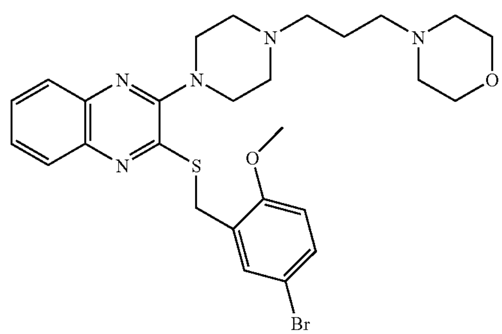 | * |
| LQ | 4-[2-(5-Bromo-2-methoxy-benzylsulfanyl)-benzylamino]-piperidine-1-carboxylic acid ethyl ester; Formate | 539.4949 | 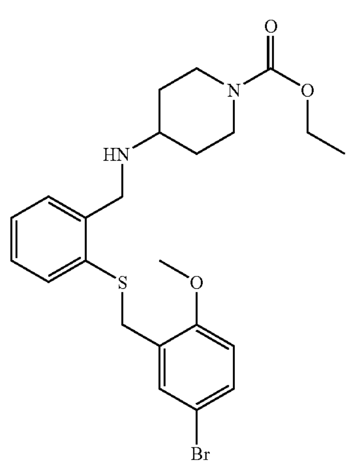 | * |

TABLE 4-continued

| ID | CHEMICAL NAME | Mol Weight (Tot) | Structure | MC4-R Binding |
|----|---------------|------------------|-----------|---------------|
| LR | 1-[2-(Naphthalen-1-ylmethylsulfanyl)-benzyl]-piperidine | 347.5242 | 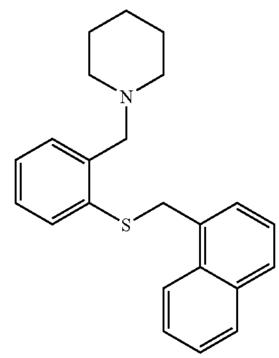 | * |
| LS | 2-{4-[2-(5-Bromo-2-methoxy-benzylsulfanyl)-benzyl]-piperazin-1-yl}-pyrimidine; Formate | 531.4779 | 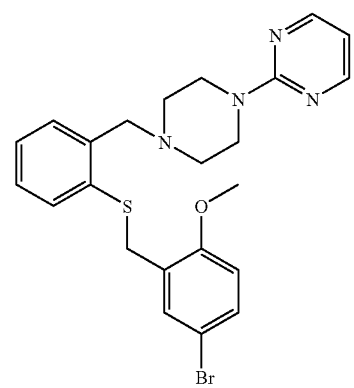 | * |
| LT | 2-[2-(6-Fluoro-naphthalen-1-ylmethylsulfanyl)-phenyl]-1,4,5,6-tetrahydro-pyrimidine; HBr | 431.3717 | 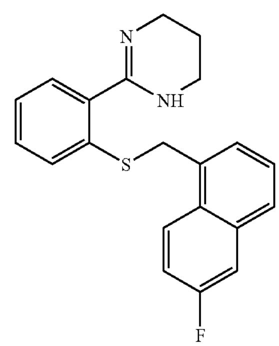 | *** |
| LU | 1-{4-[2-(5-Bromo-2-methoxy-benzylsulfanyl)-benzyl]-piperazin-1-yl}-ethanone; Formate | 495.4418 | 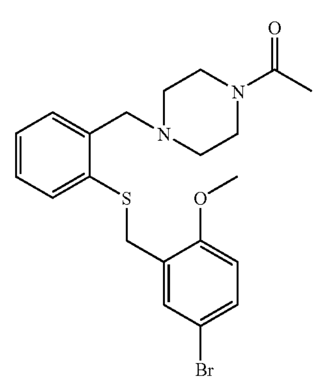 | * |

TABLE 4-continued

| ID | CHEMICAL NAME | Mol Weight (Tot) | Structure | MC4-R Binding |
|----|---------------|------------------|-----------|---------------|
| LV | 2-(2-{4-[2-(5-Bromo-2-methoxy-benzylsulfanyl)-benzyl]-piperazin-1-yl}-ethoxy)-ethanol; Formate | 541.5108 | 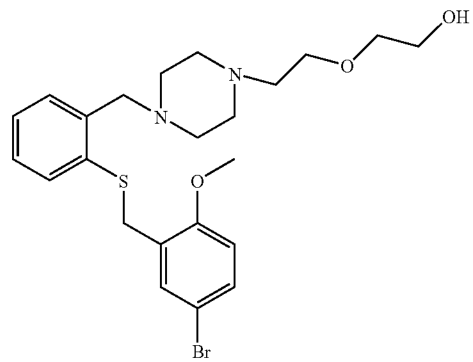 | * |
| LW | 2-{4-[2-(5-Bromo-2-methoxy-benzylsulfanyl)-benzyl]-piperazin-1-yl}-N-isopropyl-acetamide; Formate | 552.5371 | 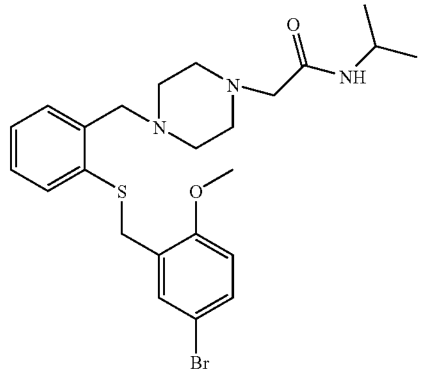 | ** |
| LX | {1-[2-(5-Bromo-2-methoxy-benzylsulfanyl)-benzyl]-piperidin-2-yl}-methanol; Formate | 482.443 | 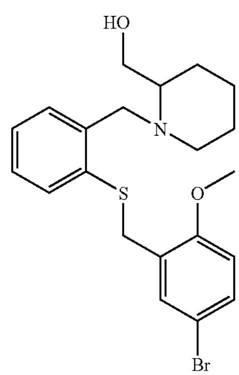 | *** |
| LY | 1-[2-(5-Bromo-2-methoxy-benzylsulfanyl)-benzyl]-2-(N-pyrrolo)methyl-pyrrolidine; Formate | 521.523 | 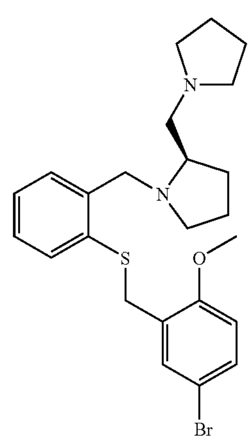 | * |

TABLE 4-continued

| ID | CHEMICAL NAME | Mol Weight (Tot) | Structure | MC4-R Binding |
|---|---|---|---|---|
| LZ | 1'-[2-(5-Bromo-2-methoxy-benzylsulfanyl)-benzyl]-[1,4']bipiperidinyl; Formate | 535.5499 | 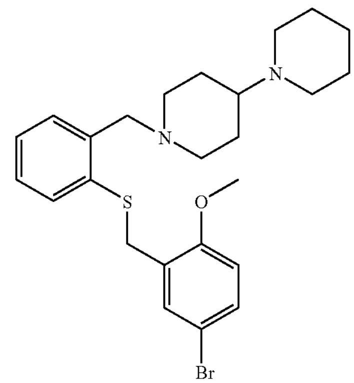 | * |
| MA | 1-[2-(5-Bromo-2-methoxy-benzylsulfanyl)-benzyl]-4-cycloheptyl-piperazine; Formate | 549.5768 | 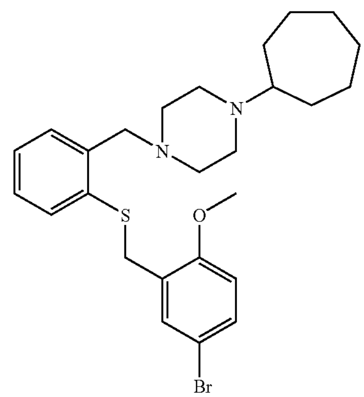 | * |
| MB | 3-{2-[2-(1,4,5,6-Tetrahydro-pyrimidin-2-yl)-phenyl]-ethyl}-1H-indole | 349.437 | 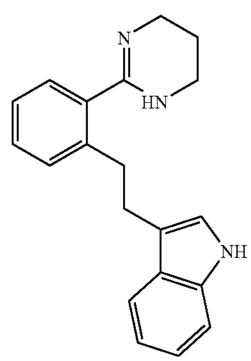 | * |
| MC | N'-[3-(5-Bromo-2-methoxy-benzylsulfanyl)-quinoxalin-2-yl]-N,N-diethyl-ethane-1,2-diamine; Formate | 521.4827 | 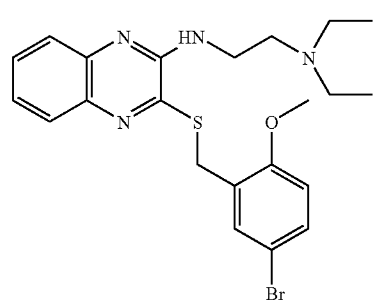 | * |

TABLE 4-continued

| ID | CHEMICAL NAME | Mol Weight (Tot) | Structure | MC4-R Binding |
|----|---------------|------------------|-----------|---------------|
| MD | N'-[3-(5-Bromo-2-methoxy-benzylsulfanyl)-quinoxalin-2-yl]-N,N-dimethyl-propane-1,3-diamine; Formate | 507.4559 | 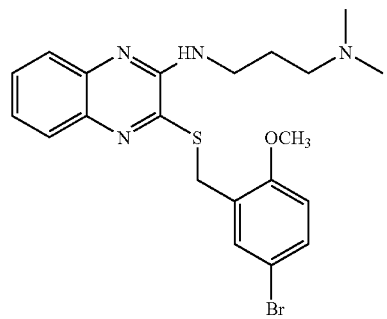 | * |
| ME | 2-(5-Bromo-2-methoxy-benzylsulfanyl)-3-[1,4]diazepan-1-yl-quinoxaline; Formate | 505.44 | 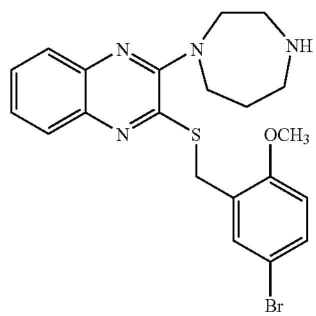 | * |
| MF | N-(4-Bromo-benzyl)-N',N'-dimethyl-N-naphthalen-1-ylmethyl-ethane-1,2-diamine | 397.358 | 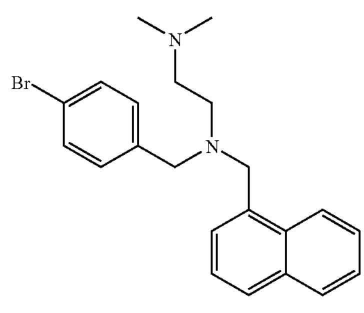 | * |
| MG | 3'-(5-Bromo-2-methoxy-benzylsulfanyl)-4-(3-morpholin-4-yl-propyl)-3,4,5,6-tetrahydro-2H-[1,2']bipyrazinyl; Formate | 568.5396 | 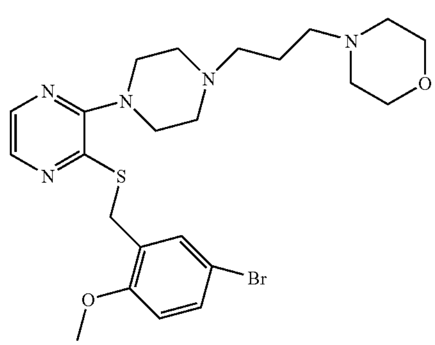 | * |

TABLE 4-continued

| ID | CHEMICAL NAME | Mol Weight (Tot) | Structure | MC4-R Binding |
|----|---------------|------------------|-----------|---------------|
| MH | {3-[3'-(5-Bromo-2-methoxy-benzylsulfanyl)-2,3,5,6-tetrahydro-[1,2']bipyrazinyl-4-yl]-propyl}-dimethyl-amine; Formate | 526.5023 | 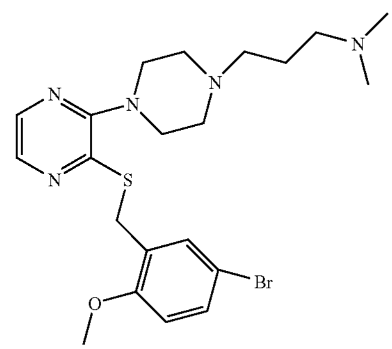 | * |
| MI | N-(3-Bromo-benzyl)-N-(5-bromo-2-methoxy-benzyl)-N',N'-dimethyl-ethane-1,2-diamine | 456.2204 | 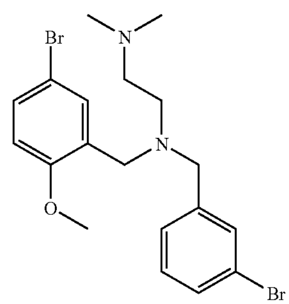 | * |
| MJ | N-(1-Benzyl-piperidin-4-yl)-2-(naphthalen-1-ylmethylsulfanyl)-benzamide | 466.6471 | 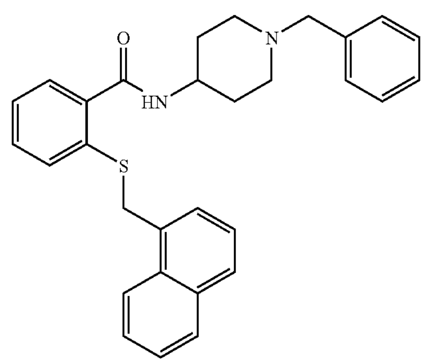 | * |
| MK | N,N-Dimethyl-N'-naphthalen-2-ylmethyl-N'-naphthalen-1-ylmethyl-ethane-1,2-diamine | 368.5218 | 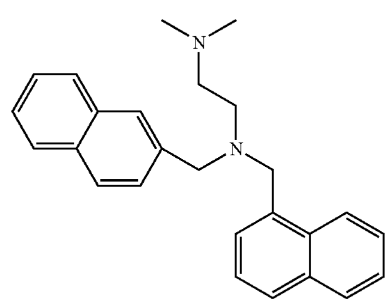 | * |

| ID | CHEMICAL NAME | Mol Weight (Tot) | Structure | MC4-R Binding |
|---|---|---|---|---|
| ML | 8-Methyl-3-[2-(naphthalen-1-ylsulfanylmethyl)-phenyl]-8-aza-bicyclo[3.2.1]octan-3-ol; Formate | 435.5915 | 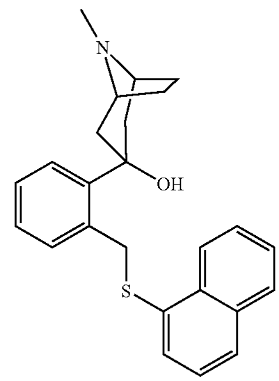 | ** |
| MM | 1-Methyl-4-[2-(naphthalen-1-ylsulfanylmethyl)-phenyl]-piperidin-4-ol; Formate | 409.5536 | 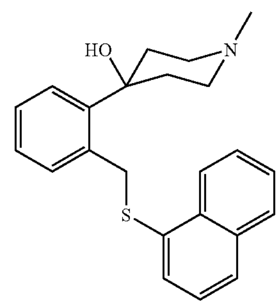 | * |
| MN | 3-[2-(Naphthalen-1-ylsulfanylmethyl)-phenyl]-1-aza-bicyclo[2.2.2]octan-3-ol; Formate | 421.5646 | 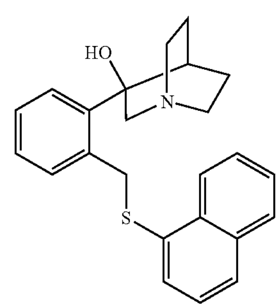 | * |
| MO | 1'-[3-(5-Bromo-2-methoxy-benzylsulfanyl)-pyrazin-2-yl]-[1,4']bipiperidinyl | 477.4686 | 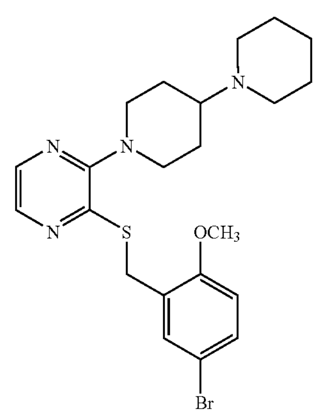 | * |

TABLE 4-continued

| ID | CHEMICAL NAME | Mol Weight (Tot) | Structure | MC4-R Binding |
|---|---|---|---|---|
| MP | [3-(5-Bromo-2-methoxy-benzylsulfanyl)-pyrazin-2-yl]-[2-(1-methyl-pyrrolidin-2-yl)-ethyl]-amine | 437.4039 | 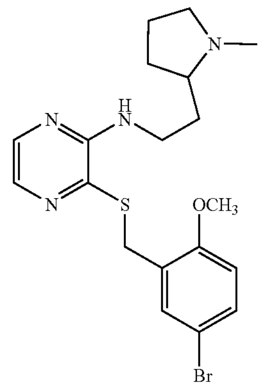 | * |
| MQ | [3-(5-Bromo-2-methoxy-benzylsulfanyl)-pyrazin-2-yl]-[3-(2-methyl-piperidin-1-yl)-propyl]-amine | 465.4576 | 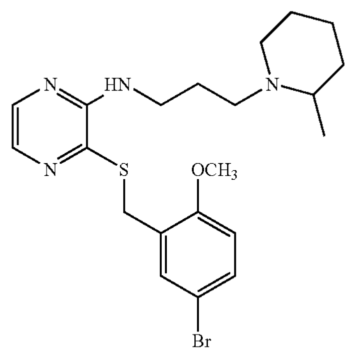 | * |
| MR | N-(3-Chloro-benzyl)-N-(2-methoxy-benzyl)-N',N'-dimethyl-ethane-1,2-diamine | 332.8731 | 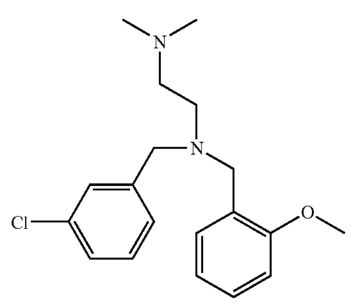 | * |
| MS | N-(3-Bromo-benzyl)-N',N'-dimethyl-N-(4-methyl-benzyl)-ethane-1,2-diamine | 381.7429 | 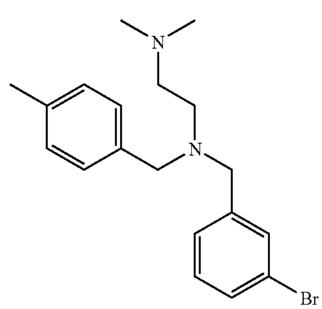 | * |

TABLE 4-continued

| ID | CHEMICAL NAME | Mol Weight (Tot) | Structure | MC4-R Binding |
|---|---|---|---|---|
| MT | N-(3-Bromo-benzyl)-N',N'-dimethyl-N-naphthalen-2-ylmethyl-ethane-1,2-diamine | 397.358 | 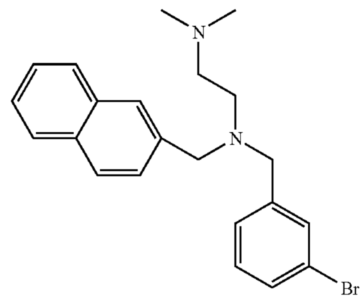 | * |
| MU | N-(3-Bromo-benzyl)-N',N'-dimethyl-N-(4-methyl-benzyl)-ethane-1,2-diamine | 361.325 | 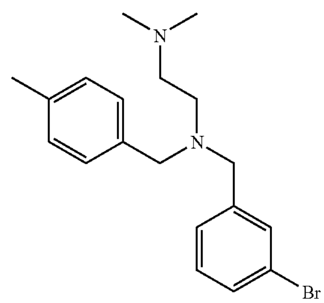 | * |
| MV | N-Benzyl-N-(2-methoxy-benzyl)-N',N'-dimethyl-ethane-1,2-diamine | 298.4283 | 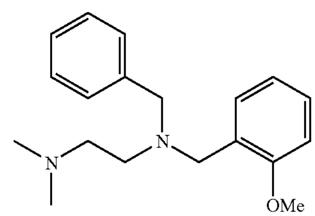 | * |
| MW | N-Benzyl-N-(2-chloro-benzyl)-N',N'-dimethyl-ethane-1,2-diamine | 302.8468 | 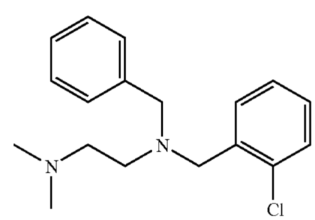 | * |
| MX | N-Benzyl-N',N'-dimethyl-N-naphthalen-1-ylmethyl-ethane-1,2-diamine | 318.4619 | 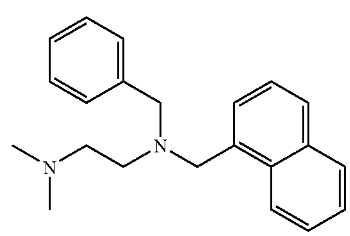 | * |
| MY | N-(5-Bromo-2-methoxy-benzyl)-N',N'-dimethyl-N-naphthalen-1-ylmethyl-ethane-1,2-diamine | 427.3843 | 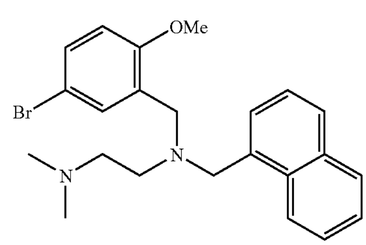 | * |

TABLE 4-continued

| ID | CHEMICAL NAME | Mol Weight (Tot) | Structure | MC4-R Binding |
|---|---|---|---|---|
| MZ | 8-Methyl-3-[2-(naphthalen-1-ylsulfanylmethyl)-phenyl]-8-aza-bicyclo[3.2.1]oct-2-ene | 371.5462 | 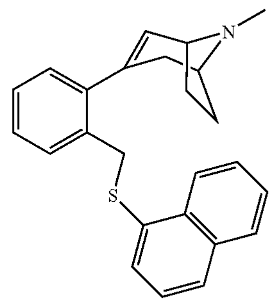 | ** |
| NA | 1-Ethyl-3-[2-(naphthalen-1-ylsulfanylmethyl)-phenyl]-piperidin-3-ol; Formate | 423.5805 | 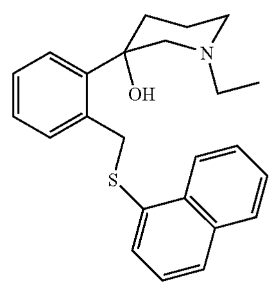 | * |
| NB | 1-Methyl-4-[2-(naphthalen-1-ylsulfanylmethyl)-phenyl]-1,2,3,6-tetrahydro-pyridine; Formate | 391.5384 | 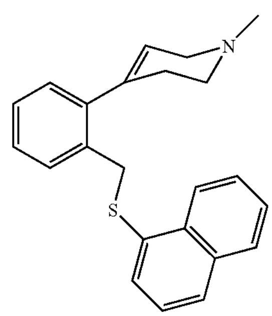 | ** |
| NC | 2-Phenyl-cyclopropanecarboxylic-acid 2-dimethylamino-ethyl)-naphthalen-1-ylmethyl-amide | 372.5102 | 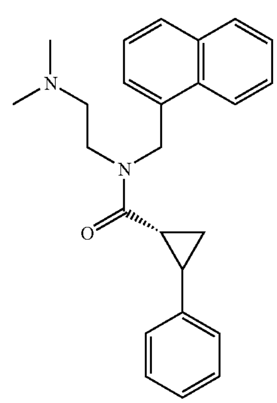 | * |

TABLE 4-continued
| ID | CHEMICAL NAME | Mol Weight (Tot) | Structure | MC4-R Binding |
|---|---|---|---|---|
| ND | N-Anthracen-9-ylmethyl-N',N'-dimethyl-N-naphthalen-1-ylmethyl-ethane-1,2-diamine | 418.5817 | 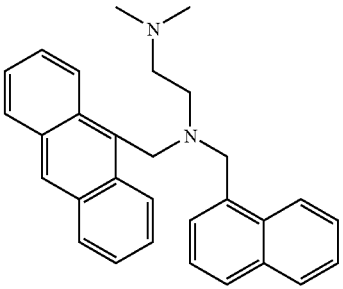 | * |
| NE | N,N-Dimethyl-N',N'-bis-naphthalen-1-ylmethyl-ethane-1,2-diamine | 368.5218 | 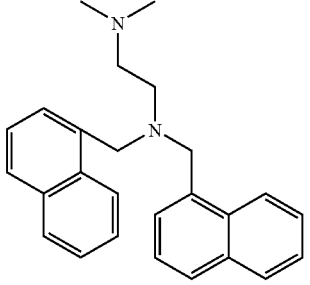 | * |
| NF | N-(2-Methoxy-naphthalen-1-ylmethyl)-N',N'-dimethyl-N-naphthalen-1-ylmethyl-ethane-1,2-diamine | 398.5481 | 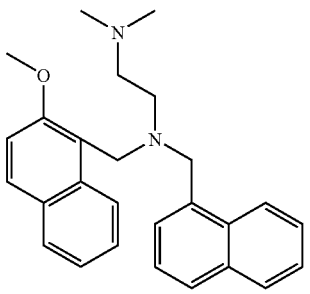 | * |
| NG | 1-[2-(5-Bromo-2-methoxy-benzylsulfanyl)-3-chloro-benzyl]-piperidine | 440.8315 | 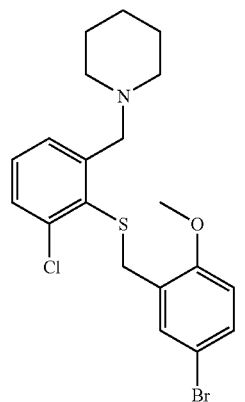 | * |

TABLE 4-continued

| ID | CHEMICAL NAME | Mol Weight (Tot) | Structure | MC4-R Binding |
|----|---------------|------------------|-----------|---------------|
| NH | 2-[3-Fluoro-2-(2-naphthalen-1-yl-ethyl)-phenyl]-1,4,5,6-tetrahydro-pyrimidine; HCl | 368.8806 | 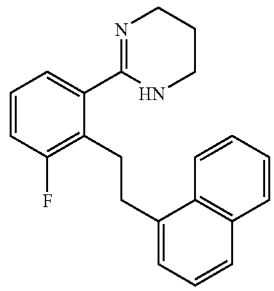 | *** |
| NI | 3-(3,4-Dichloro-phenyl)-1-(2-dimethylamino-ethyl)-1-naphthalen-1-ylmethyl-urea | 416.3496 | 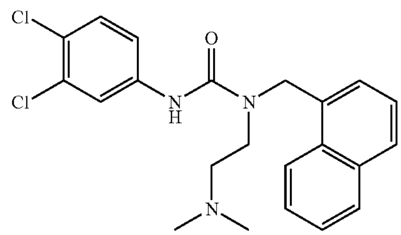 | * |
| NJ | 3-(3,5-Dichloro-phenyl)-1-(2-dimethylamino-ethyl)-1-naphthalen-1-ylmethyl-urea | 416.3496 | 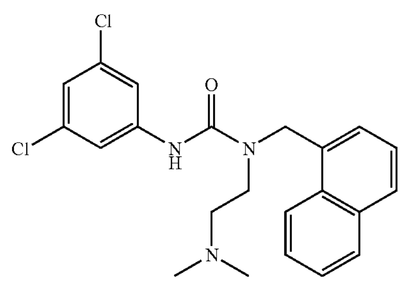 | * |
| NK | 1-(2-Dimethylamino-ethyl)-1-naphthalen-1-ylmethyl-3-(2-trifluoromethyl-phenyl)-urea | 415.4584 | 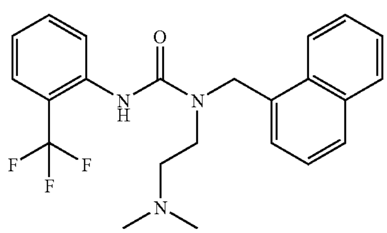 | * |
| NL | 1-(2-Dimethylamino-ethyl)-3-(4-methoxy-phenyl)-1-naphthalen-1-ylmethyl-urea | 377.4864 | 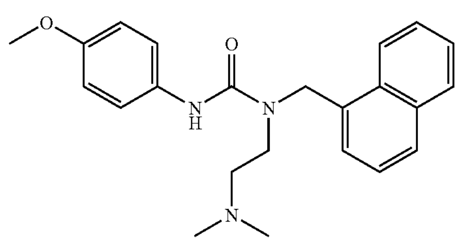 | * |
| NM | 1-(2-Dimethylamino-ethyl)-1-naphthalen-1-ylmethyl-3-phenethyl-urea | 375.5139 | 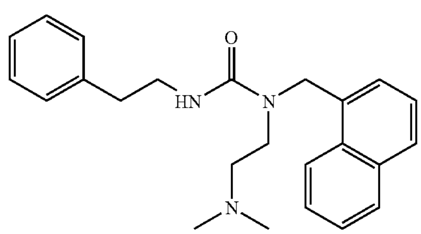 | * |

TABLE 4-continued

| ID | CHEMICAL NAME | Mol Weight (Tot) | Structure | MC4-R Binding |
|---|---|---|---|---|
| NN | 1-(2-Dimethylamino-ethyl)-1-naphthalen-1-ylmethyl-3-propyl-urea | 313.443 | 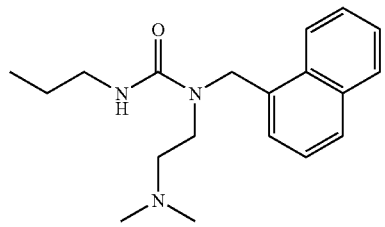 | * |
| NO | 1-(2-Dimethylamino-ethyl)-3-(4-methoxy-benzyl)-1-naphthalen-1-ylmethyl-urea | 391.5133 | 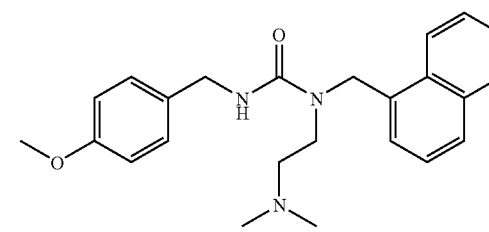 | * |
| NP | 3-(3-Cyano-phenyl)-1-(2-dimethylamino-ethyl)-1-naphthalen-1-ylmethyl-urea | 372.4699 | 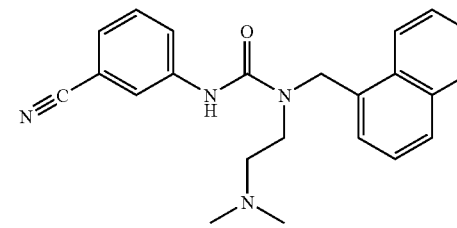 | * |
| NQ | 3-(2,6-Dichloro-pyridin-4-yl)-1-(2-dimethylamino-ethyl)-1-naphthalen-1-ylmethyl-urea | 417.3374 | 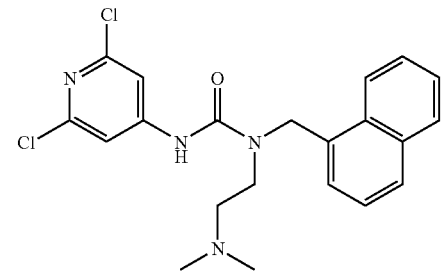 | * |
| NR | [2-(Naphthalen-2-ylmethylsulfanyl)-phenyl]-carbamic acid 2-piperidin-1-yl-ethyl ester; formate | 466.6056 | 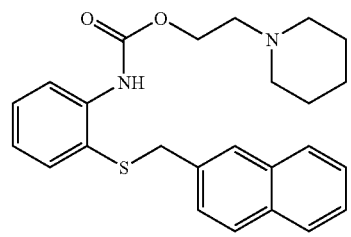 | * |
| NS | [2-(Naphthalen-2-ylmethylsulfanyl)-phenyl]-carbamic acid 1-aza-bicyclo[2.2.2]oct-3-yl ester; formate | 464.5897 | 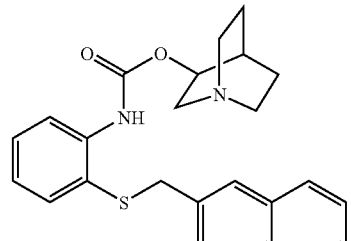 | * |

TABLE 4-continued

| ID | CHEMICAL NAME | Mol Weight (Tot) | Structure | MC4-R Binding |
|----|---------------|------------------|-----------|---------------|
| NT | [2-(5-Bromo-2-methoxy-benzylsulfanyl)-phenyl]-carbamic acid 2-piperidin-1-yl-ethyl ester | 525.4681 | 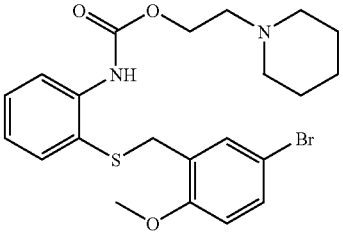 | ** |
| NU | [2-(5-Bromo-2-methoxy-benzylsulfanyl)-phenyl]-carbamic acid 1-aza-bicyclo[2.2.2]oct-3-yl ester; formate | 523.4522 | 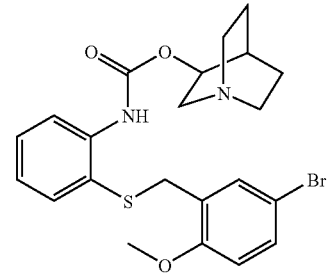 | * |
| NV | [2-(5-Bromo-2-methoxy-benzylsulfanyl)-3-chloro-benzyl]-[3-(2-methyl-piperidin-1-yl)-propyl]-amine; 2HCl | 584.8751 | 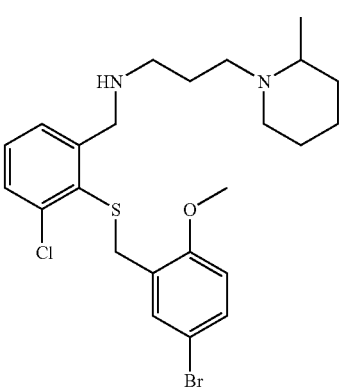 | *** |
| NW | 1-[2-(5-Bromo-2-methoxy-benzylsulfanyl)-3-chloro-benzyl]-piperazine; 2HCl | 514.7407 | 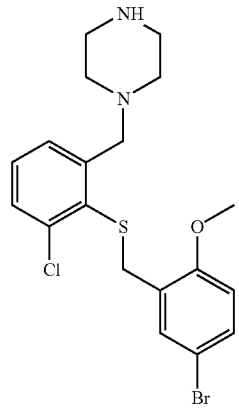 | *** |

TABLE 4-continued

| ID | CHEMICAL NAME | Mol Weight (Tot) | Structure | MC4-R Binding |
|---|---|---|---|---|
| NX | 1-[2-(5-Bromo-2-methoxy-benzylsulfanyl)-3-chloro-benzyl]-pyrrolidin-3-ol; Formate | 488.834 | 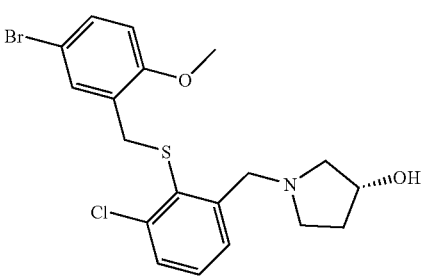 | * |
| NY | {1-[2-(5-Bromo-2-methoxy-benzylsulfanyl)-3-chloro-benzyl]-pyrrolidin-2-yl}-methanol; Formate | 502.8609 | 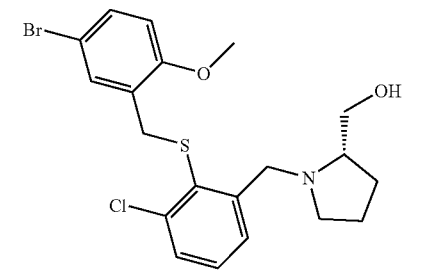 | * |
| NZ | 1-[2-(5-Bromo-2-methoxy-benzylsulfanyl)-3-chloro-benzyl]-azetidine; Formate | 458.8077 | 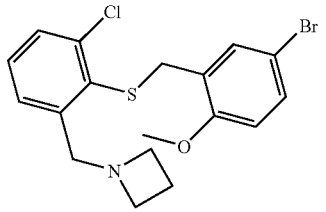 | * |
| OA | 1-[2-(5-Bromo-2-methoxy-benzylsulfanyl)-3-chloro-benzyl]-pyrrolidin-3-ol; Formate | 488.834 | 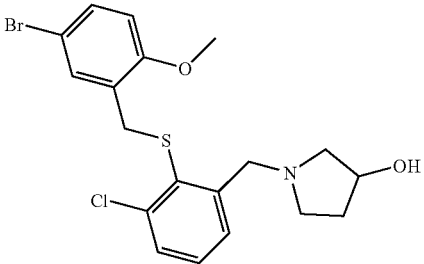 | * |
| OB | [2-(Naphthalen-1-ylmethylsulfanyl)-phenyl]-carbamic acid 1-aza-bicyclo-[2.2.2]oct-3-yl ester; Formate | 464.5897 | 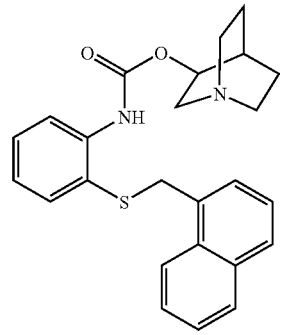 | * |

TABLE 4-continued

| ID | CHEMICAL NAME | Mol Weight (Tot) | Structure | MC4-R Binding |
|---|---|---|---|---|
| OC | [2-(2-Methyl-naphthalen-1-ylmethylsulfanyl)-phenyl]-carbamic acid 1-aza-bicyclo-[2.2.2]oct-3-yl ester; Formate | 478.6166 | 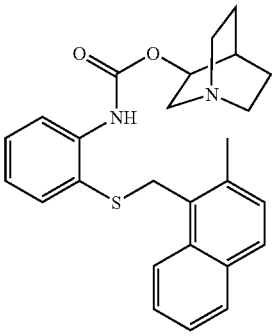 | ** |
| OD | [2-(2-Methyl-naphthalen-1-ylmethylsulfanyl)-phenyl]-carbamic acid 2-piperidin-1-yl-ethyl ester; Formate | 480.6325 | 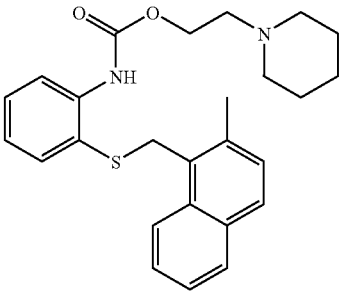 | * |
| OE | {1-[2-(5-Bromo-2-methoxy-benzylsulfanyl)-3-chloro-benzyl]-pyrrolidin-2-yl}-methanol; Formate | 502.8609 | 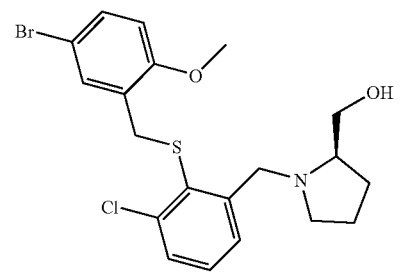 | * |
| OF | Naphthalen-2-ylmethyl-naphthalen-1-ylmethyl-(2-piperidin-1-yl-ethyl)-amine | 408.5866 | 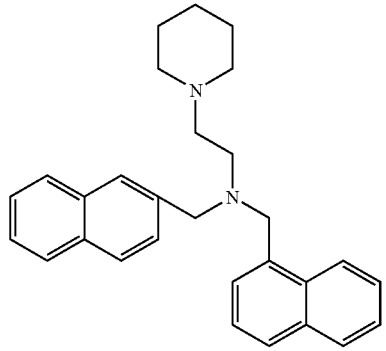 | * |

TABLE 4-continued

| ID | CHEMICAL NAME | Mol Weight (Tot) | Structure | MC4-R Binding |
|----|---------------|------------------|-----------|---------------|
| OG | 4-tert-Butyl-N-naphthalen-1-ylmethyl-N-(2-piperidin-1-yl-ethyl)-benzamide | 428.6177 | 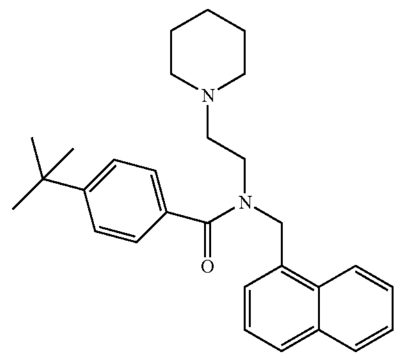 | * |
| OH | N,N-Dimethyl-N'-naphthalen-2-ylmethyl-N'-naphthalen-1-ylmethyl-propane-1,3-diamine | 382.5487 | 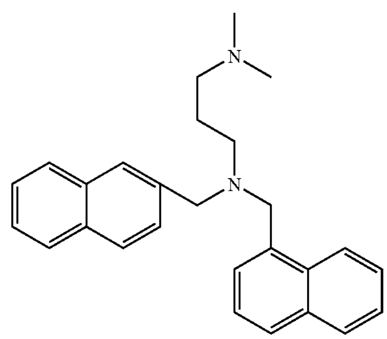 | * |
| OI | N-(5-Bromo-2-methoxy-benzyl)-N',N'-dimethyl-N-naphthalen-1-ylmethyl-propane-1,3-diamine | 441.4111 | 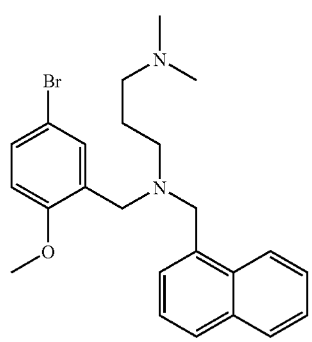 | * |
| OJ | 1-Naphthalen-1-ylmethyl-3-phenethyl-1-(2-piperidin-1-yl-ethyl)-thiourea; HCl | 468.1052 | 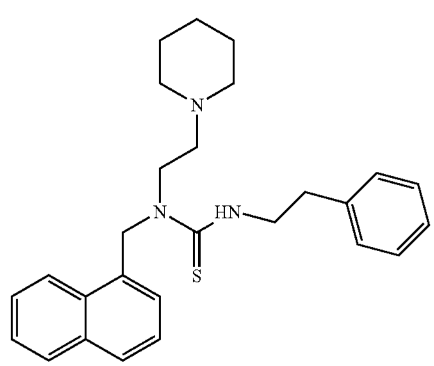 | * |

TABLE 4-continued

| ID | CHEMICAL NAME | Mol Weight (Tot) | Structure | MC4-R Binding |
|---|---|---|---|---|
| OK | 3-(4-Dimethylamino-phenyl)-1-(3-dimethylamino-propyl)-1-naphthalen-1-ylmethyl-thiourea; HCl | 457.082 | 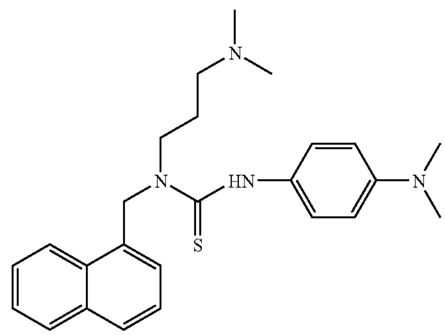 | *** |
| OL | 4-[2-(5-Bromo-2-methoxy-benzylsulfanyl)-3-chloro-benzylamino]-piperidine-1-carboxylic acid ethyl ester; Formate | 573.9397 | 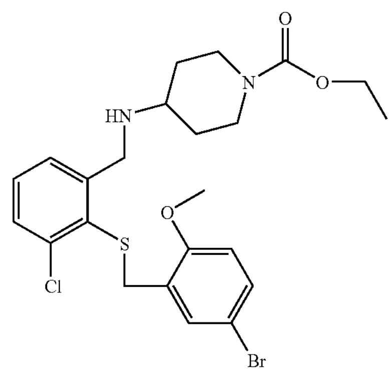 | ** |
| OM | 1-[2-(5-Bromo-2-methoxy-benzylsulfanyl)-3-chloro-benzyl]-pyrrolidin-3-ylamine; 2HCl | 514.7407 | 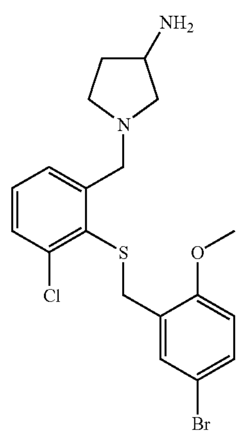 | *** |
| ON | 2-[2-(2-Naphthalen-1-yl-ethyl)-phenyl]-ethylamine; HCl | 311.8535 | 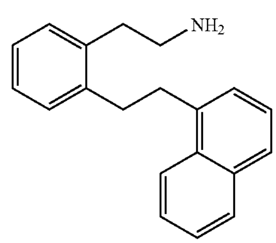 | ** |

TABLE 4-continued

| ID | CHEMICAL NAME | Mol Weight (Tot) | Structure | MC4-R Binding |
|---|---|---|---|---|
| OO | Naphthalene-2-sulfonic-acid (2-dimethylamino-ethyl)-naphthalen-1-ylmethyl-amide | 418.5597 | 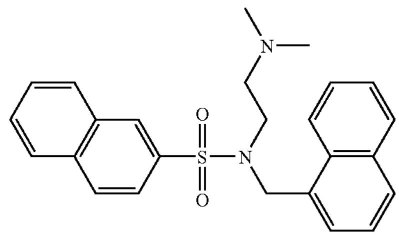 | * |
| OP | 1-[2-(5-Bromo-2-methoxy-benzylsulfanyl)-3-chloro-benzyl]-2-methoxymethyl-pyrrolidine; Formate | 516.8877 | 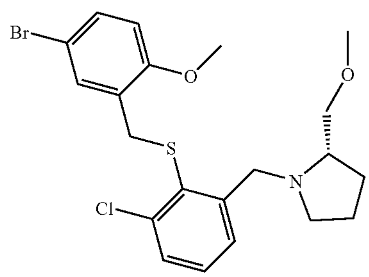 | * |
| OQ | (2-Hexyloxy-phenyl)-carbamic acid 2-piperidin-1-yl-1-piperidin-1-ylmethyl-ethyl ester; Formate | 491.6758 | 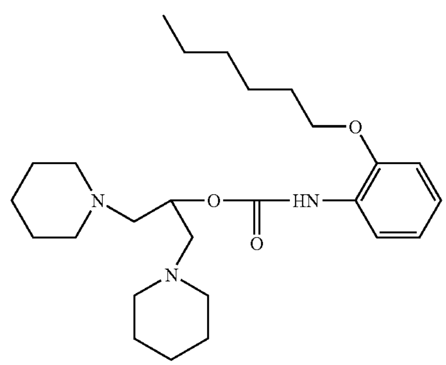 | ** |
| OR | 3-[2-(5-Bromo-2-methoxy-benzylsulfanyl)-benzyloxy]-pyrrolidine; HCl | 444.8192 | 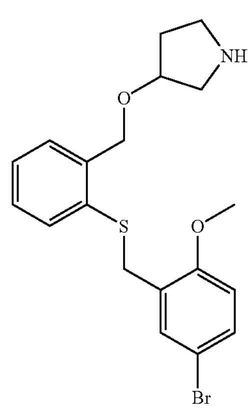 | ** |

TABLE 4-continued

| ID | CHEMICAL NAME | Mol Weight (Tot) | Structure | MC4-R Binding |
|---|---|---|---|---|
| OS | 3-[2-(5-Bromo-2-methoxy-benzylsulfanyl)-benzyloxy]-pyrrolidine; HCl | 444.8192 | 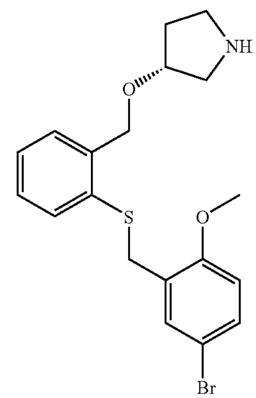 | ** |
| OT | 2-[2-(5-Bromo-2-methoxy-benzylsulfanyl)-benzyloxymethyl]-pyrrolidine; HCl | 458.8461 | 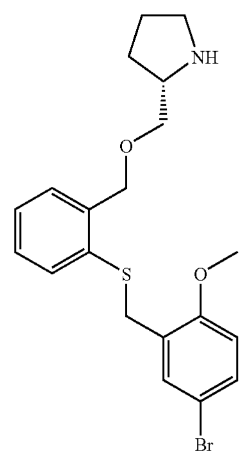 | ** |
| OU | 2-[2-(Naphthalen-1-ylsulfanylmethyl)-phenyl]-piperidine; HCl | 369.9574 | 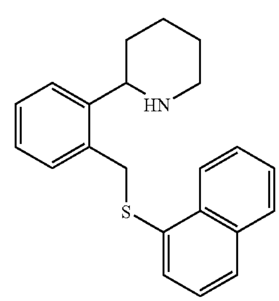 | * |
| OV | 3-[2-(5-Bromo-2-methoxy-benzylsulfanyl)-benzylamino]-propan-1-ol | 396.3482 | 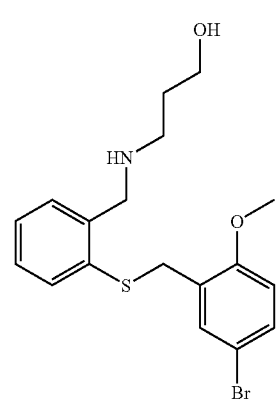 | * |

TABLE 4-continued

| ID | CHEMICAL NAME | Mol Weight (Tot) | Structure | MC4-R Binding |
|---|---|---|---|---|
| OW | 3-[2-(5-Bromo-2-methoxy-benzylsulfanyl)-benzylamino]-3-methyl-butan-1-ol | 424.402 | 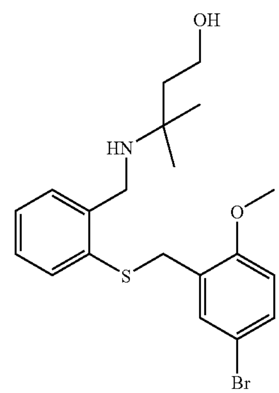 | ** |
| OX | 1-[2-(5-Bromo-2-methoxy-benzylsulfanyl)-benzyl]-pyrrolidin-3-ol | 408.3592 | 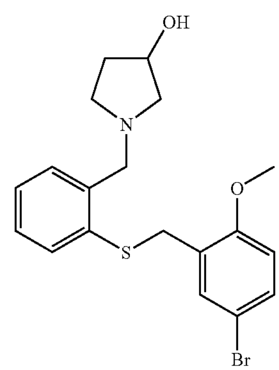 | * |
| OY | 1-[2-(5-Bromo-2-methoxy-benzylsulfanyl)-benzyl]-pyrrolidin-3-ol | 408.3592 | 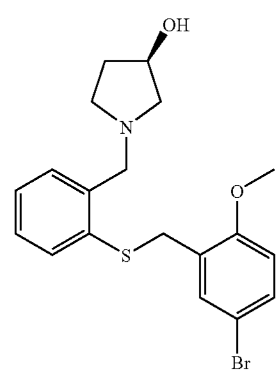 | * |
| OZ | {1-[2-(5-Bromo-2-methoxy-benzylsulfanyl)-benzyl]-pyrrolidin-2-yl}-methanol | 422.3861 | 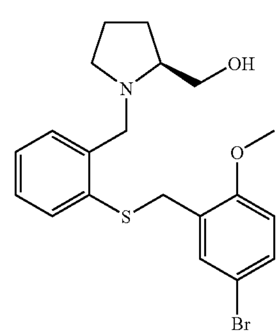 | * |

TABLE 4-continued
| ID | CHEMICAL NAME | Mol Weight (Tot) | Structure | MC4-R Binding |
|---|---|---|---|---|
| PA | {1-[2-(5-Bromo-2-methoxy-benzylsulfanyl)-benzyl]-pyrrolidin-2-yl}-methanol | 422.3861 | 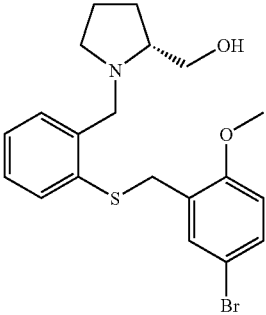 | * |
| PB | {1-[2-(Naphthalen-1-ylsulfanylmethyl)-benzyl]-piperidin-2-yl}-methanol; Formate | 423.5805 | 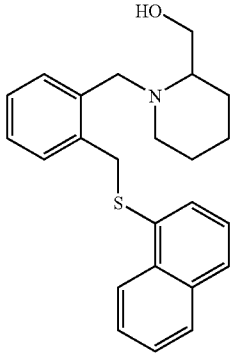 | * |
| PC | 2-[2-(Naphthalen-1-ylsulfanylmethyl)-pyrrolidin-1-yl]-ethyl-N-pyrrolidine; Formate | 386.5628 | 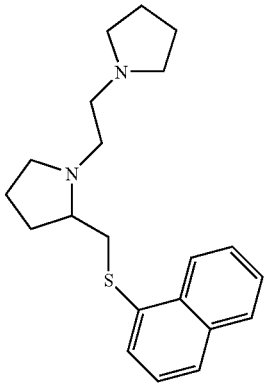 | * |
| PD | N-pyrrolyl-[1-(2-naphthalen-1-yl-ethyl)-pyrrolidin-2-ylmethyl]-amine | 308.4668 | 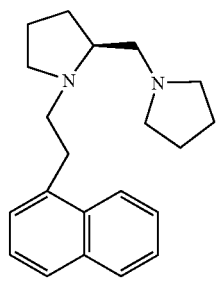 | * |

TABLE 4-continued

| ID | CHEMICAL NAME | Mol Weight (Tot) | Structure | MC4-R Binding |
|----|---------------|------------------|-----------|---------------|
| PE | 1-(2-Naphthalen-1-yl-ethyl)-piperidine-2-carboxylic acid methyl ester | 297.3972 | 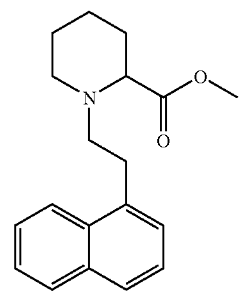 | * |
| PF | (3-Bromo-benzyl)-(1-ethyl-pyrrolidin-2-ylmethyl)-naphthalen-1-ylmethyl-amine | 437.4227 | 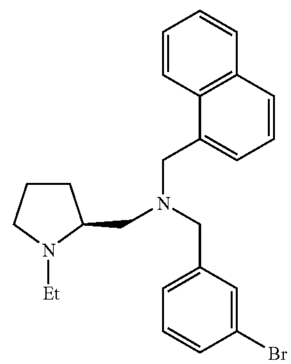 | * |
| PG | 3-[2-(5-Bromo-2-methoxy-benzylsulfanyl)-benzyloxy]-piperidine; HCl | 458.8461 | 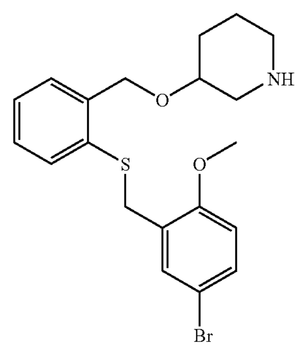 | ** |
| PH | (5-Bromo-2-methoxy-benzyl)-(1-ethyl-pyrrolidin-2-ylmethyl)-naphthalen-1-ylmethyl-amine | 467.449 | 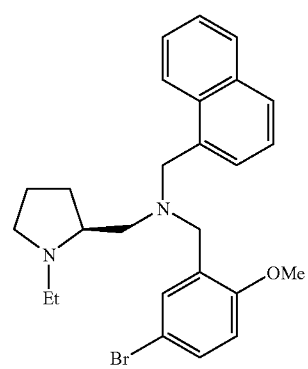 | * |

TABLE 4-continued

| ID | CHEMICAL NAME | Mol Weight (Tot) | Structure | MC4-R Binding |
|---|---|---|---|---|
| PI | (1-Ethyl-pyrrolidin-2-ylmethyl)-naphthalen-2-ylmethyl-naphthalen-1-ylmethyl-amine | 408.5866 | 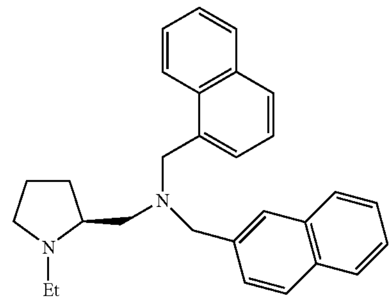 | * |
| PJ | 2-[2-(5-Bromo-2-methoxy-benzylsulfanyl)-benzyloxy-methyl]-pyrrolidine; HCl | 458.8461 | 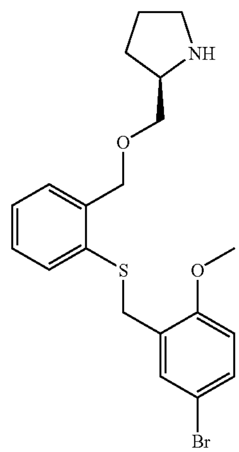 | ** |
| PK | (3-Bromo-benzyl)-(3-imidazol-1-yl-propyl)-naphthalen-1-ylmethyl amine | 434.3788 | 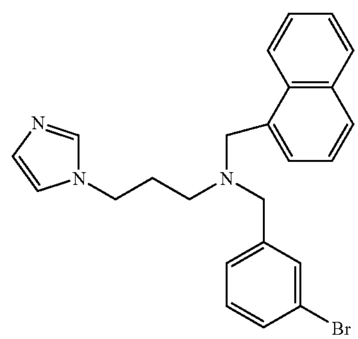 | * |
| PL | (3-Imidazol-1-yl-propyl)-naphthalen-2-ylmethyl-naphthalen-1-ylmethyl-amine | 405.5426 | 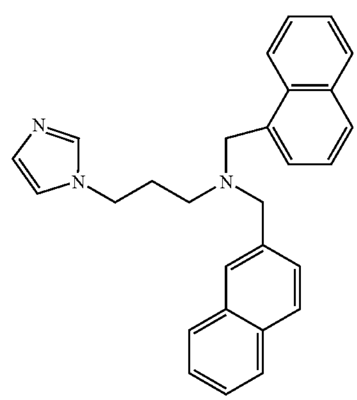 | * |

TABLE 4-continued

| ID | CHEMICAL NAME | Mol Weight (Tot) | Structure | MC4-R Binding |
|---|---|---|---|---|
| PM | [2-(Naphthalen 1-ylmethylsulfanyl)-phenyl]-carbamic acid 2-piperidin-1-yl-1-piperidin-1-ylmethyl-ethyl ester; Formate | 563.7657 | 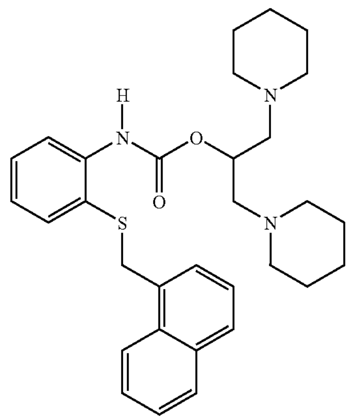 | * |
| PN | [2-(Naphthalen-1-ylmethylsulfanyl-phenyl]-carbamic acid 2-dimethylamino-ethyl ester; Formate | 426.5408 | 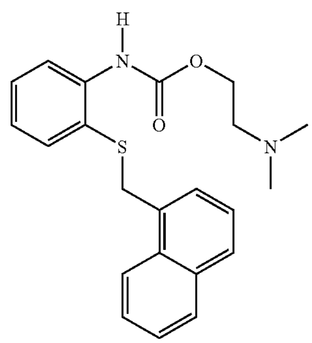 | * |
| PO | 1-[2-(Naphthalen-1-ylsulfanylmethyl)-benzyl]-piperazine; Formate | 394.542 | 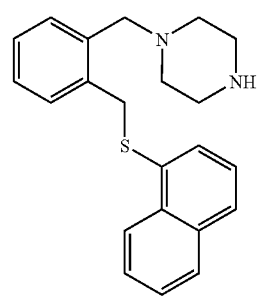 | ** |
| PP | [3-(2-Methyl-piperidin-1-yl)-propyl]-[2-(naphthalen-1-ylsulfanylmethyl)-benzyl]-amine; Formate | 464.6764 | 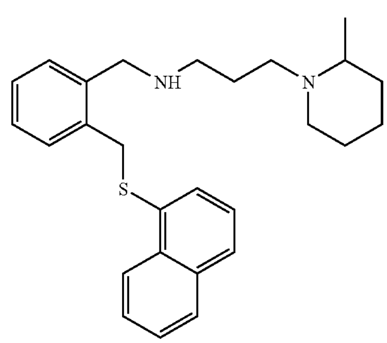 | ** |

TABLE 4-continued

| ID | CHEMICAL NAME | Mol Weight (Tot) | Structure | MC4-R Binding |
|---|---|---|---|---|
| PQ | 1-[3-Chloro-2-(naphthalen-1-ylsulfanylmethyl)-benzyl]-piperazine; HCl | 419.4168 | 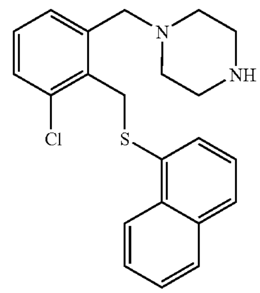 | ** |
| PR | 1-[3-Fluoro-2-(2-naphthalen-1-yl-ethyl)-benzyl]-piperazine; HCl | 384.9234 | 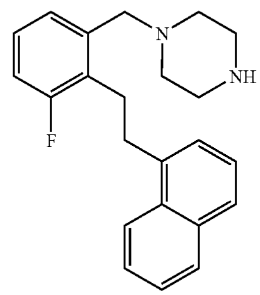 | *** |
| PS | {1-[3-Chloro-2-(naphthalen-1-ylsulfanyl-methyl)-benzyl]-piperidin-2-yl}-methanol; Formate | 458.0253 | 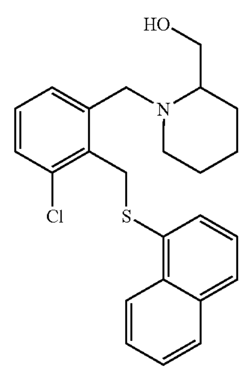 | * |
| PT | N,N-Dimethyl-N'-(2-naphthalen-1-yl-ethyl)-N'-naphthalen-1-ylmethyl-ethane-1,2-diamine; Formate | 428.5787 | 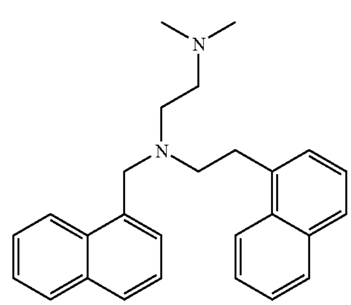 | * |

TABLE 4-continued

| ID | CHEMICAL NAME | Mol Weight (Tot) | Structure | MC4-R Binding |
|---|---|---|---|---|
| PU | {1-[2-(5-Bromo-2-methoxy-benzylsulfanyl)-3-chloro-benzyl]-piperidin-2-yl}-methanol | 470.8577 | 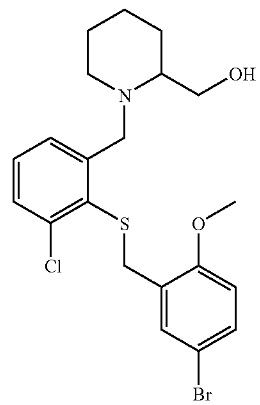 | * |
| PV | {1-[2-(2-Naphthalen-1-yl-ethyl)-benzyl]-piperidin-2-yl}-methanol; Formate | 405.5414 | 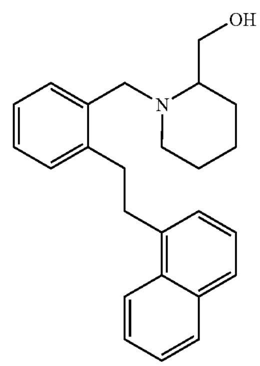 | * |
| PW | 1-[2-(2-Naphthalen-1-yl-ethyl)-benzyl]-piperazine; Formate | 376.5029 | 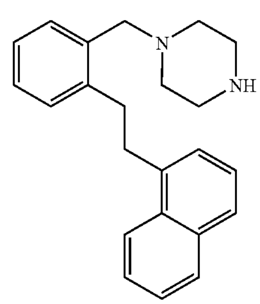 | * |
| PX | [3-(2-Methyl-piperidin-1-yl)-propyl]-[2-(2-naphthalen-1-yl-ethyl)-benzyl]-amine; Formate | 446.6373 | 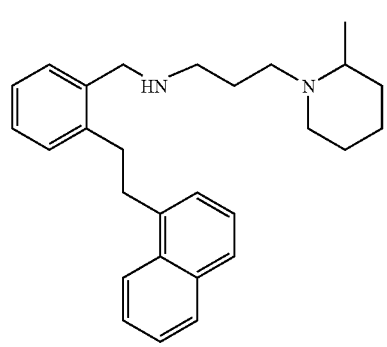 | * |

TABLE 4-continued

| ID | CHEMICAL NAME | Mol Weight (Tot) | Structure | MC4-R Binding |
|----|---------------|------------------|-----------|---------------|
| PY | 1-[2-(2-Naphthalen-1-yl-ethyl)-benzyl]-pyrrolidin-3-ylamine; Formate | 376.5029 | 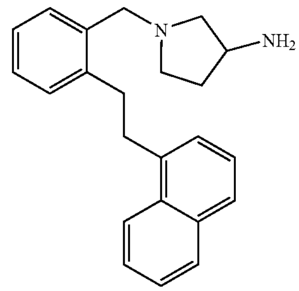 | ** |
| PZ | 5,5-Dimethyl-2-[2-(2-naphthalen-1-yl-ethyl)-phenyl]-4,5-dihydro-1H-imidazole | | 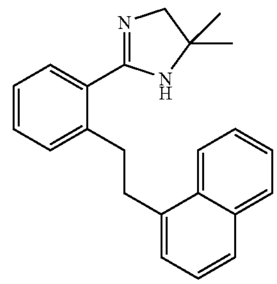 | *** |
| QA | 2-[3-Fluoro-2-(2-naphthalen-1-yl-ethyl)-phenyl]-5,5-dimethyl-4,5-dihydro-1H-imidazole | | 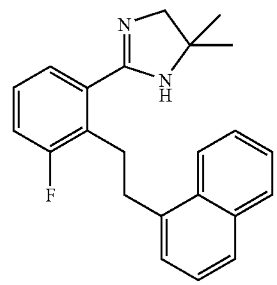 | *** |
| QB | 2-[2-(5-Bromo-2-methoxy-benzylsulfanyl)-3,5-difluoro-phenyl]-1,4,5,6-tetrahydro-pyrimidine | | 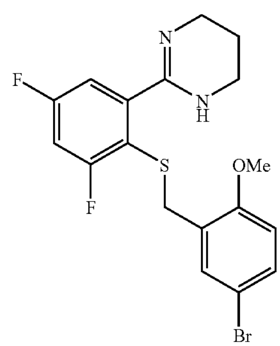 | *** |
| QC | 2-[2-(5-Bromo-2-methoxy-benzylsulfanyl)-3,5-difluoro-phenyl]-5,5-dimethyl-4,5-dihydro-1H-imidazole | | 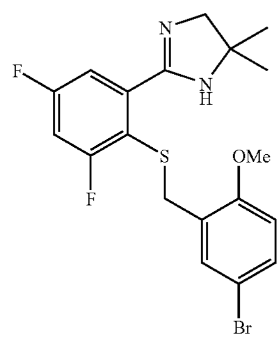 | ** |

TABLE 4-continued

| ID | CHEMICAL NAME | Mol Weight (Tot) | Structure | MC4-R Binding |
|---|---|---|---|---|
| QD | 3-(2-Naphthalen-1-yl-ethyl)-2-(1,4,5,6-tetrahydro-pyrimidin-2-yl)-phenylamine | | 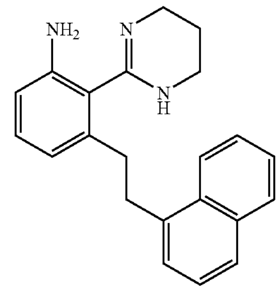 | * |
| QE | Amino-[2-(2-naphthalen-1-yl-ethyl)-phenyl]-acetonitrile | | 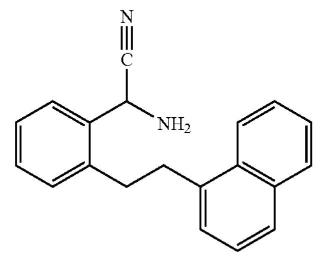 | * |
| QF | 1-[2-(2-Naphthalen-1-yl-ethyl)-phenyl]-ethane-1,2-diamine | | 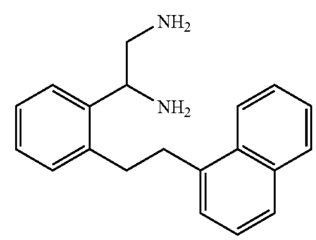 | ** |
| QG | 2-[2-(5-Bromo-2-methoxy-benzylsulfanyl)-phenyl]-4-methyl-4,5-dihydro-1H-imidazole | | 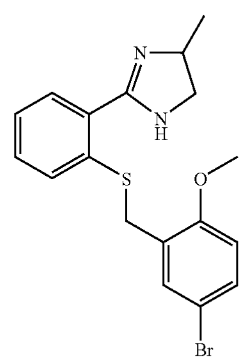 | ** |
| QH | 2-[2-(5-Bromo-2-methoxy-benzylsulfanyl)-3-fluoro-phenyl]-4-methyl-4,5-dihydro-1H-imidazole | | 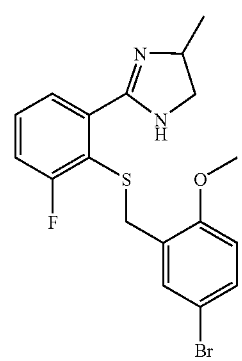 | *** |

TABLE 4-continued

| ID | CHEMICAL NAME | Mol Weight (Tot) | Structure | MC4-R Binding |
|---|---|---|---|---|
| QI | 2-[2-(5-Bromo-2-methoxy-benzylsulfanyl)-3-chloro-phenyl]-4-methyl-4,5-dihydro-1H-imidazole | | 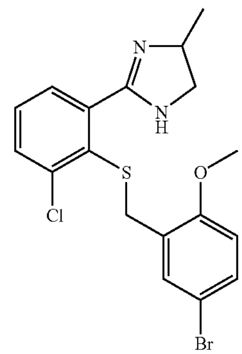 | *** |
| QJ | 2-[2-(5-Bromo-2-methoxy-benzylsulfanyl)-3,4-difluoro-phenyl]-1,4,5,6-tetrahydro-pyrimidine | | 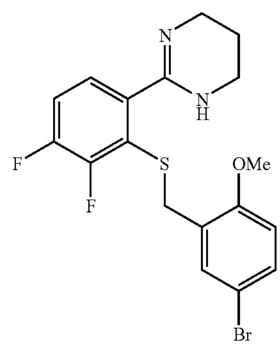 | *** |
| QK | 2-[3-Fluoro-2-(naphthalen-1-ylsulfanylmethyl)-phenyl]-5,5-dimethyl-4,5-dihydro-1H-imidazole | | 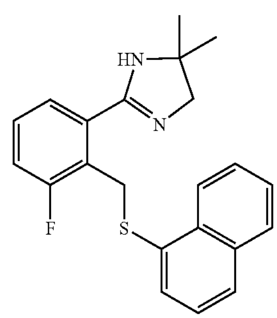 | ** |
| QL | 2-{2-[2-(5-Bromo-2-methoxy-phenyl)-1-methyl-ethyl]-phenyl}-1,4,5,6-tetrahydro-pyrimidine | | 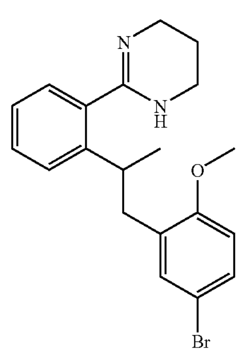 | *** |

TABLE 4-continued

| ID | CHEMICAL NAME | Mol Weight (Tot) | Structure | MC4-R Binding |
|----|---------------|------------------|-----------|---------------|
| QM | 2-[2-(5-Bromo-2-methoxy benzyl sulfanyl)-3-fluoro-4-trifluoromethyl-phenyl]-4,4-dimethyl-4,5-dihydro-1H-imidazole | | 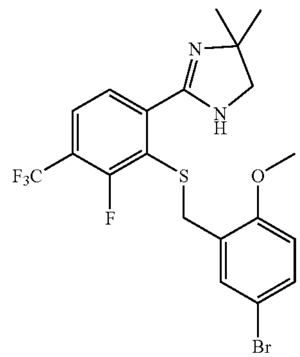 | * |
| QN | 2-[2-(5-Bromo-2-methoxy-benzyl sulfanyl)-3-fluoro-4-trifluoromethyl-phenyl]-5,5-dimethyl-1,4,5,6-tetrahydro-pyrimidine | | 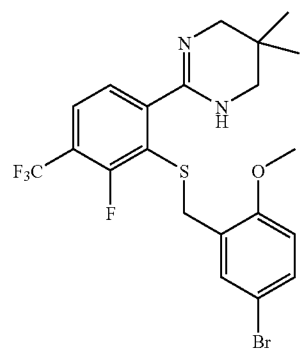 | * |
| QO | 2-[3-Methoxy-2-(2-naphthalen-1-yl-ethyl)-phenyl]-1,4,5,6-tetrahydro-pyrimidine | | 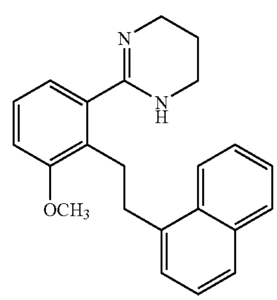 | *** |
| QP | 2-[2-(5-Bromo-2-methoxy-benzylsulfanyl)-3-chloro-phenyl]-1,4,5,6-tetrahydro-pyrimidin-5-ol | | 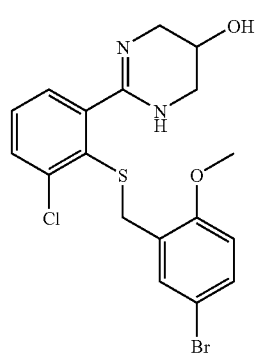 | *** |

TABLE 4-continued
| ID | CHEMICAL NAME | Mol Weight (Tot) | Structure | MC4-R Binding |
|----|---------------|------------------|-----------|---------------|
| QQ | 2-{2-[2-(5-Bromo-2-methoxy-phenyl)-ethyl]-3-methoxy-phenyl}-1,4,5,6-tetrahydro-pyrimidine | | 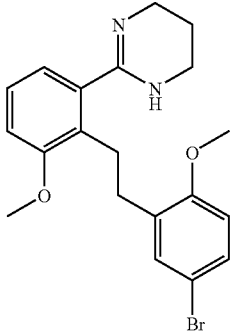 | *** |
| QR | 2-[2-(5-Bromo-2-methoxy-benzylsulfanyl)-3-chloro-phenyl]-1,4,5,6-tetrahydro-pyrimidin-5-ol | | 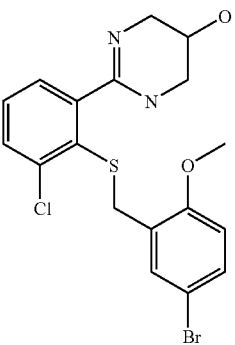 | *** |
| QS | 1-Amino-3-[2-(5-bromo-2-methoxy-phenyl)-7-chloro-benzo[b]thiophen-3-ylamino]-propan-2-ol | | 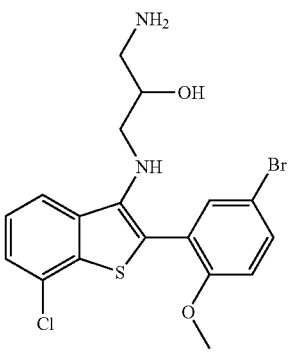 | * |
| QT | 2-[2-(1-Methyl-2-naphthalen-1-yl-ethyl)-phenyl]-1,4,5,6-tetrahydro-pyrimidine | | 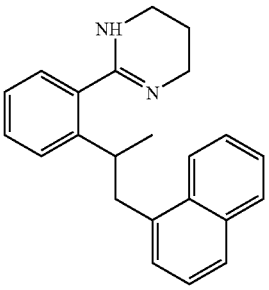 | ** |

TABLE 4-continued

| ID | CHEMICAL NAME | Mol Weight (Tot) | Structure | MC4-R Binding |
|----|---------------|------------------|-----------|---------------|
| QU | 3-(5-Bromo-2-methoxy-benzylsulfanyl)-2-fluoro-4-(1,4,5,6-tetrahydro-pyrimidin-2-yl)-phenylamine | | 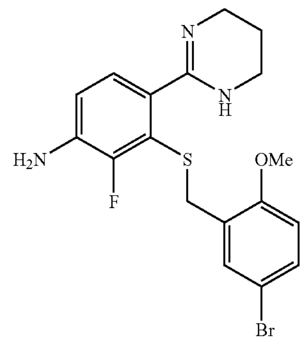 | * |
| QV | 2-{2-[2-(5-Bromo-2-methoxy-phenyl)-ethyl]-3-methyl-phenyl}-1,4,5,6-tetrahydro-pyrimidine | | 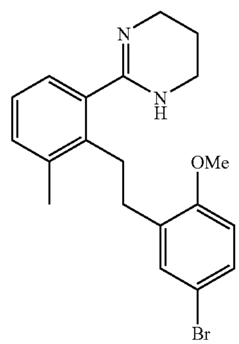 | *** |
| QW | 2-[2-(5-Bromo-2-methoxy-benzylsulfanyl)-3-fluoro-phenyl]-1,4,5,6-tetrahydro-pyrimidin-5-ol | | 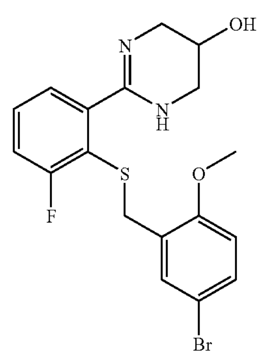 | *** |
| QX | 1-Amino-3-[2-(5-bromo-2-methoxy-phenyl)-7-fluoro-benzo[b]thiophen-3-ylamino]-propan-2-ol | | 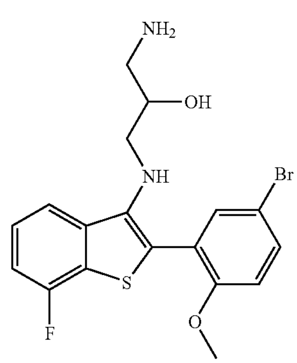 | * |

TABLE 4-continued

| ID | CHEMICAL NAME | Mol Weight (Tot) | Structure | MC4-R Binding |
|---|---|---|---|---|
| QY | 2-[3-Methoxy-2-(naphthalen-1-ylsulfanylmethyl)-phenyl]-1,4,5,6-tetrahydro-pyrimidine | | 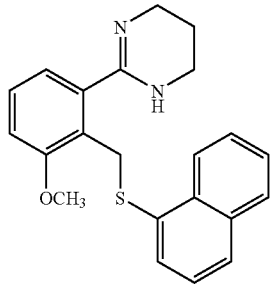 | *** |
| QZ | 2-[2-(5-Bromo-2-methoxy-benzylsulfanyl)-3-fluoro-phenyl]-1,4,5,6-tetrahydro-pyrimidin-5-ol | | 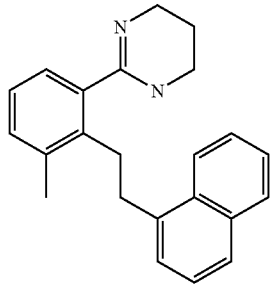 | *** |
| RA | 2-[2-(5-Bromo-2-methoxy-benzylsulfanyl)-5-methoxy-phenyl]-1,4,5,6-tetrahydro-pyrimidine | | 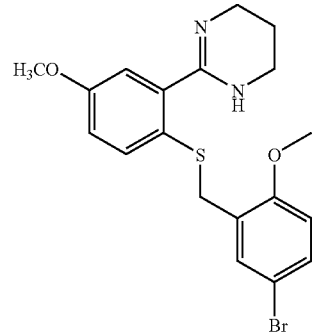 | ** |
| RB | 2-{2-[2-Chloro-6-(1,4,5,6-tetrahydro-pyrimidin-2-yl)-phenyl]-ethyl}-phenol | | 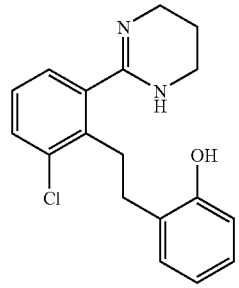 | *** |
| RC | 2-[3-Methoxy-2-(naphthalen-1-ylsulfanylmethyl)-phenyl]-1,4,5,6-tetrahydro-pyrimidin-5-ol | | 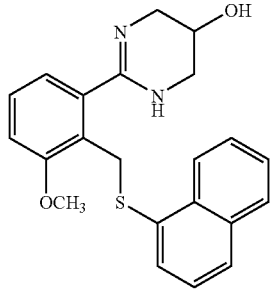 | *** |

TABLE 4-continued

| ID | CHEMICAL NAME | Mol Weight (Tot) | Structure | MC4-R Binding |
|----|---------------|------------------|-----------|---------------|
| RD | 2-{2-[2-(5-Bromo-2-methoxy-phenyl)-ethyl]-3-methyl-phenyl}-5-methyl-4,5-dihydro-1H-imidazole | | 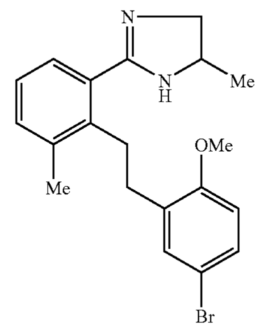 | *** |
| RE | 2-{2-[2-(5-Bromo-2-methoxy-phenyl)-ethyl]-3-methyl-phenyl}-1,4,5,6-tetrahydro-pyrimidin-5-ol | | 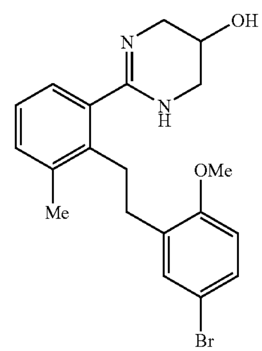 | *** |
| RF | 2-[2-(5-Bromo-2-methoxy-benzylsulfanyl)-3,4-difluoro-phenyl]-1,4,5,6-tetrahydro-pyrimidin-5-ol | | 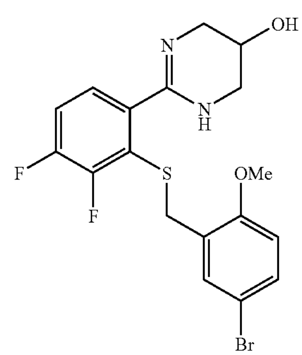 | ** |
| RG | 2-{2-[2-(5-Bromo-2-methoxy-phenyl)-ethyl]-3-chloro-phenyl}-4,4-dimethyl-4,5-dihydro-1H-imidazole | | 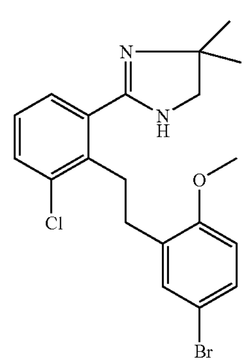 | *** |

TABLE 4-continued

| ID | CHEMICAL NAME | Mol Weight (Tot) | Structure | MC4-R Binding |
|---|---|---|---|---|
| RH | 2-[2-(5-Bromo-2-methoxy-benzylsulfanyl)-3-fluoro-4-methyl-phenyl]-1,4,5,6-tetrahydro-pyrimidine | | 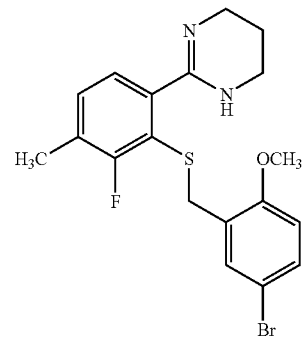 | ** |
| RI | 4,4-Dimethyl-2-[2-(naphthalen-1-ylmethylsulfanyl)-phenyl]-4,5-dihydro-oxazole | | 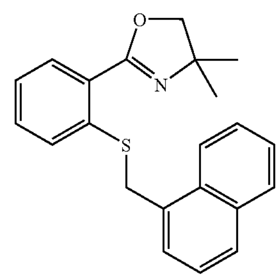 | * |
| RJ | 2-[2-(5-Bromo-2-methoxy-benzylsulfanyl)-4-methoxy-phenyl]-1,4,5,6-tetrahydro-pyrimidine | | 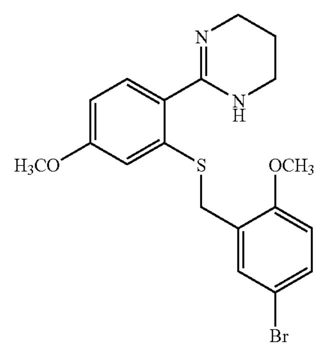 | * |
| RK | 2-[5-(5-Bromo-2-methoxy-benzyl)-2-methyl-thiophen-3-yl]-1,4,5,6-tetrahydro-pyrimidine | | 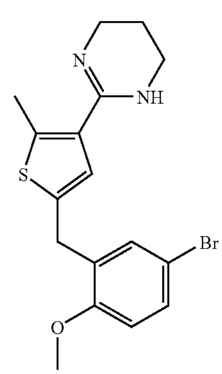 | ** |

TABLE 4-continued

| ID | CHEMICAL NAME | Mol Weight (Tot) | Structure | MC4-R Binding |
|---|---|---|---|---|
| RL | 2-{2-[2-(5-Bromo-2-methoxy-phenyl)-ethyl]-thiophen-3-yl}-1,4,5,6-tetrahydro-pyrimidine | | 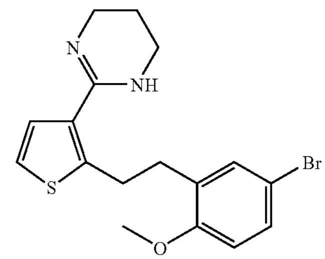 | *** |
| RM | 2-{2-[2-(5-Bromo-2-methoxy-phenyl)-ethyl]-3-ethoxy-phenyl}-1,4,5,6-tetrahydro-pyrimidine | | 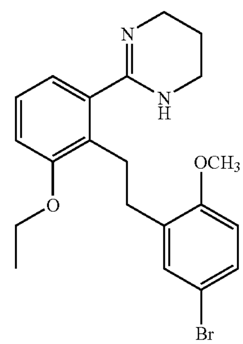 | *** |
| RN | 2-{2-[2-(5-Bromo-2-methoxy-phenyl)-ethyl]-3-isopropoxy-phenyl}-1,4,5,6-tetrahydro-pyrimidine | | 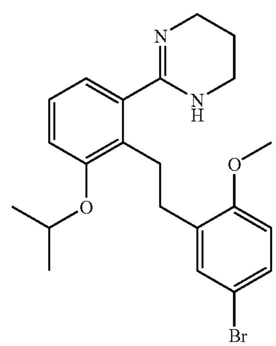 | *** |
| RO | 2-{2-[2-(5-Bromo-2-methoxy-phenyl)-ethyl]-3-fluoro-4-methoxy-phenyl}-1,4,5,6-tetrahydro-pyrimidine | | 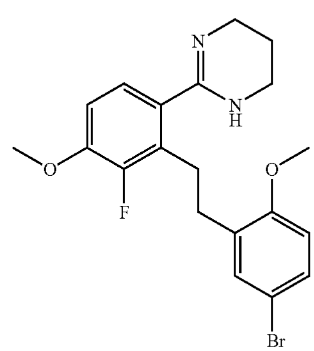 | * |

TABLE 4-continued

| ID | CHEMICAL NAME | Mol Weight (Tot) | Structure | MC4-R Binding |
|----|---------------|------------------|-----------|---------------|
| RP | 2-{2-[2-(5-Bromo-2-methoxy-phenyl)-ethyl]-3-isopropoxy-phenyl}-1,4,5,6-tetrahydro-pyrimidin-5-ol | | 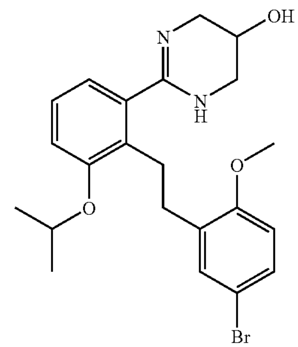 | ** |
| RQ | 2-{2-[2-(5-Bromo-2-methoxy-phenyl)-ethyl]-3-methoxy-phenyl}-1,4,5,6-tetrahydro-pyrimidin-5-ol | | 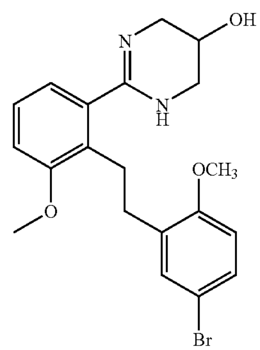 | *** |
| RS | 2-{2-[2-(5-Bromo-2-methoxy-phenyl)-ethyl]-4-methoxy-phenyl}-1,4,5,6-tetrahydro-pyrimidine | | 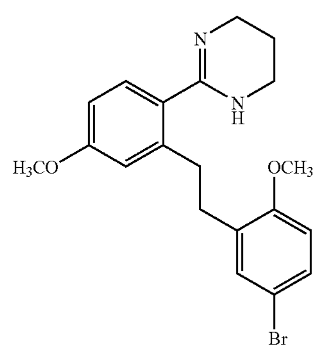 | * |
| RT | 2-{2-[2-(5-Bromo-2-methoxy-phenyl)-ethyl]-3-ethoxy-phenyl}-1,4,5,6-tetrahydro-pyrimidin-5-ol | | 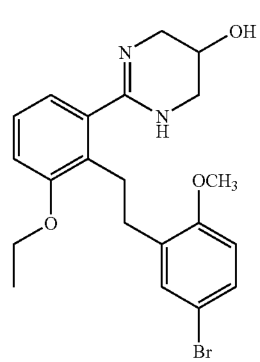 | *** |

TABLE 4-continued
| ID | CHEMICAL NAME | Mol Weight (Tot) | Structure | MC4-R Binding |
|---|---|---|---|---|
| RU | 2-[2-(5-Bromo-2-methoxy-phenyl)-ethyl]-3-(1,4,5,6-tetrahydro-pyrimidin-2-yl)-benzonitrile | | 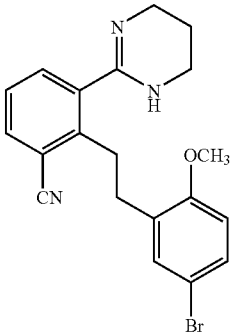 | *** |
| RV | 2-{3-Benzyloxy-2-[2-(5-bromo-2-methoxy-phenyl)-ethyl]-phenyl}-1,4,5,6-tetrahydro-pyrimidine | | 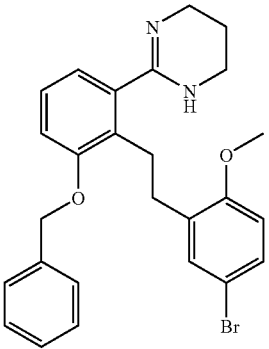 | * |
| RW | 2-{2-[2-(5-Bromo-2-methoxy-phenyl)-ethyl]-4-butyl-phenyl}-1,4,5,6-tetrahydro-pyrimidine | | 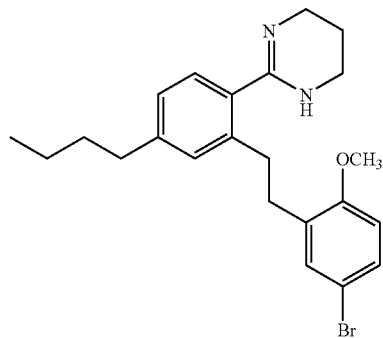 | * |
| RX | 2-{5-[2-(5-Bromo-2-methoxy-phenyl)-ethyl]-2,3-dihydro-benzo[1,4]-dioxin-6-yl}-1,4,5,6-tetrahydro-pyrimidine | | 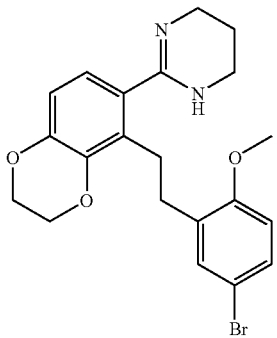 | ** |

TABLE 4-continued

| ID | CHEMICAL NAME | Mol Weight (Tot) | Structure | MC4-R Binding |
|----|---------------|------------------|-----------|---------------|
| RY | 2-{5-[2-(5-Bromo-2-methoxy-phenyl)-ethyl]-8-chloro-2,3-dihydro-benzo[1,4]dioxin-6-yl}-1,4,5,6-tetrahydro-pyrimidine | | 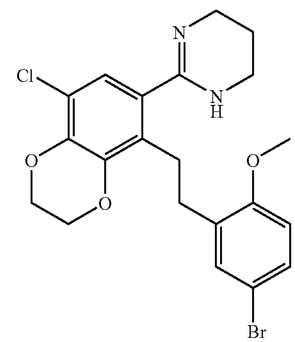 | ** |
| RZ | 2-{2-[2-(5-Bromo-2-methoxy-phenyl)-ethyl]-3-ethyl-phenyl}-1,4,5,6-tetrahydro-pyrimidine | | 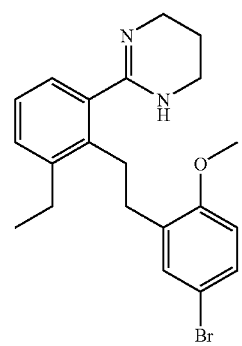 | *** |
| SA | 2-{2-[2-(5-Bromo-2-methoxy-phenyl)-ethyl]-3-propyl-phenyl}-1,4,5,6-tetrahydro-pyrimidine | | 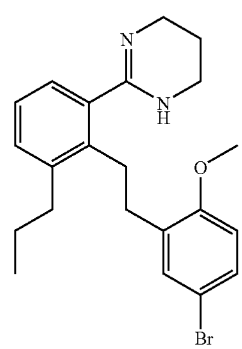 | *** |
| SB | 2-{2-[2-(5-Bromo-2-methoxy-phenyl)-ethyl]-3-butoxy-phenyl}-1,4,5,6-tetrahydro-pyrimidine | | 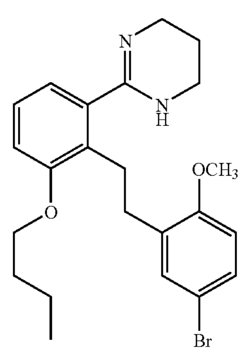 | ** |

TABLE 4-continued

| ID | CHEMICAL NAME | Mol Weight (Tot) | Structure | MC4-R Binding |
|---|---|---|---|---|
| SC | 2-{2-[2-(5-Bromo-2-methoxy-phenyl)-ethyl]-3-isobutoxy-phenyl}-1,4,5,6-tetrahydro-pyrimidine | | 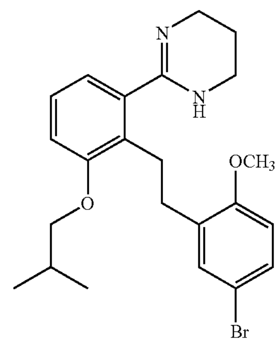 | ** |
| SD | 2-{2-[2-(5-Bromo-2-methoxy-phenyl)-ethyl]-3-butoxy-phenyl}-1,4,5,6-tetrahydro-pyrimidin-5-ol | | 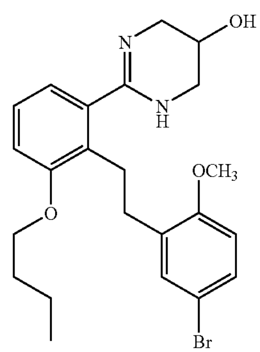 | ** |
| SE | 2-[2-(5-Bromo-2-methoxy-benzylsulfanyl)-3-fluoro-phenyl]-5-methoxy-1,4,5,6-tetrahydro-pyrimidine | | 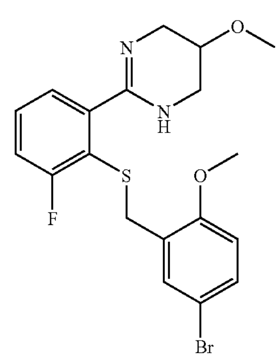 | *** |
| SF | 2-{2-[2-(5-Bromo-2-methoxy-phenyl)-ethyl]-3-chloro-phenyl}-1-methyl-1,4,5,6-tetrahydro-pyrimidine | | 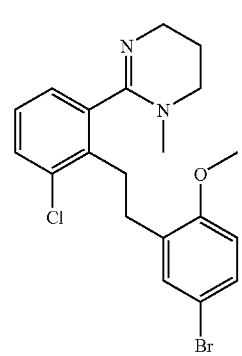 | *** |

TABLE 4-continued

| ID | CHEMICAL NAME | Mol Weight (Tot) | Structure | MC4-R Binding |
|----|---------------|------------------|-----------|---------------|
| SG | 2-[2-(5-Bromo-2-methoxy-benzylsulfanyl)-3-fluoro-phenyl]-1-methyl-4,5-dihydro-1H-imidazole | | 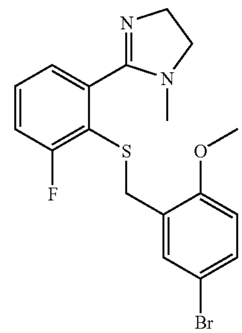 | *** |
| SH | [2-(5-Bromo-2-methoxy-benzylsulfanyl)-3-fluoro-phenyl]-1-methyl-4,5-dihydro-1H-imidazole | | 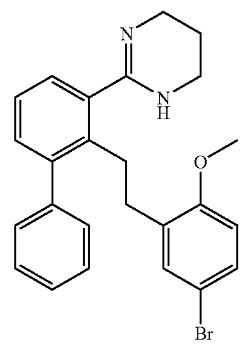 | *** |
| SI | 2-{2-[3-(1,4,5,6-Tetrahydro-pyrimidin-2-yl)-biphenyl-2-yl]-ethyl}-phenol | | 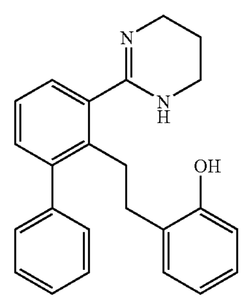 | *** |
| SJ | 2-{2-[2-(5-Bromo-2-methoxy-phenyl)-ethyl]-3-chloro-phenyl}-1-methyl-4,5-dihydro-1H-imidazole | | 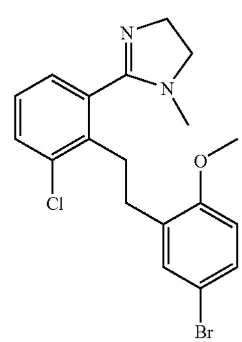 | *** |

TABLE 4-continued

| ID | CHEMICAL NAME | Mol Weight (Tot) | Structure | MC4-R Binding |
|---|---|---|---|---|
| SK | N-(3-Amino-propyl)-2-[2-(5-bromo-2-methoxy-phenyl)-ethyl]-6-methoxy-benzamide | | 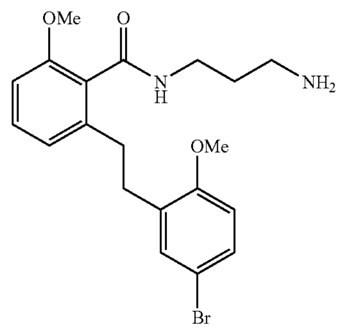 | * |
| SL | N-(3-Amino-propyl)-2-[2-(5-bromo-2-methoxy-phenyl)-ethyl]-6-methyl-benzamide | | 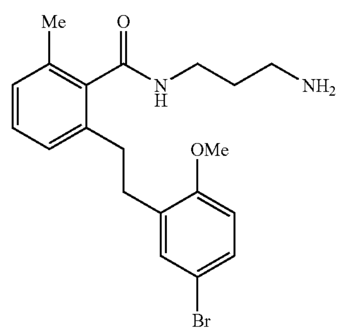 | * |
| SM | 2-[2-(5-Bromo-2-methoxy-benzylsulfanyl)-3-fluoro-phenyl]-5,6-dihydro-4H-pyrimidine-1-carboxylic acid 1-acetoxy-2-methyl-propyl ester | | 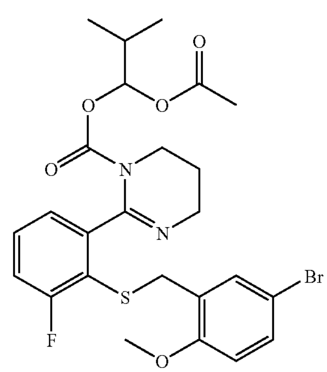 | *** |
| SN | 2-[2-(5-Bromo-2-methoxy-benzylsulfanyl)-3-fluoro-phenyl]-5,6-dihydro-4H-pyrimidine-1-carboxylic acid 1-acetoxy-ethyl ester | | 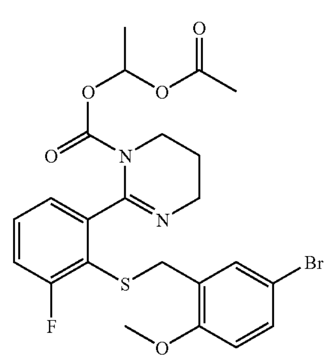 | ** |

TABLE 4-continued

| ID | CHEMICAL NAME | Mol Weight (Tot) | Structure | MC4-R Binding |
|---|---|---|---|---|
| SO | 2-{3-Methoxy-2-[2-(2-methoxy-phenyl)-ethyl]-phenyl}-1,4,5,6-tetrahydro-pyrimidine | | 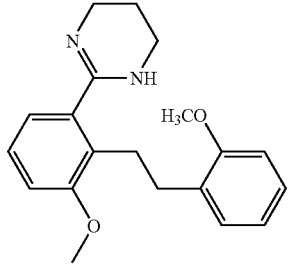 | ** |
| SP | 3-(5-Bromo-2-methoxy-phenyl)-5-chloro-3,4-dihydro-isoquinolin-1-ylamine | | 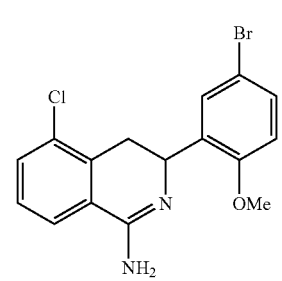 | ** |
| SQ | 2-{2-[2-(5-Bromo-2-methoxy-phenyl)-ethyl]-3-(4-methoxy-benzyloxy)-phenyl}-1,4,5,6-tetrahydro-pyrimidine | | 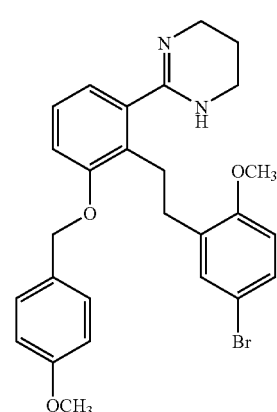 | ** |
| SR | 2-{2-[2-(5-Bromo-2-methoxy-phenyl)-ethyl]-3-chloro-phenyl}-5-methyl-1,4,5,6-tetrahydro-pyrimidin-5-ol | | 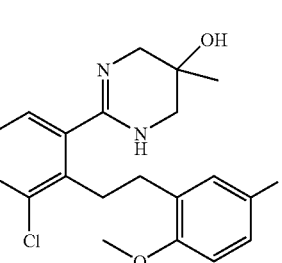 | *** |
| SS | 2-[(5-Bromo-2-methoxy-phenyl)-(3-piperidin-1-yl-propylamino)-methyl]-3-chloro-6-methyl-phenol | | 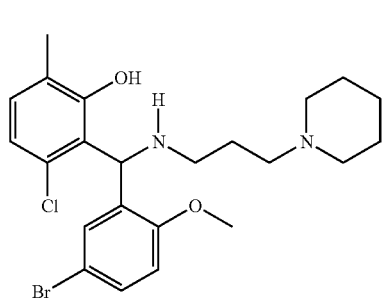 | ** |

TABLE 4-continued

| ID | CHEMICAL NAME | Mol Weight (Tot) | Structure | MC4-R Binding |
|---|---|---|---|---|
| ST | 1-{2-[2-(5-Bromo-2-methoxy-phenyl)-ethyl]-6-methyl-benzyl}-piperazine | | 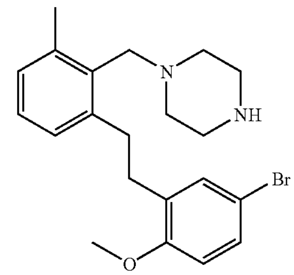 | *** |
| SU | 1-{2-[2-(5-Bromo-2-methoxy-phenyl)-ethyl]-6-methyl-benzyl}-4-methyl-piperazine | | 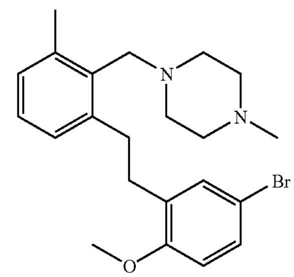 | ** |
| SV | 1-{2-[2-(5-Bromo-2-methoxy-phenyl)-ethyl]-6-methyl-benzyl)-piperidine | | 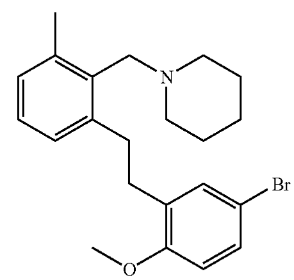 | * |
| SW | {2-[2-(5-Bromo-2-methoxy-phenyl)-ethyl]-6-methyl-benzyl}-diethyl-amine | | 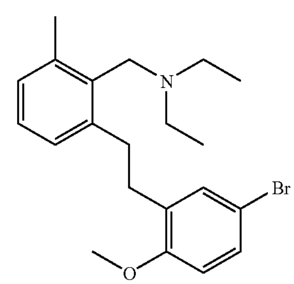 | ** |
| SY | 3-(5-Bromo-2-methoxy-phenyl)-1,2,3,4-tetrahydro-isoquinoline | | 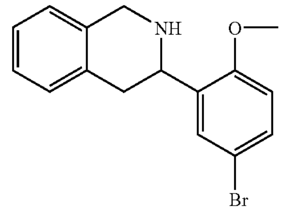 | * |

TABLE 4-continued

| ID | CHEMICAL NAME | Mol Weight (Tot) | Structure | MC4-R Binding |
|---|---|---|---|---|
| SX | 1-{2-[2-(5-Bromo-2-methoxy-phenyl)-ethyl]-3-chloro-benzyl}-piperazine | | 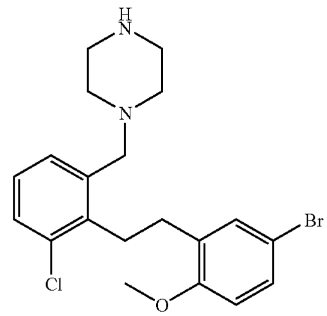 | ** |
| SY | 1-{2-[2-(5-Bromo-2-methoxy-phenyl)-ethyl]-3-chloro-benzyl}-4-methyl-piperazine | | 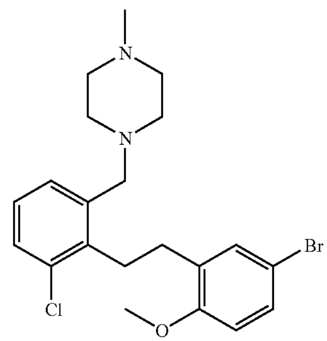 | * |
| SZ | 1-{2-[2-(5-Bromo-2-methoxy-phenyl)-ethyl]-3-chloro-benzyl}-piperidine | | 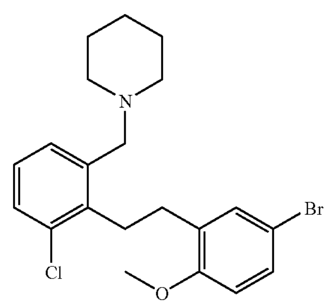 | * |
| TA | {2-[2-(5-Bromo-2-methoxy-phenyl)-ethyl]-3-chloro-benzyl}-diethyl-amine | | 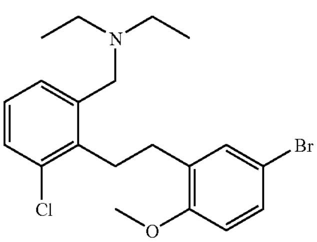 | ** |
| TB | 2-{2-[2-(5-Bromo-2-methoxy-phenyl)-ethyl]-3-chloro-phenyl}-4,5-dihydro-1H-imidazole | | 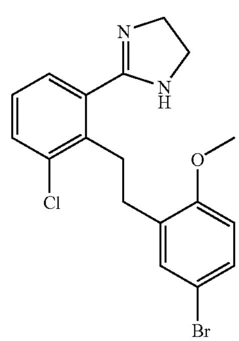 | *** |

TABLE 4-continued

| ID | CHEMICAL NAME | Mol Weight (Tot) | Structure | MC4-R Binding |
|---|---|---|---|---|
| TC | (1-{2-[2-(5-Bromo-2-methoxy-phenyl)-ethyl]-3-chloro-benzyl}-piperidin-2-yl)-methanol | | 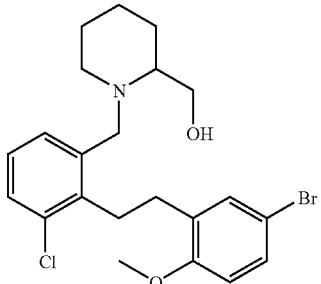 | ** |
| TD | 2-{2-[2-(5-Bromo-2-methoxy-phenyl)-ethyl]-3-propoxy-phenyl}-1,4,5,6-tetrahydro-pyrimidine | | 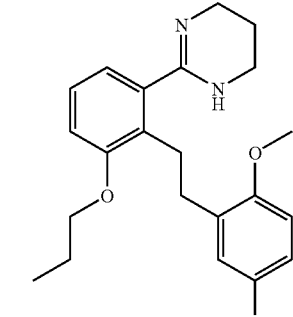 | *** |
| TE | 1-[2-(5-Bromo-2-methoxy-benzylsulfanyl)-benzyl]-4-methyl-piperazine | | 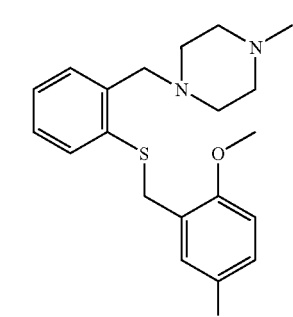 | * |
| TF | 1-{2-[2-(5-Bromo-2-methoxy-phenyl)-ethyl]-6-chloro-benzyl}-piperazine | | 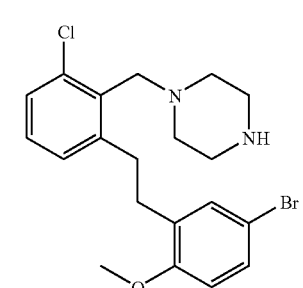 | ** |
| TG | 1-{2-[2-(5-Bromo-2-methoxy-phenyl)-ethyl]-6-chloro-benzyl}-4-methyl-piperazine | | 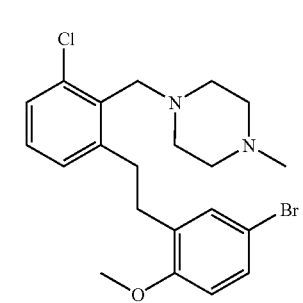 | * |

TABLE 4-continued

| ID | CHEMICAL NAME | Mol Weight (Tot) | Structure | MC4-R Binding |
|----|---------------|------------------|-----------|---------------|
| TH | 1-{2-[2-(5-Bromo-2-methoxy-phenyl)-ethyl]-6-chloro-benzyl}-piperidine | | 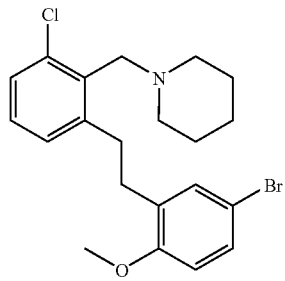 | * |
| TI | {2-[2-(5-Bromo-2-methoxy-phenyl)-ethyl]-6-chloro-benzyl}-diethyl-amine | | 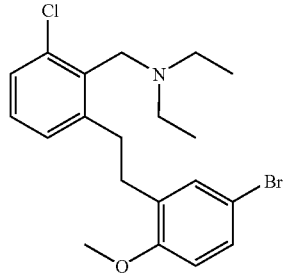 | * |
| TJ | 1-(5-Bromo-2-methoxy-benzyl)-2-(4-methoxy-benzyl)-2,3-dihydro-1H-isoindole | | 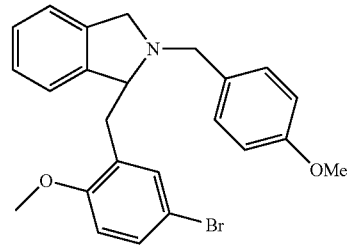 | * |
| TK | 2-{2-[2-(5-Bromo-2-methoxy-phenyl)-ethyl]-3-chloro-phenyl}-5,6-dihydro-4H-pyrimidine-1-carboxylic acid 1-acetoxy-ethyl ester | | 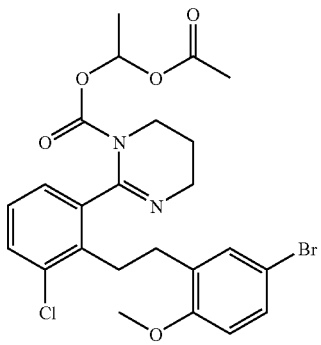 | *** |
| TL | 1-(2-{2-[2-(5-Bromo-2-methoxy-phenyl)-ethyl]-3-chloro-phenyl}-5,6-dihydro-4H-pyrimidin-1-yl)-ethanone | | 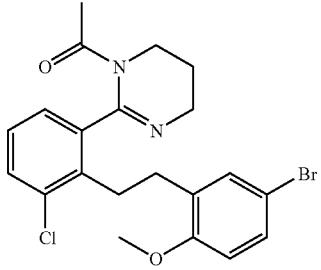 | *** |

TABLE 4-continued
| ID | CHEMICAL NAME | Mol Weight (Tot) | Structure | MC4-R Binding |
|---|---|---|---|---|
| TM | 1-{2-[2-(5-Bromo-2-methoxy-phenyl)-ethyl]-3-fluoro-benzyl}-4-methyl-piperazine | | 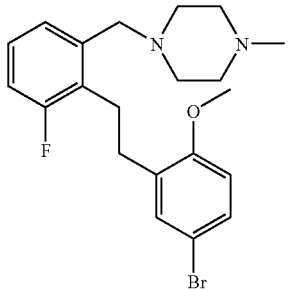 | *** |
| TN | {2-[2-(5-Bromo-2-methoxy-phenyl)-ethyl]-3-fluoro-benzyl}-diethyl-amine | | 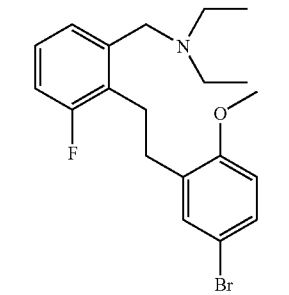 | *** |
| TO | 1-{2-[2-(5-Bromo-2-methoxy-phenyl)-ethyl]-3-fluoro-benzyl}-piperidine | | 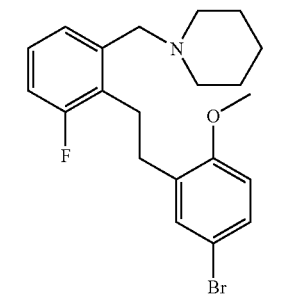 | ** |
| TP | (1-{2-[2-(5-Bromo-2-methoxy-phenyl)-ethyl]-3-fluoro-benzyl}-piperidin-2-yl)-methanol | | 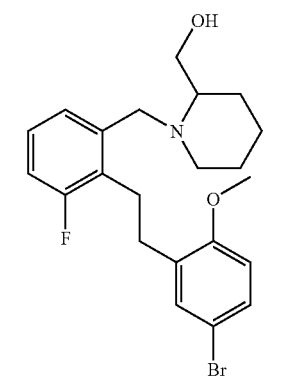 | ** |

TABLE 4-continued

| ID | CHEMICAL NAME | Mol Weight (Tot) | Structure | MC4-R Binding |
|---|---|---|---|---|
| TQ | 4-Fluoro-N-{2-[4-(2-methoxy-phenyl)-piperazin-1-yl]-ethyl}-N-pyridin-2-yl-benzamide | | 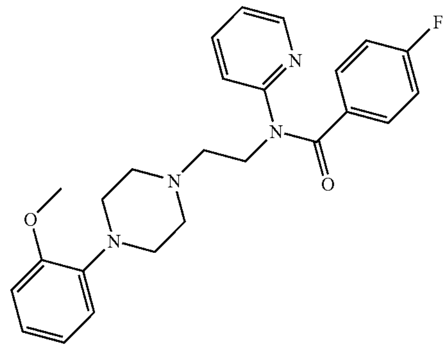 | * |
| TR | 3-(5-Bromo-2-methoxy-phenyl)-2-methyl-1,2,3,4-tetrahydro-isoquinoline | | 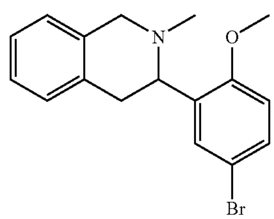 | * |
| TS | 2-{2-[2-(5-Bromo-2-methoxy-phenyl)-ethyl]-3-chloro-phenyl}-1-ethyl-4,5-dihydro-1H-imidazole | | 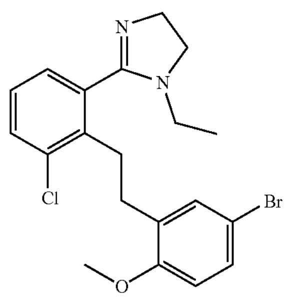 | *** |
| TT | {2-[3-(5-Bromo-2-methoxy-phenyl)-3,4-dihydro-1H-isoquinolin-2-yl]-ethyl}-diethyl-amine | | 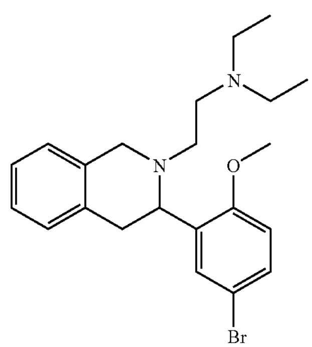 | * |
| TU | 1-(2-{2-[2-(5-Bromo-2-methoxy-phenyl)-ethyl]-3-chloro-phenyl}-4,5-dihydro-imidazol-1-yl)-ethanone | | 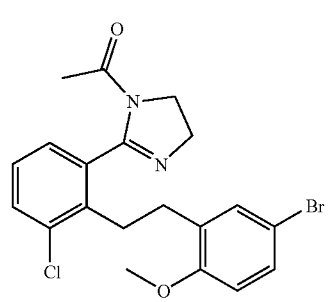 | * |

TABLE 4-continued

| ID | CHEMICAL NAME | Mol Weight (Tot) | Structure | MC4-R Binding |
|----|---------------|------------------|-----------|---------------|
| TV | 2-{2-[2-(5-Bromo-2-methoxy-phenyl)-ethyl]-3-chloro-phenyl}-4,5-dihydro-imidazole-1-carboxylic acid ethyl ester | | 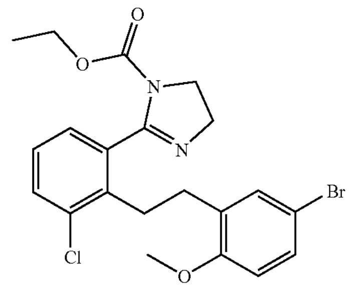 | * |
| TW | 2-{2-[2-(5-Bromo-2-methoxy-phenyl)-ethyl]-3-chloro-phenyl}-4,5-dihydro-imidazole-1-carboxylic acid isobutyl ester | | 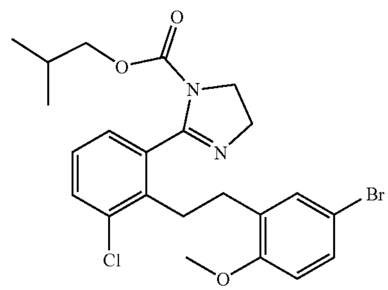 | * |
| TX | 2-{2-[2-(5-Bromo-2-methoxy-phenyl)-ethyl]-3-chloro-phenyl}-4,5-dihydro-imidazole-1-carboxylic acid tert-butyl ester | | 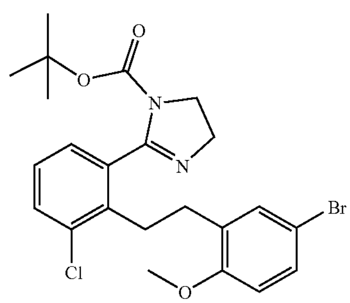 | * |
| TY | 1-(2-{2-[2-(5-Bromo-2-methoxy-phenyl)-ethyl]-3-chloro-phenyl}-4,5-dihydro-imidazol-1-yl)-2,2-dimethyl-propan-1-one | | 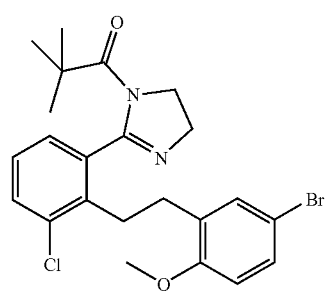 | ** |
| TZ | [1-(5-Bromo-2-methoxy-benzyl)-indan-2-yl]-dimethyl-amine | | 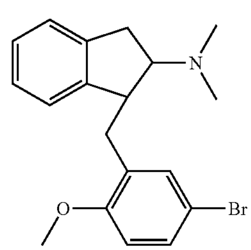 | * |

TABLE 4-continued

| ID | CHEMICAL NAME | Mol Weight (Tot) | Structure | MC4-R Binding |
|---|---|---|---|---|
| UA | 1-(5-Bromo-2-methoxy-benzyl)-2,3-dihydro-1H-isoindole | | 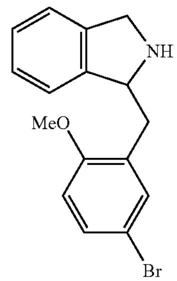 | * |
| UB | 1-(2-Methoxy-benzyl)-2-methyl-2,3-dihydro-1H-isoindole | | 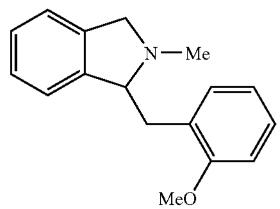 | * |
| UC | 2-Methyl-1-naphthalen-1-ylmethyl-2,3-dihydro-1H-isoindole | | 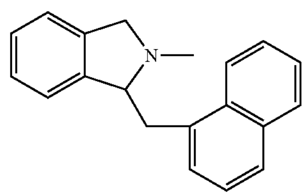 | * |
| UD | 1-{2-[3-Chloro-2-(2-naphthalen-1-yl-ethyl)-phenyl]-4,5-dihydro-imidazol-1-yl}-2,2-dimethyl-propan-1-one | | 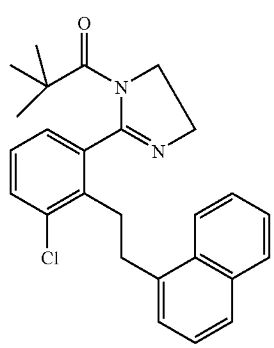 | * |
| UE | {2-[1-(5-Bromo-2-methoxy-benzyl)-1,3-dihydro-isoindol-2-yl]-ethyl}-diethyl-amine | | 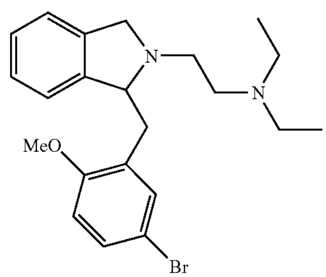 | ** |

TABLE 4-continued

| ID | CHEMICAL NAME | Mol Weight (Tot) | Structure | MC4-R Binding |
|---|---|---|---|---|
| UF | 2-[3-Chloro-2-(2-naphthalen-1-yl-ethyl)-phenyl]-1-methyl-1,4,5,6-tetrahydro-pyrimidine | | 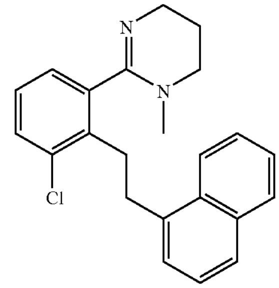 | *** |
| UG | 2-[3-Chloro-2-(2-naphthalen-1-yl-ethyl)-phenyl]-5,6-dihydro-4H-pyrimidine-1-carboxylic acid tert-butyl ester | | 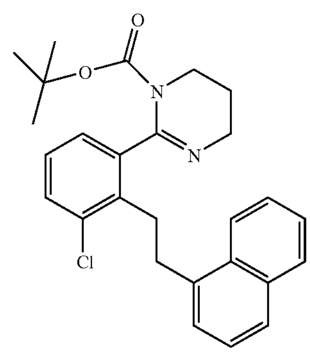 | *** |
| UH | 2-[3-Chloro-2-(2-naphthalen-1-yl-ethyl)-phenyl]-4,5-dihydro-1H-imidazole | | 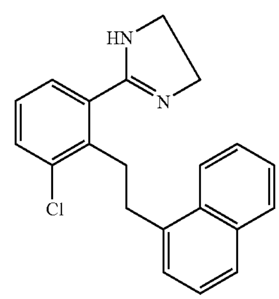 | *** |
| UI | 1-{2-[3-Chloro-2-(2-naphthalen-1-yl-ethyl)-phenyl]-4,5-dihydro-imidazol-1-yl}-ethanone | | 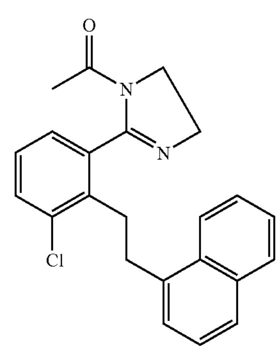 | * |

TABLE 4-continued

| ID | CHEMICAL NAME | Mol Weight (Tot) | Structure | MC4-R Binding |
|---|---|---|---|---|
| UJ | 2-[3-Chloro-2-(2-naphthalen-1-yl-ethyl)-phenyl]-4,5-dihydro-imidazole-1-carboxylic acid isobutyl ester | | 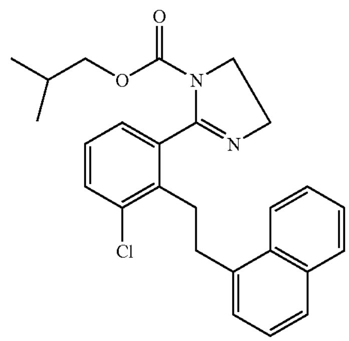 | * |
| UK | 2-[3-Chloro-2-(2-naphthalen-1-yl-ethyl)-phenyl]-4,5-dihydro-imidazole-1-carboxylic acid tert-butyl ester | | 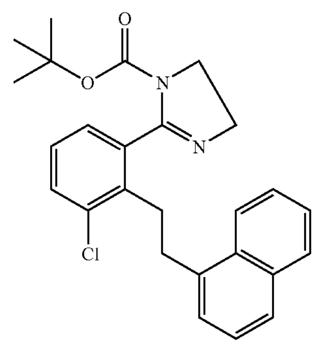 | * |
| UL | 2-[3-Chloro-2-(2-naphthalen-1-yl-ethyl)-phenyl]-4,5-dihydro-imidazole-1-carboxylic acid ethyl ester | | 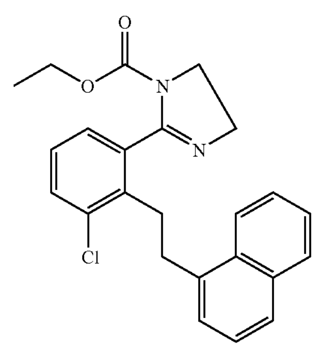 | * |
| UM | 2-[2-(5-Bromo-2-methoxy-phenyl)-ethyl]-N-(3-formylamino-propyl)-6-methyl-benzamide | | 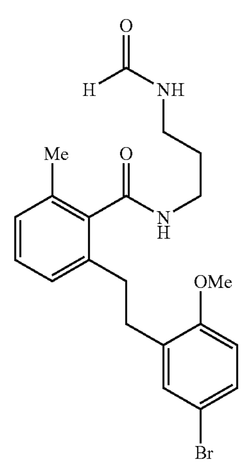 | * |

TABLE 4-continued

| ID | CHEMICAL NAME | Mol Weight (Tot) | Structure | MC4-R Binding |
|----|---------------|------------------|-----------|---------------|
| UN | 2-[3-Chloro-2-(2-naphthalen-1-yl-ethyl)-phenyl]-1-ethyl-4,5-dihydro-1H-imidazole | | 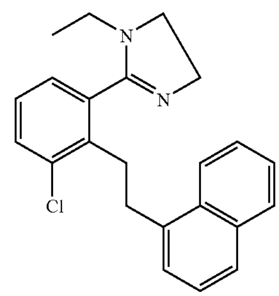 | *** |
| UO | 1-(2-{2-[2-(5-Bromo-2-methoxy-phenyl)-ethyl]-3-chloro-phenyl}-5,6-dihydro-4H-pyrimidin-1-yl)-2,2-dimethyl-propan-1-one | | 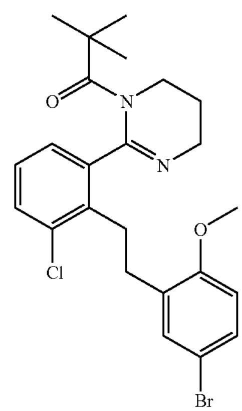 | * |
| UP | 2-{2-[2-(5-Bromo-2-methoxy-phenyl)-ethyl]-thiophen-3-yl}-4,5-dihydro-1H-imidazole | | 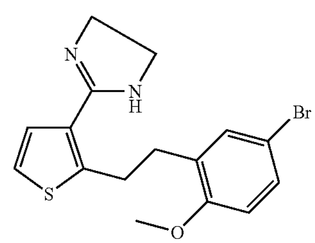 | *** |
| UQ | 2-{2-[2-(5-Bromo-2-methoxy-phenyl)-ethyl]-3-chloro-phenyl)-5,6-dihydro-4H-pyrimidine-1-carboxylic acid isobutyl ester | | 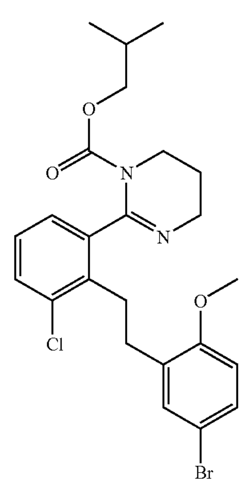 | * |

| ID | CHEMICAL NAME | Mol Weight (Tot) | Structure | MC4-R Binding |
|---|---|---|---|---|
| UR | 2-{2-[2-(5-Bromo-2-methoxy-phenyl)-ethyl]-3-chloro-phenyl)-1-isocyanomethyl-4,5-dihydro-1H-imidazole | | 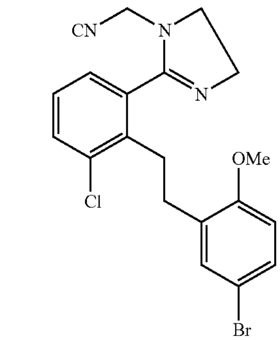 | *** |
| US | 2-{2-[2-(5-Bromo-2-methoxy-phenyl)-ethyl]-thiophen-3-yl}-1-methyl-4,5-dihydro-1H-imidazole | | 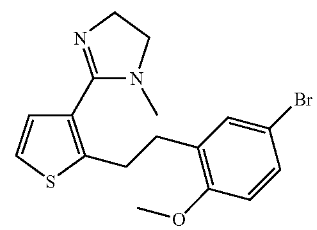 | *** |
| UT | 2-{2-[2-(5-Bromo-2-methoxy-phenyl)-ethyl]-thiophen-3-yl}-1-ethyl-4,5-dihydro-1H-imidazole | | 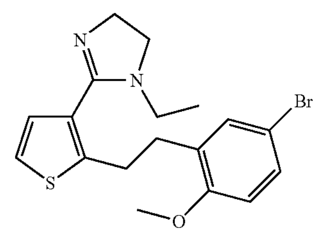 | *** |
| UU | 3-(5-Bromo-2-methoxy-benzyl)-2-methyl-2,3-dihydro-isoindol-1-one | | 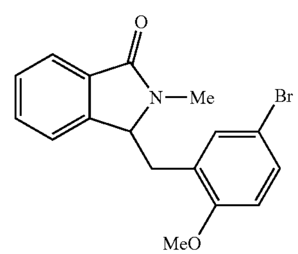 | * |
| UX | 4-(2-Methoxy-benzyl)-2-(4-methoxy-benzyl)-1,2,3,4-tetrahydro-isoquinoline | | 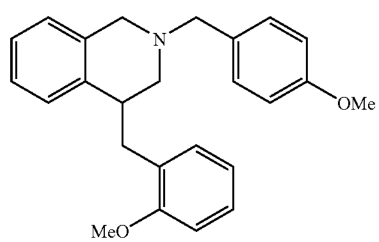 | * |
| UW | 4-(5-Bromo-2-methoxy-benzyl)-2-(4-methoxy-benzyl)-1,2,3,4-tetrahydro-isoquinoline | | 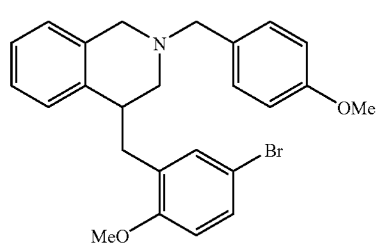 | * |

TABLE 4-continued

| ID | CHEMICAL NAME | Mol Weight (Tot) | Structure | MC4-R Binding |
|----|---------------|------------------|-----------|---------------|
| UY | 2-{2-[2-(5-Bromo-2-methoxy-phenyl)-ethyl]-3-chloro-phenyl}-1-propyl-4,5-dihydro-1H-imidazole | | 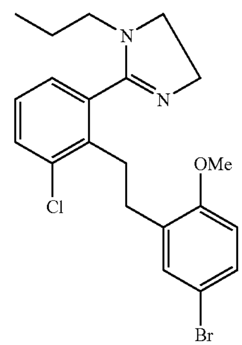 | *** |
| UZ | 2-{2-[2-(5-Bromo-2-methoxy-phenyl)-ethyl]-3-chloro-phenyl}-3a,4,5,6,7,7a-hexahydro-1H-benzoimidazole | | 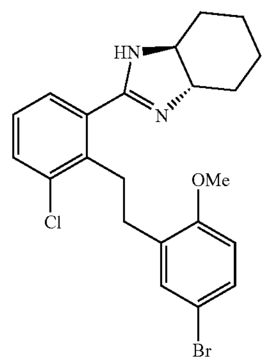 | *** |
| VA | 5,5-Dimethyl-2-[2-(naphthalen-1-ylsulfanylmethyl)-phenyl]-4,5-dihydro-1H-imidazole | | 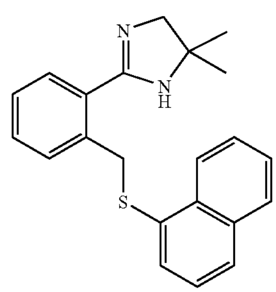 | *** |
| VB | 2-[2-(5-Bromo-2-methoxy-benzylsulfanyl)-3-chloro-phenyl]-4,4-dimethyl-4,5-dihydro-1H-imidazole | | 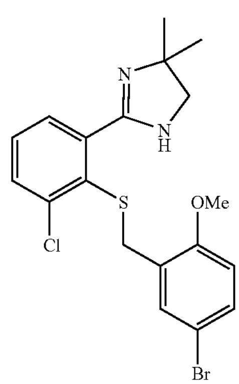 | *** |

TABLE 4-continued

| ID | CHEMICAL NAME | Mol Weight (Tot) | Structure | MC4-R Binding |
|---|---|---|---|---|
| VC | N-(5-Bromo-2-methoxy-benzyl)-N'-methyl-N-naphthalen-1-ylmethyl-ethane-1,2-diamine | | 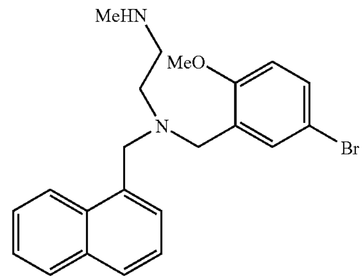 | ** |
| VD | 2-{2-[2-(5-Bromo-2-methoxy-phenyl)-ethyl]-3-chloro-phenyl}-1-ethyl-1,4,5,6-tetrahydro-pyrimidine | | 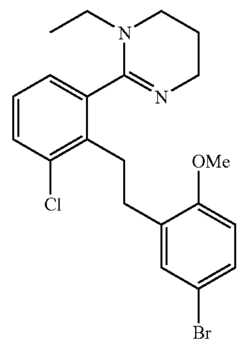 | *** |
| VE | 2-[2-(5-Bromo-2-methoxy-phenyl)-ethyl]-3-chloro-N,N,N'-trimethyl-benzamidine | | 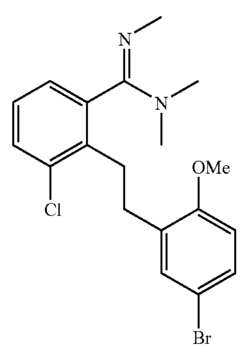 | *** |
| VF | 2-[3-Chloro-2-(2-naphthalen-1-yl-ethyl)-phenyl]-1-methyl-4,5-dihydro-1H-imidazole | | 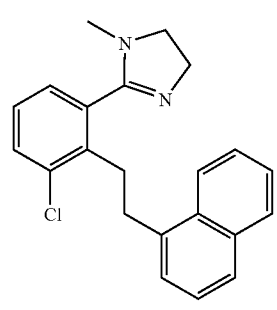 | *** |

TABLE 4-continued

| ID | CHEMICAL NAME | Mol Weight (Tot) | Structure | MC4-R Binding |
|---|---|---|---|---|
| VG | 1-Benzyl-2-{2-[2-(5-bromo-2-methoxy-phenyl)-ethyl]-3-chloro-phenyl}-4,5-dihydro-1H-imidazole | | 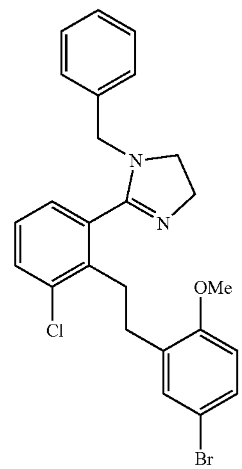 | *** |
| VH | ({2-[2-(5-Bromo-2-methoxy-phenyl)-ethyl]-3-chloro-phenyl}-pyrrolidin-1-yl-methylene)-methyl-amine | | 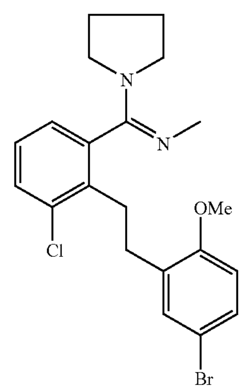 | ** |
| VI | 2-{2-[2-(5-Bromo-2-methoxy-phenyl)-ethyl]-3-chloro-phenyl}-1-isopropyl-4,5-dihydro-1H-imidazole | | 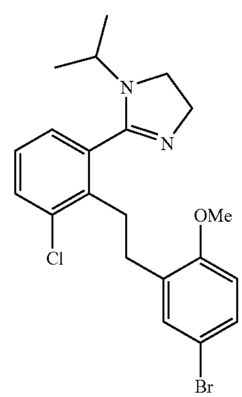 | *** |

TABLE 4-continued

| ID | CHEMICAL NAME | Mol Weight (Tot) | Structure | MC4-R Binding |
|----|---------------|------------------|-----------|---------------|
| VJ | 2-{2-[2-(5-Bromo-2-methoxy-phenyl)-ethyl]-3-chloro-phenyl}-1-(2,2,2-trifluoro-ethyl)-4,5-dihydro-1H-imidazole | | 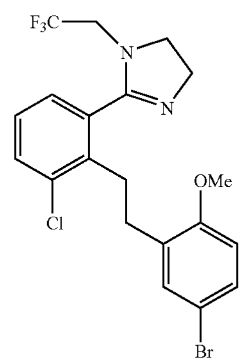 | *** |
| VK | 1-{2-[2-(5-Bromo-2-methoxy-benzylsulfanyl)-benzyloxy]-ethyl}-aziridine | | 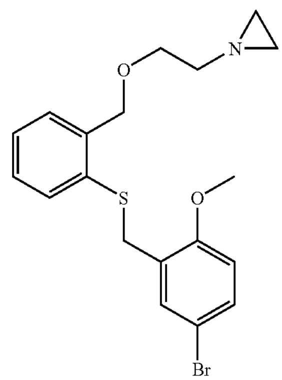 | * |
| VL | 3-[2-(5-Bromo-2-methoxy-benzylsulfanyl)-benzylamino]-3-methyl-butan-1-ol | | 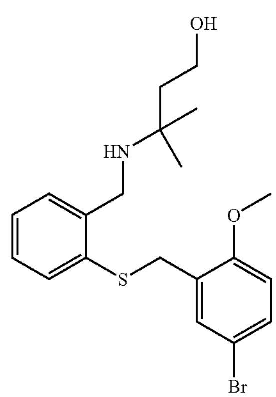 | * |
| VM | 3-Cyano-N-(2-dimethylamino-ethyl)-N-naphthalen-1-ylmethyl-benzamide | | 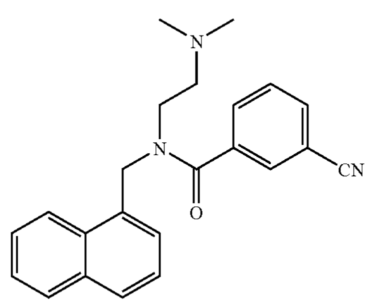 | * |

TABLE 4-continued

| ID | CHEMICAL NAME | Mol Weight (Tot) | Structure | MC4-R Binding |
|---|---|---|---|---|
| VN | N-(2-Dimethylamino-ethyl)-4-fluoro-N-naphthalen-1-ylmethyl-benzenesulfonamide | | 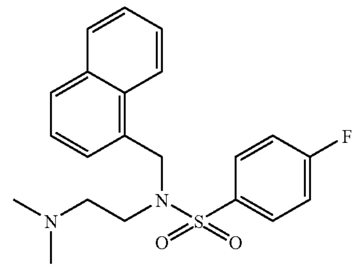 | * |
| VO | 2-Cyano-N-(2-dimethylamino-ethyl)-N-naphthalen-1-ylmethyl-benzenesulfonamide | | 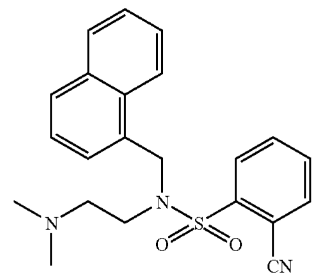 | * |
| VP | 2-[2-(Naphthalen-1-ylsulfanylmethyl)-pyrrolidin-1-yl]-ethyl-1-pyrrolidine | | 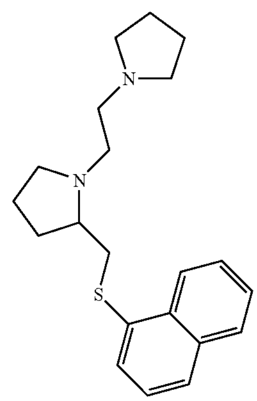 | * |
| VQ | C-{1-(2-Naphthalen-1-yl-ethyl)-pyrrolidin-2-yl]-methyl-1-pyrrolidine | | 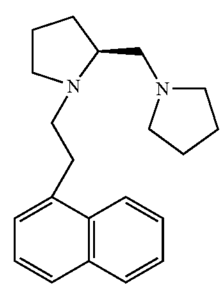 | * |
| VR | 1-(2-Naphthalen-1-yl-ethyl)-piperidine-2-carboxylic acid methyl ester | | 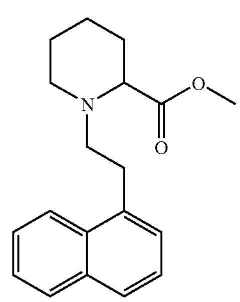 | * |

TABLE 4-continued

| ID | CHEMICAL NAME | Mol Weight (Tot) | Structure | MC4-R Binding |
|----|---------------|------------------|-----------|---------------|
| VS | (1-Ethyl-pyrrolidin-2-ylmethyl)-naphthalen-2-ylmethyl-naphthalen-1-ylmethyl-amine | | 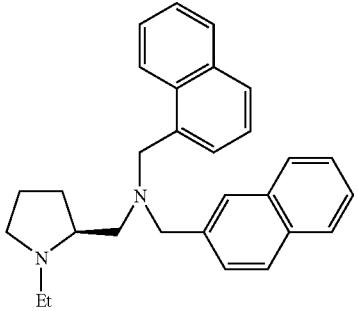 | * |
| VT | (3-Bromo-benzyl)-(3-imidazol-1-yl-propyl)-naphthalen-1-ylmethyl amine | | 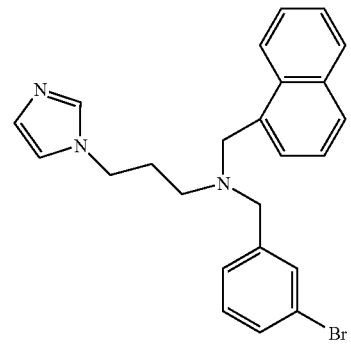 | * |
| VU | 6-[2-(Cyclohexyl-methyl-amino)-ethyl]-2-oxo-2,3-dihydro-benzoimidazole-1-carboxylic acid benzylamide | | 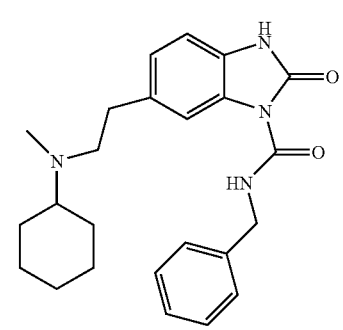 | * |
| VV | (5-Bromo-2-methoxy-benzyl)-(3-imidazol-1-yl-propyl)-naphthalen-1-ylmethyl-amine | | 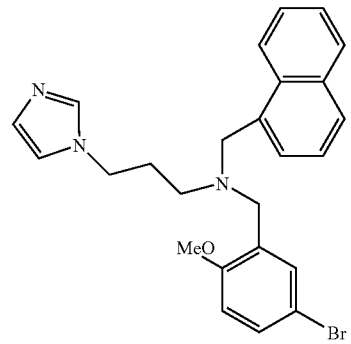 | * |

TABLE 4-continued
| ID | CHEMICAL NAME | Mol Weight (Tot) | Structure | MC4-R Binding |
|----|---------------|------------------|-----------|---------------|
| VW | (3-Imidazol-1-yl-propyl)-naphthalen-2-ylmethyl-naphthalen-1-ylmethyl-amine | | 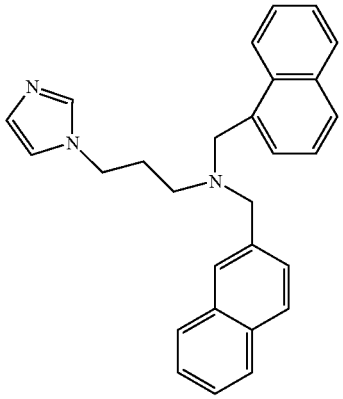 | * |
| VX | Dimethyl-[1-(2-naphthalen-1-yl-ethyl)-piperidin-2-ylmethyl]-amine | | 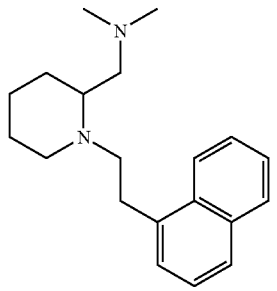 | * |
| VY | [2-(Naphthalen-1-ylmethylsulfanyl)-phenyl]-carbamic acid 2-dimethylamino-ethyl ester | | 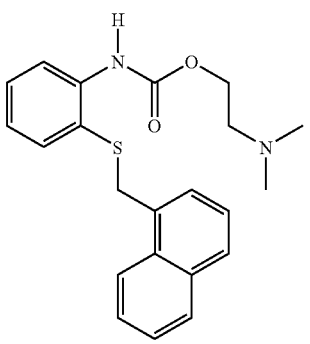 | * |
| VZ | 3-(5-Bromo-2-methoxy-benzyloxy)-1-(2-pyrrolidin-1-yl-ethyl)-piperidine | | 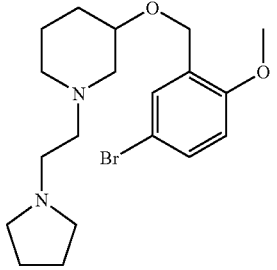 | * |

TABLE 4-continued

| ID | CHEMICAL NAME | Mol Weight (Tot) | Structure | MC4-R Binding |
|---|---|---|---|---|
| WA | C-[1-(2-Naphthalen-1-yl-ethyl)-piperidin-2-yl]-methyl-N-piperidine | | 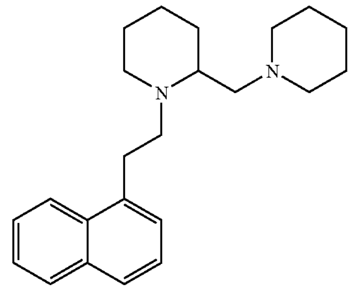 | * |
| WB | 1-[1-(2-Naphthalen-1-yl-ethyl)-piperidin-2-ylmethyl]-1H-pyrrole-2-carbonitrile | | 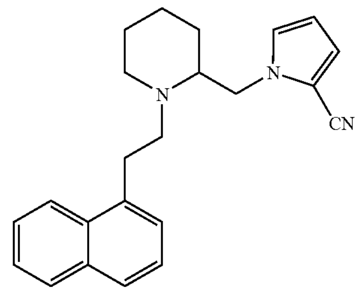 | * |
| WC | 1-[2-(Naphthalen-1-ylsulfanylmethyl)-pyrrolidin-1-yl]-2-pyrrolidin-1-yl-ethanone | | 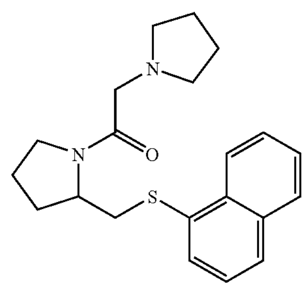 | * |
| WD | 1-{2-[2-(Naphthalen-1-ylsulfanylmethyl)-pyrrolidin-1-yl]-ethyl}-piperidine | | 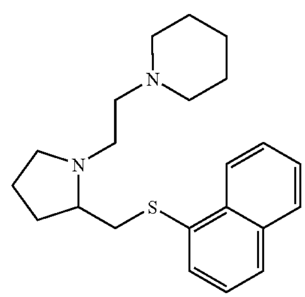 | * |
| WE | 3-(5-Bromo-2-methoxy-benzyloxy)-piperidine | | 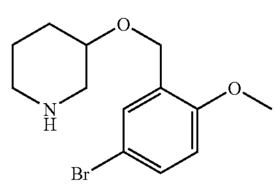 | * |
| WF | 5-(Naphthalen-1-ylsulfanylmethyl)-pyrrolidin-2-one | | 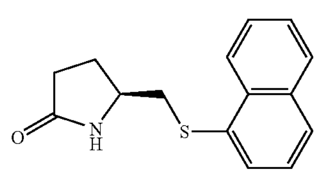 | * |

TABLE 4-continued

| ID | CHEMICAL NAME | Mol Weight (Tot) | Structure | MC4-R Binding |
|---|---|---|---|---|
| WG | 5-(Naphthalen-1-ylsulfanylmethyl)-1-(2-pyrrolidin-1-yl-ethyl)-pyrrolidin-2-one | | 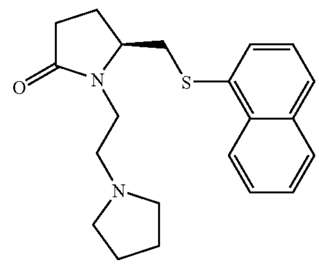 | * |
| WH | 2-[3-(5-Bromo-2-methoxy-benzyloxy)-pyrrolidin-1-yl]-ethyl-1,N-pyrrolidine | | 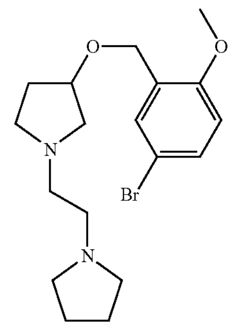 | * |
| WI | 2-{[(3-Bromo-benzyl)-naphthalen-1-ylmethyl-amino]-methyl}-piperidine 1-carboxylic acid tert-butyl ester | | 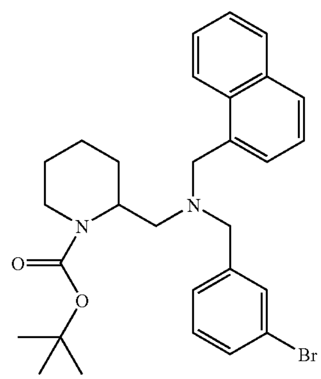 | * |
| WJ | 4-(2-Methoxy-benzyl)-2-(4-methoxy-benzyl)-1,2,3,4-tetrahydro-isoquinoline | | 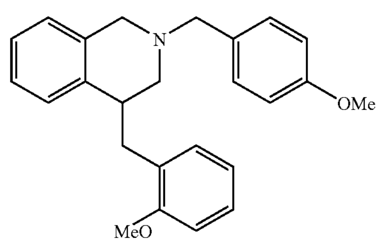 | * |
| WK | 4-(5-Bromo-2-methoxy-benzyl)-2-(4-methoxy-benzyl)-1,2,3,4-tetrahydro-isoquinoline | | 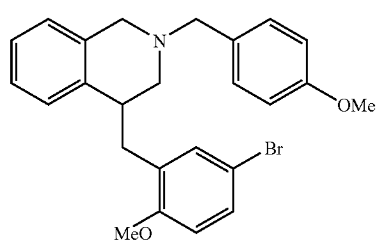 | * |

TABLE 5
| Salt | Molecular Weight | Structure |
|---|---|---|
| Parent | 347.5242 | 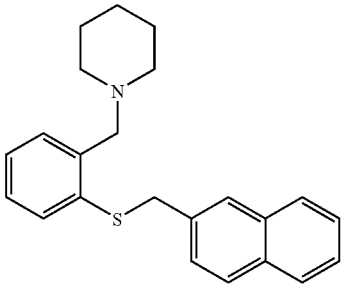 |
| Parent | 331.9091 | 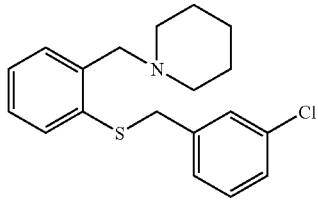 |
| Parent | 333.4453 | 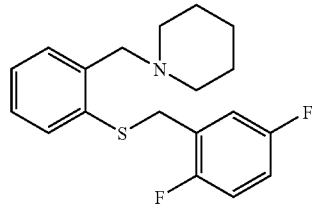 |
| Parent | 365.4626 | 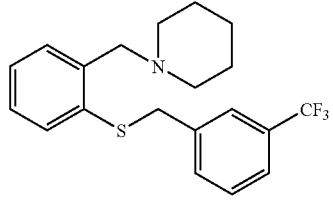 |
| Parent | 646.0503 | 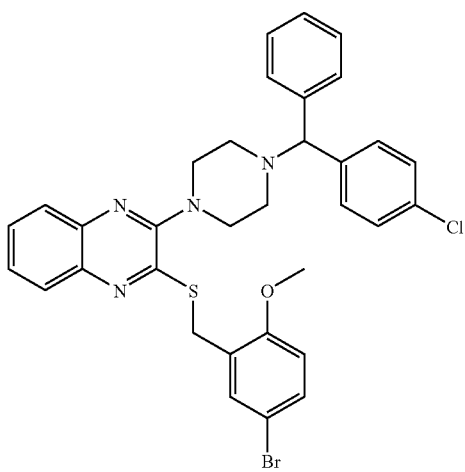 |

TABLE 5-continued

| Salt | Molecular Weight | Structure |
|------|------------------|-----------|
| Formate | 513.4192 | |
| Formate | 533.4937 | |
| Formate | 595.5646 | |
| HCl | 525.9799 | 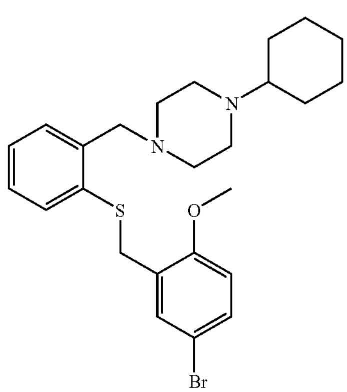 |

TABLE 5-continued
| Salt | Molecular Weight | Structure |
|---|---|---|
| Formate | 530.4901 | 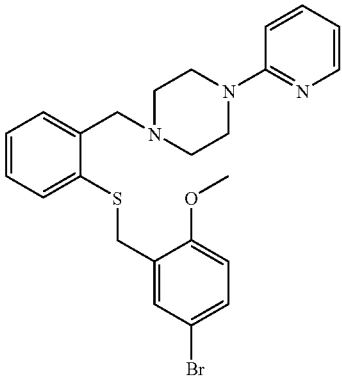 |
| Parent | 466.6471 | 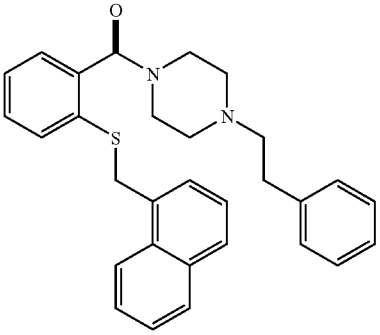 |
| Parent | 508.7277 | 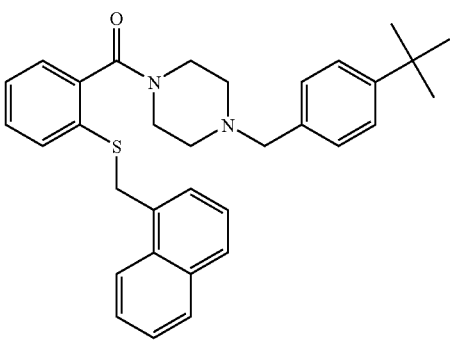 |
| Parent | 377.3244 | 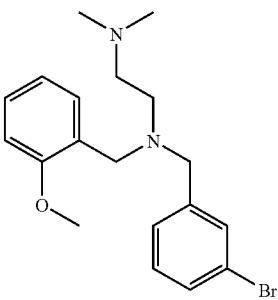 |

TABLE 5-continued
| Salt | Molecular Weight | Structure |
|---|---|---|
| Parent | 378.5383 | 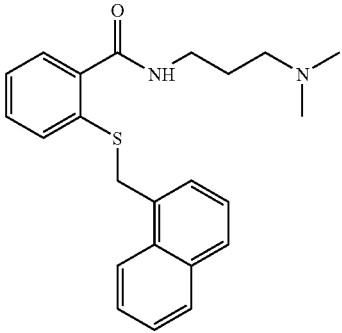 |
| Parent | 406.5921 | 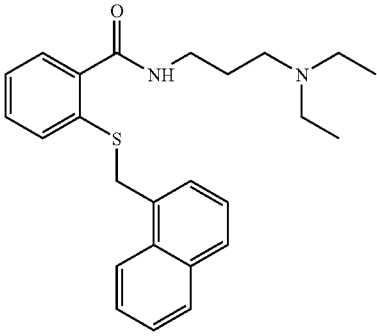 |
| Parent | 348.4882 | 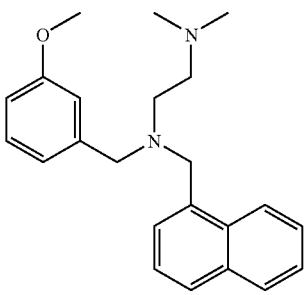 |
| Parent | 404.5762 | 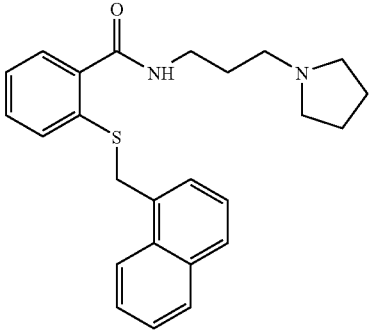 |

TABLE 5-continued

| Salt | Molecular Weight | Structure |
|---|---|---|
| Parent | 312.4552 | |
| Parent | 348.4882 | |
| Parent | 328.4546 | |
| Formate | 599.6367 | |
| Formate | 579.5194 | |

TABLE 5-continued
| Salt | Molecular Weight | Structure |
|---|---|---|
| Formate | 590.5457 | 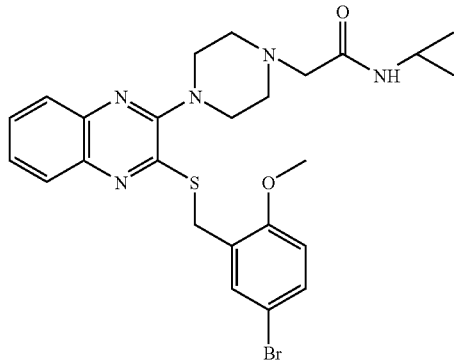 |
| Formate | 568.4987 | 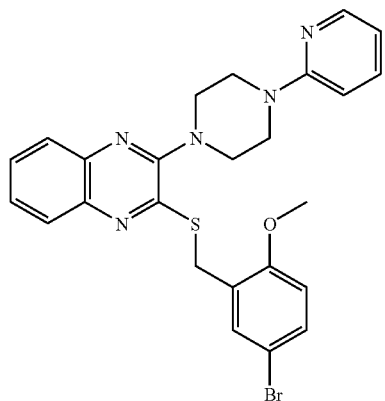 |
| Formate | 535.5096 | 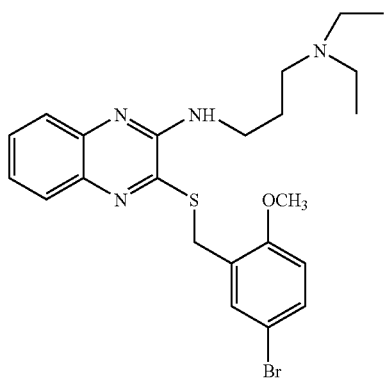 |

TABLE 5-continued
| Salt | Molecular Weight | Structure |
|---|---|---|
| Parent | 561.5456 | 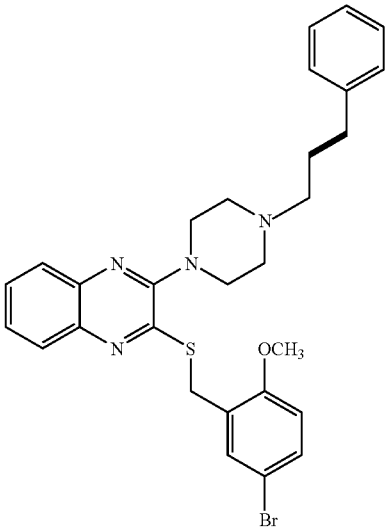 |
| Formate | 559.5316 | 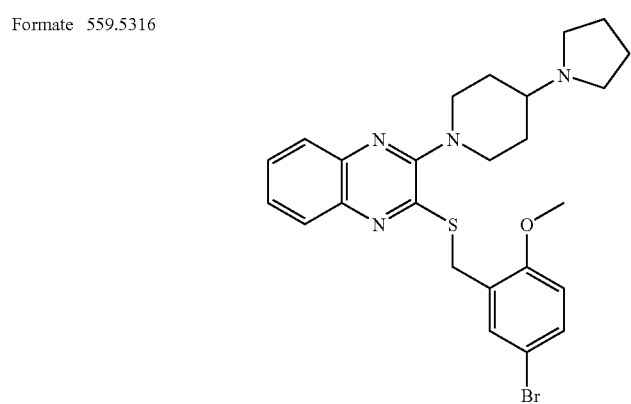 |
| Formate | 534.4815 | 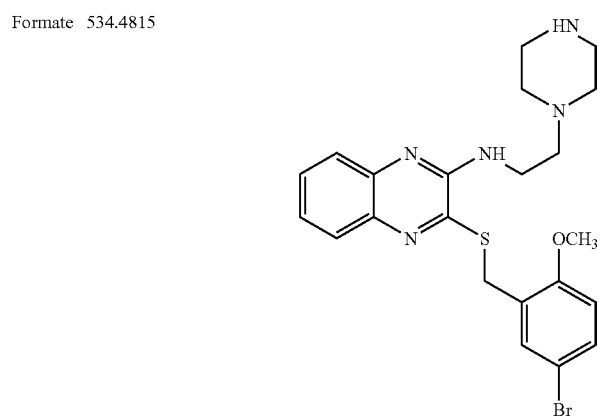 |

TABLE 5-continued
| Salt | Molecular Weight | Structure |
|---|---|---|
| Formate | 507.4559 | 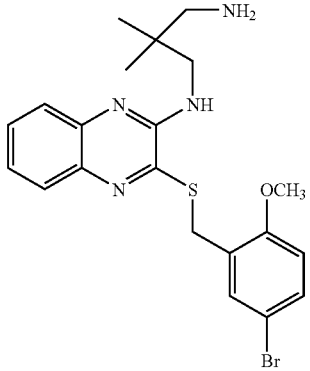 |
| Formate | 493.429 | 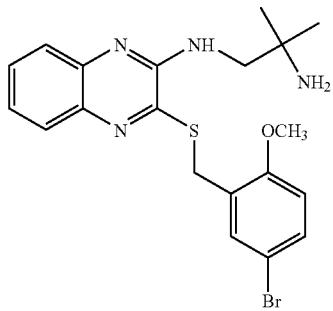 |
| Parent | 591.6153 | 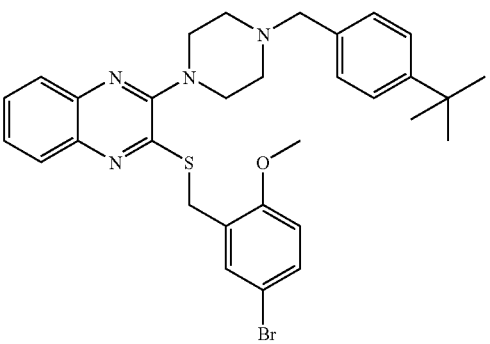 |
| Parent | 372.3079 | 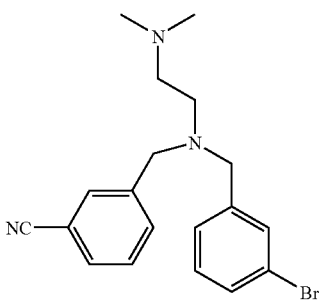 |

TABLE 5-continued

| Salt | Molecular Weight | Structure |
|---|---|---|
| Parent | 377.3244 | |
| Parent | 337.2916 | |
| Parent | 458.6678 | |
| Parent | 353.5078 | |
| Parent | 362.4717 | |

TABLE 5-continued
| Salt | Molecular Weight | Structure |
|---|---|---|
| Formate | 468.5781 | 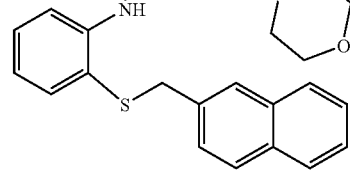 |
| Formate | 527.4406 | 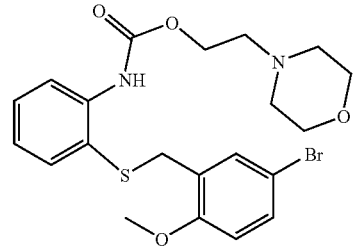 |
| Formate | 468.5781 | 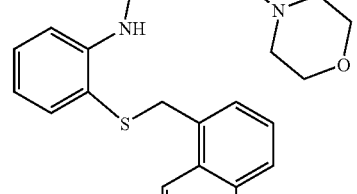 |
| Formate | 502.8609 | 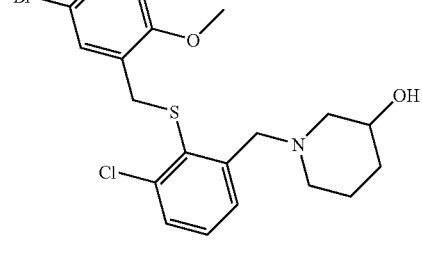 |
| Formate | 516.8877 | 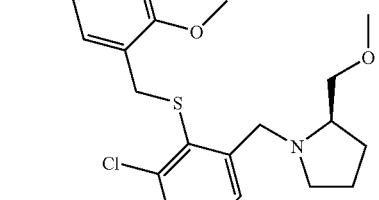 |

TABLE 5-continued
| Salt | Molecular Weight | Structure |
|---|---|---|
| Parent | 527.5285 | 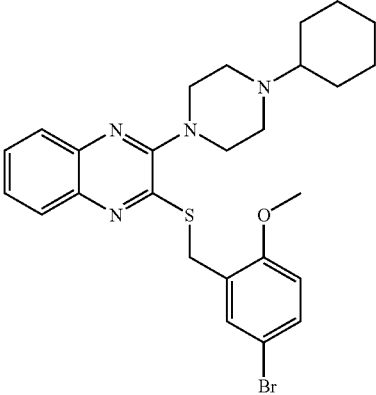 |
| Formate | 483.4339 | 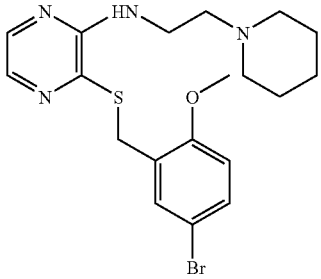 |
| Parent | 178.2774 | 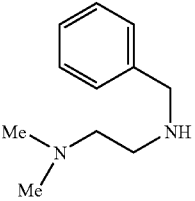 |
| Parent | 426.1942 | 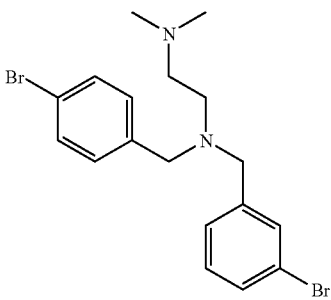 |
| Parent | 392.2957 | 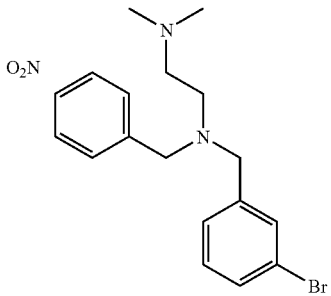 |

TABLE 5-continued
| Salt | Molecular Weight | Structure |
|---|---|---|
| Parent | 649.6519 | 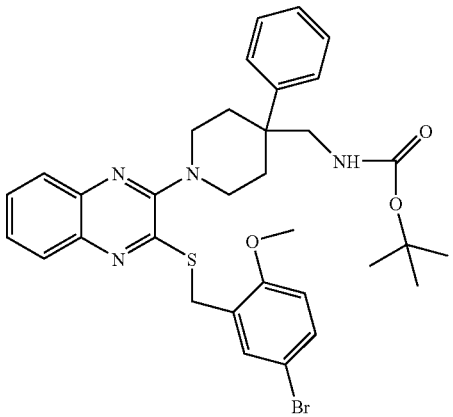 |
| Formate | 333.2297 | 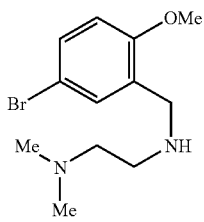 |
| Formate | 595.5646 | 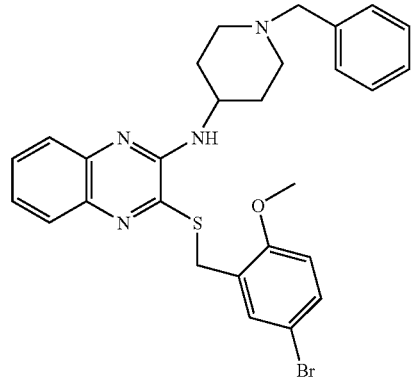 |
| Parent | 377.3244 | 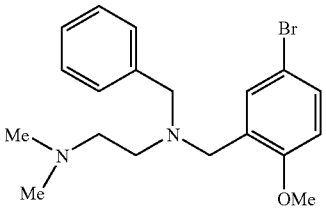 |
| Parent | 298.4283 | 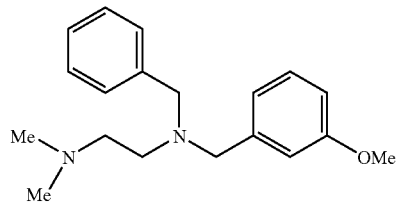 |

TABLE 5-continued
| Salt | Molecular Weight | Structure |
|---|---|---|
| Parent | 404.5762 | 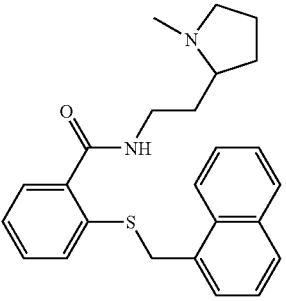 |
| Formate | 482.605 | 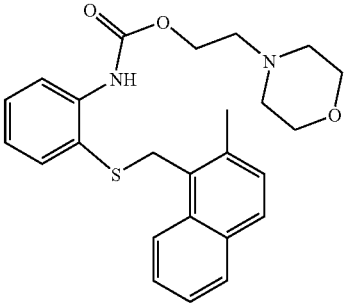 |
| Parent | 321.2376 | 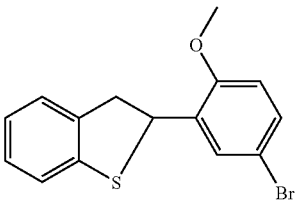 |
| Parent | 454.6122 | 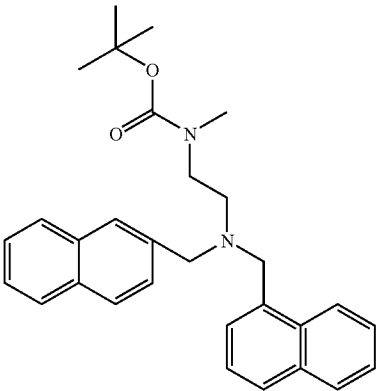 |

TABLE 5-continued
| Salt | Molecular Weight | Structure |
| --- | --- | --- |
| Parent | 513.4747 | 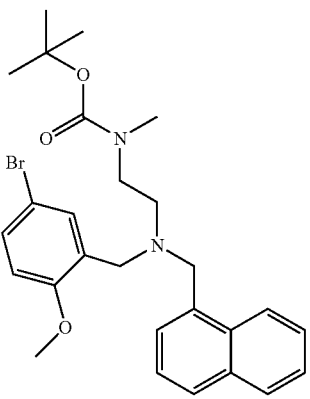 |
| Parent | 432.9709 | 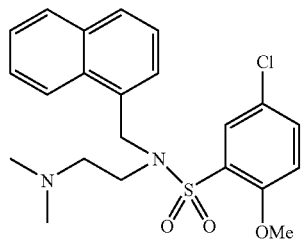 |
| Parent | 467.449 | 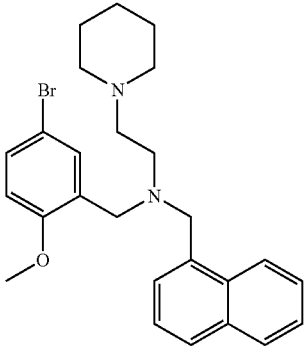 |
| Parent | 382.5267 | 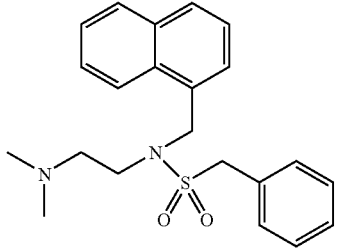 |
| Parent | 398.5261 | 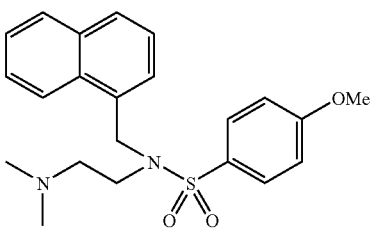 |

TABLE 5-continued

| Salt | Molecular Weight | Structure |
|---|---|---|
| HCl | 451.0753 | |
| HCl | 418.0454 | |
| HCl | 443.0552 | |
| Parent | 447.6446 | |
| Parent | 402.5603 | |

TABLE 5-continued

| Salt | Molecular Weight | Structure |
|---|---|---|
| Parent | 549.5346 | 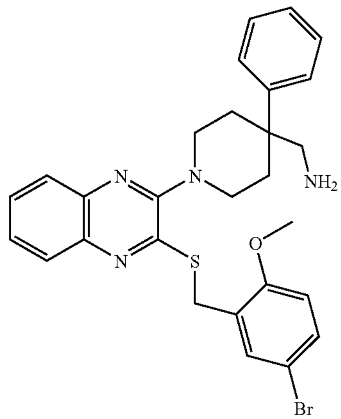 |
| Formate | 581.5377 | |
| Formate | 443.3691 | |
| Formate | 485.4497 | |

TABLE 5-continued
| Salt | Molecular Weight | Structure |
|---|---|---|
| Formate | 523.4986 | 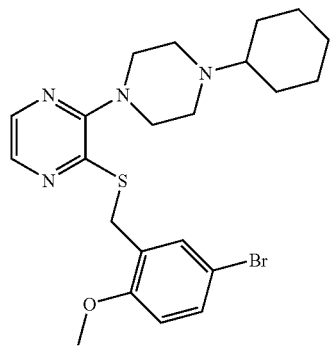 |
| Formate | 457.396 | 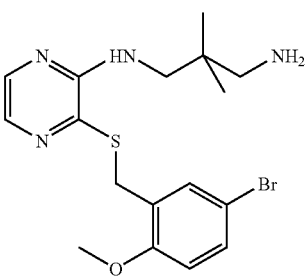 |
| Formate | 529.4595 | 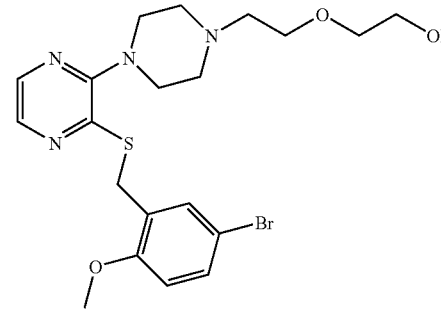 |
| Formate | 338.4082 | 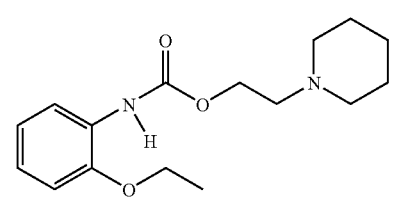 |
| Formate | 340.3808 | 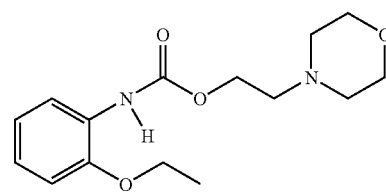 |

TABLE 5-continued
| Salt | Molecular Weight | Structure |
|---|---|---|
| HCl | 442.024 | 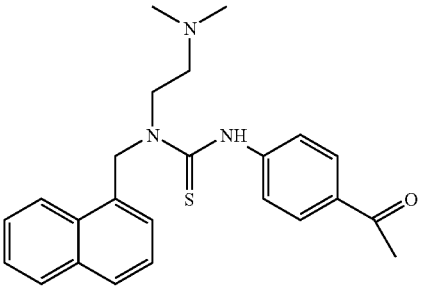 |
| Parent | 508.4765 | 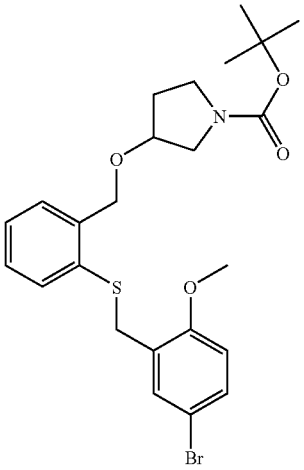 |
| Parent | 508.4765 | 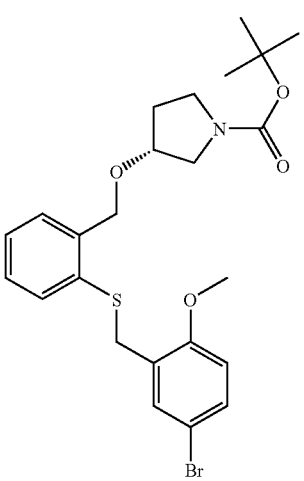 |

TABLE 5-continued

| Salt | Molecular Weight | Structure |
|---|---|---|
| Parent | 522.5034 | |
| Parent | 522.5034 | |
| Parent | 522.5034 | |

TABLE 5-continued
| Salt | Molecular Weight | Structure |
|---|---|---|
| Parent | 428.5524 | 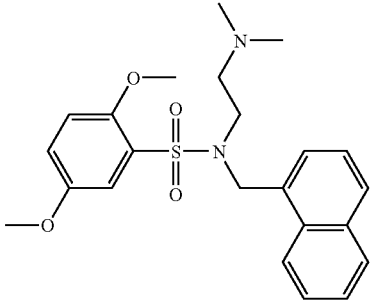 |
| Parent | 374.528 | 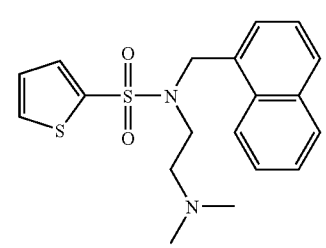 |
| Parent | 387.5029 | 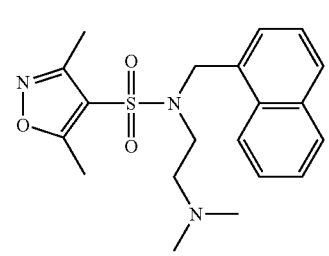 |
| Parent | 294.4399 | 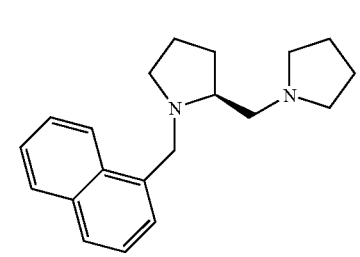 |
| Parent | 353.3024 | 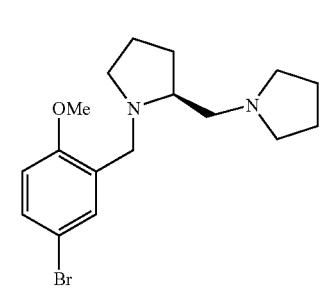 |
| Formate | 336.3924 | 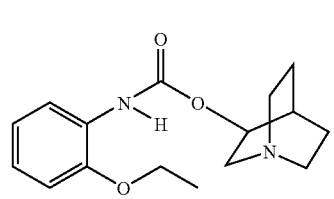 |

TABLE 5-continued

| Salt | Molecular Weight | Structure |
|---|---|---|
| Parent | 293.4118 | |
| Parent | 336.4003 | |
| Parent | 318.4619 | |
| Parent | 378.4742 | |
| Parent | 406.528 | |

TABLE 5-continued
| Salt | Molecular Weight | Structure |
|---|---|---|
| Parent | 464.4051 | 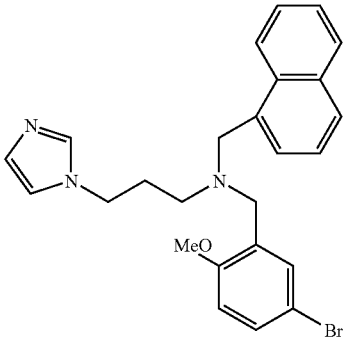 |
| Parent | 364.4473 | 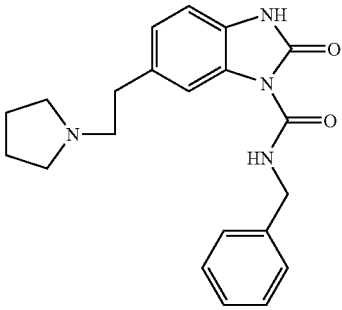 |
| Formate | 400.5463 | 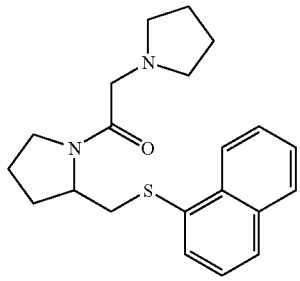 |
| Parent | 430.5902 | 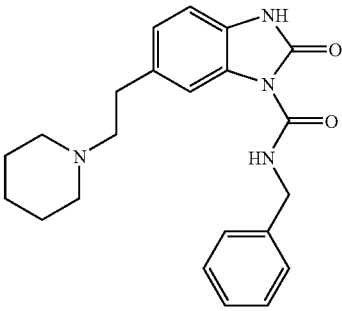 |
| Not Determined | | 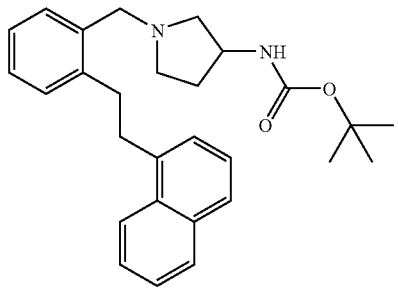 |

TABLE 5-continued

| Salt | Molecular Weight | Structure |
|---|---|---|
| HCl | 472.873 | 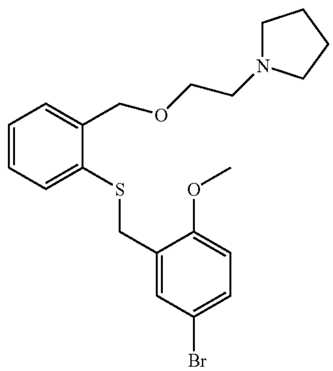 |
| Formate | 467.388 | 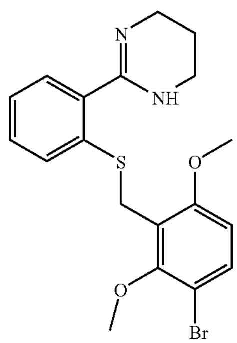 |
| Parent | 278.3538 | |
| Parent | 282.4289 | |
| Parent | 296.4558 | |

TABLE 5-continued
| Salt | Molecular Weight | Structure |
|---|---|---|
| Formate | 443.3855 | 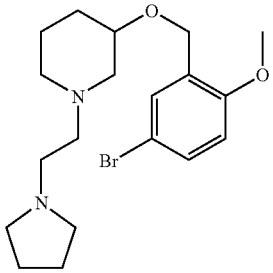 |
| Parent | 336.5206 | 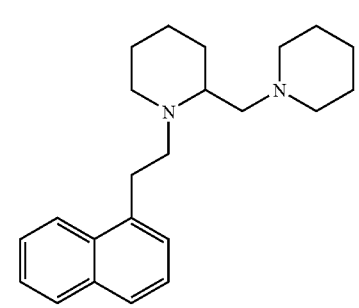 |
| Parent | 343.4717 | 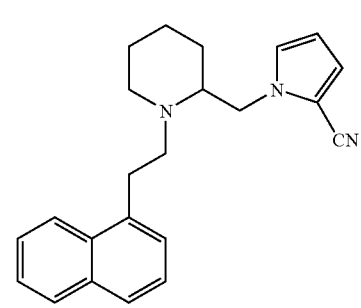 |
| Not Determined | | 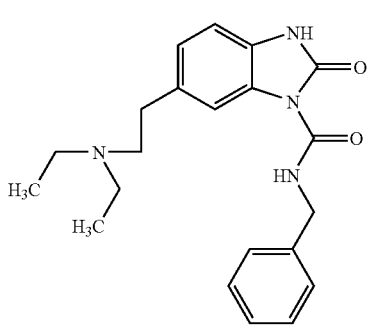 |
| Not Determined | | 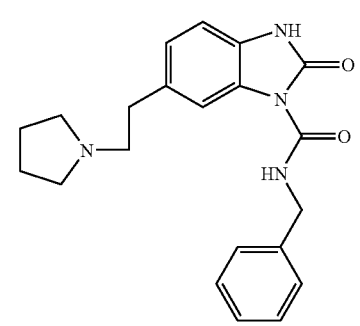 |

TABLE 5-continued

| Salt | Molecular Weight | Structure |
|---|---|---|
| | Not Determined | 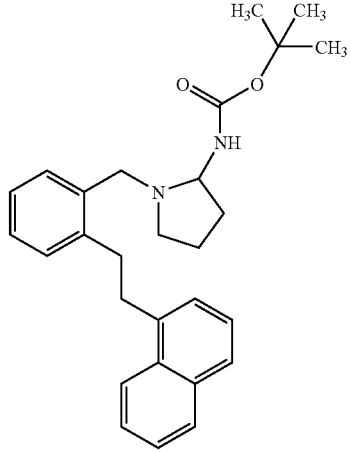 |

Example 5 cAMP Assay for MC4-R Antagonist Activity

Method

MC4 Receptors are expressed in stably transfected K293 cells. The cells are incubated in DMEM base medium (10% FBS, 1× glutamine, and 0.4 mg/ml G418) at 37° C., in an atmosphere of 6.0% $CO_2$ and 90% relative humidity. Two days before the experiment, the cells are trypsinized and 200 µl of the cell suspension (138,000 cells/ml) is deposited into 96-well Costar cell culture plates.

The test compounds are then dissolved in DMSO creating a 30 mM stock solution, which is subsequently diluted to 180, 650, 20, 6.6, 2.2 µM in OPTI-MEM (GIBCO-BRL) media with 50 µM IBMX (isobutylmethylxanthine, Sigma) minutes before the experiment.

The media is then thoroughly removed from the cell culture plates through a 12-channel straight manifold. 90 µl of OPTI-MEM media with 50 µM IBMX is added to each well (McHale et al. *FEBS Letters* 345 (1994) 147-150). The plate is then placed in an incubator set at 37° C., 6.0% $CO_2$ and 90% relative humidity. After 15 minutes of incubation, 90 µl of the test compound solutions (or a control solution of OPTI-MEM and IBMX) are added and the plates are incubated for another 10 minutes. 20 µl of the ligand MSH solution in OPTI-MEM is then added. The cell plates are incubated for an additional hour at 37° C.

After the incubation, the media mixture is removed by 12-channel straight manifold. 60 µl of 70% ethanol is added to each well. The plates are then placed on a shaker for 30 minutes to extract the cAMP. The amount of cAMP is detected by the cyclic AMP [125I] Biotrak SPA screening assay system (Amersham). The system involves adding 50 µl of 1× assay buffer into each well of an OptiPlate-96 (Packard). 50 µl of the tracer solution (cAMP-$^{125}$I) is added into each well. 5 µl of the cAMP extract is added into the mixture, followed by the addition of cAMP antiserum and 50 µl of SPA PVT-antibody binding beads. The plates are then covered with TopSeal-A (Parkard) and incubated at room temperature for up to fifteen hours before being analyzed using a TOPCOUNT machine.

Compounds O, N, AG, AL, and AM were found to be at least 100 fold more selective for MC4-R than MC1-R, MC3-R and MC5-R.

Example 6

In Vivo Assay for MC4-R Antagonist Activity

The following in vivo assay was used to test the effects of MC4-R antagonists on mice.

Male lean C57BL/6J mice were individually housed in macrolon cages (22±2 C.°; 12:12 h light/dark cycle with lights off at 6 pm). Tap water and mouse chow diet were given ad libitum. Mice were stereotaxically implanted with a chronic guide cannula aimed to the third ventricle (intracerabroventricular) one week prior to testing.

Figure 1B:
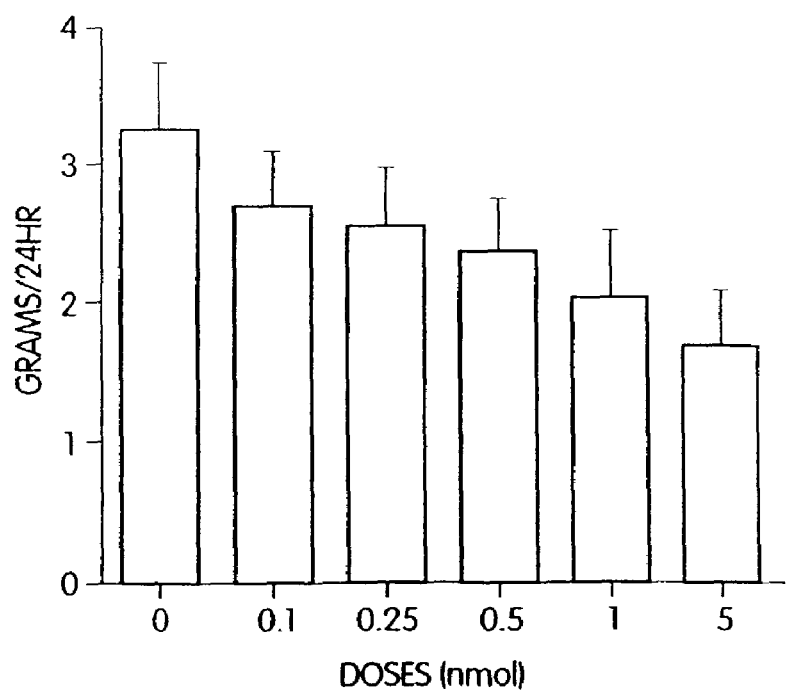

It had been previously determined that food deprived lean mice which had been injected with 0.1 nmol of MT II (a MC4-R agonist) prior to refeeding showed decreased feeding response within 1 hour of injection (FIG. 1). In previous experiments using peptidic MC4-R antagonists, it has been shown that the decreased feeding response of MT II treated food-deprived mice can be reversed by the intracerabroventricular injection of MC4-R antagonists.

In this experiment, food deprived lean mice were injected intracerabroventricularly with either Compound N or Compound O, at a dose of 15 nmol prior to injection of MT II at the dose of 0.05 nmol.

Figure 2:
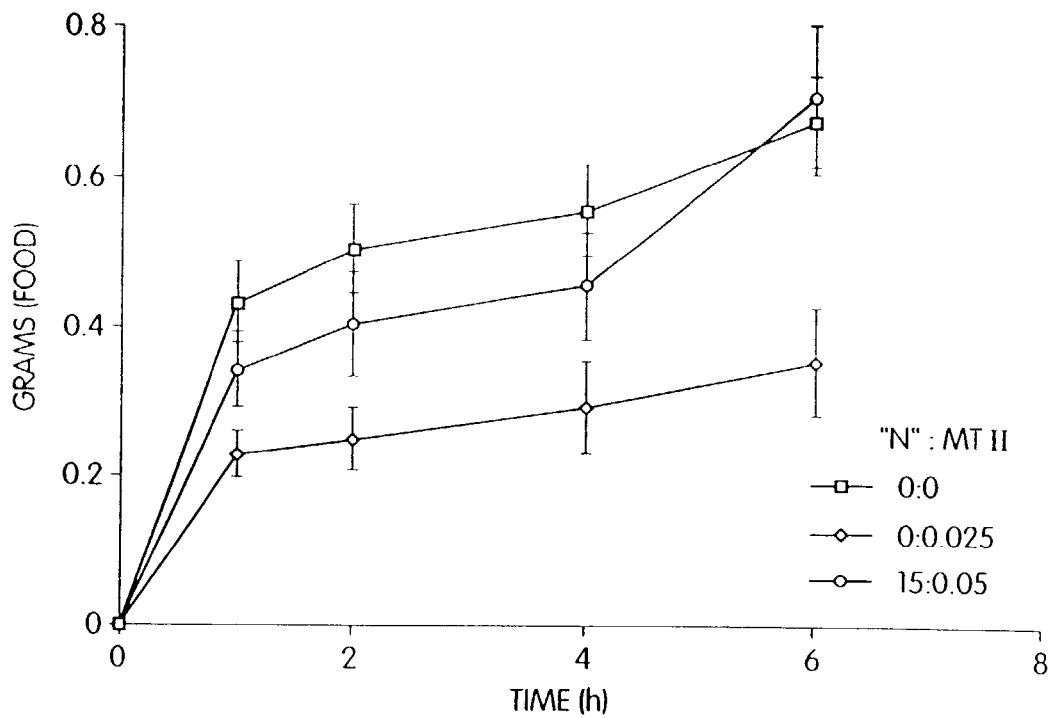
FIG. 2 is a graph depicting the effects of treating lean mice with Compound N and MT II on food intake over a six hour period.
Figure 3:
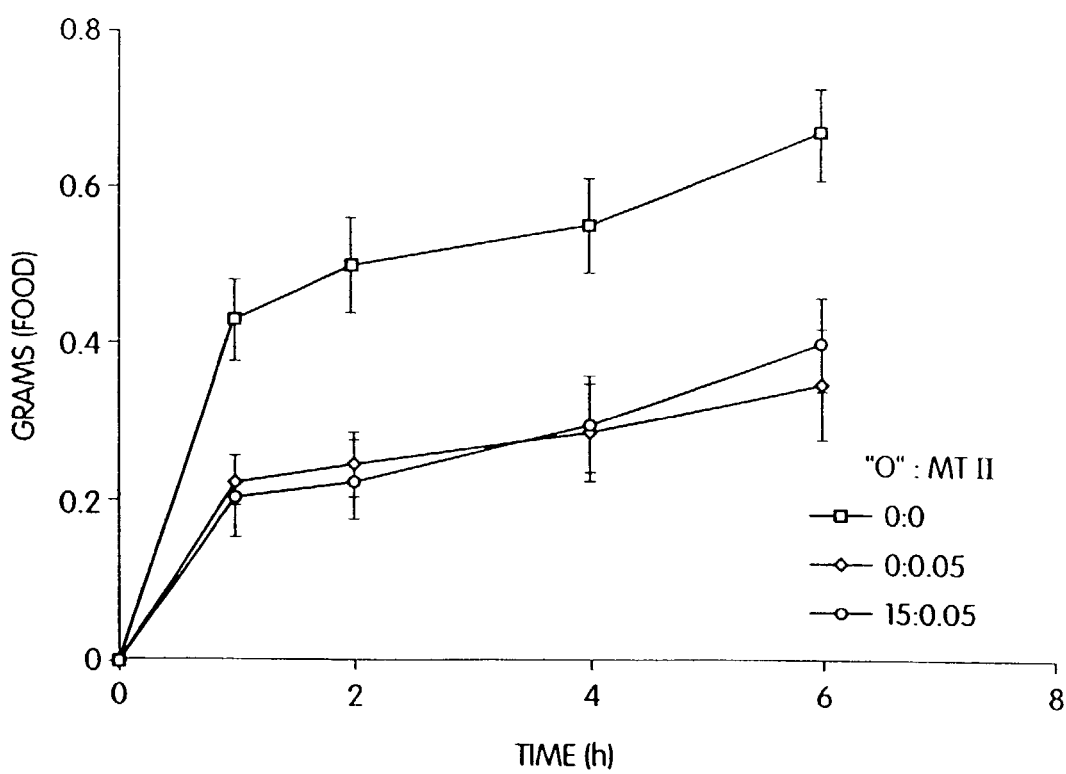
FIG. 3 is a graph depicting the effects of treating lean mice with Compound O and MT II on food intake over a six hour period.

The results of the experiment are shown in FIGS. 2 and 3. FIG. 2 shows that administration of 15 nmol of Compound N partially reverses the effect of the administration of the MC4-R agonist, MT II. FIG. 3 shows that administration of Compound O did not significantly effect the food intake of mice treated with MT II.

Example 7 cAMP Assay for MC Receptor Agonist Activity (cAMP Assay)

The cAMP assay identifies compounds which have agonist activity against MC receptors. It is used to identify the selectivity of agonist which selectively antagonize receptors of interest. The following method is outlined for MC4-R, but corresponding procedures were used for the other MC receptors, MC1-R, MC3-R, and MC5-R.

Method

MC4 Receptors are expressed in stably transfected HEK293 cells. The cells are incubated in DMEM base medium (10% FBS, 1× glutamine, and 0.4 mg/ml G418) at 37° C., in an atmosphere of 6.0% $CO_2$ and 90% relative humidity. Two days before the experiment, the cells are trypsinized and 200 μl of the cell suspension (138,000 cells/ml) is deposited into 96-well Costar cell culture plates.

The test compounds are then dissolved in DMSO creating a 30 mM stock solution, which is subsequently diluted to 180, 650, 20, 6.6, 2.2 μM in OPTI-MEM (GIBCO-BRL) media with 50 μM IBMX (isobutylmethylxanthine, Sigma) minutes before the experiment.

The media is then thoroughly removed from the cell culture plates through a 12-channel straight manifold. 90 μl of OPTI-MEM media with 50 μM IBMX is added to each well (McHale et al. *FEBS Letters* 345 (1994) 147-150). The plate is then placed in an incubator set at 37° C., 6.0% $CO_2$ and 90% relative humidity. After 15 minutes of incubation, 90 μl of the test compound solutions (or a control solution of OPTI-MEM and IBMX) are added and the plates are incubated for another 10 minutes. 20 μl of the ligand MSH solution in OPTI-MEM is then added. The cell plates are incubated for an additional hour at 37° C.

After the incubation, the media mixture is removed by 12-channel straight manifold. 60 μl of 70% ethanol is added to each well. The plates are then placed on a shaker for 30 minutes to extract the cAMP. The amount of cAMP is detected by the cyclic AMP [$^{125}$I] Biotrak SPA screening assay system (Amersham). The system involves adding 50 μl of 1× assay buffer into each well of an OptiPlate-96 (Packard). 50 μl of the tracer solution (cAMP-$^{125}$I) is added into each well. 5 μl of the cAMP extract is added into the mixture, followed by the addition of cAMP antiserum and 50 μl of SPA PVT-antibody binding beads. The plates are then covered with TopSeal-A (Packard) and incubated at room temperature for up to fifteen hours before being analyzed using a TOPCOUNT machine.

Incorporation by Reference

The entire contents of all references and patents cited herein are hereby incorporated by reference. The entire contents of U.S. Pat. No. 5,908,609 and all its references also expressly incorporated herein.

Equivalents

Those skilled in the art will recognize, or be able to ascertain using no more than routine experimentation, many equivalents to the specific embodiments and methods described herein. Such equivalents are intended to be encompassed by the scope of the following claims.

What is claimed is:
1. A compound of formula XVII:

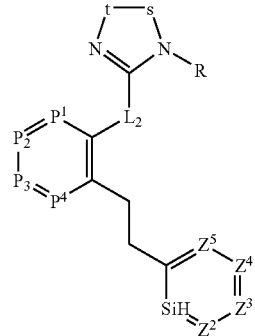

XVII or a pharmaceutically acceptable salt thereof, wherein:
$P^1$, $P^2$, $P^3$, and $P^4$ are each selected from a substituted or unsubstituted carbon;
$Z^1$ is CH or a carbon substituted with $R^7$;
$Z^2$ is CH or a carbon substituted with $R^8$;
$Z^3$, $Z^4$ and $Z^5$ are each independently selected from CH or a carbon substituted with $R^9$;
$R^7$ is $C_{1-3}$ alkoxy, $C_{1-3}$ haloalkoxy, cyano, $C_{1-3}$ cyanoalkyl, halo, $C_{1-3}$ alkyl, or $C_{1-3}$ haloalkyl;
$R^8$ is halo, $C_{1-3}$ alkyl, $C_{1-3}$ haloalkyl, or $R^7$ and $R^8$ are taken together with their intervening atoms to form a fused, 5-6 membered aromatic or nonaromatic ring having 0-2 ring heteroatoms selected from oxygen, nitrogen or sulfur;
each $R^9$ is independently selected from halo, cyano, trialkylsiloxy, $C_{1-6}$ alkyl, $C_{1-6}$ haloalkyl, $C_{1-6}$ alkoxy, $C_{1-6}$ haloalkoxy, $C_{1-6}$ alkenyl, $C_{1-6}$ alkynyl, $N(R^{10})_2$, $(C_{1-6}$ alkyl)-$N(R^{10})_2$, $O(C_{1-6}$ alkyl)-$N(R^{10})_2$, $C_{1-6}$ alkylsulfonyl, $C_{1-6}$ alkylthio, or phenyl, or two $R^9$ on neighboring carbons are taken together to form a fused, 5-6 membered aromatic or nonaromatic ring having 0-2 ring heteroatoms selected from oxygen, nitrogen, or sulfur;
each $R^{10}$ is independently selected from hydrogen, $C_{1-4}$ alkyl, or two $R^{10}$ on the same nitrogen are taken together with their intervening nitrogen to form a 5-6 membered ring having 1-2 ring heteroatoms selected from oxygen, nitrogen or sulfur;
$L_2$ is a covalent bond, a substituted or unsubstituted 1-2 carbon chain or a 2 carbon carbonyl chain, wherein one of the carbons along with the hydrogen attached thereto is optionally replaced by oxygen, $N(R^{10})$, or sulfur;
t is $CH_2$, $CHR^3$, or $CR^3R^4$, and s is $CH_2$, $CHR^5$, or $CR^5R^6$, or t-s taken together is CH=CH, $CR^3$=CH, CH=$CR^5$ or $CR^3$=$CR^5$; and have at least one feature selected from the group consisting of (i) t=$CH_2$, (ii) s=$CH_2$, (iii) t is $CHR^3$ and s is $CHR^5$ wherein $R^3$ and $R^5$ are taken together with their intervening atom or atoms to form a fused 3-7 membered non-aromatic ring having 0-2 ring heteroatoms selected from oxygen, nitrogen, or sulfur, and (iv) R and $R^5$ are taken together with their intervening atoms to form a fused pyrrolidino or piperidino ring;
$R^3$, $R^4$, $R^5$, and $R^6$ are each independently selected from $C_{1-4}$ alkyl, $C_{1-4}$ alkylcarboxyl, $C_{1-4}$ alkoxycarbonyl, $C_{1-4}$ alkylcarboxamide, or two of $R^3$, $R^4$, $R^5$, and $R^6$ are taken together with their intervening atom or atoms to form a fused 3-7 membered aromatic or non-aromatic or 3-7 membered spirocyclic ring, having 0-2 ring heteroatoms selected from oxygen, nitrogen or sulfur;

R is hydrogen or a $C_{1-8}$ alkyl or $C_{1-8}$ alkylcarbonyl that is substituted with 0-2 $R^{11}$, or R and $L_2$ are taken together with their intervening atoms to form a fused five membered ring having 1-2 ring heteroatoms selected from oxygen, nitrogen or sulfur;

each $R^{11}$ is independently selected from $C_{1-3}$ alkyl, cyano, halo, haloalkyl, $N(R^{10})_2$, $(C=O)N(R^{10})_2$, $OC(=O)N(R^{10})_2$, OH, $S(C_{1-6}$ alkyl), $SO_2(C_{1-6}$ alkyl), $SO_2N(R^{10})_2$, $C_{1-6}$ alkoxy, $C_{1-6}$ alkylcarbonyl, $C_{1-6}$ alkylcarboxyl, $C_{1-6}$ alkoxycarboxyl, $C_{5-6}$ aryl, $C_{6-10}$ arylalkyl, or a 3-6 membered heterocyclyl having 1 or 2 heteroatoms.

2. The compound of claim 1 having one or more features selected from the group consisting of:
   (a) $Z^1$ is a carbon substituted with $R^7$;
   (b) $Z^2$, $Z^3$ and $Z^5$ are each CH;
   (c) $Z^4$ is a carbon substituted with $R^9$;
   (d) $L_2$ is a covalent bond; and
   (e) R is hydrogen or $C_{1-8}$ alkyl that is substituted with 0-2 $R^{11}$.

3. The compound of claim 2 or salt thereof wherein:
   (a) $Z^1$ is a carbon substituted with $R^7$;
   (b) $Z^2$, $Z^3$ and $Z^5$ are each CH;
   (c) $Z^4$ is a carbon substituted with $R^9$;
   (d) $L^2$ is a covalent bond;
   (e) t is $CH_2$;
   (f) s is $CH_2$; and
   (g) R is hydrogen or $C_{1-8}$ alkyl that is substituted with 0-2 $R^{11}$.

4. The compound of claim 2 or salt thereof having one or more features selected from the group consisting of:
   (a) $P^1$, $P^2$, and $P^3$ are each an unsubstituted carbon, and $P^4$ is an unsubstituted carbon, or a carbon substituted with a halogen or alkoxy;
   (b) $R^7$ is alkoxy;
   (c) $R^9$ is halo, cyano or alkynyl; and
   (d) R is hydrogen, or $C_{1-4}$ alkyl that is substituted with 0-2 $R^{11}$, wherein each $R^{11}$ is independently selected from $C_{1-3}$ alkyl, cyano, halo, $C_{1-4}$ alkoxy, or a 5-6 membered heterocyclyl having 1 or 2 heteroatoms.

5. The compound of claim 2 or salt thereof wherein:
   (a) $P^1$, $P^2$, and $P^3$ are each an unsubstituted carbon, and $P^4$ is an unsubstituted carbon, or a carbon substituted with a halogen or alkoxy;
   (b) $R^7$ is alkoxy;
   (c) $R^9$ is halo, cyano or alkynyl; and
   (d) R is hydrogen, or $C_{1-4}$ alkyl that is substituted with 0-2 $R^{11}$, and each $R^{11}$ is independently selected from $C_{1-3}$ alkyl, cyano, halo, $C_{1-4}$ alkoxy, or a 5-6 membered heterocyclyl having 1 or 2 heteroatoms.

6. The compound of claim 1 or salt thereof having one or more features selected from the group consisting of:
   (a) $Z^1$ is a carbon substituted with $R^7$, $Z^2$ is a carbon substituted with $R^8$, and $R^7$ and $R^8$ are taken together to form a fused, 5-6 membered aromatic or nonaromatic ring having 0-2 ring heteroatoms selected from oxygen, nitrogen or sulfur;
   (b) $Z^3$ and $Z^5$ are each CH;
   (c) $Z^4$ is a carbon substituted with $R^9$;
   (d) $L^2$ is a covalent bond; and
   (e) R is hydrogen or $C_{1-8}$ alkyl that is substituted with 0-2 $R^{11}$.

7. The compound of claim 6 or salt thereof wherein:
   (a) $Z^1$ is a carbon substituted with $R^7$, $Z^2$ is a carbon substituted with $R^8$, and $R^7$ and $R^8$ are taken together to form a fused, 5-6 membered aromatic or nonaromatic ring having 0-2 ring heteroatoms selected from oxygen, nitrogen or sulfur;
   (b) $Z^3$ and $Z^5$ are each CH;
   (c) $Z^4$ is a carbon substituted with $R^9$;
   (d) $L^2$ is a covalent bond;
   (e) t is $CH_2$;
   (f) s is $CH_2$; and
   (g) R is hydrogen or $C_{1-8}$ alkyl that is substituted with 0-2 $R^{11}$.

8. The compound of claim 6 or salt thereof having one or more features selected from the group consisting of:
   (a) $P^1$, $P^2$, and $P^3$ are each an unsubstituted carbon, and $P^4$ is an unsubstituted carbon, or a carbon substituted with a halogen or alkoxy;
   (b) $R^7$ and $R^8$ are taken together to form a substituted or unsubstituted benzo, furano, thieno, dioxolo ring;
   (c) $R^9$ is halo, cyano or alkynyl; and
   (d) R is hydrogen, or $C_{1-4}$ alkyl that is substituted with 0-2 $R^{11}$, and each $R^{11}$ is independently selected from $C_{1-3}$ alkyl, cyano, halo, $C_{1-4}$ alkoxy, or a 5-6 membered heterocyclyl having 1 or 2 heteroatoms.

9. The compound of claim 7 or salt thereof wherein:
   (a) $P^1$, $P^2$, and $P^3$ are each an unsubstituted carbon, and $P^4$ is an unsubstituted carbon, or a carbon substituted with a halogen or alkoxy;
   (b) $R^7$ and $R^8$ are taken together to form a substituted or unsubstituted benzo, furano, thieno, dioxolo ring;
   (c) $R^9$ is halo, cyano or alkynyl; and
   (d) R is hydrogen, or $C_{1-4}$ alkyl that is substituted with 0-2 $R^{11}$, and each $R^{11}$ is independently selected from $C_{1-3}$ alkyl, cyano, halo, $C_{1-4}$ alkoxy, or a 5-6 membered heterocyclyl having 1 or 2 heteroatoms.

10. The compound of claim 1 or salt thereof having one or more features selected from the group consisting of:
    (a) $Z^1$ is a carbon substituted with $R^7$;
    (b) $Z^2$, $Z^3$ and $Z^5$ are each CH;
    (c) $Z^4$ is a carbon substituted with $R^9$;
    (d) $L^2$ is a covalent bond;
    (e) t is $CH_2$ or $CHR^3$;
    (f) s is $CHR^5$, or $CR^5R^6$, and
    (g) R is hydrogen or $C_{1-8}$ alkyl that is substituted with 0-2 $R^{11}$; wherein R and $R^5$ are optionally taken together with their intervening atoms to form a fused pyrrolidino or piperidino ring.

11. The compound of claim 10 or salt thereof wherein:
    (a) $Z^1$ is a carbon substituted with $R^7$;
    (b) $Z^2$, $Z^3$ and $Z^5$ are each CH;
    (c) $Z^4$ is a carbon substituted with $R^9$;
    (d) $L^2$ is a covalent bond;
    (e) t is $CH_2$ or $CHR^3$;
    (f) is $CHR^5$, or $CR^5R^{6,}$
    (g) R is hydrogen or $C_{1-8}$ alkyl that is substituted with 0-2 $R^{11}$, wherein $R^3$ and $R^5$ are optionally taken together with their intervening atom or atoms to form a fused 3-7 membered aromatic or non-aromatic ring or R and $R^5$ are optionally taken together with their intervening atoms to form a fused pyrrolidino or piperidino ring.

12. The compound of claim 10 or salt thereof having one or more features selected from the group consisting of:
    (a) $P^1$, $P^2$, and $P^3$ are each an unsubstituted carbon, and $P^4$ is an unsubstituted carbon, or a carbon substituted with a halogen or alkoxy;
    (b) $R^7$ is alkoxy;
    (c) $R^9$ is halo, cyano or alkynyl; and
    (d) s is $CHR^5$, wherein $R^5$ is taken together with $R^3$ to form a fused 5-6 membered non-aromatic ring, or $R^5$ is taken together with R with their intervening atoms to form a fused pyrrolidino or piperidino ring.

13. The compound of claim 11 or salt thereof wherein:
(a) $P^1$, $P^2$, and $P^3$ are each an unsubstituted carbon, and $P^4$ is an unsubstituted carbon, or a carbon substituted with a halogen or alkoxy;
(b) $R^7$ is alkoxy;
(c) $R^9$ is halo, cyano or alkynyl; and
(d) s is $CHR^5$, wherein $R^5$ is taken together with $R^3$ to form a fused 5-6 membered non-aromatic ring, or $R^5$ is taken together with R with their intervening atoms to form a fused pyrrolidino or piperidino ring.

14. The compound of claim 1 or salt thereof having one or more features selected from the group consisting of:
(a) $Z^1$ is a carbon substituted with $R^7$, $Z^2$ is a carbon substituted with $R^8$, and $R^7$ and $R^8$ are taken together to form a fused, 5-6 membered aromatic or nonaromatic ring having 0-2 ring heteroatoms selected from oxygen, nitrogen or sulfur;
(b) $Z^3$ and $Z^5$ are each CH;
(c) $Z^4$ is a carbon substituted with $R^9$;
(d) $L^2$ is a covalent bond;
(e) t is $CH_2$ or $CHR^3$;
(f) s is $CHR^5$, or $CR^5R^6$, and
(g) R is hydrogen or $C_{1-8}$ alkyl that is substituted with 0-2 $R^{11}$, or R and $R^5$ are taken together with their intervening atoms to form a fused pyrrolidino or piperidino ring.

15. The compound of claim 14 or salt thereof wherein:
(a) $Z^1$ is a carbon substituted with $R^7$, $Z^2$ is a carbon substituted with $R^8$, and $R^7$ and $R^8$ are taken together to form a fused, 5-6 membered aromatic or nonaromatic ring having 0-2 ring heteroatoms selected from oxygen, nitrogen or sulfur;
(b) $Z^3$ and $Z^5$ are each CH;
(c) $Z^4$ is a carbon substituted with $R^9$;
(d) $L^2$ is a covalent bond;
(e) t is $CH_2$ or $CHR^3$;
(f) s is $CHR^5$, or $CR^5R^6$, wherein $R^3$ and $R^5$ are optionally taken together with their intervening atom or atoms to form a fused 3-7 membered aromatic or non-aromatic ring; and
(g) R is hydrogen or $C_{1-8}$ alkyl that is substituted with 0-2 $R^{11}$, or R and $R^5$ are taken together with their intervening atoms to form a fused pyrrolidino or piperidino ring.

16. The compound of claim 14 or salt thereof having one or more features selected from the group consisting of:
(a) $P^1$, $P^2$, and $P^3$ are each an unsubstituted carbon, and $P^4$ is an unsubstituted carbon, or a carbon substituted with a halogen or alkoxy;
(b) $R^7$ and $R^8$ are taken together to form a substituted or unsubstituted benzo, furano, thieno, dioxolo ring;
(c) $R^9$ is halo, cyano or alkynyl; and
(d) s is $CHR^5$, wherein $R^5$ is taken together with $R^3$ to form a fused 5-6 membered non-aromatic ring, or $R^5$ is taken together with R with their intervening atoms to form a fused pyrrolidino or piperidino ring.

17. The compound of claim 15 or salt thereof wherein:
(a) $P^1$, $P^2$, and $P^3$ are each an unsubstituted carbon, and $P^4$ is an unsubstituted carbon, or a carbon substituted with a halogen or alkoxy;
(b) $R^7$ and $R^8$ are taken together to form a substituted or unsubstituted benzo, furano, thieno, dioxolo ring;
(c) $R^9$ is halo cyano or alkynyl; and
(d) s is $CHR^5$, wherein $R^5$ is taken together with $R^3$ to form a fused 5-6 membered non-aromatic ring, or $R^5$ is taken together with R with their intervening atoms to form a fused pyrrolidino or piperidino ring.

18. A compound selected from the group consisting of:

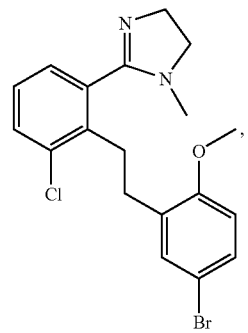

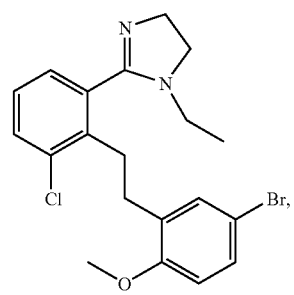

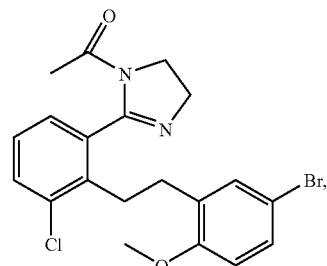

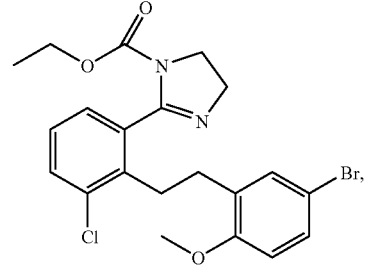

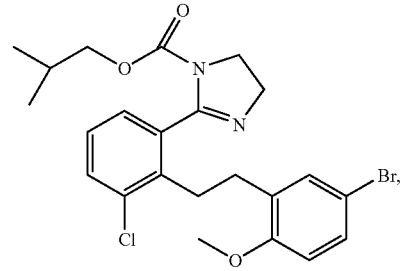

-continued
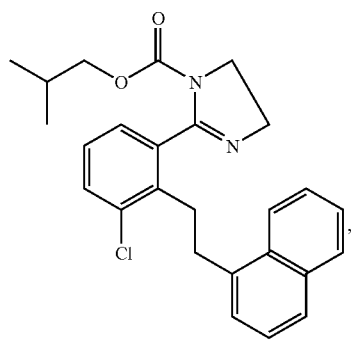
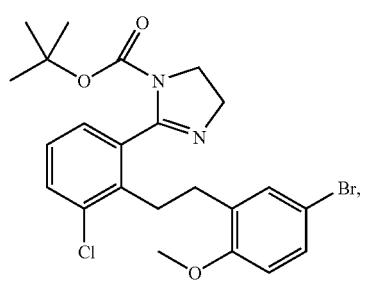
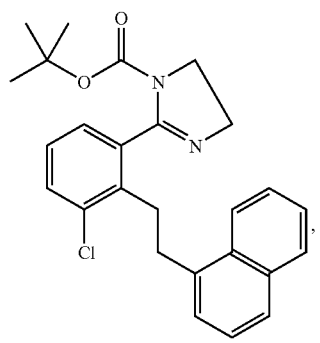
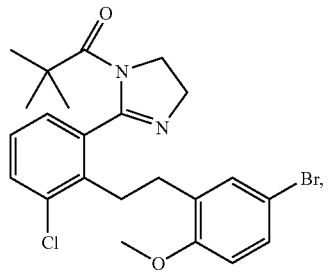
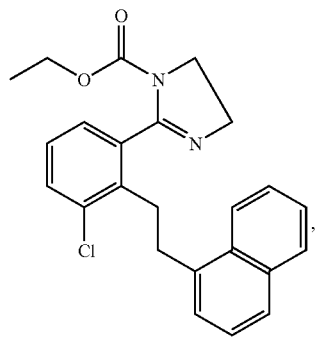
-continued
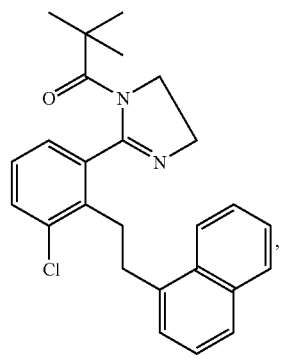
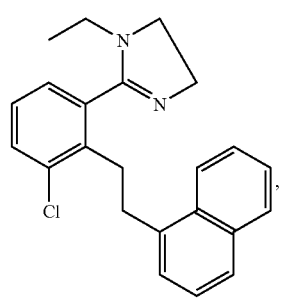
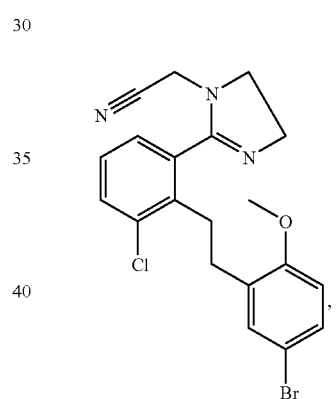
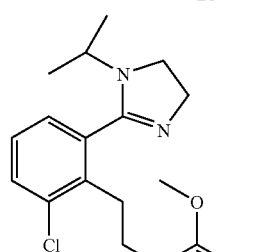
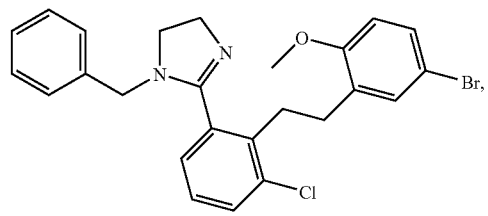

-continued
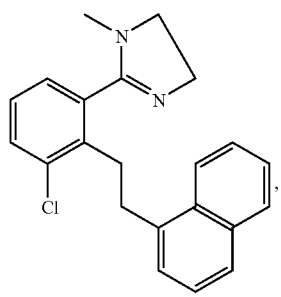
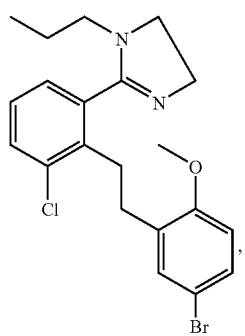
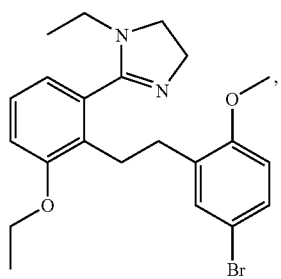
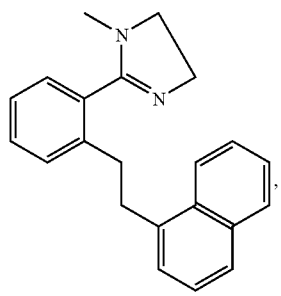
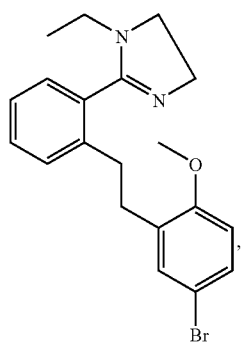
-continued
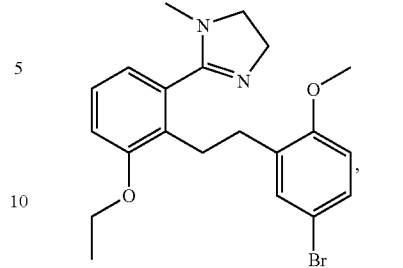
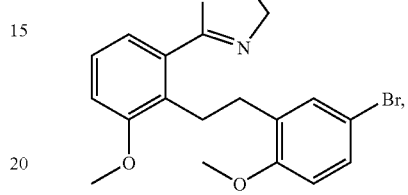
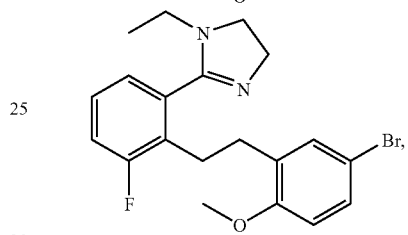
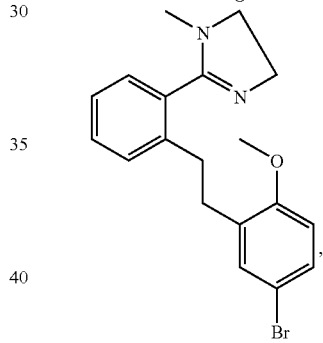
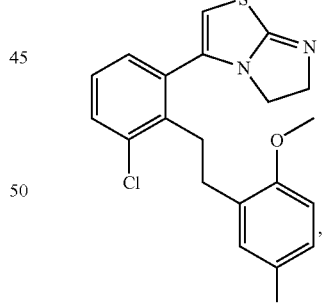
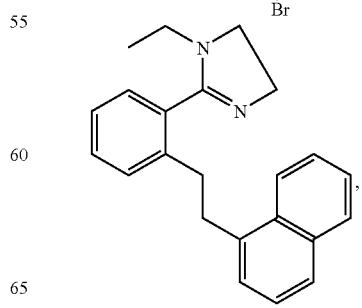

513
-continued
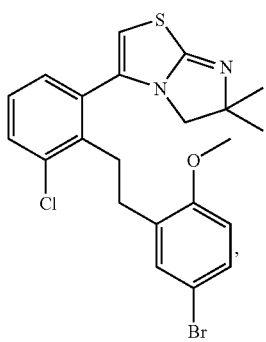
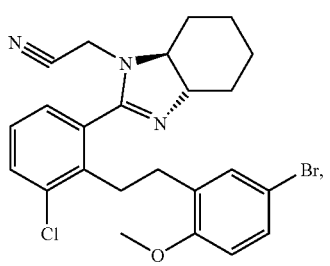
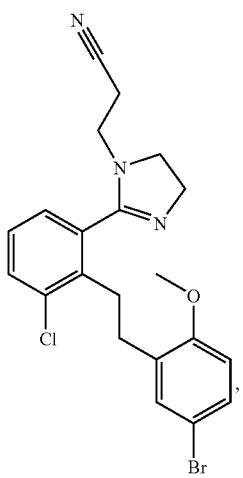
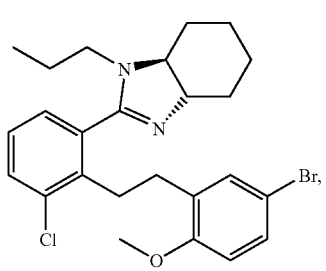
514
-continued
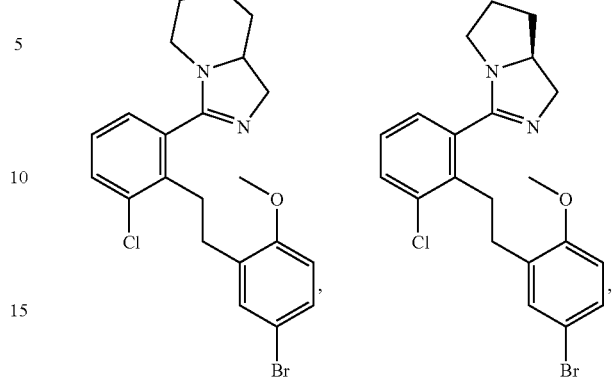
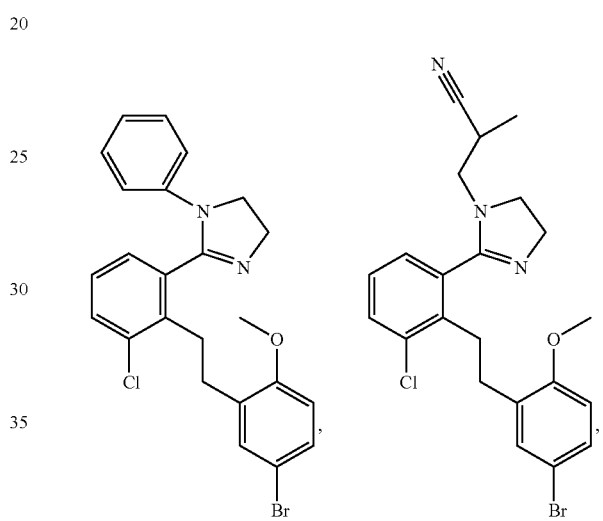
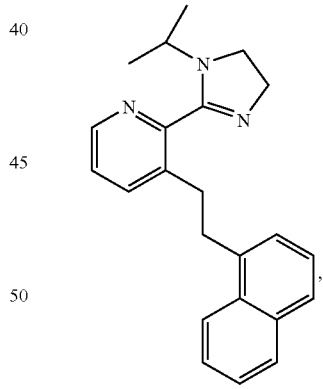
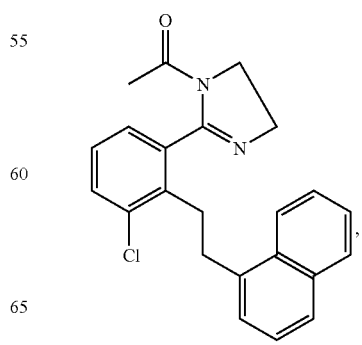

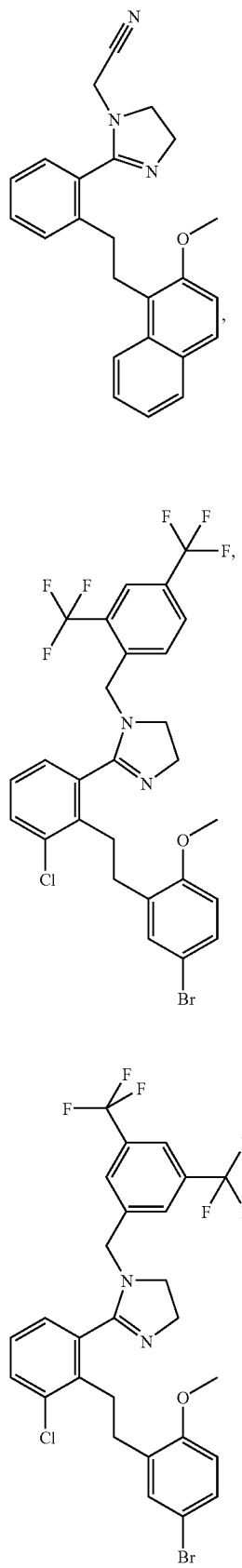
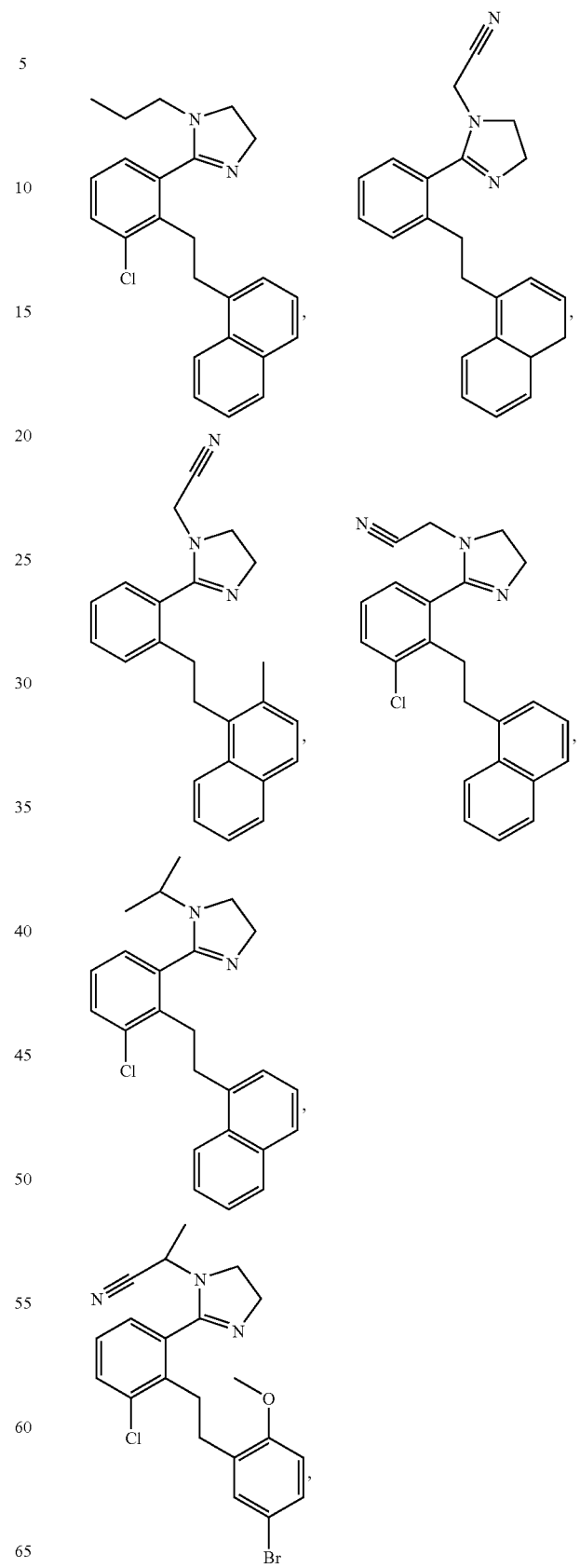

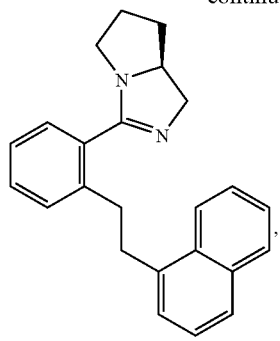
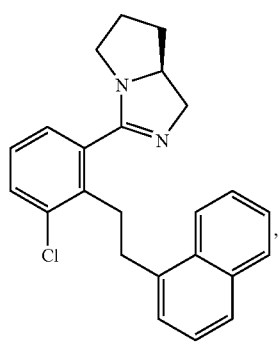
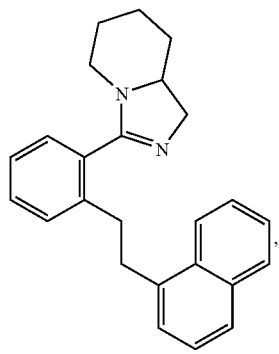
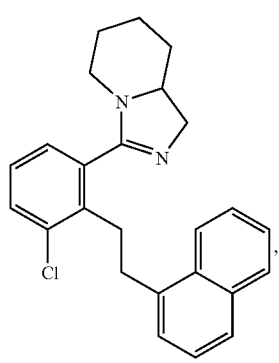
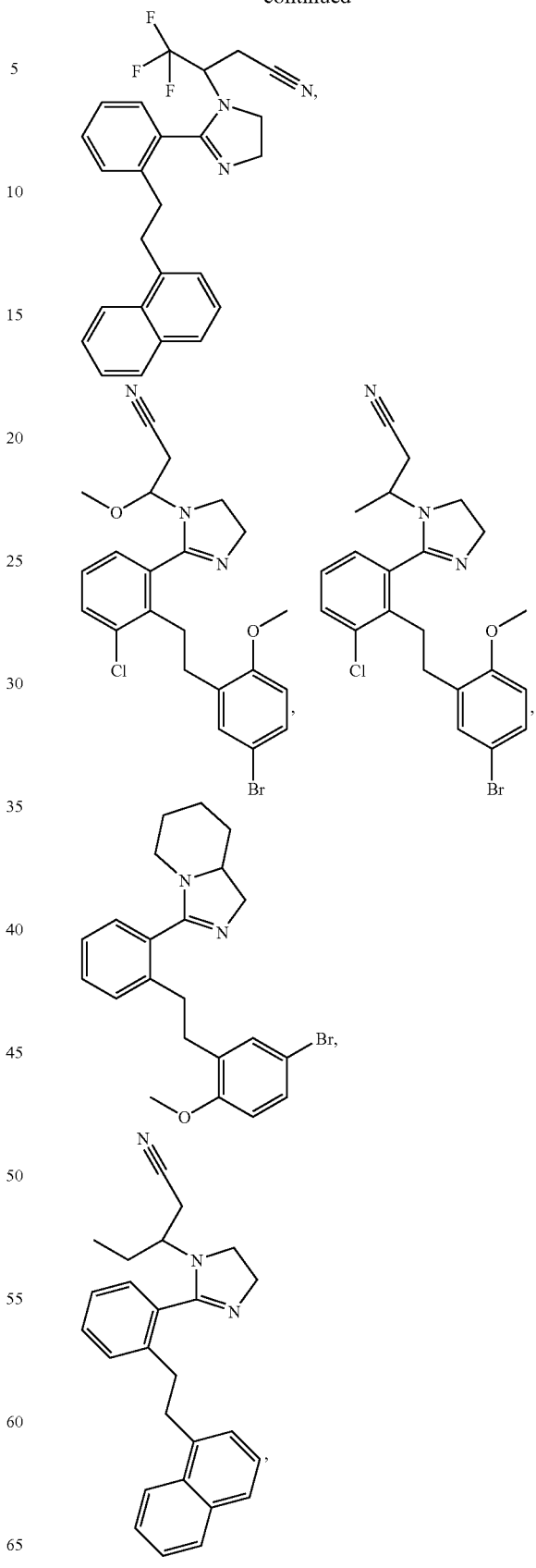

519                                    520
-continued                          -continued
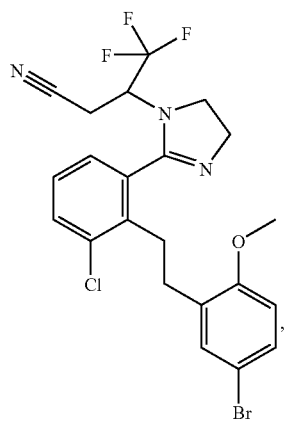
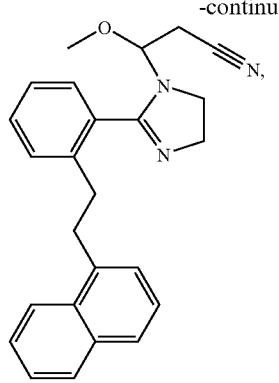
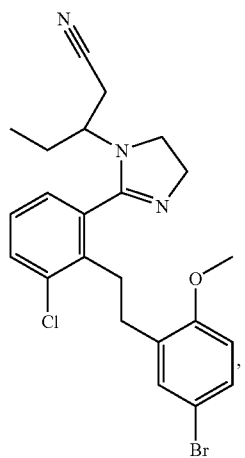
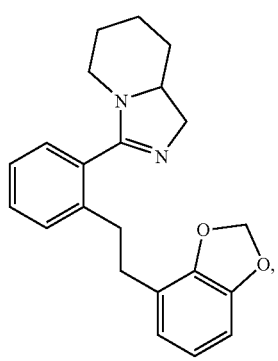
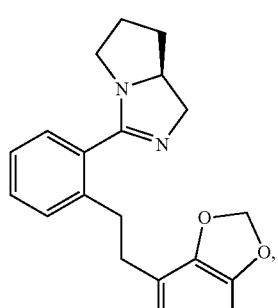
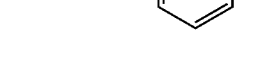
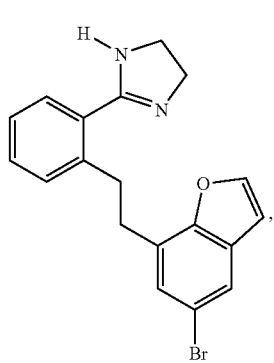
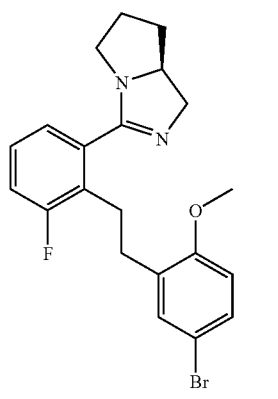
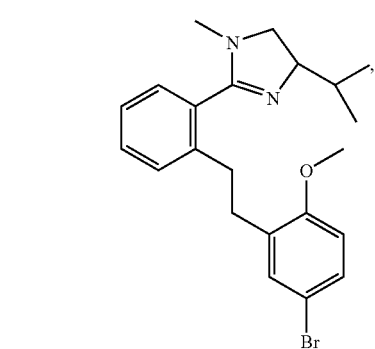

-continued
| 521 | 522 |
|---|---|
| 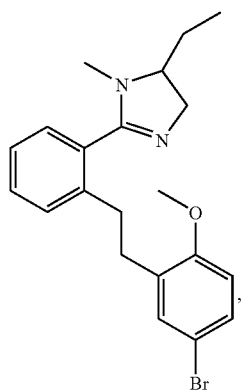 | 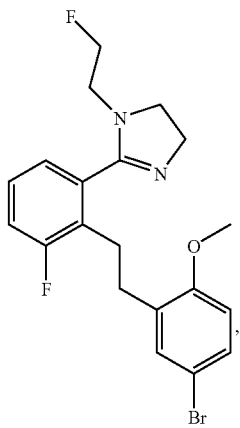 |
| 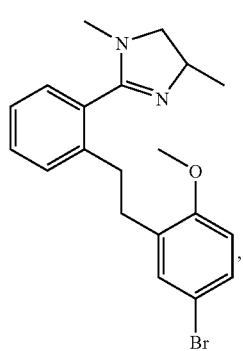 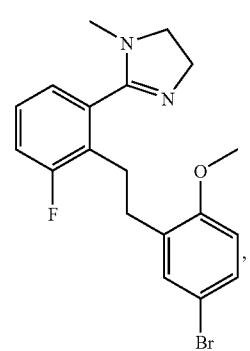 | 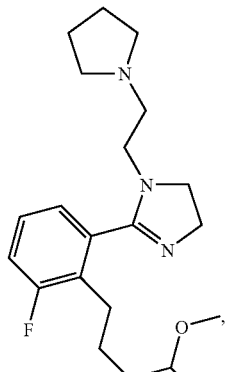 |
| 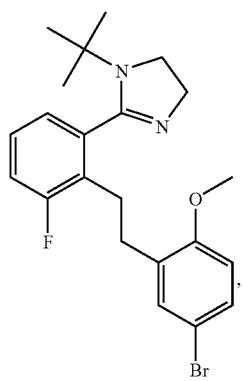 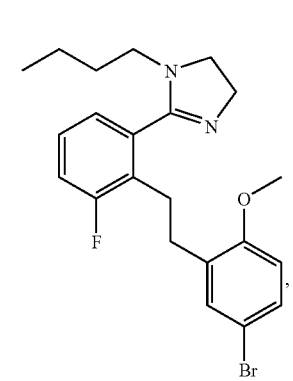 | 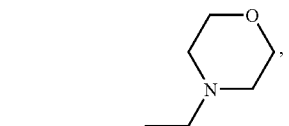 |
| 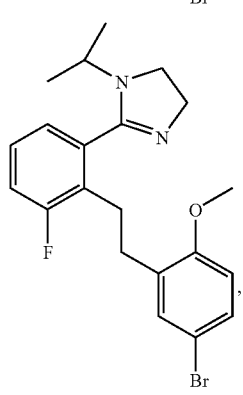 | 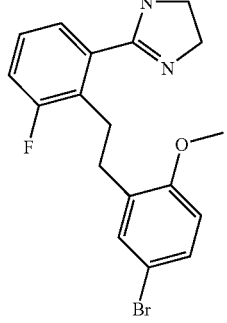 |

523
-continued
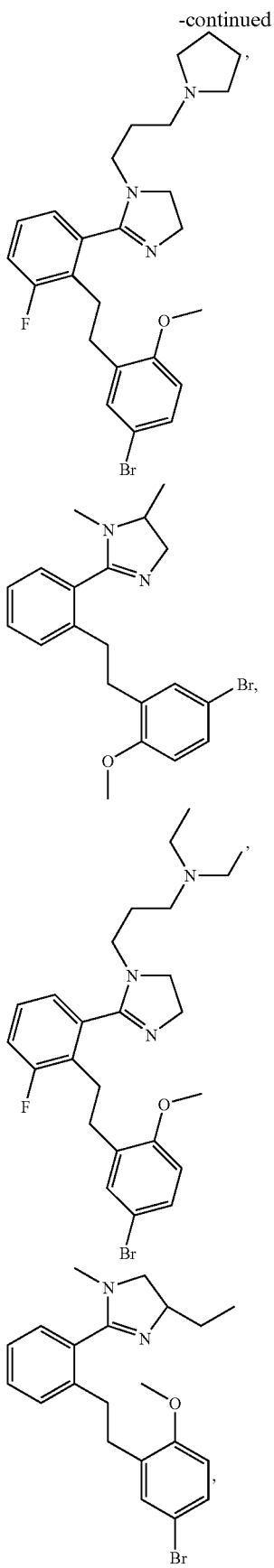
524
-continued
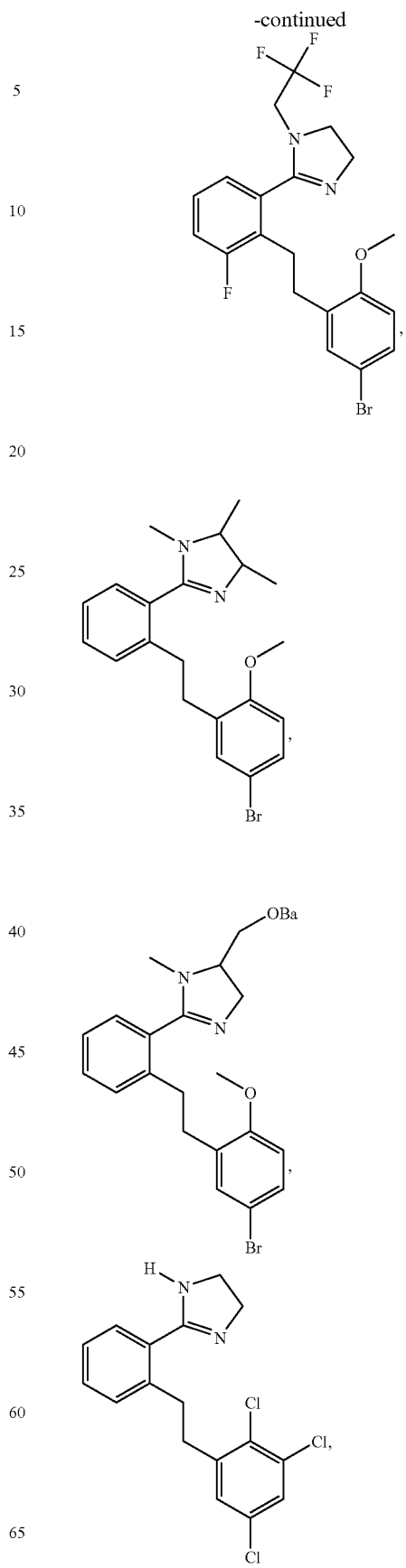

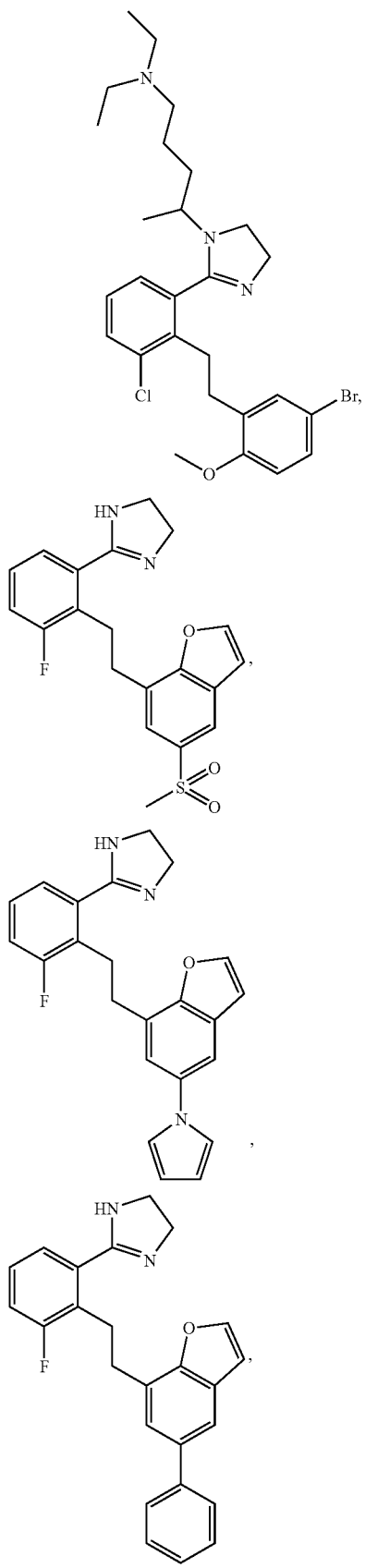
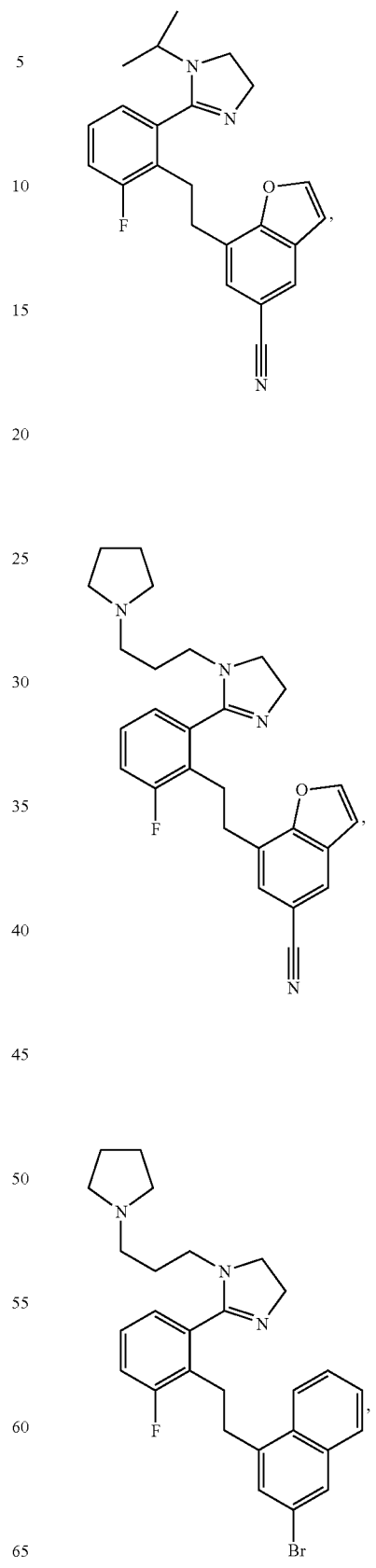

527                                528
-continued                         -continued
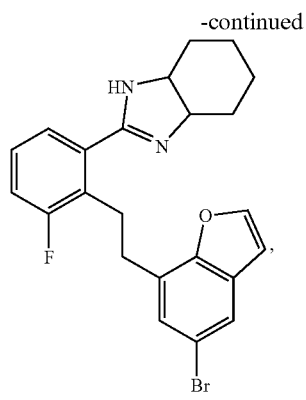
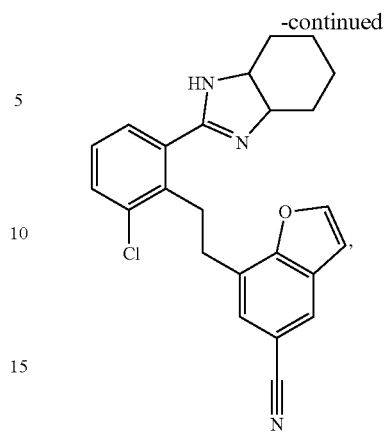
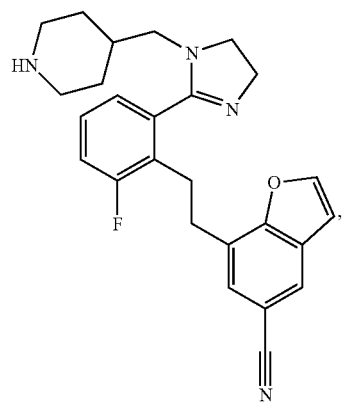
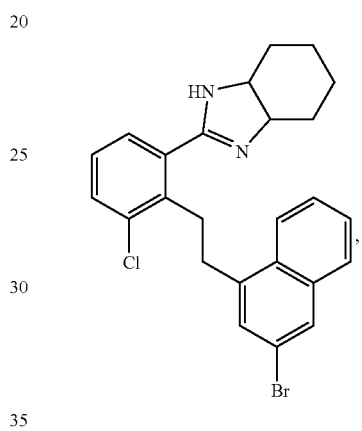
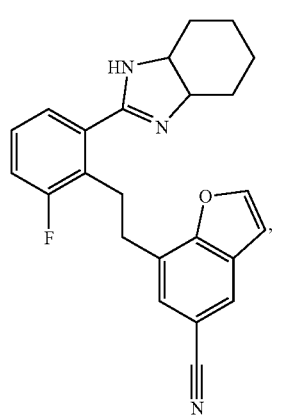
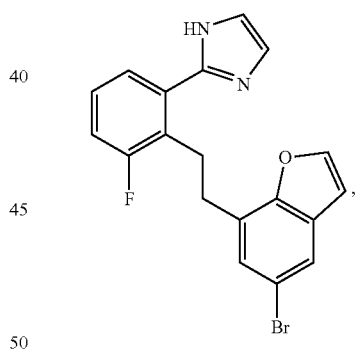
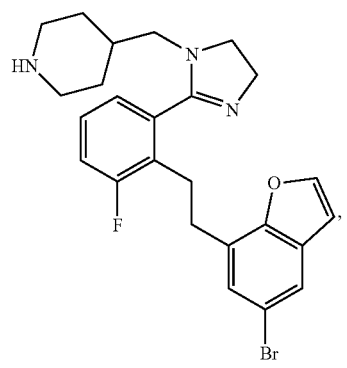
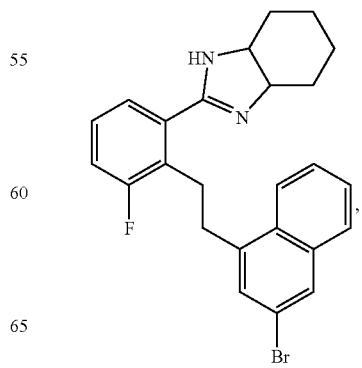

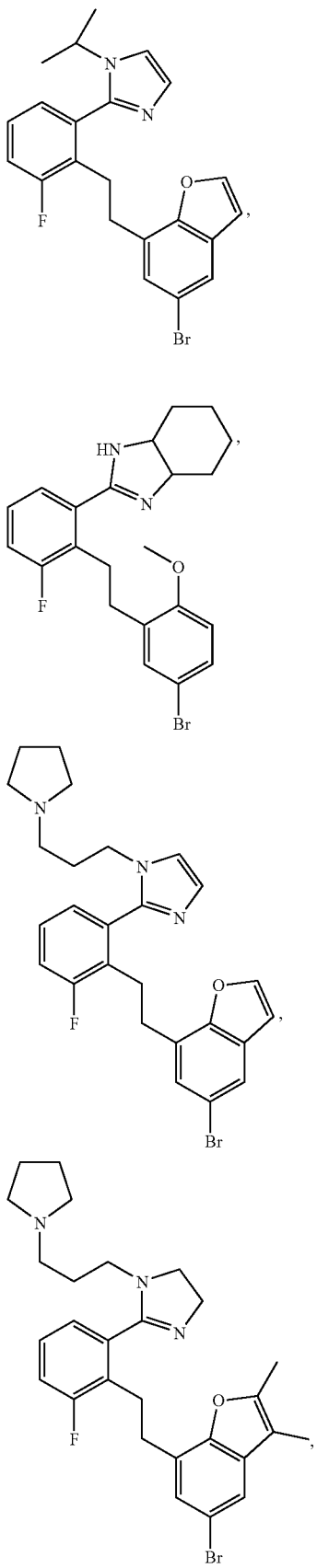
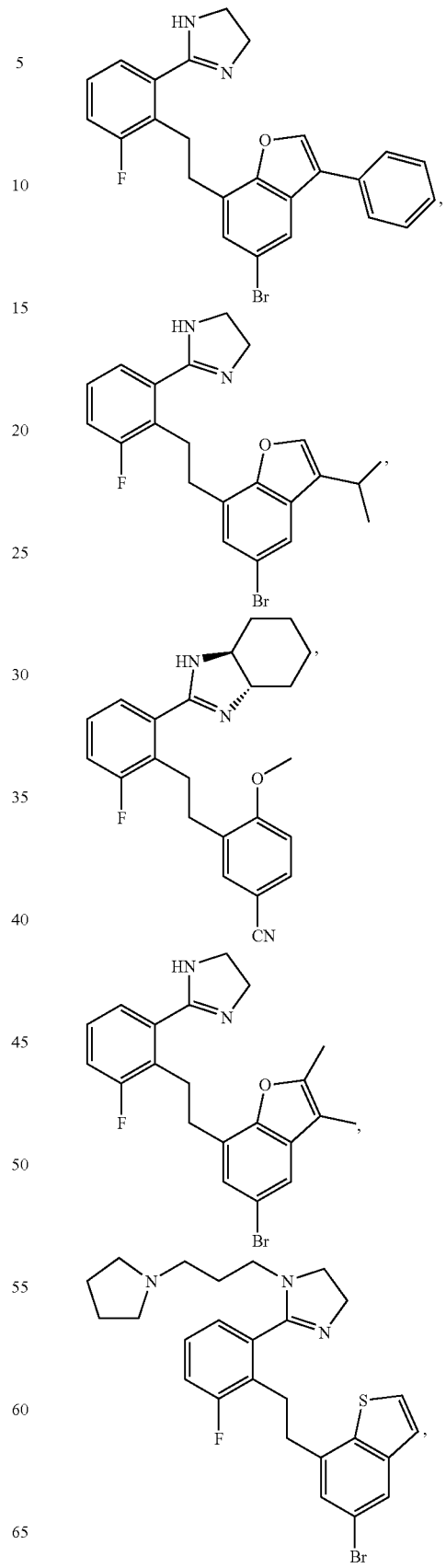

531
-continued
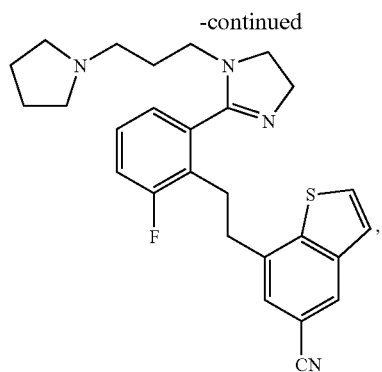
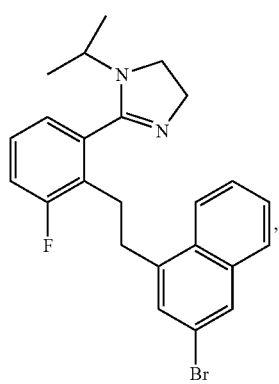
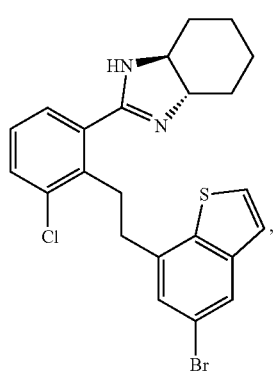
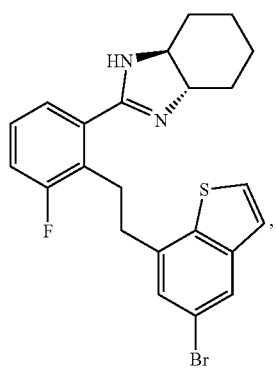
532
-continued
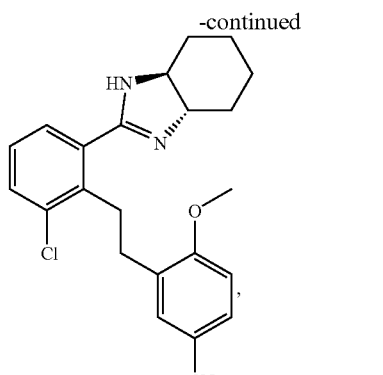
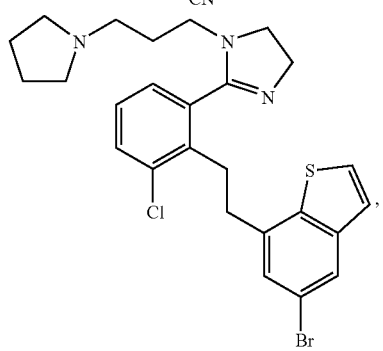
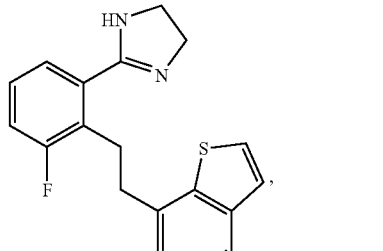
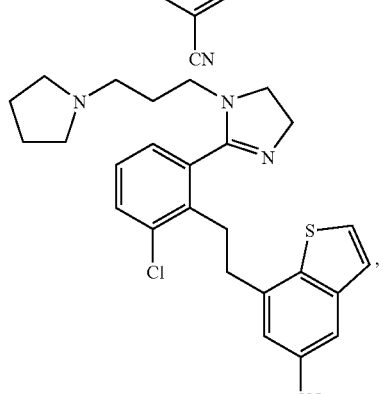
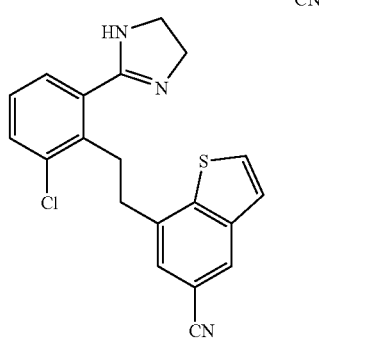

-continued
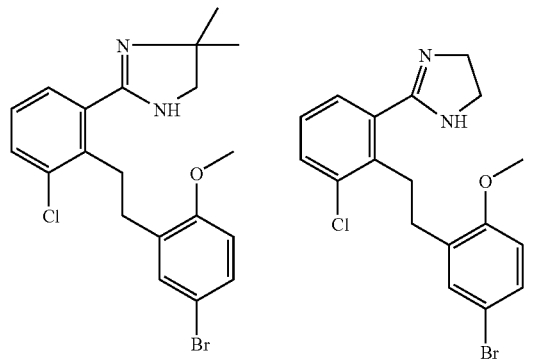
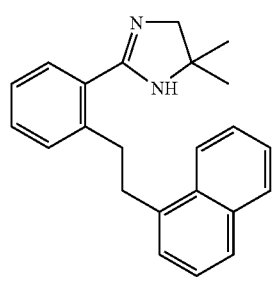
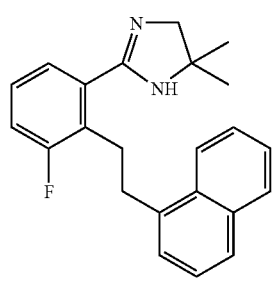
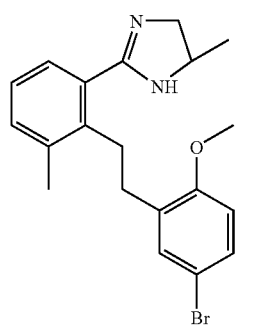
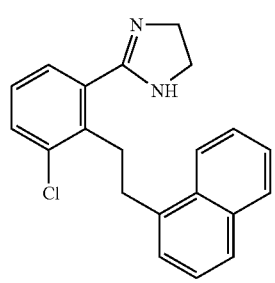
-continued
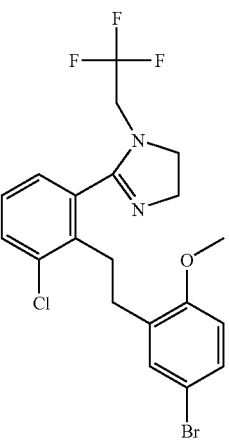 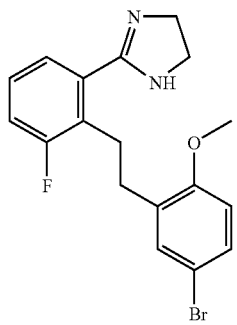
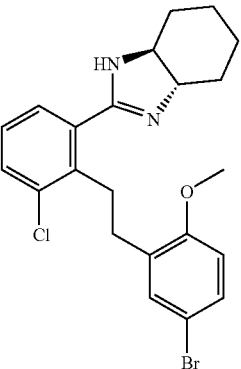 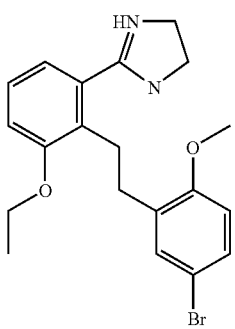
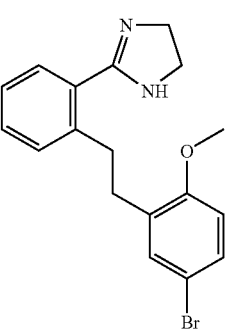 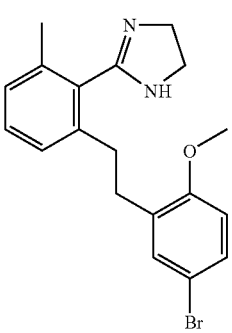

-continued
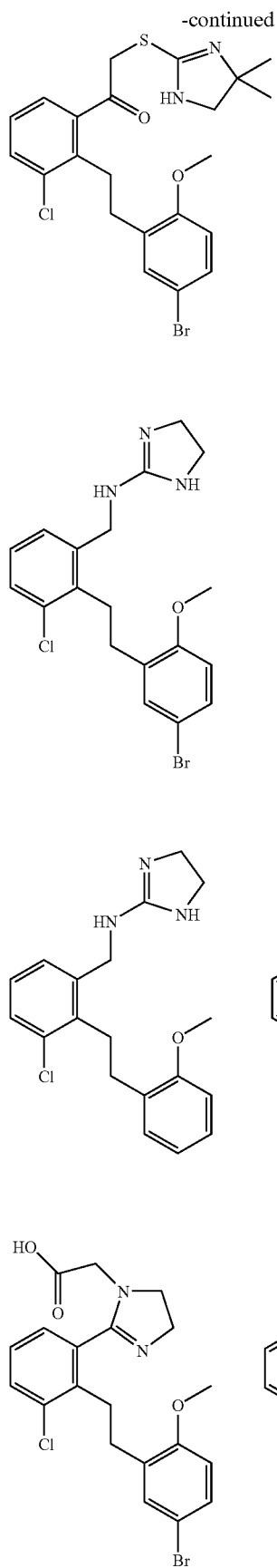
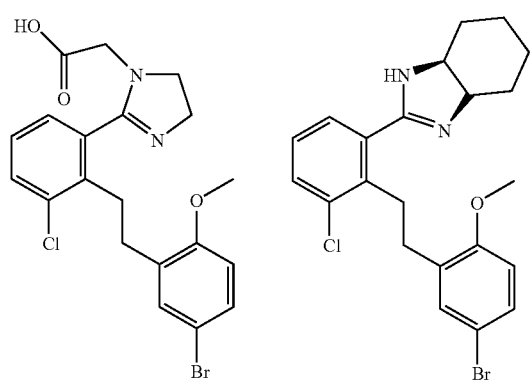
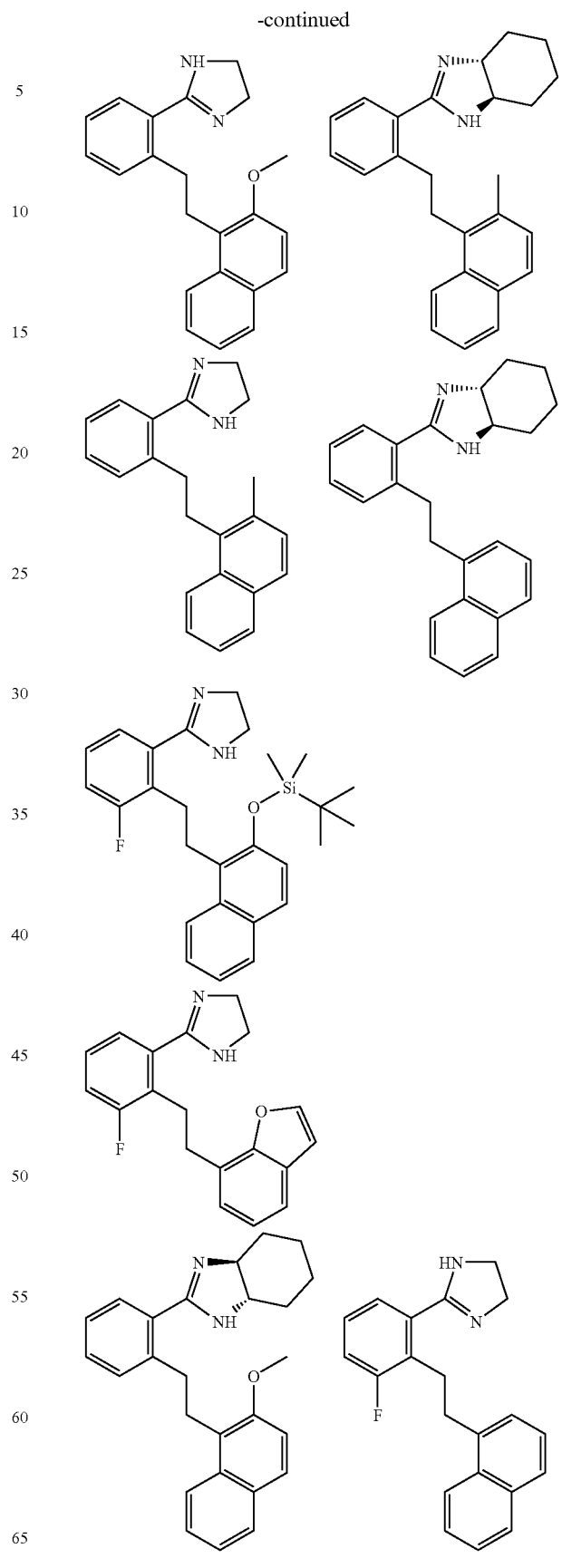

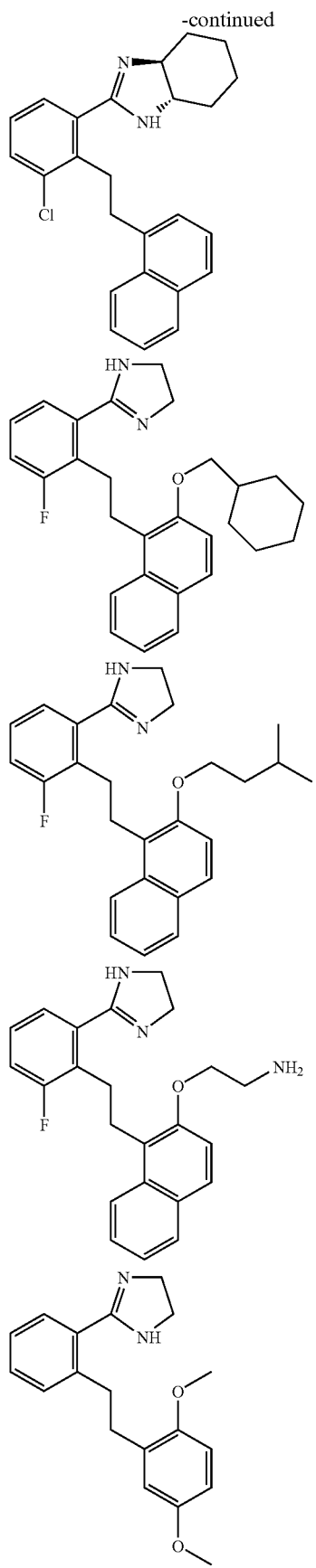
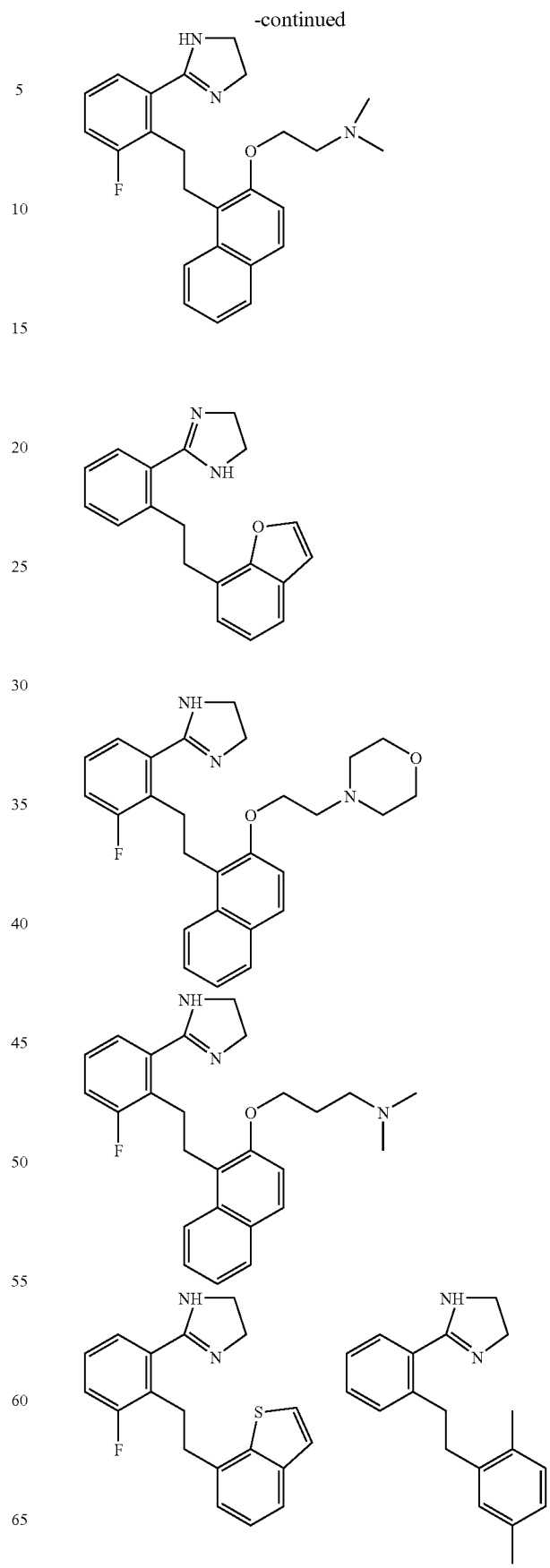

-continued
539
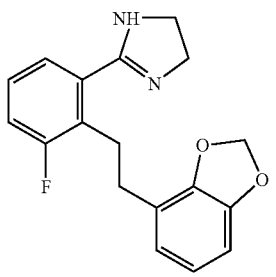
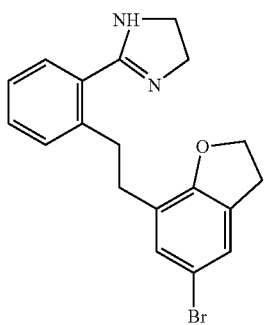
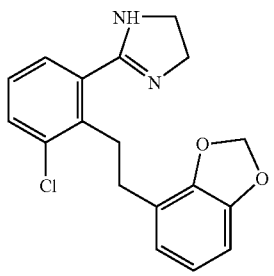
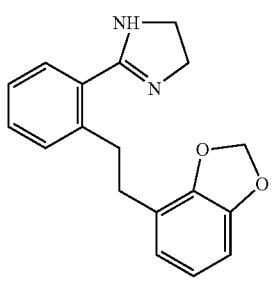
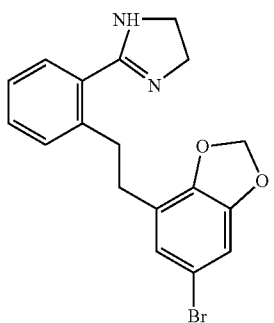
540
-continued
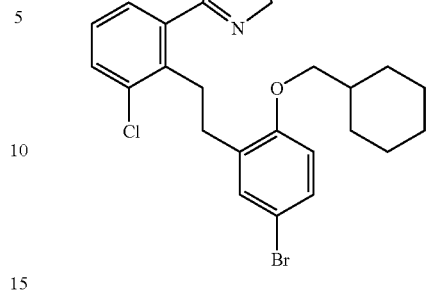
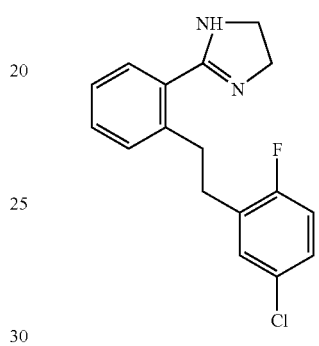
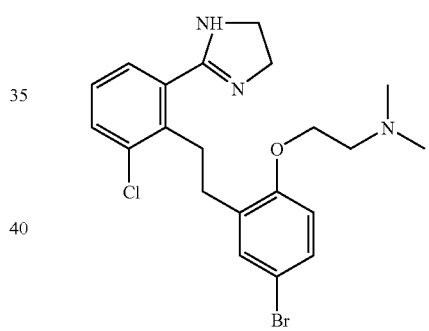
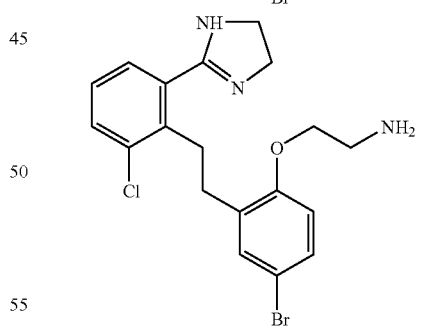
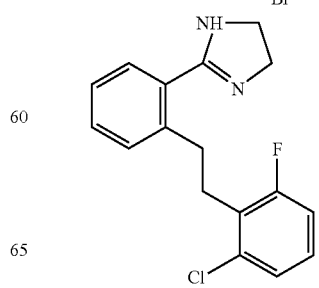

-continued
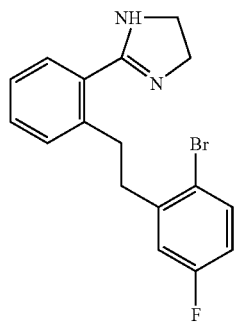
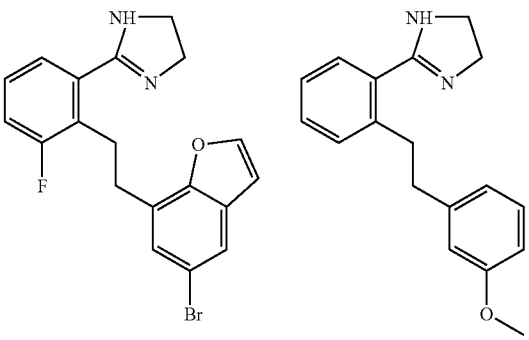
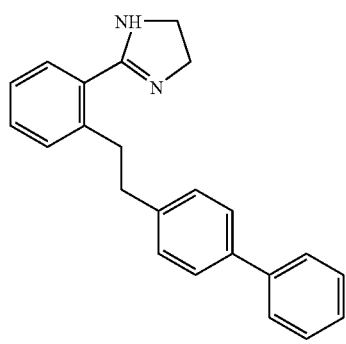
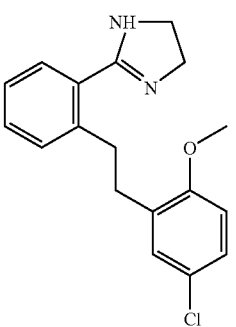
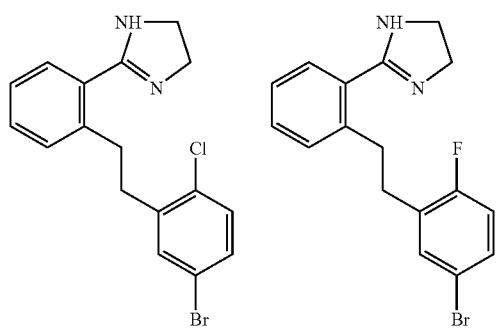
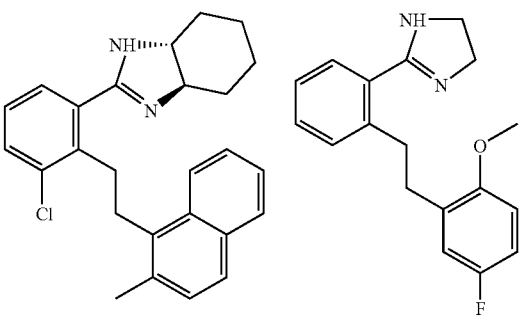
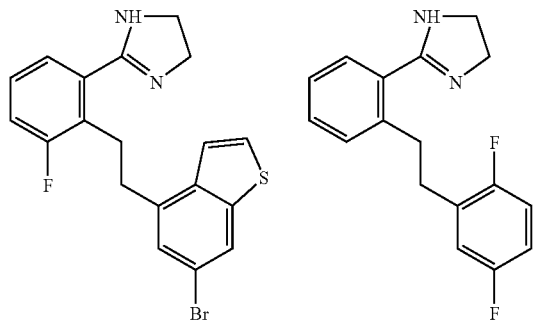
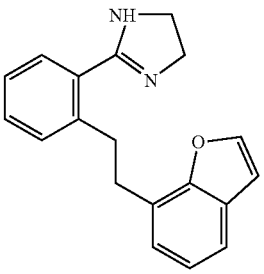
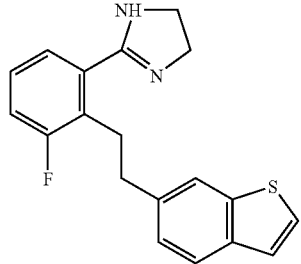
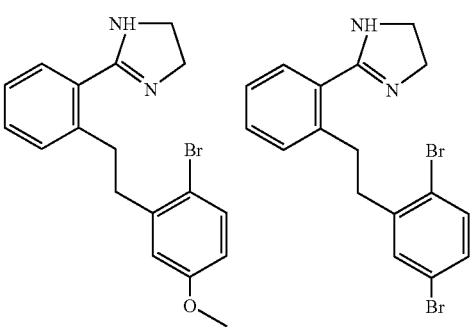

543 -continued
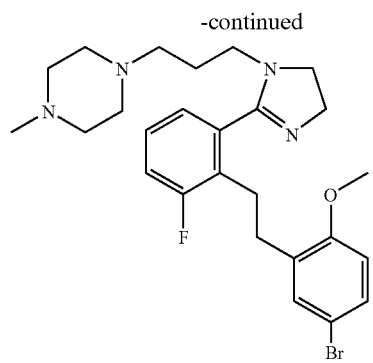
544 -continued
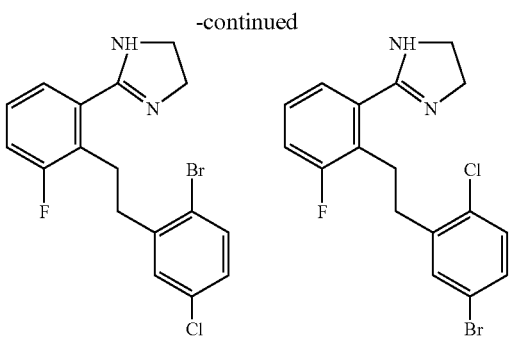
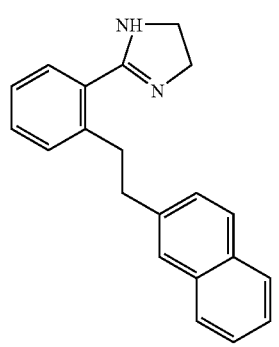
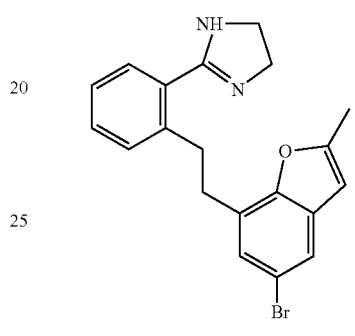
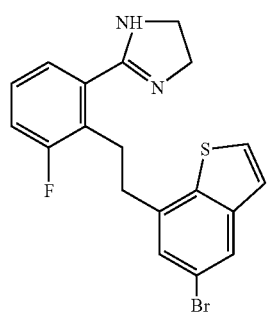
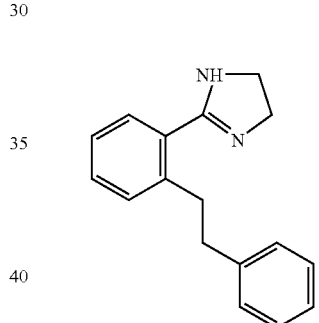
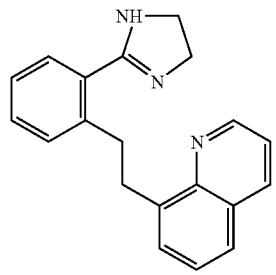
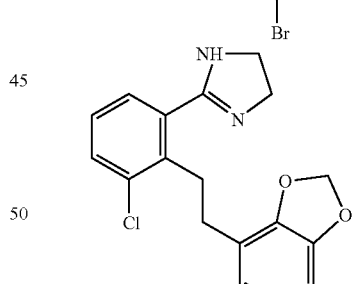
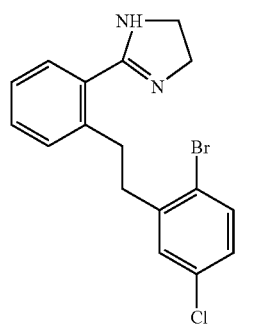
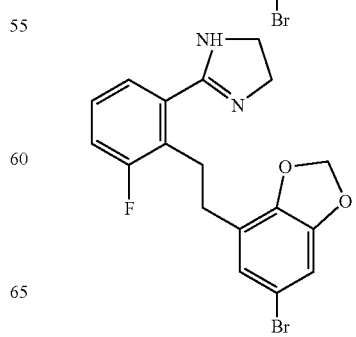

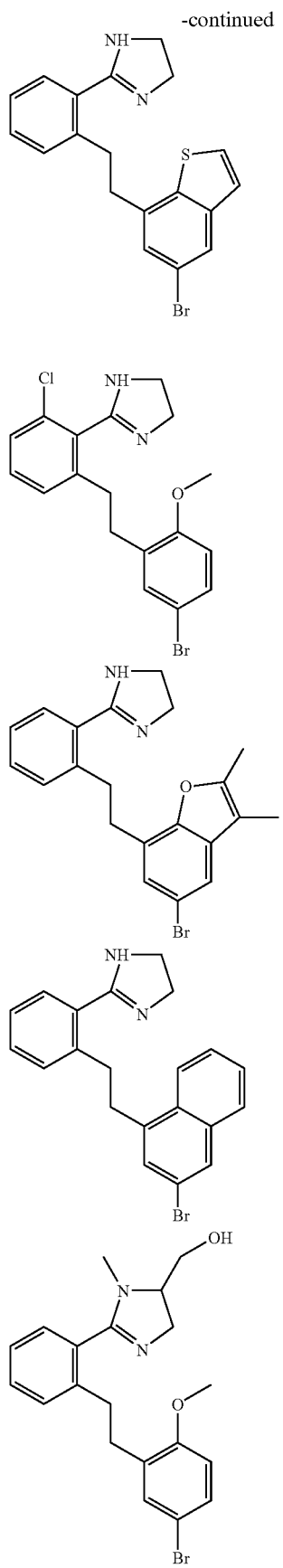
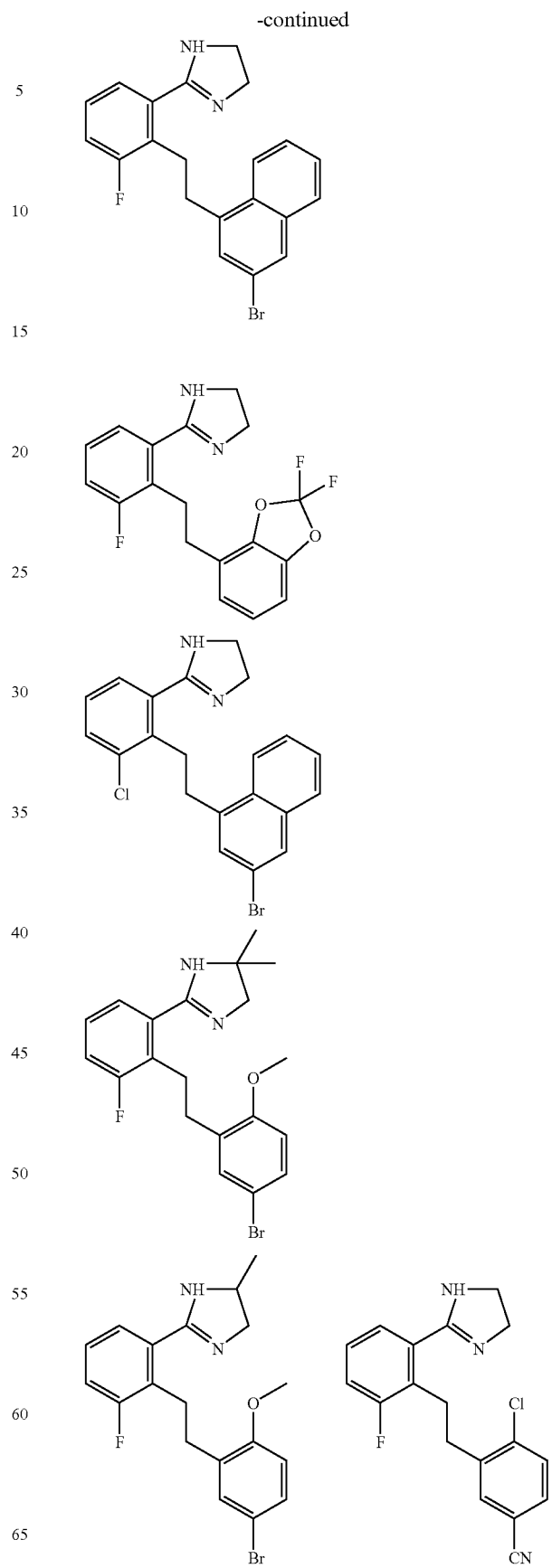

-continued
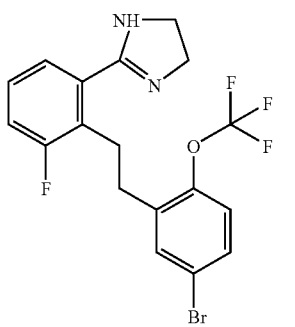
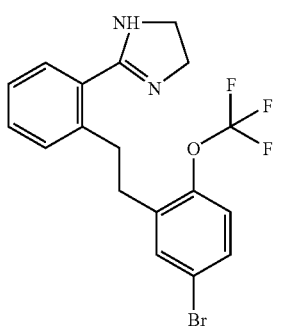
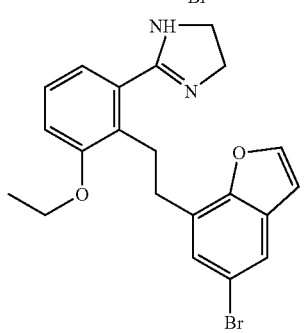
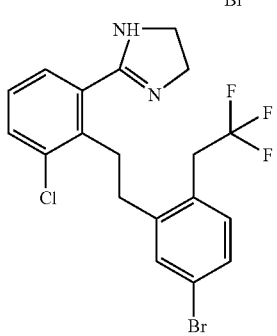
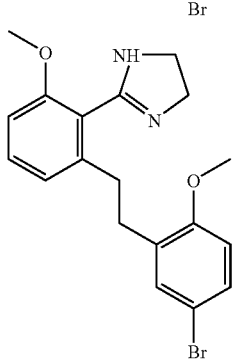
-continued
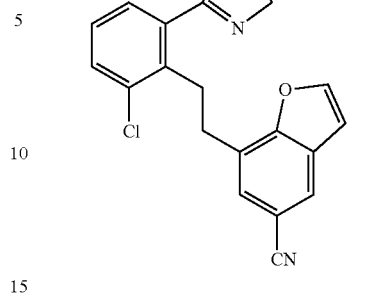
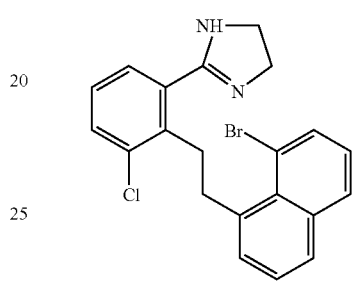
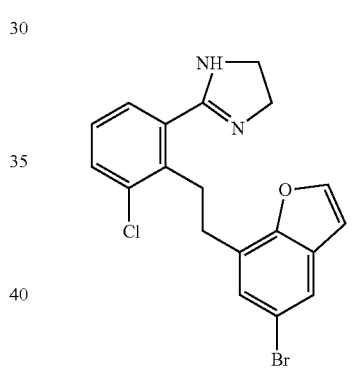
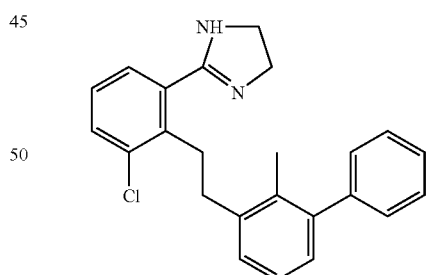
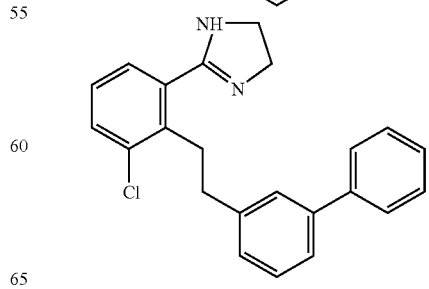

-continued
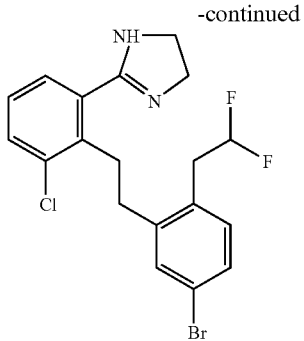
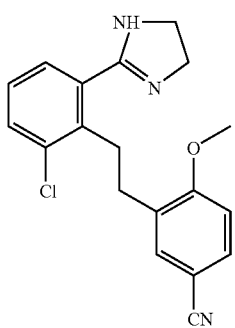
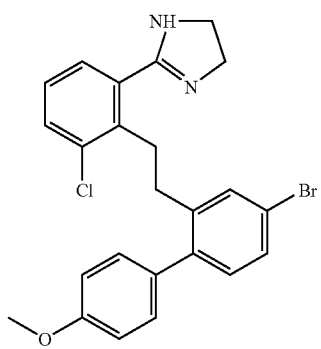
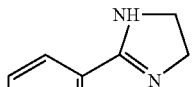
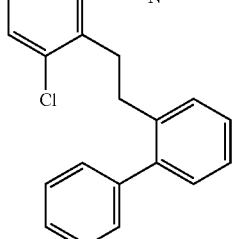
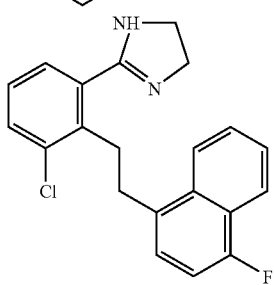
-continued
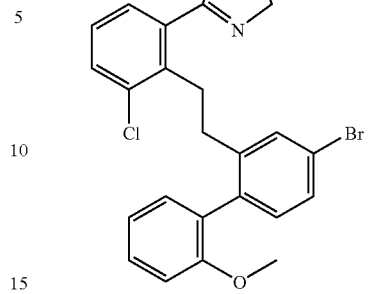
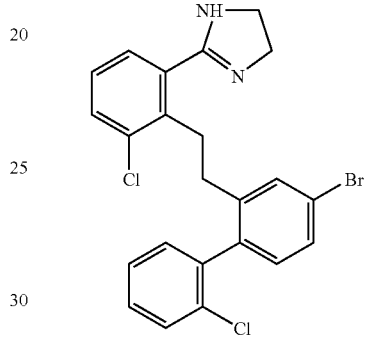
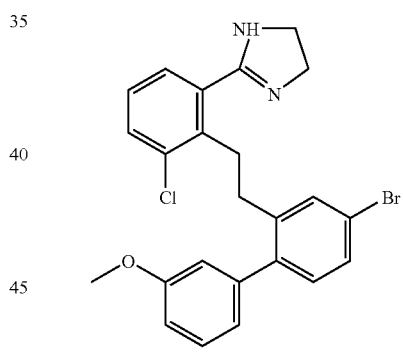
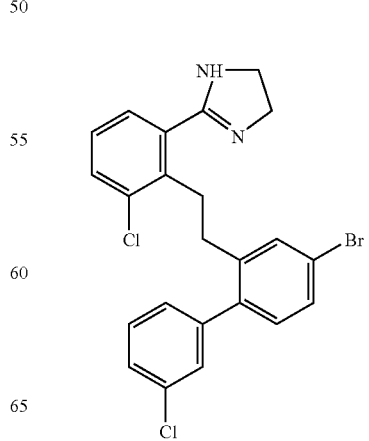

-continued
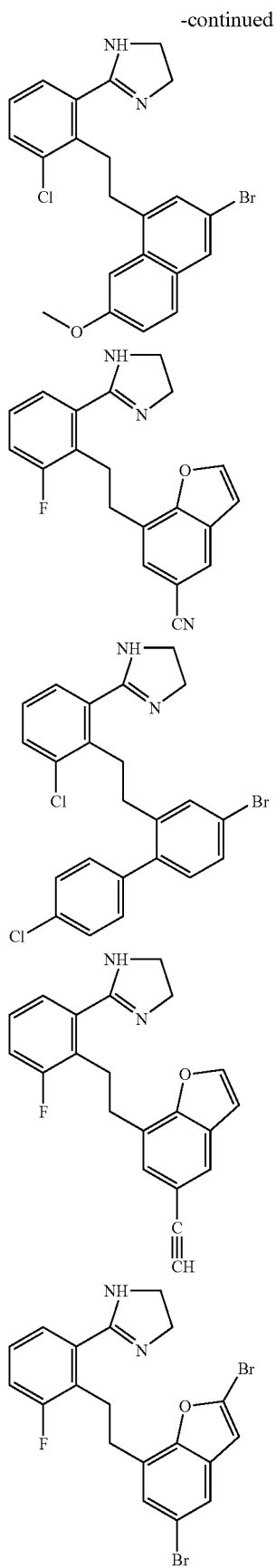
-continued
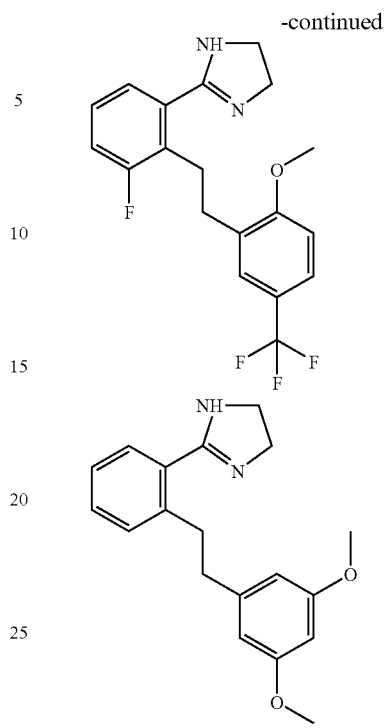
or pharmaceutically acceptable salt thereof.
19. A compound of formula:
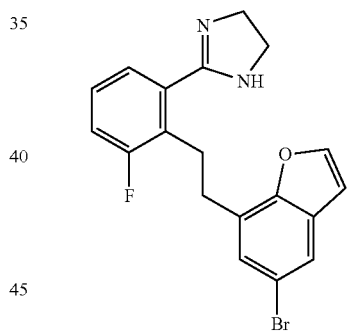
or a pharmaceutically acceptable salt thereof.
20. A compound of formula:
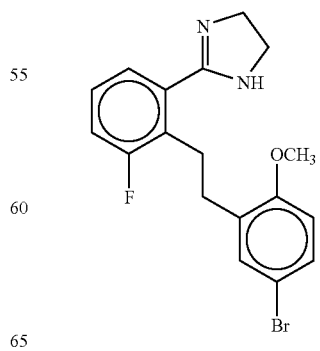
or a pharmaceutically acceptable salt thereof.

21. A pharmaceutical composition comprising a compound according to claim 1 or salt thereof and a pharmaceutically acceptable carrier.

22. A method of treating an MC4-R associated weight loss disorder in a patient in need thereof comprising administering to said patient a compound of formula (XVII) in claim 1 or salt thereof, wherein the weight loss disorder is a cachexia, aging involuntary weight loss, sarcopenia, catabolic wasting, or anorexia.

23. A method of treating an MC4-R associated weight loss disorder in a patient in need thereof comprising administering to said patient a pharmaceutical composition according to claim 21.

24. The method of claim 23, wherein the weight loss disorder is a cachexia, aging involuntary weight loss, sarcopenia, catabolic wasting, or anorexia.

25. The method of claim 22, wherein cachexia is cancer cachexia, cardiac cachexia, chronic illness cachexia, or AIDS cachexia.

26. The method of claim 23, wherein cachexia is cancer cachexia, cardiac cachexia, chronic illness cachexia, or AIDS cachexia.

27. The method of claim 22, wherein the compound is

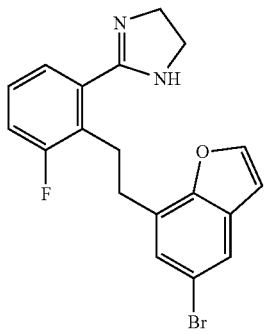

or a pharmaceutically acceptable salt thereof.

28. The method of claim 23, wherein the pharmaceutical composition comprises

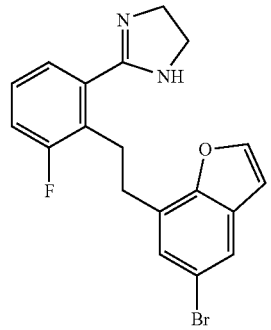

or a pharmaceutically acceptable salt thereof.

29. The method of claim 22, wherein the compound is

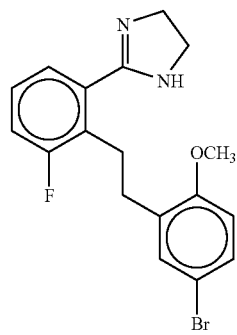

or a pharmaceutically acceptable salt thereof.

30. The method of claim 23, wherein the pharmaceutical composition comprises

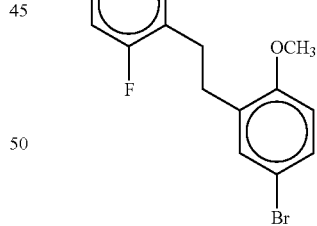

or a pharmaceutically acceptable salt thereof.

* * * * *

UNITED STATES PATENT AND TRADEMARK OFFICE
CERTIFICATE OF CORRECTION

PATENT NO. : 7,375,125 B2  Page 1 of 1
APPLICATION NO. : 10/462436
DATED : May 20, 2008
INVENTOR(S) : Tricia J. Vos et al.

It is certified that error appears in the above-identified patent and that said Letters Patent is hereby corrected as shown below:

In claim 1, column 504, lines 5-19, the structure of formula XVII should be:

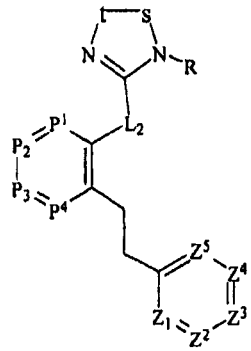

Signed and Sealed this

Ninth Day of March, 2010

David J. Kappos
*Director of the United States Patent and Trademark Office*